United States Patent
Hardy et al.

(10) Patent No.: US 10,077,243 B2
(45) Date of Patent: Sep. 18, 2018

(54) COMPOUNDS FOR TREATING DISORDERS MEDIATED BY METABOTROPIC GLUTAMATE RECEPTOR 5, AND METHODS OF USE THEREOF

(71) Applicant: Sunovion Pharmaceuticals Inc., Marlborough, MA (US)

(72) Inventors: Larry Wendell Hardy, Sturbridge, MA (US); Michele L. R. Heffernan, Worcester, MA (US); Frank Xinhe Wu, Shrewsbury, MA (US); Lakshmi D. Saraswat, Sudbury, MA (US); Kerry L. Spear, Concord, MA (US)

(73) Assignee: SUNOVION PHARMACEUTICALS INC., Marlborough, MA (US)

( * ) Notice: Subject to any disclaimer, the term of this patent is extended or adjusted under 35 U.S.C. 154(b) by 0 days.

(21) Appl. No.: 14/299,364

(22) Filed: Jun. 9, 2014

(65) Prior Publication Data

US 2014/0349992 A1    Nov. 27, 2014

Related U.S. Application Data

(63) Continuation of application No. 12/972,293, filed on Dec. 17, 2010, now Pat. No. 8,772,301.

(60) Provisional application No. 61/288,250, filed on Dec. 18, 2009.

(51) Int. Cl.

| | | |
|---|---|---|
| *A61K 31/517* | (2006.01) | |
| *C07D 487/04* | (2006.01) | |
| *C07D 239/88* | (2006.01) | |
| *C07D 403/06* | (2006.01) | |
| *C07D 405/06* | (2006.01) | |
| *C07D 417/06* | (2006.01) | |
| *C07D 471/04* | (2006.01) | |
| *C07D 487/20* | (2006.01) | |
| *C07D 401/14* | (2006.01) | |
| *C07D 413/04* | (2006.01) | |
| *C07D 471/14* | (2006.01) | |
| *C07D 471/20* | (2006.01) | |
| *C07D 487/08* | (2006.01) | |
| *C07D 491/20* | (2006.01) | |
| *C07D 498/04* | (2006.01) | |

(52) U.S. Cl.
CPC ......... *C07D 239/88* (2013.01); *C07D 401/14* (2013.01); *C07D 403/06* (2013.01); *C07D 405/06* (2013.01); *C07D 413/04* (2013.01); *C07D 417/06* (2013.01); *C07D 471/04* (2013.01); *C07D 471/14* (2013.01); *C07D 471/20* (2013.01); *C07D 487/04* (2013.01); *C07D 487/08* (2013.01); *C07D 487/20* (2013.01); *C07D 491/20* (2013.01); *C07D 498/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 5,134,127 A | 7/1992 | Stella et al. | |
| 2009/0054433 A1 | 2/2009 | Nam et al. | |
| 2009/0163545 A1* | 6/2009 | Goldfarb | 514/312 |
| 2011/0092475 A1 | 4/2011 | Hopper et al. | |
| 2011/0098313 A1 | 4/2011 | Green et al. | |

FOREIGN PATENT DOCUMENTS

| | | |
|---|---|---|
| WO | WO-2003/051315 A2 | 6/2003 |
| WO | WO-2004/087048 A2 | 10/2004 |
| WO | WO-2005/030128 A2 | 4/2005 |
| WO | WO-2005/044797 A1 | 5/2005 |
| WO | WO-2006/012577 A2 | 2/2006 |
| WO | WO-2006/048771 A1 | 5/2006 |
| WO | WO-2006/89700 A1 | 8/2006 |
| WO | WO-2006/123244 A2 | 11/2006 |
| WO | WO-2006/123249 A2 | 11/2006 |
| WO | WO-2006/123255 A2 | 11/2006 |
| WO | WO-2006/123257 A2 | 11/2006 |
| WO | WO-2006/129199 A1 | 12/2006 |
| WO | WO-2007/000771 A2 | 1/2007 |
| WO | WO-2007/023245 A1 | 3/2007 |
| WO | WO-2007/023290 A1 | 3/2007 |
| WO | WO-2007/087135 A2 | 8/2007 |
| WO | WO-2008/056259 A2 | 5/2008 |
| WO | WO-2008/112440 A1 | 9/2008 |
| WO | WO-2008/151184 A1 | 12/2008 |
| WO | WO-2008/152089 A1 | 12/2008 |
| WO | WO-2008/152090 A1 | 12/2008 |

(Continued)

OTHER PUBLICATIONS

Assay Guidance Manual Version 5.0, Eli Lilly and Company and NIH Chemical Genomics Center, www.ncgc.nih.gov/guidance/manual_toc.html, (2008).

(Continued)

*Primary Examiner* — Brian E McDowell

(57) ABSTRACT

Provided herein are compounds of formula (I):

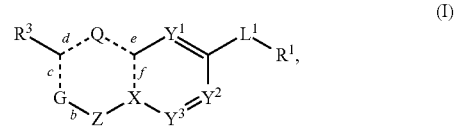

and pharmaceutical compositions thereof, useful for the treatment of disorders mediated by metabotropic glutamate receptor 5.

11 Claims, No Drawings

(56) References Cited

FOREIGN PATENT DOCUMENTS

| WO | WO-2009/099177 A1 | 8/2009 |
| WO | WO-2009/143049 A1 | 11/2009 |
| WO | WO-2011/035324 A1 | 3/2011 |
| WO | WO-2012/058128 A2 | 5/2012 |

OTHER PUBLICATIONS

Carstensen, J.T., Drug Stability: Principles & Practice, 2:379-380 (1995).
Chizh, B.A. et al., Novel approaches to targeting glutamate receptors for the treatment of chronic pain, Amino Acids, 23:169 (2002).
Goadsby, P.J. et al., Migrane—current understanding and treatment, New England Journal of Medicine, 346:257 (2002).
Handbook of Pharmaceutical Additives, 3rd Edition, Ash and Ash Eds., Gower Publishing Company: 2007.
Harrison's Principles of Internal Medicine, pp. 93-98 (Wilson et al., eds., 12th ed. 1991.
International Preliminary Report on Patentability for PCT/US2010/061147, (dated Jun. 19, 2012).
International Search Report for PCT/US2010/061147, (dated Sep. 7, 2011).
Introduction to Pharmaceutical Dosage Forms. 4th ed., Lea & Febiger, Philadelphia (1985).
Jaeschke, G. et al., mGlu5 Receptor antagonist and their therapeutic potential, Expert Opinion on Therapeutic Patents, 18:123 (2008).
Jens T. Carstensen, Drug Stability: Principles & Practice, 2d. Ed., Marcel Dekker, NY, NY, 1995, pp. 379-380.
Kinney, G.G. et al., A Novel Selective Positive Allosteric Modulator of Metabotropic Glutamate Receptor Subtype 5 has in vivo activity and antipsychotic-like effects in rat behavior models, Journal of Pharmacological Experimental Therapies, 313:199-206 (2005).
Lecoutier, L. et al., Positive Allosteric Modulation of Metabotropic Glutamate 5 Receptors Reverse N-Methyl-D-Aspartate Antagonist-Induced Alteration of Neuronal Firing in Prefrontal Cortex, Biological Psychiatry, 62:739-746 (2007).
Lindsley, C.W. et al., Progress Towards Validating the NMDA Receptor Hypofunction Hypothesis of Schizophrenia, Current Topics in Medicinal Chemistry, 6(8):771-885 (2006).
Liu, F. et al., ADX47273 [S-(4-Fluoro-phenyl)-{3-(4-Fluoro-phenyl)-[1,2,4]-oxadiazol-5-yl}-methanone]: A Novel Metabotropic Glutamate Receptor 5-Selective Positive Allosteric Modulator with Preclinical Antipsychotic-Like and Procognitive Activities, Journal of Pharmacological Experimental Therapy, 327:827-839 (2008).
O'Brien, J.A., A Family of Highly Selective Allosteric Modulatros of the Metobotropic Glutamate Receptor Subtype 5, Molecular Pharmacology, 64(3):731-740 (2003).
Pharmaceutical Preformulation and Formulation, 2nd Edition, Gibson Ed., CRC Press LLC: Boca Raton, FL, 2009.
Pieraszek, M. et al., The role of group I metabotropic glutamate receptors in schizophrenia, Amino Acids, 32:173-178 (2007).
Remington's Pharmaceutical Sciences, 18th Ed., Mack Publishing, Easton PA (1990).
Remington: The Science and Practice of Pharmacy, 21st Edition, Lippincott Williams & Wilkins: Philadelphia, PA, 2005.
Rowe et al., Handbook of Pharmaceutical Excipients, The Pharmaceutical Press and the American Pharmaceutical Association, 5 (2005).
Sharma, S. et al., Synthesis and SAR of a mGluR5 allosteric partial antagonist lead: Unexpected modulation of pharmacology with slight structural modifications to a 5-(phenylethynyl)pyrimidine scaffold, Bioorganic Medicinal Chemistry Letters, 18:4098-4101 (2008).
Stahl, S.M., The genetics of schizophrenia converge upon the NMDA glutamate receptor, CNS Spectrum, 12;583-588 (2007).
Still, et al., Rapid chromatographic technique for preparative separations with moderate resolution, Journal of Organic Chemistry, 43:2923 (1978).
Uslaner, J.M. et al., Dose-dependent effect of CDPPB, the mGluR5 positive allosteric modulator, on recognition memory is associated with GluR1 and CREB phosphorylation in the prefrontal cortex and hippocampus, Neuropharmacology, 57(5-6):531-538 (2009).
Varnes, K.J. et al., Discovery of novel positive allosteric modulators of the metabotropic glutamate receptor 5 (mGlu5), Bioorganic Medicinal Chemistry Letters, (2011).
Williams, et al., Emerging Molecular Approaches to Pain Therapy, Journal of Medicinal Chemistry, 42:1481-1485 (1999).
Written Opinion for PCT/US2010/061147, (dated Sep. 6, 2011).
Zou, M. et al., Design and synthesis of substituted N-(1,3-diphenyl-1-1 H-pyrazol-5-yl-) benzamides as positive allosteric modulators of the metabotropic glutamate receptor subtype 5", Bioorganic Medicinal Chemistry Letters, (2010).

\* cited by examiner

COMPOUNDS FOR TREATING DISORDERS MEDIATED BY METABOTROPIC GLUTAMATE RECEPTOR 5, AND METHODS OF USE THEREOF

RELATED APPLICATIONS

This application is a Continuation of U.S. patent application Ser. No. 12/972,293, filed Dec. 17, 2010, which issued as U.S. Pat. No. 8,772,301, and claims priority to U.S. Provisional Patent Application No. 61/288,250, filed on Dec. 18, 2009. The entire contents of the foregoing applications are incorporated herein by reference.

FIELD

Provided herein are compounds useful for treating disorders mediated by metabotropic glutamate receptor 5 (mGluR5), compositions comprising the compounds, and methods of use thereof.

BACKGROUND

The amino acid L-glutamate (which herein is referred to simply as glutamate) is the principal excitatory neurotransmitter in the brain and other elements of the central nervous system of mammals. Glutamate binds to neurons and activates cell surface receptors. Glutamate has significant roles in motor control, cognitive function, sensory perception, and acts as a mediator of persistent changes in the strength of synaptic signaling (synaptic plasticity), thereby modulating long term potentiation (LTP) and long term depression (LTD), which form the basis of learning and memory. Many neurological and neuropsychiatric disorders, including, but not limited to, psychosis spectrum disorders, schizophrenia and other cognitive deficits, are associated with aberrations in the function of (or the regulation by, or the regulation of) glutamate signaling systems.

Glutamate acts through two heterogeneous families of receptors: ionotropic and metabotropic glutamate receptors (mGluR). mGluRs are G protein-coupled receptors that activate intracellular second messengers when bound to glutamate. Eight subtypes of mGluRs have been cloned and classified into three groups on the basis of sequence similarities and pharmacological properties. mGluR1 and mGluR5 belong to Group I, which initiate cellular responses through a G-protein mediated mechanism and activate phospholipase C, leading to phosphoinositide hydrolysis and the mobilization of intracellular calcium (Schoepp, D. D., et al., *Neuropharmacology* 1999, 38, 1431). Two receptors that are central to the current understanding of new approaches for the treatment of the foregoing neurological and neuropsychiatric disorders are (i) an ionotropic glutamate receptor, namely the NMDA receptor [reviewed in Stahl, S. M. (2007) *CNS Spectrum* 12: 583-588], and (ii) mGluR5 [reviewed in Lindsley, C. W. et al. (2006) *Current Topics in Medicinal Chemistry* 6: 771-885; Pietraszek, M. et al. (2007) *Amino Acids* 32: 173-178]. A salient aspect of this understanding is that reduced function (hypofunction) of the NMDA receptor is involved in the symptoms of psychotic and schizophrenic diseases and disorders [Stahl, S. M. (2007) *CNS Spectrum* 12: 583-588]. Since activation of mGluR5 causes activation of the NMDA receptors that are present post-synaptically in the same cells, the exposure of the CNS to a positive allosteric modulator of mGluR5 may lead to increases in neuronal ion currents (and increased synaptic circuit firing) dependent upon the NMDA receptor [Lecourtier, L. et al. (2007) *Biological Psychiatry* 62:739-746; Uslaner, J. M. et al. (2009) *Neuropharmacology* 57: 531-538], as well as to behavioral changes that may indicate antipsychotic and pro-cognitive activities [Liu, F. et al. (2008) *J. Pharmacol. Exp. Ther.* 327: 827-839; Kinney, G. G. et al. (2005) *J. Pharmacol. Exp. Ther.* 313: 199-206]. Positive allosteric modulators of mGluR5 therefore may be of benefit in the treatment of psychotic, schizophrenic, cognitive and related neurological and neuropsychiatric diseases, either alone, or as adjunctive therapies combined with other treatments.

Moreover, since mGluR5 is expressed in both the central nervous system and the periphery (Chizh, B. A., et al., *Amino Acids* 2002, 23, 169), modulation of mGluR5 activity may be useful in the treatment of both peripheral and CNS disorders. With respect to peripheral disorders, mGluR5 negative allosteric modulators have shown efficacy in the treatment of gastrointestinal (GI) tract disorders, such as gastroesophageal reflux disease (GERD).

In the CNS, excessive activation of mGluR5 has been implicated in a number of diseases, such as various pain states, neuropsychiatric disorders such as anxiety and depression, and other neurological impairments such as drug addiction and drug withdrawal. For example, mGluR5 negative allosteric modulators are efficacious in the treatment of anxiety in a variety of animal models, including stress-induced hyperthermia and fear-potentiated startle.

Migraine is another CNS disorder relevant to mGluR5 modulation. Migraine is a chronic debilitating condition characterized by recurrent severe headaches that are often accompanied by a variety of other symptoms, such as nausea and fatigue. Pharmacologic therapies for the treatment of migraine may be divided into two classes, acute therapies for the treatment of symptoms when they arise, and chronic therapies designed to prevent the onset of migraine (prophylactics) (Goadsby, P. J., et al., *N. Engl. J. Med.* 2002, 346, 257). The best known therapeutics for the treatment of acute migraine are triptans, dual $5\text{-HT}_{1b}/5\text{-HT}_{1d}$ agonists that exert their therapeutic effects through cranial vasoconstriction. Although generally well-tolerated, their use is restricted in the presence of cardiovascular disease due to their $5\text{-HT}_{1b}$ agonism.

In contrast to the treatment for acute attacks, the current therapies for migraine prophylaxis may be subdivided into three classes: β-blockers, anticonvulsants, and antidepressants. All are moderately effective and carry substantial side-effects. Most prominent among the β-blockers is propranolol, whose side-effects include lethargy and hypotension. Valproate and topiramate are the most commonly used anticonvulsants, but, like the antidepressants, they cause side-effects such as fatigue. There is a clear medical need for a novel prophylactic therapy that is effective and free from the side-effects. Recently, an mGluR5 antagonist demonstrated efficacy in treating acute migraine in human clinical trials. The robust anxiolytic and antidepressant activities of mGluR5 antagonists should be beneficial to migraine patients, who often suffer anxiety and depression.

Other peripheral and CNS disorders relevant to mGluR5 modulation include schizophrenia, neurodegenerative diseases, levodopa-induced dyskinesia, fragile X syndrome, substance abuse/addiction, epilepsy, inflammatory, visceral and neuropathic pain, and post-traumatic stress disorder. Therefore, there is a need for effective mGluR5 modulators as therapeutics for the treatment of the aforementioned disorders.

SUMMARY

The present invention is based, at least in part, on the discovery that the compounds as disclosed herein are allosteric modulators of mGluR5, for example negative or positive allosteric modulators. Accordingly, in some aspects, the invention provides compounds of formula (I), or pharmaceutically acceptable salts, solvates, or stereoisomers thereof:

In various embodiments, a compound of formula (I) is provided:

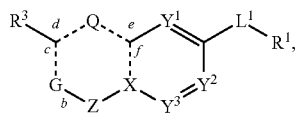
(I)

wherein;

$R^1$ is hydrogen, lower alkyl, heteroalkyl, cycloalkyl, heterocycloalkyl, alkylcycloalkyl, alkylheterocycloalkyl, alkylaryl, alkylheteroaryl, aryl or heteroaryl, each of which is optionally substituted;

$R^2$ is hydrogen, lower alkyl, lower alkenyl, heteroalkyl, cycloalkyl, heterocycloalkyl, alkylcycloalkyl, alkylheterocycloalkyl, alkylaryl, alkylheteroaryl, aryl, heteroaryl, —C(O)O$R^{12}$, or —CO—N$R^{12}$, each of which is optionally substituted;

$R^3$ is hydrogen, lower alkyl, heteroalkyl, cycloalkyl, heterocycloalkyl, alkylcycloalkyl, alkylheterocycloalkyl, alkylaryl, alkylheteroaryl, aryl or heteroaryl, each of which is optionally substituted; or $R^2$ and $R^3$ are optionally joined, together with the atoms to which they are attached, to form a mono or bicyclic ring that is carbocyclic or heterocyclic, each of which is optionally substituted;

G is CH$R^2$ or N$R^2$ when b and c are both single bonds, or G is C$R^2$ or N when one of b and c is a double bond;

Q is NH or CH$_2$ when d and e are single bonds, or N or CH when one of d or e is a double bond, or;

X is CH or N when f is a single bond, or C when f is a double bond;

Z is CH$_2$, C=O, C=S or a bond when b is a single bond, or CH or N when b is a double bond;

b, c, d, e, and f are each independently a single bond or a double bond, provided that when b is a double bond, c is a single bond; when c is a double bond, b and d are single bonds; when d is a double bond, c and e are single bonds; when e is a double bond, d and f are single bonds; and when f is a double bond, e is a single bond;

$Y^1$, $Y^2$ and $Y^3$ are each independently CH, C-halogen, C-lower alkyl, or N, provided that no more than one of $Y^2$ and $Y^3$ is N;

$L^1$ is —C≡C—, —HC=CH—, -(lower alkyl)C=C(lower alkyl)-, —CH$_2$—CH$_2$—, —CO—CH$_2$—, —CH(OH)—CH$_2$, —CH$_2$—CO—, —C$_{0-6}$alkyl-O—C$_{0-6}$alkyl-, —N$R^{12}$SO—, —SON$R^{12}$—, —N$R^{12}$SO$_2$—, —SO$_2$N$R^{12}$—, —N$R^{12}$—CO—, —CO—N$R^{12}$—,

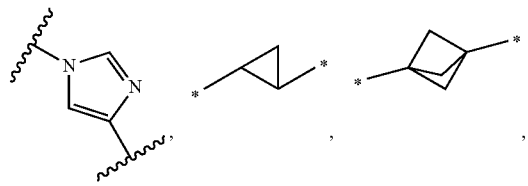

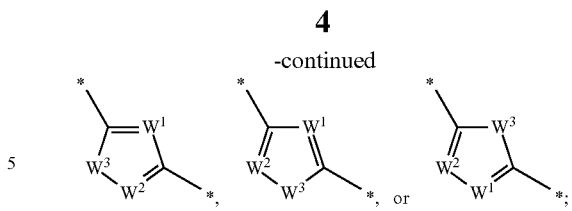

$R^{12}$ is hydrogen or lower alkyl;
$W^1$ and $W^2$ are each independently N or CH;
$W^3$ is O, S or N$R^4$; and
$R^4$ is hydrogen or lower alkyl;
or a pharmaceutically acceptable salt thereof;
provided that at least one of c and d is a double bond.

In one embodiment, at least one of G, Q, and X is a nitrogen atom. In one embodiment, at least two of G, Q, and X is a nitrogen atom. In one embodiment, both Q and G are nitrogen atoms. In one embodiment, both Q and X are nitrogen atoms.

In some aspects, the present invention provides pharmaceutical compositions and dosage forms comprising the compounds as disclosed herein. Compositions and dosage forms may comprise one or more additional active ingredients.

In some embodiments, methods are provided for the treatment of neurological disorders, such as neurodegenerative diseases, neuropsychiatric diseases, affective disorders, and loss of cognitive function, learning and memory disorders.

In some embodiments, methods are provided for the treatment, prevention, and/or management of psychosis.

In some embodiments, methods are provided for the treatment, prevention, and/or management of schizophrenia.

In some embodiments, methods are provided for the treatment, prevention, and/or management of Alzheimer's disease.

In some embodiments, methods are provided for the treatment, prevention, and/or management of cognitive disorders.

In some aspects, methods are provided for the treatment, prevention, and/or management of various conditions, disorders, or diseases mediated by mGluR5 using the compounds and compositions provided herein.

In some aspects, methods of modulating the activity of mGluR5 are provided. The method comprises contacting mGluR5 with an effective amount of a compound as disclosed herein.

In some aspects, methods of inhibiting or reducing the activity of mGluR5 are provided. The method comprises contacting mGluR5 in a cell or in a subject with an effective amount of an antagonist or a negative allosteric modulator.

In some aspects, methods of potentiating, augmenting, or increasing the activity of mGluR5 are provided, either dependently upon the presence of a sub-saturating concentration of an orthosteric agonist (such as the endogenous agonist glutamate) or independently. The method comprises contacting mGluR5 in a cell or in a subject with an effective amount of a potentiator, an allosteric agonist, or a positive allosteric modulator In some embodiments, the cell is a brain cell, such as, for example, a neuronal cell or a glial cell.

DETAILED DESCRIPTION

Definitions

Unless defined otherwise, all technical and scientific terms used herein have the same meaning as those commonly understood by one of ordinary skill in the art. All publications and patents referred to herein are incorporated by reference herein in their entirety.

As used herein, and unless otherwise indicated, the term "alkyl" refers to a linear or branched saturated monovalent hydrocarbon radical, wherein the alkyl may optionally be substituted with one or more substituents. In some embodiment, the alkyl may be optionally substituted with one or more halogen atoms. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, such as n-propyl and isopropyl), butyl (including all isomeric forms such as n-butyl, isobutyl, and t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In some embodiments, alkyl includes, but is not limited to, heteroarylalkyl (heteroaralky) such as pyridylmethyl, cycloalkylalkyl such as cyclopropylmethyl, and heterocycloalkylalkyl such as pyrrolidinomethyl, each of which is optionally substituted.

The term "heteroalkyl" includes groups in which alkyl moieties, as described above, are substituted with a heteroatom (e.g., O, N or S). One of skill in the art would be able to determine appropriate heteroalkyl moieties.

The term "bicyclic" as used herein includes fused, spiro-cylic, and bridged bicyclic compounds.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. In some embodiments, the alkenyl is optionally substituted with one or more halogen atoms. The term "alkenyl" also encompasses radicals having "cis" and "trans" configurations, or alternatively, "E" and "Z" configurations, as appreciated by those of ordinary skill in the art. As used herein, linear $C_{2-6}$ and branched $C_{3-6}$ alkenyl groups are also referred as "lower alkenyl." For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. In some embodiments, the alkynyl is optionally substituted with one or more halogen atoms. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

As used herein, and unless otherwise specified, the terms "cycloalkyl," "carbocycle" or "carbocyclic" refer to a cyclic saturated or partially unsaturated bridged and/or non-bridged monovalent hydrocarbon radical, which may be optionally substituted with one or more substituents as described herein elsewhere. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, cyclooctyl, cyclopentenyl, cyclohexenyl, decalinyl, and adamantyl.

The term "alkylcycloalkyl" includes groups in which cycloalkyl moieties are substituted with alkyl groups. One of skill in the art would be able to determine appropriate alkylcycloalkyl moieties.

As used herein, and unless otherwise specified, the term "aryl" refers to a monocyclic aromatic group and/or multi-cyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to, for example, bicyclic or tricyclic carbon rings, where at least one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents as described herein.

As used herein, and unless otherwise specified, the term "arylalkyl" or "aralkyl" refers to a monovalent alkyl group substituted with aryl, such as phenylmethyl (benzyl). In certain embodiments, both alkyl and aryl are optionally substituted with one or more substituents as described herein.

As used herein, the term "alkylaryl" includes an aryl moiety substituted with an alkyl group, such as methylphenyl (tolyl). One of skill in the art would be able to determine appropriate alkylaryl moieties.

As used herein, and unless otherwise specified, the term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl is optionally substituted with one or more substituents as described herein.

The term "alkylheteroaryl" includes groups in which a heteroaryl moiety is substituted with an alkyl group. One of skill in the art would be able to determine appropriate alkylheteroalkyl moieties.

As used herein, and unless otherwise specified, the terms "heterocyclyl," "heterocyclic" or "heterocycloalkyl" refer to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, azcanyl, azepanyl, azetidinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrofuryl, dihydrobenzisoxazinyl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, oxetanyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclyl or heterocyclic is optionally substituted with one or more substituents as described herein.

The term "alkylheterocycloalkyl" includes groups in which a heterocyclic moiety is substituted with an alkyl group. One of skill in the art would be able to determine appropriate alkylheterocycloalkyl moieties.

As used herein, and unless otherwise specified, the term "halogen", "halide" or "halo" refers to fluorine, chlorine, bromine, and/or iodine.

As used herein, and unless otherwise specified, the term "optionally substituted" refers to a group, such as an alkyl, alkenyl, alkynyl, cycloalkyl, aryl, aralkyl, heteroaryl, heteroalkyl, alkylcycloalkyl, aralkyl, heteroaralkyl, alkylaryl, alkylheteroaryl, cycloalkyl, alkylheterocycloalkyl, or heterocyclyl, which may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $M^1$; and (b) oxime (=N—OH), oxo (C=O), halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $M^1$; or (iii) R$^b$ and R$^c$ together with the N atom to which they are attached form heteroaryl or heterocyclyl, optionally substituted with one or more, in one embodiment, one, two, three, or four, substituents $M^1$. As used herein, and unless otherwise specified, all groups that can be substituted are "optionally substituted."

In one embodiment, each $M^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "stereoisomer" encompasses all enantiomerically/stereomerically pure and enantiomerically/stereomerically enriched compounds set forth herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. In some embodiments, a compound may be greater than 99.5%, greater than 99.7%, or even greater than 99.9% by weight of one stereoisomer.

As used herein and unless otherwise specified, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise specified, the term "enantiomerically pure" means a stereomerically pure composition of a compound having one chiral center. Similarly, the term "enantiomerically enriched" means a stereomerically enriched composition of a compound having one chiral center.

As used herein, and unless otherwise specified, the term "optically active" or "enantiomerically active" refers to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise specified, the term "pharmaceutically acceptable salts" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. In some embodiments, the salt is formed from hydrochloric, hydrobromic, phosphoric, or sulfuric acid. In one embodiment, the salt is formed from hydrochloride salt.

As used herein, and unless otherwise specified, the term "solvate" refers to a compound set forth herein or a salt thereof, which further includes a stoichiometric or non-stoichiometric amount of solvent bound by non-covalent intermolecular forces. Where the solvent is water, the solvate is a hydrate.

Any formula given herein is also intended to represent unlabeled forms as well as isotopically labeled forms of the compounds. For example, hydrogens represented by "H" in the formulae herein are intended to represent all isotopic forms of hydrogen (e.g., $^{1}H$, $^{2}H$ or D, or $^{3}H$); carbons represented by "C" in the formulae herein are intended to represent all isotopic forms of carbon (e.g., $^{11}C$, $^{13}C$, or $^{14}C$); nitrogens represented by "N" are intended to represent all isotopic forms of nitrogen (e.g., $^{14}N$ or $^{18}N$).

Other examples of isotopes that are included in the invention include isotopes of oxygen, sulfur, phosphorous, fluorine, iodine and chlorine, such as $^{18}F$ $^{31}P$, $^{32}P$, $^{35}S$, $^{15}O$ $^{36}Cl$ and $^{125}I$. The invention includes various isotopically labeled compounds as defined herein, for example those into which radioactive isotopes, such as $^{3}H$, $^{13}C$ and $^{14}C$ are present. In some embodiments, the atoms in the formulae herein occur in their natural abundance. In some embodiments, one or more hydrogen atom may be enriched in $^{2}H$; or/and one or more carbon atom may be enriched in $^{11}C$ $^{13}C$ $^{14}C$; or/and one or more nitrogen may be enriched in $^{14}N$. Such isotopically labeled compounds are useful in metabolic studies (with $^{14}C$), reaction kinetic studies (with, for example $^{2}H$ or $^{3}H$). detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^{2}H$ or D) may afford certain therapeutic advantages resulting from, for example, greater metabolic stability, such as increased in vivo half-life or reduced dosage requirements or an improvement in therapeutic index. It is understood that deuterium in this context is regarded as a substituent of a compound as disclosed herein. The concentration of such a heavier isotopes, specifically deuterium, may be defined by the isotopic enrichment factor. The term "isotopic enrichment factor" includes the ratio between the isotopic abundance and the natural abundance of a specified isotope, if a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Isotopically-enriched compounds as disclosed herein can generally be prepared by conventional techniques known to those skilled in the art or by processes analogous to those described in the accompanying Examples using an appropriate isotopically-enriched reagent in place of the non-enriched reagent previously employed.

The compounds as disclosed herein may exhibit the phenomenon of tautomerism. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. While the formulae cannot expressly depict all possible tautomeric forms, it is to be understood that the compounds as disclosed herein are intended to represent any tautomeric form of the depicted compounds and are not to be limited merely to a specific compound form depicted by the formula drawings. One of skill in the art by no more than routine experimentation would be able to determine which compounds may form tautomers and how to identify such tautomeric forms.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: *The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein. In some embodiments, the active ingredient is a compound as disclosed herein.

As used herein, and unless otherwise specified, the terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease (e.g., a disease or disorder related to mGluR5). In some embodiments, the therapeutic agent is a compound as disclosed herein.

As used herein, and unless otherwise indicated, the terms "treat," "treating" and "treatment" refer to the eradication or amelioration of a disease or disorder, or of one or more symptoms associated with the disease or disorder (e.g., a disease or disorder related to mGluR5). In certain embodiments, the terms refer to minimizing the spread or worsening of the disease or disorder resulting from the administration of one or more therapeutic agents to a subject with such a disease or disorder. In some embodiments, the terms refer to the administration of a compound as disclosed herein, a mixture thereof (with or without other additional active agent(s)), a solvate (e.g., hydrate), a prodrug or a pharmaceutically acceptable salt of either, after the onset of symptoms of the particular disease.

As used herein, and unless otherwise indicated, the terms "prevent," "preventing" and "prevention" refer to the prevention of the onset, recurrence or transmission of a disease or disorder, or of one or more symptoms thereof (e.g., a disease or disorder related to mGluR5). In certain embodiments, the terms refer to the treatment with or administration of a compound as disclosed herein, a mixture thereof (with or without other additional active agent(s)), a solvate (e.g., hydrate), a prodrug or a pharmaceutically acceptable salt of either, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof (e.g., a disease or disorder related to mGluR5). In some embodiments, the terms refer to management with a compound as disclosed herein. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder (e.g., a disease or disorder related to mGluR5). A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence (e.g., a disease or disorder related to mGluR5). A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In some embodiments, the subject is a human. In some embodiments, the subject is suffering from a disease or disorder related to mGluR5. In some embodiments, the subject is at risk of suffering from a disease or disorder related to mGluR5.

As used herein, and unless otherwise specified, the term "metabotropic glutamate receptor ligand" or "mGluR ligand" refers to any compound, which binds to an mGluR receptor. Unless otherwise specified, the mGluR receptor includes, but is not limited to mGluR5. Ligands include endogenous ligands for a given metabotropic glutamate receptor as well as drug molecules and other compounds, such as synthetic molecules known to bind to a particular metabotropic glutamate receptor. In some embodiments, the ligand is an allosteric modulator (e.g., a positive or negative allosteric modulator). In some embodiments, the ligand is an mGluR5 agonist. In some embodiments, the ligand is an mGluR5 antagonist. In one embodiment, the ligands include those labeled with one or more radioisotopes, such as tritium or $^{11}$C, or otherwise (e.g., fluorescently) labeled. In some embodiments, the ligand is a positron-emission tomography (PET) ligand. It is within the abilities of the skilled person to select an appropriate ligand, for example, an agonist or an antagonist, for a given metabotropic glutamate receptor.

As used herein, mGluR5 modulator is a modulator that regulates the activity of the mGluR5 receptor. An mGluR5 modulator can be a positive modulator, which increases the activity of mGluR5 receptor. An mGluR5 modulator may also be a negative modulator, which decreases the activity of the mGluR5 receptor. An mGluR5 modulator used herein may be an allosteric modulator. Such an allosteric modulator can be a positive allosteric modulator or a negative allosteric modulator.

As used herein, and unless otherwise specified, the terms "diseases" and "disorders" are used interchangeably.

Neurological Diseases and Disorders

As used herein, and unless otherwise specified, the term "neurological disorder" includes diseases, disorders or conditions of the central or peripheral nervous system of a mammal. The term "neurological disorder" includes, but is not limited to, neurodegenerative diseases, neuropsychiatric diseases, affective disorders, and loss of cognitive function, learning and memory disorders. The term "neurological disorder" also includes conditions associated with the disorder. For instance, a method of treating a neurodegenerative disorder includes methods of treating loss of memory and/or loss of cognition associated with a neurodegenerative disorder. The term "neurological disorder" also includes diseases or conditions that are implicated, at least in part, in monoamine (e.g., norepinephrine) signaling pathways (e.g., cardiovascular disease).

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxymal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Neuropsychiatric Diseases and Disorders

The term "neuropsychiatric disease" includes those neuropsychiatric diseases and disorders set forth in *The Diagnostic and Statistical Manual of Mental Disorders*, Revised, Fourth Ed., (DSM-IV-R), published by the American Psychiatric Association, which is incorporated herein by reference. Such disorders include, but are not limited to, aggression; attention disorders including attention-deficit disorder (ADD), attention-deficit-hyperactivity disorder (ADHD) and conduct disorder; delirium; delusional disorder; persisting dementia; pervasive development disorder including autism, autistic disorder and autism spectrum disorder; psychosis and psychotic disorders (including psychosis associated with affective disorders, brief reactive psychosis, brief psychotic disorder, shared psychotic disorder, and psychotic disorder due to a general medical condition and substance-induced or drug-induced psychotic disorder (e.g., caused by phencyclidine, ketamine and other dissociative anaesthetics, amphetamine, cocaine and other psychostimulants)); schizophrenia (including schizoaffective psychosis and "schizophrenia-spectrum" disorders such as schizoid or schizotypal personality disorders, or illnesses associated with psychosis (such as major depression, manic depressive (bipolar) disorder, Alzheimer's disease and post-traumatic stress syndrome) including both the positive and negative symptoms of schizophrenia and other psychoses); and sensory hyper-excitability.

The terms "attention deficit disorder" (ADD), "attention deficit disorder with hyperactivity (ADDH)," and "attention deficit/hyperactivity disorder" (AD/HD), are used herein in accordance with the accepted meanings as found in the *Diagnostic and Statistical Manual of Mental Disorders*, 4th Ed., American Psychiatric Association (DSM-IV™-R). ADD and ADHD include disorders that are most prevalent in children and are associated with increased motor activity and a decreased attention span that may result in inappropriate actions in learning and social situations.

The term "psychosis" includes mental states in which a subject suffering from psychosis undergoes a loss of contact with reality. Symptoms of pyschosis include hallucinations, delusions and impaired sight. In some embodiments, the psychosis may be associated with another neuropsychiatric disorder, for example, schizophrenia, schizophreniform disorder, schizoaffective disorder, brief psychotic disorder, bipolar disorder, clinical depression, psychosocial disorder. In some embodiments, the psychosis is related to general medical conditions, for example, brain tumors, brain damage, an epileptic disorder, dementia, multiple sclerosis, Lyme disease, Alzheimer's disease, Parkinson's disease, electrolyte disorders, hypoglycemia and AIDS. In some embodiments, the psychosis is substance-induced psychosis.

The term "schizophrenia" includes a mental disorders characterized by the disintegration of the process of thinking and emotional responsiveness, and includes symptoms such as auditory hallucinations, paranoid delusions, disorganized speech, disorganized thinking, and extensive withdrawal of the patient's interests from other people. The term "schizophrenia" also includes schizophreniform disorder and schizoaffective disorder. So-called negative symptoms of schizophrenia include affect blunting, anergia, alogia and social withdrawal. Positive symptoms of schizophrenia include delusion and hallucination. Cognitive symptoms of schizophrenia include impairment in obtaining, organizing, and using intellectual knowledge.

Affective Disorders

As used herein, and unless otherwise specified, the term "affective disorder" includes agoraphobia; anxiety and anxiety disorders (including but not limited to acute stress disorder, anxiety due to a general medical condition, dental phobia, generalized anxiety disorder, panic disorder, separation anxiety disorder, social anxiety disorder, social phobia, specific phobia, and substance-induced anxiety disorder); bipolar disorders; depression (including but not limited to dysthymia, major depressive disorder, seasonal affective disorder, seasonal depression, unipolar depression, and post-partum depression); fatigue associated with depression including but limited to chronic fatigue syndrome; mood disorders (including disorders due to a general medical condition and substance-induced mood-disorders); obsessive-compulsive disorder; panic attack; perimenopause, menopause, and male menopause; post-traumatic stress disorder; premenstrual syndrome (PMS) and premenstrual dysphoric disorder (PDD); and sleep disorders including insomnia and narcolepsy.

Cognitive Function, Learning, and Memory Disorders

As used herein, and unless otherwise specified, the terms "cognitive dysfunction," "cognitive function disorder," "learning disorder", and "memory disorder" apply to disorders that may be treated by improving mammalian brain function. The terms include disorders in which subjects exhibit symptoms of memory or learning loss, have impaired ability to learn new information or to recall previously learned information or past efforts. In some embodiments, these disorders cause marked impairment in social or occupational functioning and represent a significant decline from a previous level of functions. In some embodiments, the cognitive dysfunction may be associated with, for example, adult and childhood learning disorders; altruism; amnestic disorders (including Alzheimer's disease-related cognitive decline, normal age-related cognitive decline and persisting amnestic disorder); associative learning; attention; benign forgetfulness; cognitive deficits induced by situational stress (including but not limited to operating machinery for extended time periods or working in emergency or combat situations); cognitive disorders including dementia (associated with acquired immunodeficiency disease, Alzheimer's disease, Creutzfeldt-Jacob disease, HIV infection, Huntington's disease, ischemia, multi-infarct dementia, Parkinson's disease, perinatal hypoxia, Pick's disease, trauma, vascular problems or stroke, other general medical conditions or substance abuse); cooperativity; declarative memory; early consolidation; empathy; episodic memory; executive function; explicit memory; implicit memory; imprinting; language; late consolidation; learning (including electronic, formal, informal, multimedia and rote learning); low IQ; memory deficit; memory loss; mild cognitive impairment (MCI); non-verbal and verbal communicative skills; play; rehearsal; retrieval; semantic memory; sensory integration of environmental cues including temperature, odor, sounds, touch, and taste; social cognition; and speech disorders.

Substance Abuse and Eating Disorders

The term "substance abuse" includes a pattern of behavior in which a subject uses a substance in a abusive manner and is used herein in a manner consistent with its accepted meaning in the art. (See, e.g., DSM-IV™.) Examples of substance abuse include abuse of or addiction to canabbis, cocaine, morphine, opioids, nicotine, or alcohol; substance-abuse related disorders and addictive behaviors (including substance-induced delirium); tolerance, dependence or withdrawal from substances including alcohol, amphetamines, anxiolytics, cannabis, cocaine, hallucinogens, hypnotics, inhalants, nicotine, opioids, phencyclidine, or sedatives.

The term "eating disorder," as used herein, refers to abnormal compulsions to avoid eating or uncontrollable impulses to consume abnormally large amounts of food. Eating disorders include, but are not limited to, anorexia nervosa, binge eating, bulimia nervosa, cachexia, compulsive eating disorder, emesis, and obesity.

Pain

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, carpal tunnel syndrome, AIDS pain, arthropathy, migraine, trigeminal neuralgia, cardiac ischaemia, neuropathy arising from chronic alcohol use, and diabetic peripheral neuropathic pain (see, e.g., Harrison's *Principles of Internal Medicine*, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, the term "pain" includes pain resulting from dysfunction of the nervous system: organic pain states that share clinical features of neuropathic pain and possible common pathophysiology mechanisms, but are not initiated by an identifiable lesion in any part of the nervous system.

The term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

The term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, pain from neuropathic cancer pain, HIV/AIDS induced pain, phantom limb pain, and complex regional pain syndrome.

The term also encompasses the common clinical features of neuropathic pain including, but not limited to, sensory loss, allodynia (non-noxious stimuli produce pain), hyperalgesia and hyperpathia (delayed perception, summation, and painful after sensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including PGE2 induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes.

As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "Diabetic Peripheral Neuropathic Pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "Post-Herpetic Neuralgia", also called "Postherpetic Neuralgia (PHN)", refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

As used herein, and unless otherwise specified, the term "Trigeminal Neuralgia (TN)" refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "Complex Regional Pain Syndrome (CRPS)," formerly known as Reflex Sympathetic Dystrophy (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the term "convulsion" refers to a neurological disorder and is used interchangeably with "seizure," although there are many types of seizure, some of which have subtle or mild symptoms instead of convulsions. Seizures of all types may be caused by disorganized and sudden electrical activity in the brain. In some embodiments, convulsions are a rapid and uncontrollable shaking during which the muscles contract and relax repeatedly.

Compounds

In various embodiments, a compound of formula (I) is provided:

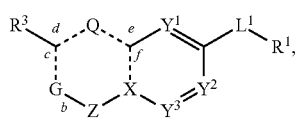

(I)

wherein.

$R^1$ is hydrogen, lower alkyl, heteroalkyl, cycloalkyl, heterocycloalkyl, alkylcycloalkyl, alkylheterocycloalkyl, alkylaryl, alkylheteroaryl, aryl or heteroaryl, each of which is optionally substituted;

$R^2$ is hydrogen, lower alkyl, lower alkenyl, heteroalkyl, cycloalkyl, heterocycloalkyl, alkylcycloalkyl, alkylheterocycloalkyl, alkylaryl, alkylheteroaryl, aryl, heteroaryl, —C(O)OR$^{12}$, or —CO—NR$^{12}$, each of which is optionally substituted;

$R^3$ is hydrogen, lower alkyl, heteroalkyl, cycloalkyl, heterocycloalkyl, alkylcycloalkyl, alkylheterocycloalkyl, alkylaryl, alkylheteroaryl, aryl or heteroaryl, each of which is optionally substituted; or $R^2$ and $R^3$ are optionally joined, together with the atoms to which they are attached, to form a mono or bicyclic ring that is carbocyclic or heterocyclic, each of which is optionally substituted;

G is CHR$^2$ or NR$^2$ when b and c are both single bonds, or G is CR$^2$ or N when one of b and c is a double bond;

Q is NH or CH$_2$ when d and e are single bonds, or N or CH when one of d or e is a double bond, or;

X is CH or N when f is a single bond, or C when f is a double bond;

Z is CH$_2$, C=O, C=S or a bond when b is a single bond, or CH or N when b is a double bond;

b, c, d, e, and f are each independently a single bond or a double bond, provided that when b is a double bond, c is a single bond; when c is a double bond, b and d are single bonds; when d is a double bond, c and e are single bonds; when e is a double bond, d and f are single bonds; and when f is a double bond, e is a single bond;

$Y^1$, $Y^2$ and $Y^3$ are each independently CH, C-halogen, C-lower alkyl, or N, provided that no more than one of $Y^2$ and $Y^3$ is N;

$L^1$ is —C≡C—, —HC=CH—, -(lower alkyl)C=C(lower alkyl)-, —CH$_2$—CH$_2$—, —CO—CH$_2$—, —CH(OH)—CH$_2$, —CH$_2$—CO—, —C$_{0-6}$alkyl-O—C$_{0-6}$alkyl-, —NR$^{12}$SO—, —SONR$^{12}$—, —NR$^{12}$SO$_2$—, —SO$_2$NR$^{12}$—, —NR$^{12}$—CO—, —CO—NR$^{12}$—, $R^{12}$ is hydrogen or lower alkyl;

$W^1$ and $W^2$ are each independently N or CH;

$W^3$ is O, S or NR$^4$; and $R^4$ is hydrogen or lower alkyl;

or a pharmaceutically acceptable salt thereof;

provided that at least one of c and d is a double bond.

In one embodiment, at least one of G, Q, and X is a nitrogen atom. In one embodiment, at least two of G, Q, and X is a nitrogen atom. In one embodiment, both Q and G are nitrogen atoms. In one embodiment, both Q and X are nitrogen atoms.

In one embodiment, at least one of d and e is a double bond.

In one embodiment, $R^1$ is hydrogen. In another embodiment, $R^1$ is optionally substituted lower alkyl. In another embodiment, $R^1$ is optionally substituted heteroalkyl. In another embodiment, $R^1$ is optionally substituted cycloalkyl. In another embodiment, $R^1$ is optionally substituted monocyclic cycloalkyl. In another embodiment, $R^1$ is optionally substituted heterocycloalkyl. In another embodiment, $R^1$ is optionally substituted monocyclic heterocycloalkyl. In another embodiment, $R^1$ is optionally substituted alkylcycloalkyl. In another embodiment, $R^1$ is optionally substituted monocyclic alkylcycloalkyl. In another embodiment, $R^1$ is optionally substituted alkylheterocycloalkyl. In another embodiment, $R^1$ is optionally substituted monocyclic alkylheterocycloalkyl. In another embodiment, $R^1$ is optionally substituted alkylaryl. In another embodiment, $R^1$ is optionally substituted monocyclic alkylaryl. In another embodiment, $R^1$ is optionally substituted alkylheteroaryl. In another embodiment, $R^1$ is optionally substituted monocyclic alkylheteroaryl. In another embodiment, $R^1$ is optionally substituted aryl. In another embodiment, $R^1$ is optionally substituted monocyclic aryl. In another embodiment, $R^1$ is optionally substituted heteroaryl. In another embodiment, $R^1$ is optionally substituted monocyclic heteroaryl.

In one embodiment, $R^2$ is hydrogen, lower alkyl, heteroalkyl, cycloalkyl, heterocycloalkyl, alkylcycloalkyl, alkylheterocycloalkyl, alkylaryl, alkylheteroaryl, aryl, or heteroaryl, each of which is optionally substituted. In one embodiment, $R^2$ is hydrogen. In another embodiment, $R^2$ is optionally substituted lower alkyl. In another embodiment, $R^2$ is optionally substituted heteroalkyl. In another embodiment, $R^2$ is optionally substituted cycloalkyl. In another embodiment, $R^2$ is optionally substituted monocyclic cycloalkyl. In another embodiment, $R^2$ is optionally substituted heterocycloalkyl. In another embodiment, $R^2$ is optionally substituted monocyclic heterocycloalkyl. In another embodiment, $R^2$ is optionally substituted alkylcycloalkyl. In another embodiment, $R^2$ is optionally substituted monocyclic alkylcycloalkyl. In another embodiment, $R^2$ is optionally substituted alkylheterocycloalkyl. In another embodiment, $R^2$ is optionally substituted monocyclic alkylheterocycloalkyl. In another embodiment, $R^2$ is optionally substituted alkylaryl. In another embodiment, $R^2$ is optionally substituted monocyclic alkylaryl. In another embodiment, $R^2$ is optionally substituted alkylheteroaryl. In another embodiment, $R^2$ is optionally substituted monocyclic alkylheteroaryl. In another embodiment, $R^2$ is optionally substituted aryl. In another embodiment, $R^2$ is optionally substituted monocyclic aryl. In another embodiment, $R^2$ is optionally substituted heteroaryl. In another embodiment, $R^2$ is optionally substituted monocyclic heteroaryl. In another embodiment $R^2$ is lower alkenyl. In another embodiment, $R^2$ is —C(O)OR$^{12}$. In another embodiment, $R^2$ is —CO—NR$^{12}$.

In one embodiment, $R^3$ is hydrogen. In another embodiment, $R^3$ is optionally substituted lower alkyl. In another embodiment, $R^3$ is optionally substituted heteroalkyl. In another embodiment, $R^3$ is optionally substituted cycloalkyl. In another embodiment, $R^3$ is optionally substituted monocyclic cycloalkyl. In another embodiment, $R^3$ is optionally substituted heterocycloalkyl. In another embodiment, $R^3$ is optionally substituted monocyclic heterocycloalkyl. In another embodiment, $R^3$ is optionally substituted alkylcycloalkyl. In another embodiment, $R^3$ is optionally substituted monocyclic alkylcycloalkyl. In another embodiment, $R^3$ is optionally substituted alkylheterocycloalkyl. In another embodiment, $R^3$ is optionally substituted monocyclic alkylheterocycloalkyl. In another embodiment, $R^3$ is optionally substituted alkylaryl. In another embodiment, $R^3$ is optionally substituted monocyclic alkylaryl. In another embodiment, $R^3$ is optionally substituted alkylheteroaryl. In another embodiment, $R^3$ is optionally substituted monocyclic alkylheteroaryl. In another embodiment, $R^3$ is optionally substituted aryl. In another embodiment, $R^3$ is optionally substituted monocyclic aryl. In another embodiment, $R^3$ is optionally substituted heteroaryl. In another embodiment, $R^3$ is optionally substituted monocyclic heteroaryl.

In another embodiment, $R^2$ and $R^3$ are linked to form a 5- to 8-membered mono or bicyclic ring that is carbocyclic or heterocyclic, any of which is optionally substituted. In another embodiment, $R^2$ and $R^3$ are linked to form a mono or bicyclic ring that is carbocyclic or heterocyclic, any of which is optionally substituted. In another embodiment, $R^2$ and $R^3$ are linked to form a monocyclic ring that is carbocyclic. In another embodiment, $R^2$ and $R^3$ are linked to form a monocyclic ring that is heterocyclic. In another embodiment $R^2$ and $R^3$ are linked to form a bicyclic ring that is carbocyclic. In another embodiment $R^2$ and $R^3$ are linked to form a bicyclic ring that is heterocyclic.

In one embodiment, G is CHR$^2$, NR$^2$, or CR$^2$. In one embodiment, G is CR$^2$. In another embodiment, G is NR$^2$. In another embodiment, G is N. In another embodiment G is CHR$^2$.

In one embodiment, Q is N. In another embodiment, Q is CH. In one embodiment, Q is NH. In one embodiment, Q is CH$_2$.

In one embodiment, X is C. In another embodiment, X is N. In another embodiment, X is CH.

In one embodiment, Z is C=O or a bond when b is a single bond, or CH or N when e is a double bond. In one embodiment, Z is CH$_2$. In another embodiment, Z is C=O. In another embodiment, Z is a bond. In another embodiment, Z is C=S.

In one embodiment, b is a single bond. In one embodiment, b is a double bond and c is a single bond. In one embodiment, c is a single bond. In one embodiment, c is a double bond, and b and d are single bonds. In one embodiment, d is a single bond. In one embodiment, d is a double bond, and c and e are single bonds. In one embodiment, e is a single bond. In one embodiment, e is a double bond, and d and f are single bonds. In one embodiment, f is a single bond. In one embodiment, f is a double bond and e is a single bond In one embodiment, $Y^1$ is CH. In another embodiment, $Y^1$ is CF. In another embodiment, $Y^1$ is N. In one embodiment $Y^1$ is C-halogen, such as C—F, C—Cl, C—Br, or C—I. In one embodiment, $Y^1$ is C-lower alkyl.

In one embodiment, $Y^2$ is CH. In another embodiment, $Y^2$ is CF. In another embodiment, $Y^2$ is N. In one embodiment $Y^2$ is C-halogen, such as C—F, C—Cl, C—Br, or C—I. In one embodiment, $Y^2$ is C-lower alkyl.

In one embodiment, $Y^3$ is CH. In another embodiment, $Y^3$ is CF. In another embodiment, $Y^3$ is N. In one embodiment $Y^3$ is C-halogen, such as C—F, C—Cl, C—Br, or C—I. In one embodiment, $Y^3$ is C-lower alkyl.

In an exemplary embodiment according to the description above no more than one of $Y^2$ and $Y^3$ is N.

In one embodiment, $L^1$ is —C≡C—, —HC═CH—, —CH$_2$—CH$_2$—, —CO—CH$_2$—, —CH(OH)—CH$_2$, —CH$_2$—CO—, —NR$^{12}$—CO—, —CO—NR$^{12}$—,

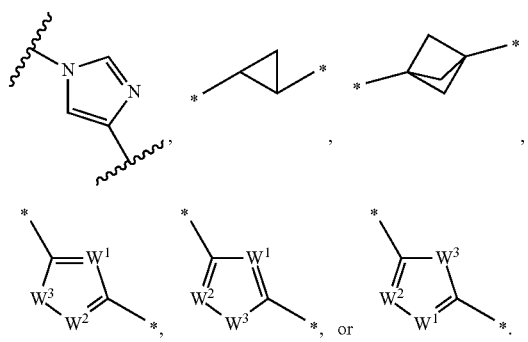

In one embodiment, L¹ is —C≡C—. In another embodiment, L¹ is (lower alkyl)-C≡C— (lower alkyl)-. In another embodiment, L¹ is —HC=CH—. In another embodiment, L¹ is —CH₂—CH₂—. In another embodiment, L¹ is —CO—CH₂—. In another embodiment, L¹ is —CH₂—CO—. In another embodiment, L¹ is —NR¹²—CO—. In another embodiment, L¹ is —CO—NR¹²—. In another embodiment, L¹ is C₀₋₆alkyl-O—C₀₋₆alkyl. In another embodiment, L¹ is —NR¹²SO—. In another embodiment, L¹ is —SONR¹²—. In another embodiment, L¹-NR¹²SO₂—. In another embodiment, L¹ is —SO₂NR¹²—. In another embodiment, L¹ is —C₀₋₆alkyl-O—C₀₋₆alkyl-. R¹² is defined herein elsewhere.

In another embodiment, L¹ is:

In another embodiment, L¹ is:

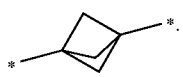

In another embodiment, L¹ is:

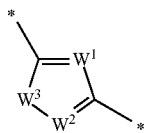

In another embodiment, L¹ is:

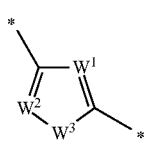

In another embodiment, L¹ is:

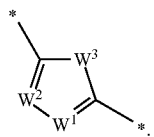

In one embodiment, R¹² is hydrogen. In another embodiment, R¹² is lower alkyl.

In one embodiment, W¹ is N. In another embodiment, W¹ is CH.

In one embodiment, W² is N. In another embodiment, W² is CH.

In one embodiment, W³ is O. In another embodiment, W³ is S. In another embodiment, W³ is NR⁴. R⁴ is defined herein elsewhere.

In one embodiment, R⁴ is hydrogen. In another embodiment, R⁴ is lower alkyl.

Any of the combinations of R¹, R², R³, G, Q, X, Z, Y¹, Y², Y³, L¹, R¹², W¹, W², W³, and R⁴ are encompassed by this disclosure and specifically provided by the invention.

In some aspects, the invention provides compounds of formula (Ia):

$$R^{3a} \underset{Z^a}{\overset{d}{\underset{G^a}{\bigwedge}}} \overset{Q^a}{\underset{X^a}{\bigwedge}} \overset{e}{\underset{Y^{3a}}{\bigwedge}} \overset{Y^{1a}}{\underset{Y^{2a}}{\bigvee}} \overset{L^{1a}}{R^{1a}}$$ (Ia)

wherein
R¹ᵃ is aryl, heteroaryl or cycloalkyl, each of which is optionally substituted;

L¹ᵃ is —C≡C—, —HC=CH—, —CH₂CH₂—, —C(O)NH—, —NHC(O)—, CH(OH)CH₂—, C(O)CH₂,

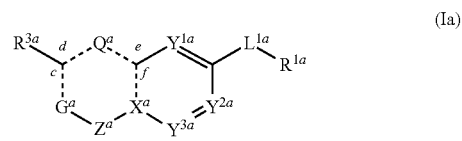

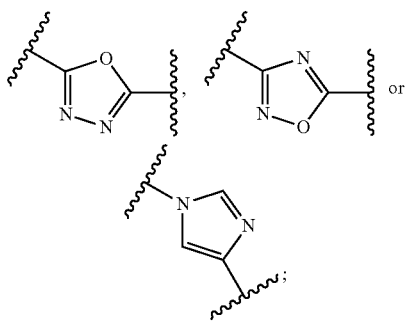

Y¹ᵃ, Y²ᵃ and Y³ᵃ are each independently CH, N, or C-halogen, provided that no more than one of Y²ᵃ and Y³ᵃ is N;

c, d e, and f are each independently single or double bonds; provided that when c is a double bond, d is a single bond; when d is a double bond, c and e are single bonds; when e is a double bond, d and f are single bonds; and when f is a double bond, e is a single bond;

Xᵃ is N when f is a single bond or C when f is a double bond;

Qᵃ is NH when d and e are single bonds or N or CH when one of d or e is a double bond;

Zᵃ is C=O or CH₂;

$G^a$ is $NR^{2a}$ when c is a single bond, or $G^a$ is $CR^{2a}$ when c is a double bond;

$R^{2a}$ is hydrogen, lower alkyl, lower alkenyl, heteroalkyl, —C(O)$R^{12a}$, —CONR$^{12a}$, or cycloalkyl, each of which is optionally substituted;

$R^{3a}$ is hydrogen, lower alkyl, cycloalkyl, heteroalkyl, or heterocycloalkyl, each of which is optionally substituted; or $R^{2a}$ and $R^{3a}$, together with the atoms to which they are attached are linked to form a monocyclic or bicyclic cycloalkyl or heterocyclic ring, each of which is optionally substituted; and $R^{12}$ is hydrogen or lower alkyl; pharmaceutically acceptable salt thereof;

provided that at least one of c and d is a double bond.

In some embodiments, at least one of $G^a$, $Q^a$, and $X^a$ is a nitrogen atom. In some embodiments, at least two of $G^a$, $Q^a$, and $X^a$ are nitrogen atoms. In some embodiments, both $Q^a$ and $G^a$ are nitrogen atoms. In some embodiments, both $Q^a$ and $X^a$ are nitrogen atoms.

In some embodiments, at least one of d and e is a double bond.

In some embodiments, $L^{1a}$ is —C≡C—. In some embodiments, $L^{1a}$ is —HC=CH—. In some embodiments, $L^{1a}$ is —CH$_2$CH$_2$—. In some embodiments, $L^{1a}$ is —C(O)NH—. In some embodiments, $L^{1a}$ is —NHC(O)—. In some embodiments, $L^{1a}$ is —CH(OH)CH$_2$—. In some embodiments, $L^{1a}$ is —C(O)CH$_2$—. In some embodiments, $L^{1a}$ is

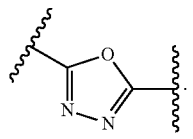 [SMILES: *c1nnc(*)o1]

In some embodiments, $L^{1a}$ is

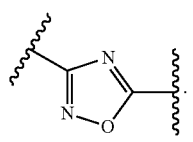 [SMILES: *c1noc(*)n1]

In some embodiments, $L^{1a}$ is

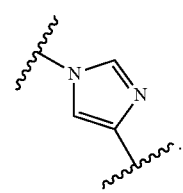 [SMILES: *c1cn(*)cn1]

In some embodiments, $Y^{1a}$ is CH or N. In some embodiments, $Y^{1a}$ is t CH. In some embodiments, $Y^{1a}$ is N. In one embodiment $Y^1$ is C-halogen, such as C—F or C—Cl In some embodiments, $Y^{2a}$ is 1 CH. In some embodiments, $Y^{2a}$ is CH. In some embodiments, $Y^{2a}$ is N. In one embodiment $Y^{2a}$ is C-halogen, such as C—F or C—Cl In some embodiments, $Y^{3a}$ is CH or N. In some embodiments, $Y^{3a}$ is CH. In some embodiments, $Y^{3a}$ is N. In one embodiment $Y^{3a}$ is C-halogen, such as C—F or C—Cl.

In some embodiments, $Z^a$ is C=O. In some embodiments, $Z^a$ is CH$_2$.

In some embodiments, $Q^a$ is N. In some embodiments, $Q^a$ is CH.

In some embodiments, $G^a$ is $NR^{2a}$ when c is a single bond, or $G^a$ is $CR^{2a}$ when c is a double bond. In some embodiments, $G^a$ is $NR^{2a}$. In some embodiments, $G^a$ is $CR^{2a}$.

In some embodiments, $X^a$ is N, $G^a$ is $CR^{2a}$, c and e are double bonds and d and f are single bonds.

In some embodiments, $X^a$ is C, $G^a$ is $NR^{2a}$, c and e are single bonds, and d and f are double bonds.

In some embodiments, $R^{1a}$ is aryl. In some embodiments $R^{1a}$ is heteroaryl. In some embodiments, $R^{1a}$ is cycloalkyl. In some embodiments, $R^{1a}$ is

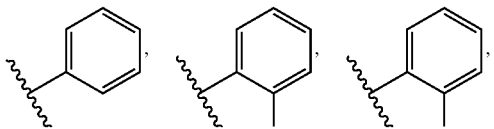

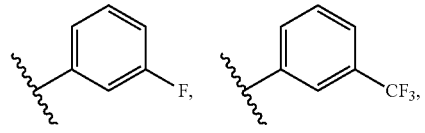

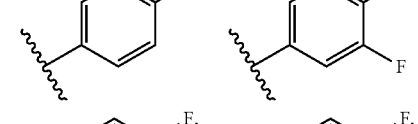

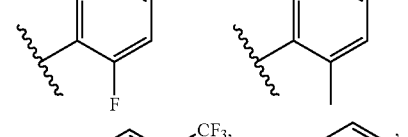

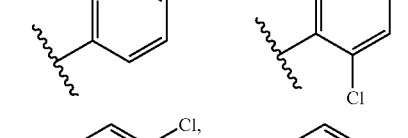

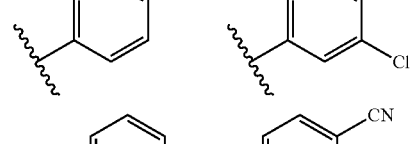

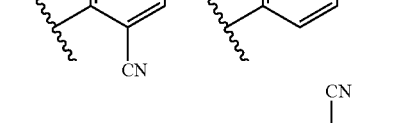

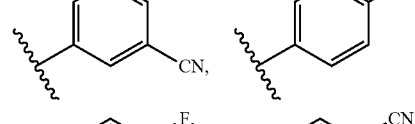

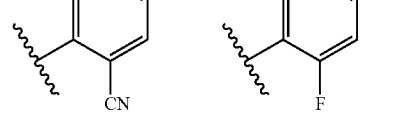

27

-continued

28

-continued

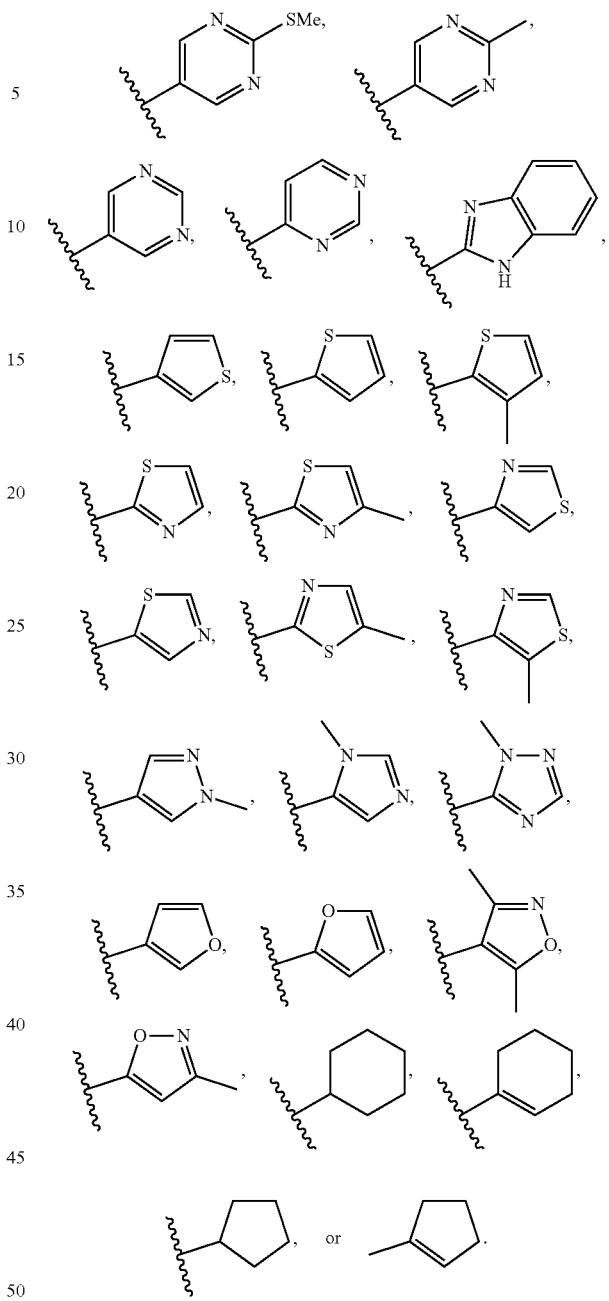

In some embodiments, $R^{2a}$ is lower alkyl, heteroalkyl, or cycloalkyl, each of which is optionally substituted. In some embodiments, $R^{2a}$ is lower alkyl. In some embodiments, $R^{2a}$ is heteroalkyl. In some embodiments, $R^{2a}$ is cycloalkyl. In some embodiments, $R^{2a}$ is alkenyl. In some embodiments, $R^{2a}$ is —C(O)R$^{12a}$. In some embodiments, $R^{2a}$ is —CONR$^{12a}$.

In some embodiments, $R^{12a}$ is hydrogen. In some embodiments, $R^{12a}$ is lower alkyl. In some embodiments, $R^{12a}$ is methyl. In some embodiments, $R^{12a}$ is ethyl.

In some embodiments, $R^{2a}$ is hydrogen, methyl, propyl, cyclopropylmethyl, methoxymethyl, hydroxymethyl, methoxyethyl, hydroxyethyl, ethoxymethyl, ethoxyethyl, isobutyl, sec-butyl, dimethylaminoethyl, —CH$_2$═CH—,

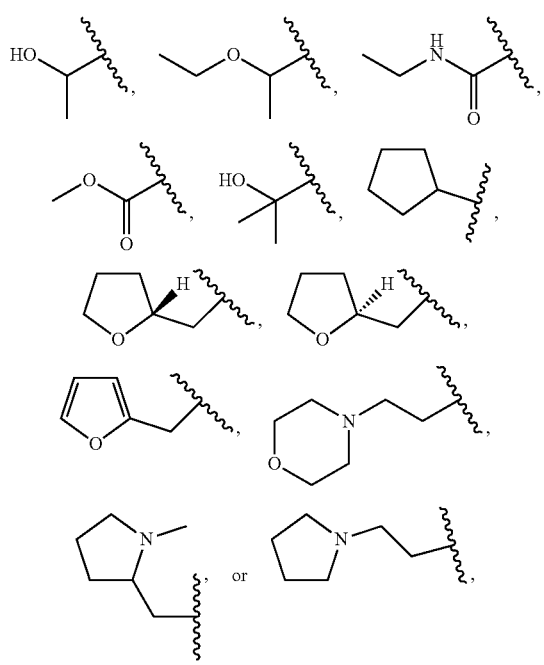

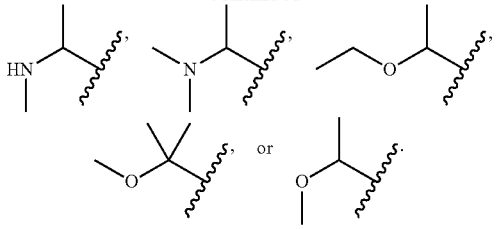

In another embodiment, $R^{2a}$ and $R^{3a}$ are linked to form a 5- to 8-membered mono or bicyclic ring that is carbocyclic or heterocyclic, any of which is optionally substituted. In another embodiment, $R^{2a}$ and $R^{3a}$ are linked to form a mono or bicyclic ring that is carbocyclic or heterocyclic, any of which is optionally substituted. In another embodiment, $R^{2a}$ and $R^{3a}$ are linked to form a monocyclic ring that is carbocyclic and is optionally substituted. In another embodiment, $R^{2a}$ and $R^{3a}$ are linked to form a monocyclic ring that is heterocyclic and is optionally substituted. In another embodiment $R^{2a}$ and $R^{3a}$ are linked to form a bicyclic ring that is carbocyclic that is optionally substituted. In another embodiment $R^{2a}$ and $R^{3a}$ are linked to form a bicyclic ring that is heterocyclic that is optionally substituted.

In some embodiments, $R^{2a}$ and $R^{3a}$ are linked to form

In some embodiments, $R^{3a}$ is hydrogen. In some embodiments, $R^{3a}$ is lower alkyl or cycloalkyl. In some embodiments, $R^{3a}$ is heteroalkyl. In some embodiments, $R^{3a}$ is heterocycloalkyl.

In some embodiments, $R^{3a}$ is hydrogen, methoxymethyl, methoxyethyl, isobutyl, sec-butyl, dimethylaminoethyl, dimethylaminomethyl,

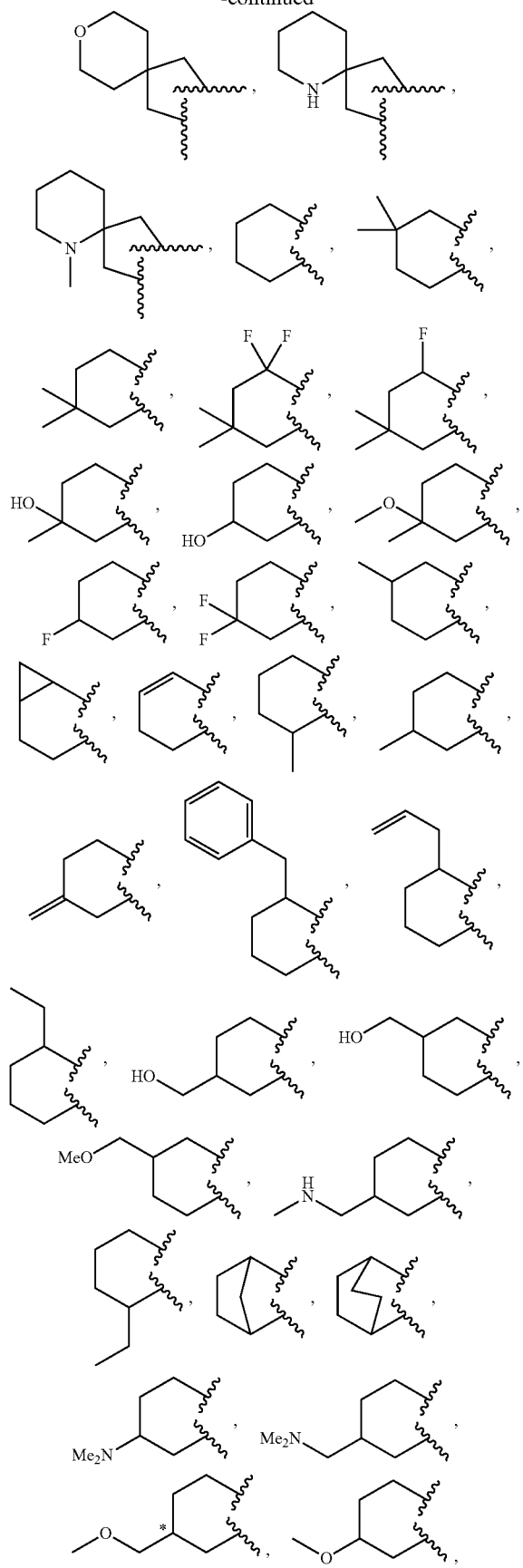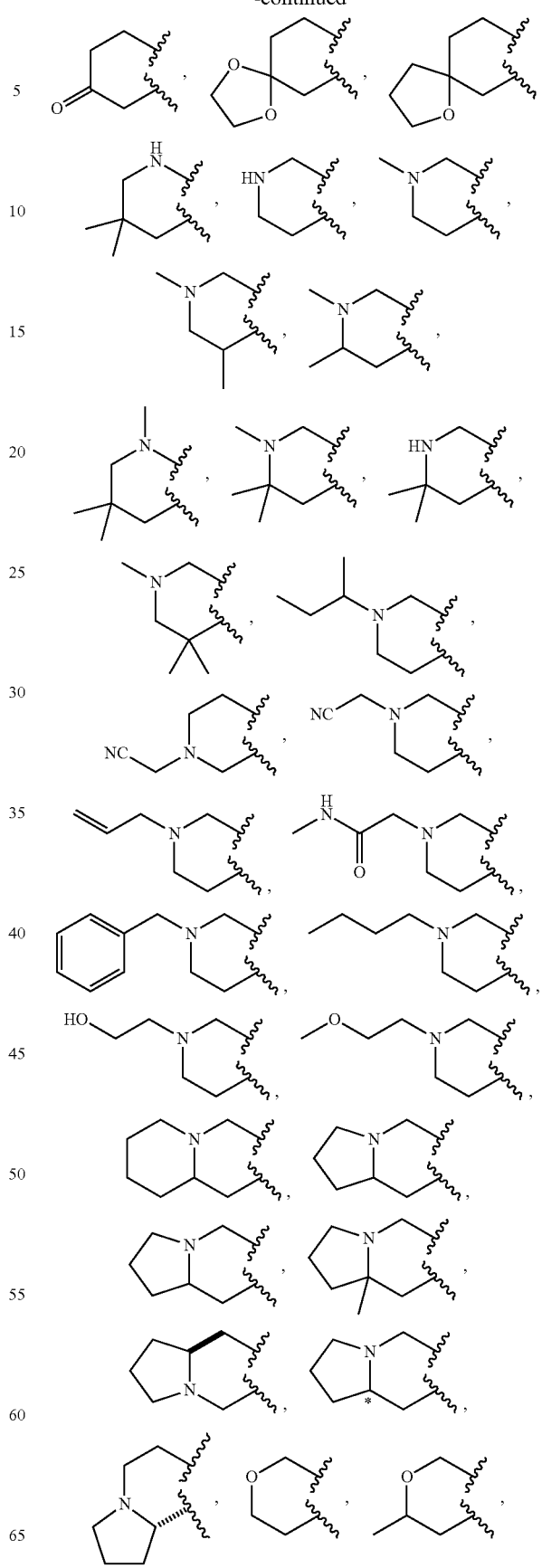

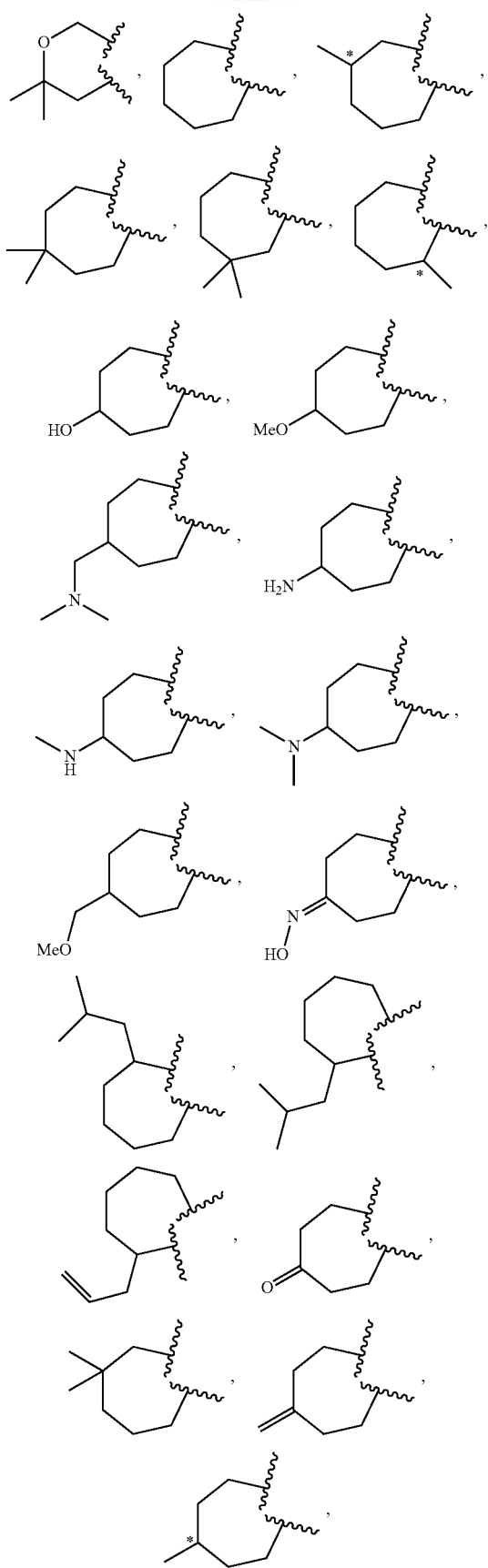
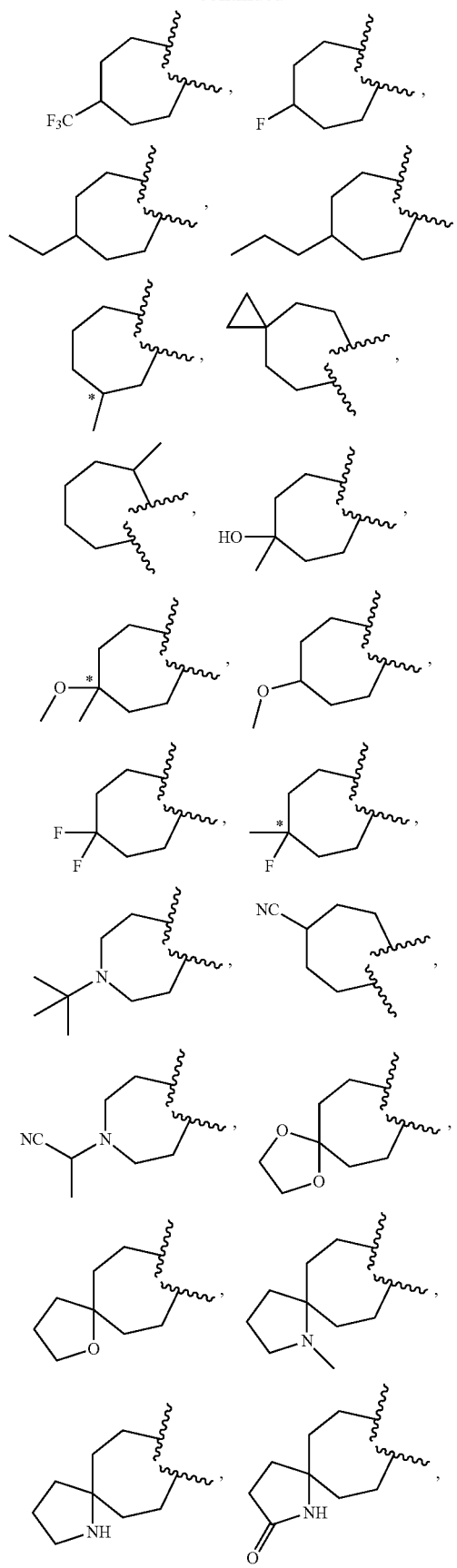

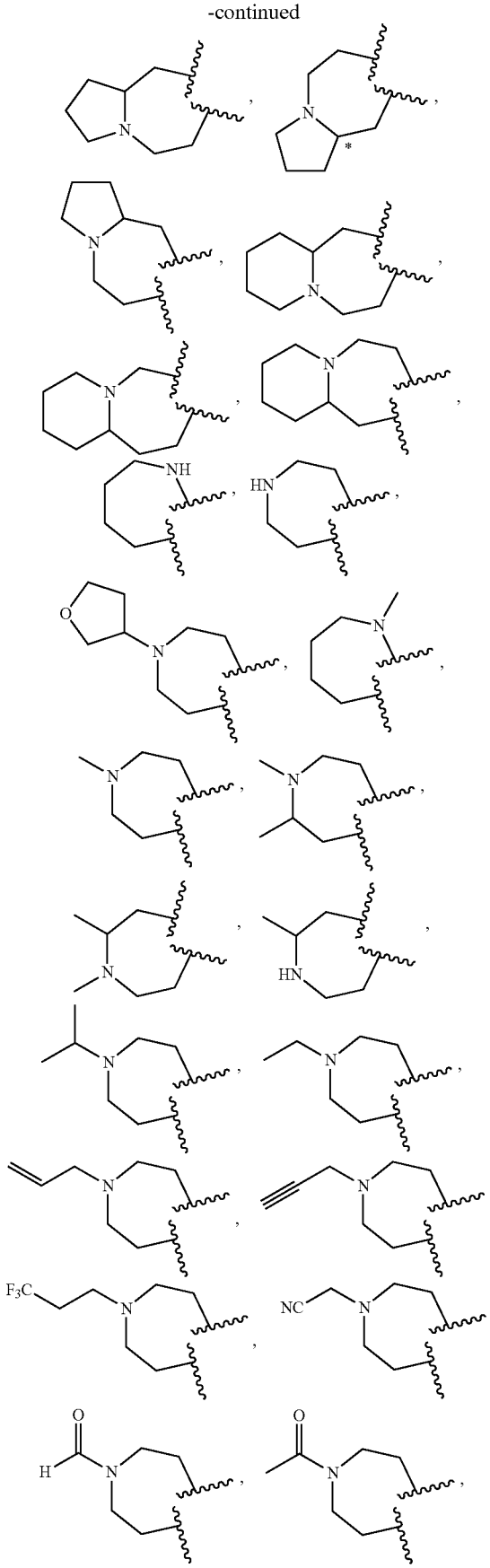
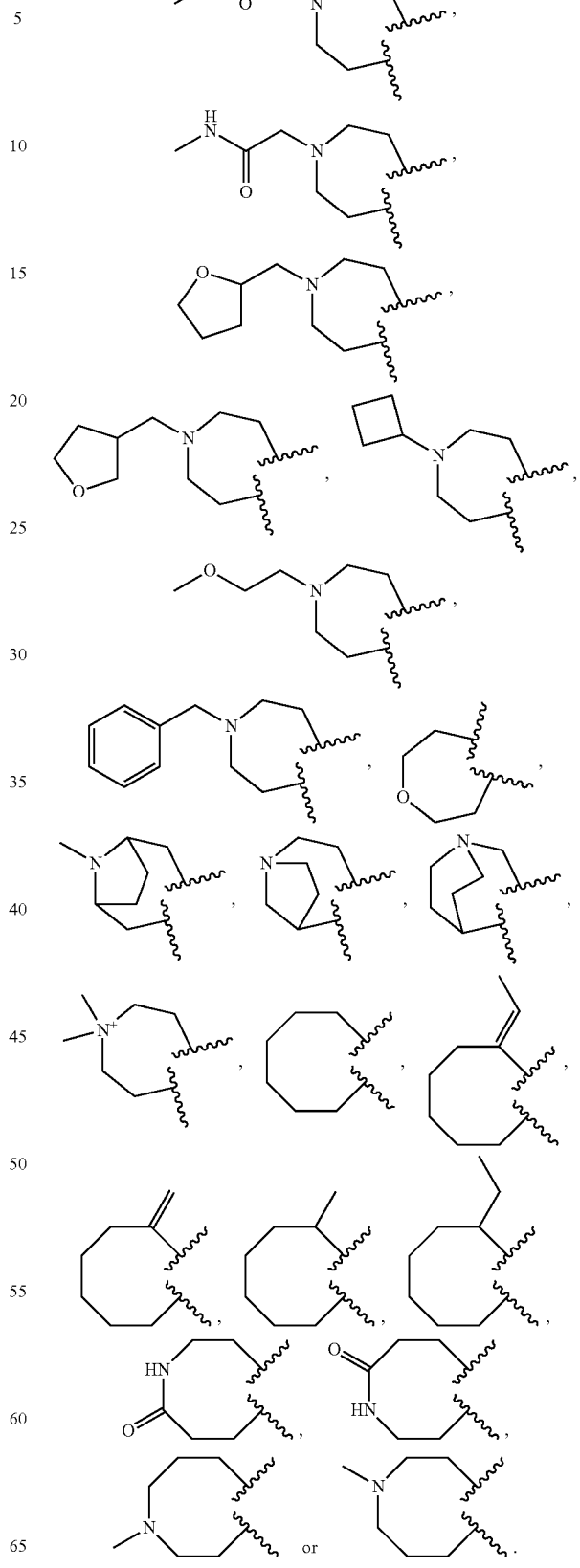

As used herein * is to denote that the enantiomers have been separated but the absolute stereochemistry of each enantiomer has not been identified.

In some embodiments, the invention provides compounds of formula Ib:

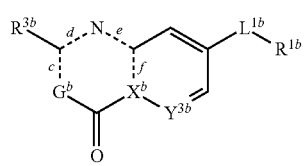

wherein $R^{1b}$ K is aryl or heteroaryl;

$L^{1b}$ is —C≡C—, —CH=CH— or —C(O)NH—;

$Y^{3b}$ is CH or N;

$X^b$ is N when f is a single bond or C when f is a double bond;

$G^b$ is $NR^{2b}$ when c is a single bond or $CR^{2a}$ when c is a double bond;

$R^{2b}$ is lower alkyl or heteroalkyl; and $R^{3b}$ is hydrogen, heteroalkyl, or heterocycloalkyl, each of which is optionally substituted; or $R^{2b}$ and $R^{3b}$, together with the atoms to which they are attached are linked to form a monocyclic or bicyclic ring that is cycloalkyl or heterocyclic, each of which is optionally substituted; and c, d e, and f are each independently single or double bonds; provided that when c is a double bond, d is a single bond; when d is a double bond, c and e are single bonds; when e is a double bond, d and f are single bonds; and when f is a double bond, e is a single bond, or a pharmaceutically acceptable salt thereof;

provided that at least one of c and d is a double bond.

In some embodiments, one of $G^b$ and $X^b$ is a nitrogen atom.

In some embodiments, $R^{1b}$ is aryl, for example,

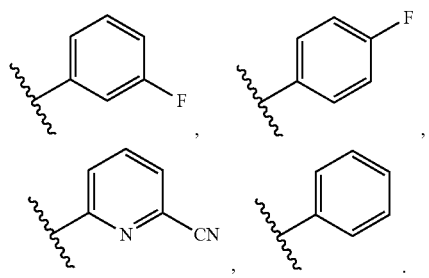

In some embodiments, $R^{1b}$ is heteroaryl, for example,

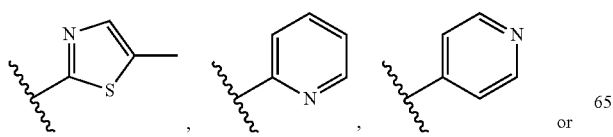

or

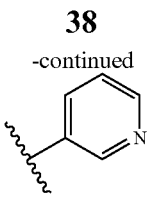

In some embodiments $R^{2b}$ is lower alkyl, such as methyl. In some embodiments, $R^{2b}$ is heteroalkyl, such as alkoxyalkyl, for example,

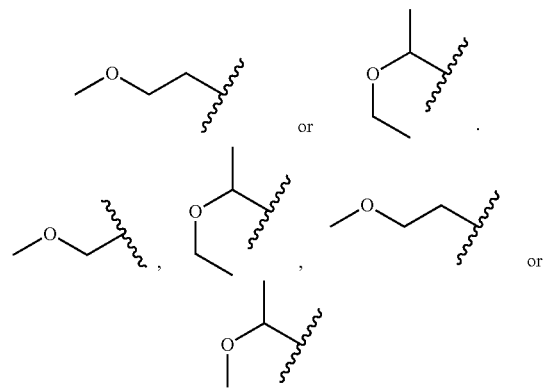

In some embodiments, $R^{3b}$ is heteroalkyl, such as alkoxyalkyl, for example,

In some embodiments, $R^{3b}$ is heterocycloalkyl, for example,

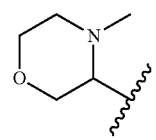

In another embodiment, $R^{2b}$ and $R^{3b}$ are linked to form a 5- to 8-membered mono or bicyclic ring that is carbocyclic or heterocyclic, any of which is optionally substituted. In another embodiment, $R^{2b}$ and $R^{3b}$ are linked to form a mono or bicyclic ring that is carbocyclic or heterocyclic, any of which is optionally substituted. In another embodiment, $R^{2b}$ and $R^{3b}$ are linked to form a monocyclic ring that is carbocyclic. In another embodiment, $R^{2b}$ and $R^{3b}$ are linked to form a monocyclic ring that is heterocyclic. In another embodiment $R^{2b}$ and $R^{3b}$ are linked to form a bicyclic ring that is carbocyclic. In another embodiment $R^{2b}$ and $R^{3b}$ are linked to form a bicyclic ring that is heterocyclic.

In some embodiments, $R^{2b}$ and $R^{3b}$ together with the atoms to which they are attached are linked to form a monocyclic or bicyclic ring that is a cycloalkyl or heterocycloalkyl ring, for example,

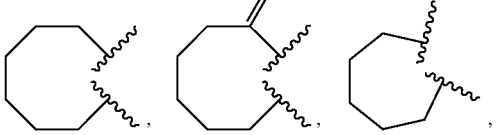

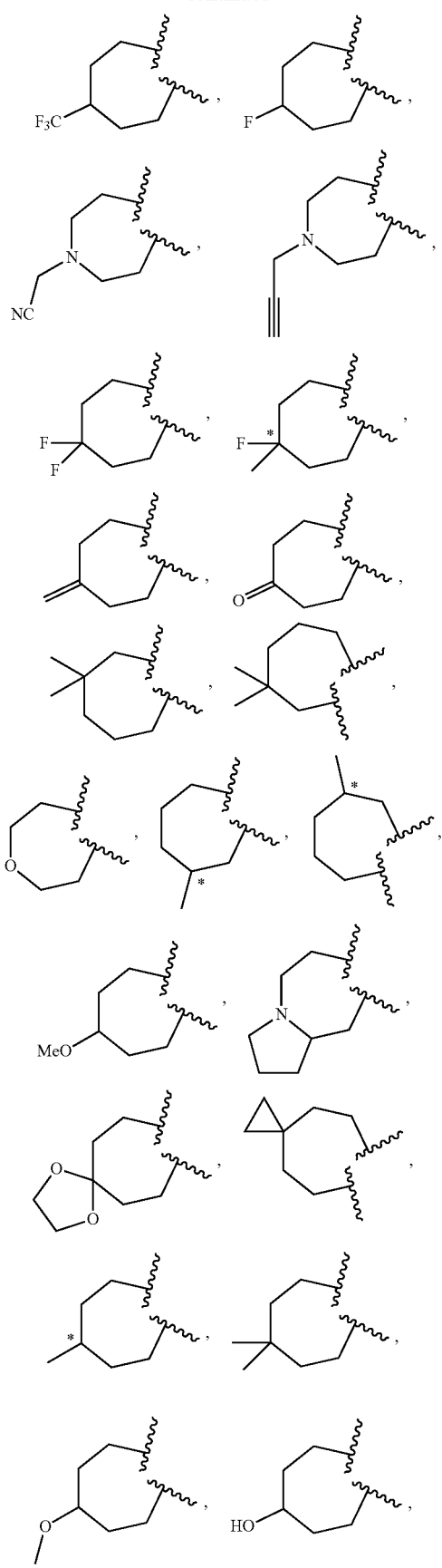
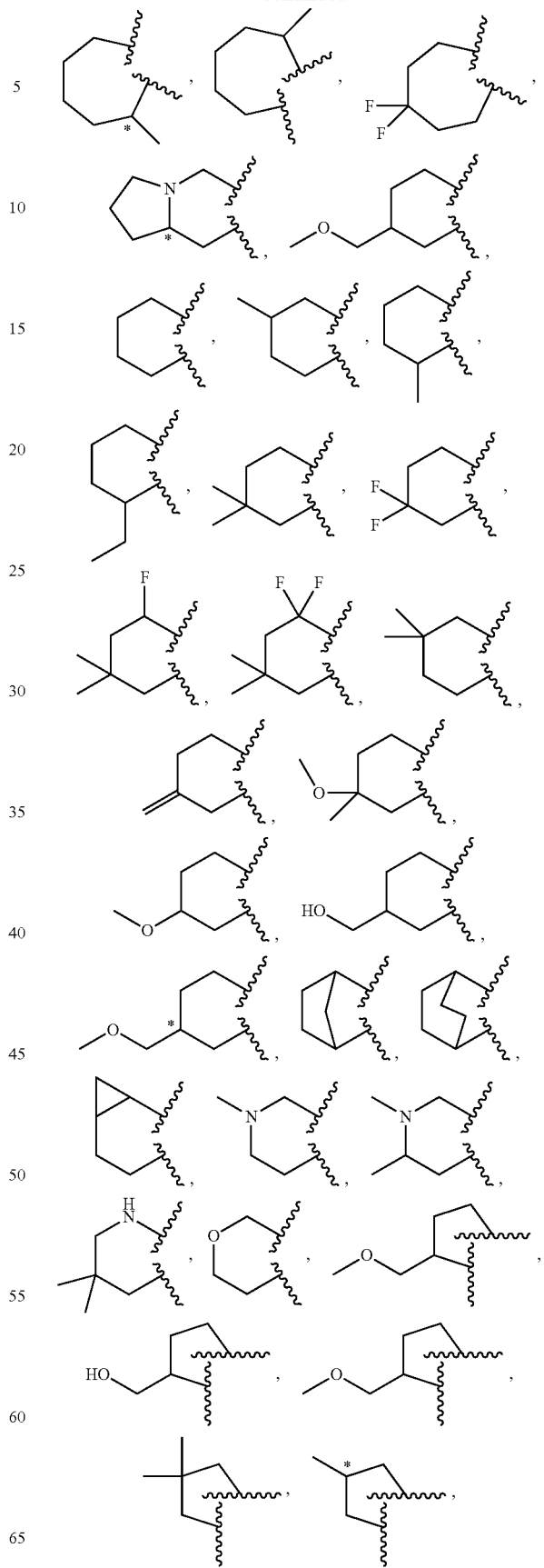

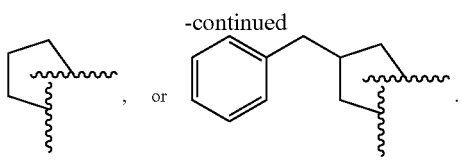

As used herein * is to denote that the enantiomers have been separated but the absolute stereochemistry of each enantiomer has not been identified.

In some embodiments, the compounds of formula (Ib) have the following substituents:

| $R^{1b}$ | $L^{2b}$ | $Y^{3b}$ | $X^b$ | $G^b$ | $R^{2b}$ & $R^{3b}$ | c, d e & f |
|---|---|---|---|---|---|---|
| 2-pyridyl | C≡C | CH | C | $NR^{2b}$ | methylcyclohexyl | c = single, d = double, e = single, f = double |
| 6-cyano-2-pyridyl | C≡C | CH | C | $NR^{2b}$ | cycloheptyl | c = single, d = double, e = single, f = double |
| 2-pyridyl | C≡C | CH | C | $NR^{2b}$ | NH-gem-dimethyl-cyclohexyl | c = single, d = double, e = single, f = double |
| 2-pyridyl | C≡C | CH | C | $NR^{2b}$ | F, gem-dimethyl-cyclohexyl | c = single, d = double, e = single, f = double |
| 2-pyridyl | C≡C | CH | C | $NR^{2b}$ | F-cycloheptyl | c = single, d = double, e = single, f = double |
| 2-pyridyl | C≡C | CH | N | $CR^{2b}$ | gem-dimethyl-cyclohexyl | c = double, d = single, e = double, f = single |
| 3-fluorophenyl | C≡C | CH | C | $NR^{2b}$ | gem-dimethyl-cyclohexyl | c = single, d = double, e = single, f = double |
| 4-pyridyl | C≡C | CH | N | $CR^{2b}$ | cycloheptyl | c = double, d = single, e = double, f = single |
| phenyl | C≡C | CH | N | $CR^{2b}$ | cycloheptyl | c = double, d = single, e = double, f = single |

-continued

| $R^{1b}$ | $L^{2b}$ | $Y^{3b}$ | $X^b$ | $G^b$ | $R^{2b}$ & $R^{3b}$ | c, d e & f |
|---|---|---|---|---|---|---|
| phenyl | C≡C | CH | N | $CR^{2b}$ | cyclooctyl | c = double, d = single, e = double, f = single |
| 3-fluorophenyl | C≡C | CH | C | $NR^{2b}$ | gem-dimethylcyclohexyl | c = single, d = double, e = single, f = double |
| pyridin-4-yl | C≡C | CH | N | $CR^{2b}$ | cyclooctyl | c = double, d = single, e = double, f = single |
| pyridin-3-yl | C≡C | CH | N | $CR^{2b}$ | cyclooctyl | c = double, d = single, e = double, f = single |
| pyridin-2-yl | C≡C | CH | C | $NR^{2b}$ | gem-dimethylcyclohexyl | c = single, d = double, e = single, f = double |
| 3-fluorophenyl | C≡C | N | C | $NR^{2b}$ | cycloheptyl | c = single, d = double, e = single, f = double |
| 4-fluorophenyl | C≡C | CH | N | $CR^{2b}$ | cycloheptyl | c = double, d = single, e = double, f = single |
| 4-fluorophenyl | C≡C | CH | N | $CR^{2b}$ | cyclooctyl | c = double, d = single, e = double, f = single |
| 3-fluorophenyl | C≡C | CH | C | $NR^{2b}$ | methylcyclohexyl | c = single, d = double, e = single, f = double |
| 3-fluorophenyl | C≡C | CH | C | $NR^{2b}$ | (methoxymethyl)cyclohexyl | c = single, d = double, e = single, f = double |

-continued

| R$^{1b}$ | L$^{2b}$ | Y$^{3b}$ | X$^b$ | G$^b$ | R$^{2b}$&R$^{3b}$ | c, d e & f |
|---|---|---|---|---|---|---|
| phenyl | C≡C | CH | C | NR$^{2b}$ | cycloheptyl | c = single<br>d = double<br>e = single<br>f = double |
| 3-fluorophenyl | C≡C | CH | C | NR$^{2b}$ | methylenecycloheptyl | c = single<br>d = double<br>e = single<br>f = double |
| 3-pyridyl | C≡C | CH | N | CR$^{2b}$ | cycloheptyl | c = double<br>d = single<br>e = double<br>f = single |
| 2-pyridyl | C≡C | CH | N | CR$^{2b}$ | methylcycloheptyl | c = double<br>d = single<br>e = double<br>f = single |
| 3-fluorophenyl | C≡C | CH | C | NR$^{2b}$ | cyclopentyl | c = single<br>d = double<br>e = single<br>f = double |
| 3-fluorophenyl | C≡C | CH | C | NR$^{2b}$ | cyclohexyl | c = single<br>d = double<br>e = single<br>f = double |
| 4-fluorophenyl | C≡C | CH | C | NR$^{2b}$ | cyclohexyl | c = single<br>d = double<br>e = single<br>f = double |
| 2-pyridyl | C≡C | CH | C | NR$^{2b}$ | dimethylcyclohexyl | c = single<br>d = double<br>e = single<br>f = double |
| 3-fluorophenyl | C≡C | CH | C | NR$^{2b}$ | N-methylpiperidinyl | c = single<br>d = double<br>e = single<br>f = double |
| 2-pyridyl | C≡C | CH | N | CR$^{2b}$ | cyclooctyl | c = double<br>d = single<br>e = double<br>f = single |

-continued

| R$^{1b}$ | L$^{2b}$ | Y$^{3b}$ | X$^b$ | G$^b$ | R$^{2b}$&R$^{3b}$ | c, d e & f |
|---|---|---|---|---|---|---|
| 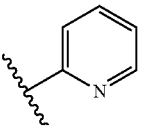 [SMILES: *c1ccccn1] | C≡C | CH | C | NR$^{2b}$ | 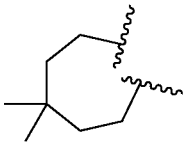 [SMILES: *CCC(C)(C)CC*] | c = single<br>d = double<br>e = single<br>f = double |
| 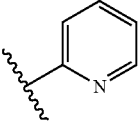 [SMILES: *c1ccccn1] | C≡C | CH | C | NR$^{2b}$ | 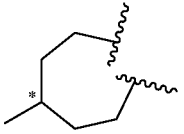 [SMILES: *CCC(C)CC*] | c = single<br>d = double<br>e = single<br>f = double |
| 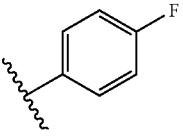 [SMILES: *c1ccc(F)cc1] | C≡C | CH | C | NR$^{2b}$ | 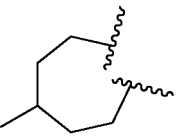 [SMILES: *CCC(C)CC*] | c = single<br>d = double<br>e = single<br>f = double |
| 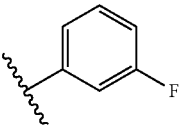 [SMILES: *c1cccc(F)c1] | C≡C | CH | C | NR$^{2b}$ | 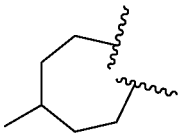 [SMILES: *CCC(C)CC*] | c = single<br>d = double<br>e = single<br>f = double |
| 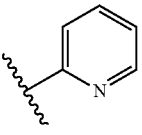 | C≡C | CH | C | NR$^{2b}$ | 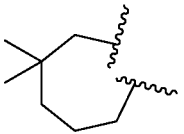 [SMILES: *CCCC(C)(C)C*] | c = single<br>d = double<br>e = single<br>f = double |
| 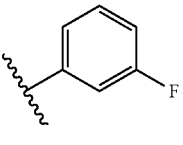 [SMILES: *c1cccc(F)c1] | C≡C | CH | C | NR$^{2b}$ | 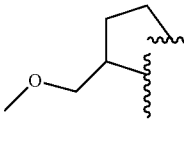 | c = single<br>d = double<br>e = single<br>f = double |
| 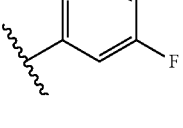 | C≡C | CH | C | NR$^{2b}$ | 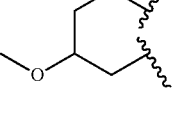 | c = single<br>d = double<br>e = single<br>f = double |
| 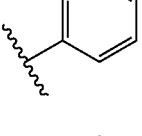 | C≡C | CH | C | NR$^{2b}$ |  | c = single<br>d = double<br>e = single<br>f = double |
| 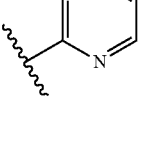 | C≡C | CH | C | NR$^{2b}$ | 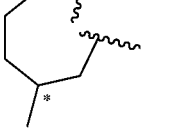 | c = single<br>d = double<br>e = single<br>f = double |
| 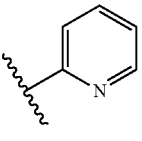 | C≡C | CH | C | NR$^{2b}$ | 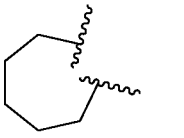 [SMILES: *CCCCC*] | c = single<br>d = double<br>e = single<br>f = double |

-continued

| $R^{1b}$ | $L^{2b}$ | $Y^{3b}$ | $X^b$ | $G^b$ | $R^{2b}$ & $R^{3b}$ | c, d e & f |
|---|---|---|---|---|---|---|
| 3-F-phenyl | C≡C | CH | C | $NR^{2b}$ | cycloheptyl with OMe | c = single, d = double, e = single, f = double |
| 2-pyridyl | C≡C | CH | N | $CR^{2b}$ | cycloheptyl | c = double, d = single, e = double, f = single |
| 2-pyridyl | C≡C | CH | C | $NR^{2b}$ | methyl-cycloheptyl | c = single, d = double, e = single, f = double |
| 3-F-phenyl | C≡C | CH | C | $NR^{2b}$ | HO-cycloheptyl | c = single, d = double, e = single, f = double |
| 2-pyridyl | C≡C | CH | C | $NR^{2b}$ | F,F-cycloheptyl | c = single, d = double, e = single, f = double |
| 2-pyridyl | C≡C | CH | C | $NR^{2b}$ | methyl-cycloheptyl (*) | c = single, d = double, e = single, f = double |
| 3-F-phenyl | C≡C | CH | C | $NR^{2b}$ | $R^{3b}$ = N-methyl-morpholinyl; $R^{2b}$ = $CH_3$ | c = single, d = double, e = single, f = double |
| 3-F-phenyl | C≡C | CH | C | $NR^{2b}$ | cyclopentyl | c = single, d = double, e = single, f = double |
| 3-F-phenyl | C≡C | CH | C | $NR^{2b}$ | benzyl-cyclopentyl | c = single, d = double, e = single, f = double |
| 3-F-phenyl | C≡C | CH | C | $NR^{2b}$ | HOCH2-cyclohexyl | c = single, d = double, e = single, f = double |

-continued

| R$^{1b}$ | L$^{2b}$ | Y$^{3b}$ | X$^b$ | G$^b$ | R$^{2b}$&R$^{3b}$ | c, d e & f |
|---|---|---|---|---|---|---|
| 3-F-phenyl | C≡C | CH | C | NR$^{2b}$ | R$^{3b}$ = CH(OCH$_3$)CH$_3$ group; R$^{2b}$ = CH$_3$ | c = single, d = double, e = single, f = double |
| 3-F-phenyl | C≡C | CH | C | NR$^{2b}$ | tetrahydropyran-3-yl | c = single, d = double, e = single, f = double |
| pyridin-2-yl | C≡C | CH | C | NR$^{2b}$ | 3,3-dimethylcyclopentyl | c = single, d = double, e = single, f = double |
| 3-F-phenyl | C≡C | CH | C | NR$^{2b}$ | hexahydroindolizinyl | c = single, d = double, e = single, f = double |
| pyridin-2-yl | C≡C | CH | N | CR$^{2b}$ | cyclohexyl-methyl | c = double, d = single, e = double, f = single |
| 3-F-phenyl | C≡C | CH | N | CR$^{2b}$ | R$^{3b}$ = H; R$^{2b}$ = CH(OEt)CH$_3$ | c = double, d = single, e = double, f = single |
| phenyl | HC=CH | CH | C | NR$^{2b}$ | cycloheptyl | c = single, d = double, e = single, f = double |
| 5-methylthiazol-2-yl | —C(O)NH— | CH | C | NR$^{2b}$ | alkenyl-cyclooctyl | c = single, d = double, e = single, f = double |
| 3-F-phenyl | C≡C | CH | C | NR$^{2b}$ | R$^{3b}$ = CH$_2$CH$_2$OCH$_3$; R$^{2b}$ = Me | c = single, d = double, e = single, f = double |

-continued

| R$^{1b}$ | L$^{2b}$ | Y$^{3b}$ | X$^b$ | G$^b$ | R$^{2b}$&R$^{3b}$ | c, d e & f |
|---|---|---|---|---|---|---|
| 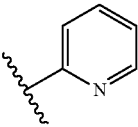 [SMILES: *c1ccccn1] | C≡C | N | C | NR$^{2b}$ | 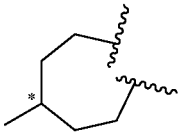 [SMILES: *CCC(C)CC*] | c = single<br>d = double<br>e = single<br>f = double |
| 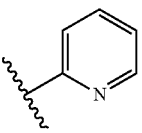 [SMILES: *c1ccccn1] | C≡C | N | C | NR$^{2b}$ | 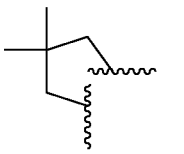 [SMILES: *CC(C)(C)C*] | c = single<br>d = double<br>e = single<br>f = double |
| 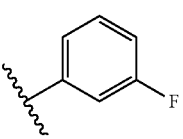 [SMILES: *c1cccc(F)c1] | C≡C | CH | C | NR$^{2b}$ | 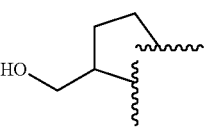 [SMILES: *CCC(*)CO] | c = single<br>d = double<br>e = single<br>f = double |
| 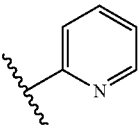 | C≡C | CH | C | NR$^{2b}$ | 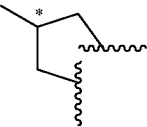 [SMILES: *CC(C)C*] | c = single<br>d = double<br>e = single<br>f = double |
| 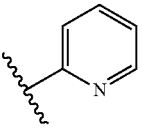 [SMILES: *c1ccccn1] | C≡C | CH | C | NR$^{2b}$ | 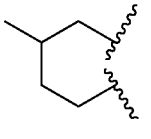 [SMILES: *CCC(C)C*] | c = single<br>d = double<br>e = single<br>f = double |
| 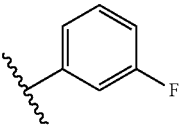 [SMILES: *c1cccc(F)c1] | C≡C | CH | C | NR$^{2b}$ | R$^{3b}$ = 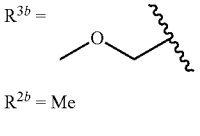<br>R$^{2b}$ = Me | c = single<br>d = double<br>e = single<br>f = double |
| 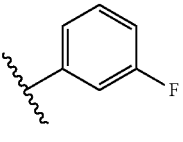 [SMILES: *c1cccc(F)c1] | C≡C | CH | C | NR$^{2b}$ | 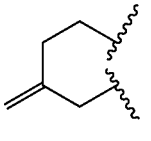 [SMILES: *CCC(=C)C*] | c = single<br>d = double<br>e = single<br>f = double |
| 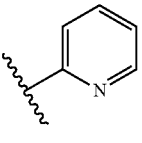 | C≡C | CH | C | NR$^{2b}$ | 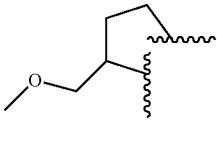 [SMILES: *CCC(*)COC] | c = single<br>d = double<br>e = single<br>f = double |
| 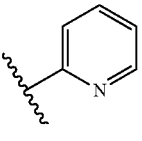 [SMILES: *c1ccccn1] | C≡C | CH | C | NR$^{2b}$ | 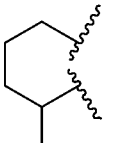 | c = single<br>d = double<br>e = single<br>f = double |
| 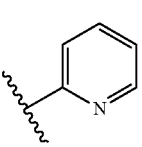 | C≡C | CH | C | NR$^{2b}$ | 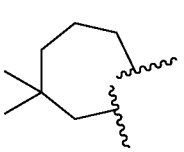 [SMILES: *CCCC(C)(C)C*] | c = single<br>d = double<br>e = single<br>f = double |

| $R^{1b}$ | $L^{2b}$ | $Y^{3b}$ | $X^b$ | $G^b$ | $R^{2b}$ & $R^{3b}$ | c, d e & f |
|---|---|---|---|---|---|---|
| 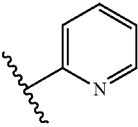 [SMILES: *c1ccccn1] | C≡C | CH | C | $NR^{2b}$ | 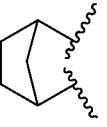 | c = single<br>d = double<br>e = single<br>f = double |
| 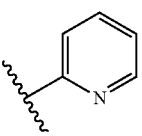 | C≡C | CH | C | $NR^{2b}$ | 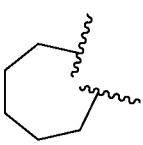 | c = single<br>d = double<br>e = single<br>f = double |
| 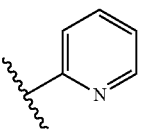 [SMILES: *c1ccccn1] | C≡C | CH | C | $NR^{2b}$ | 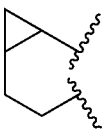 | c = single<br>d = double<br>e = single<br>f = double |
| 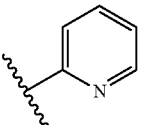 [SMILES: *c1ccccn1] | C≡C | CH | C | $NR^{2b}$ | 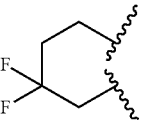 | c = single<br>d = double<br>e = single<br>f = double |
| 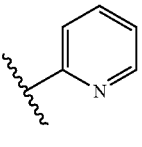 [SMILES: *c1ccccn1] | C≡C | CH | C | $NR^{2b}$ | 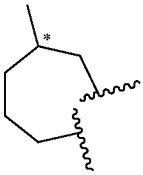 [SMILES: *CCCC(C)C*] | c = single<br>d = double<br>e = single<br>f = double |
| 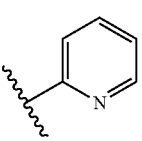 | C≡C | CH | C | $NR^{2b}$ | 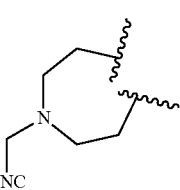 | c = single<br>d = double<br>e = single<br>f = double |
| 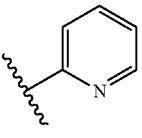 [SMILES: *c1ccccn1] | C≡C | CH | C | $NR^{2b}$ | 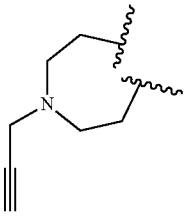 [SMILES: *CCN(CC#C)CC*] | c = single<br>d = double<br>e = single<br>f = double |
| 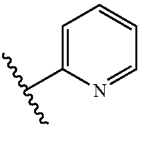 [SMILES: *c1ccccn1] | C≡C | CH | C | $NR^{2b}$ | 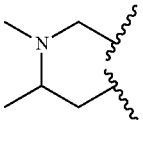 [SMILES: *CC(C)N(C)C*] | c = single<br>d = double<br>e = single<br>f = double |
| 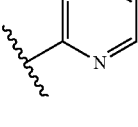 | C≡C | CH | C | $NR^{2b}$ | 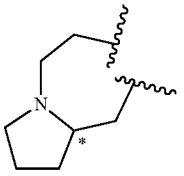 [SMILES: *CCN1CCCC1C*] | c = single<br>d = double<br>e = single<br>f = double |

-continued

| R$^{1b}$ | L$^{2b}$ | Y$^{3b}$ | X$^{b}$ | G$^{b}$ | R$^{2b}$&R$^{3b}$ | c, d e & f |
|---|---|---|---|---|---|---|
|  | C≡C | CH | C | NR$^{2b}$ | 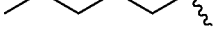 | c = single<br>d = double<br>e = single<br>f = double |
|  | C≡C | CH | C | NR$^{2b}$ | 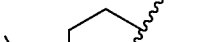 | c = single<br>d = double<br>e = single<br>f = double |
|  | C≡C | CH | C | NR$^{2b}$ | 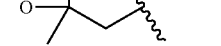 | c = single<br>d = double<br>e = single<br>f = double |
|  | C≡C | CH | C | NR$^{2b}$ | 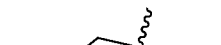 | c = single<br>d = double<br>e = single<br>f = double |
|  | C≡C | CH | C | NR$^{2b}$ |  | c = single<br>d = double<br>e = single<br>f = double |
|  | C≡C | CH | C | NR$^{2b}$ |  | c = single<br>d = double<br>e = single<br>f = double |
|  | C≡C | CH | C | NR$^{2b}$ |  | c = single<br>d = double<br>e = single<br>f = double |
|  | C≡C | CH | C | NR$^{2b}$ |  | c = single<br>d = double<br>e = single<br>f = double |

In one embodiment, the invention provides a compound of formula (II):

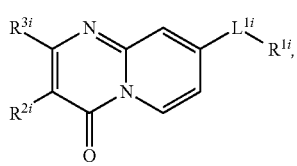

(II)

or a pharmaceutically acceptable salt, solvate, or stereoisomer thereof, wherein R$^{1i}$, R$^{2i}$ and R$^{3i}$ are each independently hydrogen, lower alkyl, heteroalkyl, cycloalkyl, heterocycloalkyl, alkylcycloalkyl, alkylheterocycloalkyl, alkylaryl, alkylheteroaryl, aryl or heteroaryl, each of which is optionally substituted, or R$^{2i}$ and R$^{3i}$ are optionally joined, together with the atoms to which they are attached, to form a mono or bicyclic ring that is carbocyclic or heterocyclic, any of which is optionally substituted;

$L^{1i}$ is —C≡C—, —HC=CH—, -(lower alkyl)-C=C-(lower alkyl)-, —CH$_2$—CH$_2$—, —CO—CH$_2$—, —CH$_2$—CO—, —NR$^{12i}$—CO—, —CO—NR$^{12i}$—C$_{0-6}$alkyl-O—C$_{0-6}$alkyl-, NR$^{12i}$SO, SONR$^{12i}$, —NR$^{12i}$SO$_2$—, —SO$_2$NR$^{12i}$—,

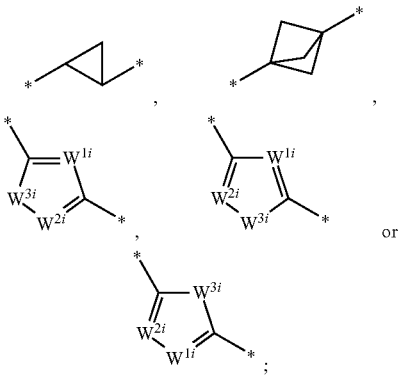

$R^{12i}$ is hydrogen or lower alkyl;
$W^{1i}$ and $W^{2i}$ are each independently N or CH;
$W^{3i}$ is O, S or NR$^{4i}$; and
$R^{4i}$ is hydrogen or lower alkyl or a pharmaceutically acceptable salt thereof.

In one embodiment, $R^{1i}$ is hydrogen. In another embodiment, $R^{1i}$ is optionally substituted lower alkyl. In another embodiment, $R^{1i}$ is optionally substituted heteroalkyl. In another embodiment, $R^{1i}$ is optionally substituted cycloalkyl. In another embodiment, $R^{1i}$ is optionally substituted monocyclic cycloalkyl. In another embodiment, $R^{1i}$ is optionally substituted heterocycloalkyl. In another embodiment, $R^{1i}$ is optionally substituted monocyclic heterocycloalkyl. In another embodiment, $R^{1i}$ is optionally substituted alkylcycloalkyl. In another embodiment, $R^{1i}$ is optionally substituted monocyclic alkylcycloalkyl. In another embodiment, $R^{1i}$ is optionally substituted alkylheterocycloalkyl. In another embodiment, $R^{1i}$ is optionally substituted monocyclic alkylheterocycloalkyl. In another embodiment, $R^{1i}$ is optionally substituted alkylaryl. In another embodiment, $R^{1i}$ is optionally substituted monocyclic alkylaryl. In another embodiment, $R^{1i}$ is optionally substituted alkylheteroaryl. In another embodiment, $R^{1i}$ is optionally substituted monocyclic alkylheteroaryl. In another embodiment, $R^{1i}$ is optionally substituted aryl. In another embodiment, $R^{1i}$ is optionally substituted monocyclic aryl. In another embodiment, $R^{1i}$ is optionally substituted heteroaryl. In another embodiment, $R^{1i}$ is optionally substituted monocyclic heteroaryl.

In one embodiment, $R^{2i}$ is hydrogen. In another embodiment, $R^{2i}$ is optionally substituted lower alkyl. In another embodiment, $R^{2i}$ is optionally substituted heteroalkyl. In another embodiment, $R^{2i}$ is optionally substituted cycloalkyl. In another embodiment, $R^{2i}$ is optionally substituted monocyclic cycloalkyl. In another embodiment, $R^{2i}$ is optionally substituted heterocycloalkyl. In another embodiment, $R^{2i}$ is optionally substituted monocyclic heterocycloalkyl. In another embodiment, $R^{2i}$ is optionally substituted alkylcycloalkyl. In another embodiment, $R^{2i}$ is optionally substituted monocyclic alkylcycloalkyl. In another embodiment, $R^{2i}$ is optionally substituted alkylheterocycloalkyl. In another embodiment, $R^{2i}$ is optionally substituted monocyclic alkylheterocycloalkyl. In another embodiment, $R^{2i}$ is optionally substituted alkylaryl. In another embodiment, $R^{2i}$ is optionally substituted monocyclic alkylaryl. In another embodiment, $R^{2i}$ is optionally substituted alkylheteroaryl. In another embodiment, $R^{2i}$ is optionally substituted monocyclic alkylheteroaryl. In another embodiment, $R^{2i}$ is optionally substituted aryl. In another embodiment, $R^{2i}$ is optionally substituted monocyclic aryl. In another embodiment, $R^{2i}$ is optionally substituted heteroaryl. In another embodiment, $R^{2i}$ is optionally substituted monocyclic heteroaryl.

In one embodiment, $R^{3i}$ is hydrogen. In another embodiment, $R^{3i}$ is optionally substituted lower alkyl. In another embodiment, $R^{3i}$ is optionally substituted heteroalkyl. In another embodiment, $R^{3i}$ is optionally substituted cycloalkyl. In another embodiment, $R^{3i}$ is optionally substituted monocyclic cycloalkyl. In another embodiment, $R^{3i}$ is optionally substituted heterocycloalkyl. In another embodiment, $R^{3i}$ is optionally substituted monocyclic heterocycloalkyl. In another embodiment, $R^{3i}$ is optionally substituted alkylcycloalkyl. In another embodiment, $R^{3i}$ is optionally substituted monocyclic alkylcycloalkyl. In another embodiment, $R^{3i}$ is optionally substituted alkylheterocycloalkyl. In another embodiment, $R^{3i}$ is optionally substituted monocyclic alkylheterocycloalkyl. In another embodiment, $R^{3i}$ is optionally substituted alkylaryl. In another embodiment, $R^{3i}$ is optionally substituted monocyclic alkylaryl. In another embodiment, $R^{3i}$ is optionally substituted alkylheteroaryl. In another embodiment, $R^{3i}$ is optionally substituted monocyclic alkylheteroaryl. In another embodiment, $R^{3i}$ is optionally substituted aryl. In another embodiment, $R^{3i}$ is optionally substituted monocyclic aryl. In another embodiment, $R^{3i}$ is optionally substituted heteroaryl. In another embodiment, $R^{3i}$ is optionally substituted monocyclic heteroaryl.

In another embodiment, $R^{2i}$ and $R^{3i}$ are combined to form a 5- to 8-membered mono or bicyclic ring that is carbocyclic or heterocyclic, any of which is optionally substituted. In another embodiment, $R^{2i}$ and $R^{3i}$ are combined to form a mono or bicyclic ring that is carbocyclic or heterocyclic, any of which is optionally substituted. In another embodiment, $R^{2i}$ and $R^{3i}$ are combined to form a monocyclic ring that is carbocyclic. In another embodiment, $R^{2i}$ and $R^{3i}$ are combined to form a monocyclic ring that is heterocyclic. In another embodiment $R^{2i}$ and $R^{3i}$ are combined to form a bicyclic ring that is carbocyclic. In another embodiment $R^{2i}$ and $R^{3i}$ are combined to form a bicyclic ring that is heterocyclic.

In one embodiment, $L^{1i}$ is —C≡C—, —HC=CH—, -(lower alkyl)-C=C-(lower alkyl)-, —CH$_2$—CH$_2$—, —CO—CH$_2$—, —CH$_2$—CO—, —NR$^{12i}$—CO—,

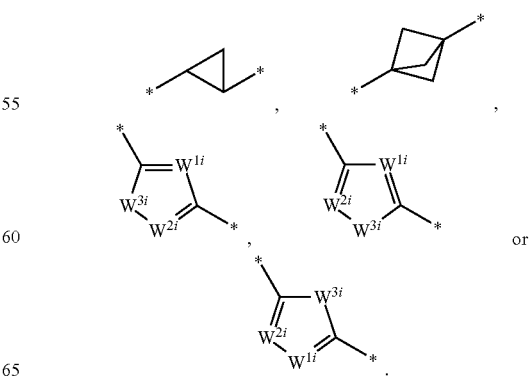

In one embodiment, $L^{1i}$ is —C≡C—. In another embodiment, $L^{1i}$ is —HC=HC—. In another embodiment, $L^{1i}$ is —CH$_2$—CH$_2$—. In another embodiment, $L^{1i}$ is —CO—CH$_2$—. In another embodiment, $L^{1i}$ is —CH$_2$—CO—. In another embodiment, $L^{1i}$ is —NR$^{12}$—CO—. In another embodiment, $L^{1i}$ is —CO—NR$^{12}$—. In another embodiment, $L^{1i}$ is —C$_{0-6}$alkyl-O—C$_{0-6}$ alkyl-. In another embodiment, $L^{1i}$ is NR$^{12i}$SO—. In another embodiment, $L^{1i}$ is —SONR$^{12i}$. In another embodiment $L^{1i}$ is —NR$^{12i}$SO$_2$—. In another embodiment, $L^{1i}$ is —SO$_2$NR$^{12i}$—. $R^{12i}$ is defined herein elsewhere.

In another embodiment, $L^{1i}$ is:

In another embodiment, $L^{1i}$ is:

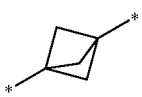

In another embodiment, $L^{1i}$ is:

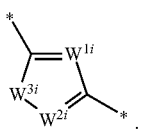

In another embodiment, $L^{1i}$ is:

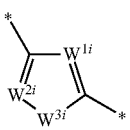

In another embodiment, $L^{1i}$ is:

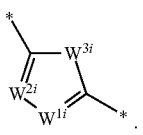

In one embodiment, $R^{12i}$ is hydrogen. In another embodiment, $R^{12i}$ is lower alkyl.

In one embodiment, $W^{1i}$ is N. In another embodiment, $W^{1i}$ is CH.

In one embodiment, $W^{2i}$ is N. In another embodiment, $W^{2i}$ is CH.

In one embodiment, $W^{3i}$ is O. In another embodiment, $W^{3i}$ is S. In another embodiment, $W^{3i}$ is NR$^{4i}$. $R^{4i}$ is defined herein elsewhere.

In one embodiment, $R^{4i}$ is hydrogen. In another embodiment, $R^{4i}$ is lower alkyl.

Any of the combinations of $R^{1i}$, $R^{2i}$, $R^{3i}$, $L^{1i}$, $R^{12i}$, $W^{1i}$, $W^{2i}$, $W^{3i}$ and $R^{4i}$ are encompassed by this disclosure and specifically provided by the invention.

In some embodiments, the compounds of formula II include, but are not limited to, the following compounds:

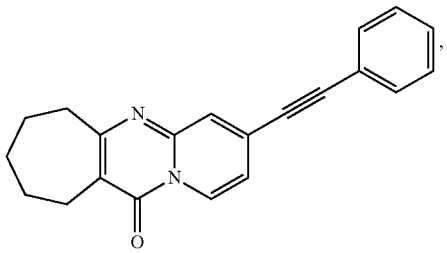

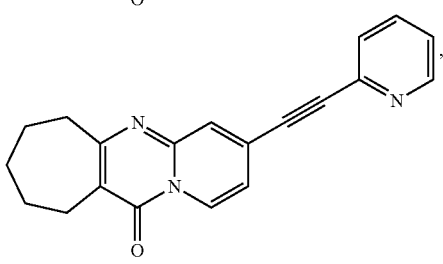

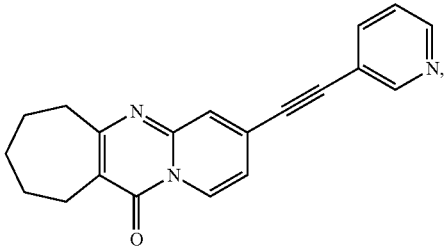

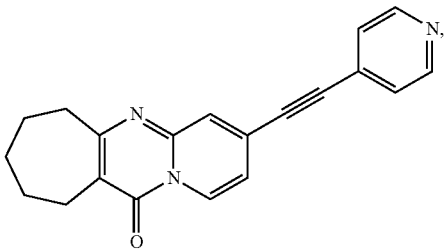

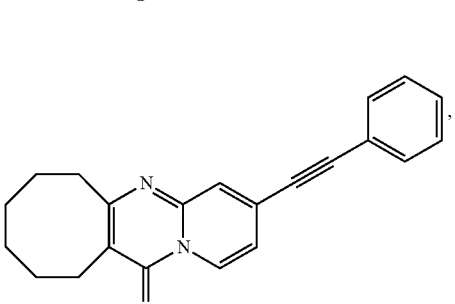

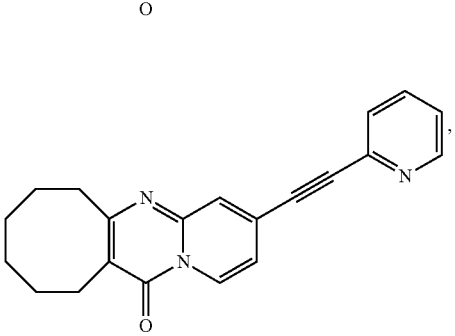

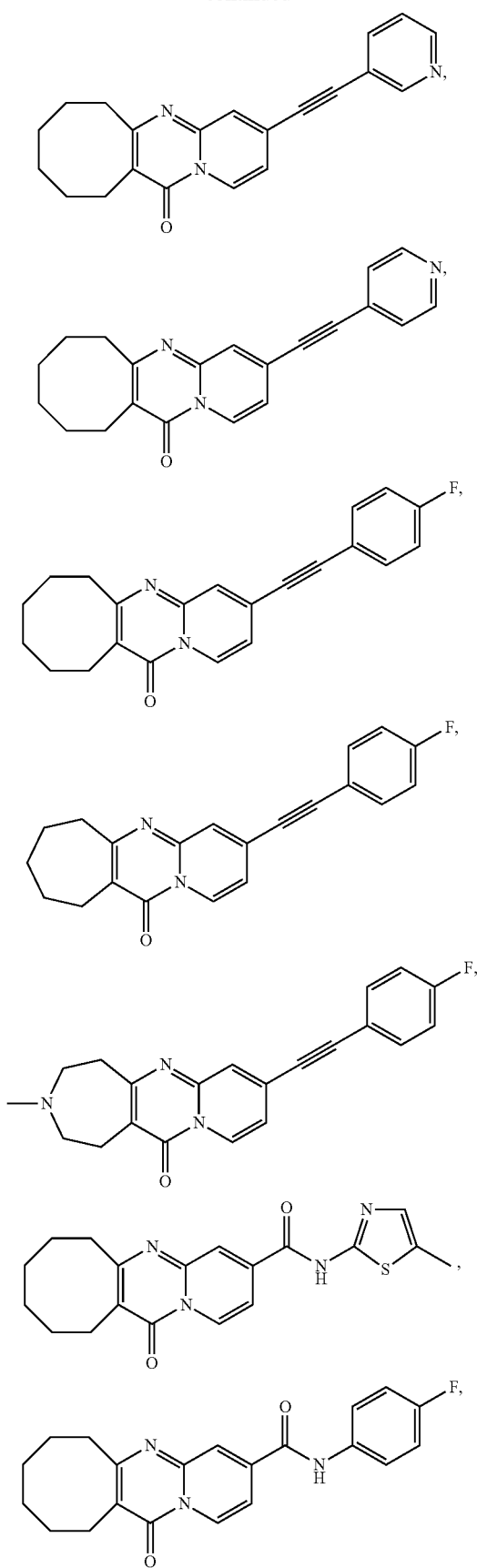
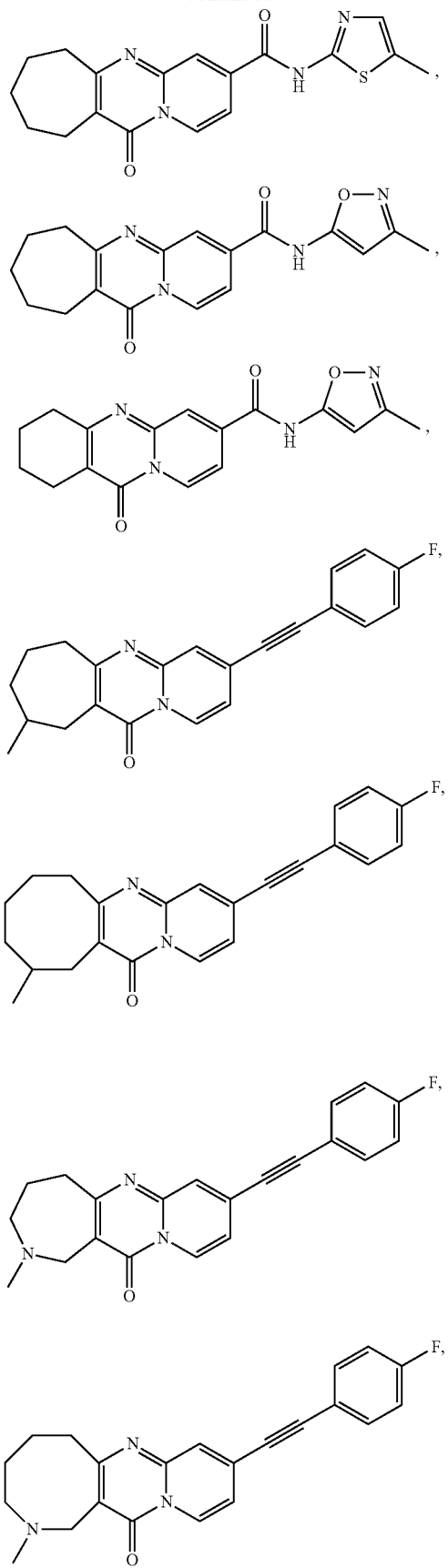

65
-continued
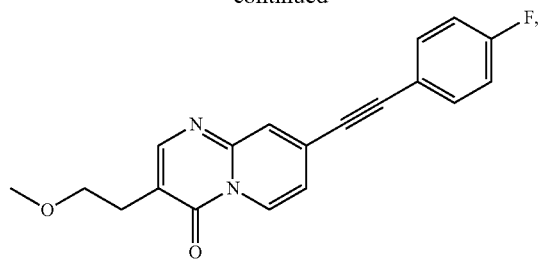
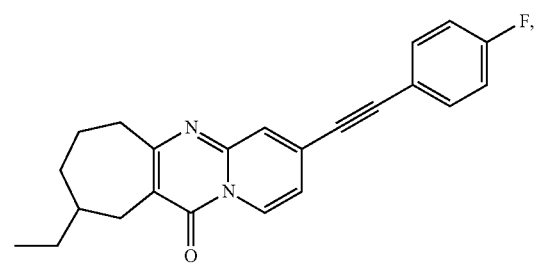
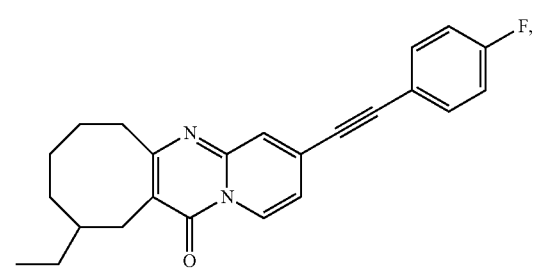
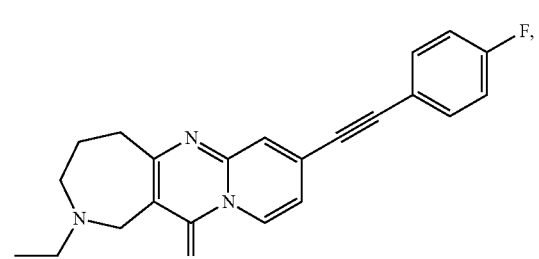
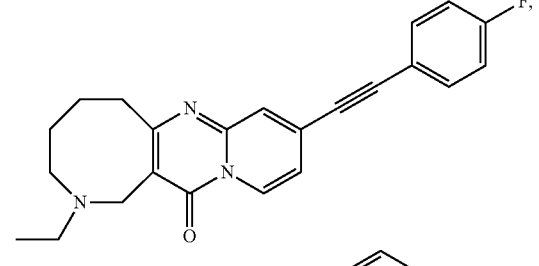
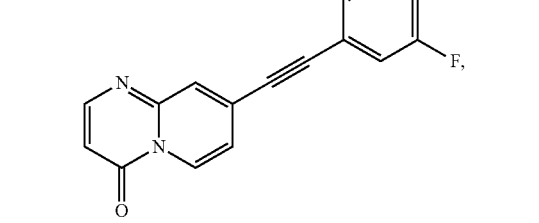
66
-continued
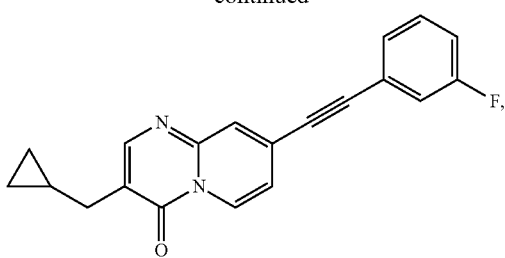
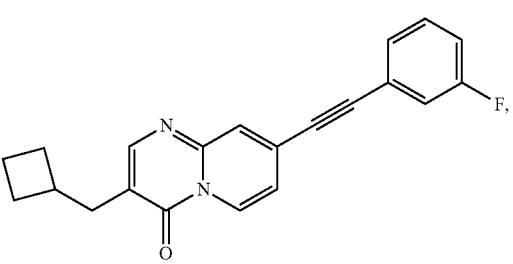
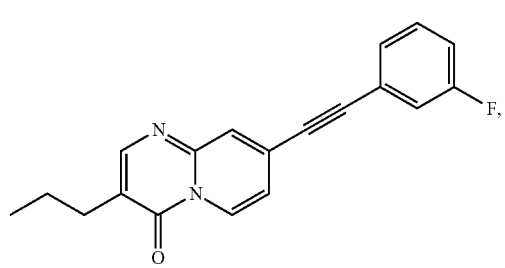
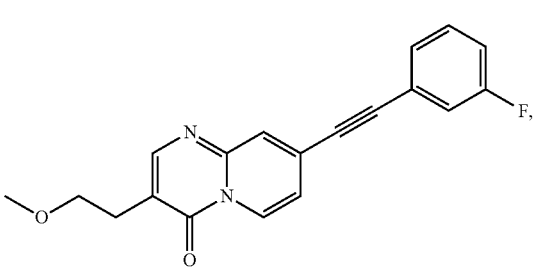
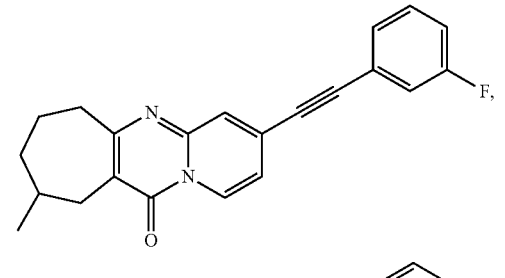
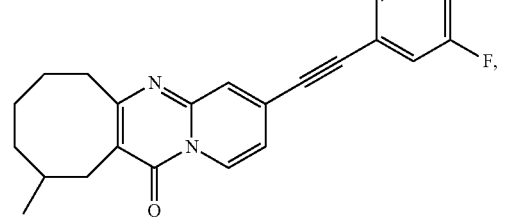

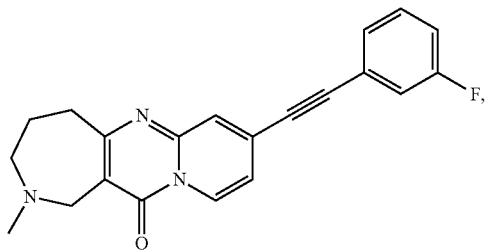

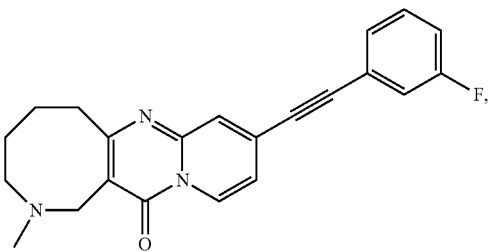

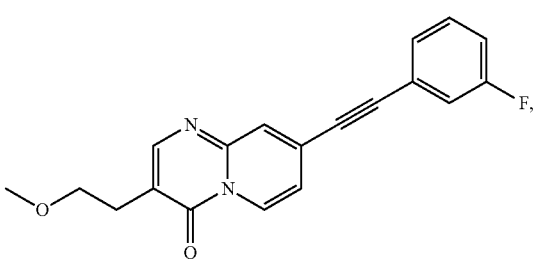

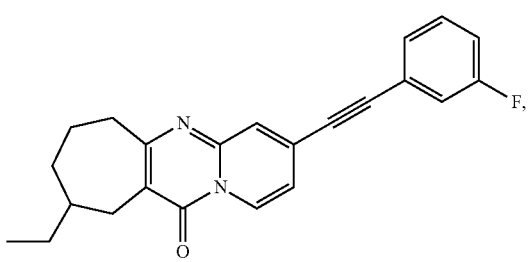

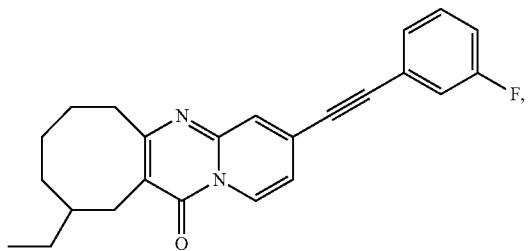

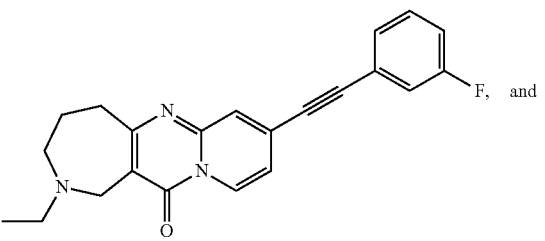

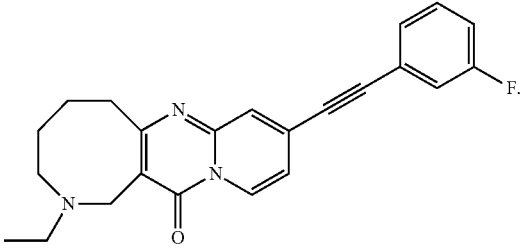

In some embodiments, a compound of formula (IIa) is provided:

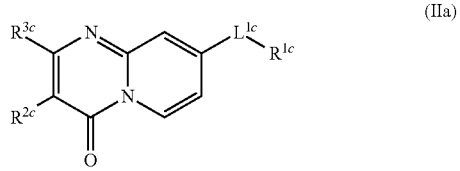

(IIa)

wherein
R$^{1c}$ is aryl or heteroaryl;
L$^{1c}$ is —C≡C—;
R$^{2c}$ is lower alkyl or heteroalkyl; and
R$^{3c}$ is hydrogen; or
R$^{2c}$ and R$^{3c}$ are linked to form a monocyclic or bicyclic ring that is carbocyclic or heterocyclic;
or a pharmaceutically acceptable salt thereof.

In another embodiment, R$^{2c}$ and R$^{3c}$ are linked to form a 5- to 8-membered mono or bicyclic ring that is carbocyclic or heterocyclic, any of which is optionally substituted. In another embodiment, R$^{2c}$ and R$^{3c}$ are linked to form a mono or bicyclic ring that is carbocyclic or heterocyclic, any of which is optionally substituted. In another embodiment, R$^{2c}$ and R$^{3c}$ are linked to form a monocyclic ring that is carbocyclic. In another embodiment, R$^{2c}$ and R$^{3c}$ are linked to form a monocyclic ring that is heterocyclic. In another embodiment R$^{2c}$ and R$^{3c}$ are linked to form a bicyclic ring that is carbocyclic. In another embodiment R$^{2c}$ and R$^{3c}$ are linked to form a bicyclic ring that is heterocyclic.

In some embodiments, the compounds of formula (IIa) have the following substituents:

| R$^{1c}$ | L$^{1c}$ | R$^{2c}$&R$^{3c}$ |
|---|---|---|
| 2-pyridyl | C≡C | gem-dimethylcyclohexyl |
| 4-pyridyl | C≡C | cycloheptyl |
| phenyl | C≡C | cycloheptyl |

-continued

| $R^{1c}$ | $L^{1c}$ | $R^{2c}$ & $R^{3c}$ |
|---|---|---|

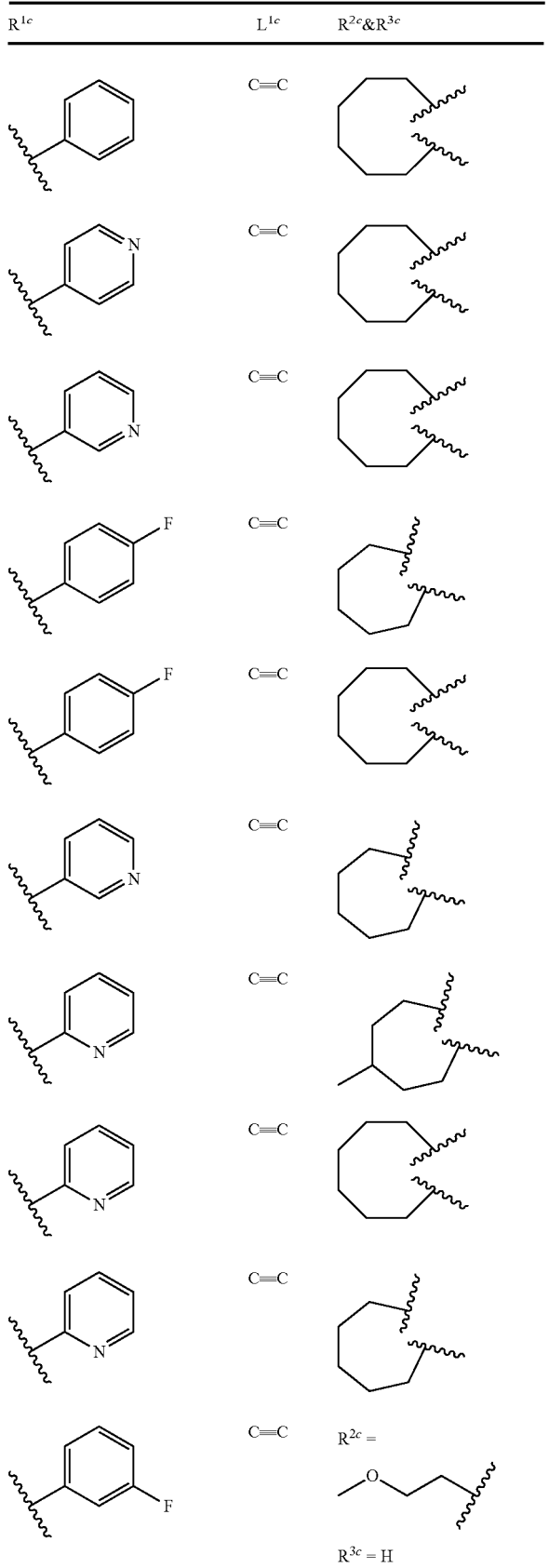

-continued

| $R^{1c}$ | $L^{1c}$ | $R^{2c}$ & $R^{3c}$ |
|---|---|---|

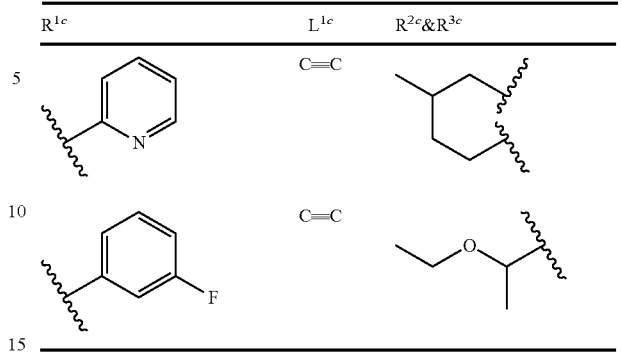

In one embodiment, there is provided a compound of formula (III):

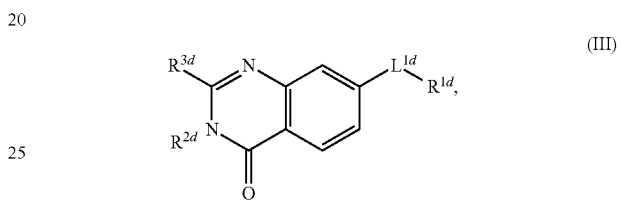

or a pharmaceutically acceptable salt, solvate, or stereoisomer thereof, wherein $R^{1d}$, $R^{2d}$ and $R^{3d}$ are each independently hydrogen, lower alkyl, heteroalkyl, cycloalkyl, heterocycloalkyl, alkylcycloalkyl, alkylheterocycloalkyl, alkylaryl, alkylheteroaryl, aryl or heteroaryl, each of which is optionally substituted; or $R^{2d}$ and $R^{3d}$ are optionally joined, together with the atoms to which they are attached, to form a mono or bicyclic ring that is carbocyclic or heterocyclic, any of which is optionally substituted;

$L^{1d}$ is —C≡C—, —HC=CH—, -(lower alkyl)-C≡C-(lower alkyl)-, —CH$_2$—CH$_2$—, —CO—CH$_2$—, —CH$_2$—CO—, —NR$^{12d}$—CO—, —CO—NR$^{12d}$—, C$_{0-6}$alkyl-O—C$_{0-6}$alkyl-, —NR$^{12d}$SO—, —SONR$^{12d}$—, —NR$^{12d}$SO$_2$, SO$_2$NR$^{12d}$—, $R^{12d}$ is hydrogen or lower alkyl
$W^{1d}$ and $W^{2d}$ are each independently N or CH;
$W^{3d}$ is O, S or NR$^{4d}$;
$R^{4d}$ is hydrogen or lower alkyl.

In one embodiment, $R^{1d}$ is hydrogen. In another embodiment, $R^{1d}$ is optionally substituted lower alkyl. In another embodiment, $R^{1d}$ is optionally substituted heteroalkyl. In another embodiment, $R^{1d}$ is optionally substituted cycloalkyl. In another embodiment, $R^{1d}$ is optionally substituted monocyclic cycloalkyl. In another embodiment, $R^{1d}$ is optionally substituted heterocycloalkyl. In another embodiment, $R^{1d}$ is optionally substituted monocyclic heterocycloalkyl. In another embodiment, $R^{1d}$ is optionally substituted alkylcycloalkyl. In another embodiment, $R^{1d}$ is optionally substituted monocyclic alkylcycloalkyl. In another embodiment, $R^{1d}$ is optionally substituted alkylheterocycloalkyl. In another embodiment, $R^{1d}$ is optionally substituted monocyclic alkylheterocycloalkyl. In another embodiment, $R^{1d}$ is optionally substituted alkylaryl. In another embodiment, $R^{1d}$ is optionally substituted monocyclic alkylaryl. In another embodiment, $R^{1d}$ is optionally substituted alkylheteroaryl. In another embodiment, $R^{1d}$ is optionally substituted monocyclic alkylheteroaryl. In another embodiment, $R^{1d}$ is optionally substituted aryl. In another embodiment, $R^{1d}$ is optionally substituted monocyclic aryl. In another embodiment, $R^{1d}$ is optionally substituted heteroaryl. In another embodiment, $R^{1d}$ is optionally substituted monocyclic heteroaryl.

In one embodiment, $R^{2d}$ is hydrogen. In another embodiment, $R^{2d}$ is optionally substituted lower alkyl. In another embodiment, $R^{2d}$ is optionally substituted heteroalkyl. In another embodiment, $R^{2d}$ is optionally substituted cycloalkyl. In another embodiment, $R^{2d}$ is optionally substituted monocyclic cycloalkyl. In another embodiment, $R^{2d}$ is optionally substituted heterocycloalkyl. In another embodiment, $R^{2d}$ is optionally substituted monocyclic heterocycloalkyl. In another embodiment, $R^{2d}$ is optionally substituted alkylcycloalkyl. In another embodiment, $R^{2d}$ is optionally substituted monocyclic alkylcycloalkyl. In another embodiment, $R^{2d}$ is optionally substituted alkylheterocycloalkyl. In another embodiment, $R^{2d}$ is optionally substituted monocyclic alkylheterocycloalkyl. In another embodiment, $R^{2d}$ is optionally substituted alkylaryl. In another embodiment, $R^{2d}$ is optionally substituted monocyclic alkylaryl. In another embodiment, $R^{2d}$ is optionally substituted alkylheteroaryl. In another embodiment, $R^{2d}$ is optionally substituted monocyclic alkylheteroaryl. In another embodiment, $R^{2d}$ is optionally substituted aryl. In another embodiment, $R^{2d}$ is optionally substituted monocyclic aryl. In another embodiment, $R^{2d}$ is optionally substituted heteroaryl. In another embodiment, $R^{2d}$ is optionally substituted monocyclic heteroaryl.

In one embodiment, $R^{3d}$ is hydrogen. In another embodiment, $R^{3d}$ is optionally substituted lower alkyl. In another embodiment, $R^{3d}$ is optionally substituted heteroalkyl. In another embodiment, $R^{3d}$ is optionally substituted cycloalkyl. In another embodiment, $R^{3d}$ is optionally substituted monocyclic cycloalkyl. In another embodiment, $R^{3d}$ is optionally substituted heterocycloalkyl. In another embodiment, $R^{3d}$ is optionally substituted monocyclic heterocycloalkyl. In another embodiment, $R^{3d}$ is optionally substituted alkylcycloalkyl. In another embodiment, $R^{3d}$ is optionally substituted monocyclic alkylcycloalkyl. In another embodiment, $R^{3d}$ is optionally substituted alkylheterocycloalkyl. In another embodiment, $R^{3d}$ is optionally substituted monocyclic alkylheterocycloalkyl. In another embodiment, $R^{3d}$ is optionally substituted alkylaryl. In another embodiment, $R^{3d}$ is optionally substituted monocyclic alkylaryl. In another embodiment, $R^{3d}$ is optionally substituted alkylheteroaryl. In another embodiment, $R^{3d}$ is optionally substituted monocyclic alkylheteroaryl. In another embodiment, $R^{3d}$ is optionally substituted aryl. In another embodiment, $R^{3d}$ is optionally substituted monocyclic aryl. In another embodiment, $R^{3d}$ is optionally substituted heteroaryl. In another embodiment, $R^{3d}$ is optionally substituted monocyclic heteroaryl.

In another embodiment, $R^{2d}$ and $R^{3d}$ are linked to form a 5- to 8-membered mono or bicyclic ring that is carbocyclic or heterocyclic, any of which is optionally substituted. In another embodiment, $R^{2d}$ and $R^{3d}$ are linked to form a mono or bicyclic ring that is carbocyclic or heterocyclic, any of which is optionally substituted. In another embodiment, $R^{2d}$ and $R^{3d}$ are linked to form a monocyclic ring that is carbocyclic. In another embodiment, $R^{2d}$ and $R^{3d}$ are linked to form a monocyclic ring that is heterocyclic. In another embodiment $R^{2d}$ and $R^{3d}$ are linked to form a bicyclic ring that is carbocyclic. In another embodiment $R^{2d}$ and $R^{3d}$ are linked to form a bicyclic ring that is heterocyclic.

In one embodiment, $L^{1d}$ is —C≡C—, —HC=CH—, —CH$_2$—CH$_2$—, —CO—CH$_2$—, —CH$_2$—CO—, NR$^{12d}$—C—, CO—NR$^{12d}$—,

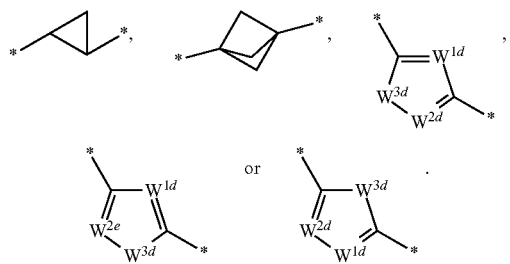

In one embodiment, $L^{1d}$ is —C≡C—. In another embodiment, $L^{1d}$ is —HC=CH—. In another embodiment, $L^{1d}$ is —CH$_2$—CH$_2$—. In another embodiment, $L^{1d}$ is —CO—CH$_2$—. In another embodiment, $L^{1d}$ is —CH$_2$—CO—. In another embodiment, $L^{1d}$ is —NR$^{12d}$CO—. In another embodiment, $L^{1d}$ is —CO—NR$^{12d}$—. In another embodiment, $L^{1d}$ is —C$_{0-6}$alkyl-O—C$_{0-6}$alkyl-. In another embodiment, $L^{1d}$ is NR$^{12d}$SO. In another embodiment, $L^{1d}$ is —SONR$^{12d}$—. In another embodiment, $L^{1d}$ is —NR$^{12d}$SO$_2$—. In another embodiment, $L^{1d}$ is —SO$_2$NR$^{12d}$—. $R^{12d}$ is defined herein elsewhere.

In another embodiment, $L^{1d}$ is:

In another embodiment, $L^{1d}$ is:

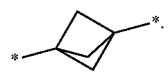

In another embodiment, $L^{1d}$ is:

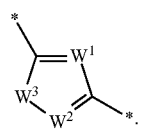

In another embodiment, $L^{1d}$ is:

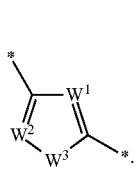

In another embodiment, $L^{1d}$ is:

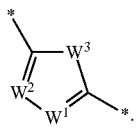

In one embodiment, $R^{12d}$ is hydrogen. In another embodiment, $R^{12d}$ is lower alkyl.

In one embodiment, $W^{1d}$ is N. In another embodiment, $W^{1d}$ is CH.

In one embodiment, $W^{2d}$ is N. In another embodiment, $W^{2d}$ is CH.

In one embodiment, $W^{3d}$ is O. In another embodiment, $W^{3d}$ is S. In another embodiment, $W^{3d}$ is $NR^{4d}$. $R^{4d}$ is defined herein elsewhere.

In one embodiment, $R^{4d}$ is hydrogen. In another embodiment, $R^{4d}$ is lower alkyl.

Any of the combinations of $R^{1d}$, $R^{2d}$, $R^{3d}$, $L^{1d}$, $R^{12d}$, $W^{1d}$, $W^{2d}$, $W^{3d}$ and $R^{4d}$ are encompassed by this disclosure and specifically provided by the invention.

In some embodiments, the compounds of formula II include, but are not limited to, the following compounds:

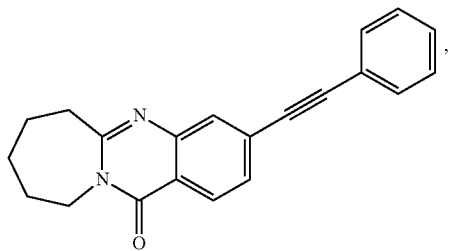

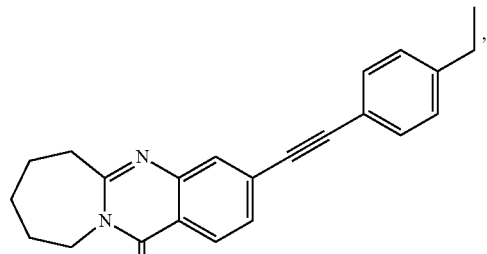

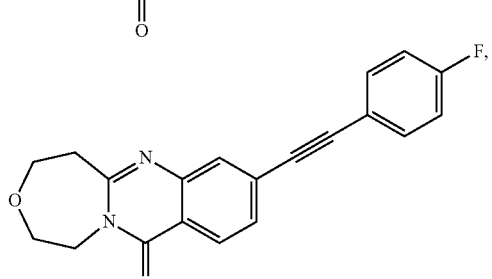

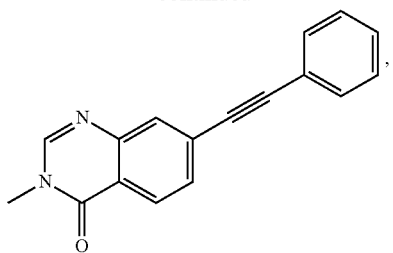

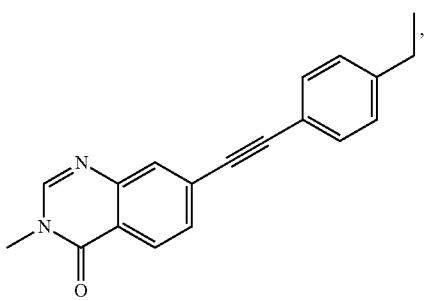

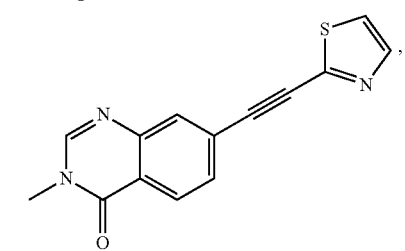

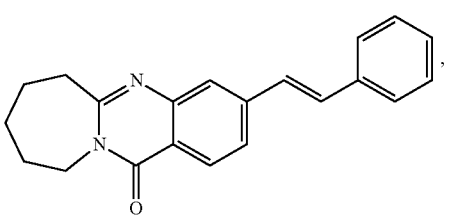

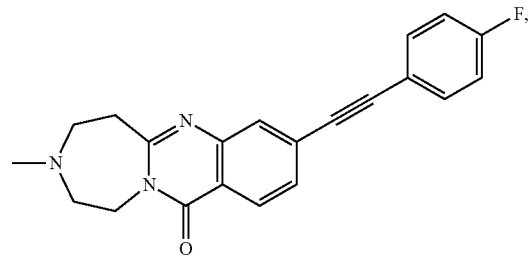

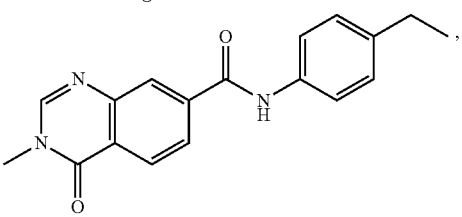

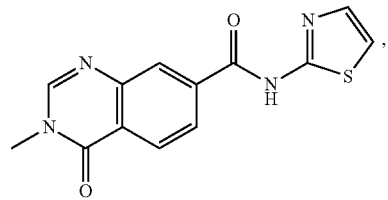

75
-continued
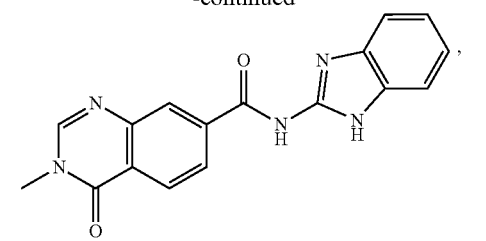
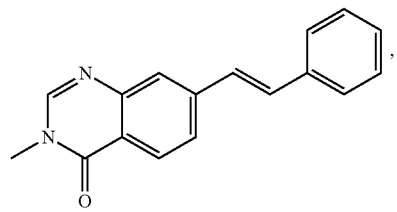
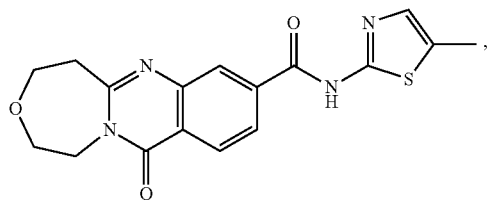
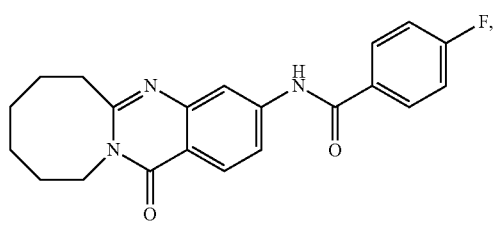
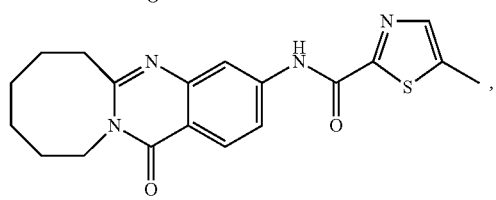
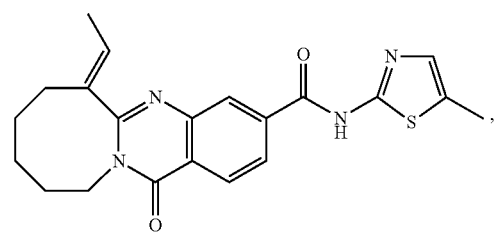
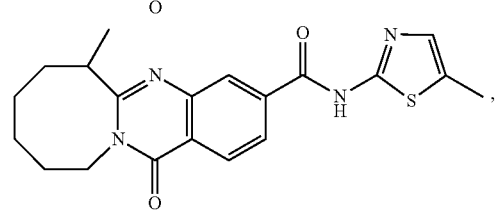
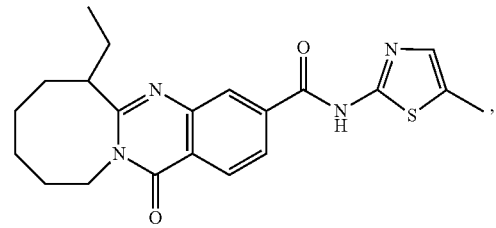
76
-continued
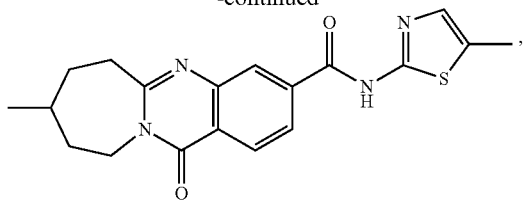
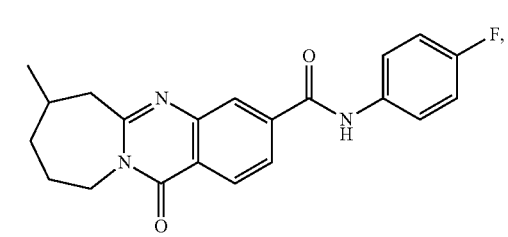
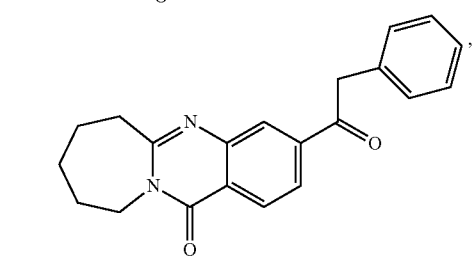
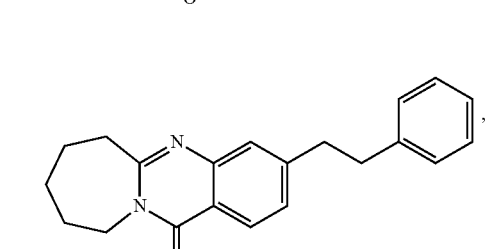
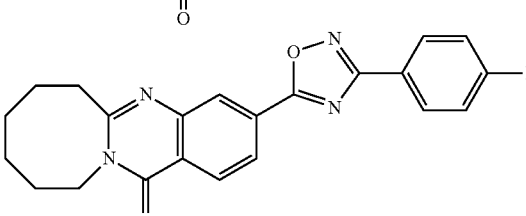
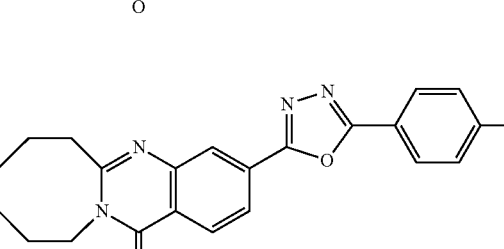
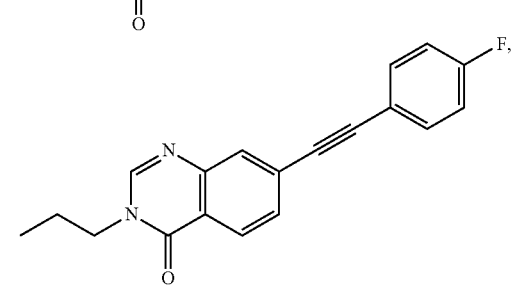

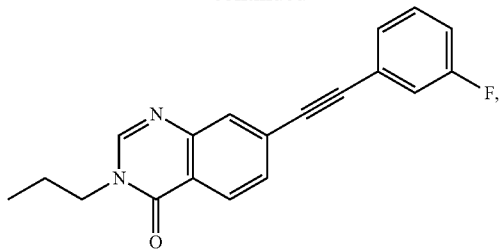

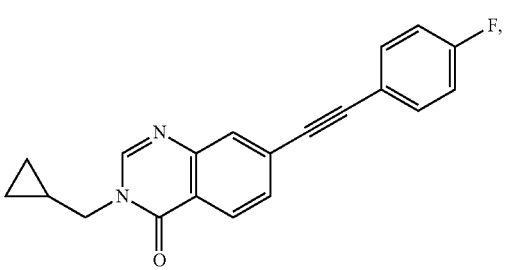

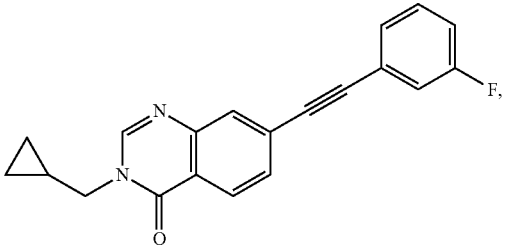

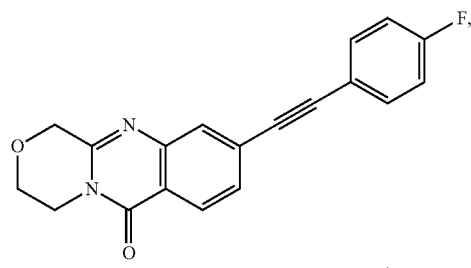

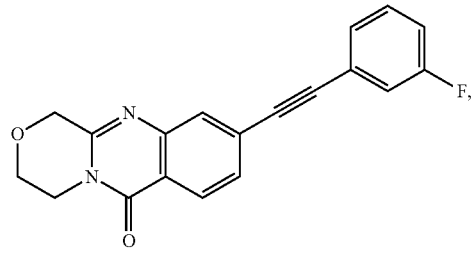

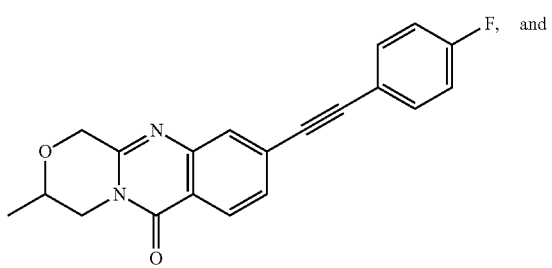

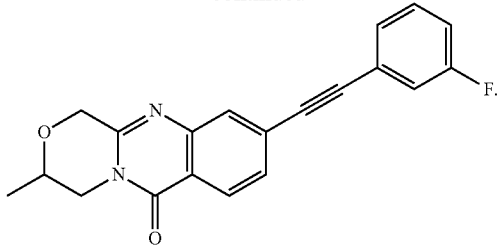

In some embodiments, compounds of formula (Ma) are provided:

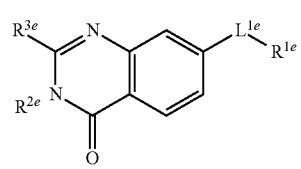

(IIIa)

wherein
$R^{1e}$ is aryl or heteroaryl;
$L^{1e}$ is —HC=CH—, —C≡C—, or —C(O)NH—;
$R^{2e}$ is lower alkyl or heteroalkyl;
$R^{3e}$ is hydrogen, lower alkyl heteroalkyl, or heterocycloalkyl; or
$R^{2e}$ and $R^{3e}$ are linked to form a monocyclic or bicyclic heterocyclic or cycloalkyl ring, each of which is optionally substituted; and pharmaceutically acceptable salts thereof.

In some embodiments, $R^{2e}$ and $R^{3e}$ are linked to form a 5- to 8-membered mono or bicyclic ring that is carbocyclic or heterocyclic, any of which is optionally substituted. In another embodiment, $R^{2e}$ and $R^{3e}$ are linked to form a mono or bicyclic ring that is carbocyclic or heterocyclic, any of which is optionally substituted. In another embodiment, $R^{2e}$ and $R^{3e}$ are linked to form a monocyclic ring that is carbocyclic. In another embodiment, $R^{2e}$ and $R^{3e}$ are linked to form a monocyclic ring that is heterocyclic. In another embodiment $R^{2e}$ and $R^{3e}$ are linked to form a bicyclic ring that is carbocyclic. In another embodiment $R^{2e}$ and $R^{3e}$ are linked to form a bicyclic ring that is heterocyclic.

In some embodiments, the compounds of formula (IIIa) have the following substituents

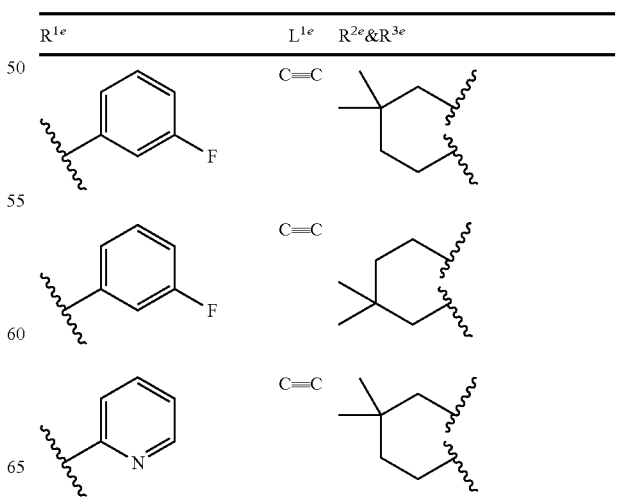

| R$^{1e}$ | L$^{1e}$ | R$^{2e}$&R$^{3e}$ |
|---|---|---|
| 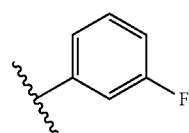 [SMILES: *c1cccc(F)c1] | C≡C | 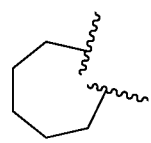 [SMILES: *CCCCC*] |
| 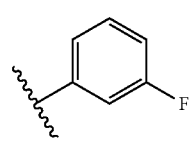 [SMILES: *c1cccc(F)c1] | C≡C | 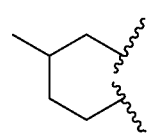 [SMILES: *CCC(C)C*] |
| 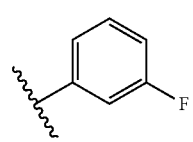 [SMILES: *c1cccc(F)c1] | C≡C | 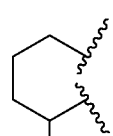 |
| 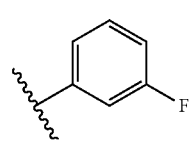 [SMILES: *c1cccc(F)c1] | C≡C | 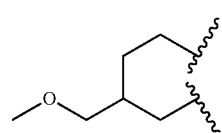 [SMILES: *CCC(C*)COC] |
| 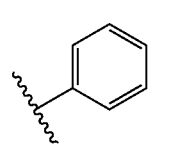 [SMILES: *c1ccccc1] | C≡C | 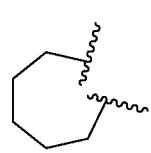 [SMILES: *CCCCC*] |
| 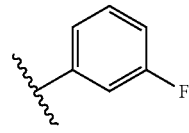 [SMILES: *c1cccc(F)c1] | C≡C | 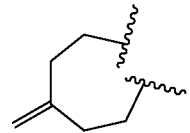 [SMILES: *CCC(=C)CC*] |
| 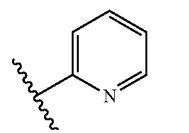 | C≡C | 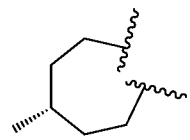 |
| 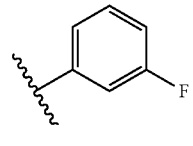 [SMILES: *c1cccc(F)c1] | C≡C | 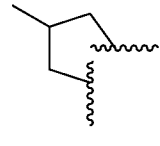 [SMILES: *CC(C)C*] |
| 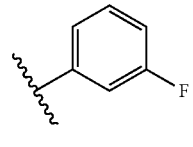 [SMILES: *c1cccc(F)c1] | C≡C | 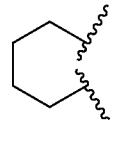 |
| 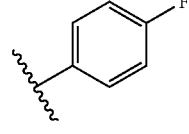 | C≡C | 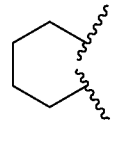 |
| R$^{1e}$ | L$^{1e}$ | R$^{2e}$&R$^{3e}$ |
|---|---|---|
| 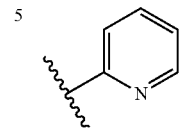 | C≡C | 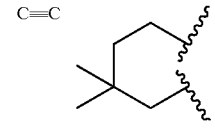 |
| 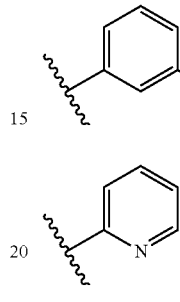 | C≡C | 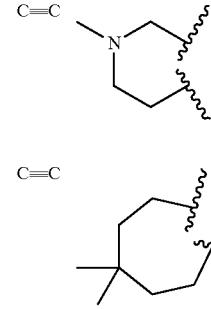 |
| 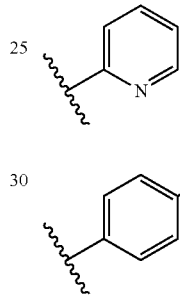 | C≡C | 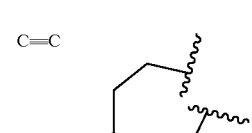 |
| 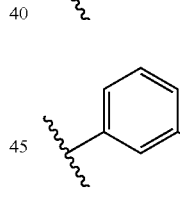 | C≡C | 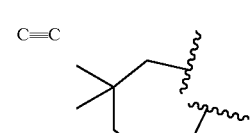 |
| 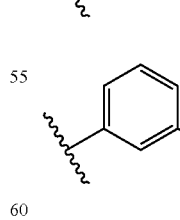 | C≡C | 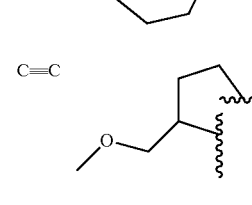 |
| 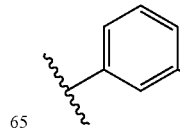 | C≡C | 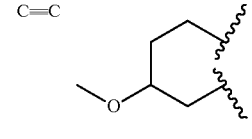 |

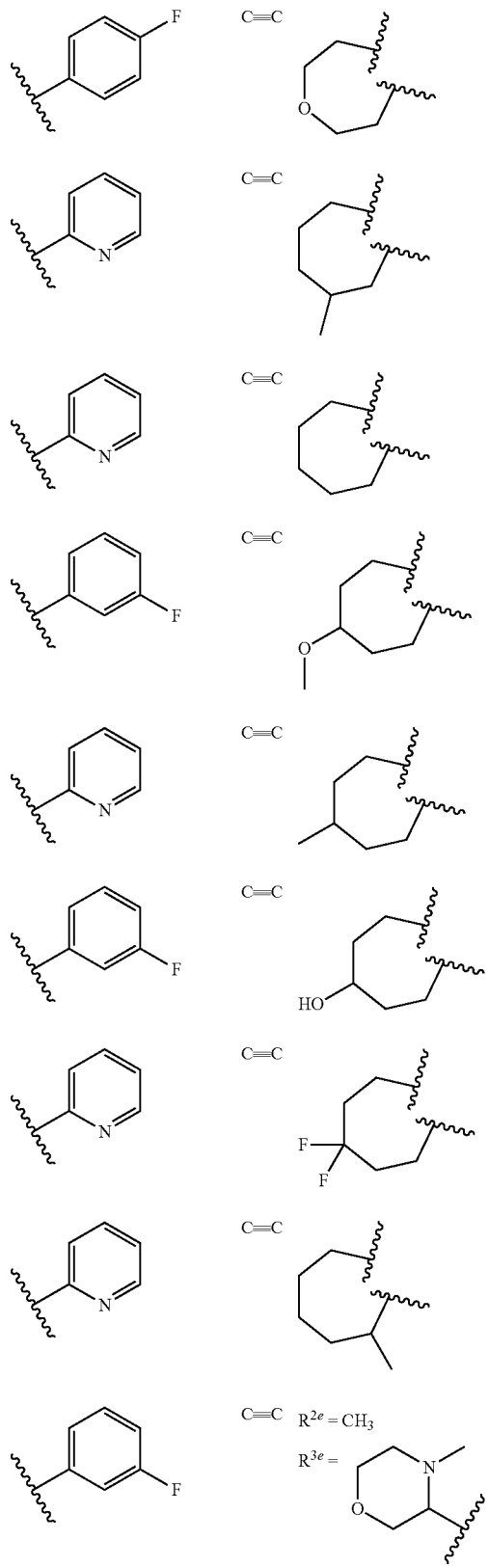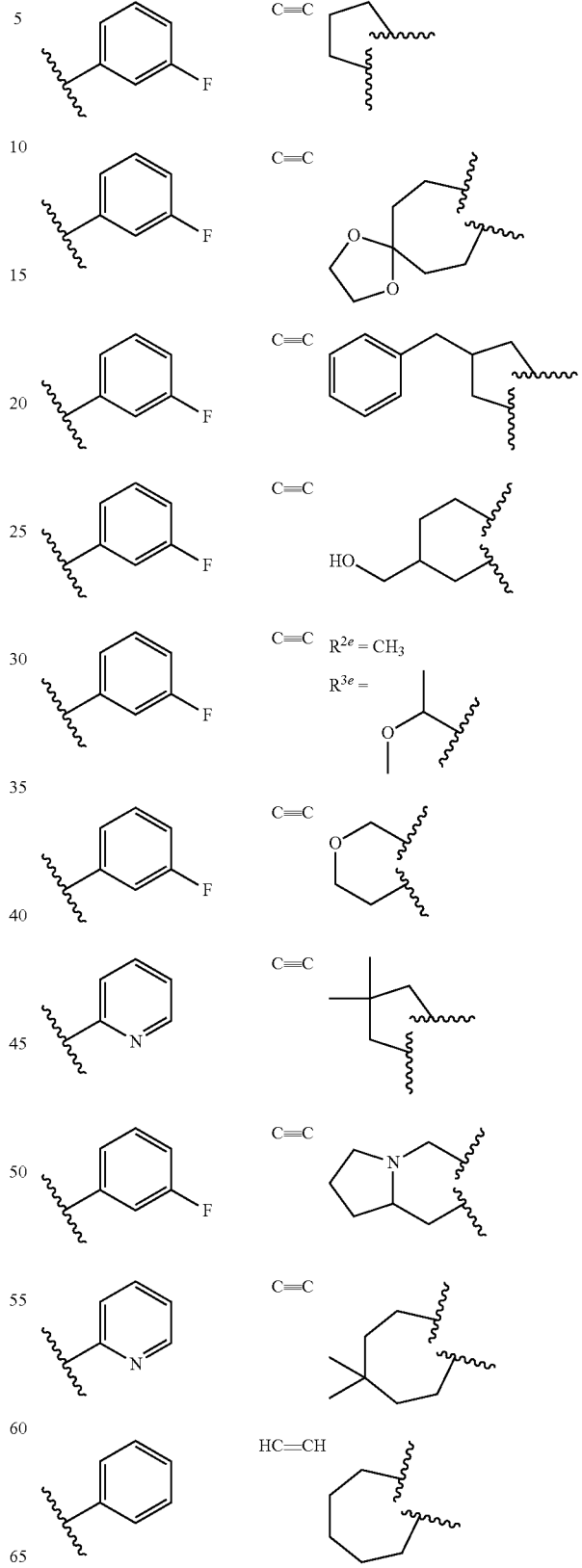

| $R^{1e}$ | $L^{1e}$ | $R^{2e}$ & $R^{3e}$ |
|---|---|---|
| 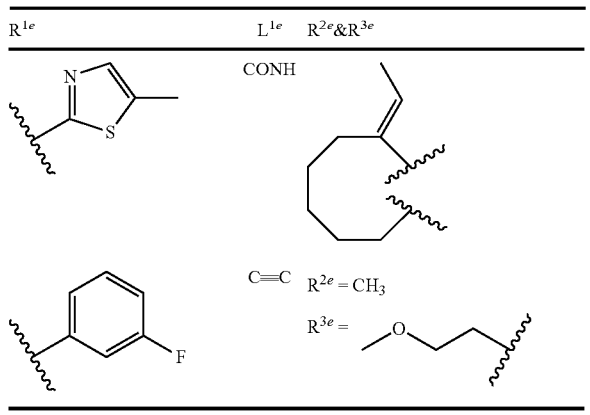 | CONH | |
| | C≡C | $R^{2e}$ = CH$_3$<br>$R^{3e}$ = 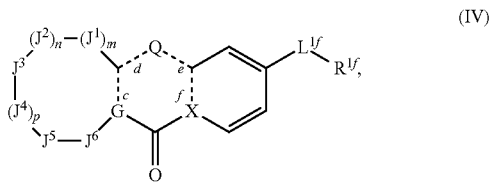 |

In one embodiment, there is provided a compound of formula (IV):

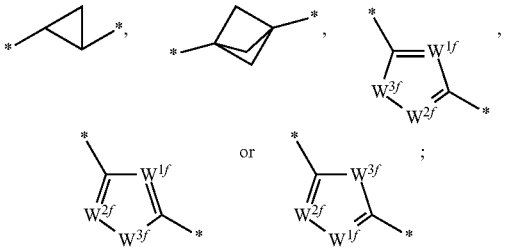

or a pharmaceutically acceptable salt, solvate, or stereoisomer thereof, wherein $R^{1f}$ is hydrogen, lower alkyl, heteroalkyl, cycloalkyl, heterocycloalkyl, alkylcycloalkyl, alkylheterocycloalkyl, alkylaryl, alkylheteroaryl, aryl or heteroaryl, each of which is optionally substituted;

$J^1$, $J^2$, $J^3$, $J^4$, $J^5$, and $J^6$ are independently CO, O, S, $NR^7$, $CR^8R^9$ or $C=CR^{10}R^{11}$, provided that there are no adjacent heteroatoms in the resulting ring;

m, n, and p are independently 0 or 1;

$R^7$ is hydrogen, cycloalkyl, heteroalkyl, acyl, heterocycloalkyl, C(O)Oalkyl, C(O)H, or lower alkyl;

$R^8$ and $R^9$ are each independently hydrogen, lower alkyl, heteroalkyl, cycloalkyl, heterocycloalkyl, alkylcycloalkyl, alkylheterocycloalkyl, alkylaryl or alkylheteroaryl, each of which is optionally substituted; or $R^8$ and $R^9$ together with the carbon atom to which they are attached are linked to form a 5-6 membered heterocyclic or cycloalkyl ring, each of which is optionally substituted;

$R^{10}$ and $R^{11}$ are each independently hydrogen or lower alkyl;

c, d, e, and f are each independently a singe or a double bond, provided that when c is a double bond, d is a single bond, when d is a double bond, c and e are single bond, when e is a double bond, d and f are single bonds, and when f is a double bond, e is a single bond;

G is N when c is a single bond, or C when c is a double bond;

Q is NH or CH$_2$ when d and e are single bonds, or N or CH when one of d or e are a double bond;

X is N when f is a single bond or C when f is a double bond;

$L^{1f}$ is —C≡C—, —HC=CH—, -(lower alkyl)-C≡C-(lower alkyl)-, —CH$_2$—CH$_2$—, —CO—CH$_2$—, —CH$_2$—CO—, —C$_{0-6}$alkyl-O—C$_{0-6}$alkyl-, —NHR$^{12}$SO—, —SONR$^{12}$—, —NR$^{12}$SO$_2$—, —SO$_2$NR$^{12}$—, —NR$^{12}$—CO—, —CO—NR$^{12}$—, $R^{12f}$ is hydrogen or lower alkyl;

$W^{1f}$ and $W^{2f}$ are each independently selected from N and CH;

$W^{3f}$ is selected from O, S, and $NR^{4f}$; and $R^4$ is selected from hydrogen and lower alkyl, or a pharmaceutically acceptable salt thereof.

In some embodiments, at least one of G, Q, and X is a nitrogen atom. In some embodiments, at least two of G, Q, and X is a nitrogen atom. In some embodiments, both Q and G are nitrogen atoms. In some embodiments, both Q and X are nitrogen atoms.

In one embodiment, $R^{1f}$ is hydrogen. In another embodiment, $R^{1f}$ is optionally substituted lower alkyl. In another embodiment, $R^{1f}$ is optionally substituted heteroalkyl. In another embodiment, $R^{1f}$ is optionally substituted cycloalkyl. In another embodiment, $R^{1f}$ is optionally substituted monocyclic cycloalkyl. In another embodiment, $R^{1f}$ is optionally substituted heterocycloalkyl. In another embodiment, $R^{1f}$ is optionally substituted monocyclic heterocycloalkyl. In another embodiment, $R^{1f}$ is optionally substituted alkylcycloalkyl. In another embodiment, $R^{1f}$ is optionally substituted monocyclic alkylcycloalkyl. In another embodiment, $R^{1f}$ is optionally substituted alkylheterocycloalkyl. In another embodiment, $R^{1f}$ is optionally substituted monocyclic alkylheterocycloalkyl. In another embodiment, $R^{1f}$ is optionally substituted alkylaryl. In another embodiment, $R^{1f}$ is optionally substituted monocyclic alkylaryl. In another embodiment, $R^{1f}$ is optionally substituted alkylheteroaryl. In another embodiment, $R^{1f}$ is optionally substituted monocyclic alkylheteroaryl. In another embodiment, $R^{1f}$ is optionally substituted aryl. In another embodiment, $R^{1f}$ is optionally substituted monocyclic aryl. In another embodiment, $R^{1f}$ is optionally substituted heteroaryl. In another embodiment, $R^{1f}$ is optionally substituted monocyclic heteroaryl.

In one embodiment, $J^1$ is O. In another embodiment, $J^1$ is S. In another embodiment, $J^1$ is $NR^7$. In another embodiment, $J^1$ is $CR^8R^9$. In another embodiment, $J^1$ is CH$_2$. In another embodiment, $J^1$ is CHR$^8$. In another embodiment, $J^1$ is C=CR$^{10}$R$^{11}$. $R^7$, $R^8$, $R^9$, $R^{10}$ and $R^{11}$ are defined herein elsewhere.

In one embodiment, $J^2$ is O. In another embodiment, $J^2$ is S. In another embodiment, $J^2$ is $NR^7$. In another embodiment, $J^2$ is $CR^8R^9$. In another embodiment, $J^2$ is CH$_2$. In another embodiment, $J^2$ is CHR$^8$. In another embodiment, $J^2$ is C=CR$^{10}$R$^{11}$. $R^7$, $R^8$, $R^9$, $R^{10}$ and $R^{11}$ are defined herein elsewhere.

In one embodiment, $J^3$ is O. In another embodiment, $J^3$ is S. In another embodiment, $J^3$ is $NR^7$. In another embodiment, $J^3$ is $CR^8R^9$. In another embodiment, $J^3$ is CH$_2$. In another embodiment, $J^3$ is CHR$^8$. In another embodiment, $J^3$ is C=CR$^{10}$R$^{11}$. $R^7$, $R^8$, $R^9$, $R^{10}$ and $R^{11}$ are defined herein elsewhere.

In one embodiment, $J^4$ is O. In another embodiment, $J^4$ is S. In another embodiment, $J^4$ is $NR^7$. In another embodiment, $J^4$ is $CR^8R^9$. In another embodiment, $J^4$ is $CH_2$. In another embodiment, $J^4$ is $CHR^8$. In another embodiment, $J^4$ is $C=CR^{10}R^{11}$. $R^7$, $R^8$, $R^9$, $R^{10}$ and $R^{11}$ are defined herein elsewhere.

In one embodiment, $J^5$ is O. In another embodiment, $J^5$ is S. In another embodiment, $J^5$ is $NR^7$. In another embodiment, $J^5$ is $CR^8R^9$. In another embodiment, $J^5$ is $CH_2$. In another embodiment, $J^5$ is $CHR^8$. In another embodiment, $J^5$ is $C=CR^{10}R^{11}$. $R^7$, $R^8$, $R^9$, $R^{10}$ and $R^{11}$ are defined herein elsewhere.

In one embodiment, $J^6$ is O. In another embodiment, $J^6$ is S. In another embodiment, $J^6$ is $NR^7$. In another embodiment, $J^6$ is $CR^8R^9$. In another embodiment, $J^6$ is $CH_2$. In another embodiment, $J^6$ is $CHR^8$. In another embodiment, $J^6$ is $C=CR^{10}R^{11}$. $R^7$, $R^8$, $R^9$, $R^{10}$ and $R^{11}$ are defined herein elsewhere.

In an exemplary embodiment according to the description above, there are no adjacent heteroatoms in the resulting ring.

In one embodiment, m is 0. In another embodiment, m is 1.

In one embodiment, n is 0. In another embodiment, n is 1.

In one embodiment, p is 0. In another embodiment, p is 1.

In one embodiment, $R^7$ is hydrogen. In another embodiment, $R^7$ is lower alkyl.

In one embodiment, $R^8$ is hydrogen. In another embodiment, $R^8$ is optionally substituted lower alkyl. In another embodiment, $R^8$ is optionally substituted heteroalkyl. In another embodiment, $R^8$ is optionally substituted cycloalkyl. In another embodiment, $R^8$ is optionally substituted monocyclic cycloalkyl. In another embodiment, $R^8$ is optionally substituted heterocycloalkyl. In another embodiment, $R^8$ is optionally substituted monocyclic heterocycloalkyl. In another embodiment, $R^8$ is optionally substituted alkylcycloalkyl. In another embodiment, $R^8$ is optionally substituted monocyclic alkylcycloalkyl. In another embodiment, $R^8$ is optionally substituted alkylheterocycloalkyl. In another embodiment, $R^8$ is optionally substituted monocyclic alkylheterocycloalkyl. In another embodiment, $R^8$ is optionally substituted alkylaryl. In another embodiment, $R^8$ is optionally substituted monocyclic alkylaryl. In another embodiment, $R^8$ is optionally substituted alkylheteroaryl. In another embodiment, $R^8$ is optionally substituted monocyclic alkylheteroaryl.

In one embodiment, $R^9$ is hydrogen. In another embodiment, $R^9$ is optionally substituted lower alkyl. In another embodiment, $R^9$ is optionally substituted heteroalkyl. In another embodiment, $R^9$ is optionally substituted cycloalkyl. In another embodiment, $R^9$ is optionally substituted monocyclic cycloalkyl. In another embodiment, $R^9$ is optionally substituted heterocycloalkyl. In another embodiment, $R^9$ is optionally substituted monocyclic heterocycloalkyl. In another embodiment, $R^9$ is optionally substituted alkylcycloalkyl. In another embodiment, $R^9$ is optionally substituted monocyclic alkylcycloalkyl. In another embodiment, $R^9$ is optionally substituted alkylheterocycloalkyl. In another embodiment, $R^9$ is optionally substituted monocyclic alkylheterocycloalkyl. In another embodiment, $R^9$ is optionally substituted alkylaryl. In another embodiment, $R^9$ is optionally substituted monocyclic alkylaryl. In another embodiment, $R^9$ is optionally substituted alkylheteroaryl. In another embodiment, $R^9$ is optionally substituted monocyclic alkylheteroaryl.

In one embodiment, $R^{10}$ is hydrogen. In another embodiment, $R^{10}$ is lower alkyl.

In one embodiment, $R^{11}$ is hydrogen. In another embodiment, $R^{11}$ is lower alkyl.

In one embodiment, G is C. In another embodiment, G is N.

In one embodiment, Q is N. In another embodiment, Q is CH.

In one embodiment, X is C. In another embodiment, X is N.

In one embodiment $L^{1f}$ is $—C\equiv C—$, $—HC=CH—$, $—CH_2—CH_2—$, $—CO—CH_2—$, $—CH_2—CO—$, $—NR^{12f}—CO—$, $—CO—NR^{12f}—$,

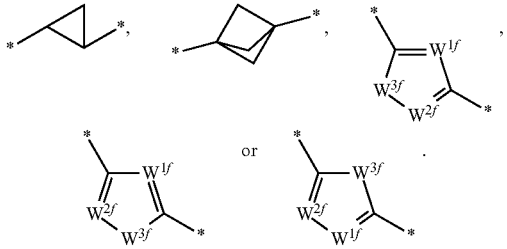

In one embodiment, $L^{1f}$ is $—C\equiv C—$. In another embodiment, $L^{1f}$ is $—HC=CH—$. In another embodiment, $L^{1f}$ is $—CH_2—CH_2—$. In another embodiment, $L^{1f}$ is $—CO—CH_2—$. In another embodiment, $L^{1f}$ is $—CH_2—CO—$. In another embodiment, $L^{1f}$ is $—NR^{12f}—CO—$. In another embodiment, $L^{1f}$ is $—CO—NR^{12f}—$. In another embodiment, $L^{1f}$ is $—C_{0-6}$alkyl-O—$C_{0-6}$ alkyl-. In another embodiment, $L^{1f}$ is $—NHR^{12f}SO—$. In another embodiment, $L^{1f}$ is $—SONR^{12f}—$. In another embodiment, $L^{1f}$ is $—NR^{12f}SO_2—$. In another embodiment, $L^{1f}$ is $—SO_2NR^{12f}—$. $R^{12f}$ is defined herein elsewhere.

In another embodiment, $L^{1f}$ is:

In another embodiment, $L^{1f}$ is:

In another embodiment, $L^{1f}$ is:

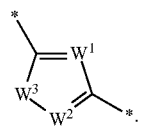

In another embodiment, $L^{1f}$ is: In another embodiment, $L^{1f}$ is:

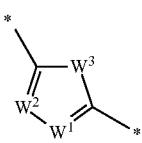

In one embodiment, $R^{12f}$ is hydrogen In another embodiment, $R^{12f}$ is lower alkyl.

In one embodiment, $W^{1f}$ is N. In another embodiment, $W^{1f}$ is CH.

In one embodiment, $W^{2f}$ is N. In another embodiment, $W^{2f}$ is CH.

In one embodiment, $W^{3f}$ is O. In another embodiment, $W^{3f}$ is S. In another embodiment, $W^{3f}$ is $NR^{4f}$. $R^{4f}$ is defined herein elsewhere.

In one embodiment, $R^{4f}$ is hydrogen. In another embodiment, $R^{4f}$ is lower alkyl.

Any of the combinations of $R^{1f}$, $J^1$, $J^2$, $J^3$, $J^4$, $J^5$, $J^6$, $R^7$, $R^8$, $R^9$, $R^{10}$, $R^{11}$, $G^4$, $Q^4$, $X^4$, $L^{1f}$, $R^{12f}$, $W^{1f}$, $W^{2f}$, $W^{3f}$, and $R^{4f}$ are encompassed by this disclosure and specifically provided by the invention.

In an exemplary embodiment according to the description above, $J^1$, $J^2$, $J^3$, $J^4$, $J^5$ and $J^6$ are $CH_2$, m is 1, n is 1, and p is 0. In another exemplary embodiment according to the description above, $J^1$, $J^2$, $J^3$, $J^4$, $J^5$ and $J^6$ are $CH_2$, m is 1, n is 1, and p is 1.

In an exemplary embodiment according to the description above, $J^2$, $J^3$, $J^4$, $J^5$ and $J^6$ are $CH_2$, m is 1, n is 1, p is selected from 0 and 1, and $J^1$ is selected from $CHR^8$, and $C=CR^{10}R^{11}$.

In an exemplary embodiment according to the description above, $J^1$, $J^3$, $J^4$, $J^5$ and $J^6$ are $CH_2$, m is 1, n is 1, p is selected from 0 and 1, and $J^2$ is $CHR^8$.

In an exemplary embodiment according to the description above, $J^1$, $J^2$, $J^4$, $J^5$ and $J^6$ are $CH_2$, m is 1, n is 1, p is selected from 0 and 1, and $J^3$ is selected from $NR^7$, O, and $CHR^8$.

In an exemplary embodiment according to the description above, $J^1$, $J^2$, $J^3$, $J^4$ and $J^6$ are $CH_2$, m is 1, n is 1, p is selected from 0 and 1, and $J^5$ is selected from $NR^7$, O, and $CHR^8$.

In some embodiments, compounds of formula IVa are provided:

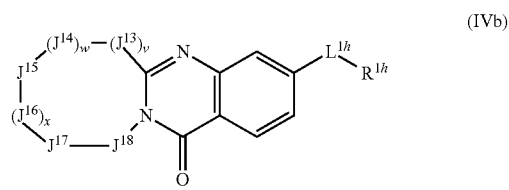

(IVa)

wherein
$R^{1g}$ is aryl or heteroaryl;
$L^{1g}$ is —C≡C—, is CONH— or

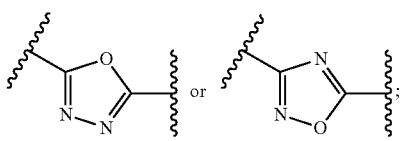

$J^7$, $J^8$, $J^9$, $J^{10}$, $J^{11}$ and $J^{12}$ are each independently CO, O, S, $NR^{20}$, $CR^{21}R^{22}$ or $C=CR^{23}R^{24}$, provided that there are no adjacent heteroatoms in the resulting ring;

s, t, and u are each independently 0 or 1;

$R^{20}$ is hydrogen, cycloalkyl, heteroalkyl, acyl, heterocyclic, C(O)Oalkyl, C(O)H, C(O)NHalkyl or lower alkyl;

$R^{21}$ and $R^{22}$ are each hydrogen, lower alkyl, heteroalkyl, cycloalkyl, heterocycloalkyl, alkylcycloalkyl, alkylheterocycloalkyl, alkylaryl or alkylheteroaryl, each of which is optionally substituted; or $R^{20}$ and $R^{21}$ together with the carbon atom to which they are attached are linked to form a 5-6 membered heterocyclic or cycloalkyl ring; and $R^{23}$ and $R^{24}$ are each independently hydrogen or lower alkyl, and pharmaceutically acceptable salts thereof.

In some embodiments, provided are compounds of formula IVb:

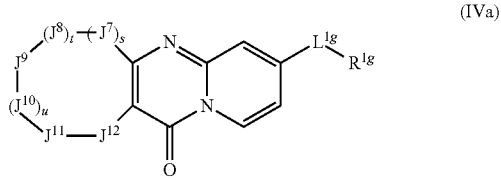

(IVb)

wherein
$R^{1h}$ is aryl, heteroaryl or heterocyclic;
$L^{1h}$ is —C≡C—, —HC=CH—, —$CH_2CH_2$—, —C(O)NH—, —NHC(O)—, CH(OH)$CH_2$—, C(O)$CH_2$,

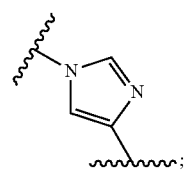 [SMILES: *c1cn(*)cn1]

$J^{13}$, $J^{14}$, $J^{15}$, $J^{16}$, $J^{17}$ and $J^{18}$ are each independently CO, O, S, $NR^{25}$, $CR^{26}R^{27}$ or $C=CR^{28}R^{29}$, provided that there are no adjacent heteroatoms in the resulting ring;

v, w, and x are each independently 0 or 1;

$R^{25}$ is hydrogen, cycloalkyl, heteroalkyl, acyl, heterocyclic, C(O)Oalkyl, C(O)H, C(O)NHalkyl or lower alkyl;

$R^{26}$ and $R^{27}$ are each hydrogen, lower alkyl, heteroalkyl, cycloalkyl, heterocycloalkyl, alkylcycloalkyl, alkylheterocycloalkyl, alkylaryl or alkylheteroaryl, each of which is optionally substituted; or $R^{26}$ and $R^{27}$ together with the carbon atom to which they are attached are linked to form a 5-6 membered heterocyclic or cycloalkyl ring; and $R^{28}$ and $R^{29}$ are each independently hydrogen or lower alkyl, or a pharmaceutically acceptable salt thereof.

In some embodiments, compounds of the invention include the compounds set forth in the examples.

Methods of Treatment, Prevention, and/or Management Binding to mGluR5 Receptor

In various embodiments, a method of binding a compound as disclosed herein to a metabotropic glutamate receptor, such as mGluR5 is provided. The method comprises contacting mGluR with an amount of compound as disclosed herein effective to bind a metabotropic glutamate receptor.

In one embodiment, a method of modulating the activity of mGluR5 via the binding of an mGluR5 ligand to mGluR5 is provided. The method comprises contacting mGluR5 with an amount of a compound as disclosed herein effective to modulate the activity of mGluR5. In one embodiment, the ligand is L-glutamate. In another embodiment, the ligand is a drug molecule or another small molecule known to have binding affinity to mGluR5. In another embodiment, the mGluR5 ligand is a radioactively labeled compound, known to bind to mGluR5. In other embodiments, binding to metabotropic glutamate receptor may be assessed using PET imaging as is known in the art, e.g. utilizing appropriate PET ligands. In some embodiments, the ligand is an allosteric modulator (e.g., a positive or negative allosteric modulator), antagonist, or inverse agonist of mGluR5.

Modulation of mGluR5 Receptor Activity

In various embodiments, a method of modulating (e.g., inhibiting or augmenting) the activity of a metabotropic glutamate receptor, such as mGluR5 is provided. The method comprises contacting the receptor, such as mGluR5, with an amount of a compound as disclosed herein, or a pharmaceutically acceptable salt thereof effective to modulate the activity of a metabotropic glutamate receptor, in vitro or in vivo. In one embodiment, mGluR5 is contacted with a compound as disclosed herein by administering to a subject a therapeutically effective amount of a compound as disclosed herein, or a pharmaceutically acceptable salt or solvate thereof. The subject may be a human.

In one embodiment, a compound as disclosed herein increases or augments the activity of metabotropic glutamate receptor, such as mGluR5. In some embodiments, the activity of mGluR5 is increased or augmented by about 1%, about 5%, about 10%, about 20%, about 30%, about 40%, about 50%, about 60%, about 70%, about 80%, about 90%, about 95%, about 99% or more, as compared with the activity obtained in the absence of a compound as disclosed herein. In one embodiment, the increase or augmentation of receptor activity is dose-dependent. Increase of mGluR5 activity may be measured using assays known in the art, for example, by in vitro functional assays as described herein elsewhere. In one embodiment, the functional assay utilizes an appropriate cell-line expressing the desired metabotropic glutamate receptor, such as mGluR5. In other embodiments, the functional assay utilizes synaptosomes isolated from brain tissue of an appropriate organism. In other embodiments, inhibition of metabotropic glutamate receptor activity may be assessed using receptor binding experiments known in the art, e.g., utilizing appropriate membrane preparations. In one embodiment, the assay involves treatment of a test subject (e.g., a mice or a rat) with a compound as disclosed herein as well as a reference compound, followed by isolation of brain tissue and ex vivo analysis of receptor occupancy. In one embodiment, the mGluR5 modulator is a positive allosteric modulator.

In certain embodiments, methods of increasing or augmenting the activity of a metabotropic glutamate receptor, such as mGluR5, in a subject (e.g., human) comprising administering to the subject an effective amount of compound as disclosed herein are provided. In some embodiments, the activity of mGluR5 is increased or augmented by about 1%, about 5%, about 10%, about 20%, about 30%, about 40%, about 50%, about 60%, about 70%, about 80%, about 90%, about 95%, about 99% or more, when measured using an assay known in the art compared to the activity obtained in the absence of administration of a compound as disclosed herein.

In one embodiment, a method of increasing or augmenting the activity of a metabotropic glutamate receptor, such as mGluR5, by a metabotropic glutamate receptor ligand is provided. In one embodiment, the method comprises contacting mGluR5 receptor with a potentiator, an allosteric agonist, or a positive allosteric modulator of the mGluR5 receptor in an amount effective to increase or augment the activity. In another embodiment, a potentiator, an allosteric agonist, or a positive allosteric modulator of the mGluR5 receptor is a compound as disclosed herein.

In one embodiment, a compound as disclosed herein inhibits or reduces the activity of metabotropic glutamate receptor, such as mGluR5. In some embodiments, the activity of mGluR5 is inhibited or reduced by about 1%, about 5%, about 10%, about 20%, about 30%, about 40%, about 50%, about 60%, about 70%, about 80%, about 90%, about 95%, about 99% or more, as compared with the activity obtained without contacting with the compounds as disclosed herein. In one embodiment, the inhibition or reduction of receptor activity is dose-dependent Inhibition of mGluR5 activity may be measured using assays known in the art, for example, the in vitro functional assays as described herein elsewhere. In one embodiment, the functional assay utilizes an appropriate cell-line expressing the desired metabotropic glutamate receptor, such as mGluR5. In other embodiments, the functional assay utilizes synaptosomes isolated from brain tissue of an appropriate organism. In other embodiments, inhibition of metabotropic glutamate receptor activity may be assessed using receptor binding experiments known in the art, e.g. utilizing appropriate membrane preparations. In one embodiment, the assay involves treatment of a test subject (e.g., a mice or a rat) with a compound set forth herein as well as a reference compound, followed by isolation of brain tissue and ex vivo analysis of receptor occupancy. In one embodiment, the mGluR5 modulator is a negative allosteric modulator.

In certain embodiments, methods of inhibiting or reducing the activity of a metabotropic glutamate receptor, such as mGluR5, in a subject (e.g., human) comprising administering to the subject an effective amount of a compound as disclosed herein are provided. In some embodiments, the activity of mGluR5 is inhibited or reduced by about 1%, about 5%, about 10%, about 20%, about 30%, about 40%, about 50%, about 60%, about 70%, about 80%, about 90%, about 95%, about 99% or more, when measured using an assay known in the art and compared to the activity obtained in the absence of administration of a compound as disclosed herein.

In one embodiment, a method of inhibiting or reducing the activity of a metabotropic glutamate receptor, such as mGluR5, by a metabotropic glutamate receptor ligand is provided. In one embodiment, the method comprises contacting mGluR5 receptor with an amount of an antagonist, an inverse agonist, or an allosteric modulator of the mGluR5 receptor effective to inhibit or reduce the activity of the metabotropic glutamate receptor. In another embodiment, an antagonist, an inverse agonist, or an allosteric modulator of the mGluR5 receptor is a compound as disclosed herein.

Treatment, Prevention, and/or Management of mGluR5 Related Disorders and Conditions In certain embodiments, a method of treating, preventing, and/or managing a neurological disorder, such as a neurodegenerative disorder, neuropsychiatric disorder, affective disorder, or a cognitive function, tearing or memory disorder, comprising administering to a subject in need thereof an effective amount of a compound as disclosed herein is provided.

In certain embodiments, a method of treating psychosis, schizophrenia, or a cognitive disorder (such as Alzheimer's disease), comprising administering to a subject in need thereof an effective amount of a compound as disclosed herein is provided. In one embodiment, the compounds as disclosed herein inhibit the activity of mGluR5. In certain embodiments, the compounds as disclosed herein are positive allosteric modulators of mGluR5. In other embodiments, the compounds as disclosed herein are antagonists of mGluR5. In certain embodiments, the compounds as disclosed herein are selective for mGluR5 over other CNS-related targets. In one embodiment, the compounds as disclosed herein are highly brain penetrable in mammals, such as rodents, and human. In some embodiments, inhibition or potentiation of mGluR5 activity may be assessed by functional assays as described herein elsewhere. In certain embodiments, the efficacious concentration of the compounds set forth herein is less than 10 nM, less than 100 nM, less than 1 µM, less than 10 µM, less than 100 µM, or less than 1 mM. In other embodiments, compound's activity may be assessed in various art-recognized animal models.

In some embodiments, a method of treating, preventing, and/or managing a neurodegenerative disease [including but not limited to Alzheimer's disease (including the accompanying symptoms of mild, moderate, or severe cognitive impairment); amyotropic lateral sclerosis (ALS); anoxic and ischemic injuries; ataxia and convulsion (including for the treatment and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g. spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor), and dystonia (including axial dystonia, dystonic writer's cramp, hemiplegic dystonia, paroxymal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; and viral infection induced neurodegeneration (including but limited to neurodegeneration caused by caused by acquired immunodeficiency syndrome (AIDS) and encephalopathies)], comprising administering to a subject in need thereof an effective amount of a compound as disclosed herein is provided. For example, without being limited by a particular theory, mGluR5 modulators may be effective in treating Parkinson's disease, and efficacious in a variety of animal models for Parkinson's disease. See, e.g., Jaeschke, G., et al., *Expert Opin. Ther. Pat.* 2008, 18, 123; Glatthar R., et al., WO 2006/89700 A1.

In some embodiments, a method of treating, preventing, and/or managing a neuropsychiatric disorder (including but limited to: aggression; attention disorders including attention-deficit disorder (ADD), attention-deficit-hyperactivity disorder (ADHD) and conduct disorder; delirium; delusional disorder; persisting dementia; pervasive development disorder including autism, autistic disorder and autism spectrum disorder; psychosis and psychotic disorders (including psychosis associated with affective disorders, brief reactive psychosis, brief psychotic disorder, shared psychotic disorder, psychotic disorder due to a general medical condition and substance-induced or drug-induced psychotic disorder (e.g., caused by phencyclidine, ketamine and other dissociative anaesthetics, amphetamine, cocaine and other psychostimulants)); schizophrenia (including schizoaffective psychosis and "schizophrenia-spectrum" disorders such as schizoid or schizotypal personality disorders, or illnesses associated with psychosis (such as major depression, manic depressive (bipolar) disorder, Alzheimer's disease and post-traumatic stress syndrome) including both the positive and negative symptoms of schizophrenia and other psychoses); and sensory hyper-excitability), comprising administering to a subject in need thereof an effective amount of a compound as disclosed herein is provided.

In some embodiments, a method of treating, preventing and/or managing disorders of cognition, learning or memory or of improving cognitive function, memory and learning abilities (including but not limited to: adult and childhood learning disorders; altruism; amnestic disorders (including Alzheimer's disease-related cognitive decline, normal age-related cognitive decline and persisting amnestic disorder); associative learning; attention; benign forgetfulness; cognitive deficits induced by situational stress (including but not limited to operating machinery for extended time periods or working in emergency or combat situations); cognitive disorders including dementia (associated with acquired immunodeficiency disease, Alzheimer's disease, Creutzfeldt-Jacob disease, HIV infection, Huntington's disease, ischemia, multi-infarct dementia, Parkinson's disease, perinatal hypoxia, Pick's disease, trauma, vascular problems or stroke, other general medical conditions or substance abuse); cooperativity; declarative memory; early consolidation; empathy; episodic memory; executive function; explicit memory; implicit memory; imprinting; language; late consolidation; learning (including electronic, formal, informal, multimedia and rote learning); low IQ; memory deficit; memory loss; mild cognitive impairment (MCI); non-verbal and verbal communicative skills; play; rehearsal; retrieval, semantic memory; sensory integration of environmental cues including temperature, odor, sounds, touch, and taste; social cognition; and speech disorders), comprising administering to a subject in need thereof an effective amount of a compound as disclosed herein is provided.

In some embodiments, a method of treating, preventing, and/or managing gastrointestinal disorders (including but not limited to acid reflux; dyspepsia; gastroesophageal reflux disorder (GERD); and irritable bowel syndrome), comprising administering to a subject in need thereof an effective amount of a as disclosed herein is provided. For example, without being limited by a particular theory, mGluR5 modulators may be effective in treating gastrointestinal disorders in human. See, e.g., Jaeschke, G., et al., *Expert Opin. Ther. Pat.* 2008, 18, 123; Bolea C., et al., WO 2004/78728 A1.

In some embodiments, a method of treating, preventing, and/or managing all categories of pain (including but not limited to: pain described in terms of stimulus or nerve response; somatic pain (normal nerve response to a noxious stimulus); neuropathic pain (abnormal response of a injured or altered sensory pathway often without clear noxious input, and including chemotherapy-induced neuropathy, diabetic peripheral neuropathic pain, HIV/AIDS peripheral neuropathy, neuropathic cancer pain, and post-herpetic neuralgia); abdominal pain; acute thermal hyperalgesia; allodynia; burns; causalgia; central pain; complex regional pain syndrome (CRPS); dental pain; dual mechanism pain; dysesthesia; ear ache; episiotomy pain; eye pain; fibromyalgia; gynecological pain including dysmeorrhoea; headache (including acute and chronic tension headache and cluster headache); heart pain; hyperalgesia; hyperesthesia; hyperpathia; itching conditions including contact dermatitis, pruritis, and itch due to atopic dermatitis and hemodialysis; labor pain; low back pain; mechanical allodynia; mixed etiology pain; musculo-skeletal pain including that following physical trauma; neck pain; orofacial pain; pain associated with cystitis; pain cause by convulsion; pain resulting from dysfunction of the nervous system (i.e., organic pain states that share clinical features of neuropathic pain and possibly common pathophysiology mechanism, but are not initiated by an identifiable lesion in any part of the nervous system); pain that is a symptom or a result of a disease state or syndrome (such as AIDS pain, ankylosing spondylitis; arthritis pain, cancer pain, cardiac ischaemia, carpal tunnel syndrome, diabetic peripheral neuropathic pain, episcleritis, gout, inflammation, irritable bowel syndrome, migraine, neuropathy arising from chronic alcohol use, repetitive motion injury, pain from autoimmune diseases, pain from respiratory diseases, scar pain, sciatica; scleritis; and trigeminal neuralgia); pain that is categorized in terms of its severity (mild, moderate, or severe pain); pain that is categorized temporally (chronic pain and acute pain); phantom limb pain; post-surgical pain; reflex sympathetic dystrophy; sinus pain; and visceral pain) comprising administering to a subject in need thereof an effective amount of a compound as disclosed herein is provided. See e.g., Jaeschke, G., et al., *Expert Opin. Ther. Pat.* 2008, 18, 123; Cosford, N. D. P., et al., WO 2003/51315 A2.

In some embodiments, a method of treating, preventing, and/or managing migraine, comprising administering to a subject in need thereof an effective amount of a compound as disclosed herein is provided For example, without being limited by a particular theory, mGluR5 modulators may be effective in the treatment and prevention of migraine in human, and may have comparable efficacy to triptans in treating migraine. See, e.g., Jaeschke, G., et al., *Expert Opin. Ther. Pat.* 2008, 18, 123.

In some embodiments, a method of treating, preventing, and/or managing substance abuse disorder or eating disorder (including but not limited to the abuse of or addiction to canabbis, cocaine, morphine, opioid, nicotine, or alcohol; substance-abuse related disorders and addictive behaviors (including substance-induced delirium); tolerance, dependence or withdrawal from substances including alcohol, amphetamines, anxiolytics, cannabis, cocaine, hallucinogens, hypnotics, inhalants, nicotine, opioids, phencyclidine, or sedatives; anorexia nervosa; binge eating; bulimia nervosa; cachexia; compulsive eating disorder; emesis; and obesity) comprising administering to a subject in need thereof an effective amount of a compound as disclosed herein is provided. See e.g., Jaeschke, G., et al., *Expert Opin. Ther. Pat.* 2008, 18, 123.

In other embodiments, a method of treating, preventing, and/or managing a disorder of the genitourinary tract or a sexual disorder (including but limited to: lower urinary tract disorder; overactive bladder; urinary incontinence including without limitation involuntary voiding of urine, dribbling or leakage of urine, stress urinary incontinence (SUI), urge incontinence, urinary exertional incontinence, reflex incontinence, passive incontinence, and overflow incontinence; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psychosexual dysfunction, including without limitation, inhibited sexual desire, inhibited sexual excitement, inhibited female orgasm, inhibited male orgasm, functional dyspareunia, functional vaginismus, and atypical psychosexual dysfunction), comprising administering to a subject in need thereof an effective amount of a compound as disclosed herein is provided.

In other embodiments, a method of treating, preventing, and/or managing cancer, including but not limited to, oral cancer and glioneuronal cancer, comprising administering to a subject in need thereof an effective amount of a compound as disclosed herein is provided.

In some embodiments, a compound as disclosed herein is active in at least one model, which can be used to measure the activity of the compounds and estimate their efficacy in treating a disorder related to mGluR5. For example, when the model is for depression (e.g., mean immobility), the compounds are active when they inhibit mean immobility of a test subject by about 5%, about 10%, about 20%, about 30%, about 40%, about 50%, about 60%, about 70%, about 80%, about 90%, about 95%, about 99%, or more, when compared to vehicle. In some embodiments, the compound as disclosed herein produce a similar disparity in measured endpoint between treated animals and animals administered vehicle.

Other exemplary diseases and conditions that may be treated, prevented, and/or managed using the methods, compounds as disclosed herein and compositions thereof, include, but are not limited to: metabolic diseases including diabetes and pulmonary/respiratory diseases including asthma, chronic obstructive pulmonary disease (COPD), chronic bronchitis, cystic fibrosis, and emphysema.

In one embodiment, the compounds described herein treat, prevent, and/or manage a neurological disorder, without causing addiction to said compounds. Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound set forth herein will be that amount of the compound which is the lowest dose effective to produce a therapeutic or prophylactic effect. Such an effective dose will generally depend upon the factors described above. Generally, oral, intravenous, intracerebroventricular, and subcutaneous doses of the compounds set forth herein for a patient will range from about 0.005 mg per kilogram to about 5 mg per kilogram of body weight per day. In one embodiment, the oral dose of a compound set forth herein will range from about 10 mg to about 300 mg per day. In another embodiment, the oral dose of a compound set forth herein will range from about 20 mg to about 250 mg per day. In another embodiment, the oral dose of a compound set forth herein will range from about 100 mg to about 300 mg per day. In another embodiment, the oral dose of a compound set forth herein will range from about 10 mg to about 100 mg per day. In another embodiment, the oral dose of a compound set forth herein will range from about 25 mg to about 50 mg per day. In another embodiment, the oral dose of a compound set forth herein will range from about 50 mg to about 200 mg per day. Each of the above-recited dosage ranges may be formulated as a single or multiple unit dosage formulations.

In some embodiments, the compounds disclosed herein may be used in combination with one or more second active agents to treat, prevent, and/or manage disorders described herein.

Pharmaceutical Compositions and Dosage Forms

Pharmaceutical compositions can be used in the preparation of individual, single unit dosage forms. Pharmaceutical compositions and dosage forms provided herein comprise a compound set forth herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences,* 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound set forth herein in an amount of from about 0.10 to about 500 mg. In other embodiments, dosage forms comprise a compound set forth herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound set forth herein, and any optional additional active agents concurrently administered to the patient.

Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's *The Science and Practice of Pharmacy*, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound set forth herein, and optional excipients, such as anhydrous lactose, microcrystalline cellulose, polyvinylpyrrolidone, stearic acid, colloidal anhydrous silica, and gelatin.

Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound set forth herein. See, e.g., U.S. Pat. No. 5,134,127, which is incorporated herein by reference.

Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound set forth herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

I. EXAMPLES

Certain embodiments are illustrated by the following non-limiting examples.

A. Synthesis of Compounds

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Aldrich in Sure-Seal bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates (Merck Art 5719) and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (See, e.g., Still et al., J. Org. Chem., 43: 2923 (1978)) was performed using silica gel 60 (Merck Art 9385) or various MPLC systems.

The compound structures in the examples below were confirmed by one or more of the following methods: proton magnetic resonance spectroscopy, mass spectroscopy, and melting point. Proton magnetic resonance ($^1$H NMR) spectra were determined using an NMR spectrometer operating at 400 MHz field strength. Chemical shifts are reported in the form of delta (δ) values given in parts per million (ppm) relative to an internal standard, such as tetramethylsilane (TMS). Alternatively, $^1$H NMR spectra were referenced to signals from residual protons in deuterated solvents as follows: $CDCl_3$=7.25 ppm; DMSO-$d^6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

As used herein, and unless otherwise specified, "4 Å MS" means 4 angstrom molecular sieves, "Ac" means acetyl, "aq" means aqueous, "BINAP" means 2,2'-bis(diphenylphosphino)-1,1'-binaphthyl, "cat." means catalytic, "DCE" means 1,2-dichloroethane, "DAST" means (diethylamino)sulfur trifluoride ($Et_2NSF_3$), "DCM" means dichloromethane, "Dess-Martin reagent" means 1,1,1-tris(acetyloxy)-1,1-dihydro-1,2-benziodoxol-3-(1H)-one (also called DMP), "DIEA" means diisopropylethylamine, "DMAP" means 4-dimethylaminopyridine, "DME" means 1,2-dimethoxyethane, "DMF" means dimethylformamide, "DMF-DMA" means N,N-dimethylformamide dimethylacetal, "DMSO" means dimethyl sulfoxide, "EDCI" means N-(3-dimethylaminopropyl)-N'-ethylcarbodiimide hydrochloride, "equiv" and "eq" mean equivalent(s), "Et" means ethyl, "EtOAc" means ethyl acetate, "EtOH" means ethanol, "Fmoc" means 9-fluorenylmethoxycarbonyl, "h" or "hr" means hour(s), "HOBt" means hydroxybenzotriazole, "LDA" means lithium diisopropylamide, "m-CPBA" means 3-chloro-perbenzoic acid, "Me" means methyl, "MeCN" means acetonitrile, "MeOH" means methanol, "Ms" means mesyl ($CH_3SO_2$—), "min" means minute(s), "NMP" means N-methylpyrrolidone, "PE" means petroleum ether, "PPA" means polyphosphoric acid, "RT" or "rt" means room temperature, "Selectfluor" means 1-(chloromethyl)-4-fluoro-1,4-diazoniabicyclo[2.2.0]octane ditetrafluoroborate, "TBDMSCl" means tert-butyldimethylsilyl chloride, "t-BuOH" means tert-butanol, "t-BuONa" means sodium tert-butoxide, "TBTU" means 2-(1H-benzotriazole-1-yl)-1,1,3,3-tetramethyluronium tetrafluoroborate, "TEA" means triethylamine, "Tebbe Reagent" means μ-chloro[di(cyclopenta-2,4-dien-1-yl)]dimethyl(μ-methylene)titaniumaluminum, "TFA" means trifluoroacetic acid, "THF" means tetrahydrofuran, "TMSI" means iodotrimethylsilane, "o-Tol" means o-tolyl (2-$CH_3C_6H_4$), "m-Tol" means p-tolyl (4-$CH_3C_6H_4$), "Ts" means tosyl (p-$CH_3C_6H_4SO_2$), and "Xantphos" means 4,5-bis(diphenylphosphino)-9,9-dimethylxanthene. For those compounds containing basic nitrogen center(s), its HCl salt was prepared by treating the freebase with excess HCl etherate solution.

mGluR5 PAM $EC_{50}$ values: +++++<10 nM; ++++ is between 10 and 30 nM; +++ is between 30 and 100 nM; ++ is between 100 and 300 nM; + is between 300 and 1,000 nM. Fold shift at 10 μM: +++>3; ++ is between 2.0 and 2.9; + is between 1.5 and 1.9.

Example 1.1. Synthesis of 7-((4-fluorophenyl)ethynyl)quinazolin-4(3H)-one

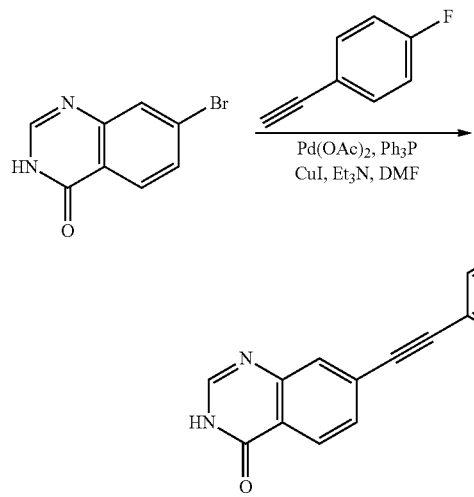

A flask was charged with 7-bromoquinazolin-4(3H)-one (60 mg, 0.27 mmol, 1 equiv), 1-ethynyl-4-fluorobenzene (81 mg, 0.675 mmol, 2.5 equiv), Pd(OAc)$_2$ (12.2 mg, 0.054 mmol, 0.2 equiv), PPh$_3$ (63.7 mg, 0.24 mmol, 0.9 equiv), CuI (10.3 mg, 0.054 mmol, 0.2 equiv), Et$_3$N (0.3 mL) and DMF (6 mL). A vacuum was applied and the reaction mixture was back filled with nitrogen three times. The mixture was stirred at 70° C. for 3.5 hours. After it was cooled to room temperature, the reaction mixture was diluted with H$_2$O and extracted with ethyl acetate (3×50 mL). The combined organic layers were washed with brine and dried over anhydrous sodium sulfate, then concentrated under reduced pressure and purified by column chromatography to give the desired product. MS (ESI): 265 (MH$^+$); $^1$H NMR (300 MHz, DMSO-d$^6$) δ 12.38-12.33 (m, 1H), 8.13 (s, 2H), 7.81 (s, 1H), 7.69-7.54 (m, 3H), 7.39-7.29 (m, 2H).

Example 1.2. Synthesis of 7-((3-fluorophenyl)ethynyl)quinazolin-4(3H)-one

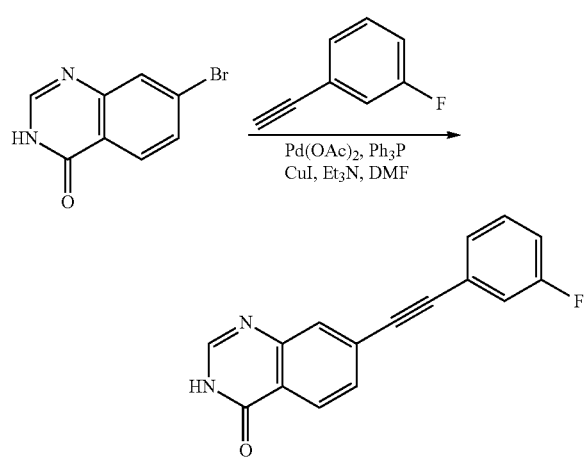

The title compound was prepared from 7-bromoquinazolin-4(3H)-one and 1-ethynyl-3-fluorobenzene according to the experimental procedure as described in Example 1.1. MS (ESI): 265 (MH$^+$); $^1$H NMR (300 MHz, DMSO-d$^6$) δ 12.37 (s, 1H), 8.14 (s, 2H), 7.83 (s, 1H), 7.68-7.64 (m, 1H), 7.53-7.49 (m, 3H), 7.36-7.33 (m, 1H). mGluR5 PAM EC$_{50}$: +.

Example 1.3. Synthesis of 3-methyl-7-(phenylethynyl)quinazolin-4(3H)-one

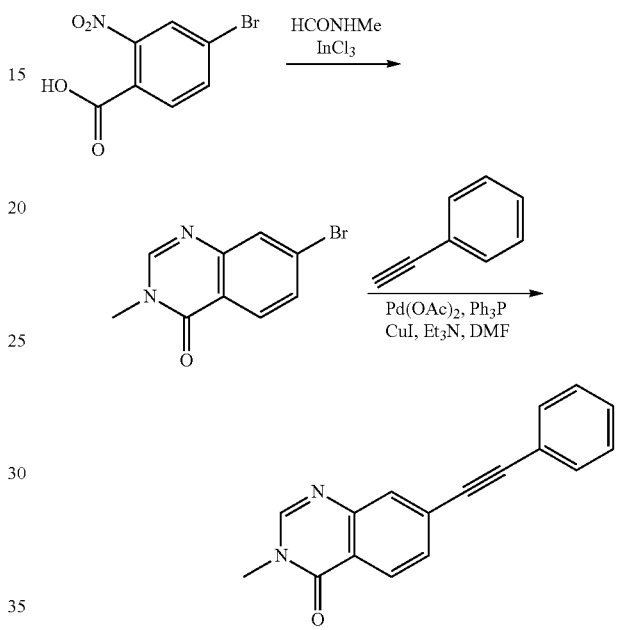

Example 1.3a. Synthesis of 7-bromo-3-methylquinazolin-4(3H)-one

A solution of 4-bromo-2-nitrobenzoic acid (1 g, 4.1 mmol) and InCl$_3$ (0.88 g, 4 mmol) in N-methylformamide (6 mL, 100 mmol) was stirred at reflux overnight (ca. 18 h). After it was cooled to room temperature, the mixture was diluted with H$_2$O (30 mL) and extracted with ethyl acetate (3×30 mL). The combined organic layers were washed with brine, and dried over Na$_2$SO$_4$. After filtration and concentration, the crude product was purified by column chromatography to give the desired product (0.5 g). MS (ESI): 239 (MH$^+$).

Example 1.3b. Synthesis of 3-methyl-7-(phenylethynyl)quinazolin-4(3H)-one

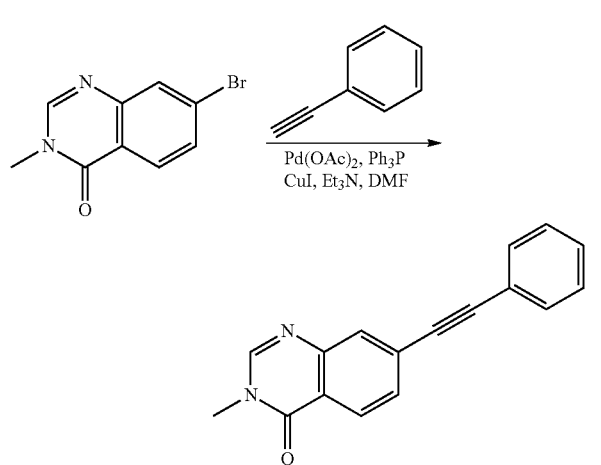

The title compound was prepared according to the experimental procedure as described in Example 1.1. MS (ESI): 261 (MH⁺); ¹H NMR (300 MHz, CDCl₃) δ 8.31-8.29 (d, J=8.25 Hz, 1H), 8.08 (s, 1H), 7.87 (s, 1H), 7.65-7.58 (m, 3H), 7.41-7.39 (m, 3H), 3.61 (s, 3H). mGluR5 PAM EC$_{50}$: ++.

Example 1.4. Synthesis of 7-((4-ethylphenyl)ethynyl)-3-methylquinazolin-4(3H)-one

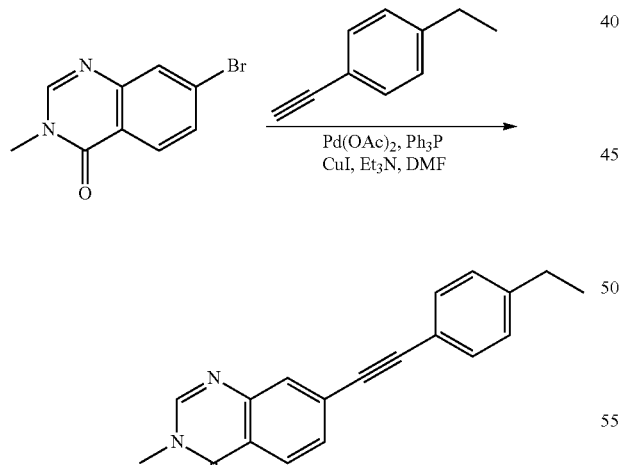

The title compound was prepared according to the experimental procedure as described in Example 1.1. MS (ESI): 289 (MH⁺); ¹H NMR (300 MHz, DMSO-d⁶) δ 8.41 (s, 1H), 8.17-8.14 (d, J=8.22 Hz, 1H), 7.80-7.79 (d, J=1.05 Hz, 1H), 7.66-7.23 (dd, J=8.25, 1.44 Hz, 1H), 7.56-7.53 (d, J=8.01 Hz, 2H), 7.32-7.29 (d, J=8.10 Hz, 2H), 3.50 (s, 3H), 2.69-2.62 (m, 2H), 1.22-1.17 (t, J=7.56 Hz, 3H).

Example 1.5. Synthesis of 3-methyl-7-(thiazol-2-ylethenyl)quinazolin-4(3H)-one

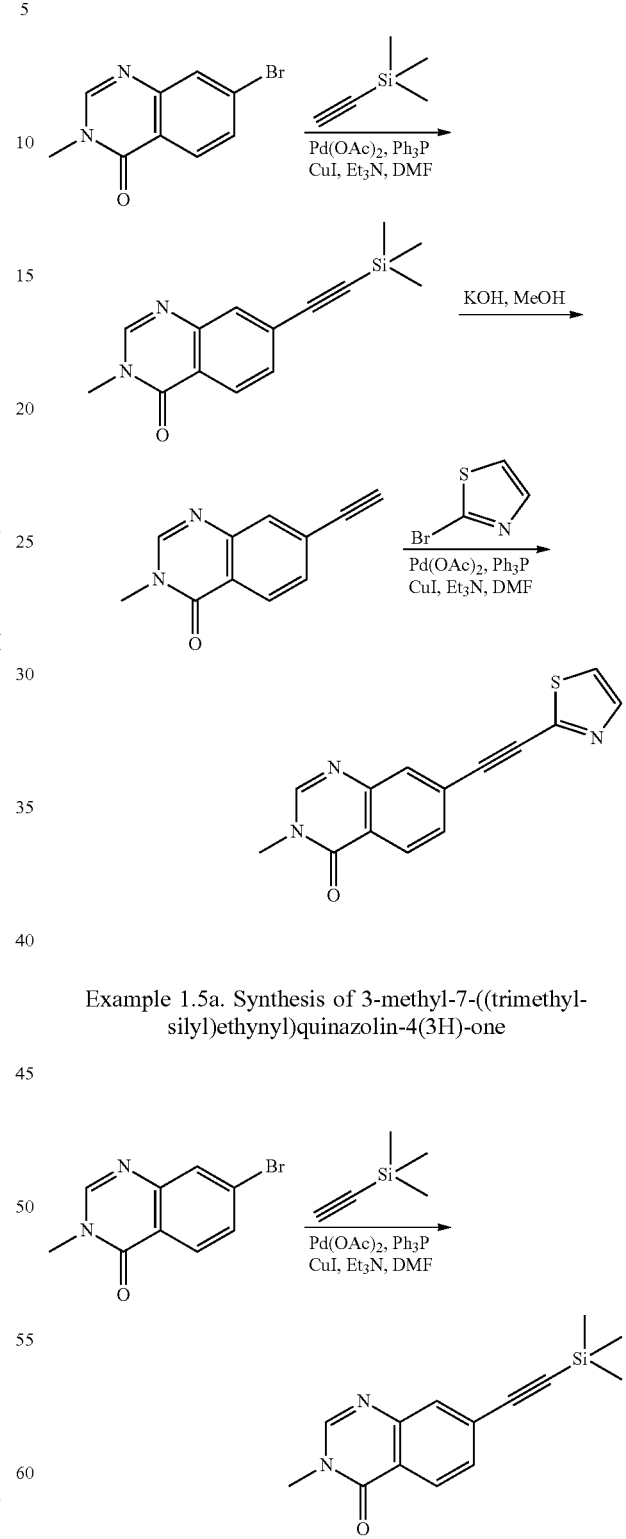

Example 1.5a. Synthesis of 3-methyl-7-((trimethylsilyl)ethynyl)quinazolin-4(3H)-one The title compound was prepared according to the experimental procedure as described in Example 5.1d. MS (ESI): 257 (MH⁺).

Example 1.5b. Synthesis of 7-ethynyl-3-methylquinazolin-4(3H)-one

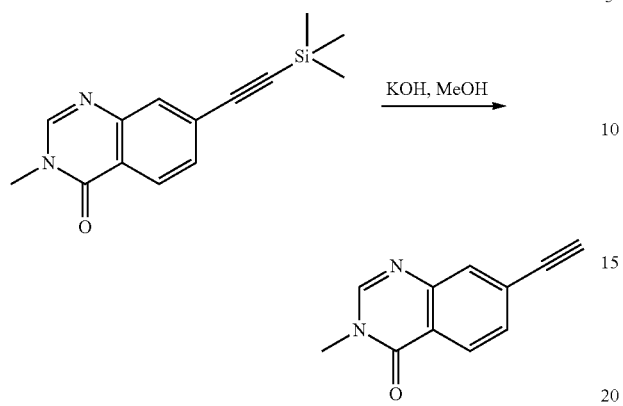

The title compound was prepared according to the experimental procedure as described in Example 5.1e. MS (ESI): 185 (MH+).

Example 1.5c. Synthesis of 3-methyl-7-(thiazol-2-ylethynyl)quinazolin-4(3H)-one

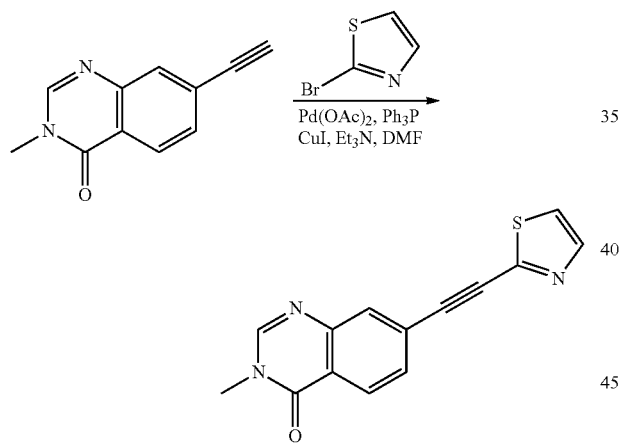

The title compound was prepared according to the experimental procedure as described in Example 1.1. MS (ESI): 268 (MH+); $^1$H NMR (300 MHz, CD$_3$OD) δ 8.37 (s, 1H), 8.32-8.30 (d, J=8.40 Hz, 1H), 7.98-7.93 (m, 2H), 7.81-7.80 (d, J=3.30 Hz, 1H), 7.77-7.74 (d, J=8.25 Hz, 1H), 3.62 (m, 3H). mGluR5 PAM EC$_{50}$: +.

Example 1.6. Synthesis of 7-((4-fluorophenyl)ethynyl)-3-propylquinazolin-4(3H)-one

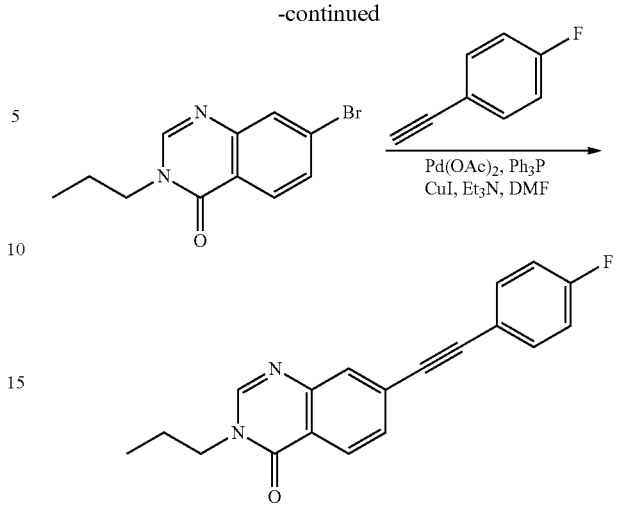

Example 1.6a. Synthesis of 7-bromo-3-propylquinazolin-4(3H)-one

To a mixture of 7-bromoquinazolin-4(3H)-one (0.2 g, 0.89 mmol) and DMF (20 mL) was added sodium hydride (85 mg, 3.5 mmol) in portions. The reaction mixture was stirred at room temperature for 15 min 1-iodopropane (0.18 g, 1.1 mmol) was added dropwise. After stirring for 30 min., the reaction mixture was quenched with water (20 mL) and extracted with ethyl acetate (3×50 mL). The combined organic layers were dried over Na$_2$SO$_4$. After filtration and concentration, the residue was purified by silica gel chromatography to give the desired product. MS (ESI): 267, 269 (MH+).

Example 1.6b. Synthesis of 7((4-fluorophenyl)ethynyl)-3-propylquinazolin-4(3H)-one

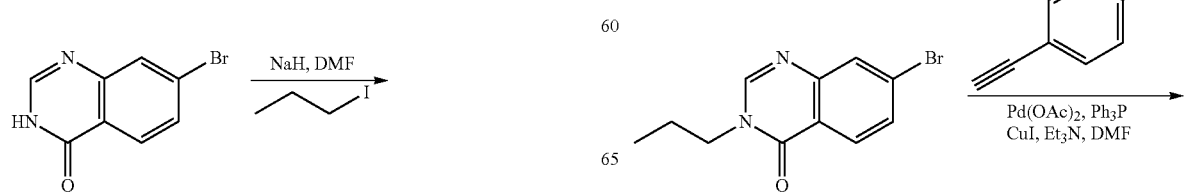

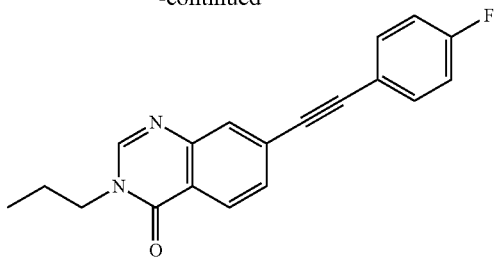

The title compound was prepared according to the experimental procedure as described in Example 1.1. MS (ESI): 307 (M+H⁺); ¹H NMR (300 MHz, CDCl₃) δ 8.31-8.28 (d, J=8.22 Hz, 1H), 8.05 (s, 1H), 7.85-7.84 (d, J=1.14 Hz, 1H), 7.62-7.55 (m, 3H), 7.12-7.07 (t, J=8.72 Hz, 2H), 4.00-3.96 (t, J=7.23 Hz, 2H), 1.89-1.82 (m, 2H), 1.05-1.00 (t, J=7.43 Hz, 3H). mGluR5 PAM EC₅₀: ++. Fold shift at 10 μM: ++.

Example 1.7. Synthesis of 7-((3-fluorophenyl)ethynyl)-3-propylquinazolin-4(3H)-one

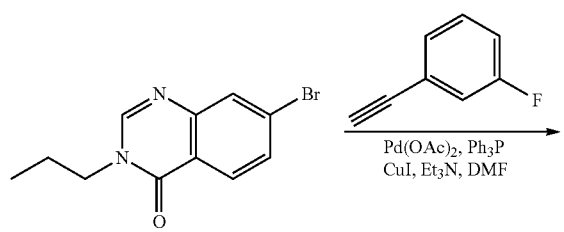

The title compound was prepared according to the experimental procedure as described in Example 1.6a and Example 1.1. MS (ESI): 307 (MH⁺); ¹H NMR (300 MHz, CDCl₃) δ 8.31-8.29 (d, J=8.25 Hz, 1H), 8.05 (s, 1H), 7.88 (s, 1H), 7.64-7.60 (d, J=8.27 Hz, 1H), 7.38-7.30 (m, 3H), 7.14-7.07 (m, 1H), 4.01-3.96 (t, J=7.20 Hz, 2H), 1.92-1.80 (m, 2H), 1.05-1.00 (t, J=7.41 Hz, 3H). mGluR5 PAM EC₅₀: ++++. Fold shift at 10 μM: +++.

Example 1.8. Synthesis of 3-(cyclopropylmethyl)-7-((3-fluorophenyl) ethynyl) quinazolin-4(3H)-one

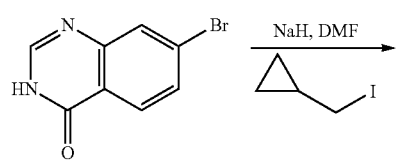

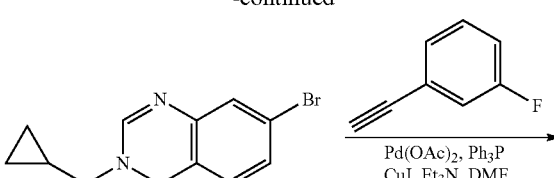

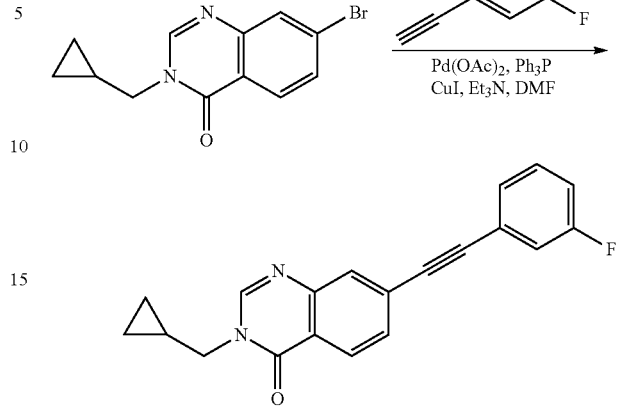

The title compound was prepared according to the experimental procedure described in Example 1.6a and Example 1.1. MS (ESI): 319 (MH⁺); ¹H NMR (300 MHz, CDCl₃) δ 8.32-8.29 (d, J=8.31 Hz, 1H), 8.14 (s, 1H), 7.87 (s, 1H), 7.64-7.61 (d, J=8.22 Hz, 1H), 7.38-7.30 (m, 3H), 7.14-7.08 (m, 1H), 3.90-3.88 (d, J=7.17 Hz, 2H), 1.34-1.27 (m, 1H), 0.73-0.64 (m, 2H), 0.48-0.44 (m, 2H). mGluR5 PAM EC₅₀: +++. Fold shift at 10 μM: ++.

Example 1.9. Synthesis of 3-(cyclopropylmethyl)-7-((4-fluorophenyl) ethynyl)quinazolin-4(3H)-one

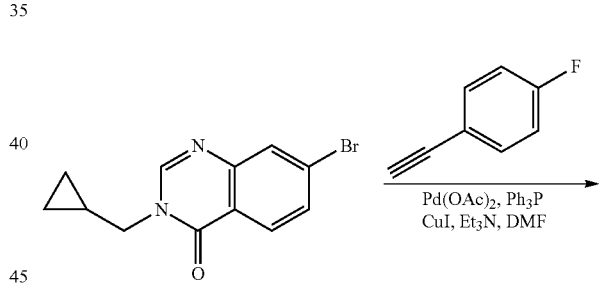

The title compound was prepared according to the experimental procedure described in Example 1.6a and Example 1.1. MS (ESI): 319 (MH⁺); ¹H NMR (300 MHz, CDCl₃) δ 8.31-8.28 (d, J=8.75 Hz, 1H), 8.14 (s, 1H), 7.85 (s, 1H), 7.63-7.56 (m, 3H), 7.13-7.07 (t, J=8.67 Hz, 2H), 3.90-3.88 (d, J=7.17 Hz, 2H), 1.36-1.27 (m, 1H), 0.70-0.64 (m, 2H), 0.48-0.44 (m, 2H). mGluR5 PAM EC₅₀: ++. Fold shift at 10 μM: +++.

Example 1.10. Synthesis of 3-cyclopentyl-7-((4-fluorophenyl)ethynyl)quinazolin-4(3H)-one

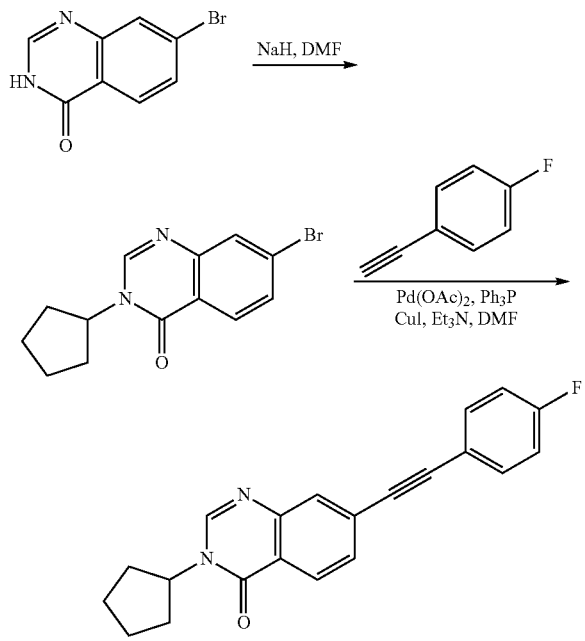

The title compound was prepared according to the experimental procedure described in Example 1.6a and Example 1.1. MS (ESI): 333 (MH⁺); ¹H NMR (300 MHz, CDCl₃) δ 8.30-8.27 (d, J=8.28 Hz, 1H), 8.14 (s, 1H), 7.84 (s, 1H), 7.62-7.56 (m, 3H), 7.13-7.17 (m, 2H), 5.22-5.17 (m, 1H), 2.27-2.22 (m, 2H), 1.96-1.78 (m, 6H). mGluR5 PAM EC$_{50}$: +++. Fold shift at 10 μM: ++.

Example 1.11. Synthesis of 3-cyclopentyl-7-((3-fluorophenyl)ethynyl)quinazolin-4(3H)-one

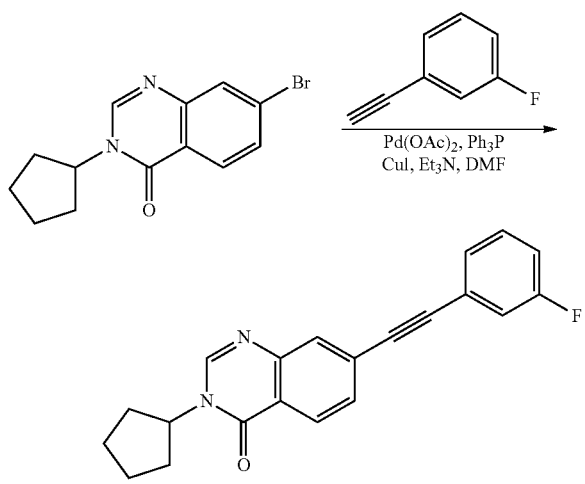

The title compound was prepared according to the experimental procedure described in Example 1.6a and Example 1.1. MS (ESI): 333 (MH⁺); ¹H NMR (300 MHz, CDCl₃) δ 8.31-8.28 (d, J=8.31 Hz, 1H), 8.15 (s, 1H), 7.85 (s, 1H), 7.63-7.60 (d, J=8.28 Hz, 1H), 7.38-7.30 (m, 3H), 7.14-7.07 (m, 1H), 5.22-5.15 (m, 1H), 2.31-2.23 (m, 2H), 1.96-1.76 (m, 6H). mGluR5 PAM EC$_{50}$: ++++. Fold shift at 10 μM: +.

Example 1.12. Synthesis of 7-((4-fluorophenyl)ethynyl)-3-(2-methoxyethyl)quinazolin-4(3H)-one

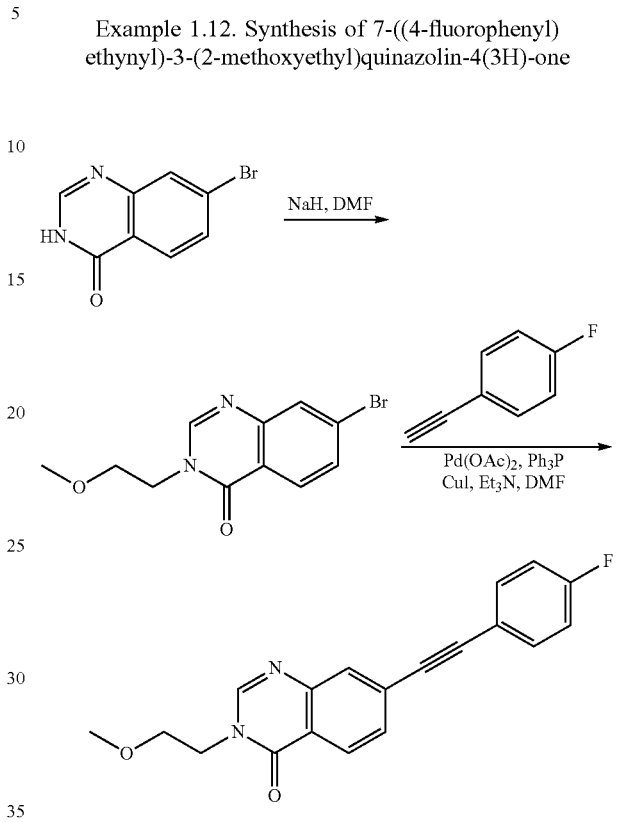

The title compound was prepared according to the experimental procedure described in Example 1.6a and Example 1.1. MS (ESI): 323 (MH⁺); ¹H NMR (300 MHz, CDCl₃) δ 8.30-8.27 (d, J=8.10 Hz, 1H), 8.12 (s, 1H), 7.85 (s, 1H), 7.62-7.56 (m, 3H), 7.12-7.07 (m, 2H), 4.22-4.18 (t, J=9.66 Hz, 2H), 3.71-3.68 (t, J=4.98 Hz, 2H), 3.35 (s, 3H). mGluR5 PAM EC$_{50}$: +++. Fold shift at 10 μM: +++.

Example 1.13. Synthesis of 7-((4-fluorophenyl)ethynyl)-3-((tetrahydrofuran-2-yl)methyl)quinazolin-4(3H)-one

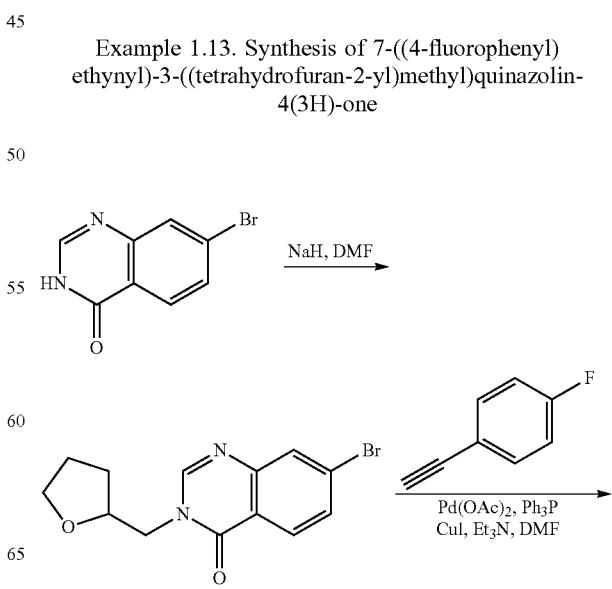

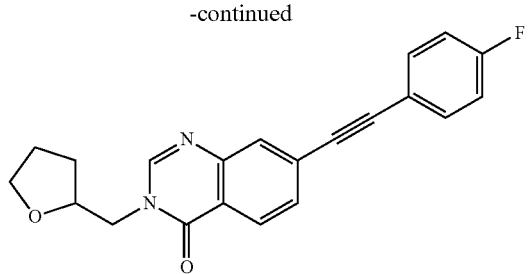

The title compound was prepared according to the experimental procedure described in Example 1.6a and Example 1.1. MS (ESI): 349 (MH$^+$); $^1$H NMR (300 MHz, CDCl$_3$) δ 8.29-8.27 (d, J=8.28 Hz, 1H), 8.18 (s, 1H), 7.85 (s, 1H), 7.62-7.55 (m, 3H), 7.12-7.06 (m, 2H), 4.40-4.35 (d, J=13.79 Hz, 1H), 4.28-4.20 (m, 1H), 3.93-3.74 (m, 3H), 2.18-2.07 (m, 1H), 1.97-1.87 (m, 2H), 1.64-1.56 (m, 1H). mGluR5 PAM EC$_{50}$: +++. Fold shift at 10 μM: ++.

Example 1.14. Synthesis of 7-((4-fluorophenyl)ethynyl)-3-(furan-2-ylmethyl)quinazolin-4(3H)-one

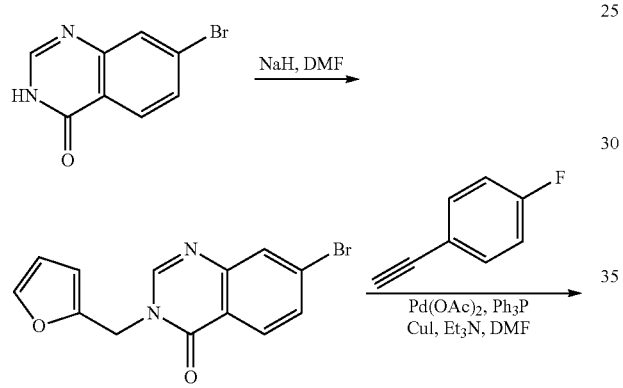

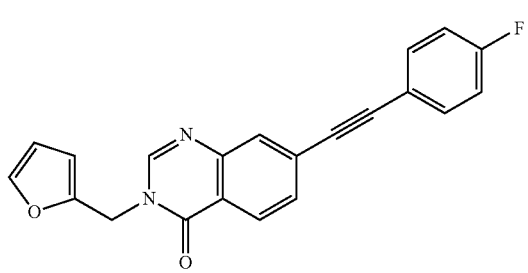

The title compound was prepared according to the experimental procedure described in Example 1.6a and Example 1.1. MS (ESI): 345 (MH$^+$); $^1$H NMR (300 MHz, CDCl$_3$) δ 8.30-8.27 (d, J=8.67 Hz, 1H), 8.20 (s, 1H), 7.85 (s, 1H), 7.79-7.73 (m, 3H), 7.41-7.33 (m, 1H), 7.12-7.06 (t, J=8.69 Hz, 2H), 6.50 (s, 1H), 6.37 (s, 1H), 5.20 (s, 2H). mGluR5 PAM EC$_{50}$: +. Fold shift at 10 μM: +++.

Example 1.15 and Example 1.16. Separation of Racemic 7-((4-fluorophenyl)ethynyl)-3-((tetrahydrofuran-2-yl)methyl)quinazolin-4(3H)-one into (S)-7-((4-fluorophenyl)ethynyl)-3-((tetrahydrofuran-2-yl)methyl)quinazolin-4(3H)-one and (R)-7-((4-fluorophenyl)ethynyl)-3-((tetrahydrofuran-2-yl)methyl)quinazolin-4(3H)-one

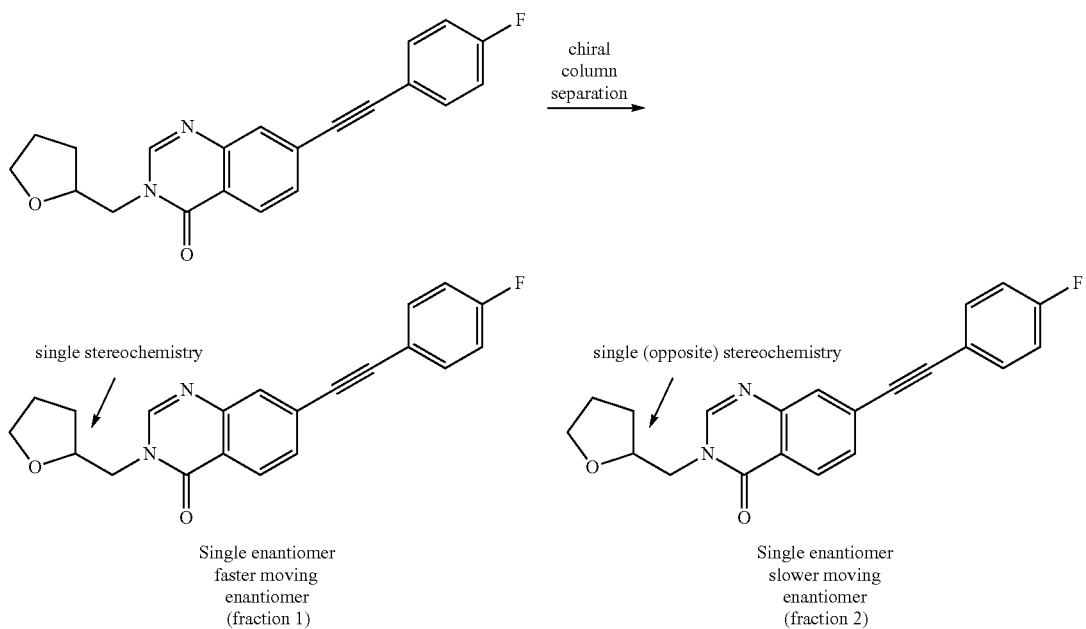

Racemic 7-((4-fluorophenyl)ethynyl)-3-((tetrahydrofuran-2-yl)methyl)quinazolin-4(3H)-one was separated into the corresponding two single enantiomer compounds (S)-7-((4-fluorophenyl)ethynyl)-3-((tetrahydrofuran-2-yl)methyl)quinazolin-4(3H)-one and (R)-7-((4-fluorophenyl)ethynyl)-3-((tetrahydrofuran-2-yl)methyl)quinazolin-4(3H)-one using chiral chromatography with an isocratic SFC method. The column used was a 3.0×25.0 cm RegisPack from Regis Technologies (Morton Grove, Ill.). The $CO_2$ co-solvent was ethanol with 0.1% isopropylamine. Isocratic Method: 55% Co-solvent at 80 mL/min System Pressure: 120 bar. Column Temperature 25° C.

Faster moving enantiomer (fraction 1): Retention time=2.31 min 100% ee. mGluR5 PAM $EC_{50}$: ++++. Fold shift at 10 μM: ++.

Slower moving enantiomer (fraction 2): Retention time=3.59 min 99.2% ee. mGluR5 PAM $EC_{50}$: ++.

Example 1.17. Synthesis of 3-(2-methoxyethyl)-7-(pyridin-4-ylethynyl)quinazolin-4(3H)-one

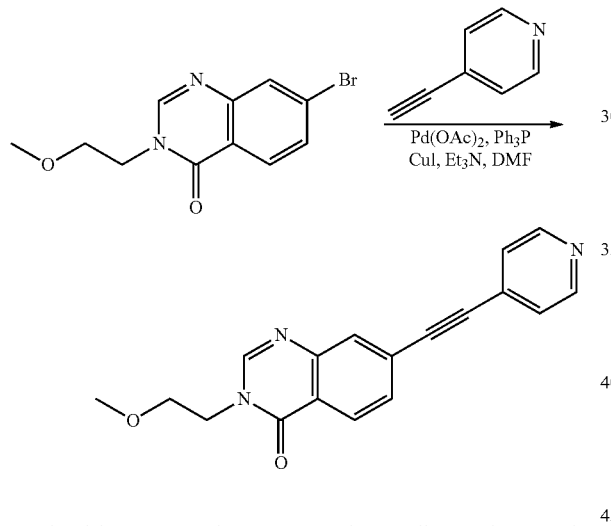

The title compound was prepared according to the experimental procedure described in Example 1.6a and Example 1.1. MS (ESI): 306 (MH$^+$). mGluR5 PAM $EC_{50}$: ++. Fold shift at 10 μM: ++.

Example 1.18. Synthesis of 3-(2-methoxyethyl)-7-(pyridin-3-ylethynyl)quinazolin-4(3H)-one

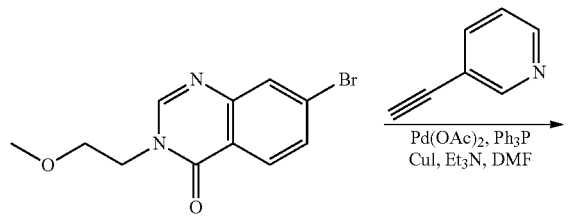

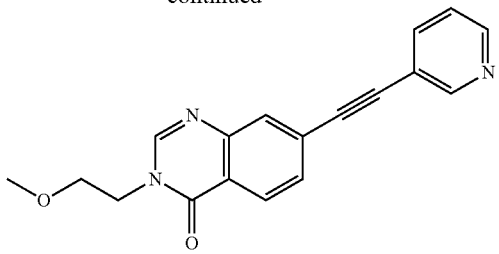

The title compound was prepared according to the experimental procedure described in Example 1.6a and Example 1.1. MS (ESI): 306 (MH$^+$).

Example 1.19. Synthesis of 3-(sec-butyl)-7-((3-fluorophenyl)ethynyl)quinazolin-4(3H)-one

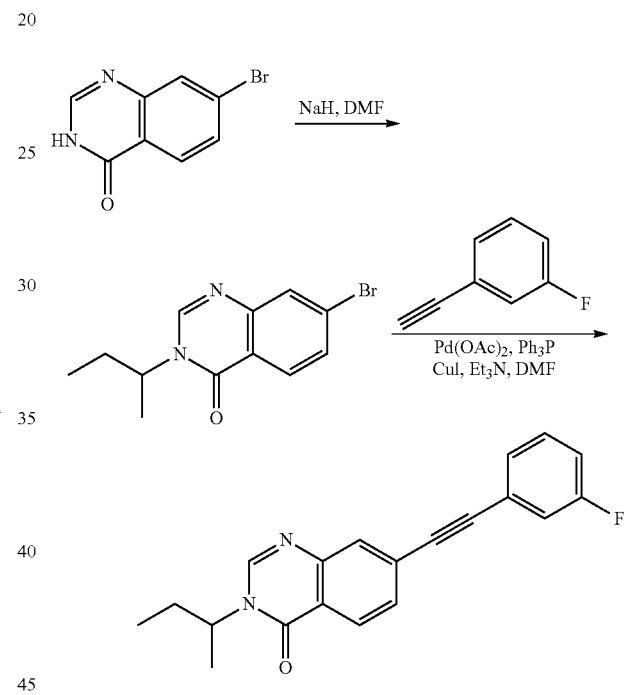

The title compound was prepared according to the experimental procedure described in Example 1.6a and Example 1.1. MS (ESI): 321 (MH$^+$); $^1$H NMR (300 MHz, CDCl$_3$) δ 8.32-8.29 (d, J=8.37 Hz, 1H), 8.08 (s, 1H), 7.87 (s, 1H), 7.64-7.61 (d, J=8.28 Hz, 1H), 7.39-7.35 (m, 2H), 7.28 (s, 1H), 7.14-7.08 (m, 1H), 5.01-4.94 (m, 1H), 1.92-1.82 (m, 2H), 1.51-1.48 (d, J=6.96 Hz, 3H), 0.99-0.94 (t, J=7.5 Hz, 3H). mGluR5 PAM $EC_{50}$: +++++. Fold shift at 10 μM: ++.

Example 1.20. Synthesis of 7-((3-fluorophenyl)ethynyl)-3-isobutylquinazolin-4(3H)-one

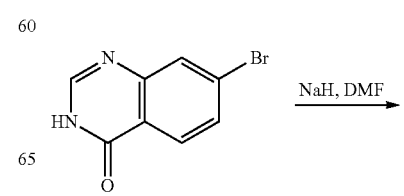

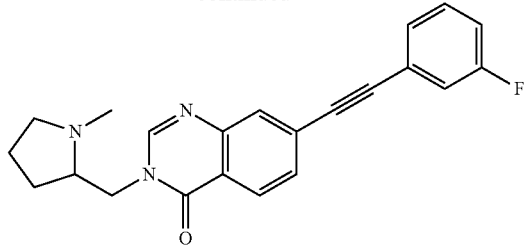

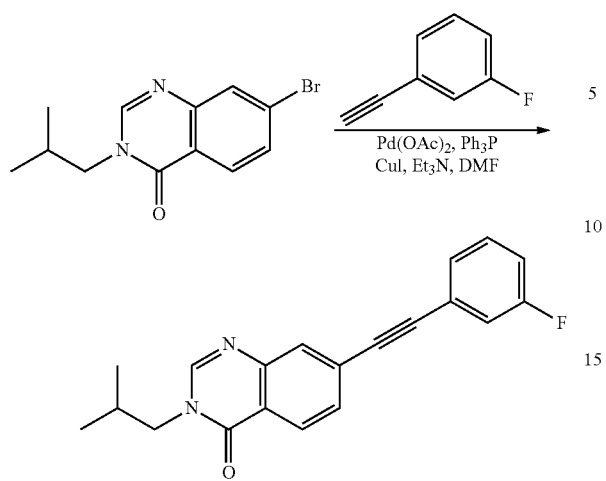

The title compound was prepared according to the experimental procedure described in Example 1.6a and Example 1.1. MS (ESI): 321 (MH+); 1H NMR (300 MHz, CDCl3) δ 8.31-8.29 (d, J=8.31 Hz, 1H), 8.02 (s, 1H), 7.86 (s, 1H), 7.64-7.61 (d, J=8.27 Hz, 1H), 7.38-7.35 (m, 2H), 7.32-7.28 (m, 1H), 7.14-7.07 (m, 1H), 3.84-3.81 (d, J=7.35 Hz, 2H), 2.28-2.19 (m, 1H), 1.03-1.00 (d, J=8.69 Hz, 6H). mGluR5 PAM EC50: +++. Fold shift at 10 μM: ++.

Example 1.21. Synthesis of 7-((3-fluorophenyl)ethynyl)-3-((1-methylpyrrolidin-2-yl)methyl)quinazolin-4(3H)-one

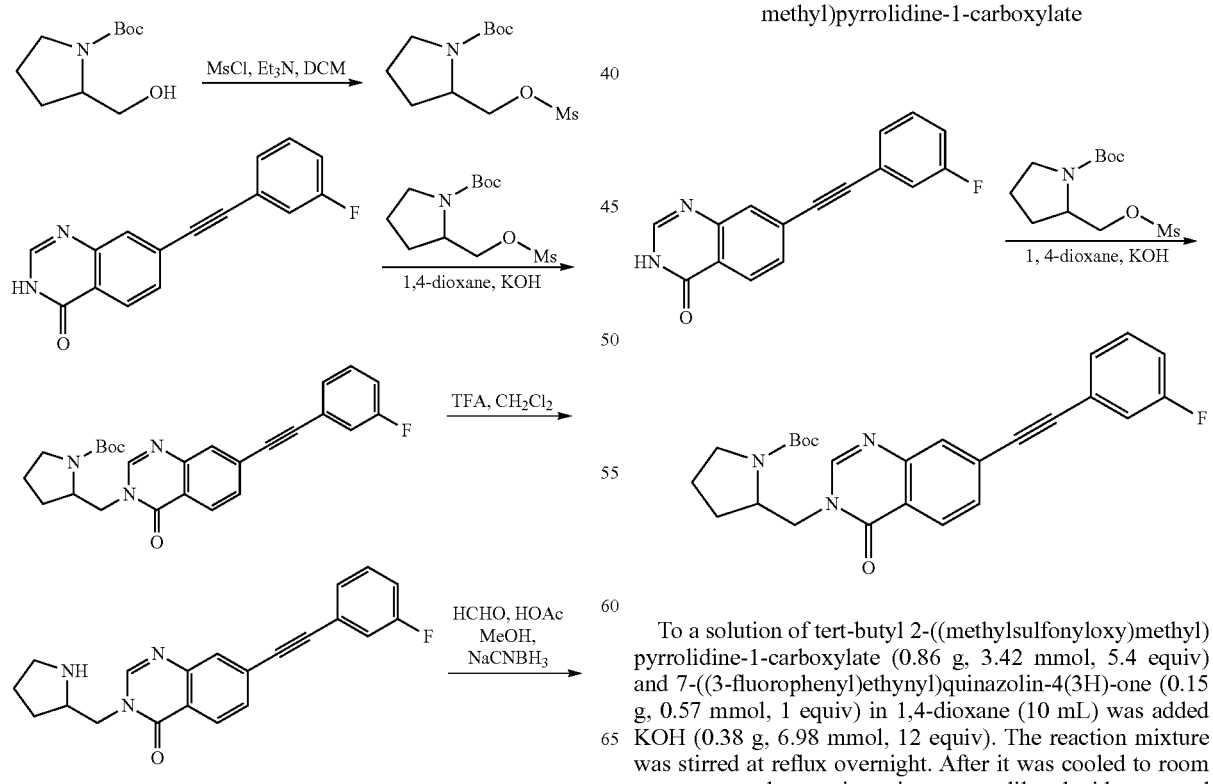

Example 1.21a. Synthesis of tert-butyl 2-((methylsulfonyloxy)methyl)pyrrolidine-1-carboxylate

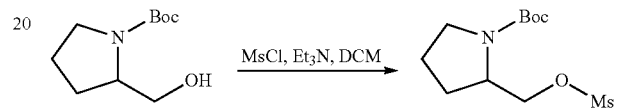

To a solution of tert-butyl 2-(hydroxymethyl)pyrrolidine-1-carboxylate (1.00 g, 4.97 mmol, 1.0 equiv) and Et3N (1.06 g, 10.5 mmol, 2.1 equiv) in DCM (15 mL) was added dropwise MsCl (0.85 g, 7.40 mmol, 1.5 equiv) at 0° C. Then the reaction mixture was stirred at room temperature for 3 h. After the mixture was washed with brine, the organic layer was separated, dried over Na2SO4, filtered, and concentrated to give 1.8 g of the crude product, which was used for the nest step without further purification.

Example 1.21b. Synthesis of tert-butyl 2-((7-((3-fluorophenyl)ethynyl)-4-oxoquinazolin-3(4H)-yl)methyl)pyrrolidine-1-carboxylate To a solution of tert-butyl 2-((methylsulfonyloxy)methyl)pyrrolidine-1-carboxylate (0.86 g, 3.42 mmol, 5.4 equiv) and 7-((3-fluorophenyl)ethynyl)quinazolin-4(3H)-one (0.15 g, 0.57 mmol, 1 equiv) in 1,4-dioxane (10 mL) was added KOH (0.38 g, 6.98 mmol, 12 equiv). The reaction mixture was stirred at reflux overnight. After it was cooled to room temperature, the reaction mixture was diluted with saturated NaCl and extracted with ethyl acetate (3×50 mL). The combined organic layers were dried over Na₂SO₄. After filtration and concentration, the residue was purified by silica gel chromatography to give 0.74 g of the desired product. MS (ESI): 448 (MH⁺).

Example 1.21c. Synthesis of 7-((3-fluorophenyl)ethynyl)-3-(pyrrolidin-2-ylmethyl)quinazolin-4(3H)-one

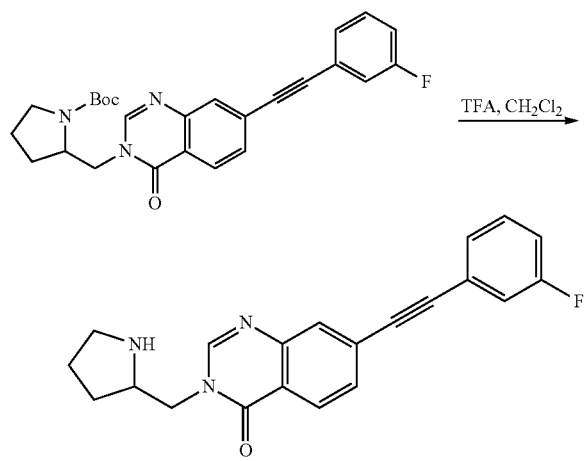

A mixture of tert-butyl 2-474(3-fluorophenyl)ethynyl)-4-oxoquinazolin-3(4H)-yl)methyl)pyrrolidine-1-carboxylate (0.74 g) and TFA (4 mL) in dichloromethane (4 mL) was stirred at room temperature for 2.5 h. Then the reaction mixture was adjusted pH to 8-9 with saturated NaHCO₃ and extracted with ethyl acetate (3×50 mL). The combined organic layers were dried over Na₂SO₄ and concentrated to give the crude product (0.4 g), which was used for the next step without further purification. MS (ESI): 348 (MH⁺).

Example 1.21d. Synthesis of the HCl Salt of 7-((3-fluorophenyl)ethynyl)-3-((1-methylpyrrolidin-2-yl)methyl)quinazolin-4(3H)-one

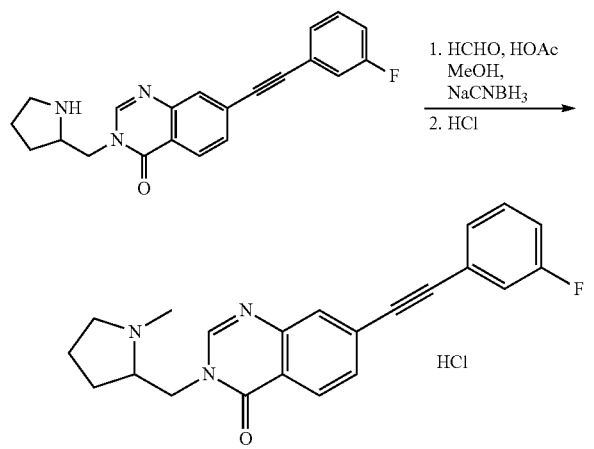

To a solution of 7-((3-fluorophenyl)ethynyl)-3-(pyrrolidin-2-ylmethyl)quinazolin-4(3H)-one (0.4 g, 1.15 mmol, 1 equiv), 37% HCHO (0.7 mL, 2.3 mmol, 2 equiv) and HOAc (1 d) in MeOH (20 mL) was added NaCNBH₃ in portions. After the reaction mixture was stirred at room temperature for 1 h, the solvent was removed, diluted with saturated NaHCO₃ and extracted with ethyl acetate (3×50 mL). The combined organic layers were dried over Na₂SO₄. After filtration and concentration, the residue was purified by silica gel chromatography to give 42 mg of the desired product. The product was then converted to the corresponding HCl salt. MS (ESI): 362 (MH⁺).

¹H NMR (300 MHz, CD₃OD) δ 8.20 (s, 1H), 8.36-8.33 (d, J=8.4 Hz, 1H), 7.91 (s, 1H), 7.80-7.77 (d, J=9.0 Hz, 1H), 7.51-7.42 (m, 2H), 7.38-7.35 (m, 1H), 7.25-7.18 (m, 1H), 4.86-4.54 (m, 2H), 3.89-3.79 (m, 2H), 3.28-3.22 (m, 1H), 3.12 (s, 3H), 2.47-2.36 (m, 1H), 2.23-2.06 (m, 2H), 2.02-1.93 (m, 1H). mGluR5 PAM EC₅₀: ++.

Example 2.1. Synthesis of 7-((3-fluorophenyl)ethynyl)-2-(2-methoxyethyl)-3-methylquinazolin-4(3H)-one

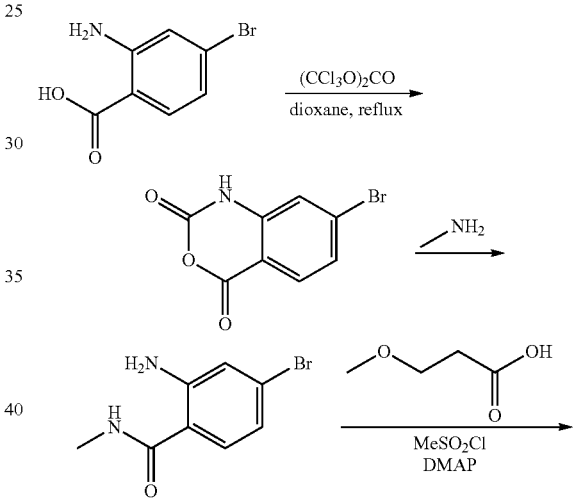

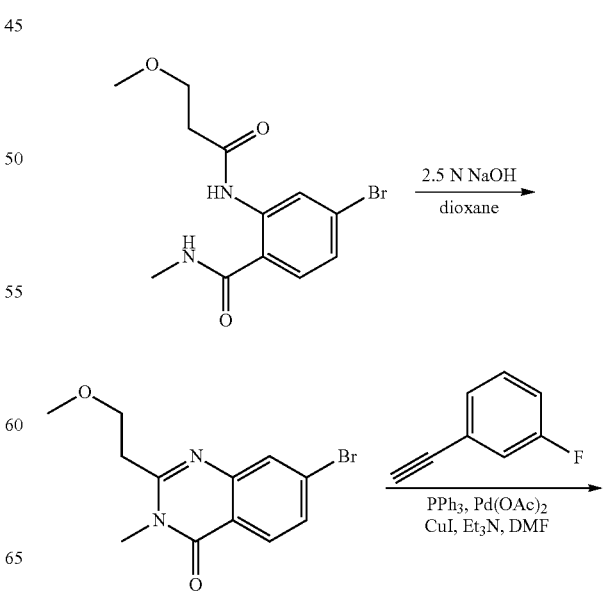

-continued

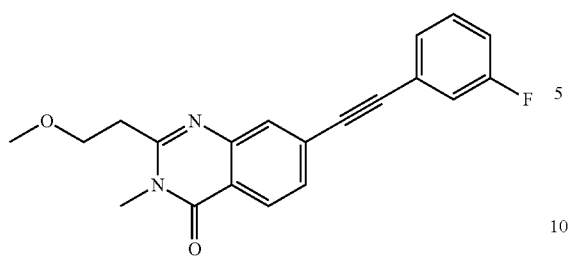

Example 2.1a. Synthesis of 2-amino-4-bromo-N-methylbenzamide

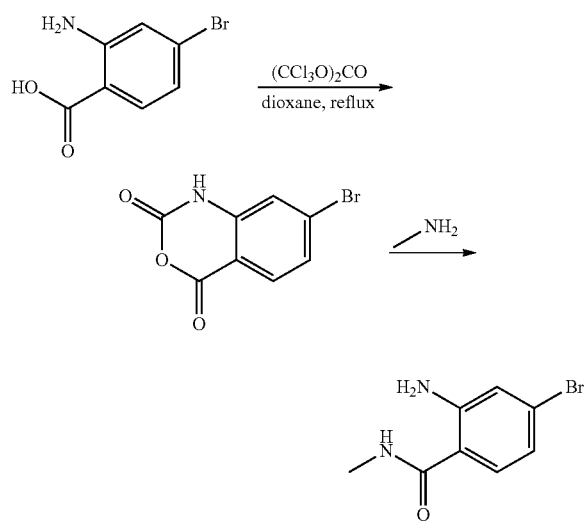

To a mixture of 2-amino-4-bromobenzoic acid (5.0 g, 23.1 mmol) and dioxane (50 mL) was added triphosgene (2.3 g, 7.75 mmol). The reaction mixture was heated to reflux and stirred for 4 h. Methylamine (40% in water, 2 mL, 23.1 mmol) was added dropwise after the mixture was cooled to room temperature. After stirring for 30 min, the solution was evaporated under reduced pressure and the residue was redissolved in DCM which was washed with sat. NaHCO$_3$ aqueous solution, dried over Na$_2$SO$_4$, filtered, and evaporated to give 4.6 g of the target compound. MS (ESI): 229, 231 (MH$^+$).

Example 2.1b. Synthesis of 4-bromo-2-(3-methoxypropanamido)-N-methylbenzamide

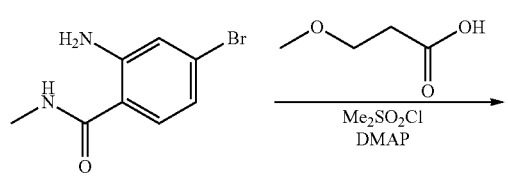

-continued

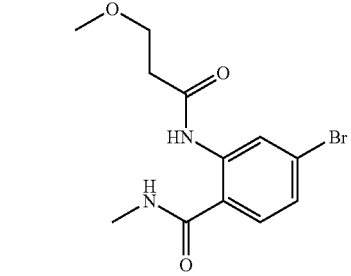

To a mixture of 3-methoxypropanoic acid (0.25 mL, 2.62 mmol), DMAP (0.64 g, 5.24 mmol) and dry DCM (5 mL) was added methanesulfonyl chloride (0.22 mL, 2.88 mmol) dropwise at 0° C. under nitrogen atmosphere. 2-Amino-4-bromo-N-methylbenzamide (0.3 g, 1.31 mmol) was added after stirring for 1 h, and the temperature was allowed to rise to room temperature slowly. The reaction mixture was quenched with sat. NH$_4$Cl solution after 3 h and extracted with ethyl acetate (3×10 mL). The combined organic layers were washed with NaHCO$_3$, dried over Na$_2$SO$_4$, filtered, and evaporated to give 0.39 g of the target compound. MS (ESI): 315, 317 (MH$^+$).

Example 2.1c. Synthesis of 7-bromo-2-(2-methoxyethyl)-3-methylquinazolin-4(3H)-one

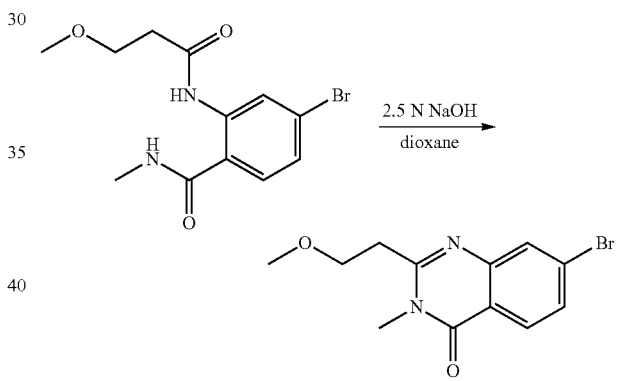

The mixture of 4-bromo-2-(3-methoxypropanamido)-N-methylbenzamide (0.05 g, 0.159 mmol), 2.5 N NaOH (1 mL) and dioxane (1 mL) was stirred for 3 h at room temperature, then diluted with water, and extracted with ethyl acetate (3×10 mL). The combined organic layers were washed with brine (3×10 mL), dried over Na$_2$SO$_4$, filtered, and evaporated to give 59 mg of the target compound. MS (ESI): 297, 299 (MH$^+$).

Example 2.1d. Synthesis of 7-((3-fluorophenyl)ethynyl)-2-(2-methoxyethyl)-3-methylquinazolin-4(3H)-one

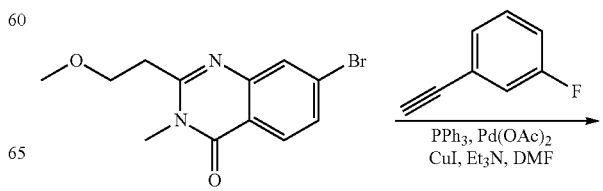

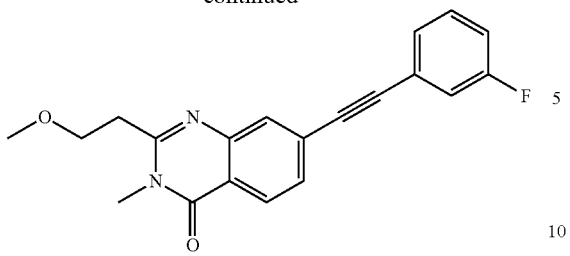

The title compound was prepared according to the experimental procedure described in Example 1.1. MS (ESI): 337 (MH+); $^1$H NMR (300 MHz, CDCl$_3$) δ 8.26-8.23 (d, J=8.25 Hz, 1H), 7.81 (s, 1H), 7.57-7.54 (d, J=8.30 Hz, 1H), 7.38-7.34 (m, 2H), 7.27-7.26 (m, 1H), 7.15-7.07 (m, 1H), 3.98-3.93 (t, J=6.60 Hz, 2H), 3.67 (s, 3H), 3.43 (s, 3H), 3.15-3.10 (t, J=6.69 Hz, 2H). mGluR5 PAM EC$_{50}$: +++++. Fold shift at 10 μM: +.

Example 2.2. Synthesis of 7-((3-fluorophenyl)ethynyl)-3-methyl-2-(tetrahydrofuran-3-yl)quinazolin-4(3H)-one

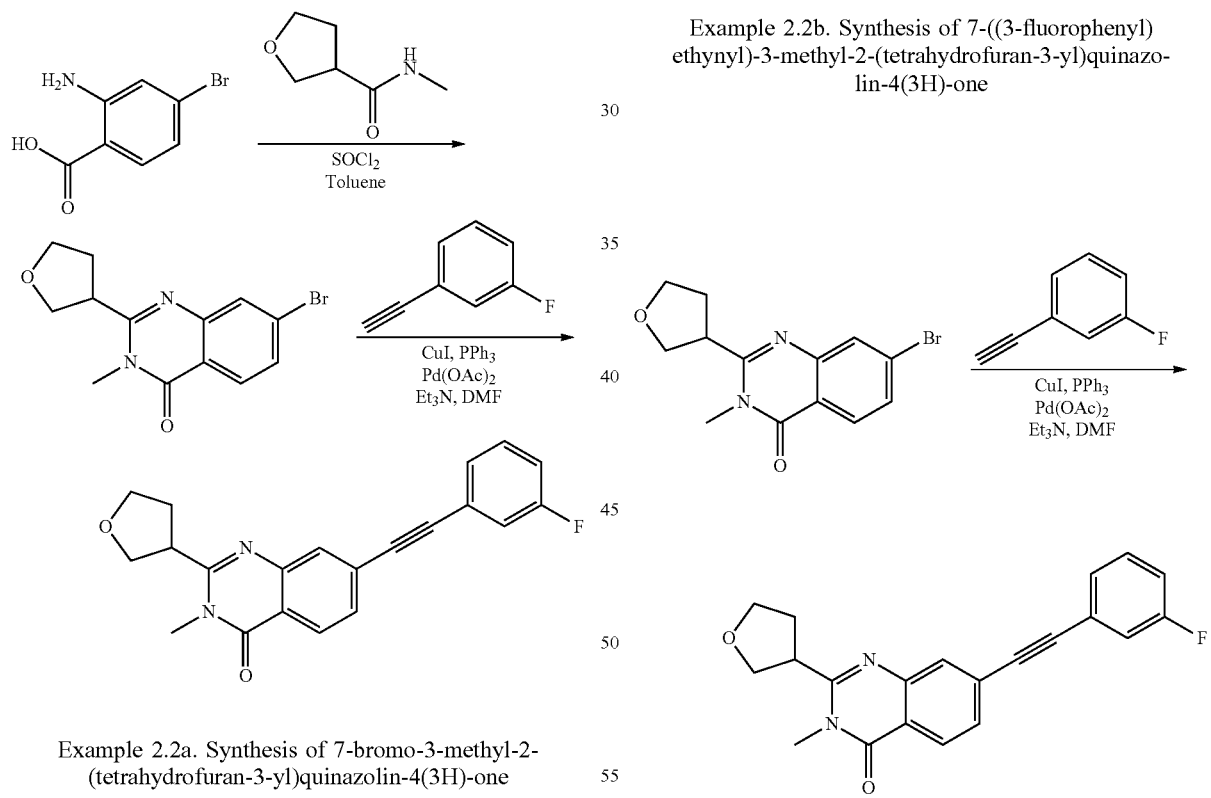

Example 2.2a. Synthesis of 7-bromo-3-methyl-2-(tetrahydrofuran-3-yl)quinazolin-4(3H)-one

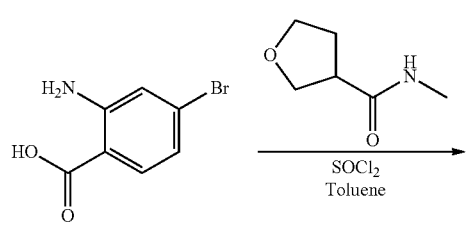

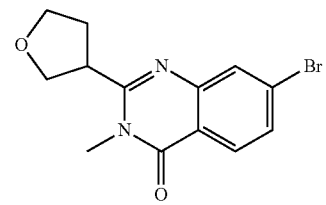

The mixture of 2-amino-4-bromobenzoic acid (349 mg, 1.62 mmol), N-methyltetrahydrofuran-3-carboxamide (190 mg, 1.47 mmol), SOCl$_2$ (0.13 mL, 1.76 mmol) and toluene (10 mL) was stirred at 80° C. for 5 h, and Na$_2$CO$_3$ aqueous solution was added after the mixture was cooled to room temperature. The water layer was extracted with ethyl acetate (3×10 mL) and the combined organic layers were dried over Na$_2$SO$_4$, filtered, and evaporated to give the desired product, which was directly used for the next step. MS (ESI): 309, 311 (MH+).

Example 2.2b. Synthesis of 7-((3-fluorophenyl)ethynyl)-3-methyl-2-(tetrahydrofuran-3-yl)quinazolin-4(3H)-one The title compound was prepared according to the experimental procedure described in Example 1.1. MS (ESI): 349 (MH+); $^1$H NMR (300 MHz, CDCl$_3$) δ 8.34-8.32 (d, J=8.16 Hz, 1H), 7.77 (s, 1H), 7.62-7.56 (d, J=8.16 Hz, 1H), 7.38-7.34 (m, 2H), 7.27-7.24 (m, 1H), 7.15-7.07 (m, 1H), 4.25-4.22 (d, J=6.99 Hz, 2H), 4.13-3.97 (m, 2H), 3.71-3.61 (m, 4H), 2.54-2.46 (m, 1H), 2.43-2.31 (m, 1H). mGluR5 PAM EC$_{50}$: +.

Example 2.3. Synthesis of 7-((3-fluorophenyl)ethynyl)-3-methyl-2-(tetrahydrofuran-2-yl)quinazolin-4(3H)-one

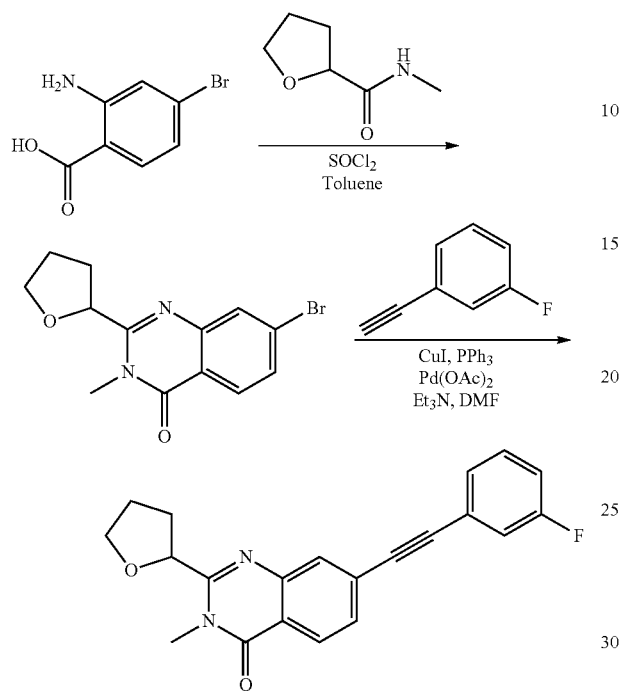

The title compound was prepared according to the experimental procedure described in Example 2.2a and Example 1.1. MS (ESI): 349 (MH+); $^1$H NMR (300 MHz, CDCl$_3$) δ 8.27-8.25 (d, J=8.25 Hz, 1H), 7.88 (s, 1H), 7.60-7.56 (d, J=8.25 Hz, 1H), 7.38-7.32 (m, 2H), 7.27-7.25 (m, 1H), 7.13-7.07 (m, 1H), 5.11-5.07 (m, 1H), 4.06-3.94 (m, 2H), 3.76 (s, 3H), 2.82-2.76 (m, 1H), 2.24-2.18 (m, 2H), 2.11-2.02 (m, 1H). mGluR5 PAM EC$_{50}$: +.

Example 2.4. Synthesis of 7-((3-fluorophenyl)ethynyl)-3-methyl-2-(1-methylpyrrolidin-2-yl)quinazolin-4(3H)-one

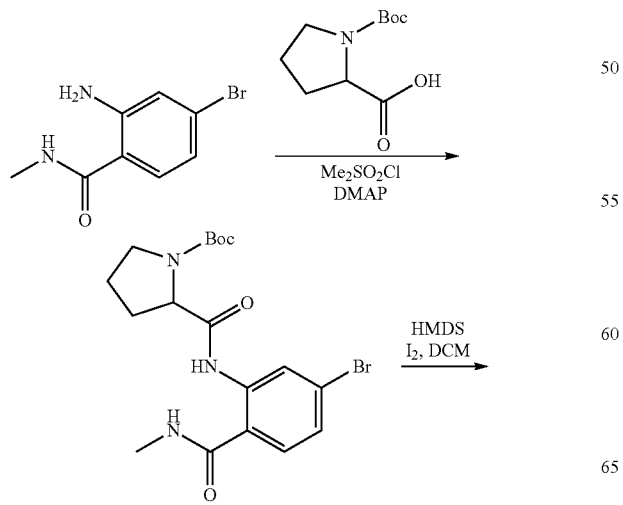

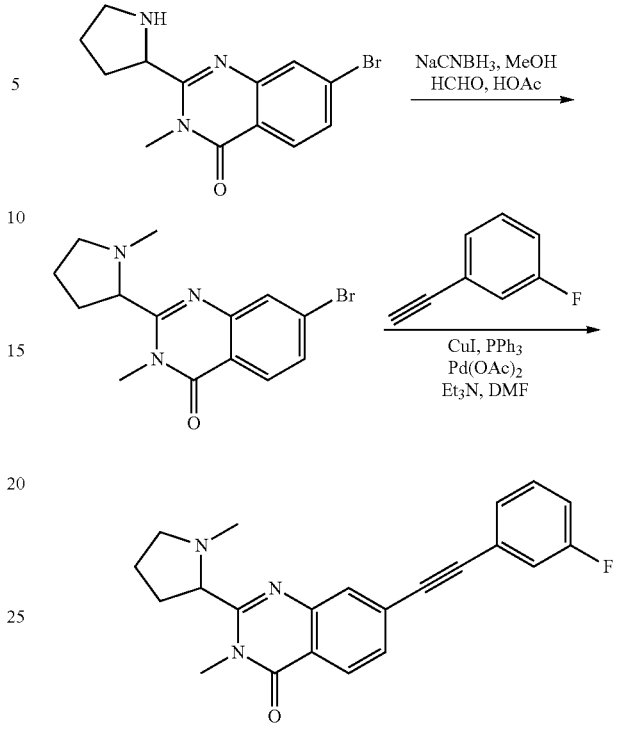

Example 2.4a. Synthesis of tert-butyl 2-(5-bromo-2-(methylcarbamoyl)phenylcarbamoyl)pyrrolidine-1-carboxylate

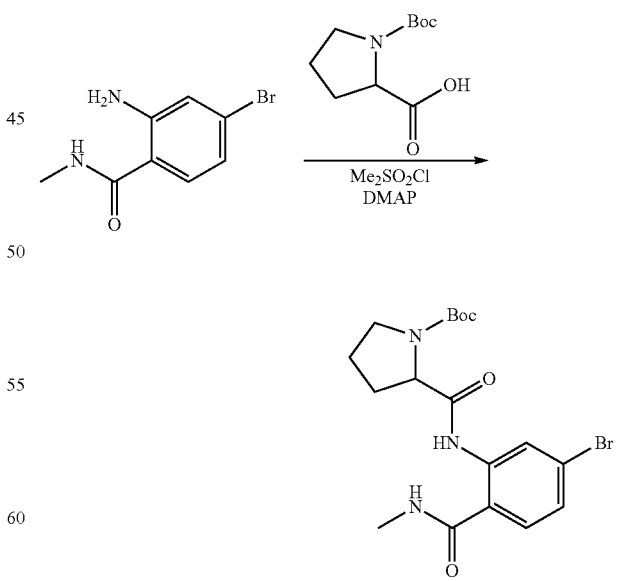

The title compound was prepared according to the experimental procedure described in Example 2.1b. MS (ESI): 426, 428 (MH+).

Example 2.4b. Synthesis of 7-bromo-3-methyl-2-(pyrrolidin-2-yl)quinazolin-4(3H)-one

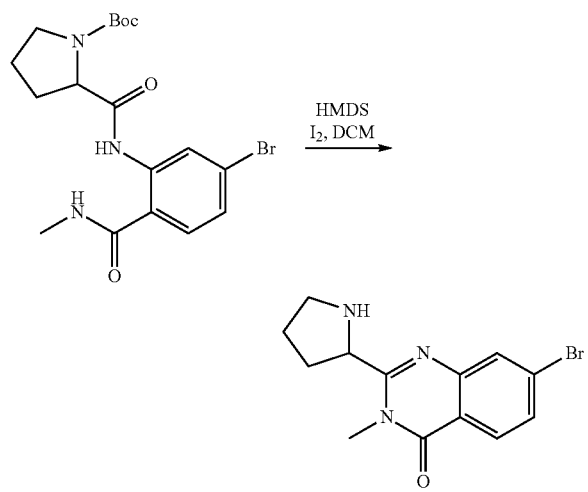

The mixture of tert-butyl 2-(5-bromo-2-(methylcarbamoyl)phenylcarbamoyl)pyrrolidine-1-carboxylate (0.2 g, 0.47 mmol), hexamethyldisilazane (0.39 mL, 1.88 mmol), I$_2$ (0.24 g, 0.94 mmol), and DCM (10 mL) was refluxed for 5 h under nitrogen atmosphere. Na$_2$S$_2$O$_3$ aqueous solution was added to quench the reaction followed by cooling to room temperature. The organic layer was separated and the water layer was extracted with ethyl acetate (3×10 mL). The combined organic layers were washed with brine, dried over Na$_2$SO$_4$, filtered, and evaporated to give the desired product, which was directly used for the next step. MS (ESI): 308, 310 (MH$^+$).

Example 2.4c. Synthesis of 7-bromo-3-methyl-2-(1-methylpyrrolidin-2-yl)-quinazolin-4(3H)-one

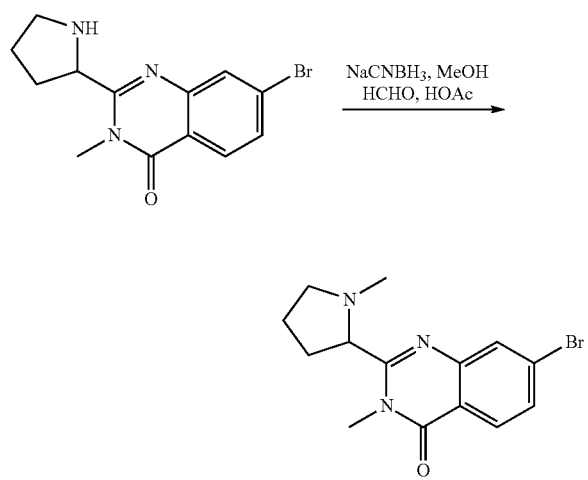 [SMILES: Cn1c(C2CCCN2)nc2cc(Br)ccc2c1=O ; CN1CCCC1c1nc2cc(Br)ccc2c(=O)n1C]

The title compound was prepared according to the experimental procedure described in Example 1.21d. MS (ESI): 322, 324 (MH$^+$).

Example 2.4d. Synthesis of the HCl Salt of 7-((3-fluorophenyl)ethynyl)-3-methyl-2-(tetrahydrofuran-3-yl)quinazolin-4(3H)-one

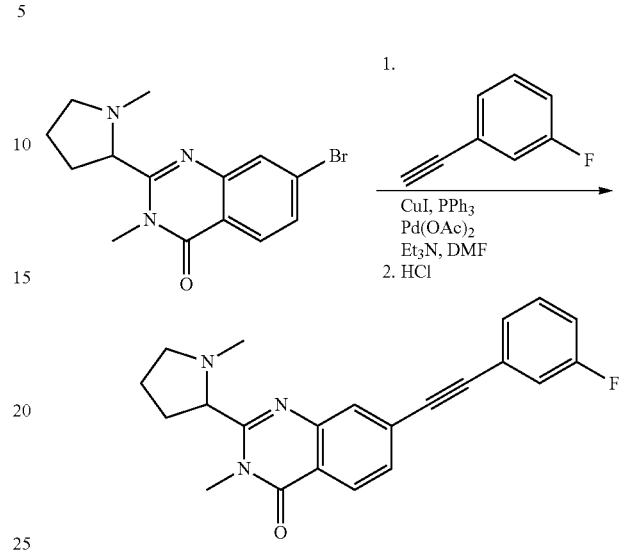

The title compound was prepared according to the experimental procedure described in Example 1.1. The mixture of 7-((3-fluorophenyl)ethynyl)-3-methyl-2-(tetrahydrofuran-3-yl)quinazolin-4(3H)-one and DCM was treated with HCl/Et$_2$O, filtered to give the desired HCl salt. MS (ESI): 362 (MH$^+$); $^1$H NMR (300 MHz, CD$_3$OD) δ 8.29-8.26 (d, J=8.19 Hz, 1H), 7.95 (s, 1H), 7.74-7.71 (dd, J=8.27, 1.55 Hz, 1H), 7.48-7.41 (m, 2H), 7.37-7.33 (m, 1H), 7.27-7.21 (m, 1H), 5.04-4.98 (m, 1H), 3.99-3.95 (m, 1H), 3.62 (s, 3H), 3.46-3.38 (m, 1H), 3.09 (s, 3H), 2.93-2.87 (m, 1H), 2.40-2.30 (m, 1H), 2.24-2.11 (m, 2H). mGluR5 PAM EC$_{50}$: ++. Fold shift at 10 μM: ++.

Example 2.5. Synthesis of 7-((3-fluorophenyl)ethynyl)-3-methyl-2-(1-methylpyrrolidin-3-yl)quinazolin-4(3H)-one

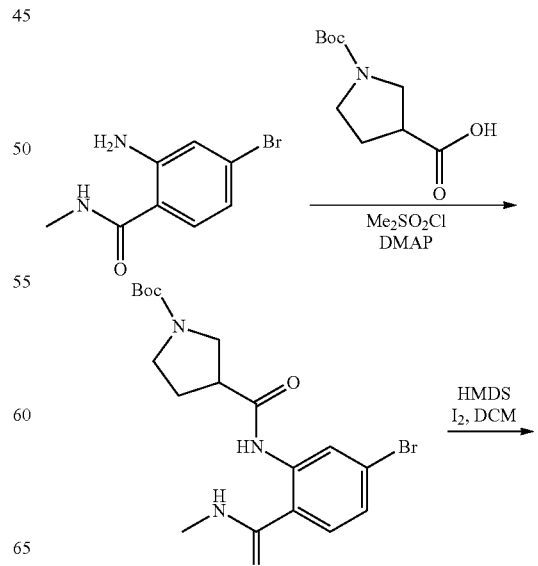

-continued

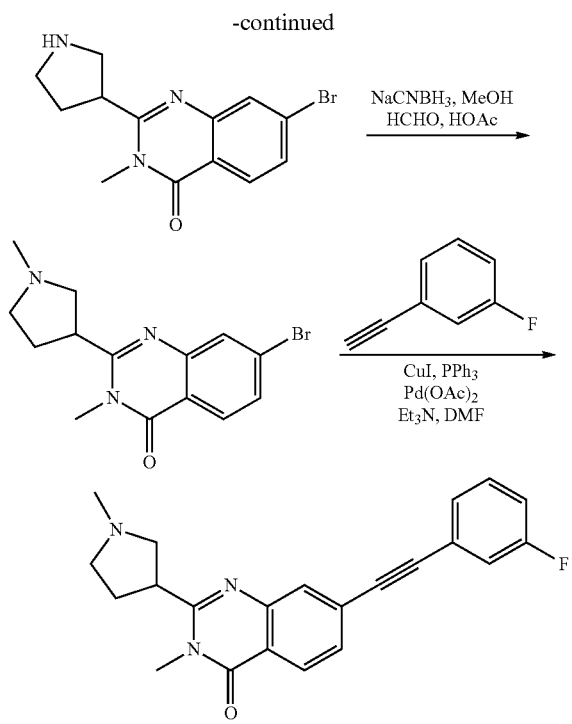

The title compound was prepared according to the experimental procedure described in Example 2.1b, Example 2.4b, Example 1.21d, and Example 1.1. MS (ESI): 362 (MH+); 1H NMR (300 MHz, CD3OD) δ 8.23-8.21 (d, J=8.28 Hz, 1H), 7.96-7.89 (dd, J=19.66, 1.26 Hz, 1H), 7.67-7.64 (d, J=8.28 Hz, 1H), 7.50-7.40 (m, 2H), 7.35-7.32 (m, 1H), 7.24-7.18 (m, 1H), 4.40-4.36 (d, J=11.68 Hz, 1H), 4.24-4.03 (m, 1H), 3.87-3.82 (m, 1H), 3.70 (s, 3H), 3.12 (s, 3H), 2.92-2.77 (m, 1H), 2.71-2.60 (m, 1H), 2.50-2.25 (m, 2H).

Example 2.6. Synthesis of 7-((3-fluorophenyl)ethynyl)-3-methyl-2-(pyrrolidin-1-ylmethyl)quinazolin-4(3H)-one

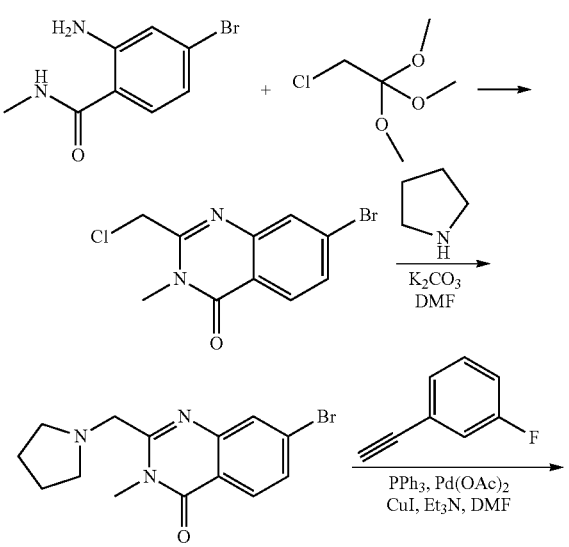

-continued

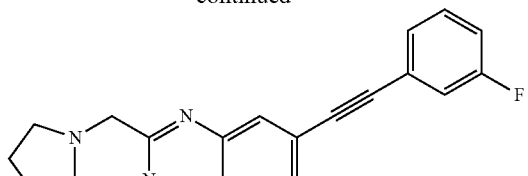

Example 2.6a. Synthesis of 7-bromo-2-(chloromethyl)-3-methylquinazolin-4(3H)-one

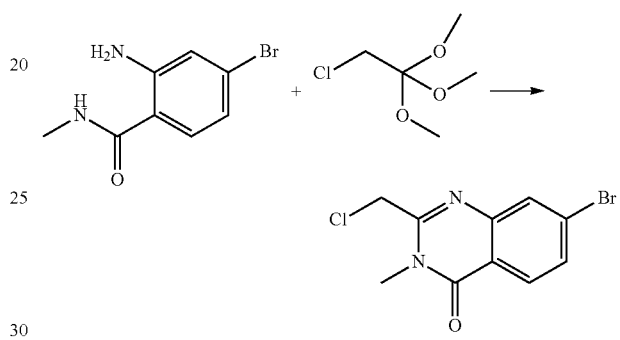

The mixture of 2-amino-4-bromo-N-methylbenzamide (0.4 g, 1.75 mmol) and 2-chloro-1,1,1-trimethoxyethane (4 mL) was stirred at 110° C. for 6 h. After the solution was evaporated under reduced pressure, ice cooled ethyl acetate was used to wash the residue to give 0.25 g of the desired product which was used for the next step without further purification. MS (ESI): 287, 289 (MH+).

Example 2.6b. Synthesis of 7-bromo-3-methyl-2-(pyrrolidin-1-ylmethyl)quinazolin-4(3H)-one

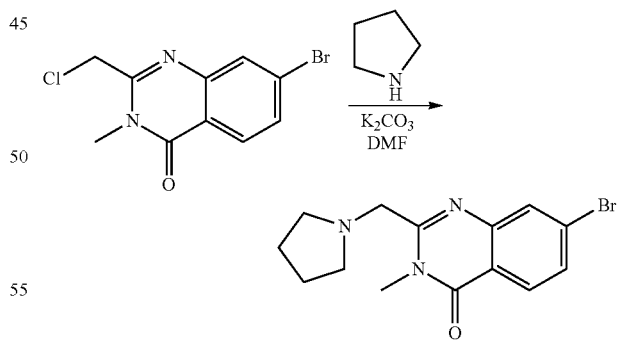

The mixture of 7-bromo-2-(chloromethyl)-3-methylquinazolin-4(3H)-one (125 mg, 0.43 mmol), pyrrolidine (65 mg, 0.91 mmol), K2CO3 (244 mg, 1.768 mmol) and DMF (10 mL) was stirred at room temperature for 30 min. Then water was added and the mixture was extracted with ethyl acetate (3×10 mL). The combined organic layers were washed with brine (3×10 mL), dried over Na2SO4, filtered and evaporated to give 100 mg of the desired product. MS (ESI): 322, 324 (MH+).

Example 2.6c. Synthesis of the HCl Salt of 7-((3-fluorophenyl)ethynyl)-3-methyl-2-(pyrrolidin-1-ylmethyl)quinazolin-4(3H)-one

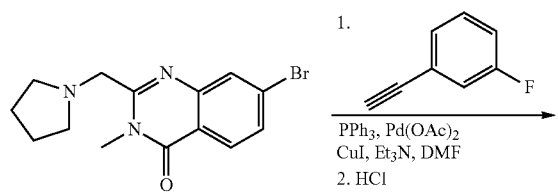

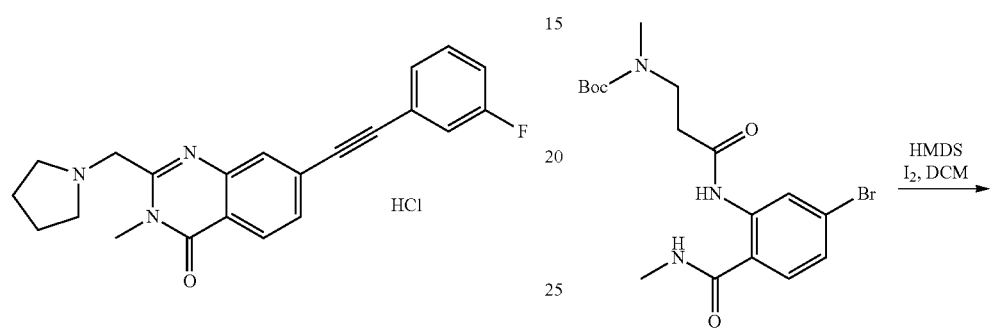

The title compound was prepared according to the experimental procedure described in Example 1.1. The product was then converted to the corresponding HCl salt. MS (ESI): 362 (MH+); $^1$H NMR (300 MHz, CD$_3$OD) δ 8.28-8.25 (d, J=8.16 Hz, 1H), 7.95 (s, 1H), 7.71-7.69 (dd, J=8.28, 1.53 Hz, 1H), 7.50-7.40 (m, 2H), 7.36-7.32 (m, 1H), 7.24-7.18 (m, 1H), 4.05-4.00 (m, 2H), 3.59 (s, 3H), 3.40-3.35 (m, 4H), 2.28-2.17 (m, 4H). mGluR5 PAM EC$_{50}$: ++.

Example 2.7. Synthesis of 2-((dimethylamino)methyl)-7-((3-fluorophenyl)ethynyl)-3-methylquinazolin-4(3H)-one

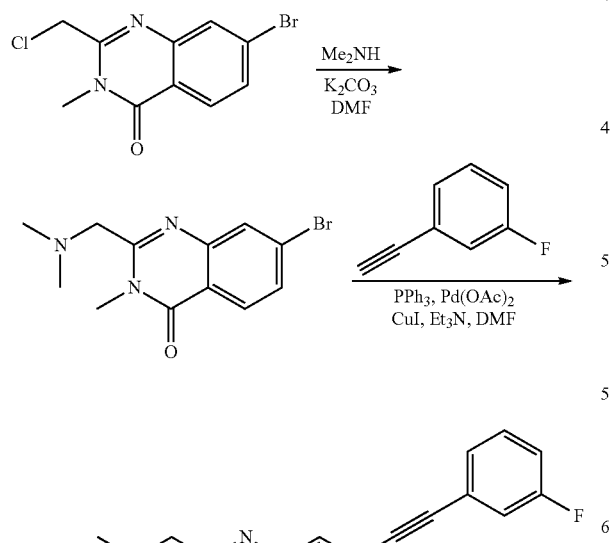

The title compound was prepared according to the experimental procedure described in Example 2.6b and Example 1.1. MS (ESI): 336 (MH+); $^1$H NMR (300 MHz, CD$_3$OD) δ 8.28-8.25 (d, J=8.28 Hz, 1H), 7.95 (s, 1H), 7.73-7.69 (d, J=8.25 Hz, 1H), 7.48-7.44 (m, 2H), 7.36-7.32 (m, 1H), 7.26-7.16 (m, 1H), 4.75 (s, 2H), 3.58 (s, 3H), 3.18 (s, 6H). mGluR5 PAM EC$_{50}$: +++. Fold shift at 10 μM: ++.

Example 2.8. Synthesis of the HCl Salt of 2-(2-(dimethylamino)ethyl)-7-((3-fluorophenyl)ethynyl)-3-methylquinazolin-4(3H)-one

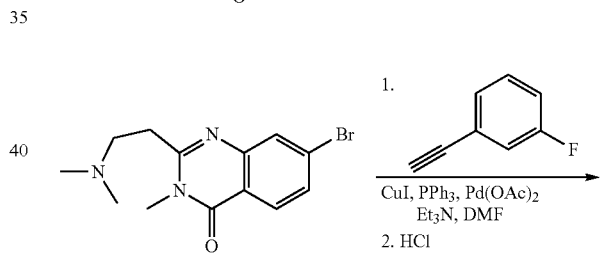

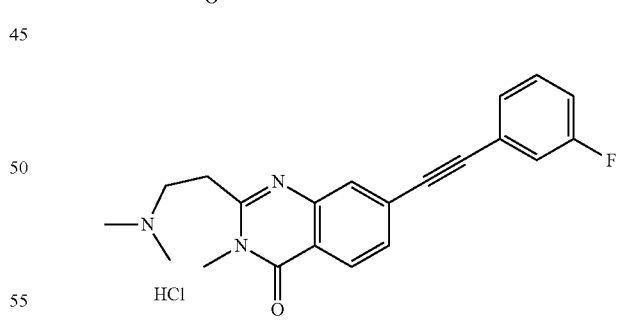

The title compound was prepared according to the experimental procedure as described in Example 2.4b, Example 1.21d, and Example 1.1. The product was then converted to the corresponding HCl salt. MS (ESI): 350 (MH+); $^1$H NMR (300 MHz, CD$_3$OD) δ 8.24-8.22 (d, J=8.28 Hz, 1H), 7.97 (s, 1H), 7.68-7.65 (dd, J=8.30, 1.52 Hz, 1H), 7.48-7.41 (m, 2H), 7.36-7.32 (m, 1H), 7.26-7.20 (m, 1H), 3.77-3.73 (t, J=5.97 Hz, 2H), 3.67 (s, 3H), 3.48-3.44 (t, J=5.91 Hz, 2H), 3.5807 (s, 6H).

Example 2.9. Synthesis of 7-((3-fluorophenyl)ethynyl)-3-methyl-2-(4-methylmorpholin-3-yl)quinazolin-4(3H)-one

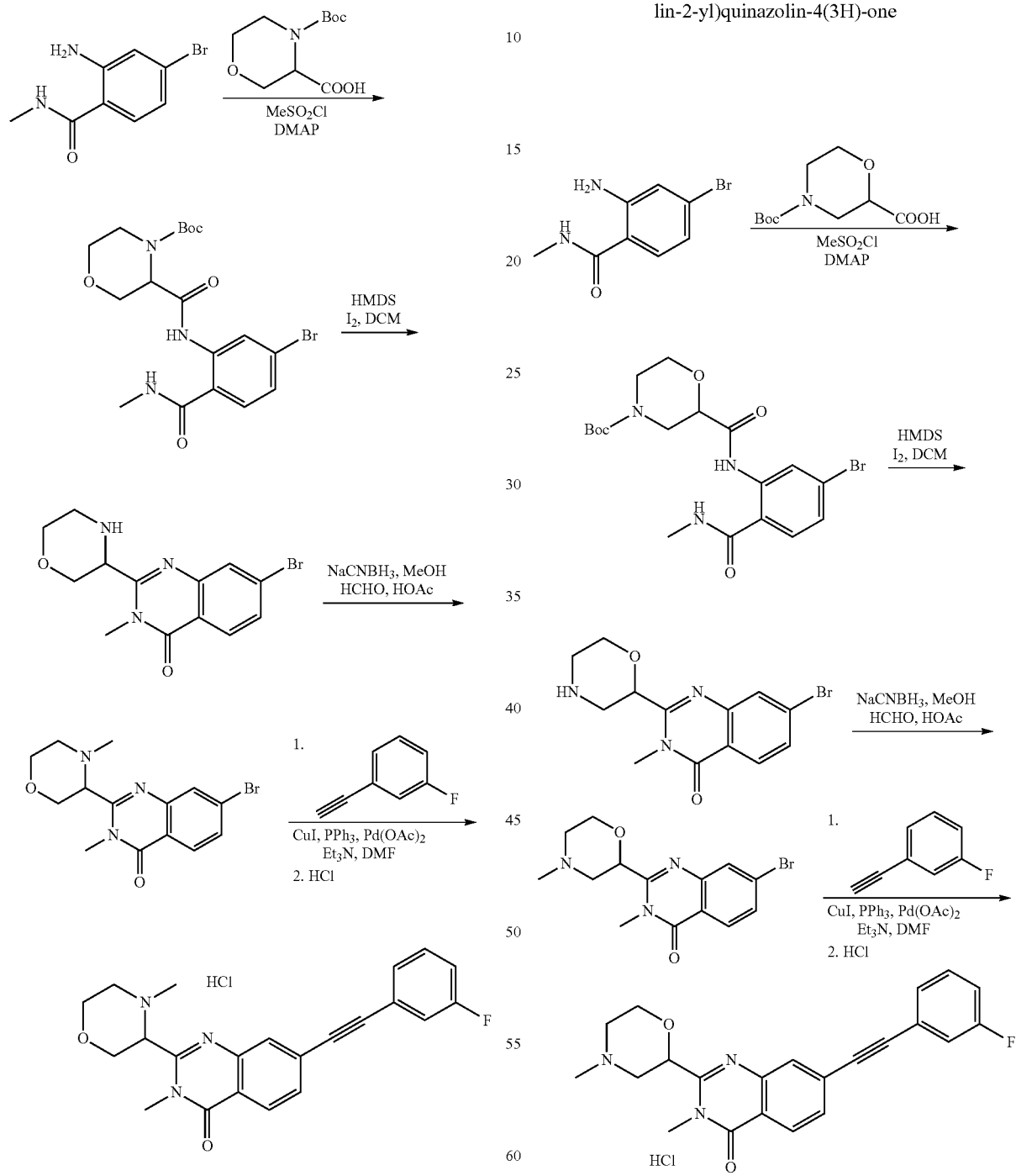

The title compound was prepared according to the experimental procedure described in Example 2.1b, Example 2.4b, Example 1.21d, and Example 1.1. The product was then converted to the corresponding HCl salt. MS (ESI): 378 (MH+); $^1$H NMR (300 MHz, CD$_3$OD) δ 8.29-8.26 (d, J=8.28 Hz, 1H), 7.95 (s, 1H), 7.75-7.72 (d, J=8.27 Hz, 1H), 7.49- 7.41 (m, 2H), 7.37-7.32 (m, 1H), 7.26-7.19 (m, 1H), 5.10-5.16 (d, J=10.5, 3.6 Hz, 1H), 4.56-4.50 (m, 1H), 4.27-4.22 (m, 1H), 4.02-3.93 (m, 1H), 3.75-3.71 (m, 2H), 3.68 (s, 3H), 3.62-3.57 (m, 1H), 3.01 (s, 3H). mGluR5 PAM EC$_{50}$: +++++.

Example 2.10. Synthesis of the HCl Salt of 7-((3-fluorophenyl)ethynyl)-3-methyl-2-(4-methylmorpholin-2-yl)quinazolin-4(3H)-one The title compound was prepared according to the experimental procedure described in Example 2.1b, Example 2.4b, Example 1.21d, and Example 1.1. The product was then converted to the corresponding HCl salt. MS (ESI): 378 (MH+).

Example 2.11. Synthesis of 7-((3-fluorophenyl)ethynyl)-2-(1-methoxyethyl)-3-methylquinazolin-4(3H)-one

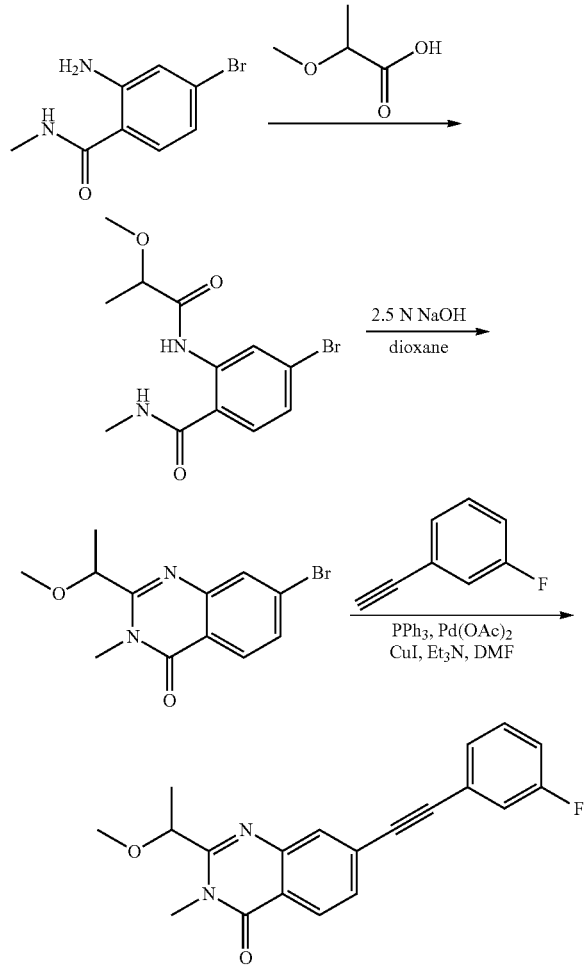

The title compound was prepared according to the experimental procedure described in Example 2.1b, Example 2.1c, and Example 1.1. MS (ESI): 337 (MH+); $^1$H NMR (300 MHz, CDCl$_3$) δ 8.27-8.24 (d, J=8.16 Hz, 1H), 7.86 (s, 1H), 7.60-7.56 (d, J=8.21 Hz, 1H), 7.38-7.33 (m, 2H), 7.25-7.20 (m, 1H), 7.12-7.05 (m, 1H), 4.65 (q, J=6.69 Hz, 1H), 3.74 (s, 3H), 3.40 (s, 3H), 1.65-1.60 (d, J=6.69 Hz, 3H). mGluR5 PAM EC$_{50}$: +++++. Fold shift at 10 μM: ++.

Example 2.12. Synthesis of 7-((3-fluorophenyl)ethynyl)-2-isobutyl-3-methylquinazolin-4(3H)-one

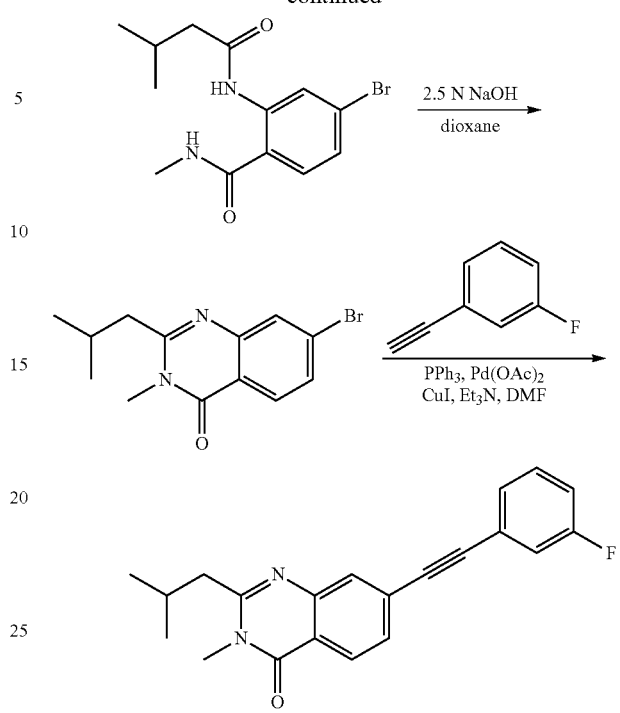

The title compound was prepared according to the experimental procedure described in Example 2.1b, Example 2.1c, and Example 1.1. MS (ESI): 335 (MH+); $^1$H NMR (300 MHz, CDCl$_3$) δ 8.26-8.23 (d, J=8.25 Hz, 1H), 7.83 (s, 1H), 7.57-7.53 (d, J=8.25 Hz, 1H), 7.40-7.33 (m, 2H), 7.26-7.25 (m, 1H), 7.12-7.05 (m, 1H), 3.62 (s, 3H), 2.75-2.72 (d, J=7.05 Hz, 2H), 2.38-2.29 (m, 1H), 1.10-1.05 (d, J=6.63 Hz, 6H). mGluR5 PAM EC$_{50}$: +++. Fold shift at 10 μM: +.

Example 2.13. Synthesis of 7-((3-fluorophenyl)ethynyl)-2-(2-methoxyethyl)quinazolin-4(3H)-one

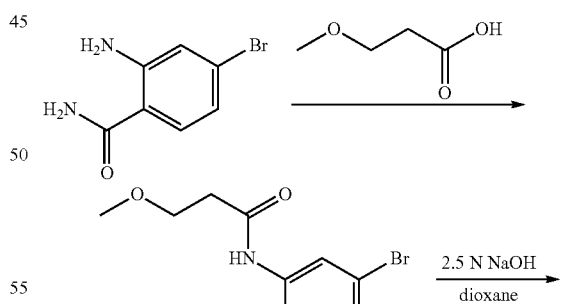

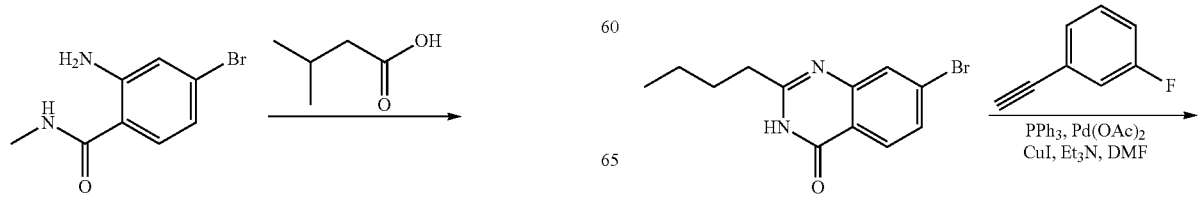

-continued

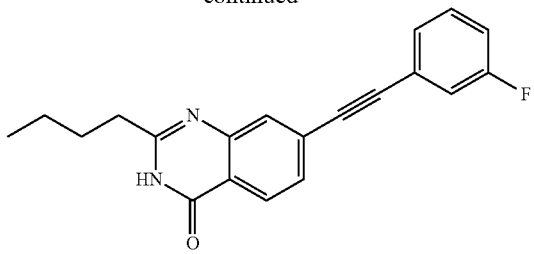

The title compound was prepared according to the experimental procedure described in Example 2.1b, Example 2.1c, and Example 1.1. MS (ESI): 323 (MH+); $^1$H NMR (300 MHz, CDCl$_3$) δ 10.00 (brs, 1H), 8.26-8.23 (d, J=8.19 Hz, 1H), 7.80 (s, 1H), 7.59-7.56 (dd, J=8.21, 1.5 Hz, 1H), 7.38-7.35 (m, 2H), 7.29-7.28 (m, 1H), 7.14-7.07 (m, 1H), 3.84-3.80 (t, J=5.2 Hz, 2H), 3.49 (s, 3H), 3.03-2.99 (t, J=5.5 Hz, 2H). mGluR5 PAM EC$_{50}$: ++. Fold shift at 10 µM: ++.

Example 2.14. Synthesis of 2-(sec-butyl)-7-((3-fluorophenyl)ethynyl)-3-methylquinazolin-4(3H)-one

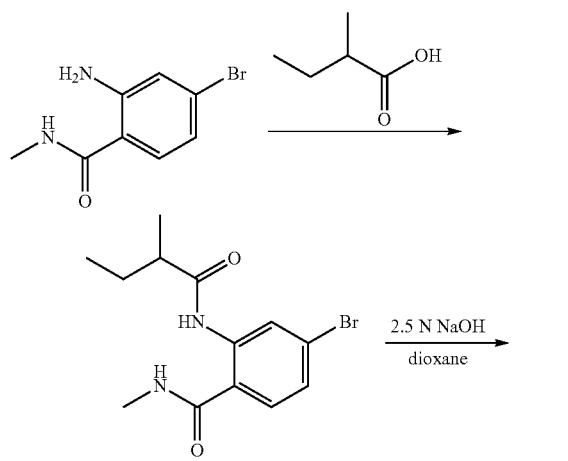

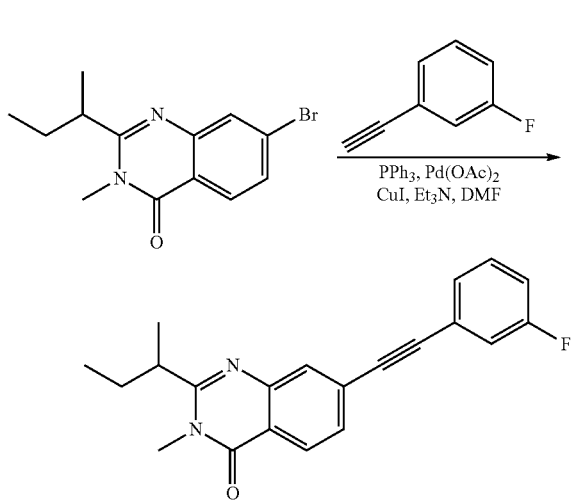

The title compound was prepared according to the experimental procedure described in Example 2.1b, Example 2.1c, and Example 1.1. MS (ESI): 335 (MH+); $^1$H NMR (300 MHz, CDCl$_3$) δ 8.26-8.23 (d, J=8.40 Hz, 1H), 7.85 (s, 1H), 7.55-7.52 (dd, J=8.1, 1.5 Hz, 1H), 7.38-7.33 (m, 2H), 7.25-7.20 (m, 1H), 7.12-7.05 (m, 1H), 3.68 (s, 3H), 3.02-2.95 (m, 1H), 2.05-1.96 (m, 1H), 1.72-1.57 (m, 1H), 1.38-1.36 (d, J=6.6 Hz, 3H), 1.02-0.97 (t, J=7.5 Hz, 3H). mGluR5 PAM EC$_{50}$: +.

Example 2.15. Synthesis of the HCl Salt of 2-(1-methoxyethyl)-3-methyl-7-(pyridin-2-ylethynyl)quinazolin-4(3H)-one

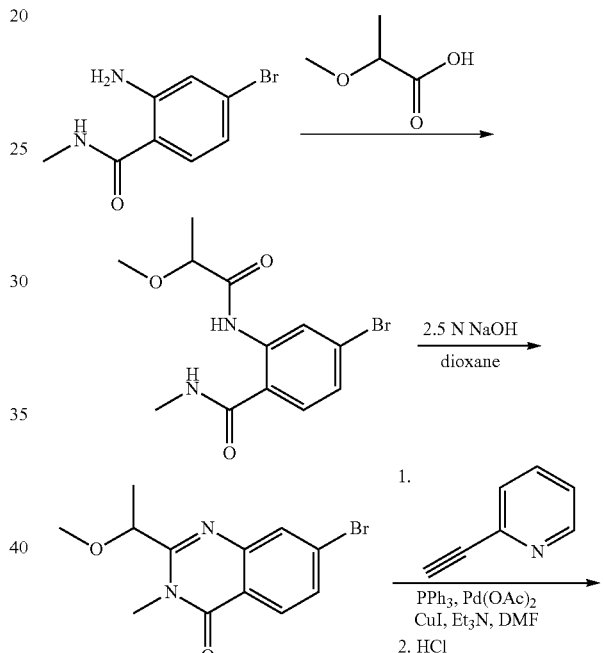

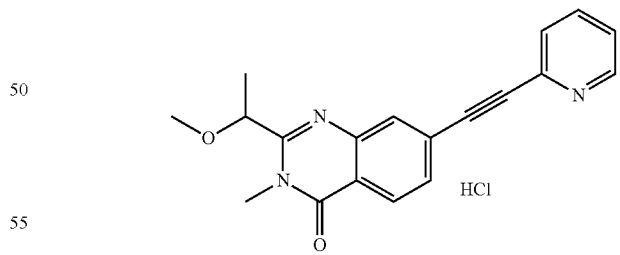

The title compound was prepared according to the experimental procedure described in Example 2.1b, Example 2.1c, and Example 1.1. The product was then converted to the corresponding HCl salt. MS (ESI): 320 (MH+); $^1$H NMR (300 MHz, CD$_3$OD) δ 8.95-8.93 (d, J=5.7 Hz, 1H), 8.70-8.64 (m, 1H), 8.48-8.45 (d, J=8.3 Hz, 1H), 8.36-8.34 (d, J=7.4 Hz, 2H), 8.17-8.11 (m, 1H), 8.06-8.03 (dd, J=8.2, 1.3 Hz, 1H), 5.13-5.07 (m, 1H), 3.85 (s, 3H), 3.60 (s, 3H), 1.69-1.67 (d, J=6.6 Hz, 3H).

Example 2.16. Synthesis of the HCl Salt of 2-(methoxymethyl)-3-methyl-7-(pyridin-2-ylethynyl)quinazolin-4(3H)-one

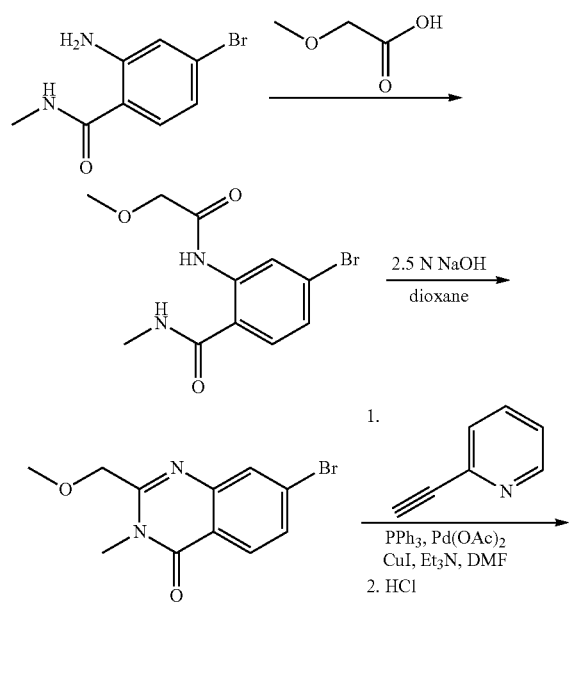

The title compound was prepared according to the experimental procedure described in Example 2.1b, Example 2.1c, and Example 1.1. The product was then converted to the corresponding HCl salt. MS (ESI): 306 (MH+); $^1$H NMR (300 MHz, CD$_3$OD) δ 8.94-8.92 (d, J=5.3 Hz, 1H), 8.68-8.62 (m, 1H), 8.48-8.45 (d, J=8.8 Hz, 1H), 8.35-8.32 (d, J=8.6 Hz, 2H), 8.12-8.02 (m, 2H), 4.99 (s, 2H), 3.72 (s, 3H), 3.67 (s, 3H).

Example 2.17. Synthesis of the HCl Salt of 2-(2-methoxypropan-2-yl)-3-methyl-7-(pyridin-2-ylethynyl)quinazolin-4(3H)-one

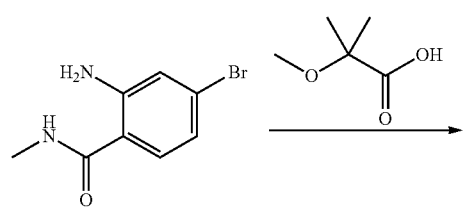

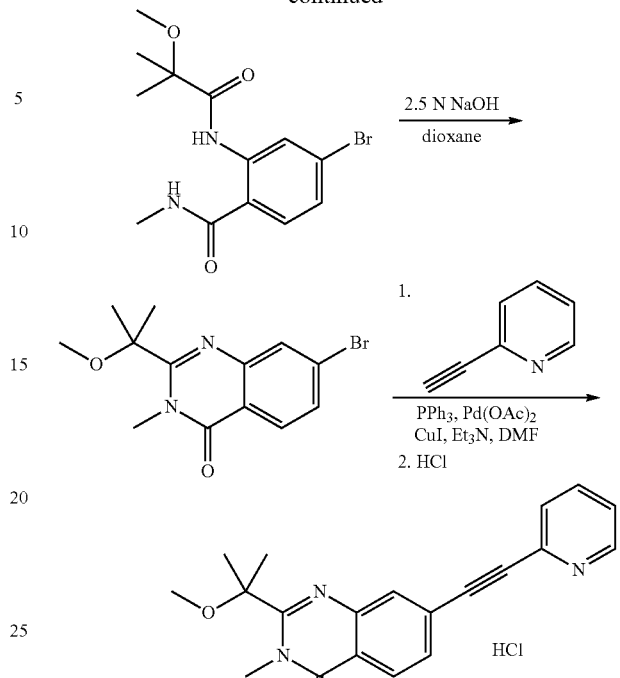

The title compound was prepared according to the experimental procedure described in Example 2.1b, Example 2.1c, and Example 1.1. The product was then converted to the corresponding HCl salt. MS (ESI): 334 (MH+); $^1$H NMR (300 MHz, CD$_3$OD) δ 8.93-8.91 (d, J=5.2 Hz, 1H), 8.71-8.66 (dt, J=8.0, 1.5 Hz, 1H), 8.35-8.32 (d, J=8.2 Hz, 2H), 8.13-8.08 (m, 2H), 7.84-7.81 (dd, J=8.2, 1.5 Hz, 1H), 3.95 (s, 3H), 3.26 (s, 3H), 1.75 (s, 6H).

Example 2.18. Synthesis of 7-((3-fluorophenyl)ethynyl)-2-(methoxymethyl)-3-methylquinazolin-4(3H)-one

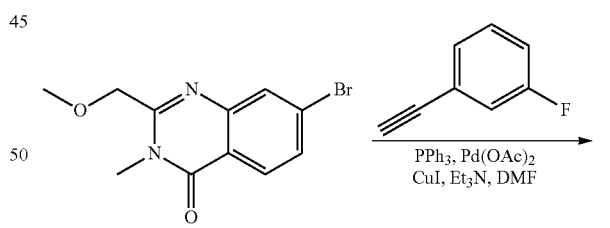

The title compound was prepared according to the experimental procedure described in Example 1.1. MS (ESI): 323 (MH+); $^1$H NMR (300 MHz, CDCl$_3$) δ 8.29-8.26 (d, J=8.22 Hz, 1H), 7.86 (s, 1H), 7.63-7.60 (d, J=8.21 Hz, 1H), 7.38-

7.35 (m, 2H), 7.30-7.27 (m, 1H), 7.12-7.09 (m, 1H), 4.60 (s, 2H), 3.72 (s, 3H), 3.51 (s, 3H). mGluR5 PAM EC$_{50}$: ++++. Fold shift at 10 μM: ++.

Example 2.19. Synthesis of the HCl Salt of 2-(1-ethoxyethyl)-3-methyl-7-(pyridin-2-ylethynyl)quinazolin-4(3H)-one

Example 2.20. Synthesis of the 2HCl Salt of 3-methyl-2-(1-(methylamino)ethyl)-7-(pyridin-2-ylethynyl)quinazolin-4(3H)-one

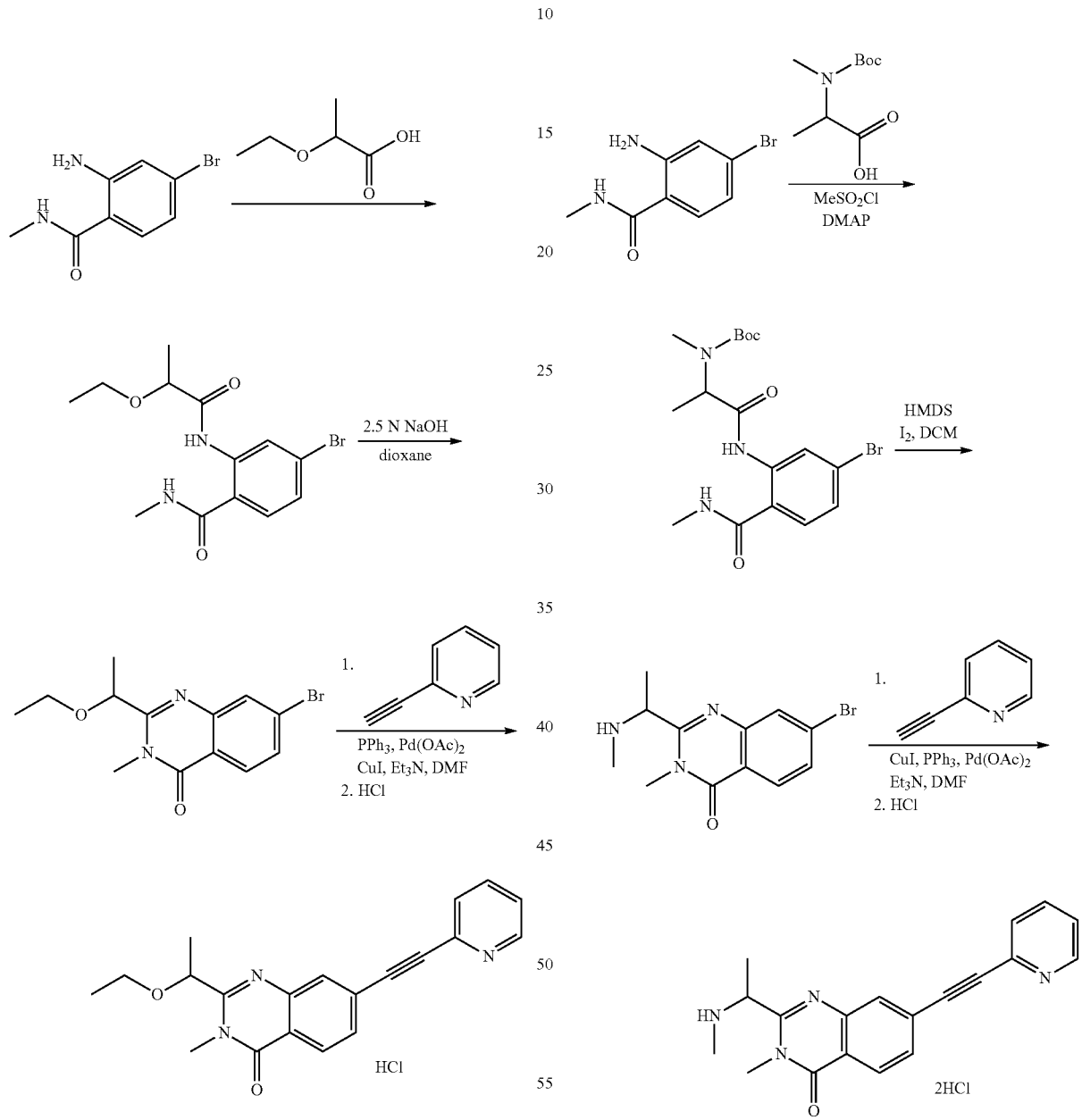

The title compound was prepared according to the experimental procedure described in Example 2.1b, Example 2.1c, and Example 1.1. The product was then converted to the corresponding HCl salt. MS (ESI): 334 (MH$^+$); $^1$H NMR (300 MHz, CD$_3$OD) δ 8.91-8.89 (d, J=4.9 Hz, 1H), 8.63-8.57 (dt, J=8.0, 1.5 Hz, 1H), 8.45-8.42 (d, J=8.2 Hz, 1H), 8.30-8.26 (m, 2H), 8.08-8.05 (m, 1H), 8.00-7.97 (dd, J=8.2, 1.4 Hz, 1H), 5.16-5.09 (q, 1H), 3.77 (s, 3H), 3.75-3.71 (q, 2H), 1.69-1.66 (d, J=6.3 Hz, 3H), 1.37-1.31 (t, J=7.0 Hz, 3H).

The title compound was prepared according to the experimental procedure described in Example 2.1b, Example 2.4b, and Example 1.1. The product was then converted to the corresponding 2HCl salt. MS (ESI): 319 (MH$^+$); $^1$H NMR (300 MHz, CD$_3$OD) δ 8.94-8.92 (d, J=5.9 Hz, 1H), 8.71-8.66 (dt, J=8.0, 1.5 Hz, 1H), 8.38-8.32 (m, 2H), 8.14-8.09 (m, 2H), 7.88-7.85 (dd, J=8.2, 1.5 Hz, 1H), 4.87-4.83 (m, 1H), 3.69 (s, 3H), 2.86 (s, 3H), 1.75-1.72 (d, J=6.9 Hz, 3H).

Example 2.21. Synthesis of 2-(1-(dimethylamino) ethyl)-3-methyl-7-(pyridin-2-ylethynyl)quinazolin-4 (3H)-one

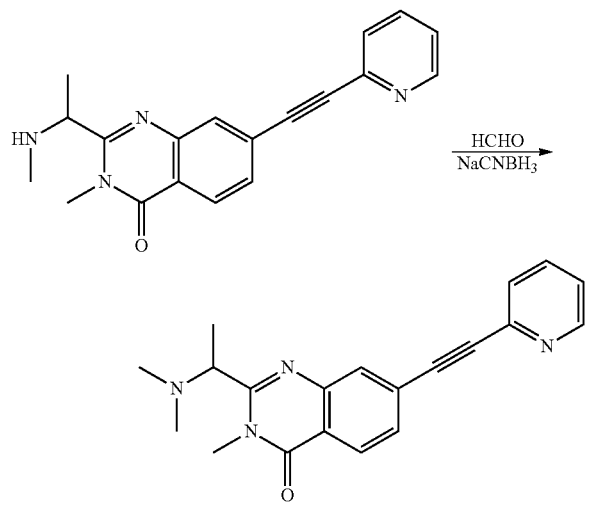

The title compound was prepared according to the experimental procedure described in Example 1.21d. MS (ESI): 333 (MH$^+$); $^1$H NMR (300 MHz, CD$_3$OD) δ 8.94-8.92 (d, J=8.0 Hz, 1H), 8.71-8.66 (dt, J=8.0, 1.5 Hz, 1H), 8.38-8.32 (m, 2H), 8.17-8.10 (m, 2H), 7.88-7.85 (dd, J=8.2, 1.5 Hz, 1H), 5.02-4.95 (m, 1H), 3.70 (s, 3H), 3.16 (s, 3H), 3.03 (s, 3H), 1.78-1.76 (d, J=6.9 Hz, 3H). mGluR5 PAM EC$_{50}$: ++.

Example 2.22. Synthesis of the 2HCl Salt of 2-(1-(isopropyl(methyl)amino)ethyl)-3-methyl-7-(pyridin-2-ylethynyl)quinazolin-4(3H)-one

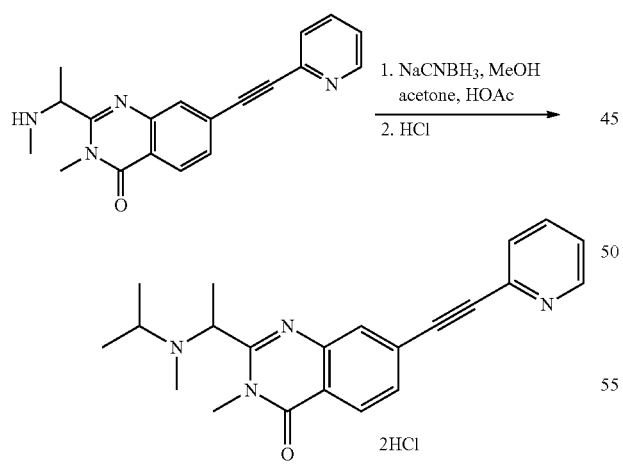

The title compound was prepared according to the experimental procedure described in Example 1.21d. The product was then converted to the corresponding 2HCl salt. MS (ESI): 361 (MH$^+$); $^1$H NMR (300 MHz, CD$_3$OD) δ 8.91-8.89 (d, J=5.0 Hz, 1H), 8.65-8.60 (m, 1H), 8.39-8.36 (d, J=8.3 Hz, 1H), 8.30-8.27 (d, J=8.0 Hz, 1H), 8.13 (s, 1H), 8.09-8.04 (dt, J=5.70, 1.1 Hz, 1H), 7.89-7.86 (dd, J=8.2, 1.5 Hz, 1H), 5.06-5.04 (m, 1H), 3.82-3.76 (m, 1H), 3.69 (s, 3H), 2.89 (s, 3H), 1.76-1.73 (d, J=6.6 Hz, 3H), 1.48-1.45 (d, J=6.6 Hz, 3H), 1.34-1.32 (d, J=6.9 Hz, 3H). mGluR5 PAM EC$_{50}$: +.

Example 2.23. Synthesis of the 2HCl Salt of 2-(1-(cyclobutyl(methyl)amino)ethyl)-3-methyl-7-(pyridin-2-ylethynyl)quinazolin-4(3H)-one

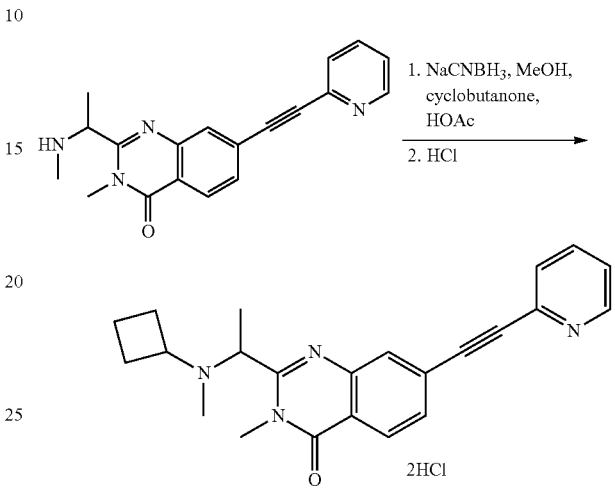

The title compound was prepared according to the experimental procedure described in Example 1.21d. The product was then converted to the corresponding 2HCl salt. MS (ESI): 373 (MH$^+$); $^1$H NMR (300 MHz, CD$_3$OD) δ 8.95-8.93 (d, J=5.8 Hz, 1H), 8.70-8.67 (dt, J=8.0, 1.4 Hz, 1H), 8.38-8.35 (m, 2H), 8.20-8.10 (m, 2H), 7.90-7.87 (dd, J=8.2, 1.4 Hz, 1H), 5.03-4.94 (m, 1H), 4.23-4.09 (m, 1H), 3.72 (s, 3H), 3.21-3.18 (m, 1H), 3.06-2.97 (m, 3H), 2.39-2.10 (m, 3H), 1.78-1.76 (d, J=6.6 Hz, 3H), 0.91-0.78 (m, 1H), 0.46-0.36 (m, 1H). mGluR5 PAM EC$_{50}$: +.

Example 2.24. Synthesis of the 2HCl Salt of 2-(azetidin-2-yl)-3-methyl-7-(pyridin-2-ylethynyl) quinazolin-4(3H)-one

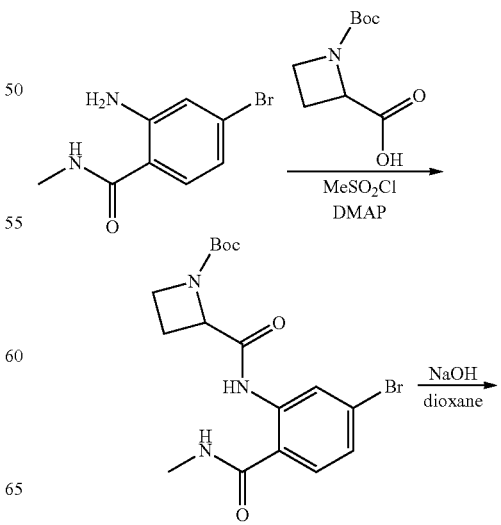

145

-continued

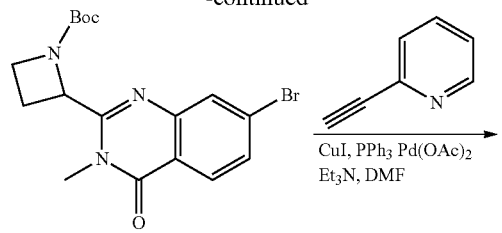

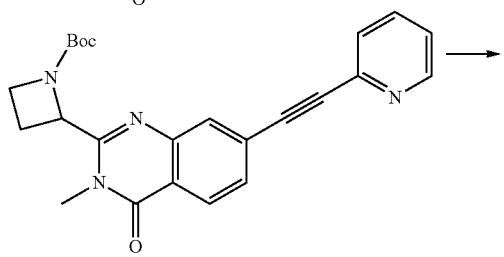

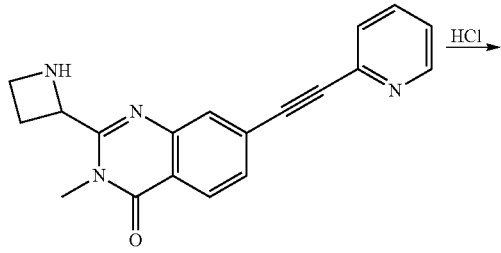

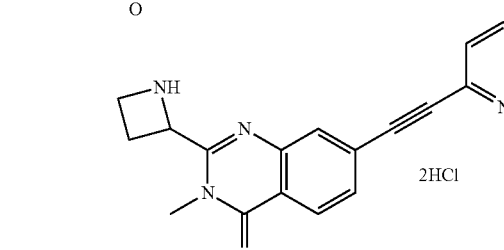

The title compound was prepared according to the experimental procedure described in Example 2.1b, Example 2.1c, Example 1.1, and Example 1.21c. The product was then converted to the corresponding 2HCl salt. MS (ESI): 317 (MH⁺); ¹H NMR (300 MHz, CD₃OD) δ 8.85-8.83 (d, J=5.6 Hz, 1H), 8.51-8.46 (t, J=7.7 Hz, 1H), 8.38-7.35 (d, J=8.2 Hz, 1H), 8.19-8.16 (m, 2H), 7.97-7.93 (t, J=6.6 Hz, 1H), 7.88-7.84 (d, J=8.2 Hz, 1H), 5.92-5.86 (t, J=8.7 Hz, 1H), 4.37-4.28 (m, 1H), 4.15-4.08 (m, 1H), 3.51 (s, 3H), 3.19-3.11 (m, 1H), 2.88-2.78 (m, 1H).

Example 2.25. Synthesis of the 2HCl Salt of 3-methyl-2-(1-methylazetidin-2-yl)-7-(pyridin-2-ylethynyl)quinazolin-4(3H)-one

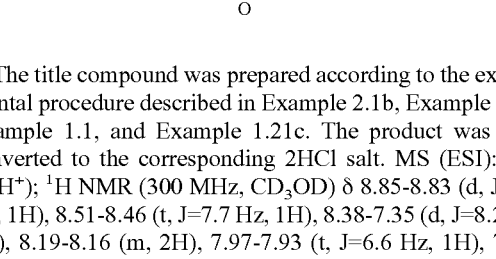

146

-continued

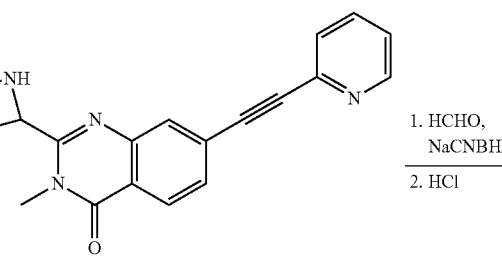

The title compound was prepared according to the experimental procedure described in Example 1.21d. The product was then converted to the corresponding 2HCl salt. MS (ESI): 331 (MH⁺); ¹H NMR (300 MHz, CD₃OD) δ 8.94-8.92 (d, J=5.8 Hz, 1H), 8.71-8.65 (t, J=8.0 Hz, 1H), 8.39-8.33 (t, J=8.4 Hz, 2H), 8.22-8.21 (d, J=1.14 Hz, 1H), 8.14-8.09 (t, J=6.85 Hz, 1H), 7.90-7.87 (dd, J=8.2, 1.5 Hz, 1H), 5.92-5.85 (t, J=9.1 Hz, 1H), 4.31-4.23 (m, 2H), 3.51 (s, 3H), 3.14 (s, 3H), 3.12-3.05 (m, 1H), 2.81-2.74 (m, 1H).

Example 2.26. Synthesis of the 2HCl Salt of 2-(azetidin-3-yl)-3-methyl-7-(pyridin-2-ylethynyl)quinazolin-4(3H)-one

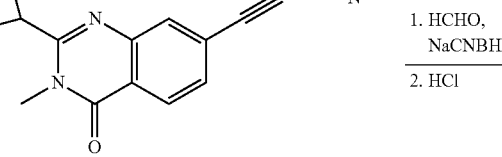

-continued

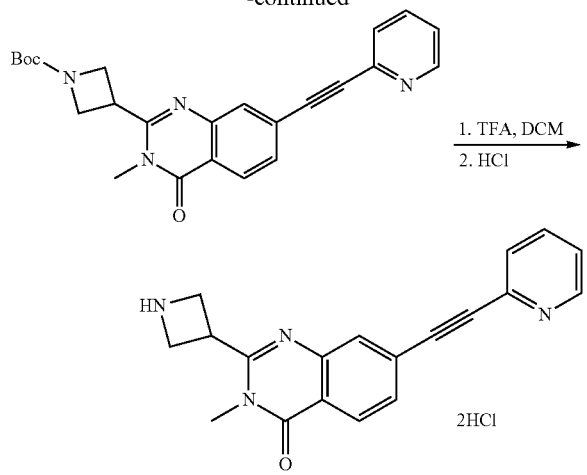

1. TFA, DCM
2. HCl

2HCl

Example 2.26a. Synthesis of tert-butyl 3-(5-bromo-2-(methylcarbamoyl)phenylcarbamoyl)azetidine-1-carboxylate

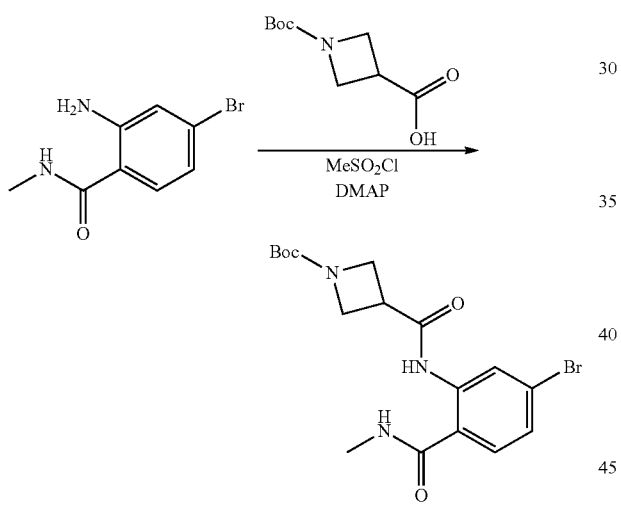

MeSO₂Cl
DMAP

The title compound was prepared according to the experimental procedure described in Example 2.1b.

Example 2.26b. Synthesis of 2-(azetidin-3-yl)-7-bromo-3-methylquinazolin-4(3H)-one

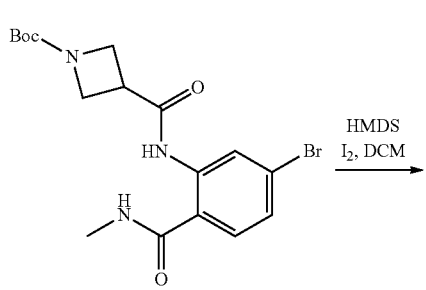

HMDS
I₂, DCM

-continued

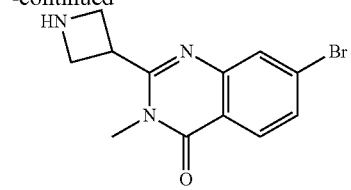

The title compound was prepared according to the experimental procedure described in Example 2.4b.

Example 2.26c. Synthesis of tert-butyl 3-(7-bromo-3-methyl-4-oxo-3,4-dihydroquinazolin-2-yl)azetidine-1-carboxylate

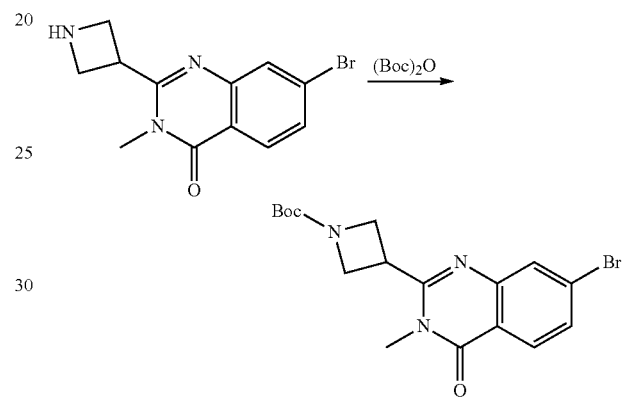

(Boc)₂O

The title compound was prepared according to the experimental procedure described in Example 6.20a.

Example 2.26d. Synthesis of tert-butyl 3-(3-methyl-4-oxo-7-(pyridin-2-ylethynyl)-3,4-dihydroquinazolin-2-yl)azetidine-1-carboxylate

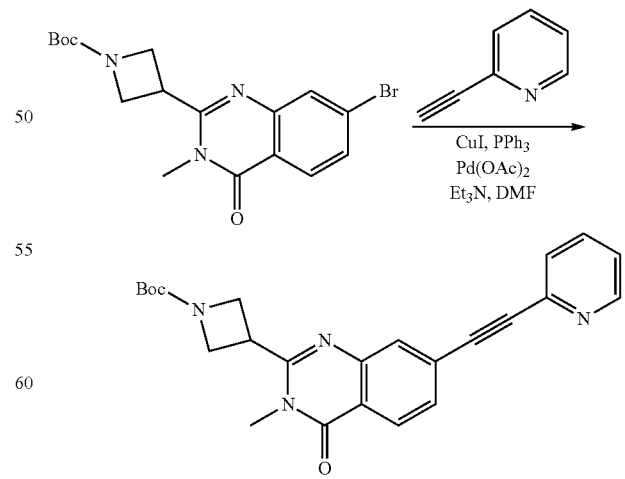

CuI, PPh₃
Pd(OAc)₂
Et₃N, DMF

The title compound was prepared according to the experimental procedure described in Example 1.1.

Example 2.26e. Synthesis of the 2HCl Salt of 2-(azetidin-3-yl)-3-methyl-7-(pyridin-2-ylethynyl)quinazolin-4(3H)-one

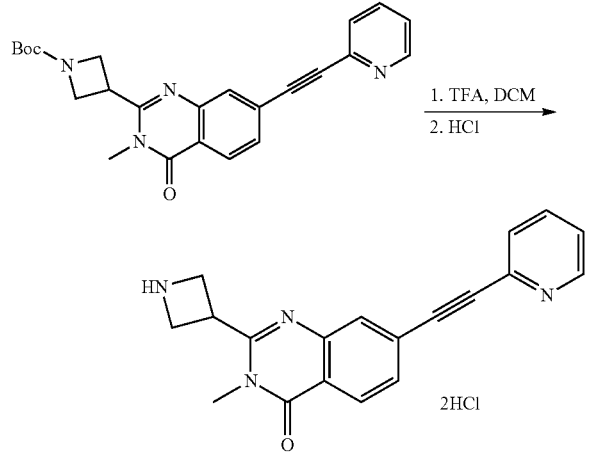

The title compound was prepared according to the experimental procedure described in Example 1.21c. The product was then converted to the corresponding 2HCl salt. MS (ESI): 317 (MH+); 1H NMR (300 MHz, CD3OD) δ 8.94-8.92 (d, J=5.4 Hz, 1H), 8.71-8.65 (m, 1H), 8.35-8.32 (d, J=8.1 Hz, 2H), 8.15-8.09 (m, 2H), 7.86-7.82 (dd, J=8.2, 1.5 Hz, 1H), 4.73-4.48 (m, 5H), 3.53 (s, 3H).

Example 2.27. Synthesis of the 2HCl Salt of 3-methyl-2-(1-methylazetidin-3-yl)-7-(pyridin-2-ylethynyl)quinazolin-4(3H)-one

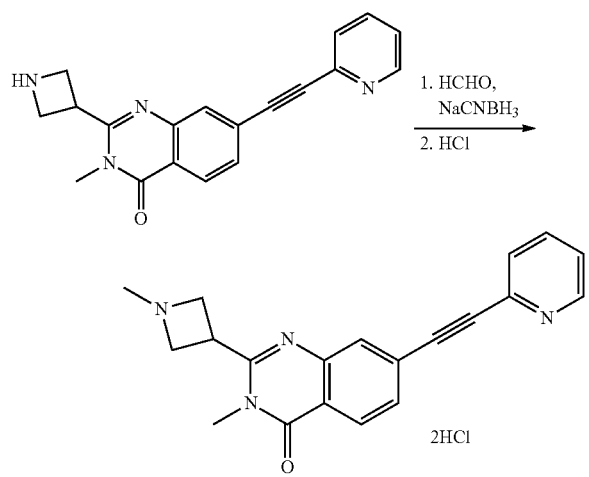

The title compound was prepared according to the experimental procedure described in Example 1.21d. The product was then converted to the corresponding 2HCl salt. MS (ESI): 331 (MH+); 1H NMR (300 MHz, CD3OD) δ 8.29-8.26 (d, J=8.22 Hz, 1H), 7.86 (s, 1H), 7.63-7.60 (d, J=8.21 Hz, 1H), 7.38-7.35 (m, 2H), 7.30-7.27 (m, 1H), 7.12-7.09 (m, 1H), 4.80 (m, 1H), 4.65-4.50 (m, 2H), 4.50-4.40 (m, 2H), 3.51 (s, 3H), 3.04 (s, 3H).

Example 2.28. Synthesis of the 2HCl Salt of 2-(1-isopropylazetidin-3-yl)-3-methyl-7-(pyridin-2-ylethynyl)quinazolin-4(3H)-one

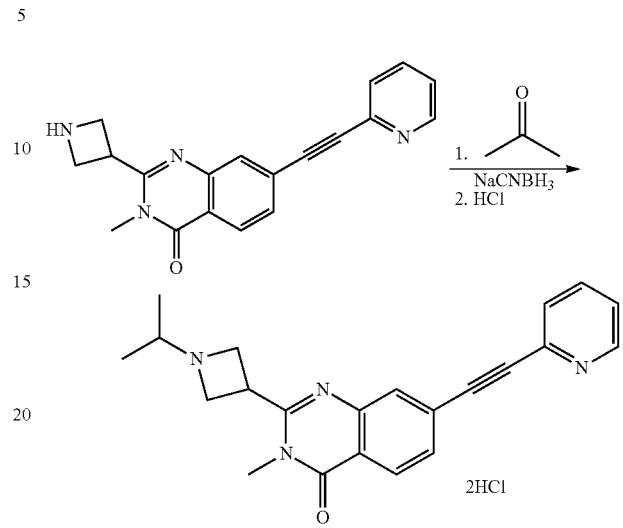

The title compound was prepared according to the experimental procedure described in Example 1.21d. The product was then converted to the corresponding 2HCl salt. MS (ESI): 359 (MH+); 1H NMR (300 MHz, CD3OD) δ 8.93-8.91 (d, J=5.6 Hz, 1H), 8.70-8.65 (m, 1H), 8.37-8.32 (m, 2H), 8.19-8.08 (m, 2H), 7.86-7.82 (m, 1H), 4.83-4.78 (m, 1H), 4.67-4.52 (m, 4H), 3.58-3.54 (m, 4H), 1.36-1.33 (m, 6H).

Example 2.29. Synthesis of 2-(3-(3-methyl-4-oxo-7-(pyridin-2-ylethynyl)-3,4-dihydroquinazolin-2-yl)azetidin-1-yl)acetonitrile

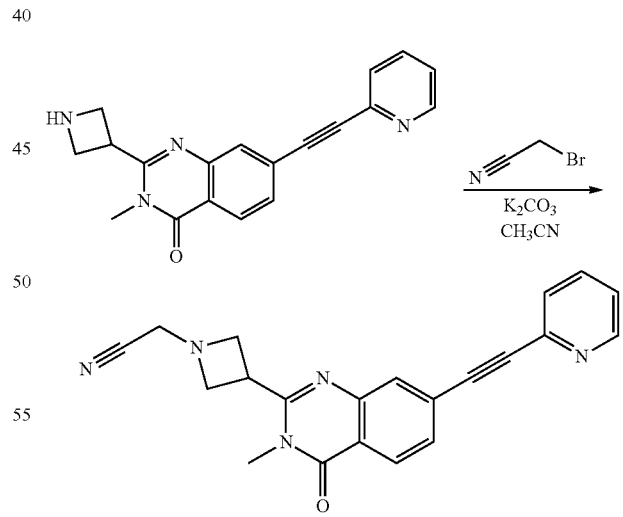

The mixture of 2-(azetidin-3-yl)-3-methyl-7-(pyridin-2-ylethynyl)quinazolin-4(3H)-one (100 mg, 0.316 mmol), 2-bromoacetonitrile (0.024 mL, 0.348 mmol), K2CO3 (87 mg, 0.632 mmol) and CH3CN (5 mL) was stirred at room temperature for 3 h, then diluted with water (10 mL). The mixture was then extracted with ethyl acetate (3×10 mL). The combined organic layers were dried over Na2SO4, filtered, and evaporated to give the crude product, which was purified by column chromatography to give 50 mg of the desired product. MS (ESI): 356 (MH+); $^1$H NMR (300 MHz, CDCl$_3$) δ 8.68-8.67 (d, J=4.4 Hz, 1H), 8.27-8.24 (d, J=8.2 Hz, 1H), 7.95 (s, 1H), 7.77-7.71 (m, 1H), 7.67-7.64 (dd, J=8.2, 1.5 Hz, 1H), 7.60-7.58 (d, J=7.8 Hz, 1H), 7.33-7.28 (m, 1H), 3.92-3.89 (m, 5H), 3.56 (s, 2H), 3.50 (s, 3H).

Example 2.30. Synthesis of the HCl Salt of 3-methyl-2-(oxetan-2-yl)-7-(pyridin-2-ylethynyl)quinazolin-4(3H)-one

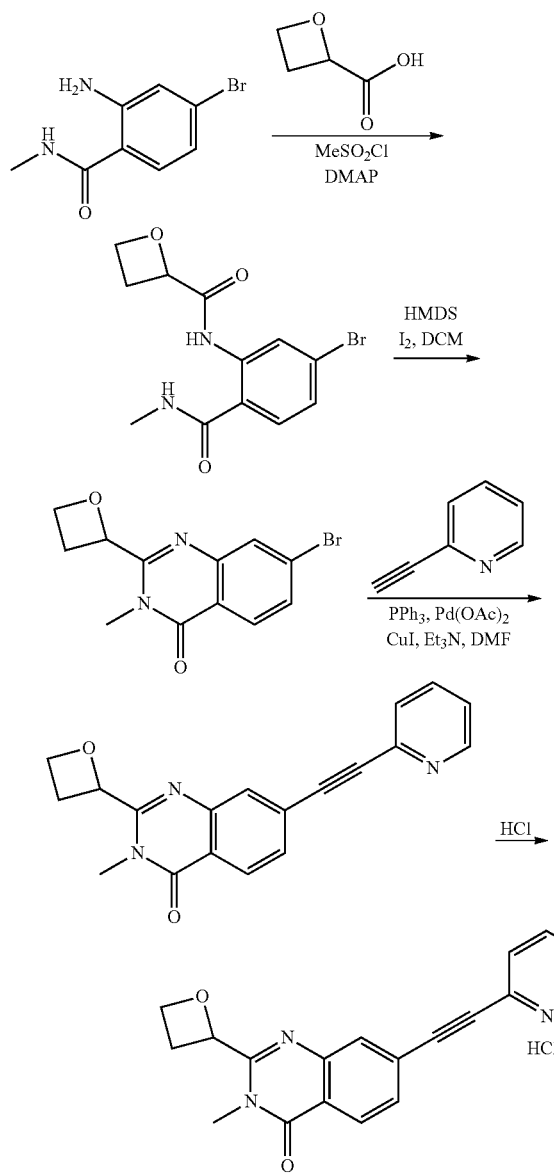

The title compound was prepared according to the experimental procedure described in Example 2.1b, Example 2.4b, and Example 1.1. The product was then converted to the corresponding HCl salt. MS (ESI): 318 (MH+); $^1$H NMR (300 MHz, CD$_3$OD) δ 8.68-8.66 (d, J=4.7 Hz, 1H), 8.30-8.28 (d, J=8.2 Hz, 1H), 8.01-8.00 (d, J=0.9 Hz, 1H), 7.77-7.69 (m, 2H), 7.61-7.58 (d, J=7.8 Hz, 1H), 7.33-7.29 (m, 1H), 5.85-5.80 (dd, J=7.8, 6.6 Hz, 1H), 4.85-4.79 (m, 1H), 4.72-4.65 (m, 1H), 3.65-3.60 (m, 1H), 3.57 (s, 3H), 3.07-3.01 (m, 1H).

Example 3.1. Synthesis of 6-((3-fluorophenyl)ethynyl)-2,3-dihydropyrrolo[2,1-b]quinazolin-9(1H)-one

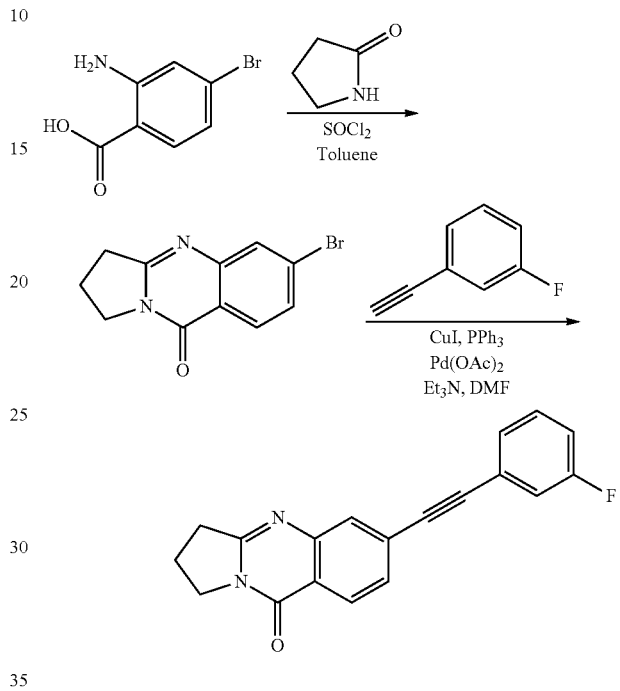

The title compound was prepared according to the experimental procedure as described in Example 2.2a and Example 1.1. MS (ESI): 305 (MH+); $^1$H NMR (300 MHz, CDCl$_3$) δ 8.28-8.25 (d, J=8.16 Hz, 1H), 7.80 (s, 1H), 7.58-7.55 (d, J=8.24 Hz, 1H), 7.38-7.34 (m, 2H), 7.28-7.26 (m, 1H), 7.13-7.06 (m, 1H), 4.25-4.20 (t, J=7.23 Hz, 2H), 3.23-3.18 (t, J=7.95 Hz, 2H), 2.37-2.27 (m, 2H). mGluR5 PAM EC$_{50}$: +++++. Fold shift at 10 μM: +.

Example 3.2. Synthesis of the HCl Salt of 6-(pyridin-2-ylethynyl)-2,3-dihydropyrrolo[2,1-b]quinazolin-9(1H)-one

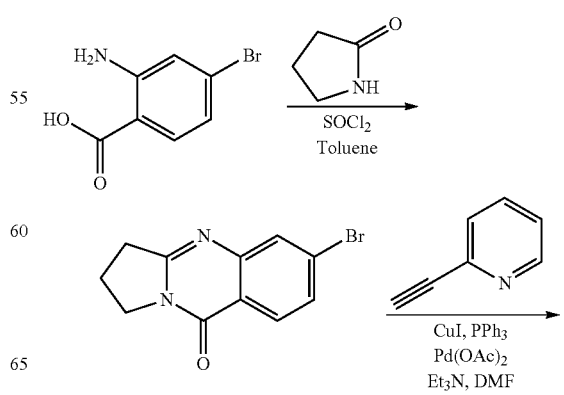

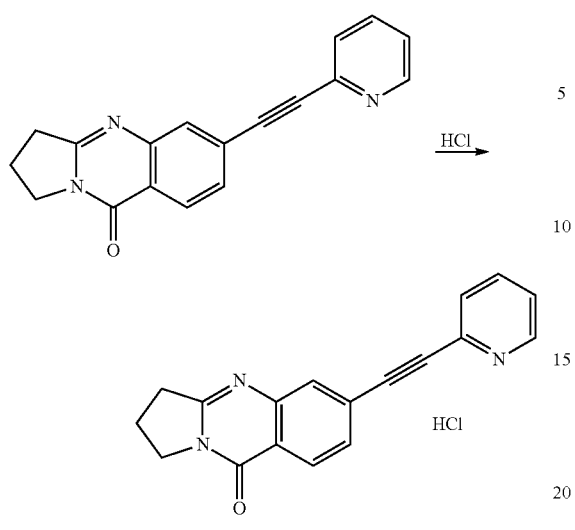

The title compound was prepared according to the experimental procedure as described in Example 2.2a and Example 1.1. The product was then converted to the corresponding HCl salt. MS (ESI): 288 (MH$^+$); $^1$H NMR (300 MHz, DMSO-d$^6$) δ 8.73-8.72 (d, J=4.43 Hz, 1H), 8.23-8.20 (d, J=8.22 Hz, 1H), 8.09-8.03 (m, 1H), 7.96 (s, 1H), 7.89-7.86 (d, J=7.80 Hz, 1H), 7.77-7.74 (dd, J=8.22, 1.38 Hz, 1H), 7.63-7.58 (m, 1H), 4.14-4.09 (t, J=7.3 Hz, 2H), 3.28-3.22 (t, J=7.89 Hz, 2H), 2.29-2.19 (m, 2H).

Example 3.3. Synthesis of the HCl Salt of 6-((3-fluorophenyl)ethynyl)-1-((methylamino)methyl)-2,3-dihydropyrrolo[2,1-b]quinazolin-9(1H)-one

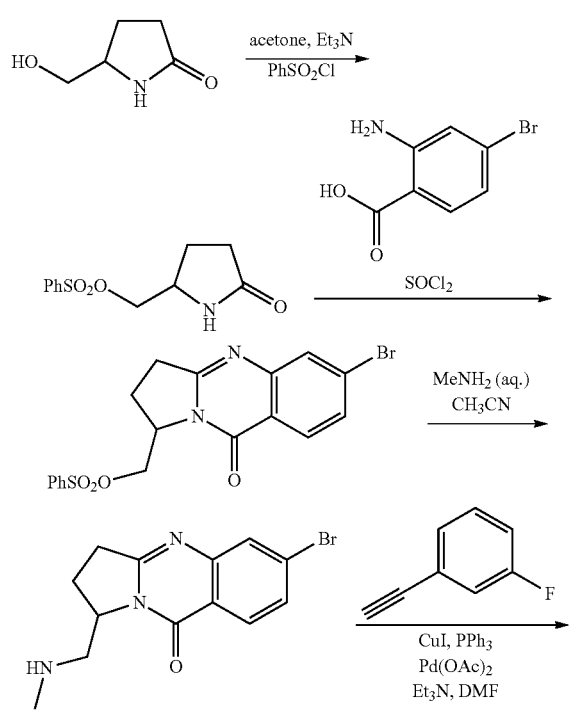

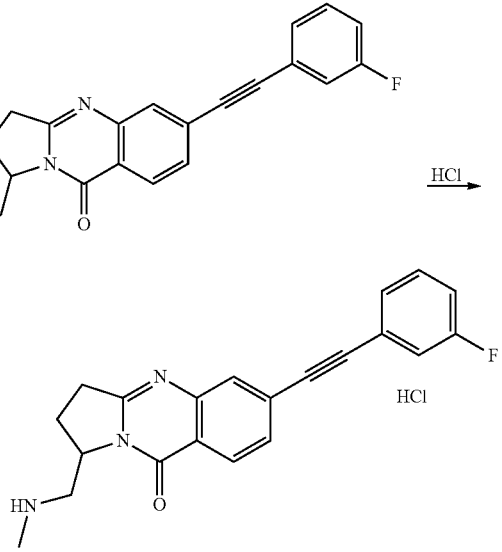

Example 3.3a. Synthesis of (5-oxopyrrolidin-2-yl)methyl benzenesulfonate

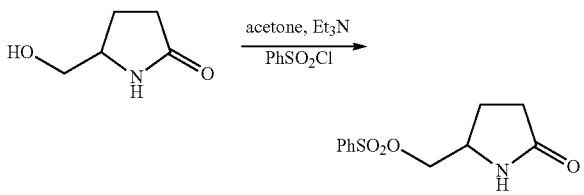

To a stirred solution of 5-(hydroxymethyl)pyrrolidin-2-one (1.0 g, 8.7 mmol) in acetone (80 mL) was added Et$_3$N (1.8 g, 17.4 mmol) and benzenesulfonyl chloride (3.1 g, 17.4 mmol). The mixture was stirred for 3 h at room temperature. Then the reaction mixture was filtered and concentrated, and the crude product was purified by column chromatography to give the desired product. MS (ESI): 256 (MH$^+$).

Example 3.3b. Synthesis of (6-bromo-9-oxo-1,2,3,9-tetrahydropyrrolo[2,1-b]quinazolin-1-yl)methyl benzenesulfonate

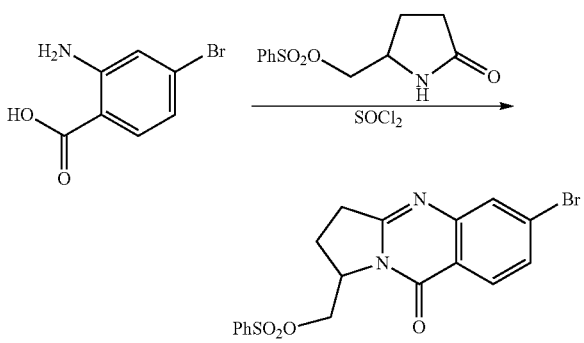

The title compound was prepared according to the experimental procedure as described in Example 2.2a. MS (ESI): 435, 437 (MH+).

Example 3.3c. Synthesis of 6-bromo-1-((methylamino)methyl)-2,3-dihydro pyrrolo[2,1-b]quinazolin-9(1H)-one

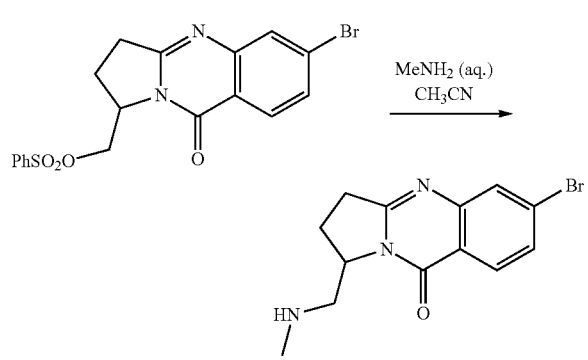

To the solution of (6-bromo-9-oxo-1,2,3,9-tetrahydropyrrolo[2,1-b]quinazolin-1-yl) methyl benzenesulfonate (100 mg, 0.23 mmol) in acetonitrile (4 mL) was added aq. methylamine (2 mL). The reaction mixture was stirred at 60° C. for 4 h. After concentration, the crude product was purified by column chromatography to give the desired product. MS (ESI): 308, 310 (MH+).

Example 3.3d. Synthesis of the HCl Salt of 64(3-fluorophenyl)ethynyl)-1-((methylamino)methyl)-2,3-dihydropyrrolo[2,1-b]quinazolin-9(1H)-one

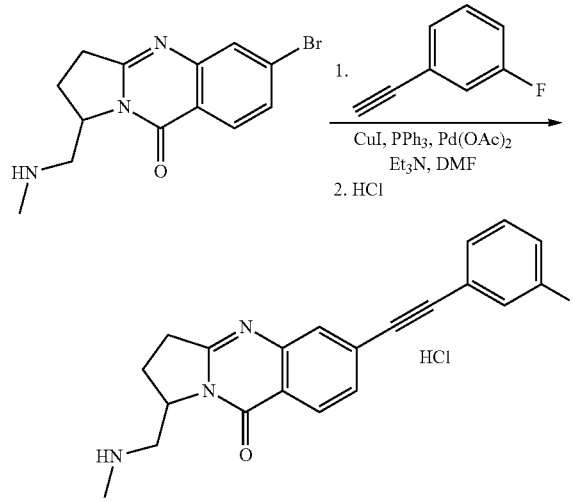

The title compound was prepared according to the experimental procedure as described in Example 1.1. The product was then converted to the corresponding HCl salt. MS (ESI): 348 (MH+). MS (ESI): 348 (MH+); $^1$H NMR (300 MHz, DMSO-d$^6$) δ 8.96-8.83 (m, 2H), 8.18-8.15 (d, J=8.16 Hz, 1H), 7.81 (s, 1H), 7.67-7.64 (dd, J=8.19, 1.53 Hz, 1H), 7.56-7.47 (m, 3H), 7.37-7.30 (m, 1H), 4.96-4.94 (m, 1H), 3.42-3.31 (m, 3H), 3.06-2.79 (m, 1H), 2.66-2.55 (m, 3H), 2.47-2.35 (m, 1H), 2.79-2.22 (m, 1H).

Example 3.4. Synthesis of the HCl Salt of 1-((dimethylamino)methyl)-6-((3-fluorophenyl)ethynyl)-2,3-dihydropyrrolo[2,1-b]quinazolin-9(1H)-one

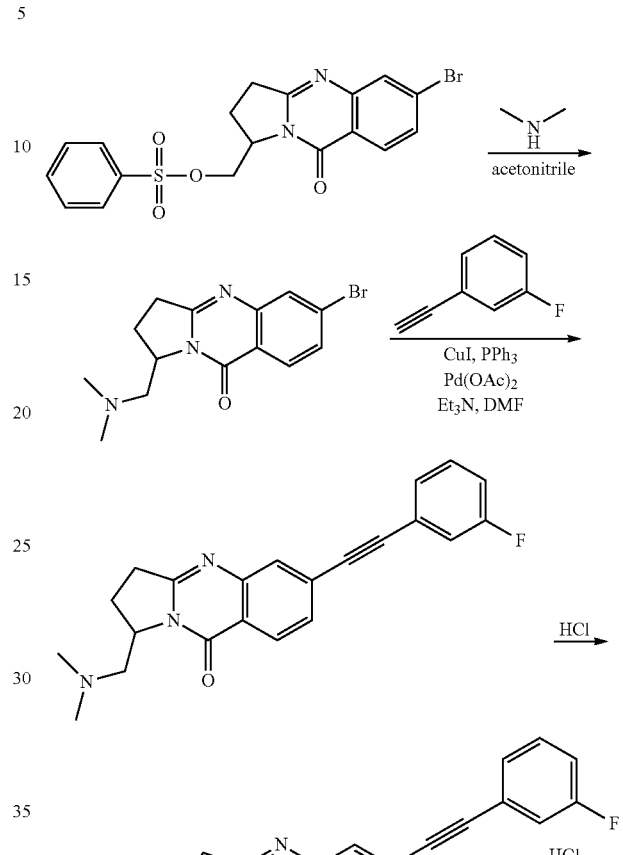

The title compound was prepared according to the experimental procedure as described in Example 3.3c and Example 1.1. The product was then converted to the corresponding HCl salt. MS (ESI): 362 (MH+); $^1$H NMR (300 MHz, CD$_3$OD) δ 8.36-8.33 (d, J=8.37 Hz, 1H), 7.85 (s, 1H), 7.79-7.76 (dd, J=8.30, 1.31 Hz, 1H), 7.51-7.43 (m, 2H), 7.38-7.34 (m, 1H), 7.26-7.19 (m, 1H), 5.25-5.22 (m, 1H), 3.86-3.80 (m, 1H), 3.59-3.45 (m, 2H), 3.38-3.33 (m, 1H), 3.19 (s, 3H), 3.05 (s, 3H), 2.77-2.70 (m, 1H), 2.30-2.18 (m, 1H). mGluR5 PAM EC$_{50}$: ++.

Example 3.5. Synthesis of 6-((3-fluorophenyl)ethynyl)-1-(hydroxymethyl)-2,3-dihydropyrrolo[2,1-b]quinazolin-9(1H)-one

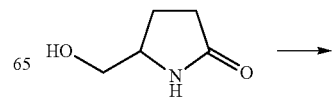

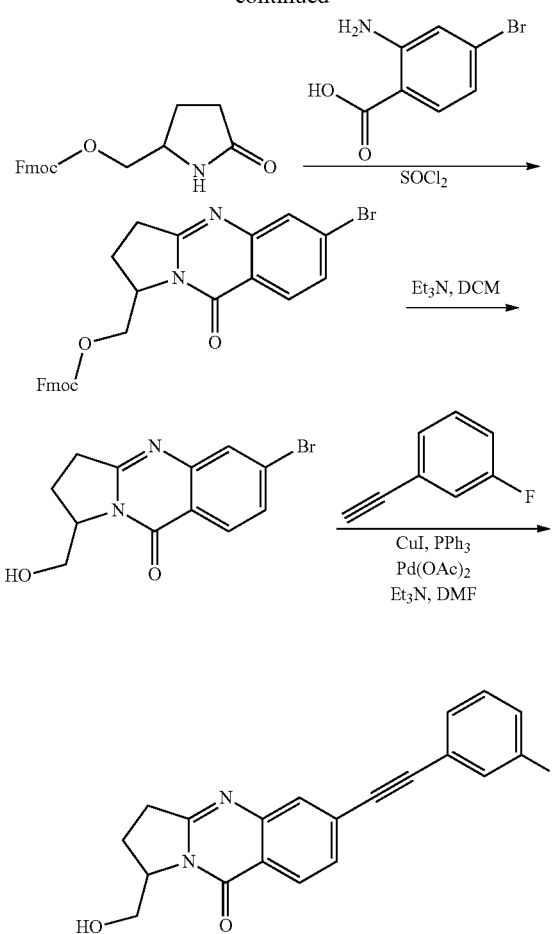

Example 3.5a. Synthesis of (9H-fluoren-9-yl)methyl (5-oxopyrrolidin-2-yl)methyl carbonate

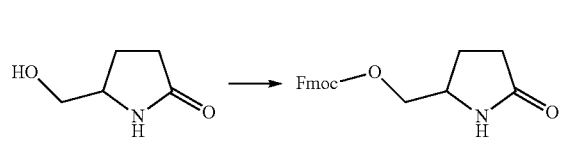

The title compound was prepared according to the experimental procedure as described in Example 5.1a.

Example 3.5b. Synthesis of (9H-fluoren-9-yl)methyl (6-bromo-9-oxo-1,2,3,9-tetrahydropyrrolo[2,1-b]quinazolin-1-yl)methyl carbonate

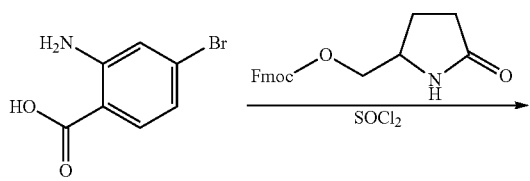

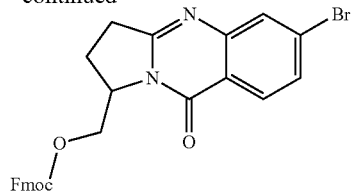

The title compound was prepared according to the experimental procedure as described in Example 2.2a.

Example 3.5c. Synthesis of 6-bromo-1-(hydroxymethyl)-2,3-dihydropyrrolo[2,1-b]quinazolin-9(1H)-one

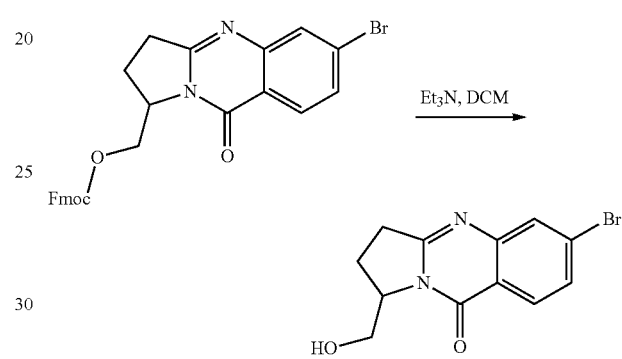

The title compound was prepared according to the experimental procedure as described in Example 3.17b.

Example 3.5d. Synthesis of 64(3-fluorophenyl)ethynyl)-1-(hydroxymethyl)-2,3-dihydropyrrolo[2,1-b]quinazolin-9(1H)-one

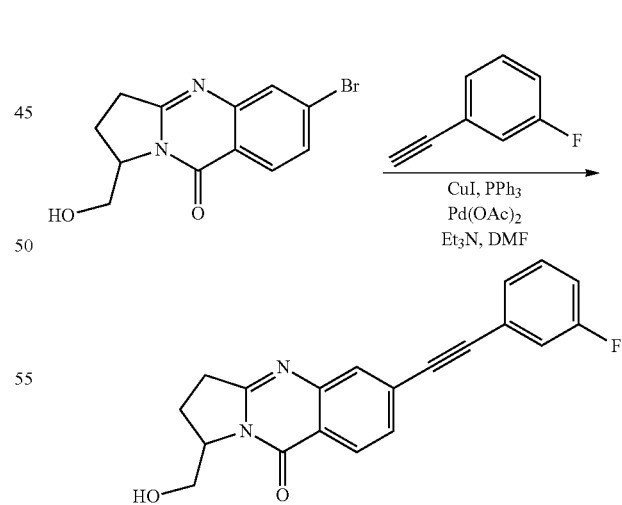

The title compound was prepared according to the experimental procedure as described in Example 1.1. MS (ESI): 358 (MH⁺); ¹H NMR (300 MHz, CD₃OD) δ 8.90-8.88 (d, J=5.0 Hz, 1H), 8.61-8.55 (t, J=7.9 Hz, 1H), 8.40-8.37 (d, J=8.3 Hz, 1H), 8.28-8.25 (d, J=7.9 Hz, 1H), 8.06-8.01 (m, 2H), 7.91-7.88 (d, J=8.3 Hz, 1H), 4.19 (s, 2H), 3.80-3.75 (t, J=5.1 Hz, 4H), 3.36 (s, 2H), 1.90-1.76 (broad, 4H). mGluR5 PAM $EC_{50}$: +++. Fold shift at 10 μM: +++.

Example 3.6. Synthesis of 6-((3-fluorophenyl)ethynyl)-1-(methoxymethyl)-2,3-dihydropyrrolo[2,1-b]quinazolin-9(1H)-one

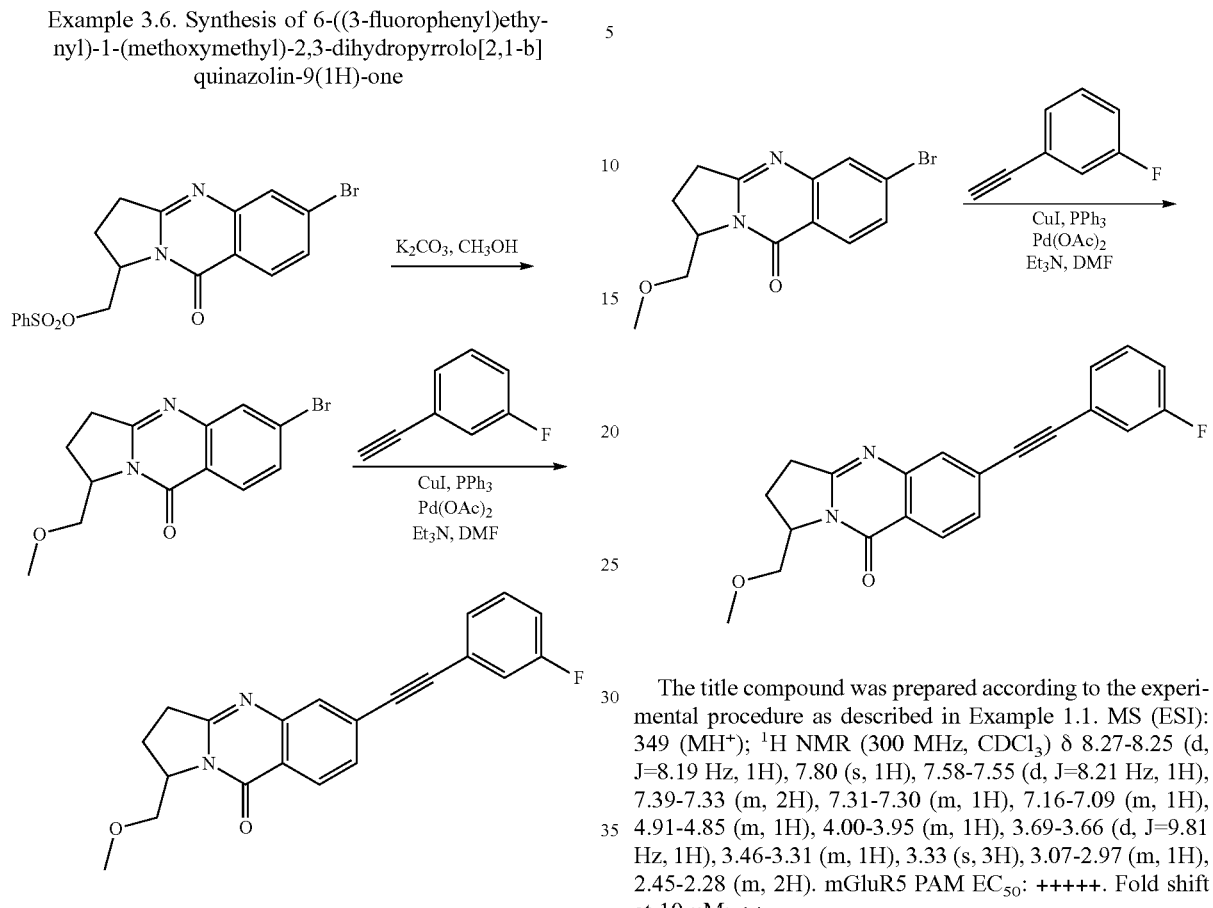

Example 3.6a. Synthesis of 6-bromo-1-(methoxymethyl)-2,3-dihydropyrrolo[2,1-b]quinazolin-9(1H)-one A solution of 6-bromo-9-oxo-1,2,3,9-tetrahydropyrrolo[2,1-b]quinazolin-1-yl benzenesulfonate (300 mg, 0.69 mmol) and potassium carbonate (290 mg, 2.1 mmol) in methanol (80 mL) was stirred at reflux for 2 h. After it was cooled to room temperature, the mixture was concentrated and purified by silica-gel chromatography to give the desired product. MS (ESI): 309, 311 ($MH^+$).

Example 3.6b. Synthesis of 64(3-fluorophenyl)ethynyl)-1-(methoxymethyl)-2,3-dihydropyrrolo[2,1-b]quinazolin-9(1H)-one The title compound was prepared according to the experimental procedure as described in Example 1.1. MS (ESI): 349 ($MH^+$); $^1$H NMR (300 MHz, $CDCl_3$) δ 8.27-8.25 (d, J=8.19 Hz, 1H), 7.80 (s, 1H), 7.58-7.55 (d, J=8.21 Hz, 1H), 7.39-7.33 (m, 2H), 7.31-7.30 (m, 1H), 7.16-7.09 (m, 1H), 4.91-4.85 (m, 1H), 4.00-3.95 (m, 1H), 3.69-3.66 (d, J=9.81 Hz, 1H), 3.46-3.31 (m, 1H), 3.33 (s, 3H), 3.07-2.97 (m, 1H), 2.45-2.28 (m, 2H). mGluR5 PAM $EC_{50}$: +++++. Fold shift at 10 μM: ++.

Example 3.7. Synthesis of the HCl Salt of 1-(methoxymethyl)-6-(pyridin-2-ylethynyl)-2,3-dihydropyrrolo[2,1-b]quinazolin-9(1H)-one

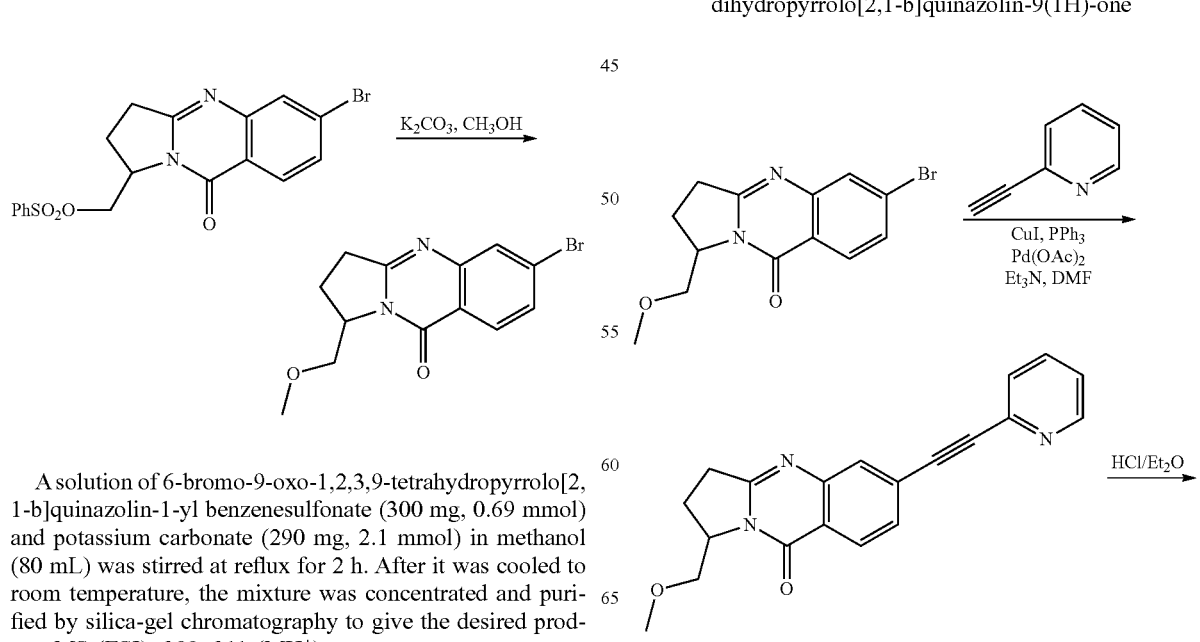

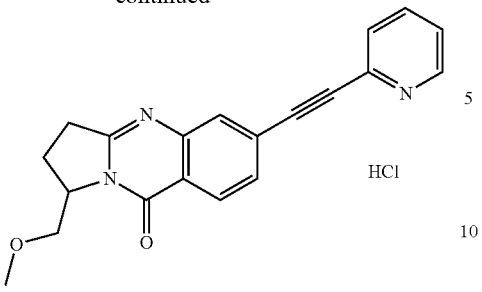

The title compound was prepared according to the experimental procedure as described in Example 1.1. The product was then converted to the corresponding HCl salt. MS (ESI): 332 (MH+); $^1$H NMR (300 MHz, DMSO-d$^6$) δ 8.68-8.66 (d, J=4.86 Hz, 1H), 8.19-8.16 (d, J=8.19 Hz, 1H), 7.97-7.92 (m, 1H), 7.82-7.76 (m, 2H), 7.69-7.66 (d, J=7.62 Hz, 1H), 7.53-7.48 (m, 1H), 4.81-4.77 (m, 1H), 3.84-3.79 (m, 1H), 3.64-3.60 (d, J=9.75 Hz, 1H), 3.26-3.17 (m, 4H), 3.02-2.98 (m, 1H), 2.39-2.31 (m, 1H), 2.17-2.10 (m, 1H). mGluR5 PAM EC$_{50}$: +++. Fold shift at 10 μM: +++.

Example 3.8. Synthesis of 64(3-fluorophenyl)ethynyl)-2-methyl-2,3-dihydropyrrolo[2,1-b]quinazolin-9(1H)-one

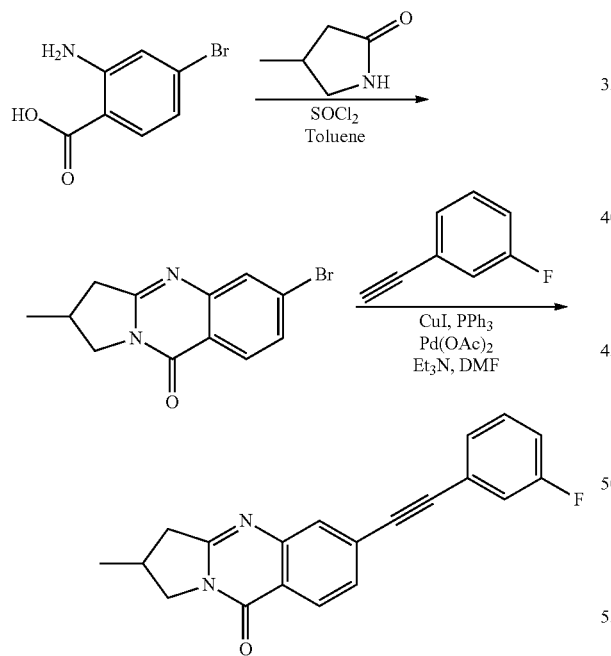

The title compound was prepared according to the experimental procedure as described in Example 2.2a and Example 1.1. MS (ESI): 319 (MH+); $^1$H NMR (300 MHz, CDCl$_3$) δ 8.28-8.25 (d, J=8.19 Hz, 1H), 7.77 (s, 1H), 7.58-7.55 (d, J=8.24 Hz, 1H), 7.41-7.34 (m, 2H), 7.32-7.28 (m, 1H), 7.13-7.06 (m, 1H), 4.40-4.34 (m, 1H), 3.78-3.72 (m, 1H), 3.35-3.27 (m, 1H), 2.87-2.71 (m, 2H), 1.30-1.28 (d, J=6.63 Hz, 3H). mGluR5 PAM EC$_{50}$: +++++. Fold shift at 10 μM: ++.

Example 3.9. Synthesis of 6-((3-fluorophenyl)ethynyl)-2-isobutyl-2,3-dihydropyrrolo[2,1-b]quinazolin-9(1H)-one

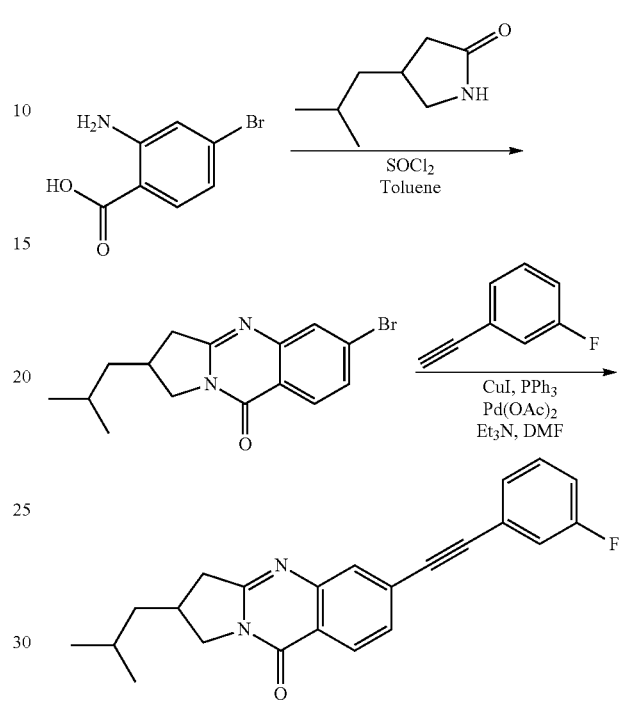

The title compound was prepared according to the experimental procedure as described in Example 2.2a and Example 1.1. MS (ESI): 361 (MH+); $^1$H NMR (300 MHz, CDCl$_3$) δ 8.28-8.25 (d, J=8.25 Hz, 1H), 7.79 (s, 1H), 7.58-7.55 (d, J=8.22 Hz, 1H), 7.37-7.34 (m, 2H), 7.32-7.28 (m, 1H), 7.13-7.07 (m, 1H), 4.44-4.37 (m, 1H), 3.76-3.69 (m, 1H), 3.32-3.24 (m, 1H), 2.90-2.81 (m, 1H), 2.76-2.65 (m, 1H), 1.76-1.67 (m, 1H), 1.52-1.47 (t, J=7.28 Hz, 2H), 1.00-0.97 (d, J=6.54 Hz, 6H). mGluR5 PAM EC$_{50}$: ++++.

Example 3.10. Synthesis of 2-benzyl-64(3-fluorophenyl)ethynyl)-2,3-dihydropyrrolo[2,1-b]quinazolin-9(1H)-one

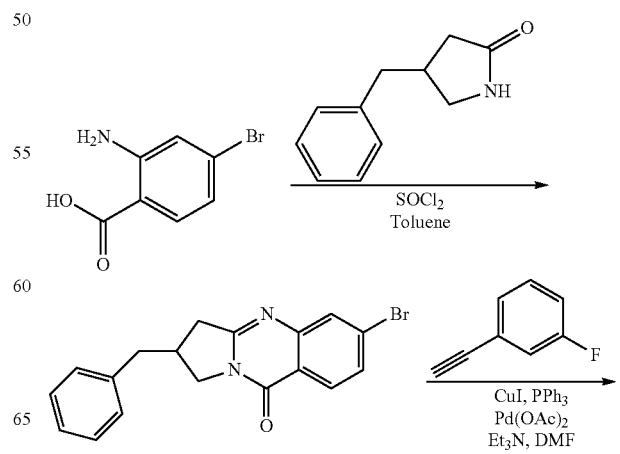

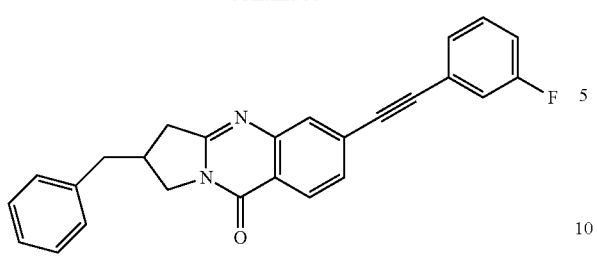

The title compound was prepared according to the experimental procedure as described in Example 2.2a and Example 1.1. MS (ESI): 395 (MH+); $^1$H NMR (300 MHz, CDCl$_3$) δ 8.27-8.24 (d, J=8.16 Hz, 1H), 7.79 (s, 1H), 7.59-7.55 (d, J=8.21 Hz, 1H), 7.38-7.33 (m, 4H), 7.30-7.29 (m, 1H), 7.26-7.22 (m, 3H), 7.14-7.07 (m, 1H), 4.31-4.24 (m, 1H), 3.95-3.89 (m, 1H), 3.32-3.22 (m, 1H), 3.03-2.84 (m, 4H). mGluR5 PAM EC$_{50}$: +++++. Fold shift at 10 μM: ++.

Example 3.11. Synthesis of the HCl Salt of 2-methyl-6-(pyridin-2-ylethynyl)-2,3-dihydropyrrolo[2,1-b]quinazolin-9(1H)-one

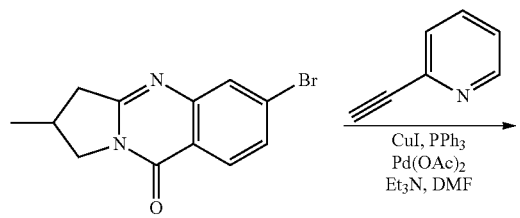

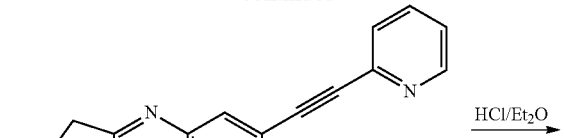

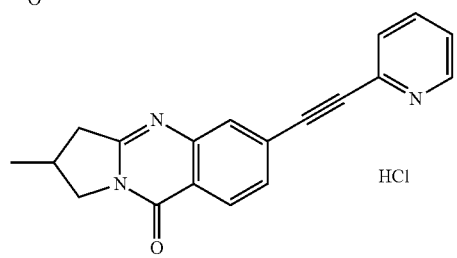

The title compound was prepared according to the experimental procedure as described in Example 1.1. The product was then converted to the corresponding HCl salt. MS (ESI): 302 (MH+); $^1$H NMR (300 MHz, DMSO-d$^6$) δ 8.72-8.71 (d, J=4.38 Hz, 1H), 8.21-8.18 (d, J=8.22 Hz, 1H), 8.08-8.02 (m, 1H), 7.93-7.92 (d, J=1.08 Hz, 1H), 7.88-7.85 (d, J=7.80 Hz, 1H), 7.76-7.72 (d, J=8.22 Hz, 1H), 7.62-7.58 (dd, J=7.60, 1.04 Hz, 1H), 5.45 (s, 1H), 4.30-4.23 (dd, J=11.76, 6.69 Hz, 1H), 3.69-3.63 (dd, J=11.76, 6.69 Hz, 1H), 3.40-3.31 (m, 1H), 2.93-2.85 (m, 1H), 2.76-2.69 (m, 1H), 1.18-1.16 (d, J=6.6 Hz, 3H). mGluR5 PAM EC$_{50}$: ++++. Fold shift at 10 μM: +++.

Example 3.12 and Example 3.13. Separation of (S)-2-methyl-6-(pyridin-2-ylethynyl)-2,3-dihydropyrrolo[2,1-b]quinazolin-9(1H)-one and (R)-2-methyl-6-(pyridin-2-ylethynyl)-2,3-dihydropyrrolo[2,1-b]quinazolin-9(1H)-one

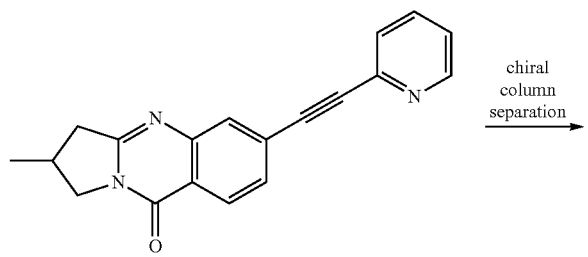

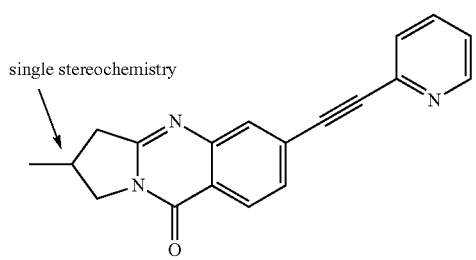

Single enantiomer
faster moving enantiomer (fraction 1)

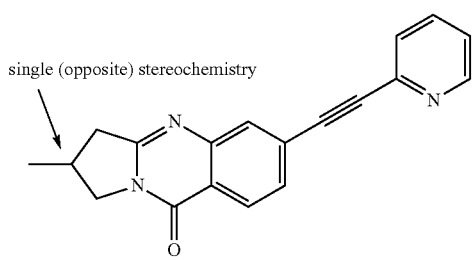

Single enantiomer
slower moving enantiomer (fraction 2)

Racemic 2-methyl-6-(pyridin-2-ylethynyl)-2,3-dihydropyrrolo[2,1-b]quinazolin-9(1H)-one was separated into the corresponding two single enantiomer compounds S)-2-methyl-6-(pyridin-2-ylethynyl)-2,3-dihydropyrrolo[2,1-b]quinazolin-9(1H)-one and (R)-2-methyl-6-(pyridin-2-ylethynyl)-2,3-dihydropyrrolo[2,1-b]quinazolin-9(1H)-one using chiral chromatography with an isocratic SFC method. The column used was a 3.0×25.0 cm RegisPack from Regis Technologies (Morton Grove, Ill.). The $CO_2$ co-solvent was methanol:isopropanol (1:1) with 1% isopropylamine. Isocratic Method: 50% Co-solvent at 70 mL/min System Pressure: 200 bar. Column Temperature 25° C.

Faster moving enantiomer (fraction 1) Retention time=2.1 min 100% ee. mGluR5 PAM $EC_{50}$: +++. Fold shift at 10 μM: ++.

Slower moving enantiomer (fraction 2): Retention time=3.3 min. 95.6% ee. mGluR5 PAM $EC_{50}$: ++++. Fold shift at 10 μM: +++.

Example 3.14. Synthesis of 1-methyl-6-(pyridin-2-ylethynyl)-2,3-dihydropyrrolo[2,1-b]quinazolin-9(1H)-one

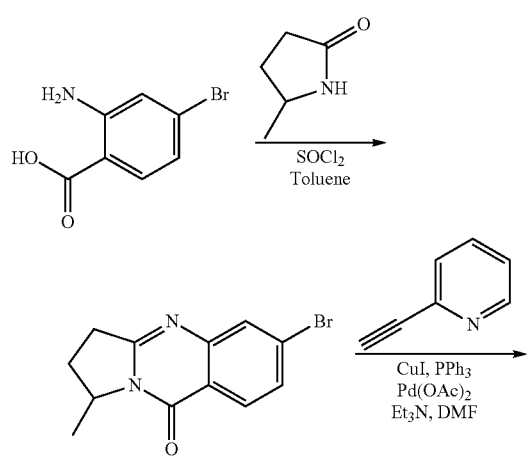

The title compound was prepared according to the experimental procedure as described in Example 2.2a and Example 1.1. MS (ESI): 302 (MH+); $^1$H NMR (300 MHz, $CD_3OD$) δ 8.99-8.97 (dd, J=5.08, 0.83 Hz, 1H), 8.76-8.70 (t, J=7.99 Hz, 1H), 8.47-8.45 (d, J=8.28 Hz, 1H), 8.42-8.39 (d, J=7.98 Hz, 1H), 8.19-8.14 (m, 2H), 8.07-8.04 (dd, J=8.28, 1.38 Hz, 1H), 5.08-5.02 (m, 1H), 3.81-3.72 (m, 1H), 3.58-3.47 (m, 1H), 2.74-2.66 (m, 1H), 2.22-2.15 (m, 1H), 1.63-1.61 (d, J=6.54 Hz, 3H). mGluR5 PAM $EC_{50}$: ++.

Example 3.15. Synthesis of the HCl Salt of 6'-((3-fluorophenyl)ethynyl)-1'H-spiro[piperidine-2,2'-pyrrolo[2,1-b]quinazolin]-9'(3'H)-one

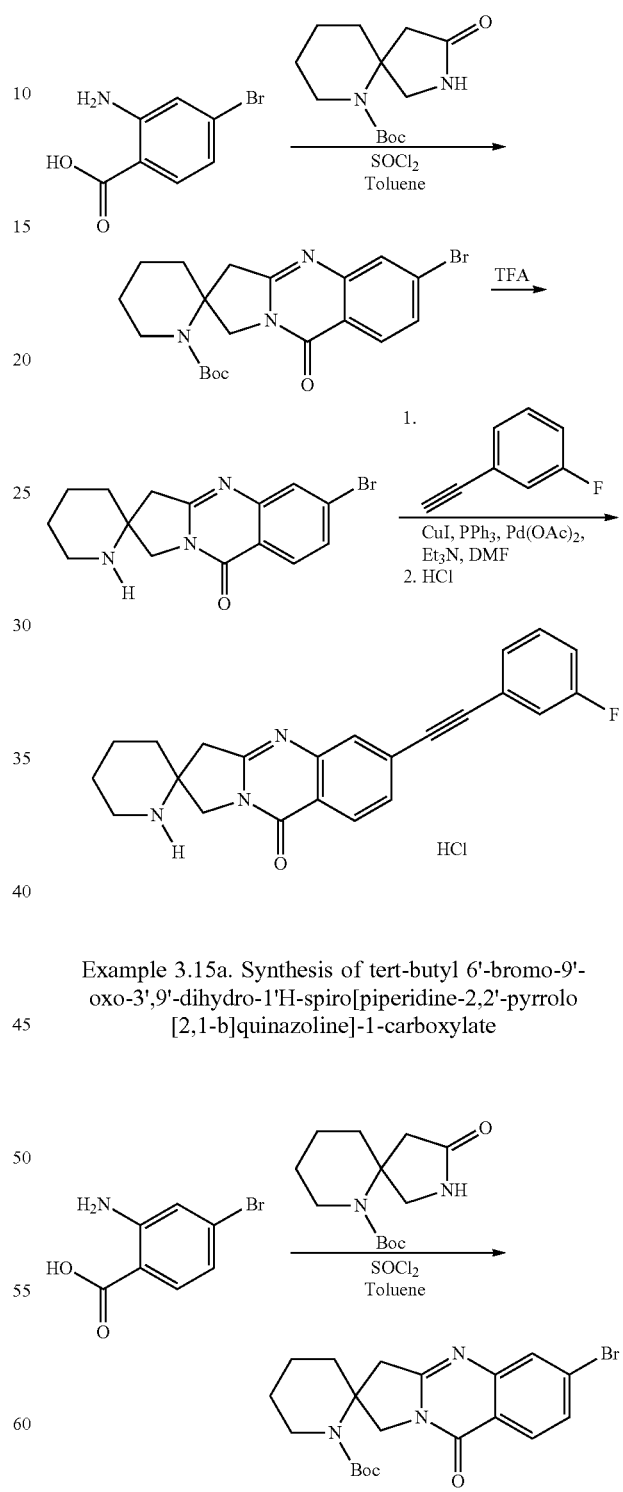

Example 3.15a. Synthesis of tert-butyl 6'-bromo-9'-oxo-3',9'-dihydro-1'H-spiro[piperidine-2,2'-pyrrolo[2,1-b]quinazoline]-1-carboxylate The title compound was prepared according to the experimental procedure as described in Example 2.2a. MS (ESI): 434, 436 (MH+).

Example 3.15b. Synthesis of 6'-bromo-1'H-spiro[piperidine-2,2'-pyrrolo[2,1-b]quinazolin]-9'(3'H)-one

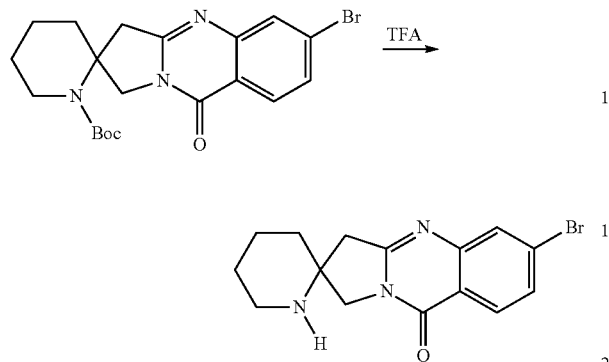

The title compound was prepared according to the experimental procedure as described in Example 1.21c. MS (ESI): 334, 336 (MH+)

Example 3.15c. Synthesis of the HCl Salt of 6'((3-fluorophenyl)ethynyl)-1'H-spiro[piperidine-2,2'-pyrrolo[2,1-b]quinazolin]-9'(3' H)-one

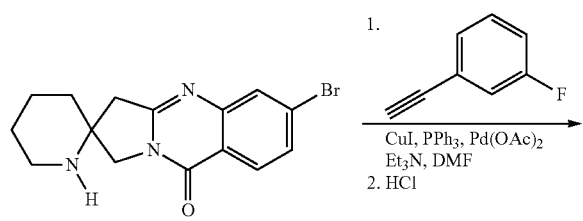

The title compound was prepared according to the experimental procedure as described in Example 1.1. The title compound was then converted to the corresponding HCl salt. MS (ESI): 374 (MH+); $^1$H NMR (300 MHz, CD$_3$OD) δ 8.29-8.26 (d, J=8.61 Hz, 1H), 7.84 (s, 1H), 7.74-7.71 (dd, J=8.25, 1.52 Hz, 1H), 7.78-7.42 (m, 2H), 7.39-7.34 (m, 1H), 7.25-7.21 (m, 1H), 4.66-4.61 (d, J=13.86 Hz, 1H), 4.36-4.31 (d, J=13.92 Hz, 1H), 3.67 (s, 2H), 3.42-3.41 (m, 2H), 2.14-2.03 (m, 2H), 1.88 (broad, 4H).

Example 3.16. Synthesis of 6'-((3-fluorophenyl)ethynyl)-1-methyl-1'H-spiro[piperidine-2,2'-pyrrolo[2,1-b]quinazolin]-9'(3' H)-one

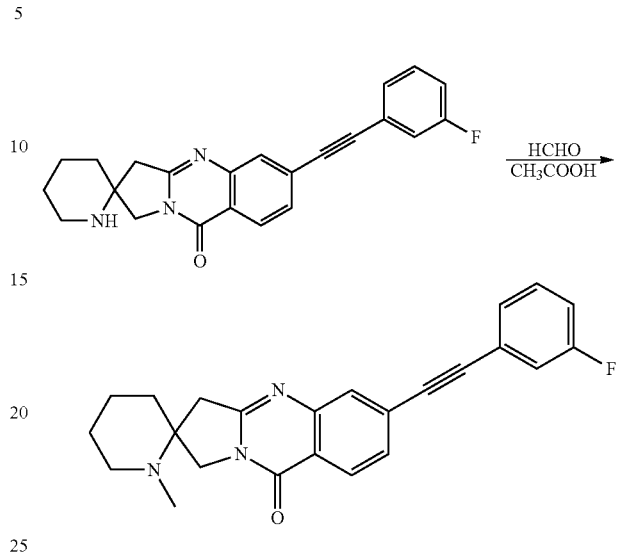

The title compound was prepared according to the experimental procedure as described in Example 1.21d. MS (ESI): 388 (MH+); $^1$H NMR (300 MHz, DMSO-d$^6$) δ 8.28-8.25 (d, J=8.27 Hz, 1H), 7.79 (s, 1H), 7.59-7.55 (dd, J=8.24, 1.52 Hz, 1H) 7.38-7.34 (m, 2H), 7.30-7.29 (m, 1H), 7.28-7.26 (m, 1H), 7.14-7.07 (m, 1H), 4.48-4.44 (d, J=13.42 Hz, 1H), 4.11-4.09 (d, J=6.75 Hz, 1H), 3.86-3.81 (d, J=13.42 Hz, 1H), 3.44-3.38 (d, J=18.33 Hz, 1H), 3.06-3.00 (d, J=18.36 Hz, 1H), 2.60-2.57 (m, 2H), 2.14 (s, 3H), 1.86-1.82 (m, 2H), 1.71-1.59 (m, 2H), 1.02-0.99 (d, J=6.72 Hz, 1H). mGluR5 PAM EC$_{50}$: ++.

Example 3.17. Synthesis of the HCl Salt of 6'-((3-fluorophenyl)ethynyl)-1'H-spiro[piperidine-4,2'-pyrrolo[2,1-b]quinazolin]-9'(3H)-one

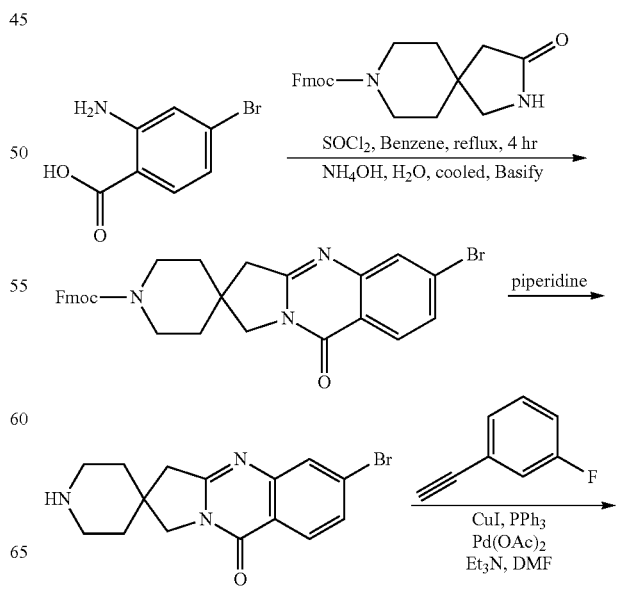

-continued

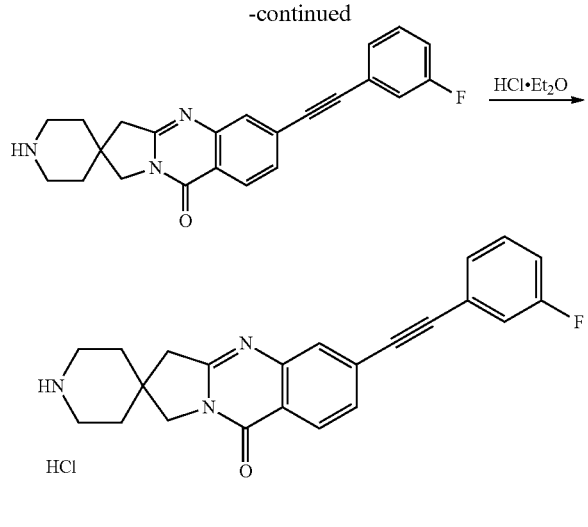

Example 3.17a. Synthesis of (9H-fluoren-9-yl)methyl 6'-bromo-9'-oxo-3',9'-dihydro-1'H-spiro[piperidine-4,2'-pyrrolo[2,1-b]quinazoline]-1-carboxylate

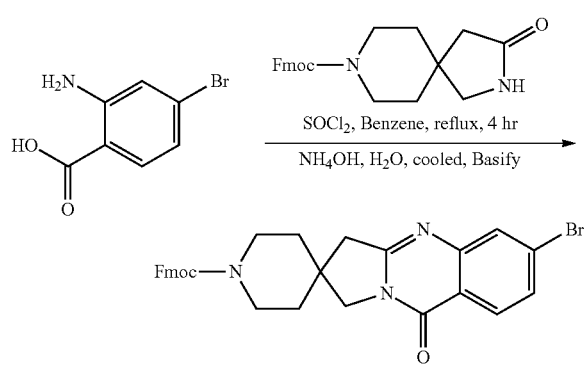

The title compound was prepared according to the experimental procedure as described in Example 2.2a.

Example 3.17b. Synthesis of 6'-bromo-1'H-spiro[piperidine-4,2'-pyrrolo[2,1-b]quinazolin]-9'(3'H)-one

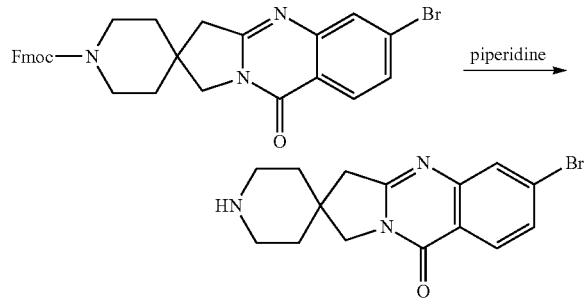

A solution of (9H-fluoren-9-yl)methyl 6'-bromo-9'-oxo-3',9'-dihydro-1'H-spiro[piperidine-4,2'-pyrrolo[2,1-b]quinazoline]-1-carboxylate (0.6 g, 1.1 mmol, 1 equiv) and piperidine (4 mL) in DCM (50 mL) was stirred at room temperature overnight. The reaction mixture was then diluted with water and extracted with ethyl acetate (3×100 mL). The combined organic layers were dried over $Na_2SO_4$. After filtration and concentration, the residue was purified by silica gel chromatography to give the desired product.

Example 3.17c. Synthesis of the HCl Salt of 6'4(3-fluorophenyl)ethynyl)-1'H-spiro[piperidine-4,2'-pyrrolo[2,1-b]quinazolin]-9'(3'H)-one

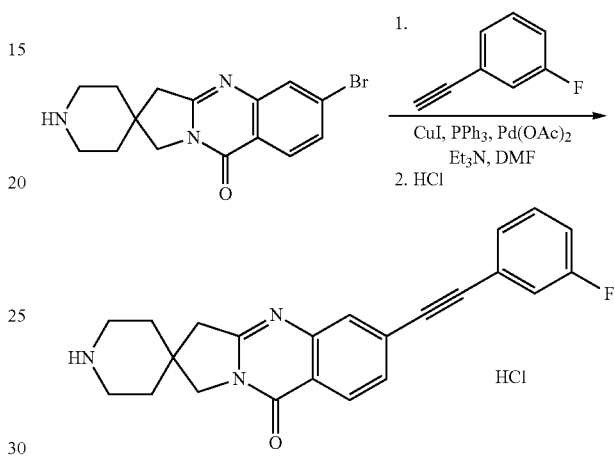

The title compound was prepared according to the experimental procedure as described in Example 1.1. The compound was then converted to the corresponding HCl salt. MS (ESI): 374 (M+H$^+$); $^1$H NMR (300 MHz, CD$_3$OD) δ 8.34-8.31 (d, J=8.25 Hz, 1H), 7.85-7.80 (m, 2H), 7.50-7.43 (m, 2H), 7.40-7.36 (m, 1H), 7.27-7.20 (m, 1H), 4.28 (s, 2H), 3.54 (s, 2H), 3.38-3.36 (m, 5H), 2.12-2.08 (m, 3H).

Example 3.18. Synthesis of 2-(hydroxymethyl)-6-(pyridin-2-ylethynyl)-2,3-dihydropyrrolo[2,1-b]quinazolin-9(1H)-one

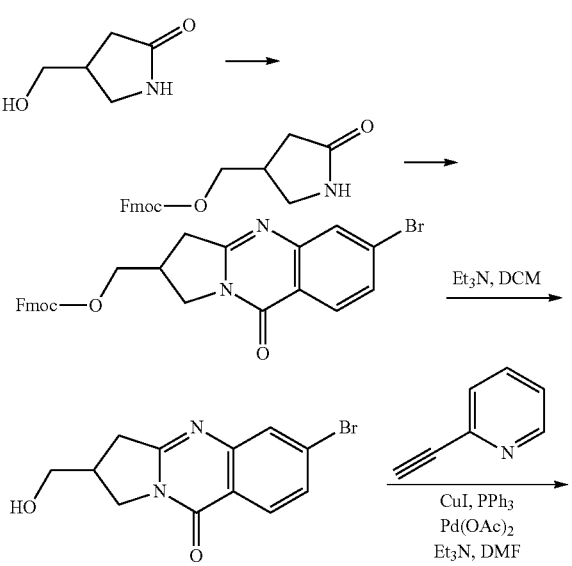

171
-continued

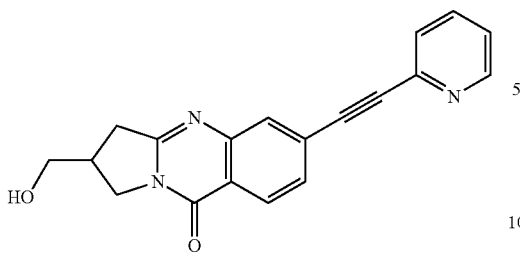

The title compound was prepared according to the experimental procedure as described in Example 5.1a, Example 2.2a, 3.17b, and Example 1.1. MS (ESI): 318 (MH+); $^1$H NMR (300 MHz, DMSO-d$^6$) δ 8.87-8.68 (d, J=4.44 Hz, 1H), 8.19-8.16 (d, J=8.25 Hz, 1H), 8.01-7.96 (m, 1H), 7.87-7.80 (m, 2H), 7.71-7.68 (d, J=8.34 Hz, 1H), 7.56-7.52 (m, 1H), 4.19-4.12 (m, 1H), 3.94-3.88 (m, 1H), 3.54-3.44 (m, 2H), 3.52-3.24 (m, 1H), 3.03-2.95 (m, 1H), 2.72 (m, 1H). mGluR5 PAM EC$_{50}$: ++.

Example 3.19. Synthesis of the HCl Salt of 2-(methoxymethyl)-6-(pyridin-2-ylethynyl)-2,3-dihydropyrrolo[2,1-b]quinazolin-9(1H)-one

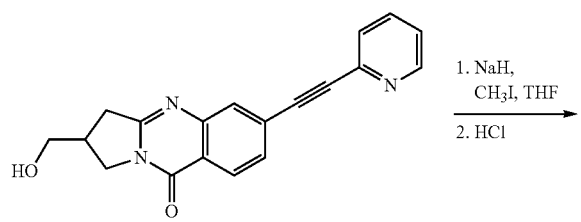

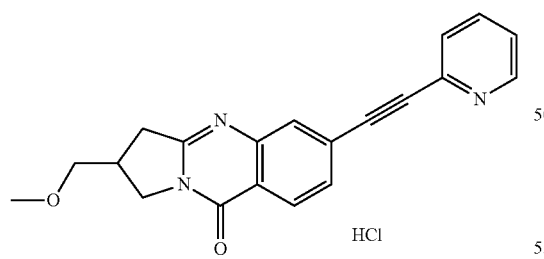

The title compound was prepared according to the experimental procedure as described in Example 4.25. The product was then converted to the corresponding HCl salt. MS (ESI): 332 (MH+); $^1$H NMR (300 MHz, CD$_3$OD) δ 8.92-8.90 (d, J=5.55 Hz, 1H), 8.64-8.58 (m, 1H), 8.43-8.40 (d, J=8.22 Hz, 1H), 8.31-8.28 (d, J=8.01 Hz, 1H), 8.09-8.04 (m, 2H), 7.97-7.95 (d, J=8.28 Hz, 1H), 4.47-4.41 (m, 1H), 4.20-4.14 (m, 1H), 3.68-3.58 (m, 3H), 3.40 (s, 3H), 3.33-3.32 (m, 1H), 3.12-3.08 (m, 1H). mGluR5 PAM EC$_{50}$: +++.

172

Example 3.20. Synthesis of 2,2-dimethyl-6-(pyridin-2-ylethynyl)-2,3-dihydropyrrolo[2,1-b]quinazolin-9(1H)-one

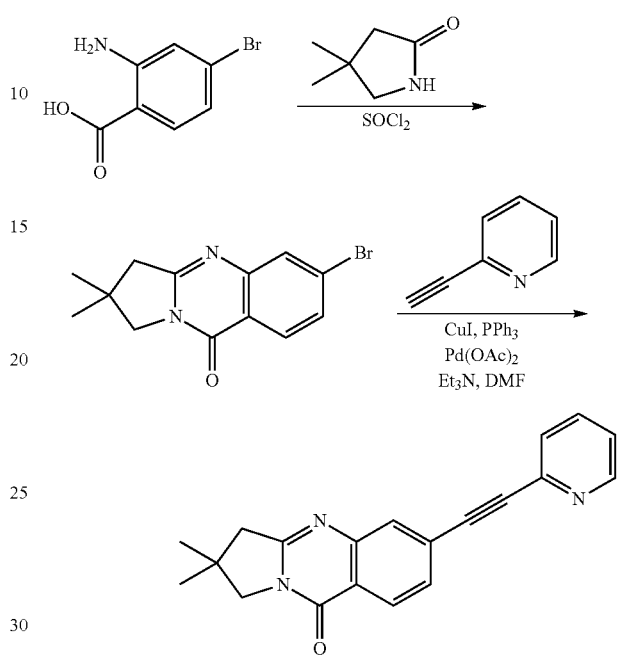

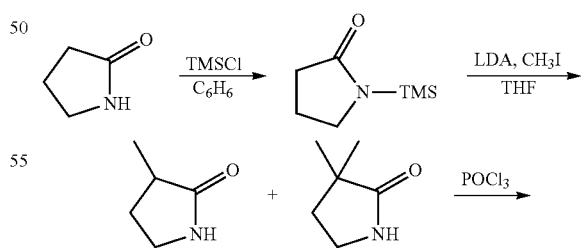

The title compound was prepared according to the experimental procedure as described in Example 2.2a and Example 1.1. MS (ESI): 316 (MH+); $^1$H NMR (300 MHz, DMSO-d$^6$) δ 8.68-8.67 (d, J=4.62 Hz, 1H), 8.19-8.16 (d, J=8.22 Hz, 1H), 7.99-7.97 (m, 1H), 7.84-7.78 (m, 2H), 7.70-7.67 (d, J=8.19 Hz, 1H), 7.54-7.50 (m, 1H), 3.84 (s, 2H), 2.98 (s, 2H), 1.20 (s, 6H). mGluR5 PAM EC$_{50}$: +++++. Fold shift at 10 μM: +++.

Example 3.21. Synthesis of the HCl Salt of 3-methyl-6-(pyridin-2-ylethynyl)-2,3-dihydropyrrolo[2,1-b]quinazolin-9(1H)-one

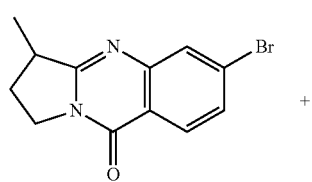

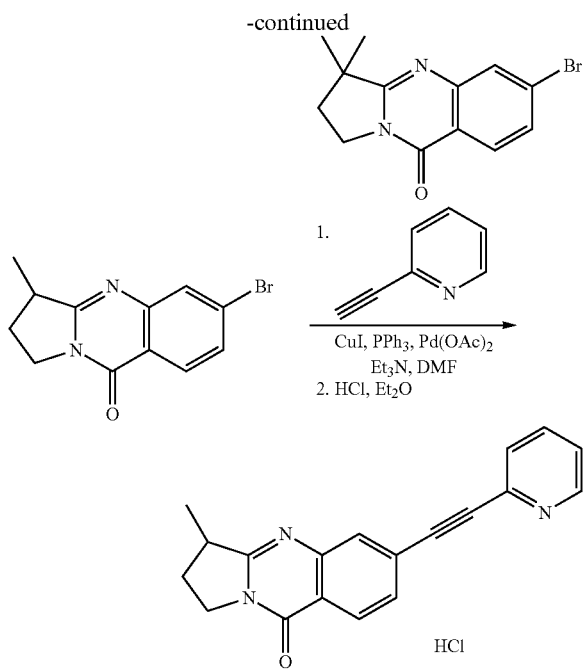

Example 3.21a. Synthesis of N-trimethylsilyl-2-pyrrolidinone

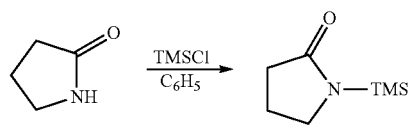 [SMILES: "TMSCl" ; O=C1CCCN1 ; C[Si](C)(C)N1CCCC1=O ; "C6H5"]

A solution of 30.0 g (353 mmol) of 2-pyrrolidinone and 35.5 g (353 mmol) of triethylamine in 250 mL of benzene was refluxed, during which 210 mL (179.8 g, 1655 mmol) of chlorotrimethysilane was added dropwise over 1 h. After 12 h, the solution was cooled, filtered and the precipitate was washed with benzene. Concentration of the filtrate under vacuum pressure gave a yellow oil, which was distilled (0.3 mmHg) to give 37.1 g of N-timethylsilyl-2-pyrrolidinone as a colorless oil. MS (ESI): 158 (MH+).

Example 3.21b. Synthesis of 3-methyl-2-pyrrolidinone and 3,3-dimethylpyrrolidin-2-one

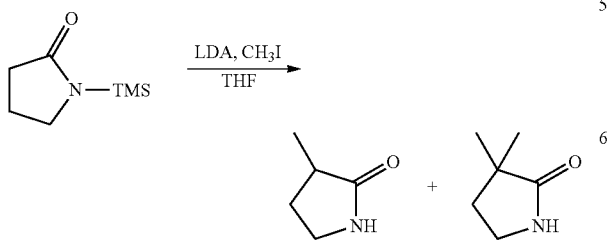

A solution of lithium diisopropylamide in 100 mL of THF (prepared from 4.88 mL (3.54 g, 35.0 mmol) of diisopropylamine and 22.1 mL of 2.5 M n-butyllithium in hexane) was treated with 3.80 g (35.0 mmol) of N-trimethylsilyl-2-pyrrolidinone at −78° C. After one hour, 4.48 g (35.0 mmol) of iodomethane was added at −78° C. The solution was warmed to 0° C. and stirred for 12 hours. The reaction mixture was then quenched with water and extracted with ethyl acetate. The organic layer was then dried over MgSO4. After removal of solvent, 2.8 g of the crude product was obtained which was directly used for the next step without further purification.

Example 3.21c. Synthesis of 6-bromo-3-methyl-2,3-dihydropyrrolo[2,1-b]-quinazolin-9(1H)-one and 6-bromo-3,3-dimethyl-2,3-dihydropyrrolo[2,1-b]quinazolin-9(1H)-one

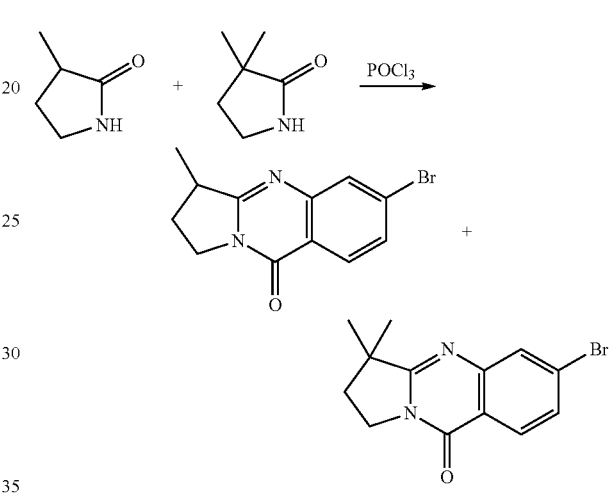

The title compounds were prepared according to the experimental procedure described in Example 4.27b. The title compounds were separated in this step.

Example 3.21d. Synthesis of the HCl Salt of 3-methyl-6-(pyridin-2-ylethynyl)-2,3-dihydropyrrolo[2,1-b]quinazolin-9(1H)-one

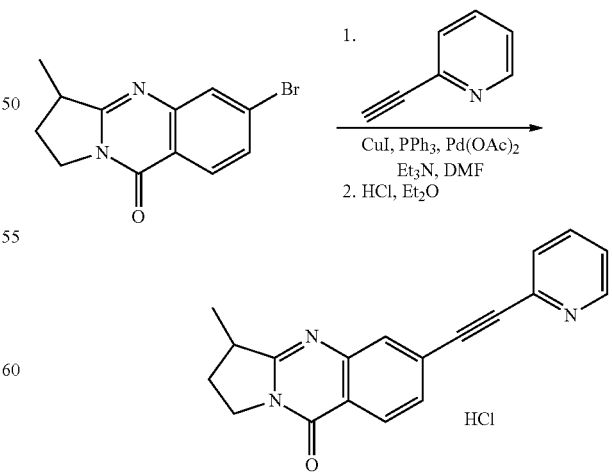

The title compound was prepared according to the experimental procedure described in Example 1.1. The product was then converted to the corresponding HCl salt. MS (ESI): 302 (MH$^+$); $^1$H NMR (300 MHz, CD$_3$OD) δ 8.94-8.92 (d, J=5.6 Hz, 1H), 8.66-8.61 (t, J=8.0 Hz, 1H), 8.43-8.41 (d, J=8.3 Hz, 1H), 8.33-8.31 (d, J=8.0 Hz, 1H), 8.16 (s, 1H), 8.11-8.06 (t, J=6.0 Hz, 1H), 7.98-7.95 (dd, J=8.3, 1.3 Hz, 1H), 4.46-4.37 (m, 1H), 4.26-4.16 (m, 1H), 3.84-3.78 (m, 1H), 2.72-2.63 (m, 1H), 2.12-2.05 (m, 1H), 1.63-1.60 (d, J=7.1 Hz, 3H).

Example 3.22. Synthesis of the HCl salt 3,3-dimethyl-6-(pyridin-2-ylethynyl)-2,3-dihydropyrrolo[2,1-b]quinazolin-9(1H)-one

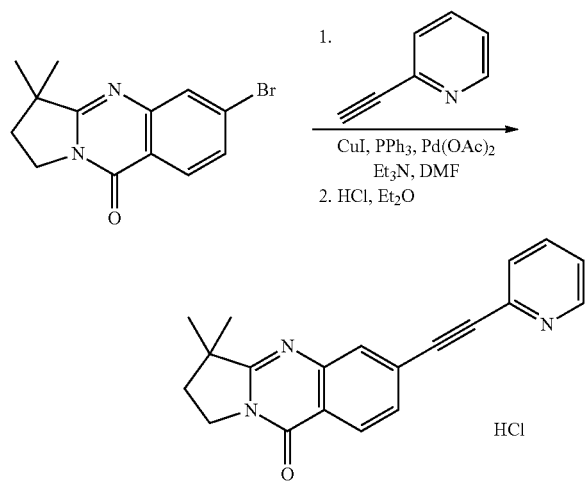

The title compound was prepared according to the experimental procedure as described in Example 1.1. The product was then converted to the corresponding HCl salt. MS (ESI): 316 (MH$^+$); $^1$H NMR (300 MHz, CD$_3$OD) δ 8.67-8.66 (d, J=4.7 Hz, 1H), 8.19-8.16 (d, J=8.3 Hz, 1H), 7.97-7.92 (m, 1H), 7.88 (s, 1H), 7.78-7.75 (d, J=7.8 Hz, 1H), 7.68-7.65 (dd, J=8.2, 1.3 Hz, 1H), 7.52-7.48 (m, 1H), 4.08-4.03 (t, J=7.1 Hz, 2H), 2.11-2.06 (t, J=7.1 Hz, 2H), 1.36 (s, 6H).

Example 3.23. Synthesis of the HCl Salt of 2,2-dimethyl-6-(pyridin-2-ylethynyl)-2,3-dihydropyrrolo[2,1-b]quinazolin-9(1H)-one

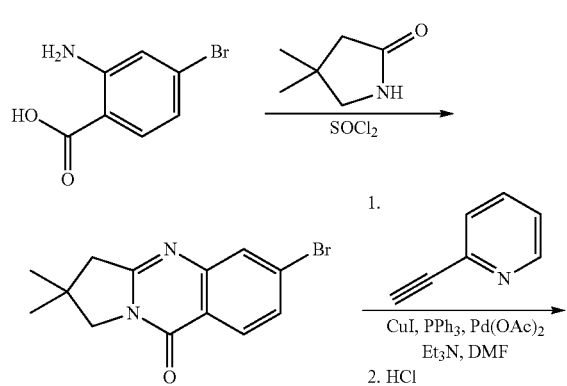

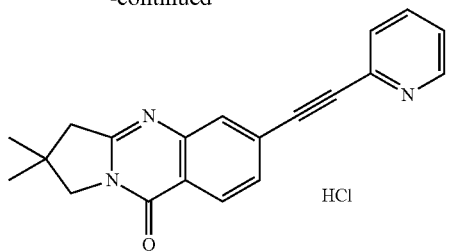

The title compound was prepared according to the experimental procedure as described in Example 2.2a and Example 1.1. The product was then converted to the corresponding HCl salt. MS (ESI): 316 (MH$^+$); $^1$H NMR (300 MHz, CD$_3$OD) δ 8.91-8.89 (d, J=5.85 Hz, 1H), 8.62-8.56 (t, J=7.93 Hz, 1H), 8.42-8.39 (d, J=8.28 Hz, 1H), 8.29-8.26 (d, J=8.10 Hz, 1H), 8.07-8.02 (m, 2H), 7.94-7.91 (dd, J=7.93, 1.40 Hz, 1H), 4.07 (s, 2H), 3.28 (s, 2H), 1.36 (s, 6H). mGluR5 PAM EC$_{50}$: +++++. Fold shift at 10 μM: +++.

Example 3.24. Synthesis of the HCl Salt of 6'-(pyridin-2-ylethynyl)-2,3,5,6-tetrahydro-1'H-spiro[pyran-4,2'-pyrrolo[2,1-b]quinazolin]-9'(3'H)-one

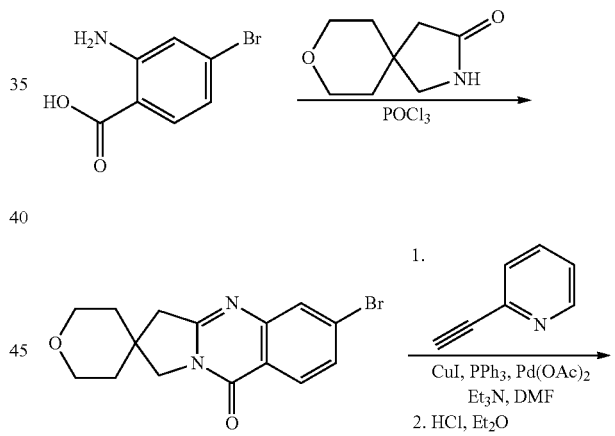

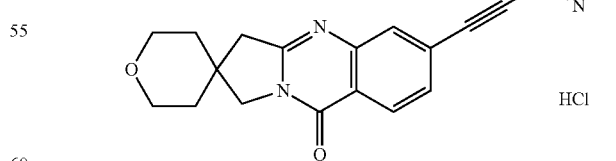

The title compound was prepared according to the experimental procedures as described in Example 4.27b and Example 1.1. The product was then converted to the corresponding HCl salt. mGluR5 PAM EC$_{50}$: ++++. Fold shift at 10 μM: +++.

Example 3.25. Synthesis of 3-(pyridin-2-ylethynyl)-8,9-dihydro-6H-6,9-methanopyrido[2,1-b]quinazolin-11(7H)-one

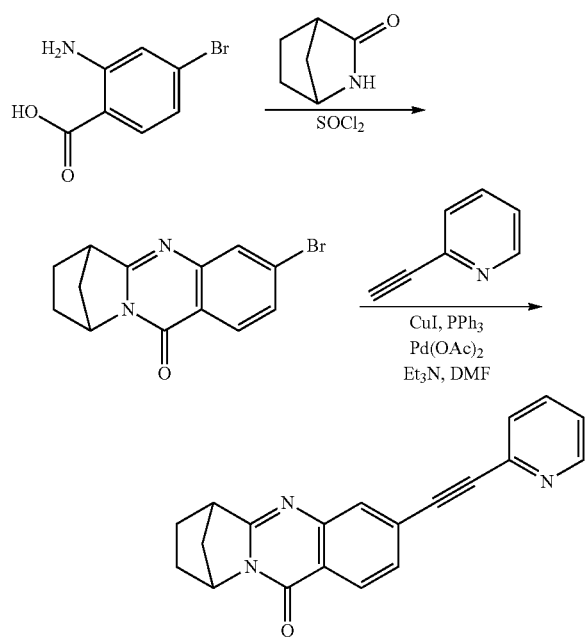

The title compound was prepared according to the experimental procedure as described in Example 2.2a and Example 1.1. MS (ESI): 314 (MH$^+$); $^1$H NMR (300 MHz, CD$_3$OD) δ 8.95-8.93 (d, J=5.64 Hz, 1H), 8.71-8.68 (t, J=7.97 Hz, 1H), 8.43-8.40 (d, J=8.25 Hz, 1H), 8.36-8.33 (d, J=8.04 Hz, 1H), 8.14-8.09 (m, 2H), 7.98-7.95 (dd, J=8.28, 1.35 Hz, 1H), 5.37 (s, 1H), 3.87-3.86 (m, 1H), 2.45-2.31 (m, 2H), 2.27-2.20 (m, 1H), 2.04-2.00 (d, J=10.41 Hz, 1H), 1.88-1.75 (m, 2H). mGluR5 PAM EC$_{50}$: ++++. ++++. Fold shift at 10 μM: +.

Example 4.1. Synthesis of 9-((3-fluorophenyl)ethynyl)-3,4-dihydro-[1,4]oxazino[3,4-b]quinzolin-6(1H)-one

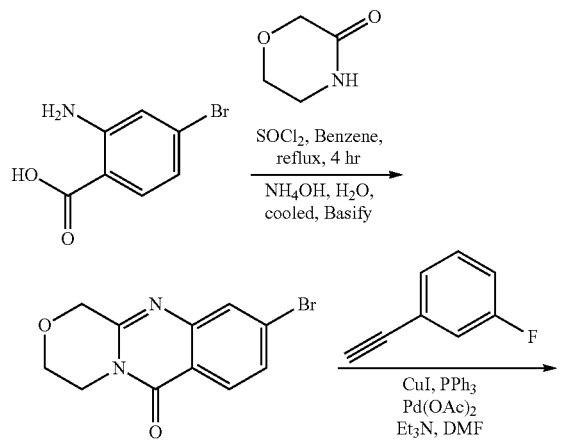

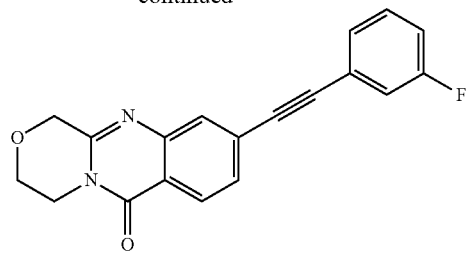

The title compound was prepared according to the experimental procedure as described in Example 2.2a and Example 1.1. MS (ESI): 321 (M+H$^+$); $^1$H NMR (300 MHz, CDCl$_3$) δ 8.17-8.14 (d, J=8.67 Hz, 1H), 7.75 (s, 1H), 7.64-7.61 (d, J=8.52 Hz, 1H), 7.51 (s, 3H), 7.36-7.32 (m, 1H), 4.71 (s, 2H), 4.09 (t, 2H), 3.91 (t, 2H). mGluR5 PAM EC$_{50}$: +++++.

Example 4.2. Synthesis of 9-((4-fluorophenyl)ethynyl)-3,4-dihydro-[1,4]oxazino[3,4-b]quinazolin-6(1H)-one

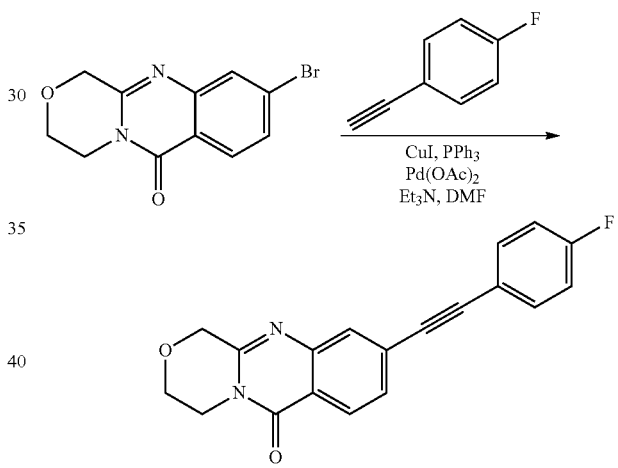

The title compound was prepared according to the experimental procedure as described in Example 1.1. MS (ESI): 321 (MH$^+$) δ $^1$H NMR (300 MHz, CDCl$_3$) δ 8.27-8.24 (d, J=8.88 Hz, 1H), 7.75 (s, 1H), 7.58-7.56 (d, J=6.51 Hz, 3H), 7.12-7.07 (t, J=8.15 Hz, 2H), 4.78 (s, 2H), 4.16-4.10 (m, 4H). mGluR5 PAM EC$_{50}$: +++.

Example 4.3. Synthesis of the HCl Salt of 9-(pyridin-2-ylethynyl)-3,4-dihydro-[1,4]oxazino[3,4-b]quinazolin-6(1H)-one

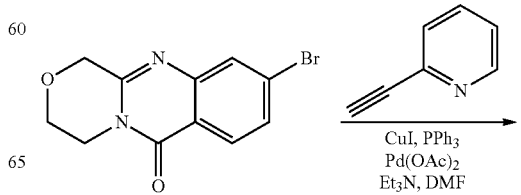

-continued

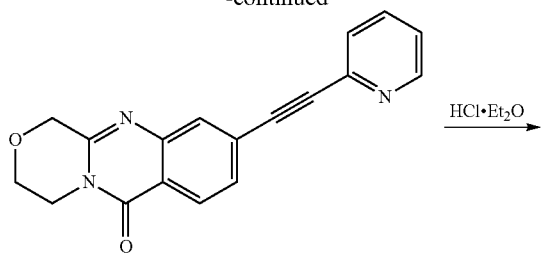

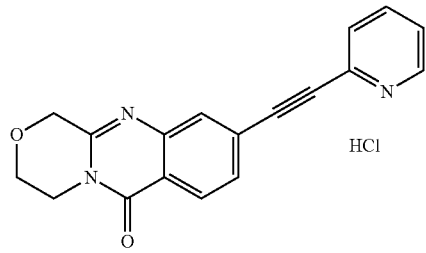

The title compound was prepared according to the experimental procedure as described in Example 1.1. The product was then converted to the corresponding HCl salt. MS (ESI): 304 (M+H$^+$); $^1$H NMR (300 MHz, DMSO-d$^6$) δ 8.723-8.707 (d, J=4.50 Hz, 1H), 8.202-8.175 (d, J=8.224 Hz, 1H), 8.084-8.036 (m, 2H), 7.874-7.855 (m, 2H), 7.716-7.688 (m, 1H), 7.624-7.583 (m, 1H), 4.745 (s, 2H), 4.115-4.081 (t, J=5.1 Hz, 2H), 3.935-3.901 (t, J=5.1 Hz, 2H).

Example 4.4. Synthesis of 3-((3-fluorophenyl)ethynyl)-8,9-dihydro-6H-pyrido[2,1-b]quinazolin-11(7H)-one

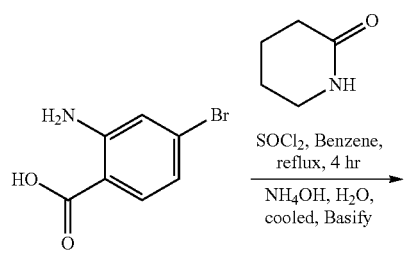

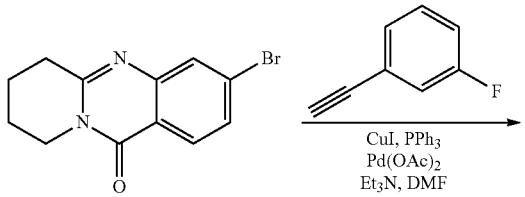

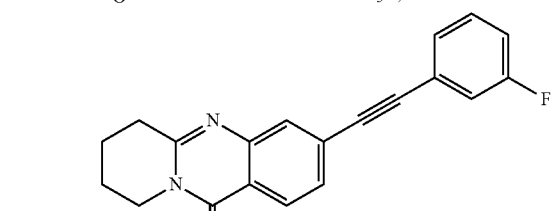

The title compound was prepared according to the experimental procedure as described in Example 2.2a and Example 1.1. MS (ESI): 319 (M+H$^+$); $^1$H NMR (300 MHz, CDCl$_3$) δ 8.26-8.23 (d, J=8.25, Hz, 1H), 7.76 (s, 1H), 7.75-7.53 (dd, J=8.24, 1.43 Hz, 1H), 7.38-7.32 (m, 2H), 7.30-7.26 (m, 1H), 7.13-7.07 (m, 1H), 4.12-4.08 (t, J=6.0 Hz, 2H), 3.05-3.00 (t, J=6.12 Hz, 2H), 2.08-1.94 (m, 4H). mGluR5 PAM EC$_{50}$: +++++. Fold shift at 10 μM: ++.

Example 4.5. Synthesis of 3-((4-fluorophenyl)ethynyl)-8,9-dihydro-6H-pyrido[2,1-b]quinazolin-11(7H)-one

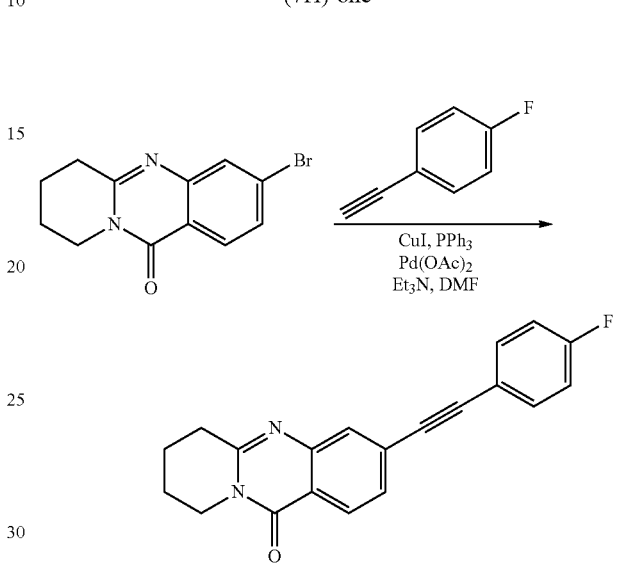

The title compound was prepared according to the experimental procedure as described in Example 1.1. MS (ESI): 319 (M+H$^+$); $^1$H NMR (300 MHz, CDCl$_3$) δ 8.23-8.20 (d, J=8.22 Hz, 1H), 7.72 (s, 1H), 7.57-7.44 (m, 3H), 7.10-7.04 (t, J=8.48 Hz, 2H), 4.09-4.05 (t, J=5.84, Hz, 2H), 3.02-2.98 (t, J=6.30, Hz, 2H), 2.25-1.95 (m, 4H). mGluR5 PAM EC$_{50}$: +++++.

Example 4.6. Synthesis of the HCl Salt of 3-(pyridin-2-ylethynyl)-8,9-dihydro-6H-pyrido[2,1-b]quinazolin-11(7H)-one

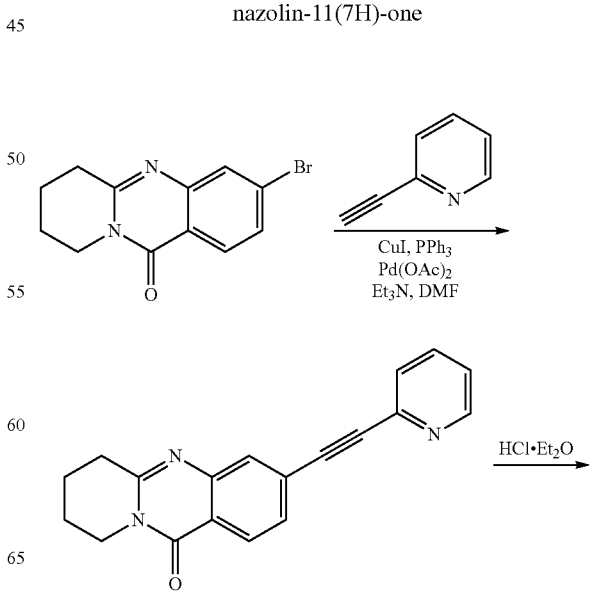

-continued

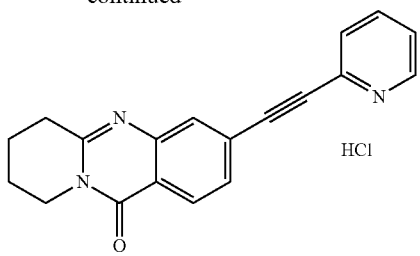

The title compound was prepared according to the experimental procedure as described in Example 1.1. The product was then converted to the corresponding HCl salt. MS (ESI): 302 (M+H$^+$); $^1$H NMR (300 MHz, DMSO-d$^6$) δ 8.71-8.69 (d, J=4.62 Hz, 1H), 8.26-8.22 (d, J=8.78 Hz, 1H), 8.10 (s, 1H), 8.02-7.97 (t, J=7.70 Hz, 1H), 7.85-7.81 (m, 2H), 7.58-7.54 (m, 1H), 3.98-3.94 (t, J=5.97 Hz, 2H), 3.22-3.18 (t, J=6.35 Hz, 2H), 2.01-1.86 (m, 4H).

Example 4.7. Synthesis of 6-allyl-3-((3-fluorophenyl)ethynyl)-8,9-dihydro-6H-Pyrido[2,1-b]quinazolin-11(7H)-one

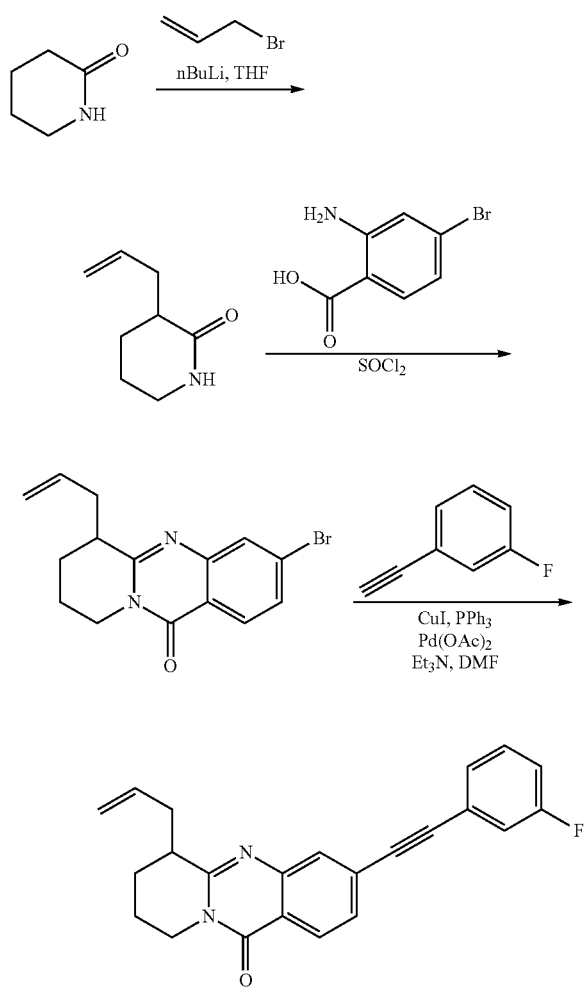

Example 4.7a. Synthesis of 3-allylpiperidin-2-one

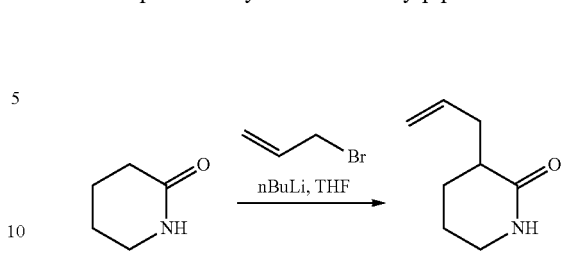

To a solution of piperidin-2-one (0.5 g, 5.0 mmol, 1 equiv) in dry THF (10.0 mL) was added nBuLi (4.2 ml, 10.5 mmol, 2.1 equiv) dropwise at 0° C. The mixture was then cooled to −75° C. and excess 3-bromoprop-1-ene was added to the mixture. The reaction mixture was kept at −78° C. for 1 h, quenched with NH$_4$Cl solution and extracted with ethyl acetate (3×20 mL). The combined organic layers were dried over Na$_2$SO$_4$ and concentrated under reduced pressure to give the desired product, which was directly used for the next step without further purification.

Example 4.7b. Synthesis of 6-allyl-3-bromo-8,9-dihydro-6H-pyrido[2,1-b]quinazolin-11(7H)-one

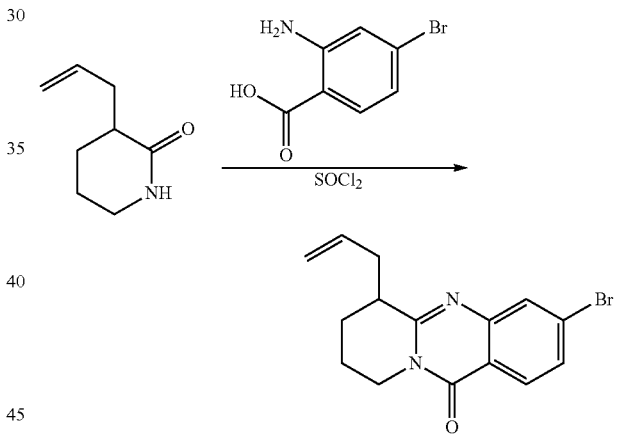

The title compound was prepared according to the experimental procedure as described in Example 2.2a.

Example 4.7c. Synthesis of 6-allyl-3-((3-fluorophenyl)ethynyl)-8,9-dihydro-6H-pyrido[2,1-b]quinazolin-11(7H)-one

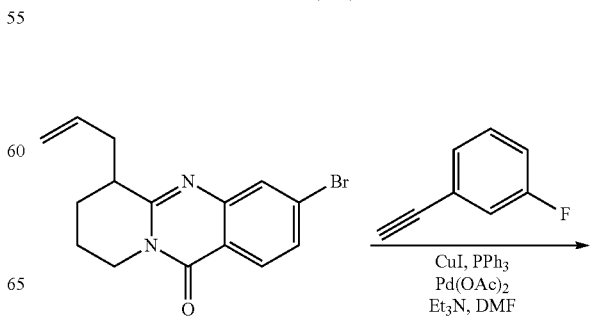

-continued

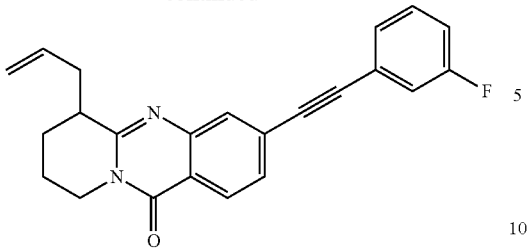

The title compound was prepared according to the experimental procedure as described in Example 1.1. MS (ESI): 359 (M+H⁺); ¹H NMR (300 MHz, CDCl₃) δ 8.26-8.23 (d, J=7.83 Hz, 1H), 7.82 (s, 1H), 7.56-7.53 (dd, J=8.74, 1.52 Hz, 1H), 7.38-7.35 (m, 2H), 7.28-7.26 (m, 1H), 7.12-7.09 (m, 1H), 5.96-5.82 (m, 1H), 5.19-5.11 (m, 2H), 4.19-4.16 (m, 1H), 4.02-4.00 (m, 1H), 3.01-2.94 (m, 2H), 2.54-2.53 (m, 1H), 2.10-1.96 (m, 3H), 1.72-1.69 (m, 1H). mGluR5 PAM EC$_{50}$: ++++. Fold shift at 10 μM: +.

Example 4.8. Synthesis of 6-ethyl-3-((3-fluorophenyl)ethynyl)-8,9-dihydro-6H-pyrido[2,1-b]quinazolin-11(7H)-one

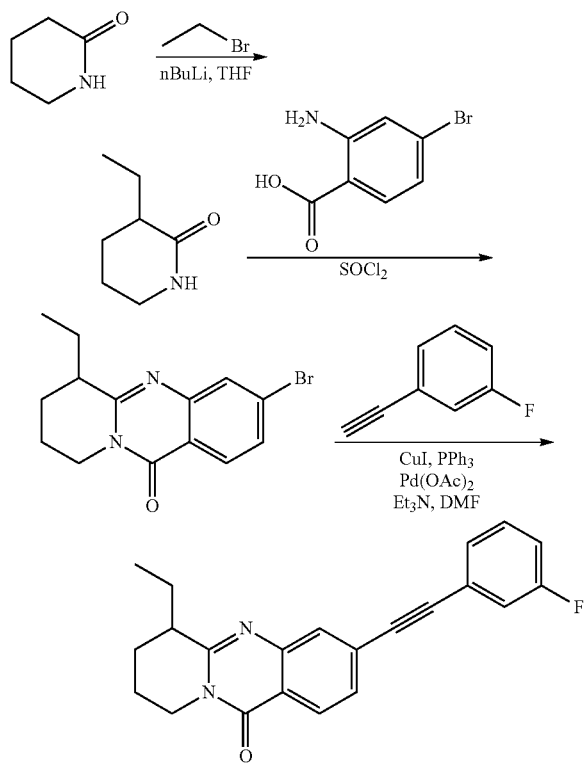

The title compound was prepared according to the experimental procedure as described in Example 4.7a, Example 2.2a and Example 1.1. MS (ESI): 347 (M+H⁺); ¹H NMR (300 MHz, CDCl₃) δ 8.26-8.23 (d, J=8.01 Hz, 1H), 7.82 (s, 1H), 7.55-7.52 (dd, J=8.27, 1.49 Hz, 1H), 7.38-7.34 (m, 2H), 7.28-7.27 (m, 1H), 7.11-7.09 (m, 1H), 4.22-4.13 (m, 1H), 4.07-3.99 (m, 1H), 2.86-2.81 (m, 1H), 2.27-1.94 (m, 4H), 1.81-1.68 (m, 2H), 1.10-1.02 (m, 3H). mGluR5 PAM EC$_{50}$: ++. Fold shift at 10 μM: +.

Example 4.9. Synthesis of 6-benzyl-3-((3-fluorophenyl)ethynyl)-8,9-dihydro-6H-pyrido[2,1-b]quinazolin-11(7H)-one

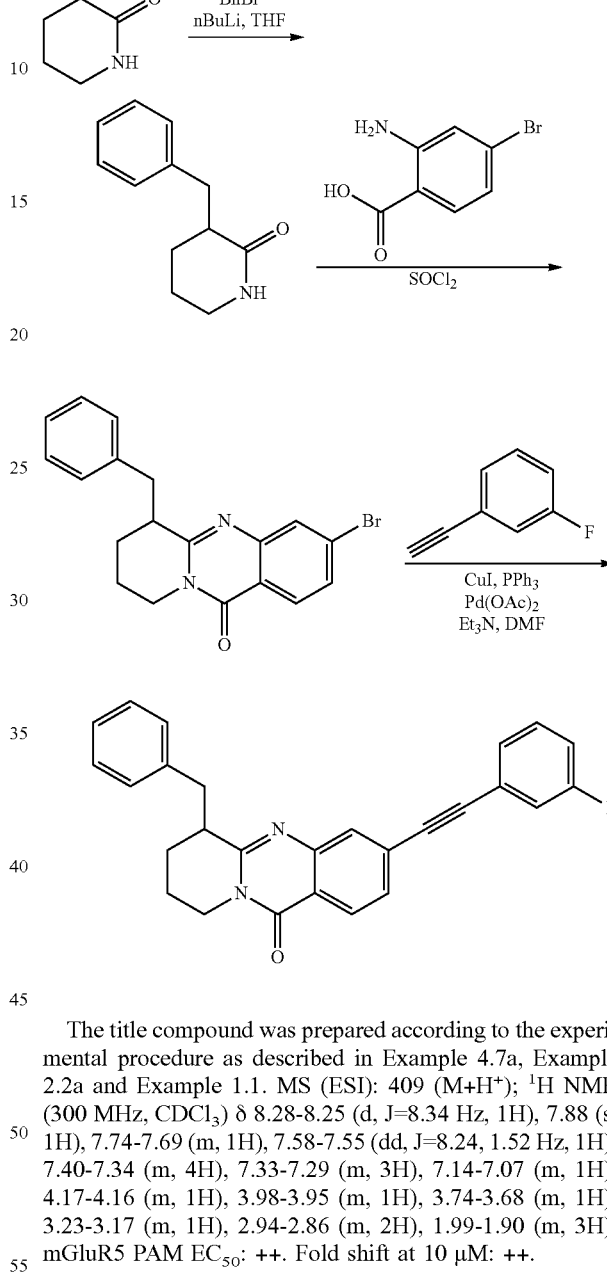

The title compound was prepared according to the experimental procedure as described in Example 4.7a, Example 2.2a and Example 1.1. MS (ESI): 409 (M+H⁺); ¹H NMR (300 MHz, CDCl₃) δ 8.28-8.25 (d, J=8.34 Hz, 1H), 7.88 (s, 1H), 7.74-7.69 (m, 1H), 7.58-7.55 (dd, J=8.24, 1.52 Hz, 1H), 7.40-7.34 (m, 4H), 7.33-7.29 (m, 3H), 7.14-7.07 (m, 1H), 4.17-4.16 (m, 1H), 3.98-3.95 (m, 1H), 3.74-3.68 (m, 1H), 3.23-3.17 (m, 1H), 2.94-2.86 (m, 2H), 1.99-1.90 (m, 3H). mGluR5 PAM EC$_{50}$: ++. Fold shift at 10 μM: ++.

Example 4.10. Synthesis of 3-((3-fluorophenyl)ethynyl)-7-methyl-8,9-dihydro-6H-pyrido[2,1-b]quinazolin-11(7H)-one

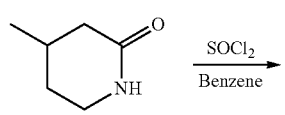

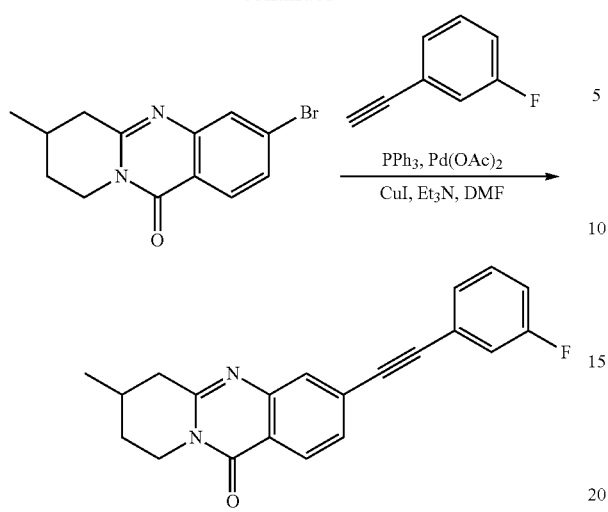

The title compound was prepared according to the experimental procedure as described in Example 2.2a and Example 1.1. MS (ESI): 333 (MH+); ¹H NMR (300 MHz, CDCl₃) δ 8.26-8.23 (d, J=8.27 Hz, 1H), 7.77 (s, 1H), 7.56-7.52 (dd, J=8.74, 1.52 Hz, 1H), 7.38-7.34 (m, 2H), 7.30-7.25 (m, 1H), 7.14-7.06 (m, 1H), 4.41-4.33 (m, 1H), 3.88-3.78 (m, 1H), 3.16-3.08 (m, 1H), 2.67-2.58 (m, 1H), 2.23-2.09 (m, 2H), 1.62-1.55 (m, 1H), 1.18-1.16 (d, J=6.6 Hz, 3H). mGluR5 PAM EC$_{50}$: +++++.

Example 4.11 and Example 4.12. Synthesis of 7-methyl-3-(pyridin-2-ylethynyl)-8,9-dihydro-6H-pyrido[2,1-b]quinazolin-11(7H)-one and 8-methyl-3-(pyridin-2-ylethynyl)-8,9-dihydro-6H-pyrido[2,1-b]quinazolin-11(7H)-one

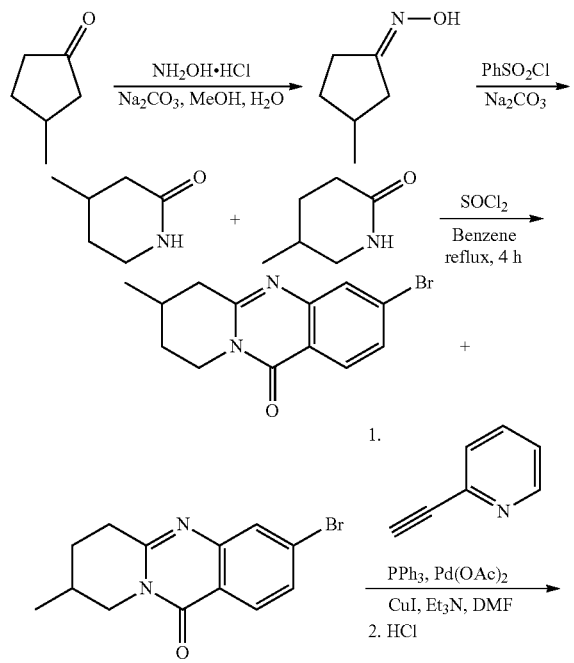

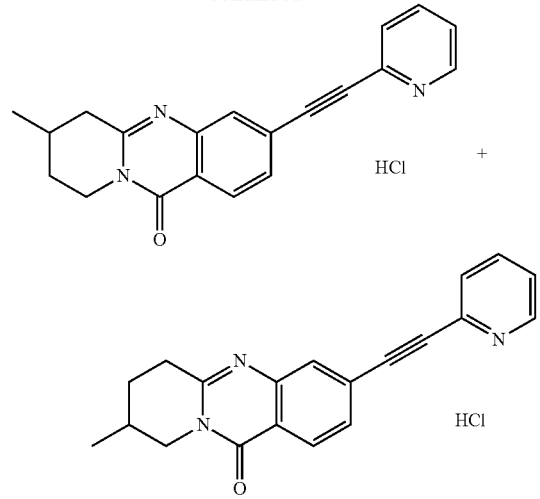

Example 4.11a. Synthesis of 3-methylcyclopentanone oxime

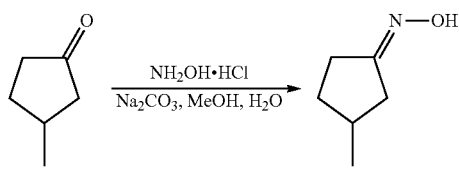

A solution of 3-methylcyclopentanone (2 g, 20.4 mmol), hydroxylamine hydrochloride (2.6 g, 40.8 mmol) and Na₂CO₃ (6.48 g, 61.2 mmol) in MeOH/water (20 mL/12 mL) was stirred at room temperature for 5 h. The solvent was then removed from the reaction mixture under reduced pressure. The residue was partitioned between ethyl acetate and water, and the organic layer was washed with brine, dried over anhydrous sodium sulfate, and stripped of all solvents under reduced pressure to provide the crude for the next step.

Example 4.11b. Synthesis of 4-methylpiperidin-2-one and 5-methylpiperidin-2-one

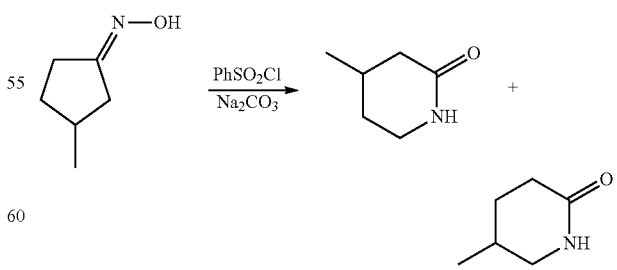

To a solution of 3-methylcyclopentanone oxime (2 g, 17.7 mmol) and Na₂CO₃ (7.5 g, 70.8 mmol) in acetone (100 mL) and water (100 mL) was added phenylsulfonyl chloride (6.18 g, 35.4 mmol) dropwise at 0° C. The reaction mixture was stirred overnight, quenched with water, and extracted with DCM (3×200 mL). The combined organic layers were dried over Na$_2$SO$_4$ and concentrated under reduced pressure to give the desired product.

Example 4.11c and Example 4.12c. Synthesis of 3-bromo-7-methyl-8,9-dihydro-6H-pyrido[2,1-b]quinazolin-11(7H)-one and 3-bromo-8-methyl-8,9-dihydro-6H-pyrido[2,1-b]quinazolin-11(7H)-one

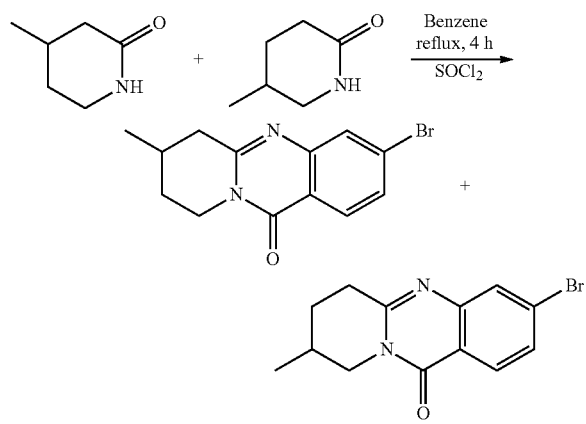

The title compounds were prepared according to the experimental procedure as described in Example 2.2a.

Example 4.11d and Example 4.12d. Synthesis of the HCl Salt of 7-methyl-3-(pyridin-2-ylethynyl)-8,9-dihydro-6H-pyrido[2,1-b]quinazolin-11(7H)-one and HCl Salt of 8-methyl-3-(pyridin-2-ylethynyl)-8,9-dihydro-6H-pyrido[2,1-b]quinazolin-11(7H)-one

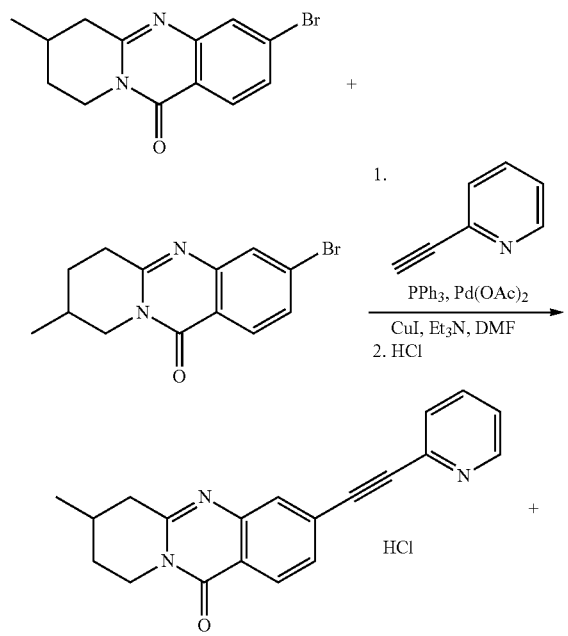

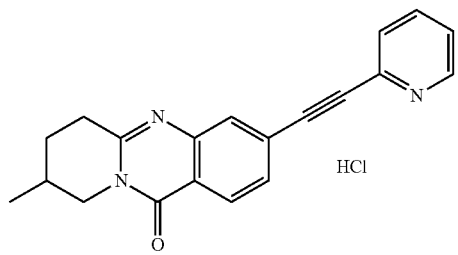

The title compound was prepared according to the experimental procedure as described in Example 1.1. The products were then converted to the corresponding HCl salt.

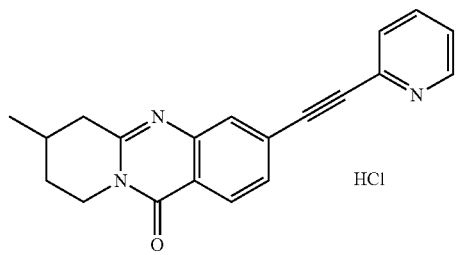 [SMILES: CC1CCn2c(nc3cc(C#Cc4ccccn4)ccc3c2=O)C1 ; Cl]

7-methyl-3-(pyridin-2-ylethynyl)-8,9-dihydro-6H-pyrido[2,1-b]quinazolin-11(7H)-one MS (ESI): 316 (M+H$^+$); $^1$H NMR (300 MHz, DMSO-d$^6$) δ 8.72-8.70 (d, J=4.56 Hz, 1H), 8.26-8.24 (d, J=8.28 Hz, 1H), 8.16 (s, 1H), 8.05-7.99 (m, 1H), 7.88-7.83 (m, 2H), 7.60-7.56 (m, 1H), 4.25-4.17 (m, 1H), 3.80-3.70 (m, 1H), 3.37-3.30 (dd, J=17.84, 3.73 Hz, 1H), 2.87-2.78 (m, 1H), 2.12-2.09 (m, 2H), 1.66-1.57 (m, 1H), 1.10-1.08 (d, J=6.6 Hz, 3H). mGluR5 PAM EC$_{50}$: +++. Fold shift at 10 μM: +.

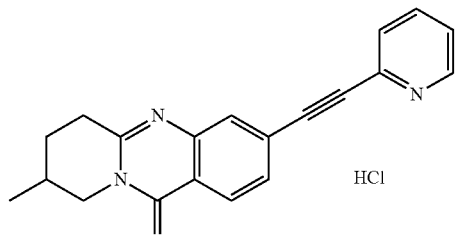

8-methyl-3-(pyridin-2-ylethynyl)-8,9-dihydro-6H-pyrido[2,1-b]quinazolin-11(7H)-one MS (ESI): 316 (M+H$^+$); $^1$H NMR (300 MHz, DMSO-d$^6$) δ 8.71-8.70 (d, J=4.47 Hz, 1H), 8.26-8.24 (d, J=8.28 Hz, 1H), 8.11 (s, 1H), 8.023-7.98 (m, 1H), 7.86-7.81 (t, J=7.56 Hz, 2H), 7.58-7.54 (m, 1H), 4.31-4.25 (dd, J=13.67, 4.76 Hz, 1H), 3.31-3.19 (m, 3H), 2.11-2.096 (m, 2H), 1.56-1.50 (m, 1H), 1.10-1.08 (d, J=6.51 Hz, 3H). mGluR5 PAM EC$_{50}$: ++++. Fold shift at 10 μM: +.

Example 4.13 and Example 4.14. Synthesis of 3-((3-fluorophenyl)ethynyl)-7,7-dimethyl-8,9-dihydro-6H-pyrido[2,1-b]quinazolin-11(7H)-one and 3-((3-fluorophenyl)ethynyl)-8,8-dimethyl-8,9-dihydro-6H-pyrido[2,1-b]quinazolin-11(7H)-one

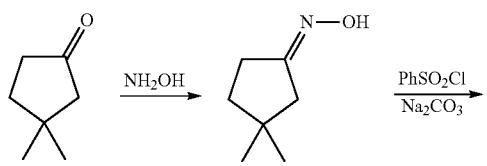

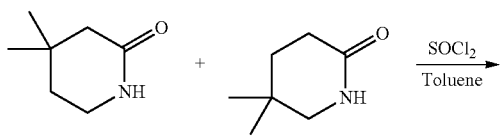

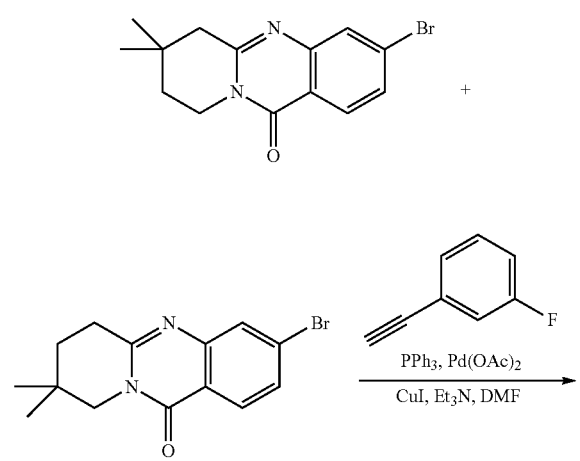

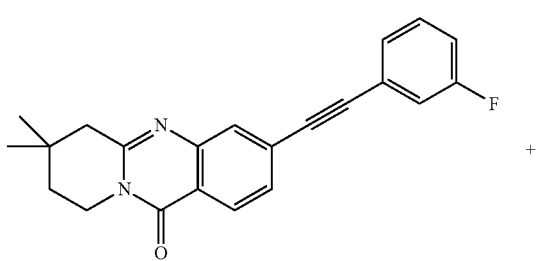

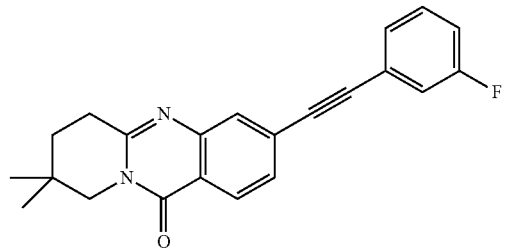

The title compound was prepared according to the experimental procedure as described in Example 4.11a, Example 4.11b, Example 2.2a, and Example 1.1.

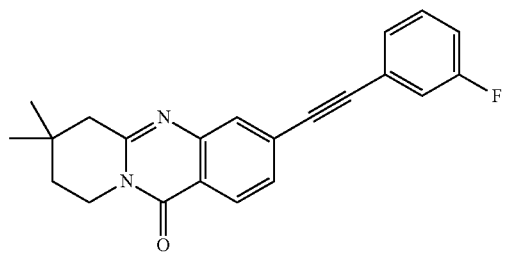 [SMILES: CC1(C)CCn2c(nc3cc(C#Cc4cccc(F)c4)ccc3c2=O)C1]

3-((3-fluorophenyl)ethynyl)-7,7-dimethyl-8,9-dihydro-6H-pyrido[2,1-b]quinazolin-11(7H)-one MS (ESI): 347 (MH$^+$); $^1$H NMR (300 MHz, CDCl$_3$) δ 8.27-8.24 (d, J=8.2 Hz, 1H), 7.76 (s, 1H), 7.56-7.53 (d, J=8.21, 1H), 7.37-7.35 (m, 2H), 7.30-7.25 (m, 1H), 7.14-7.05 (m, 1H), 4.12-4.08 (t, J=6.6 Hz, 2H), 2.80 (s, 2H), 1.87-1.83 (t, J=6.6 Hz, 2H), 1.14 (s, 6H). mGluR5 PAM EC$_{50}$: +++++. Fold shift at 10 μM: ++.

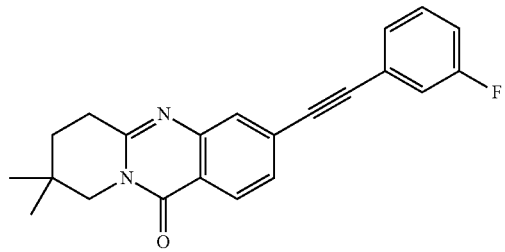 [SMILES: CC1(C)CCc2nc3cc(C#Cc4cccc(F)c4)ccc3c(=O)n2C1]

3-((3-fluorophenyl)ethynyl)-8,8-dimethyl-8,9-dihydro-6H-pyrido[2,1-b]quinazolin-11(7H)-one MS (ESI): 347 (MH$^+$); $^1$H NMR (300 MHz, CDCl$_3$) δ 8.27-8.24 (d, J=8.2 Hz, 1H), 7.76 (s, 1H), 7.56-7.53 (dd, J=8.21, 1.5 Hz, 1H), 7.37-7.35 (m, 2H), 7.27-7.25 (m, 1H), 7.14-7.05 (m, 1H), 3.84 (s, 2H), 3.06-3.01 (t, J=7.1 Hz, 2H), 1.79-1.74 (t, J=7.1 Hz, 2H), 1.12 (s, 6H). mGluR5 PAM EC$_{50}$: +++++. Fold shift at 10 μM: ++.

Example 4.15 and Example 4.16. Synthesis of the HCl Salt of 7,7-dimethyl-3-(pyridin-2-ylethynyl)-8,9-dihydro-6H-pyrido[2,1-b]quinazolin-11(7H)-one and HCl Salt of 8,8-dimethyl-3-(pyridin-2-ylethynyl)-8,9-dihydro-6H-pyrido[2,1-b]quinazolin-11(7H)-one

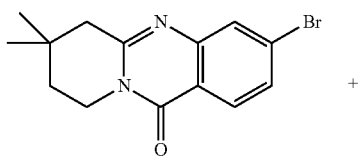

+

Example 4.17. Synthesis of 3-((3-fluorophenyl)ethynyl)-9-methyl-8,9-dihydro-6H-pyrido[2,1-b]quinazolin-11(7H)-one

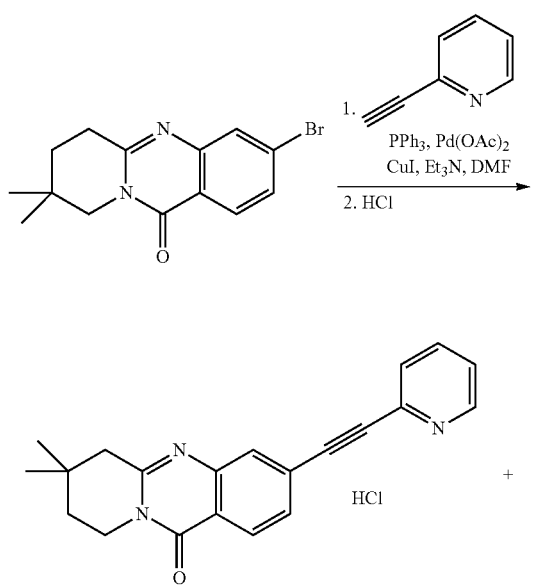

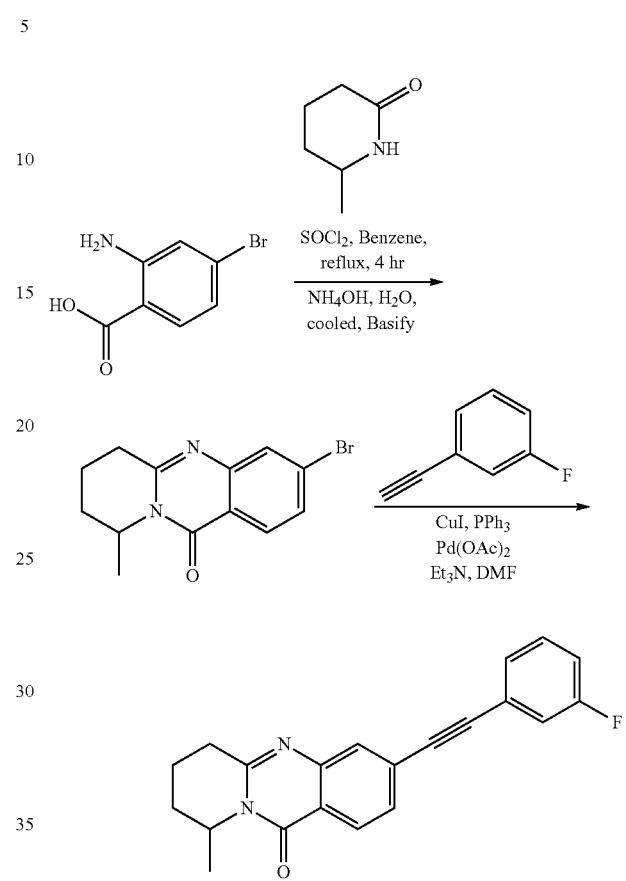

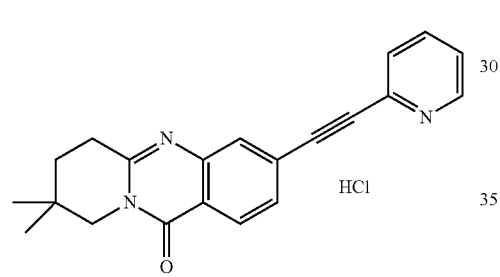

The title compounds were prepared according to the experimental procedures as described in Example 1.1. The products were then converted to the corresponding HCl salts.

8,8-dimethyl-3-(pyridin-2-ylethynyl)-8,9-dihydro-6H-pyrido[2,1-b]quinazolin-11(7H)-one MS (ESI): 330 (MH+); 1H NMR (300 MHz, CD3OD) δ 8.95-8.93 (d, J=5.7 Hz, 1H), 8.68-8.63 (dt, J=8.0, 1.5 Hz, 1H), 8.46-8.44 (d, J=8.3 Hz, 1H), 8.35-8.33 (d, J=8.0 Hz, 1H), 8.13-8.08 (m, 2H), 8.03-8.00 (dd, J=8.3, 1.4 Hz, 1H), 3.89 (s, 2H), 3.41-3.36 (t, J=6.8 Hz, 2H), 1.91-1.87 (t, J=6.8 Hz, 2H), 1.20 (s, 6H). mGluR5 PAM EC50: +++++. Fold shift at 10 μM: +++.

7,7-dimethyl-3-(pyridin-2-ylethynyl)-8,9-dihydro-6H-pyrido[2,1-b]quinazolin-11(7H)-one MS (ESI): 330 (MH+); 1H NMR (300 MHz, CD3OD) δ 8.89-8.87 (d, J=5.9 Hz, 1H), 8.53-8.52 (m, 1H), 8.46-8.44 (d, J=8.3 Hz, 1H), 8.24-8.21 (d, J=8.0 Hz, 1H), 8.03-7.97 (m, 3H), 4.22-4.12 (t, J=6.5, 1.4 Hz, 2H), 3.11 (s, 2H), 2.02-1.99 (t, J=6.4 Hz, 2H), 1.23 (s, 6H). mGluR5 PAM EC50: +++++. Fold shift at 10 μM: +++.

The title compound was prepared according to the experimental procedure as described in Example 2.2a and Example 1.1. MS (ESI): 333 (MH+); 1H NMR (300 MHz, CDCl3) δ 8.27-8.24 (d, J=8.2 Hz, 1H), 7.74 (s, 1H), 7.55-7.51 (d, J=8.21, 1H), 7.37-7.35 (m, 2H), 7.30-7.28 (m, 1H), 7.11-7.07 (m, 1H), 5.12-5.10 (m, 1H), 3.09-3.01 (m, 2H), 2.02-1.98 (m, 4H), 1.43-1.41 (d, J=6.6 Hz, 3H). mGluR5 PAM EC50: ++++.

Example 4.18. Synthesis of the HCl Salt of 9-methyl-3-(pyridin-2-ylethynyl)-8,9-dihydro-6H-pyrido[2,1-b]quinazolin-11(7H)-one

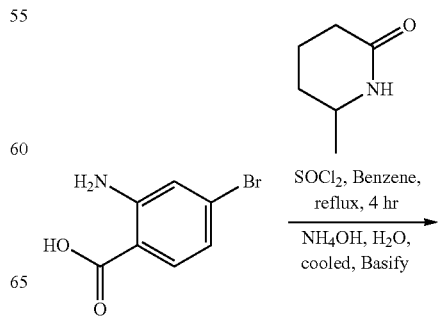

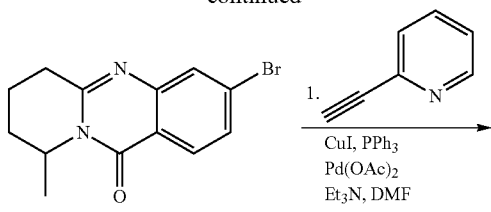

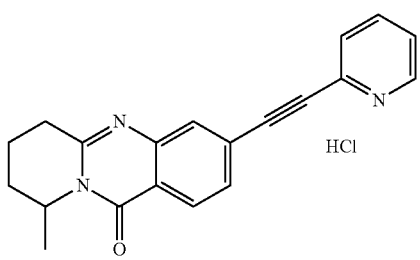

The title compound was prepared according to the experimental procedure as described in Example 2.2a and Example 1.1. The product was then converted to the corresponding HCl salt. MS (ESI): 316 (MH+); ¹H NMR (300 MHz, CD$_3$OD) δ 8.70-8.68 (d, J=4.3 Hz, 1H), 8.25-8.22 (d, J=8.2 Hz, 1H), 8.02 (s, 1H), 8.00-7.94 (m, 1H), 7.83-7.77 (m, 2H), 7.56-7.51 (m, 1H), 4.98-4.90 (m, 1H), 3.39-3.10 (m, 2H), 2.00-1.87 (m, 4H), 1.34-1.32 (d, J=6.6 Hz, 3H). mGluR5 PAM EC$_{50}$: ++++. Fold shift at 10 μM: ++.

Example 4.19. Synthesis of the HCl Salt of 9-ethyl-3-(pyridin-2-ylethynyl)-8,9-dihydro-6H-pyrido[2,1-b]quinazolin-11(7H)-one

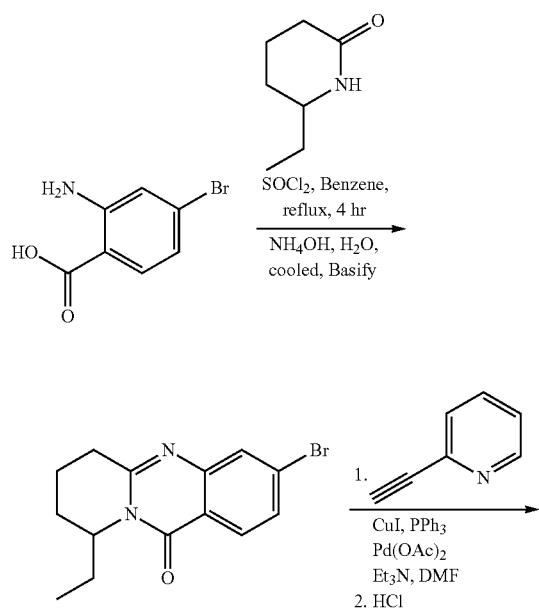

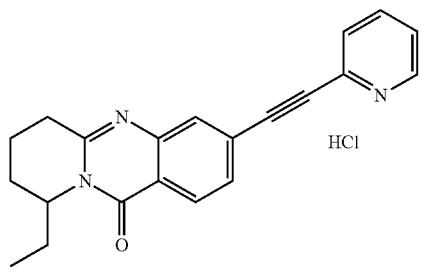

The title compound was prepared according to the experimental procedure as described in Example 2.2a and Example 1.1. The product was then converted to the corresponding HCl salt. MS (ESI): 333 (MH+); ¹H NMR (300 MHz, CD$_3$OD) δ 8.70-8.68 (d, J=4.5 Hz, 1H), 8.25-8.22 (d, J=8.2 Hz, 1H), 8.06 (s, 1H), 8.00-7.95 (m, 1H), 7.84-7.79 (m, 2H), 7.56-7.52 (m, 1H), 4.70-4.65 (m, 1H), 3.25-3.14 (m, 2H), 2.10-2.06 (m, 1H), 1.88-1.84 (m, 3H), 1.74-1.61 (m, 2H), 0.96-0.91 (t, J=7.3 Hz, 3H). mGluR5 PAM EC$_{50}$: ++++. Fold shift at 10 μM: ++.

Example 4.20. Synthesis of 3-((3-fluorophenyl)ethynyl)-8H-pyrido[2,1-b]quinazolin-11(9H)-one

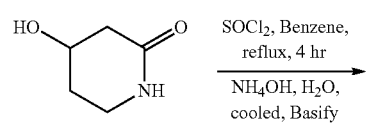

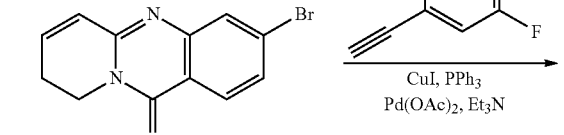

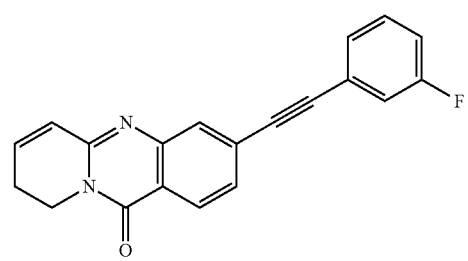

The title compound was prepared according to the experimental procedure as described in Example 2.2a and Example 1.1. MS (ESI): 317 (M+H+); ¹H NMR (300 MHz, CDCl$_3$) δ 8.28-8.25 (d, J=8.22 Hz, 1H), 7.82 (s, 1H), 7.58-7.55 (dd, J=8.72, 1.47 Hz, 1H), 7.38-7.35 (m, 2H), 7.29-7.28 (m, 1H), 7.13-7.07 (m, 1H), 6.78-6.71 (m, 1H), 6.54-6.50 (m, 1H), 4.32-4.27 (t, J=7.01 Hz, 2H), 2.66-2.59 (m, 2H). mGluR5 PAM EC$_{50}$: ++++.

Example 4.21. Synthesis of 3'4(3-fluorophenyl)ethynyl)-6',7'-dihydrospiro[[1,3]dioxolane-2,8'-pyrido[2,1-b]quinazolin]-11'(9'H)-one

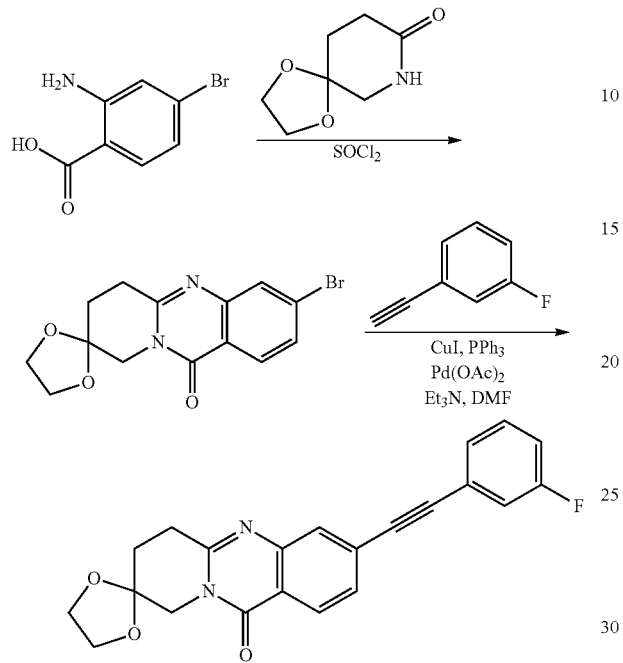

The title compound was prepared according to the experimental procedure as described in Example 2.2a and Example 1.1. MS (ESI): 377 (M+H$^+$); $^1$H NMR (300 MHz, CDCl$_3$) δ 8.26-8.23 (d, J=8.19 Hz, 1H), 7.78 (s, 1H), 7.57-7.54 (dd, J=8.24, 1.52 Hz, 1H), 7.41-7.30 (m, 2H), 7.29-7.26 (m, 1H), 7.14-7.08 (m, 1H), 4.09 (broad s, 6H), 3.21-3.16 (t, J=7.10 Hz, 2H), 2.22-2.18 (t, J=7.11 Hz, 2H). mGluR5 PAM EC$_{50}$: ++++. Fold shift at 10 µM: ++.

Example 4.22. Synthesis of 3-((3-fluorophenyl)ethynyl)-6H-pyrido[2,1-b]quinazoline-8,11(7H,9H)-dione

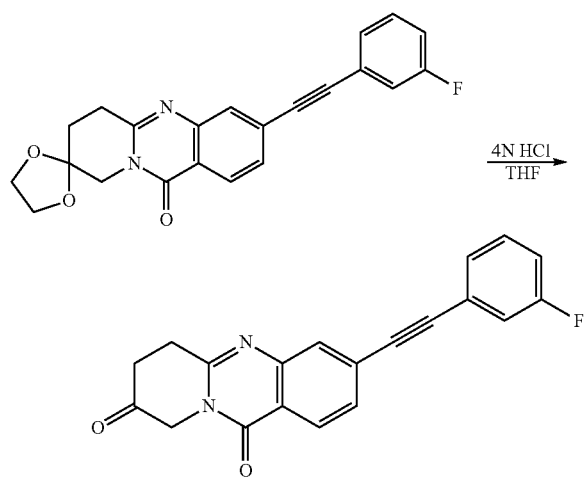

A solution of 3'((3-fluorophenyl)ethynyl)-6',7'-dihydrospiro[[1,3]dioxolane-2,8'-pyrido[2,1-b]quinazolin]-11' (9'H)-one (0.5 g, 1.3 mmol) and 4N HCl (4 mL) in THF (20 mL) was heated at reflux for 4 h. After it was cooled to room temperature, the reaction mixture was quenched with Na$_2$CO$_3$ solution and extracted with ethyl acetate (3×50 mL). The combined organic layers were dried over Na$_2$SO$_4$. After filtration and concentration, the residue was purified by silica gel chromatography to give the desired product. MS (ESI): 333 (MH$^+$); $^1$H NMR (300 MHz, CDCl$_3$) δ 8.28-8.25 (d, J=8.19 Hz, 1H), 7.82 (s, 1H), 7.63-7.60 (dd, J=8.22, 1.50 Hz, 1H), 7.39-7.35 (m, 2H), 7.28-7.27 (m, 1H), 7.15-7.09 (m, 1H), 4.28 (s, 2H), 3.34-3.30 (t, 2H), 2.85-2.81 (t, 2H). mGluR5 PAM EC$_{50}$: +++. Fold shift at 10 µM: +.

Example 4.23. Synthesis of 3-((3-fluorophenyl)ethynyl)-8-hydroxy-8,9-dihydro-6H-pyrido[2,1-b]quinazolin-11(7H)-one

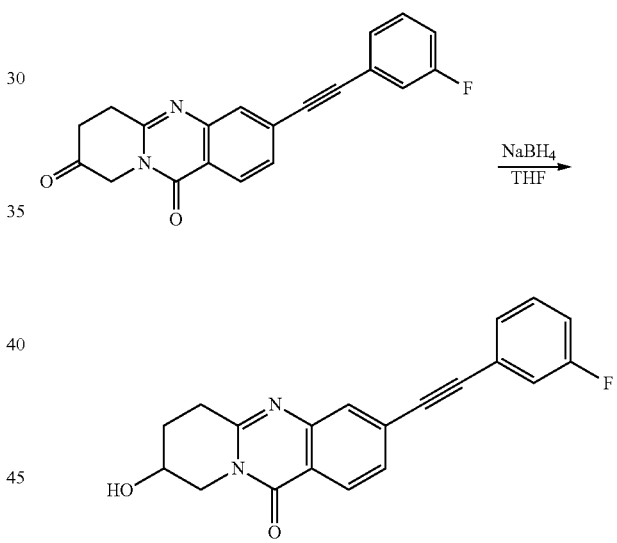

To a solution of 3-((3-fluorophenyl)ethynyl)-6H-pyrido[2,1-b]quinazoline-8,11 (7H,9H)-dione (0.2 g, 0.6 mmol, 1 equiv) in THF (15 mL) was added NaBH$_4$ (45.6 mg, 1.2 mmol, 2 equiv) in portions. After stirring at rt for 30 minute, the reaction mixture was quenched with water and extracted with ethyl acetate (3×50 mL). The combined organic layers were dried over Na$_2$SO$_4$. After filtration and concentration, the residue was purified by silica gel chromatography to give the desired product. MS (ESI): 335 (M+H$^+$); $^1$H NMR (300 MHz, CDCl$_3$) δ 8.24-8.21 (d, J=8.19 Hz, 1H), 7.76 (s, 1H), 7.56-7.53 (dd, J=8.22, 1.41 Hz, 1H), 7.37-7.34 (m, 2H), 7.27-7.26 (m, 1H), 7.13-7.06 (m, 1H), 4.53-4.51 (m, 1H), 4.34-4.28 (m, 1H), 4.05-3.99 (m, 1H), 3.52-3.22 (m, 1H), 3.03-2.93 (m, 1H), 2.23-2.16 (m, 1H), 2.11-2.02 (m, 2H). mGluR5 PAM EC$_{50}$: +++. Fold shift at 10 µM: ++.

Example 4.24. Synthesis of the HCl Salt of 8-hydroxy-3-(pyridin-2-ylethynyl)-8,9-dihydro-6H-pyrido[2,1-b]quinazolin-11(7H)-one

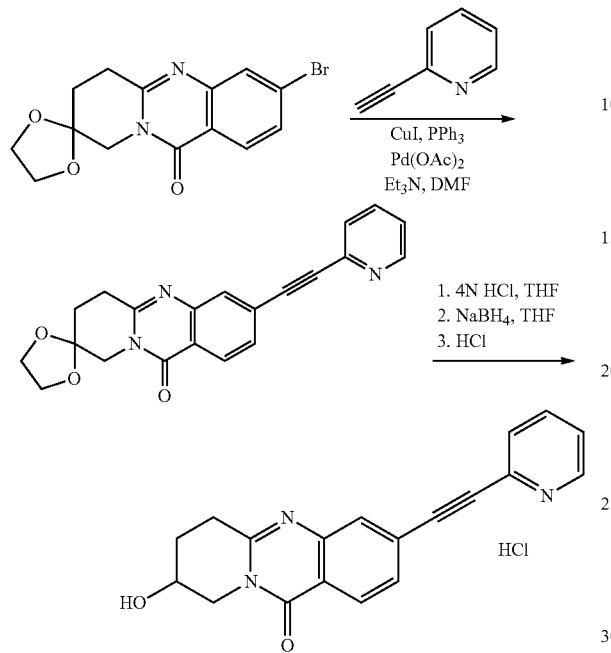

The title compound was prepared according to the experimental procedure as described in Example 1.1, Example 4.22, and Example 4.23. The product was then converted to the corresponding HCl salt. MS (ESI): 318 (M+H⁺); ¹H NMR (300 MHz, CD₃OD) δ 8.86-8.84 (d, J=4.952 Hz, 1H), 8.49-8.41 (m, 2H), 8.19-8.16 (d, J=7.954 Hz, 1H), 8.00-7.92 (m, 3H), 4.51-4.47 (m, 1H), 4.34-4.29 (dd, J=5.08, 3.37 Hz, 1H), 4.01-3.95 (dd, J=7.25, 1.63 Hz, 1H), 3.54-3.43 (m, 1H), 3.28-3.21 (m, 1H), 2.21-2.12 (m, 2H). mGluR5 PAM EC₅₀: +.

Example 4.25. Synthesis of 3-((3-fluorophenyl)ethynyl)-8-methoxy-8,9-dihydro-6H-pyrido[2,1-b]quinazolin-11(7H)-one

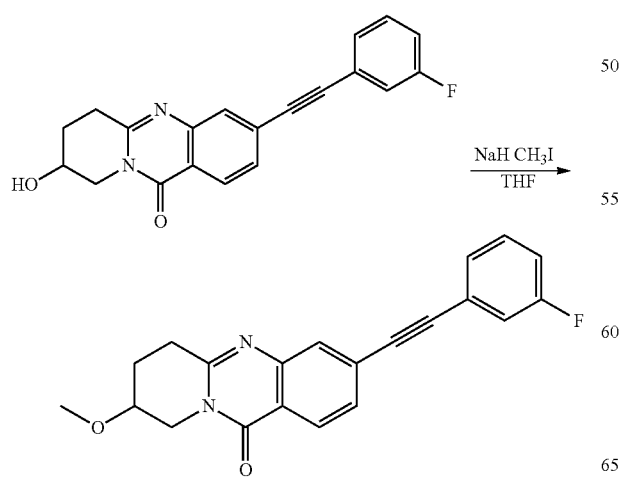

To a solution of 3-((3-fluorophenyl)ethynyl)-8-hydroxy-8,9-dihydro-6H-pyrido[2,1-b]quinazolin-11(7H)-one (0.2 g, 0.6 mmol, 1 equiv) in THF (15 mL) was added NaH (57.6 mg, 2.4 mmol, 4 equiv) in portions. After stirring at rt for 1 h, the reaction mixture was quenched with water and extracted with ethyl acetate (3×50 mL). The combined organic layers were dried over Na₂SO₄. After filtration and concentration, the residue was purified using silica gel chromatography to give the desired product. MS (ESI): 349 (M+H⁺); ¹H NMR (300 MHz, CDCl₃) δ 8.27-8.24 (d, J=8.46 Hz, 1H), 8.01 (s, 1H), 7.62-7.50 (d, J=8.19 Hz, 1H), 7.37-7.35 (m, 2H), 7.30-7.28 (m, 1H), 7.14-7.09 (m, 1H), 4.58-4.57 (m, 1H), 4.02-4.00 (m, 1H), 3.87-3.81 (m, 1H), 3.42 (s, 3H), 3.33-3.20 (m, 2H), 2.26-2.15 (m, 2H). mGluR5 PAM EC₅₀: +++++. Fold shift at 10 μM: +.

Example 4.26. Synthesis of the HCl Salt of 8-methoxy-3-(pyridin-2-ylethynyl)-8,9-dihydro-6H-pyrido[2,1-b]quinazolin-11(7H)-one

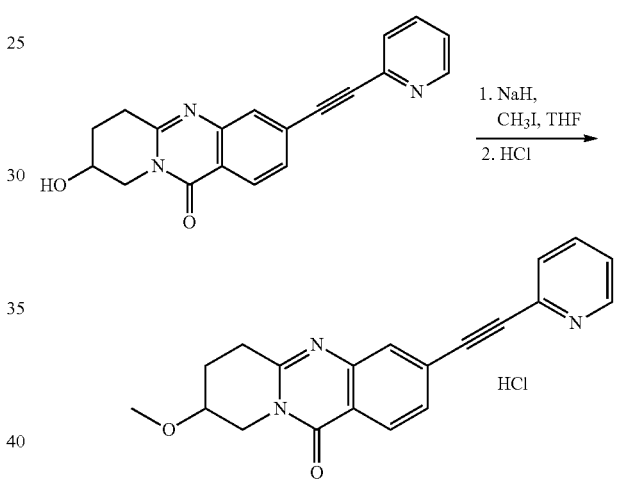

The title compound was prepared according to the experimental procedure as described in Example 4.25. The product was then converted to the corresponding HCl salt. MS (ESI): 332 (M+H⁺); ¹H NMR (300 MHz, CD₃OD) δ 8.93-8.91 (d, J=5.07 Hz, 1H), 8.65-8.59 (dt, J=7.59, 1.47 Hz, 1H), 8.45-8.42 (d, J=8.28 Hz, 1H), 8.32-8.29 (d, J=7.98 Hz, 1H), 8.10-7.99 (m, 3H), 4.57-4.52 (d, J=12.66 Hz, 1H), 4.15-4.12 (m, 1H), 3.96-3.90 (dd, J=14.82, 3.24 Hz, 1H), 3.45 (s, 3H), 3.33 (s, 1H)?, 2.32-2.29 (m, 1H), 2.23-2.17 (m, 1H). mGluR5 PAM EC₅₀: +++. Fold shift at 10 μM: ++.

Example 4.27. Synthesis of the HCl Salt of 4-(pyridin-2-ylethynyl)-9,9a-dihydro-1H-cyclopropa[3,4]pyrrolo[2,1-b]quinazolin-7(1aH)-one

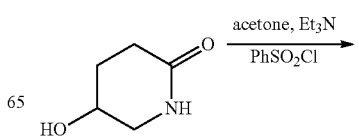

-continued

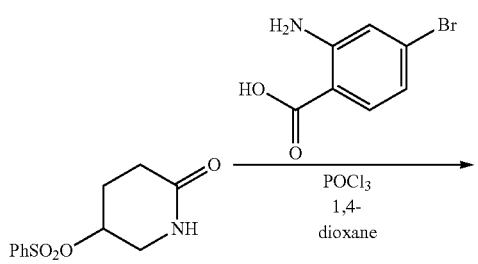

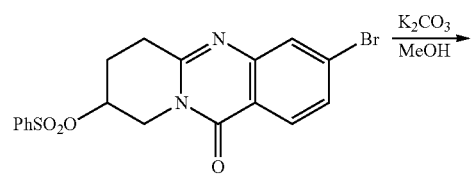

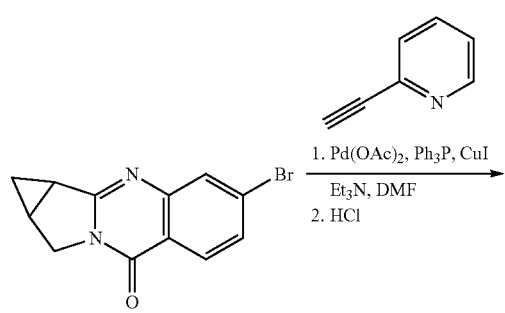

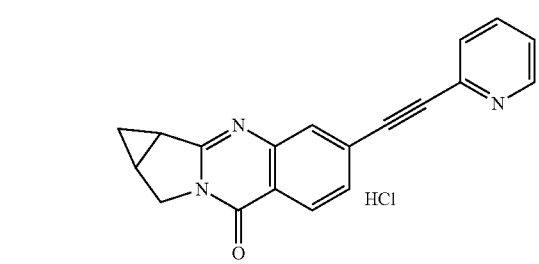

Example 4.27a. Synthesis of 6-oxopiperidin-3-yl benzenesulfonate

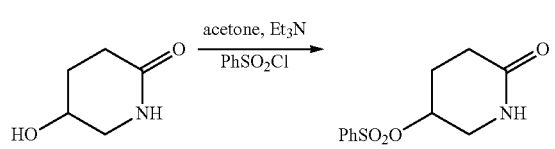

The title compound was prepared according to the experimental procedure as described in Example 3.3a.

Example 4.27b. Synthesis of 3-bromo-11-oxo-7,8,9,11-tetrahydro-6H-pyrido[2,1-b]quinazolin-8-yl 4-bromobenzenesulfonate

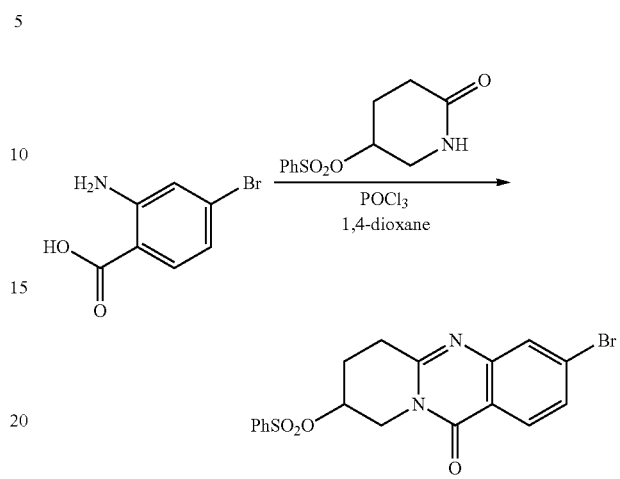

A solution of 2-amino-4-bromobenzoic acid (1.4 g, 6.6 mmol, 1.1 equiv), 6-oxopiperidin-3-yl 4-bromobenzenesulfonate (2 g, 6.0 mmol, 1 equiv), and phosphoryl trichloride (4 mL) in 1,4-dioxane (100 mL) was stirred at 80° C. for two hours. After it was cooled to room temperature, the reaction mixture was diluted with water and extracted with ethyl acetate (3×100 mL). The combined organic layers were dried over $Na_2SO_4$. After filtration and concentration, the residue was purified by silica gel chromatography to give the desired product.

Example 4.27c. Synthesis of 4-bromo-9,9a-dihydro-1H-cyclopropa[3,4]pyrrolo[2,1-b]quinazolin-7 (1aH)-one

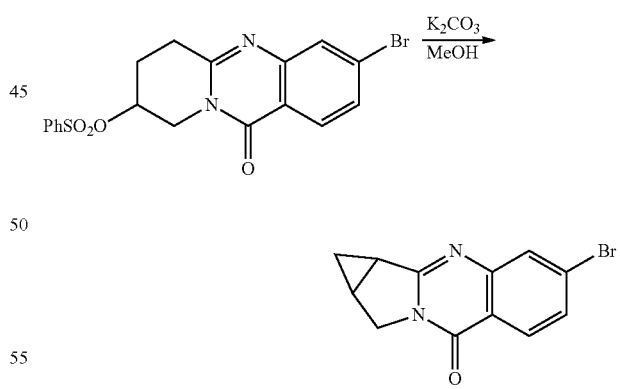

A solution of 3-bromo-11-oxo-7,8,9,11-tetrahydro-6H-pyrido[2,1-b]quinazolin-8-yl 4-bromobenzenesulfonate (0.5 g, 0.98 mmol, 1.1 equiv) and $K_2CO_3$ in MeOH (100 mL) was stirred at reflux for two hours. After it was cooled to room temperature, the reaction mixture was diluted with water and extracted with ethyl acetate (3×100 mL). The combined organic layers were dried over $Na_2SO_4$. After filtration and concentration, the residue was purified by silica gel chromatography to give the desired product.

Example 4.27d. Synthesis of the HCl Salt of 4-(pyridin-2-ylethynyl)-9,9a-dihydro-1H-cyclopropa[3,4]pyrrolo[2,1-b]quinazolin-7(1aH)-one

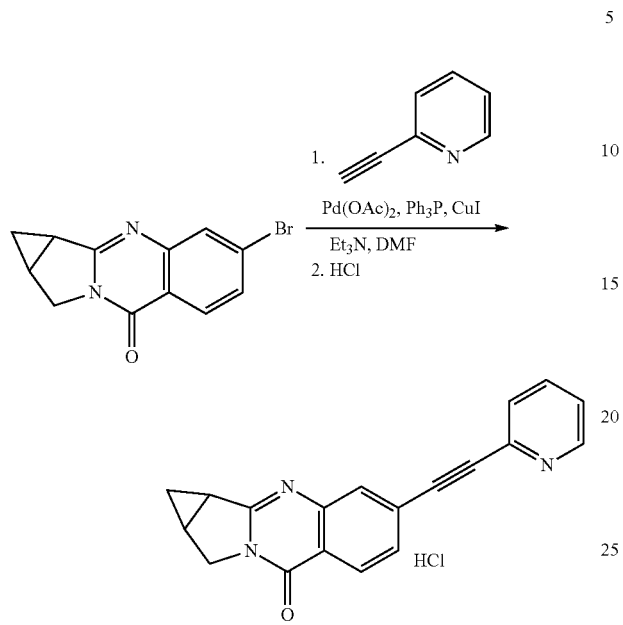

The title compound was prepared according to the experimental procedure as described in Example 1.1. The compound was then converted to the corresponding HCl salt. MS (ESI): 300 (M+H$^+$); $^1$H NMR (300 MHz, CDCl$_3$) δ 8.91-8.89 (d, J=5.22 Hz, 1H), 8.63-8.57 (t, J=7.94 Hz, 1H), 8.39-8.36 (d, J=8.22 Hz, 1H), 8.29-8.27 (d, J=8.07 Hz, 1H), 8.08-8.02 (m, 2H), 7.94-7.91 (d, J=8.27 Hz, 1H), 4.38-4.36 (m, 2H), 3.00-2.99 (m, 1H), 2.67-2.67 (m, 1H), 1.79-1.75 (m, 1H), 1.19-1.16 (m, 1H). mGluR5 PAM EC$_{50}$: +++.

Example 4.28. Synthesis of 3-((3-fluorophenyl)ethynyl)-8-methylene-8,9-dihydro-6H-pyrido[2,1-b]quinazolin-11(7H)-one

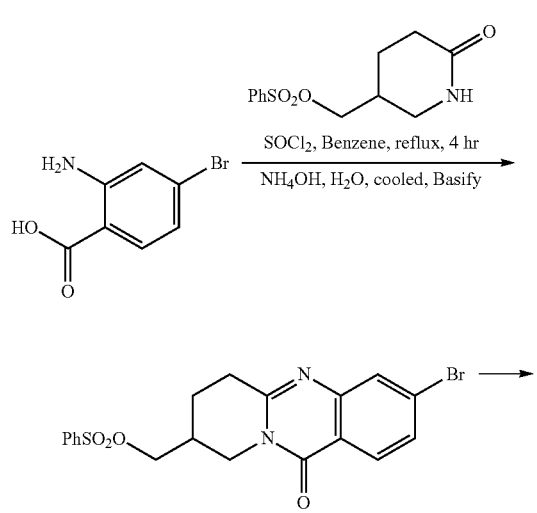

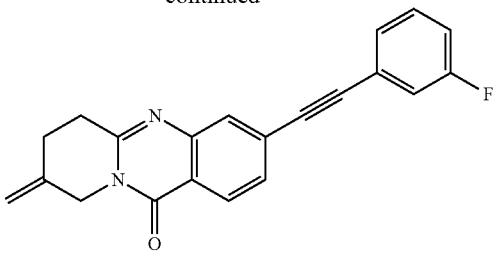

Example 4.28a. Synthesis of (3-bromo-11-oxo-7,8,9,11-tetrahydro-6H-pyrido[2,1-b]quinazolin-8-yl)methyl benzenesulfonate

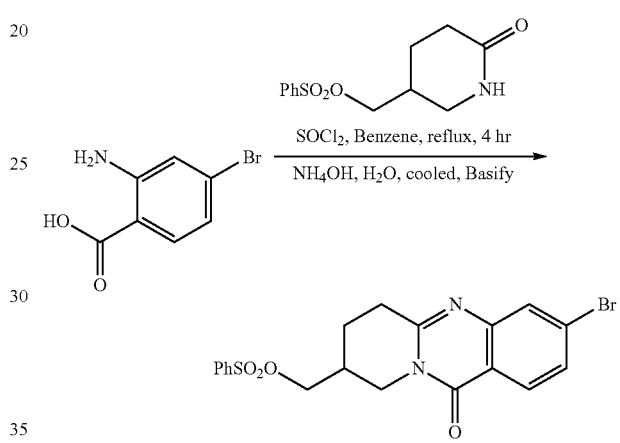

The title compound was prepared according to the experimental procedure as described in Example 2.2a.

Example 4.28b. Synthesis of 3-((3-fluorophenyl)ethynyl)-8-methylene-8,9-dihydro-6H-pyrido[2,1-b]quinazolin-11(7H)-one

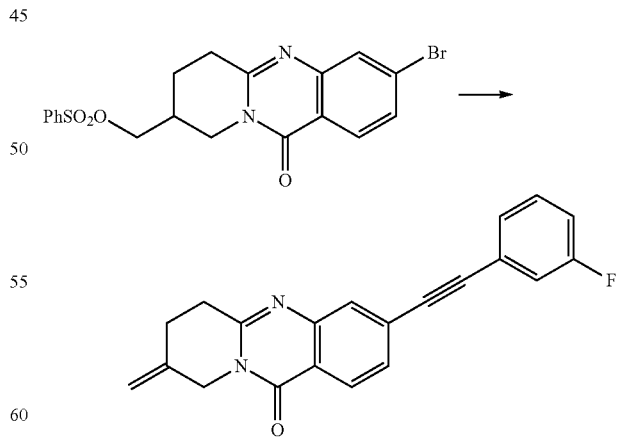

The title compound was prepared according to the experimental procedure as described in Example 1.1. MS (ESI): 331 (M+H$^+$); $^1$H NMR (300 MHz, CDCl$_3$) δ 8.27-8.24 (d, J=8.46 Hz, 1H), 8.01 (s, 1H), 7.62-7.50 (d, J=8.19 Hz, 1H), 7.37-7.35 (m, 2H), 7.30-7.28 (m, 1H), 7.14-7.09 (m, 1H), 5.22 (s, 1H), 5.12 (s, 1H), 4.73 (s, 2H), 3.11-3.06 (t, J=6.60 Hz, 2H), 2.72-2.68 (t, J=7.5 Hz, 2H). mGluR5 PAM EC$_{50}$: ++++. Fold shift at 10 µM: ++.

Example 4.29. Synthesis of the HCl Salt of 8-methylene-3-(pyridin-2-ylethynyl)-8,9-dihydro-6H-pyrido[2,1-b]quinazolin-11(7H)-one The title compound was prepared according to the experimental procedure as described in Example 3.3a, Example 2.2a, and Example 1.1. The product was then converted to the corresponding HCl salt. MS (ESI): 314 (M+H$^+$); $^1$H NMR (300 MHz, CDCl$_3$) δ 8.900-8.882 (d, J=5.553 Hz, 1H), 8.578-8.525 (t, J=7.939 Hz, 1H), 8.461-8.433 (d, J=8.284 Hz, 1H), 8.264-8.237 (d, J=7.954 Hz, 1H), 8.064-7.977 (m, 3H), 5.357 (s, 1H), 5.285 (s, 1H), 4.792 (s, 2H), 3.401-3.356 (t, J=6.783 Hz, 2H), 2.829-2.784 (t, J=6.768 Hz, 2H).

Example 4.30. Synthesis of the HCl Salt of 8-(dimethylamino)-3-((3-fluorophenyl)ethynyl)-8,9-dihydro-6H-pyrido[2,1-b]quinazolin-11(7H)-one

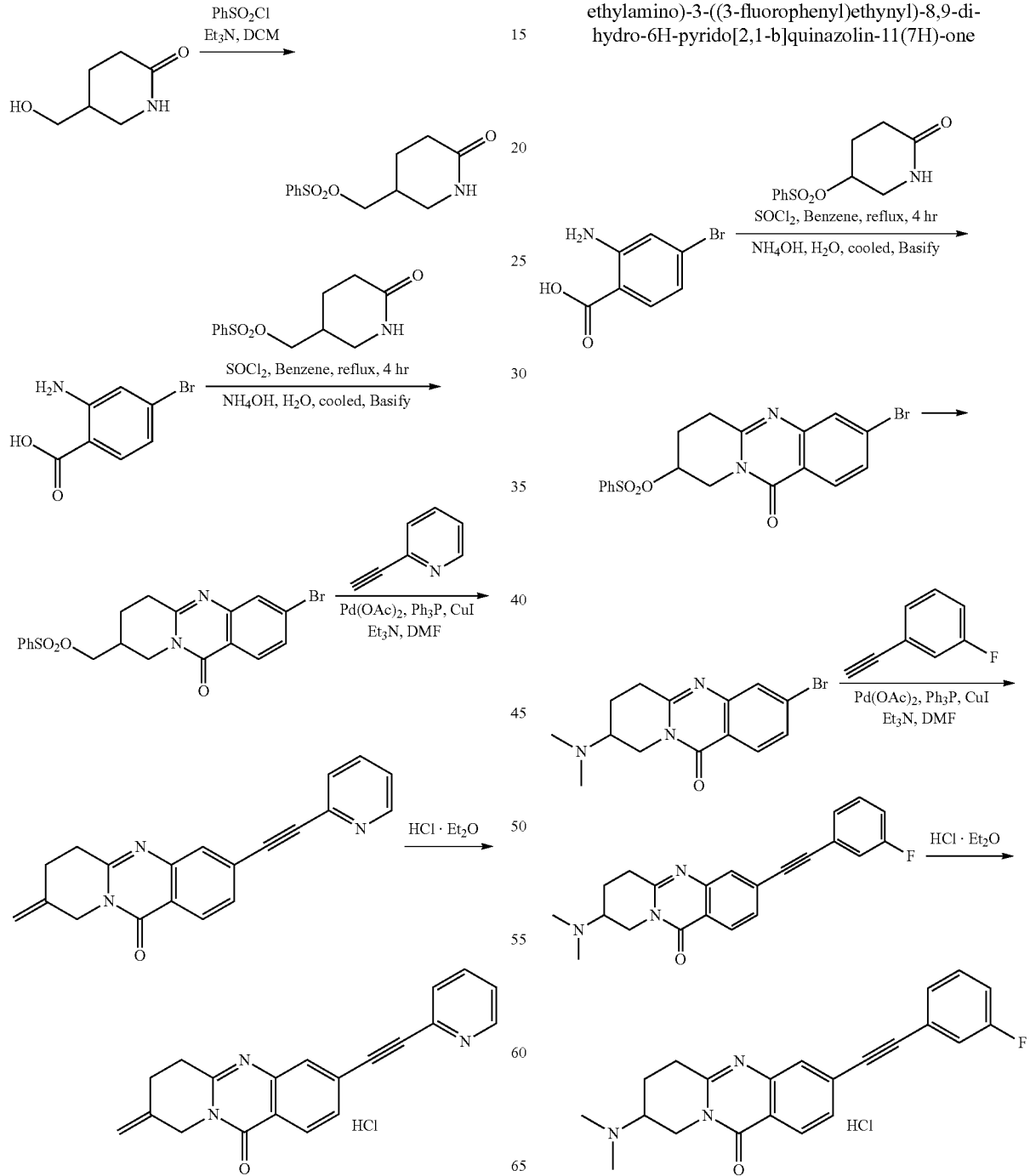

Example 4.30a. Synthesis of 3-bromo-11-oxo-7,8,9,11-tetrahydro-6H-pyrido[2,1-b]quinazolin-8-yl benzenesulfonate

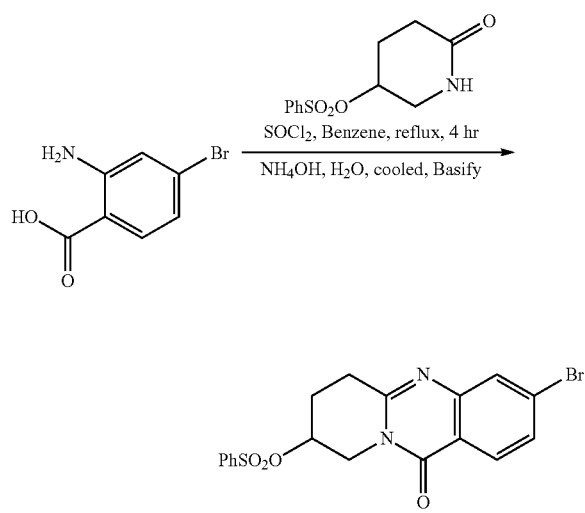

The title compound was prepared according to the experimental procedure as described in Example 2.2a.

Example 4.30b. Synthesis of 3-bromo-8-(dimethylamino)-8,9-dihydro-6H-pyrido[2,1-b]quinazolin-11(7H)-one

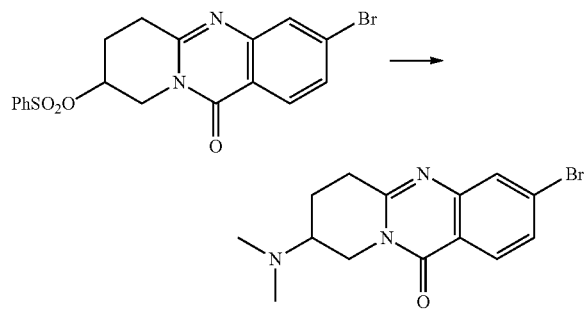

A solution of 3-bromo-11-oxo-7,8,9,11-tetrahydro-6H-pyrido[2,1-b]quinazolin-8-yl benzenesulfonate (0.15 g, 0.34 mmol, 1 equiv) and excess aq. dimethylamine in acetonitrile (6 mL) was stirred at 70° C. for 3 hours. After it was cooled to rt, the reaction mixture was diluted with water and extracted with ethyl acetate (3×20 mL). The combined organic layers were dried over $Na_2SO_4$. After filtration and concentration, the residue was purified by silica gel chromatography to give the desired product.

Example 4.30c. Synthesis of the HCl Salt of 8-(dimethylamino)-3-((3-fluorophenyl)ethynyl)-8,9-dihydro-6H-pyrido[2,1-b]quinazolin-11(7H)-one

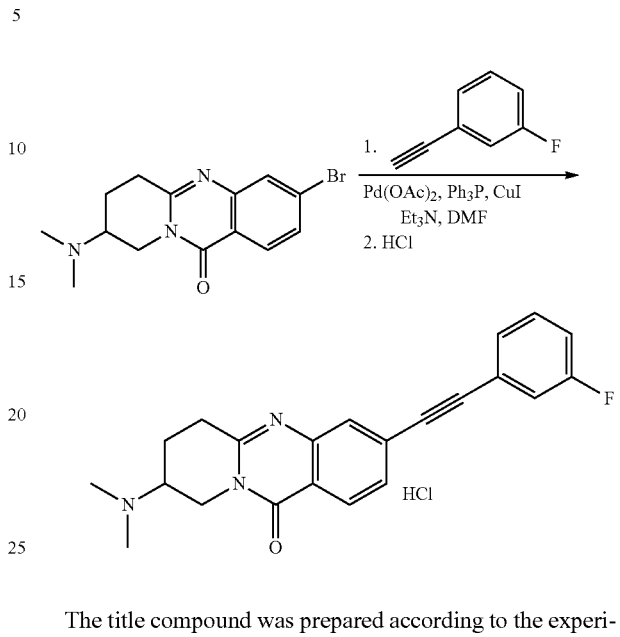

The title compound was prepared according to the experimental procedure as described in Example 1.1. The product was then converted to the corresponding HCl salt. MS (ESI): 362 (M+H⁺); $^1$H NMR (300 MHz, CDCl$_3$) δ 8.26-8.23 (d, J=8.28 Hz, 1H), 7.76 (s, 1H), 7.56-7.53 (dd, J=8.24, 1.46 Hz, 1H), 7.37-7.34 (m, 2H), 7.27-7.23 (m, 1H), 7.13-7.06 (m, 1H), 4.18-4.15 (m, 2H), 3.19-3.09 (m, 1H), 3.00-2.90 (m, 1H), 2.87-2.78 (m, 1H), 2.38 (s, 6H), 2.22-2.12 (m, 1H), 2.02-1.92 (m, 1H). mGluR5 PAM EC$_{50}$: ++. Fold shift at 10 µM: +.

Example 4.31. Synthesis of 3-((3-fluorophenyl)ethynyl)-8-(hydroxymethyl)-8,9-dihydro-6H-pyrido[2,1-b]quinazolin-11(7H)-one

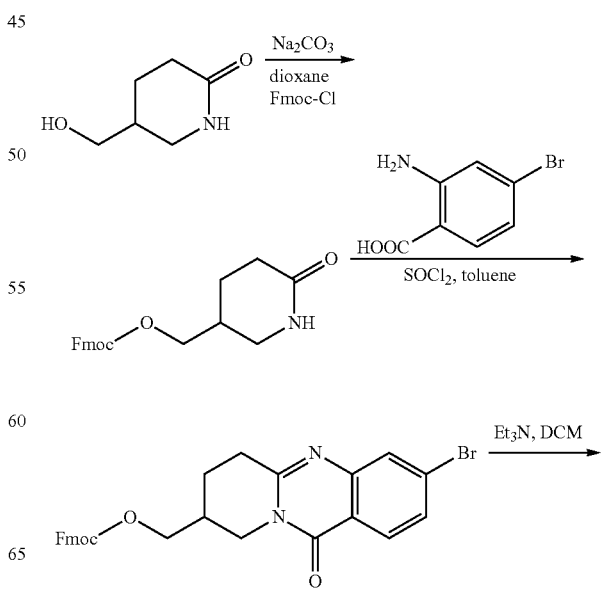

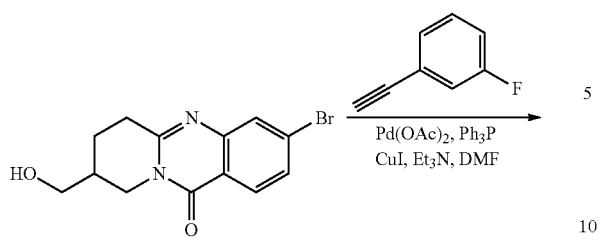

Example 4.31a. Synthesis of (9H-fluoren-9-yl)methyl (6-oxopiperidin-3-yl)methyl carbonate The title compound was prepared according to the experimental procedure as described in Example 5.1a.

Example 4.31b. Synthesis of (9H-fluoren-9-yl) methyl (3-bromo-11-oxo-7,8,9,11-tetrahydro-6H-pyrido[2,1-b]quinazolin-8-yl)methyl carbonate

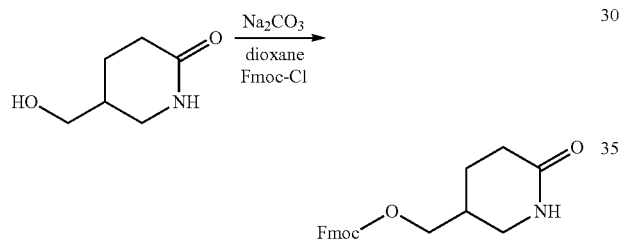

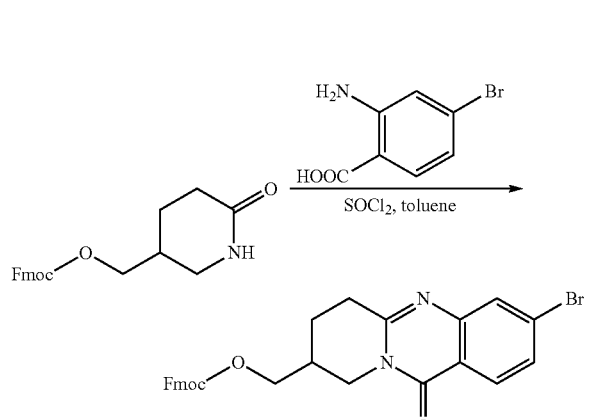

The title compound was prepared according to the experimental procedure as described in Example 2.2a.

Example 4.31c. Synthesis of 3-bromo-8-(hydroxymethyl)-8,9-dihydro-6H-pyrido[2,1-b]quinazolin-11(7H)-one

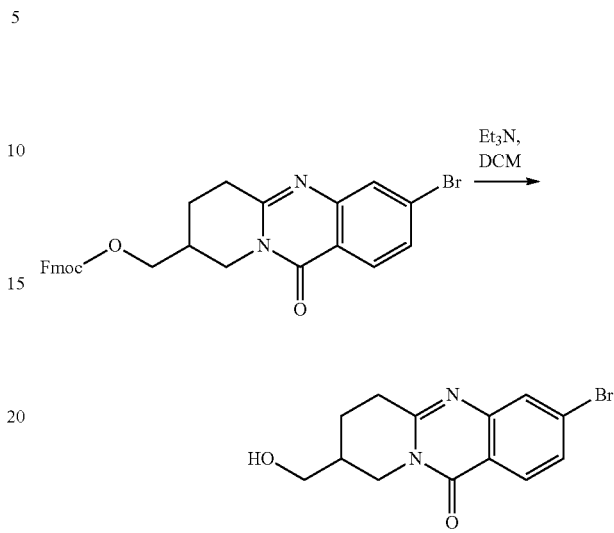

The title compound was prepared according to the experimental procedure as described in Example 3.17b.

Example 4.31d. Synthesis of 3-((3-fluorophenyl)ethynyl)-8-(hydroxymethyl)-8,9-dihydro-6H-pyrido[2,1-b]quinazolin-11(7H)-one The title compound was prepared according to the experimental procedure as described in Example 1.1. MS (ESI): 349 (MH+); $^1$H NMR (300 MHz, CDCl$_3$) δ 8.26-8.22 (d, J=8.04 Hz, 1H), 7.77 (s, 1H), 7.56-7.54 (d, J=8.22 Hz, 1H), 7.36-7.31 (m, 2H), 7.28 (s, 1H), 7.13-7.10 (m, 1H), 4.40-4.37 (dd, J=14.1, 5.1 Hz, 1H), 3.86-3.64 (m, 3H), 3.11-2.93 (m, 2H), 2.34-2.24 (m, 1H), 2.20-2.11 (m, 1H), 1.80 (s, 1H), 1.73-1.67 (m, 1H). mGluR5 PAM EC$_{50}$: +++++. Fold shift at 10 μM: +++.

Example 4.32. Synthesis of the HCl Salt of 8-(hydroxymethyl)-3-(pyridin-2-ylethynyl)-8,9-dihydro-6H-pyrido[2,1-b]quinazolin-11(7H)-one

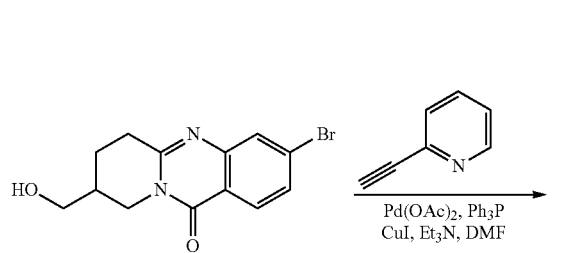

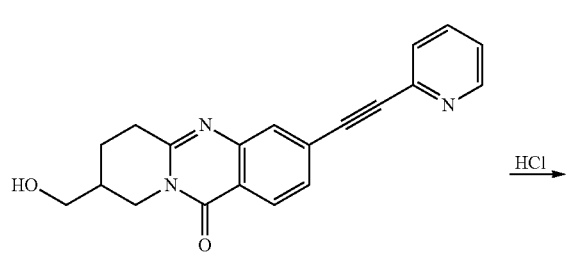

The title compound was prepared according to the experimental procedure as described in Example 1.1. The product was then converted to the corresponding HCl salt. MS (ESI): 332 (MH+); $^1$H NMR (300 MHz, CD$_3$OD) δ 8.87-8.85 (d, J=5.49 Hz, 1H), 8.50-8.42 (m, 2H), 8.20-8.17 (d, J=7.83 Hz, 1H), 8.01-7.93 (m, 3H), 4.57-4.51 (m, 1H), 3.77-3.64 (m, 3H), 3.39-3.36 (m, 2H), 2.30-2.28 (m, 1H), 2.17-2.14 (m, 1H), 1.83-1.79 (m, 1H). mGluR5 PAM EC$_{50}$: ++.

Example 4.33. Synthesis of 3-((3-fluorophenyl)ethynyl)-8-(methoxymethyl)-8,9-dihydro-6H-pyrido[2,1-b]quinazolin-11(7H)-one

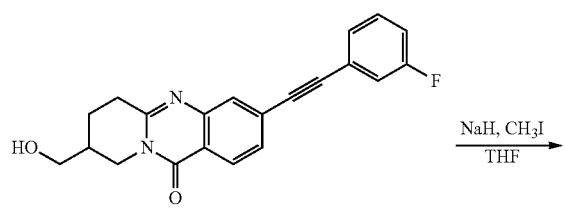

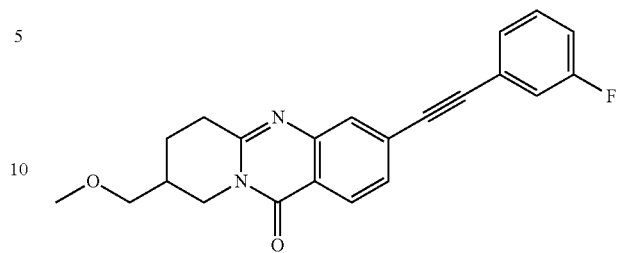

The title compound was prepared according to the experimental procedure as described in Example 4.25. MS (ESI): 346 (MH+); $^1$H NMR (300 MHz, CDCl$_3$) δ 8.27-8.24 (d, J=8.25 Hz, 1H), 7.76 (s, 1H), 7.56-7.53 (d, J=8.25 Hz, 1H), 7.37-7.34 (m, 2H), 7.27-7.26 (m, 1H), 7.13-7.07 (m, 1H), 4.49-4.43 (m, 1H), 3.71-3.63 (m, 1H), 3.46-3.42 (m, 2H), 3.40 (s, 3H), 3.12-2.98 (m, 2H), 2.35-2.29 (m, 1H), 2.14-2.04 (m, 1H), 1.74-1.60 (m, 1H). mGluR5 PAM EC$_{50}$: +++++. Fold shift at 10 μM: ++.

Example 4.34. Synthesis of the HCl Salt of 8-(methoxymethyl)-3-(pyridin-2-ylethynyl)-8,9-dihydro-6H-pyrido[2,1-b]quinazolin-11(7H)-one

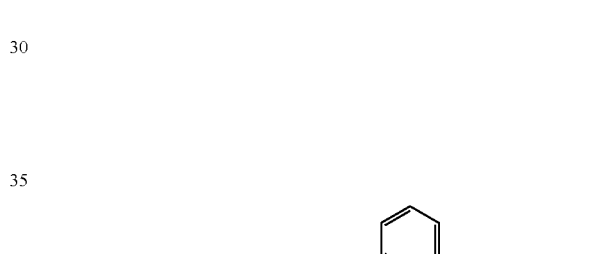

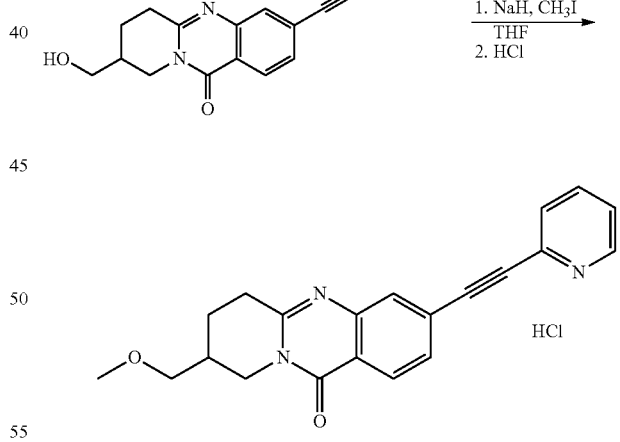

The title compound was prepared according to the experimental procedure as described in Example 4.25. The product was then converted to the corresponding HCl salt. MS (ESI): 346 (MH+); $^1$H NMR (300 MHz, DMSO-d$^6$) δ 8.67-8.65 (d, J=4.77 Hz, 1H), 8.19-8.17 (d, J=8.22 Hz, 1H), 7.95-7.89 (dt, J=7.8, 1.43 Hz, 1H), 7.83 (s, 1H), 7.77-7.74 (m, 1H), 7.70-7.67 (m, 1H), 7.51-7.47 (m, 1H), 4.32-4.26 (dd, J=13.79, 5.15 Hz, 1H), 3.60-3.57 (m, 1H), 3.42-3.37 (m, 2H), 3.29 (s, 3H), 3.07-2.99 (m, 2H), 2.32-2.27 (m, 1H), 1.99-1.93 (m, 1H), 1.62-1.52 (m, 1H). mGluR5 PAM EC$_{50}$: ++++. Fold shift at 10 μM: +++.

Example 4.34a and Example 4.34b. (S)-8-(methoxymethyl)-3-(pyridin-2-ylethynyl)-8,9-dihydro-6H-pyrido[2,1-b]quinazolin-11(7H)-one and (R)-8-(methoxymethyl)-3-(pyridin-2-ylethynyl)-8,9-dihydro-6H-pyrido[2,1-b]quinazolin-11(7H)-one

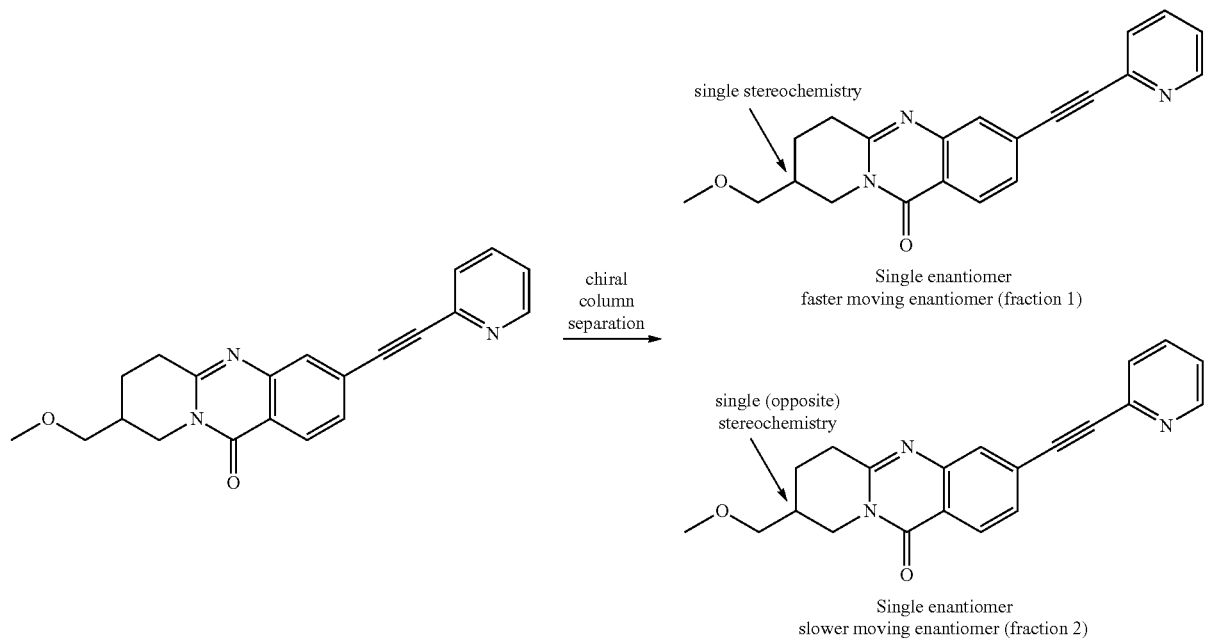 [SMILES: COCC1CCc2nc3cc(C#Cc4ccccn4)ccc3c(=O)n2C1 ; COCC1CCc2nc3cc(C#Cc4ccccn4)ccc3c(=O)n2C1 ; COCC1CCc2nc3cc(C#Cc4ccccn4)ccc3c(=O)n2C1]

Racemic 8-(methoxymethyl)-3-(pyridin-2-ylethynyl)-8,9-dihydro-6H-pyrido[2,1-b]quinazolin-11(7H)-one was separated into the corresponding two single enantiomer compounds (S)-8-(methoxymethyl)-3-(pyridin-2-ylethynyl)-8,9-dihydro-6H-pyrido[2,1-b]quinazolin-11(7H)-one and (R)-8-(methoxymethyl)-3-(pyridin-2-ylethynyl)-8,9-dihydro-6H-pyrido[2,1-b]quinazolin-11(7H)-one using chiral chromatography with an isocratic SFC method. The column used was a 3.0×25.0 cm RegisPack from Regis Technologies (Morton Grove, Ill.). The $CO_2$ co-solvent was isopropanol with 1% isopropylamine. Isocratic Method: 35% Co-solvent at 80 mL/min System Pressure: 100 bar. Column Temperature 25° C.

Faster moving enantiomer (fraction 1): Retention time=1.9 min 97.9% ee. mGluR5 PAM $EC_{50}$: +++. Fold shift at 10 μM: +++.

Slower moving enantiomer (fraction 2): Retention time=2.2 min. 97.0% ee. mGluR5 PAM $EC_{50}$: +++. Fold shift at 10 μM: ++.

Example 4.35. Synthesis of the HCl Salt of 3-((3-fluorophenyl)ethynyl)-8-((methylamino)methyl)-8,9-dihydro-6H-pyrido[2,1-b]quinazolin-11(7H)-one

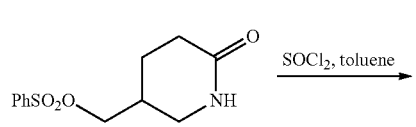

-continued

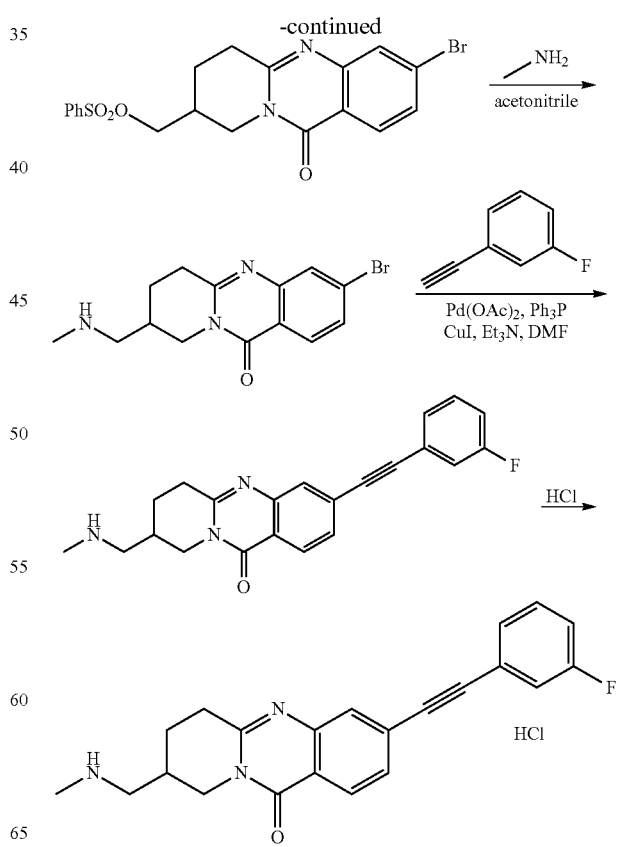

The title compound was prepared according to the experimental procedure as described in Example 2.2a, Example 3.3c, and Example 1.1. The product was then converted to the corresponding HCl salt. MS (ESI): 362 (MH+); 1H NMR (300 MHz, DMSO-d6) δ 8.98-8.91 (broad, 2H), 8.19-8.16 (d, J=8.34 Hz, 1H), 7.82 (dd, J=8.2, 1.4 Hz, 1H), 7.67-7.64 (dd, J=8.14, 1.38 Hz, 1H), 7.56-7.47 (m, 1H), 7.37-7.31 (m, 1H), 4.43-4.36 (m, 1H), 3.60-3.52 (m, 1H), 3.20-2.91 (m, 4H), 2.59-2.56 (m, 3H), 2.45-2.43 (m, 1H), 2.12-2.05 (m, 1H), 1.74-1.64 (m, 1H).

Example 4.36. Synthesis of the HCl Salt of 8-((dimethylamino)methyl)-3-((3-fluorophenyl)ethynyl)-8,9-dihydro-6H-pyrido[2,1-b]quinazolin-11(7H)-one

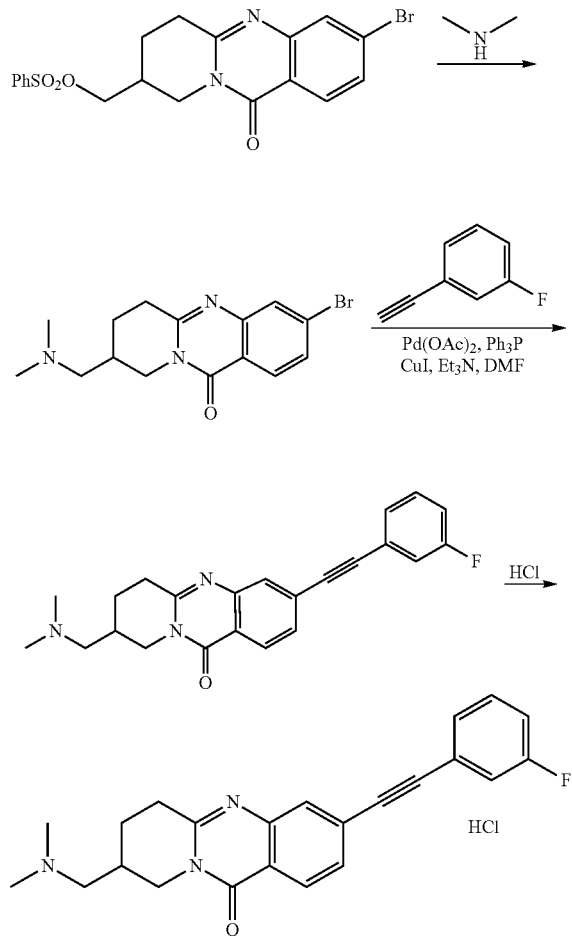

The title compound was prepared according to the experimental procedure as described in Example 3.3c and Example 1.1. The product was then converted to the corresponding HCl salt. MS (ESI): 376 (MH+); 1H NMR (300 MHz, DMSO-d6) δ 9.99-9.97 (s, 1H), 8.18-8.15 (d, J=8.16 Hz, 1H), 7.79 (s, 1H), 7.65-7.62 (dd, J=8.25, 1.56 Hz, 1H), 7.56-7.46 (m, 1H), 7.38-7.31 (m, 1H), 4.42-4.35 (m, 1H), 3.60-3.52 (m, 1H), 3.29-3.11 (m, 2H), 3.06-2.97 (m, 2H), 2.82 (s, 3H), 2.78 (s, 3H), 2.56-2.51 (m, 1H), 2.14-2.08 (m, 1H), 1.74-1.64 (m, 1H). mGluR5 PAM EC50: +.

Example 4.37. Synthesis of the HCl Salt of 7-(hydroxymethyl)-3-(pyridin-2-ylethynyl)-8,9-dihydro-6H-pyrido[2,1-b]quinazolin-11(7H)-one

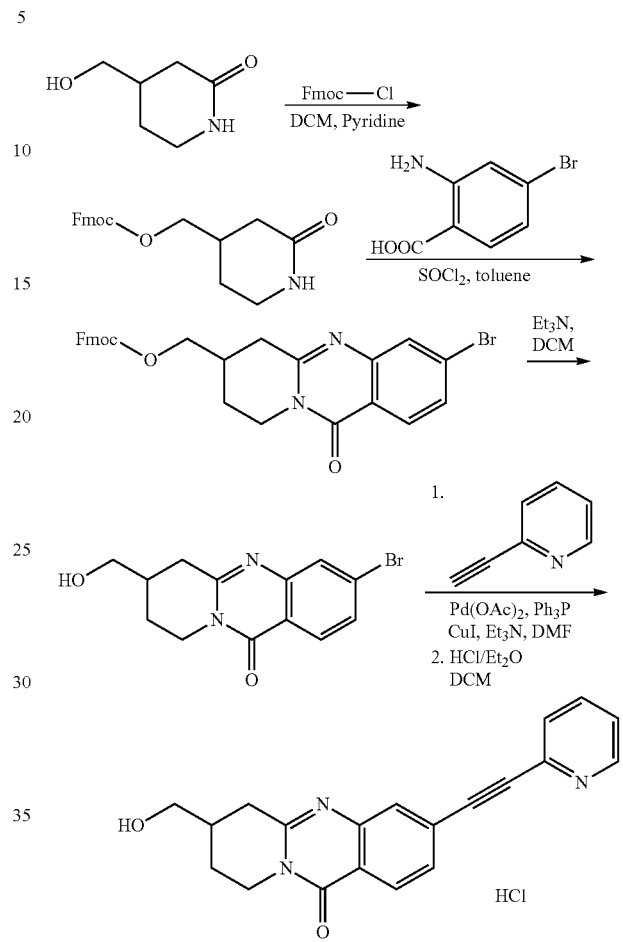

The title compound was prepared according to the experimental procedure as described in Example 5.1a, Example 2.2a, Example 3.17b, and Example 1.1. The product was then converted to the corresponding HCl salt. MS (ESI): 332 (MH+); 1H NMR (300 MHz, CD3OD) δ 8.88-8.87 (d, J=5.31 Hz, 1H), 8.53-8.47 (t, J=7.94 Hz, 1H), 8.45-8.42 (d, J=8.25 Hz, 1H), 8.23-8.20 (d, J=7.95 Hz, 1H), 8.02-7.95 (m, 3H), 4.55-4.47 (m, 1H), 3.98-3.89 (m, 1H), 3.74-3.62 (m, 2H), 3.42-3.36 (m, 1H), 3.18-3.08 (m, 1H), 2.34-2.26 (m, 2H), 1.87-1.84 (m, 1H). mGluR5 PAM EC50: +++. Fold shift at 10 μM: ++.

Example 4.38. Synthesis of the HCl Salt of 7-(methoxymethyl)-3-(pyridin-2-ylethynyl)-8,9-dihydro-6H-pyrido[2,1-b]quinazolin-11(7H)-one

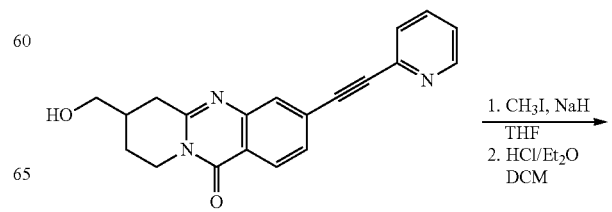

-continued

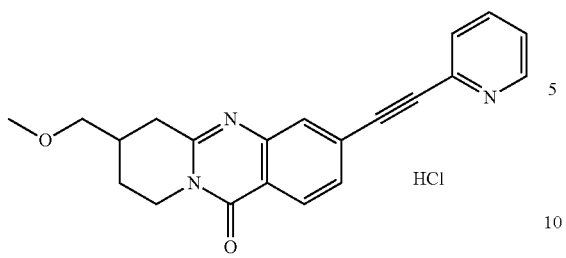

The title compound was prepared according to the experimental procedure as described in Example 4.25. The product was then converted to the corresponding HCl salt. MS (ESI): 346 (MH$^+$); $^1$H NMR (300 MHz, CD$_3$OD) δ 8.88-8.87 (d, J=5.34 Hz, 1H), 8.53-8.48 (t, J=7.95 Hz, 1H), 8.45-8.43 (d, J=8.25 Hz, 1H), 8.23-8.20 (d, J=7.95 Hz, 1H), 8.02-7.96 (m, 3H), 4.52-4.44 (m, 1H), 3.98-3.88 (m, 3H), 3.57-3.47 (m, 1H), 3.40 (s, 3H), 3.18-3.09 (m, 1H), 2.47-2.42 (m, 1H), 2.32-2.55 (m, 1H), 1.90-1.83 (m, 1H).

Example 4.39. Synthesis of the HCl Salt of 3-methyl-9-(pyridin-2-ylethynyl)-3,4-dihydro-[1,4]oxazino[3,4-b]quinazolin-6(1H)-one

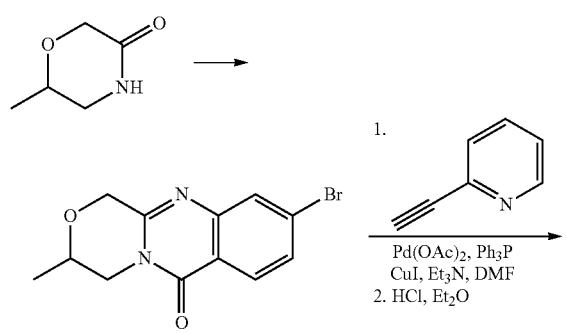

The title compound was prepared according to the experimental procedure as described in Example 2.2a and Example 1.1. The product was then converted to the corresponding HCl salt. MS (ESI): 318 (MH$^+$); $^1$H NMR (300 MHz, CD$_3$OD) δ 8.97-8.95 (d, J=5.58 Hz, 1H), 8.74-8.68 (dt, J=7.98, 1.50 Hz, 1H), 8.46-8.43 (d, J=8.28 Hz, 1H), 8.39-8.37 (d, J=8.04 Hz, 1H), 8.12-8.17 (dt, J=5.5, 1.2 Hz, 1H), 8.11-8.09 (s, 1H), 8.01-7.98 (dd, J=8.30, 1.34 Hz, 1H), 5.22-5.02 (m, 2H), 4.21-4.15 (dd, J=6.97, 1.48 Hz, 1H), 4.21-4.15 (m, 1H), 3.59-3.50 (m, 1H), 1.48-1.46 (d, J=6.0 Hz, 3H).

Example 4.40. Synthesis of the HCl Salt of 3,3-dimethyl-9-(pyridin-2-ylethynyl)-3,4-dihydro-[1,4]oxazino[3,4-b]quinazolin-6(1H)-one

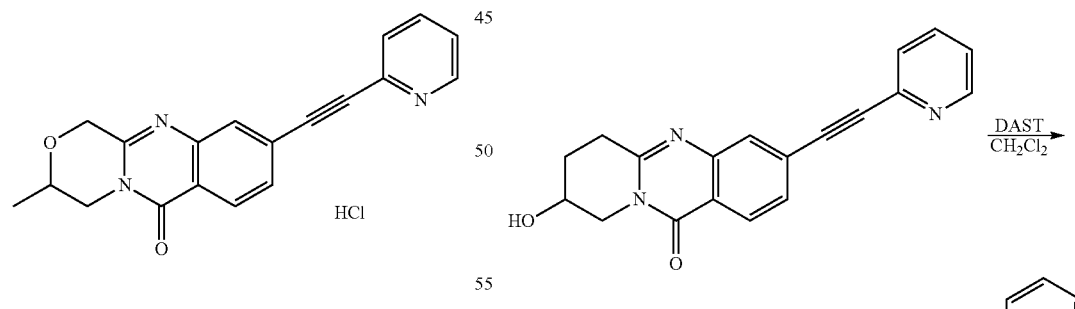

The title compound was prepared according to the experimental procedure as described in Example 2.2a and Example 1.1. The product was then converted to the corresponding HCl salt. MS (ESI): 332 (MH$^+$); $^1$H NMR (300 MHz, DMSO-d$^6$) δ 8.68-8.67 (d, J=5.01 Hz, 1H), 8.21-8.18 (d, J=8.25 Hz, 1H), 8.05-7.99 (t, J=7.76 Hz, 1H), 7.84-7.83 (m, 2H), 7.72-7.69 (d, J=8.25 Hz, 1H), 7.59-7.55 (m, 1H), 4.68 (s, 2H), 3.89 (s, 2H), 1.28 (s, 6H). mGluR5 PAM EC$_{50}$: ++++. Fold shift at 10 μM: +.

Example 4.41. Synthesis of 8-fluoro-3-(pyridin-2-ylethynyl)-8,9-dihydro-6H-pyrido[2,1-b]quinazolin-11(7H)-one To a stirred solution of 8-hydroxy-3-(pyridin-2-ylethynyl)-8,9-dihydro-6H-pyrido[2,1-b]quinazolin-11(7H)-one (100 mg, 0.315 mmol, 1 eq) in DCM was added excess DAST under N₂ at −78° C. After stirring at the same temperature for 3 hours, the reaction mixture was quenched with water (20 mL) and extracted with ethyl acetate (3×20 mL). The combined organic layers were dried over Na$_2$SO$_4$ and concentrated under reduced pressure to give the desired product, which was purified by silica gel chromatography. MS (ESI): 320 (MH⁺); ¹H NMR (300 MHz, DMSO-d⁶) δ 8.65-8.65 (d, J=3.30 Hz, 1H), 8.17-8.14 (d, J=8.16 Hz, 1H), 7.92-7.87 (t, J=7.5 Hz, 1H), 7.79 (s, 1H), 7.74-7.72 (d, J=7.71 Hz, 1H), 7.67-7.64 (d, J=8.04 Hz, 1H), 7.48-7.47 (m, 1H), 5.50-5.34 (d, J=48.6 Hz, 1H), 4.62-4.52 (t, J=15.9 Hz, 1H), 3.93-3.79 (dd, J=38.1, 15.3 Hz, 1H), 2.96-2.94 (m, 2H), 2.45-2.10 (m, 2H).

Example 4.42. Synthesis of 8,8-difluoro-3-(pyridin-2-ylethynyl)-8,9-dihydro-6H-pyrido[2,1-b]quinazolin-11(7H)-one

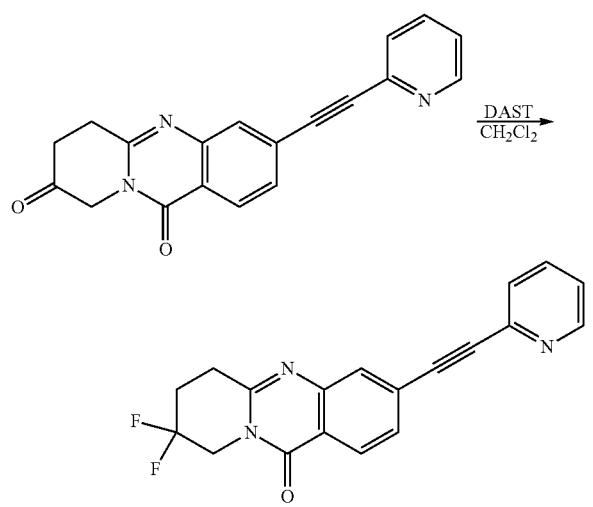

The title compound was prepared according to the experimental procedure as described in Example 4.41. MS (ESI): 338 (MH⁺); ¹H NMR (300 MHz, DMSO-d⁶) δ 8.67-8.65 (d, J=4.02 Hz, 1H), 8.20-8.17 (d, J=8.10 Hz, 1H), 7.95-7.90 (m, 1H), 7.84 (s, 1H), 7.77-7.69 (m, 2H), 7.51-7.47 (m, 1H), 4.67-4.26 (m, 4H), 3.17-3.13 (m, 2H). mGluR5 PAM EC$_{50}$: ++++. Fold shift at 10 μM: ++.

Example 4.43. Synthesis of the HCl Salt of 8-(pyridin-2-ylethynyl)-1,2,3,10b-tetrahydrocyclopropa[3,4]pyrido[2,1-b]quinazolin-5(1aH)-one

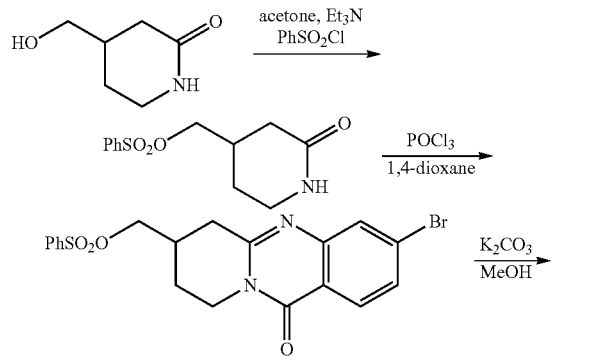

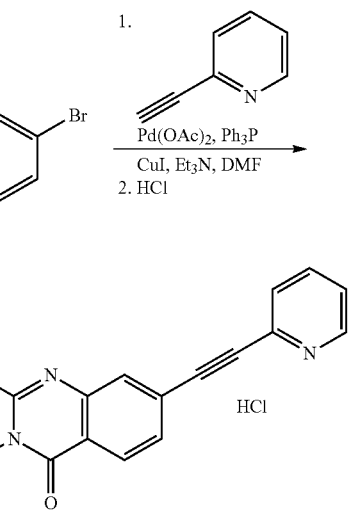

The title compound was prepared according to the experimental procedure as described in Example 3.3a, 4.27b, Example 4.27c, and Example 1.1. The product was then converted to the corresponding HCl salt. MS (ESI): 314 (MH⁺); ¹H NMR (300 MHz, CDCl₃) δ 8.68-8.66 (d, J=4.71 Hz, 1H), 8.24-8.21 (d, J=8.19 Hz, 1H), 7.84 (d, J=0.9 Hz, 1H), 7.76-7.71 (dt, J=7.8, 1.8 Hz, 1H), 7.61-7.57 (m, 2H), 7.32-7.28 (m, 1H), 4.89-4.82 (dd, J=14.4, 3.0 Hz, 1H), 3.15-3.10 (t, J=4.5 Hz, 1H), 2.37-2.30 (m, 2H), 2.10-1.92 (m, 2H), 1.39-1.34 (m, 1H), 1.27-1.18 (m, 1H). mGluR5 PAM EC$_{50}$: ++++. Fold shift at 10 μM: ++.

Example 4.44. Synthesis of the HCl Salt of 6,6-difluoro-8,8-dimethyl-3-(pyridin-2-ylethynyl)-8,9-dihydro-6H-pyrido[2,1-b]quinazolin-11(7H)-one

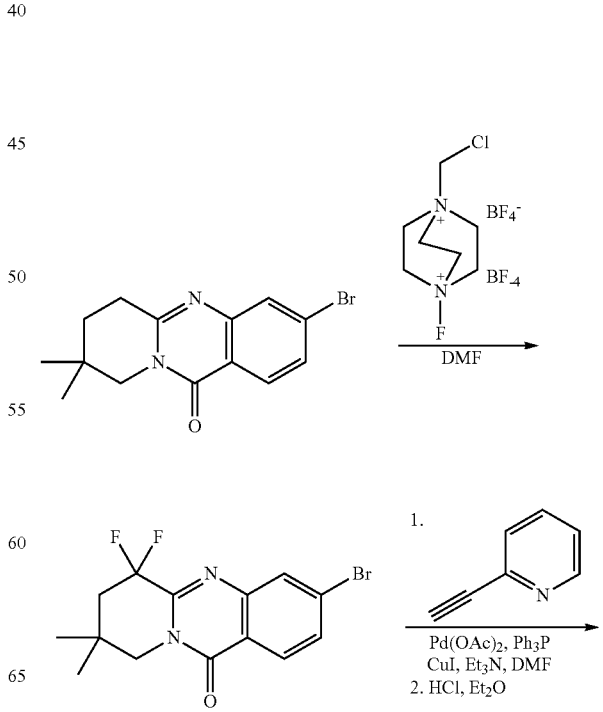

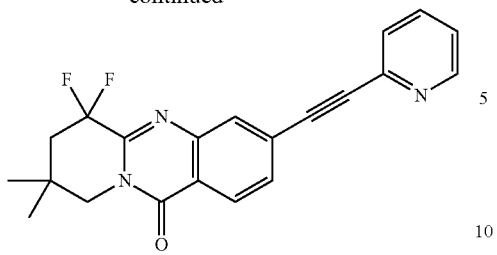

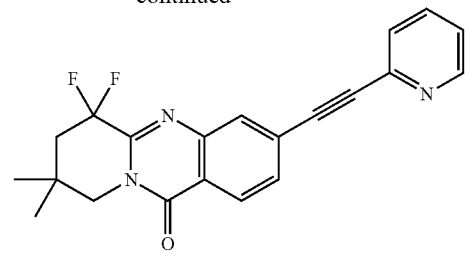

Example 4.44a. Synthesis of 3-bromo-6,6-difluoro-8,8-dimethyl-8,9-dihydro-6H-pyrido[2,1-b]quinazolin-11(7H)-one

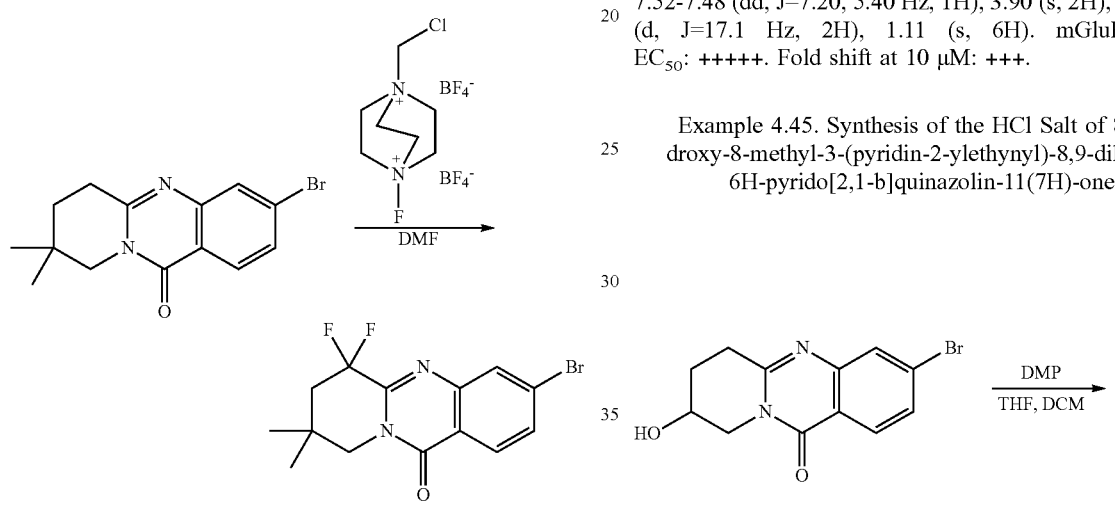

To a solution of 3-bromo-8,8-dimethyl-8,9-dihydro-6H-pyrido[2,1-b]quinazolin-11 (7H)-one (0.1 g, 0.327 mmol, 1 eq) in DMF (5 mL), Selectfluor (0.47 g, 1.31 mmol, 4 eq) was added. The reaction mixture was heated to 90° C. and stirred for 3 h. After it was cooled to room temperature, the reaction mixture was diluted with water and extracted with ethyl acetate (3×50 mL), dried over Na$_2$SO$_4$. After filtration and concentration, 120 mg of the desired product was obtained, which was directly used for the next step without further purification. MS (ESI): 343, 345 (MH$^+$).

Example 4.44b. Synthesis of the HCl Salt of 6,6-difluoro-8,8-dimethyl-3-(pyridin-2-ylethynyl)-8,9-dihydro-6H-pyrido[2,1-b]quinazolin-11(7H)-one The title compound was prepared according to the experimental procedure as described in Example 1.1. The product was then converted to the corresponding HCl salt. MS (ESI): 366 (MH$^+$); $^1$H NMR (300 MHz, DMSO-d$^6$) δ 8.68-8.66 (d, J=4.14 Hz, 1H), 8.25-8.22 (d, J=8.22 Hz, 1H), 8.02 (s, 1H), 7.96-7.91 (t, J=9.45 Hz, 1H), 7.82-7.76 (t, J=9.60 Hz, 2H), 7.52-7.48 (dd, J=7.20, 5.40 Hz, 1H), 3.90 (s, 2H), 2.43-2.38 (d, J=17.1 Hz, 2H), 1.11 (s, 6H). mGluR5 PAM EC$_{50}$: +++++. Fold shift at 10 μM: +++.

Example 4.45. Synthesis of the HCl Salt of 8-hydroxy-8-methyl-3-(pyridin-2-ylethynyl)-8,9-dihydro-6H-pyrido[2,1-b]quinazolin-11(7H)-one

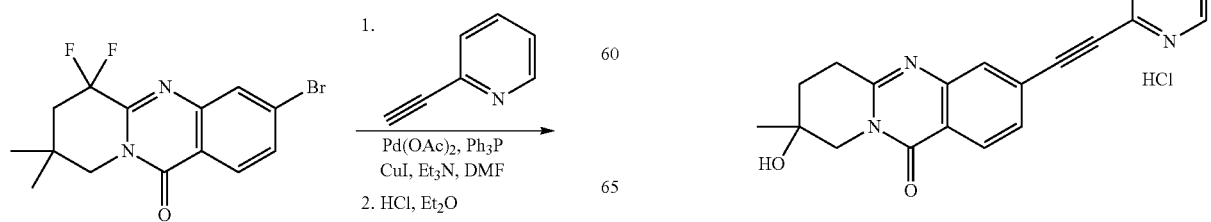

Example 4.45a. Synthesis of 3-bromo-6H-pyrido[2,1-b]quinazoline-8,11(7H,9H)-dione

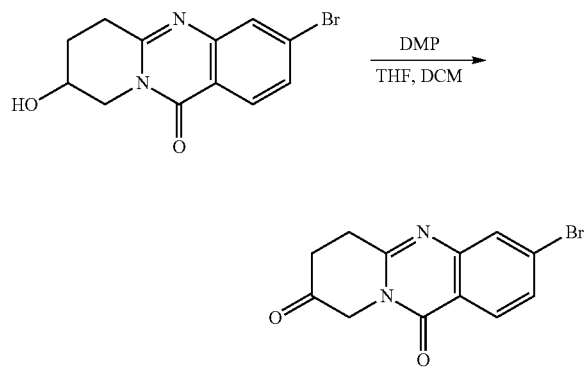

To a solution of 3-bromo-8-hydroxy-8,9-dihydro-6H-pyrido[2,1-b]quinazolin-11(7H)-one (1 g, 3.4 mmol, 1 equiv) in THF (30 mL) and DCM (20 mL) at 0° C. was added Dess-Martin reagent (2.9 g, 6.8 mmol, 2 equiv). The resulting mixture was stirred at rt for 3 h. After that, 60 mL of aq. Na$_2$S$_2$O$_3$ was added. The mixture was extracted with ethyl acetate (3×100 mL), dried over Na$_2$SO$_4$. After filtration and concentration, 700 mg of the desired product was obtained, which was directly used for the next step without further purification. MS (ESI): 293, 295 (MH$^+$).

Example 4.45b. Synthesis of 3-bromo-8-hydroxy-8-methyl-8,9-dihydro-6H-pyrido[2,1-b]quinazolin-11(7H)-one

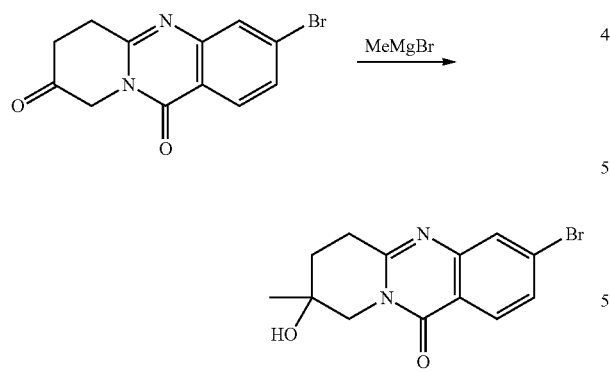

To a solution of 3-bromo-6H-pyrido[2,1-b]quinazoline-8,11(7H,9H)-dione (0.04 g, 1.37 mmol, 1 equiv) in dry THF was added CH$_3$MgBr (0.27 mL, 2.74 mmol, 2 equiv) dropwise at 0° C. The resulting mixture was stirred for 4 h at 0° C. The reaction was quenched with saturated NH$_4$Cl, extracted with EtOAc, and dried over Na$_2$SO$_4$. The organic extract was concentrated under reduced pressure to give the desired product. MS (ESI): 309, 311 (MH$^+$).

Example 4.45c. Synthesis of the HCl Salt of 8-hydroxy-8-methyl-3-(pyridin-2-ylethynyl)-8,9-dihydro-6H-pyrido[2,1-b]quinazolin-11(7H)-one

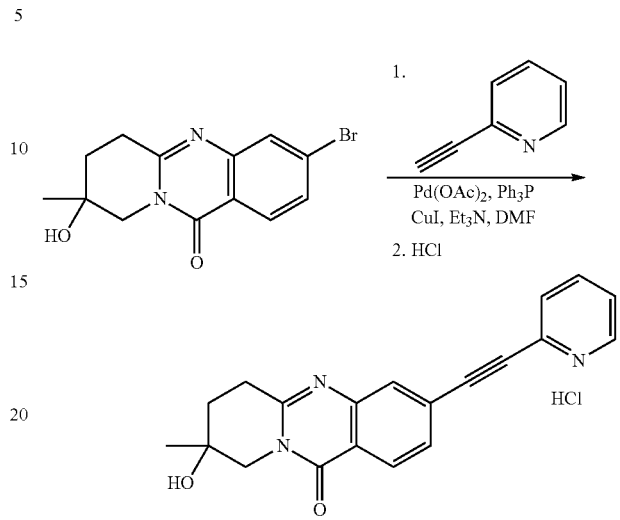

The title compound was prepared according to the experimental procedure as described in Example 1.1. The product was then converted to the corresponding HCl salt. MS (ESI): 332 (MH$^+$). MS (ESI): 332 (MH$^+$); $^1$H NMR (300 MHz, CD$_3$OD) δ 8.77-8.76 (d, J=4.68 Hz, 1H), 8.41-8.38 (d, J=8.64 Hz, 1H), 8.27-8.22 (t, J=7.80 Hz, 1H), 8.02-7.99 (d, J=8.01 Hz, 1H), 7.94-7.92 (m, 2H), 7.79-7.74 (t, J=6.00 Hz, 1H), 4.42-4.37 (d, J=15.01 Hz, 1H), 3.69-3.64 (d, J=14.53 Hz, 1H), 3.48-3.45 (m, 1H), 3.28-3.21 (m, 1H), 2.08-2.03 (m, 2H), 1.51 (s, 3H). mGluR5 PAM EC$_{50}$: ++. Fold shift at 10 μM: ++.

Example 4.46. Synthesis of the HCl Salt of 8-methoxy-8-methyl-3-(pyridin-2-ylethynyl)-8,9-dihydro-6H-pyrido[2,1-b]quinazolin-11(7H)-one

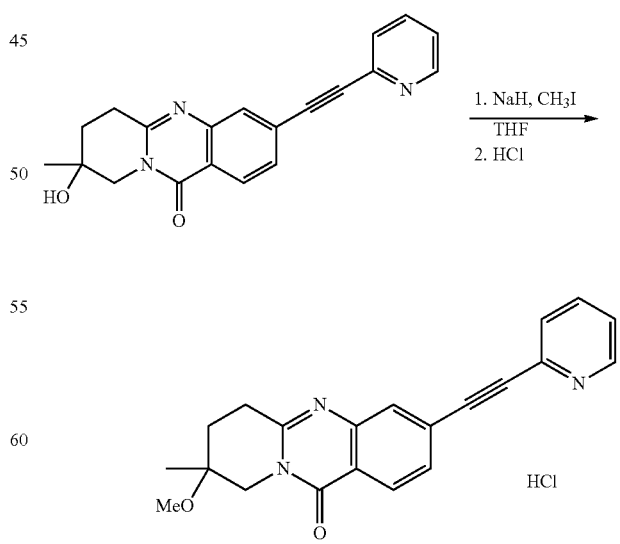

To a solution of 8-hydroxy-8-methyl-3-(pyridin-2-ylethynyl)-8,9-dihydro-6H-pyrido[2,1-b]quinazolin-11(7H)-one (20 mg, 0.06 mmol, 1 equiv) and NaH (5.4 mg, 0.09 mmol, 1.5 equiv) in dry THF was added CH₃I (25.5 mg, 0.18 mmol, 3 equiv) at rt. The resulting mixture was heated at 60° C. and stirred for 2 hours. After cooling to rt, the reaction mixture was quenched with water and extracted with ethyl acetate, and dried over Na₂SO₄. The organic extract was concentrated under reduced pressure and purified by column chromatography to give 5 mg of the desired product. The product was then converted to the corresponding HCl salt. MS (ESI): 346 (MH⁺); ¹H NMR (300 MHz, CD₃OD) δ 8.84-8.82 (d, J=5.19 Hz, 1H), 8.43-8.39 (m, 2H), 8.15-8.12 (d, J=7.92 Hz, 1H), 7.97 (s, 1H), 7.94-7.90 (m, 2H), 4.67-4.61 (dd, J=14.67, 2.31 Hz, 1H), 3.61-3.56 (d, J=14.71 Hz, 2H), 3.26 (s, 3H), 3.24-3.08 (m, 1H), 2.38-2.26 (m, 1H), 2.08-1.95 (m, 1H), 1.48 (s, 3H). mGluR5 PAM EC₅₀: ++++. Fold shift at 10 µM: +++.

Example 4.47. Synthesis of the HCl Salt of 6-fluoro-8,8-dimethyl-3-(pyridin-2-ylethynyl)-8,9-dihydro-6H-pyrido[2,1-b]quinazolin-11(7H)-one

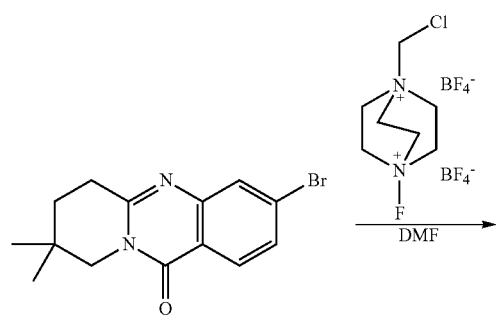

Example 4.47a. Synthesis of 3-bromo-6-fluoro-8,8-dimethyl-8,9-dihydro-6H-pyrido[2,1-b]quinazolin-11(7H)-one

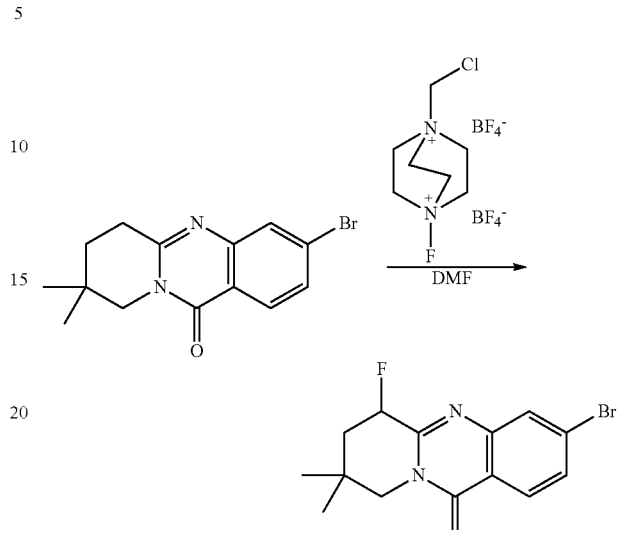

To a solution of 3-bromo-8,8-dimethyl-8,9-dihydro-6H-pyrido[2,1-b]quinazolin-11 (7H)-one (0.1 g, 0.327 mmol, 1 equiv) in DMF (5 mL), Selectfluor (0.12 g, 0.327 mmol, 1 eq) was added. The reaction mixture was heated to 90° C. and stirred for 3 hours. After cooling to room temperature, the reaction mixture was diluted with water and extracted with ethyl acetate (3×50 mL), dried over Na₂SO₄. After filtration and concentration, 80 mg of the desired product was obtained, which was directly used for the next step without further purification.

Example 4.47b. Synthesis of the HCl Salt of 6-fluoro-8,8-dimethyl-3-(pyridin-2-ylethynyl)-8,9-dihydro-6H-pyrido[2,1-b]quinazolin-11(7H)-one

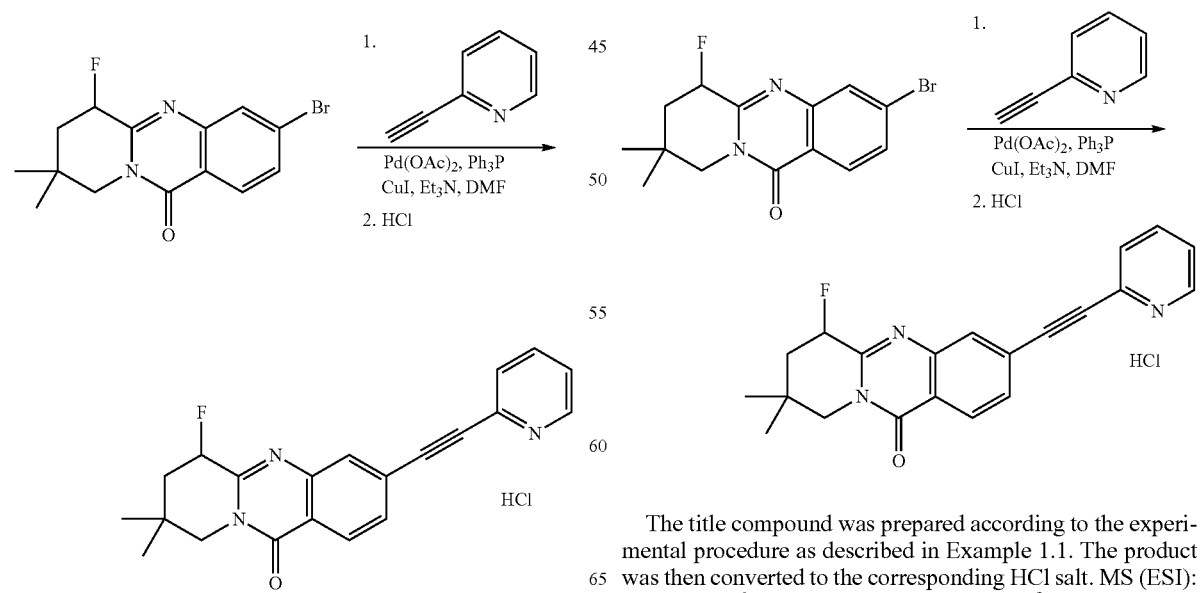

The title compound was prepared according to the experimental procedure as described in Example 1.1. The product was then converted to the corresponding HCl salt. MS (ESI): 348 (MH⁺); ¹H NMR (300 MHz, DMSO-d⁶) δ 8.71-8.70 (d, J=4.59 Hz, 1H), 8.24-8.21 (d, J=8.22 Hz, 1H), 8.06-8.00 (td, J=7.77, 1.51 Hz, 1H), 7.96 (s, 1H), 7.85-7.83 (d, J=7.80 Hz, 1H), 7.78-7.75 (d, J=8.25 Hz, 1H), 7.59-7.56 (dd, J=6.60, 5.10 Hz, 1H), 5.75-5.55 (dt, J=5.48, 5.52 Hz, 1H), 3.93-3.76 (dd, J=36.60, 13.50 Hz, 2H), 2.25-1.95 (m, 2H), 1.08-1.04 (d, J=9.66 Hz, 6H). mGluR5 PAM $EC_{50}$: +++++. Fold shift at 10 μM: +++.

Example 4.48. Synthesis of the HCl Salt of 3-(pyridin-2-ylethynyl)-8,9-dihydro-6H-6,9-ethanopyrido[2,1-b]quinazolin-11(7H)-one

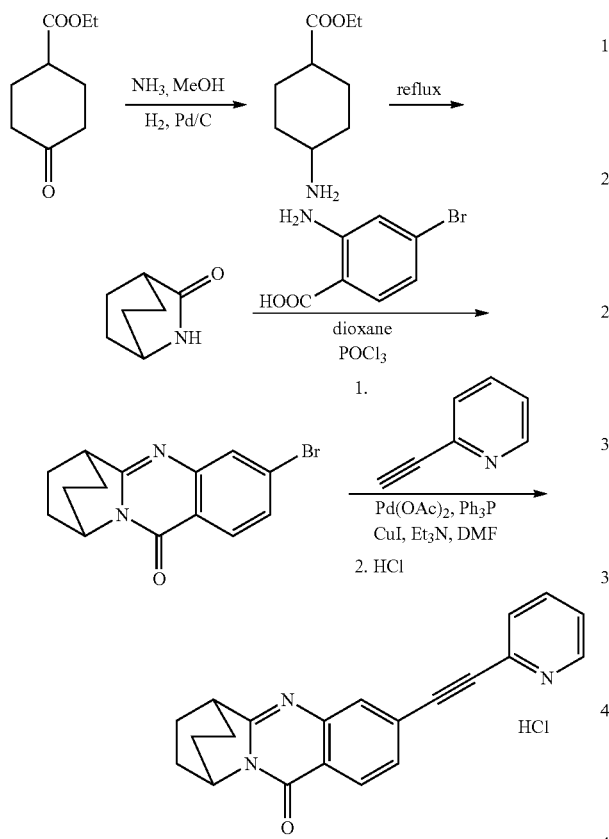

Example 4.48a. Synthesis of ethyl 4-aminocyclohexanecarboxylate

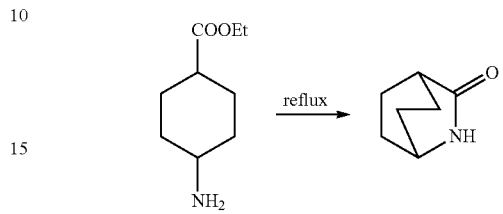

Ethyl 4-oxocyclohexanecarboxylate (3.0 g, 17.65 mmol) was dissolved in 150 mL methanol saturated with ammonia at 0° C., and to the solution was added wet 10% Pd/C catalyst (4.0 g). The mixture was stirred at room temperature under hydrogen (1 atm) for about 36 h. Then the catalyst was then removed by filtration and the filtrate was concentrated to give the crude product, which was purified by chromatography on silica gel to give 2.0 g of the desired product. MS (ESI): 172 (MH+).

Example 4.48b. Synthesis of 2-azabicyclo[2.2.2]octan-3-one

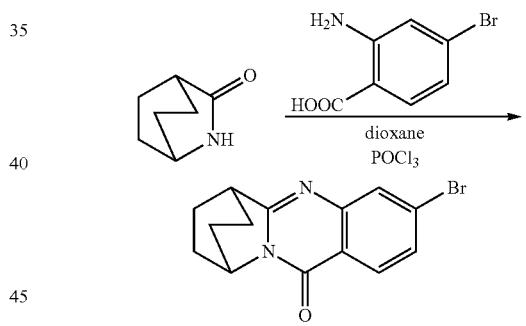

A solution of ethyl 4-aminocyclohexanecarboxylate (0.6 g, 3.49 mmol), toluene (1 mL) in oil bath (170° C.) was heated for 2-3 h to dryness. After cooling to rt, the reaction mixture was diluted with water and extracted with ethyl acetate (3×30 mL). The combined organic layers were dried over $Na_2SO_4$. After filtration and concentration, 300 mg of the desired product was obtained by column chromatography purification. MS (ESI): 126 (MH+).

Example 4.48c. Synthesis of 3-bromo-8,9-dihydro-6H-6,9-ethanopyrido[2,1-b]quinazolin-11(7H)-one

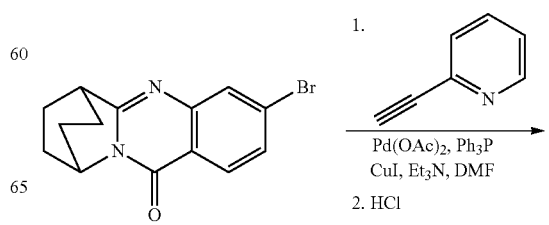

The title compound was prepared according to the experimental procedure as described in Example 4.27b. MS (ESI): 305, 307 (MH+).

Example 4.48d. Synthesis of the HCl Salt of 3-(pyridin-2-ylethynyl)-8,9-dihydro-6H-6,9-ethanopyrido[2,1-b]quinazolin-11(7H)-one -continued

The title compound was prepared according to the experimental procedure as described in Example 1.1. The product was then converted to the corresponding HCl salt. MS (ESI): 328 (MH⁺). MS (ESI): 328 (MH⁺); ¹H NMR (300 MHz, CD₃OD) δ 8.97-8.95 (d, J=5.34 Hz, 1H), 8.71-8.66 (t, J=7.97 Hz, 1H), 8.51-8.48 (d, J=8.28 Hz, 1H), 8.38-8.35 (d, J=8.04 Hz, 1H), 8.16-8.11 (t, J=6.30 Hz, 2H), 8.05-8.02 (d, J=8.28 Hz, 1H), 5.48 (s, 1H), 3.53 (s, 1H), 2.22-2.08 (m, 4H), 1.95-1.88 (m, 4H). mGluR5 PAM EC₅₀: +++++. Fold shift at 10 μM: ++.

Example 4.49. Synthesis of the 2HCl Salt of 13a-methyl-8-(pyridin-2-ylethynyl)-2,3,13,13a-tetrahydro-1H-pyrrolo[1',2':4,5]pyrazino[2,1-b]quinazolin-11 (5H)-one

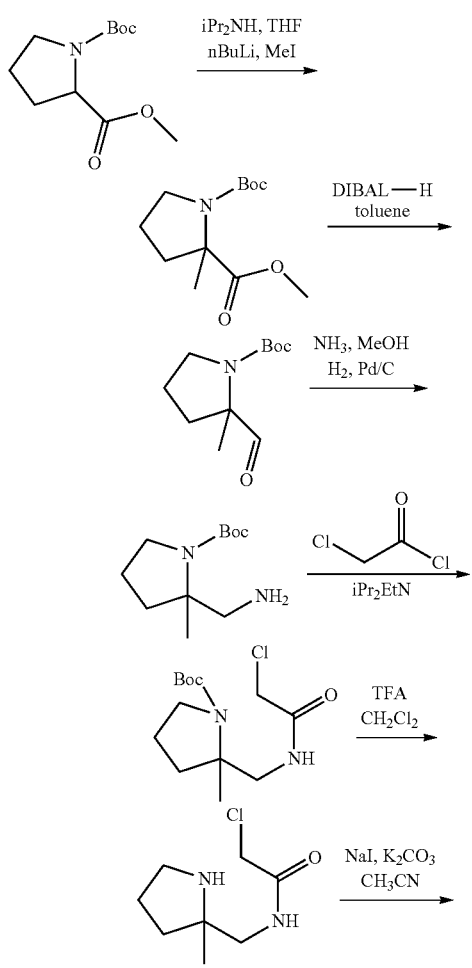

-continued

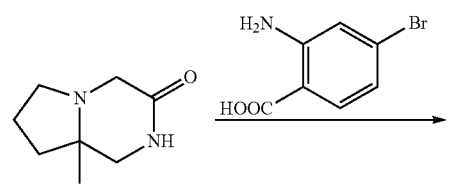

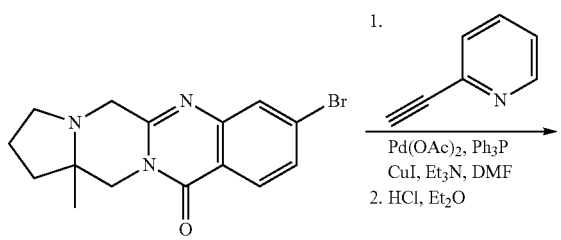

Example 4.49a. Synthesis of 1-tert-butyl 2-methyl 2-methylpyrrolidine-1,2-dicarboxylate

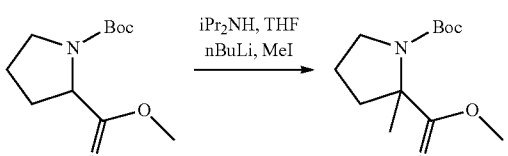

To a solution of diisopropylamine (1.59 g, 15.7 mmol) in THF (10 mL) was added n-BuLi (7.54 mL, 2.5 M in n-hexane) dropwise at 0° C. Then the solution was stirred at the same temperature for 30 min 1-tert-butyl 2-methyl pyrrolidine-1,2-dicarboxylate (3.0 g, 13.0 mmol) was dissolved in 50 mL THF and cooled to −78° C. To the solution was added prepared lithium diisopropylamide (15.7 mmol) dropwise. After the reaction mixture was kept at −78° C. for 3 h, MeI (1.6 mL, 25.7 mmol) was added. The mixture was allowed to warm to 0° C. and stirred for 2 h. Then the reaction mixture was quenched with water (30 mL) and extracted with EtOAc (3×50 mL). The combined organic layers were dried over Na₂SO₄ and concentrated under vacuum to give 2 g of the crude product. MS (ESI): 244 (MH⁺).

Example 4.49b. Synthesis of tert-butyl 2-formyl-2-methylpyrrolidine-1-carboxylate

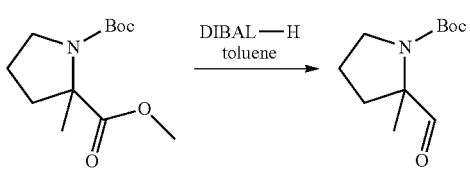

To a solution of 1-tert-butyl 2-methyl 2-methylpyrrolidine-1,2-dicarboxylate (3.5 g, 14.3 mmol) in toluene at −78° C. was added DIBAL-H (17.6 mL, 30 mmol, 1.7 M) dropwise, while maintaining the reaction temperature below −65° C. The reaction was stirred at −78° C. for 2 hr and then quenched with methanol (10 mL). The mixture was then diluted with ethyl acetate (50 mL), saturated NH$_4$Cl was added and the mixture was stirred vigorously for 20 min at room temperature. The two phases were then separated and the aqueous layer was extracted with DCM (3×50 mL). The combined organics were then washed with brine, dried over Na$_2$SO$_4$, concentrated in vacuo and purified by column chromatography to give 3 g of the desired product.

Example 4.49c. Synthesis of tert-butyl 2-(aminomethyl)-2-methylpyrrolidine-1-carboxylate

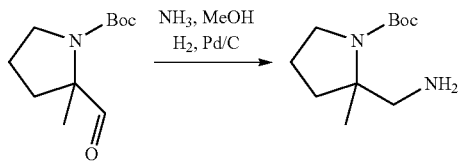

The title compound was prepared according to the experimental procedure as described in Example 4.48a. MS (ESI): 215 (MH$^+$).

Example 4.49d. Synthesis of tert-butyl 2-((2-chloroacetamido)methyl)-2-methylpyrrolidine-1-carboxylate

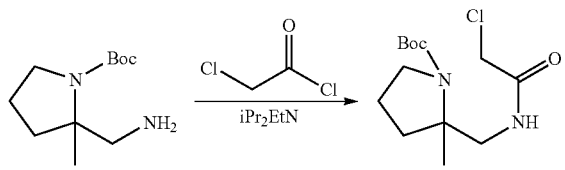

A solution of tert-butyl 2-(aminomethyl)-2-methylpyrrolidine-1-carboxylate (1.2 g), excess 2-chloroacetyl chloride (2 mL) and diisopropyl ethyl amine (2 mL) in DCM was stirred at room temperature for about 2 h. The reaction was monitored by LC-MS. After the solution was concentrated in vacuo, 0.7 g of the desired product was obtained by column chromatography purification. MS (ESI): 291, 293 (MH$^+$).

Example 4.49e. Synthesis of 2-chloro-N-((2-methylpyrrolidin-2-yl)methyl)acetamide

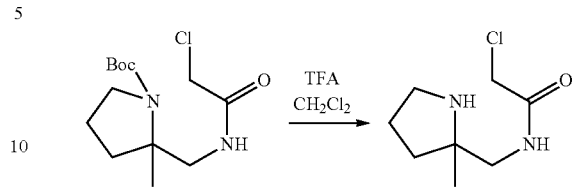

A solution of tert-butyl 2-((2-chloroacetamido)methyl)-2-methylpyrrolidine-1-carboxylate (0.7 g, 4.8 mmol) and TFA (3 mL) in DCM was stirred at room temperature for about 3 h. Then the solution was concentrated to give 300 mg of the crude product, which was directly used for the next step. MS (ESI): 191, 193 (MH$^+$).

Example 4.49f. Synthesis of 8a-methylhexahydropyrrolo[1,2-a]pyrazin-3(4H)-one

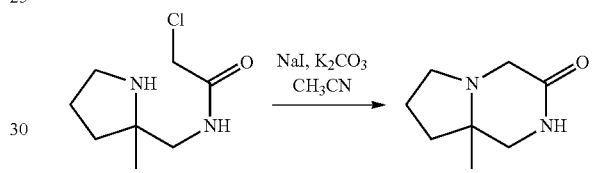

A solution of 2-chloro-N-((2-methylpyrrolidin-2-yl)methyl)acetamide (~300 mg), K$_2$CO$_3$ (1.0 g, 7.2 mmol) and a catalytic amount of NaI in CH$_3$CN was stirred at 80° C. for about 3 h. The reaction was monitored by LC-MS. After cooling to room temperature, the suspension was diluted with water (30 mL) and extracted with DCM (8×100 mL). Then the combined organic layers were concentrated to give 120 mg of the desired product, which was directly used for the next step without further purification. MS (ESI): 155 (MH$^+$).

Example 4.49g. Synthesis of 8-bromo-13a-methyl-2,3,13,13a-tetrahydro-1H-pyrrolo[1',2':4,5]pyrazino[2,1-b]quinazolin-11(5H)-one

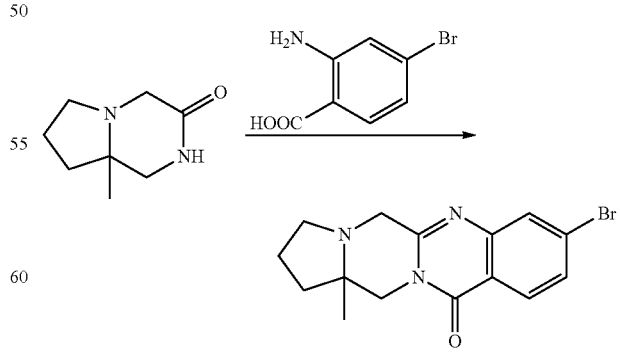

The title compound was prepared according to the experimental procedure as described in Example 4.27b. MS (ESI): 334, 336 (MH$^+$).

Example 4.49h. Synthesis of the 2HCl Salt of 13a-methyl-8-(pyridin-2-ylethynyl)-2,3,13,13a-tetrahydro-1H-pyrrolo[1',2':4,5]pyrazino[2,1-b]quinazolin-11(5H)-one

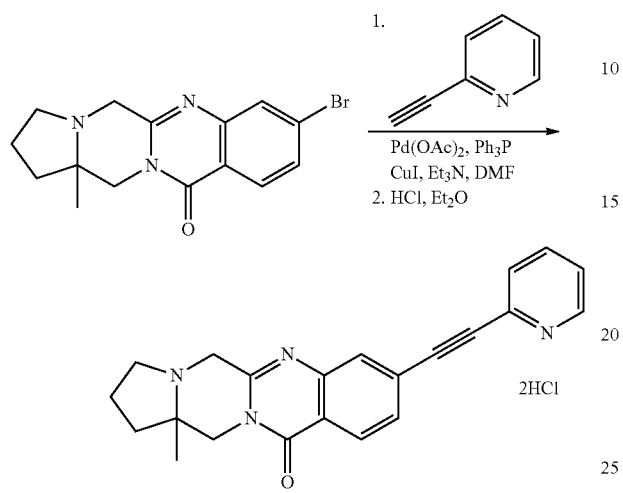

The title compound was prepared according to the experimental procedure as described in Example 1.1. The product was then converted to the corresponding 2HCl salt. MS (ESI): 357 (MH$^+$); $^1$H NMR (300 MHz, CD$_3$OD) δ 8.94-8.92 (d, J=5.6 Hz, 1H), 8.70-8.65 (t, J=8.0 Hz, 1H), 8.42-8.39 (d, J=8.2 Hz, 1H), 8.35-8.33 (d, J=7.9 Hz, 1H), 8.13-8.09 (m, 2H), 7.93-7.90 (d, J=8.3 Hz, 1H), 4.80-4.75 (d, J=14.7 Hz, 1H), 4.67-4.62 (d, J=14.7 Hz, 1H), 4.54-4.49 (d, J=14.7 Hz, 1H), 4.43-4.38 (d, J=14.7 Hz, 1H), 3.95-3.91 (d, J=9.9 Hz, 1H), 3.27-3.24 (m, 1H), 2.17-2.13 (m, 4H), 1.62 (s, 3H). mGluR5 PAM EC$_{50}$: +++.

Example 4.50. Synthesis of 1-fluoro-8,8-dimethyl-3-(pyridin-2-ylethynyl)-8,9-dihydro-6H-pyrido[2,1-b]quinazolin-11(7H)-one

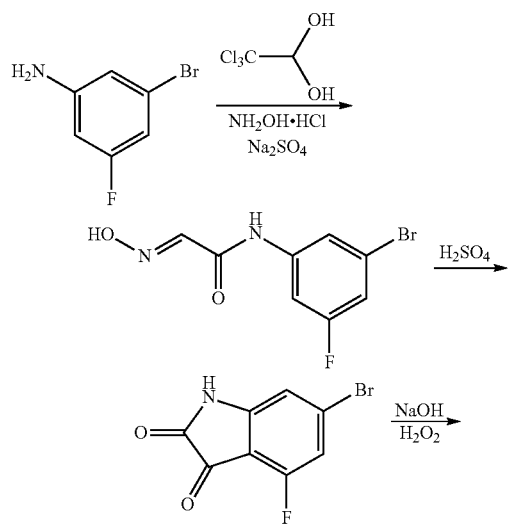

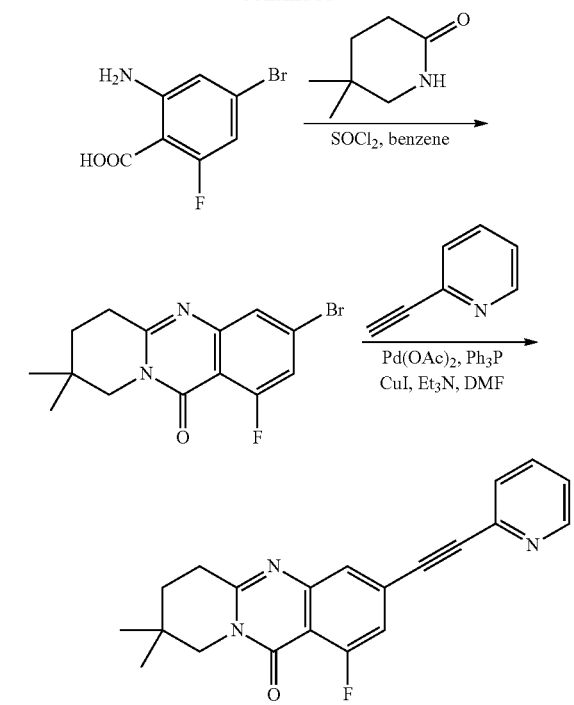

Example 4.50a. Synthesis of (E)-N-(3-bromo-5-fluorophenyl)-2-(hydroxyimino)acetamide

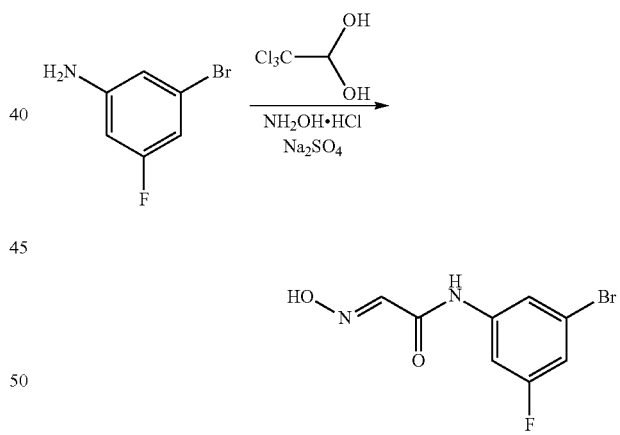

A mixture of 3-bromo-5-fluoroaniline (4.0 g, 21.1 mmol, 1.0 equiv) in conc. HCl (10 mL) and water (100 mL) was heated until it became a clear solution. 2,2,2-trichloroethane-1,1-diol (3.83 g, 23.2 mmol, 1.1 equiv) and Na$_2$SO$_4$ (22.5 g, 158.5 mmol, 7.3 equiv.) was pre-warmed to 50° C. and added to the mixture. To the stirred mixture was then added an aqueous solution of hydroxylammonium chloride (4.39 g, 63.2 mmol, 3.0 equiv) dropwise. The resulting mixture was refluxed for 1 h. After it was cooled to room temperature, the precipitate was filtered and washed with excess water, dried under vacuum to provide 6.13 g of crude product, which was used into the next step without further purification. MS (ESI): 259, 261 (MH$^-$).

Example 4.50b. Synthesis of 6-bromo-4-fluoroindoline-2,3-dione

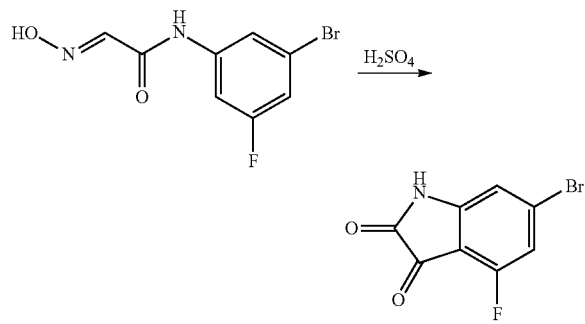

(E)-N-(3-bromo-5-fluorophenyl)-2-(hydroxyimino)acetamide (6.13 g, 23.6 mmol) was slowly added to a solution of conc. $H_2SO_4$ (30 mL) in an ice bath. The temperature of the reaction mixture was maintained below 50° C. After completion of the addition, the solution was heated to 90° C. for 1 h. After it was cooled to rt, the mixture was poured into ice-water and stirred vigorously for 1 h. The insoluble solid was filtered and washed with water, dried under vacuum to provide 7.4 g of crude product, which was used into the next step without further purification. MS (ESI): 242, 244 (MH$^-$).

Example 4.50c. Synthesis of 2-amino-4-bromo-6-fluorobenzoic acid

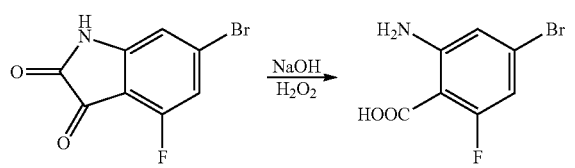

To a solution of 6-bromo-4-fluoroindoline-2,3-dione (7.4 g, 31.8 mmol) in 1 M NaOH (100 mL) was added 38% $H_2O_2$ (13 mL) dropwise. The resulting solution was stirred at rt for 2 h. The mixture was filtered and the filtrate was acidified using hydrochloric acid (2 N) till pH became around 2. The precipitate was formed and filtered, washed with water, dried under vacuum to give 2.8 g of the desired product. MS (ESI): 232, 234 (MH$^-$).

Example 4.50d. Synthesis of 1-fluoro-8,8-dimethyl-3-(pyridin-2-ylethynyl)-8,9-dihydro-6H-pyrido[2,1-b]quinazolin-11(7H)-one

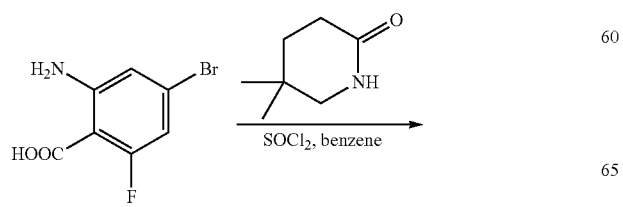

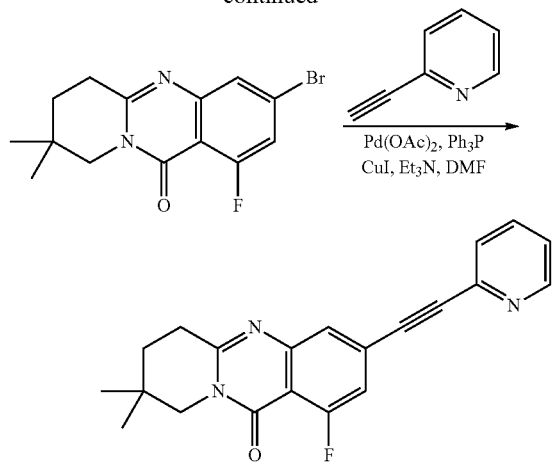

The title compound is prepared according to the experimental procedure as described in Example 2.2a and Example 1.1. MS (ESI): 348 (MH$^+$); $^1$H NMR (300 MHz, CDCl$_3$) δ 8.68-8.67 (d, J=4.8 Hz, 1H), 7.74-7.72 (d, J=4.5 Hz, 2H), 7.47-7.43 (dd, J=9.0, 2.4 Hz, 1H), 7.31-7.24 (m, 2H), 3.83 (s, 2H), 3.04-3.00 (t, J=6.9 Hz, 2H), 1.87-1.82 (t, J=6.9 Hz, 2H), 1.12 (s, 6H).

Example 4.51. Synthesis of 1-chloro-8,8-dimethyl-3-(pyridin-2-ylethynyl)-8,9-dihydro-6H-pyrido[2,1-b]quinazolin-11(7H)-one

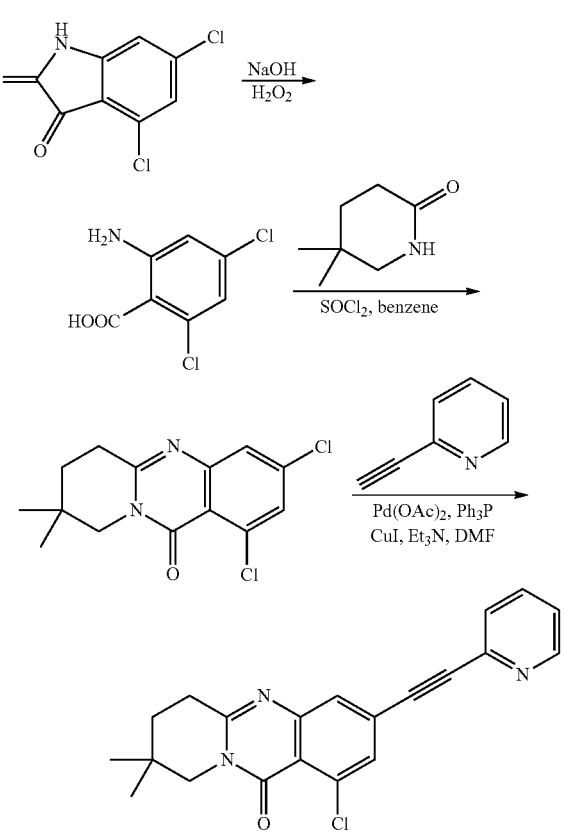

The title compound was prepared according to the experimental procedures described in Example 4.50c, Example 2.2a and Example 1.1. MS (ESI): 364, 366 (MH$^+$).

Example 5.1. Synthesis of the HCl Salt of 9-((5-methylthiazol-2-yl)ethynyl)-3,4-dihydro-1H-pyrazino[2,1-b]quinazolin-6(2H)-one

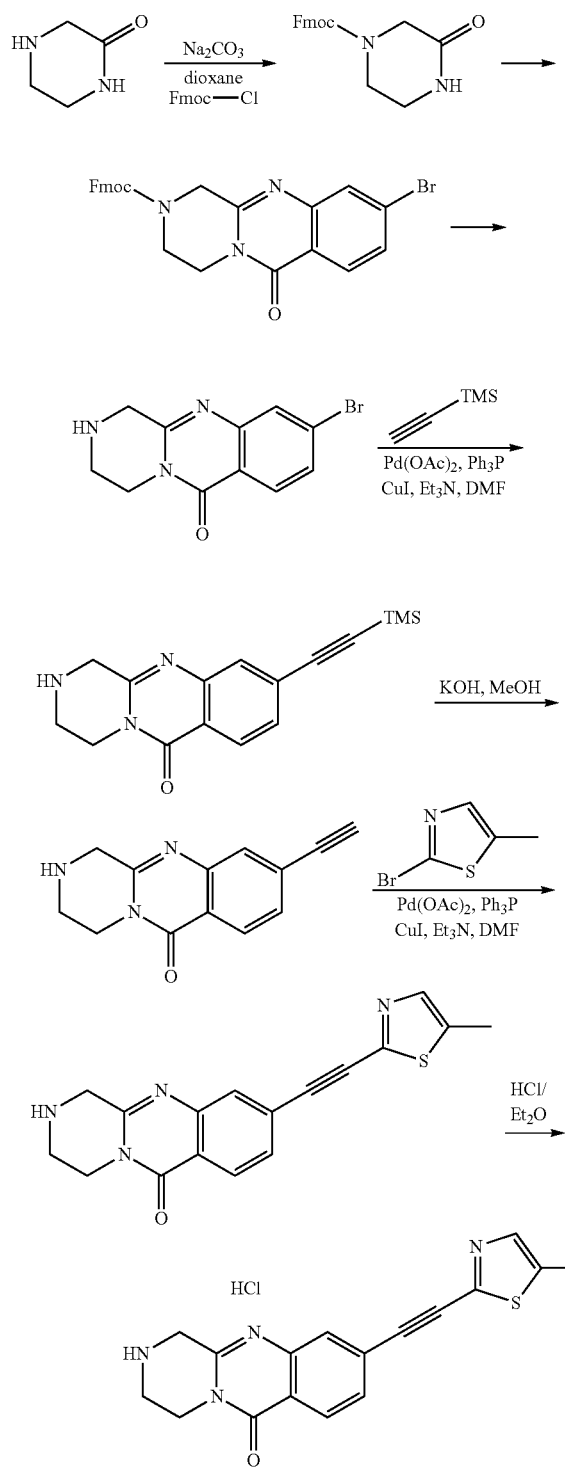

Example 5.1a. Synthesis of (9H-fluoren-9-yl)methyl 3-oxopiperazine-1-carboxylate

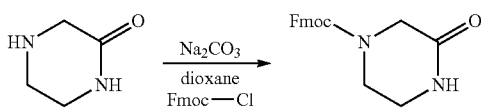

To a solution of piperazin-2-one (2 g, 20 mmol, 1 equiv), Na$_2$CO$_3$ (4.2 g, 40 mmol, 2 equiv) and water (20 mL) in 1,4-dioxane (60 mL) was added Fmoc-Cl (5.7 g, 22 mmol, 1.1 equiv) at 0° C. After the reaction mixture was stirred at room temperature for 4 h, it was diluted with saturated NaCl (200 mL). The solution was extracted with ethyl acetate (3×50 mL) and dried over Na$_2$SO$_4$. The combined organic layers were concentrated to give 6.7 g of the desired product, which was directly used for the next step without further purification. MS (ESI): 323 (MH$^+$).

Example 5.1b. (9H-fluoren-9-yl)methyl 9-bromo-6-oxo-3,4-dihydro-1H-pyrazino[2,1-b]quinazoline-2(6H)-carboxylate

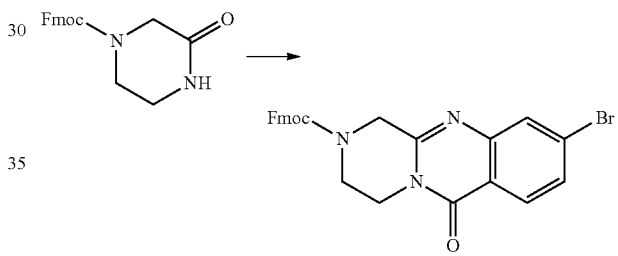

The title compound was prepared according to the experimental as described in Example 2.2b. MS (ESI): 502 (MH$^+$).

Example 5.1c. Synthesis of 9-bromo-3,4-dihydro-1H-pyrazino[2,1-b]quinazolin-6(2H)-one

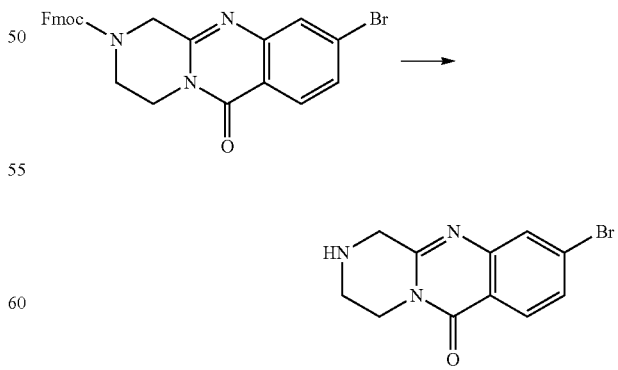

The title compound was prepared according to the experimental procedure as described in Example 3.17b. MS (ESI): 280/282 (MH$^+$).

Example 5.1d. Synthesis of 9-((trimethylsilyl)ethynyl)-3,4-dihydro-1H-pyrazino[2,1-b]quinazolin-6(2H)-one

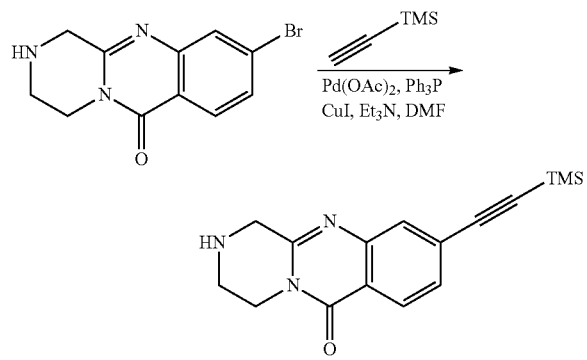

A flask was charged with 9-bromo-3,4-dihydro-1H-pyrazino[2,1-b]quinazolin-6(2H)-one (200 mg, 0.71 mmol, 1 equiv), ethynyltrimethylsilane (206 mg, 2.1 mmol, 3 equiv), Pd(OAc)$_2$ (31.5 mg, 0.14 mmol, 0.2 equiv), PPh$_3$ (165 mg, 0.63 mmol, 0.9 equiv), CuI (13 mg, 0.07 mmol, 0.1 equiv), Et$_3$N (353 mg, 3.5 mmol, 5 equiv) and DMF (20 mL). A vacuum was applied and the reaction mixture was back filled with nitrogen three times. The mixture was stirred at 70° C. for 3.5 hours. After it was cooled to room temperature, the reaction mixture was diluted with H$_2$O and extracted with ethyl acetate (2×50 mL). The combined organic layers were washed with brine and dried over anhydrous sodium sulfate, then concentrated under reduced pressure. 120 mg of desired product was obtained MS (ESI): 298 (MH$^+$).

Example 5.1e. Synthesis of 9-ethynyl-3,4-dihydro-1H-pyrazino[2,1-b]quinazolin-6(2H)-one

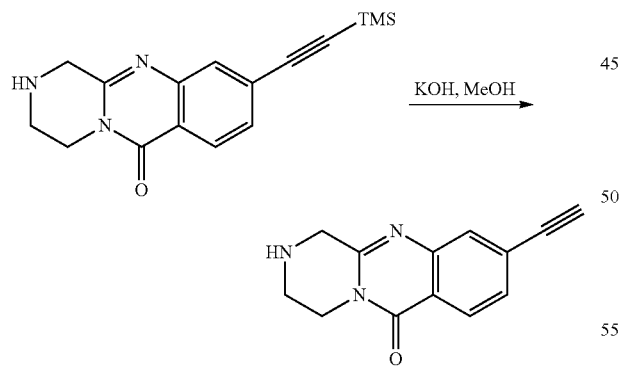

To a solution of 9-((trimethylsilyl)ethynyl)-3,4-dihydro-1H-pyrazino[2,1-b]quinazolin-6(2H)-one (120 mg) in MeOH (50 mL) was added 1 N KOH (2 mL). The mixture was stirred at room temperature for 1 h. Then the reaction mixture was adjusted pH to 8 and extracted with ethyl acetate three times. The combined organic layers were dried over Na$_2$SO$_4$ and concentrated to give the desired product (60 mg), which was purified by column chromatography. MS (ESI): 226 (MH$^+$).

Example 5.1f. Synthesis of the HCl Salt of 94(5-methylthiazol-2-yl)ethynyl)-3,4-dihydro-1H-pyrazino[2,1-b]quinazolin-6(2H)-one

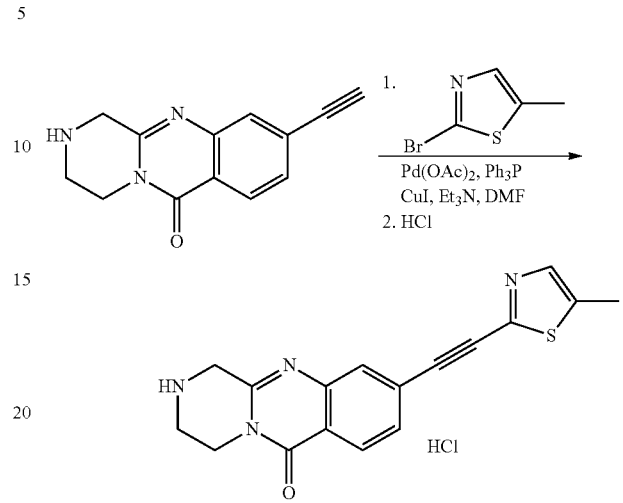

The title compound was prepared according to the experimental procedure as described in Example 1.1. The product was then converted to the corresponding HCl salt. MS (ESI): 323 (MH$^+$).

Example 5.2. Synthesis of 2-methyl-9-((5-methylthiazol-2-yl)ethynyl)-3,4-dihydro-1H-pyrazino[2,1-b]quinazolin-6(2H)-one

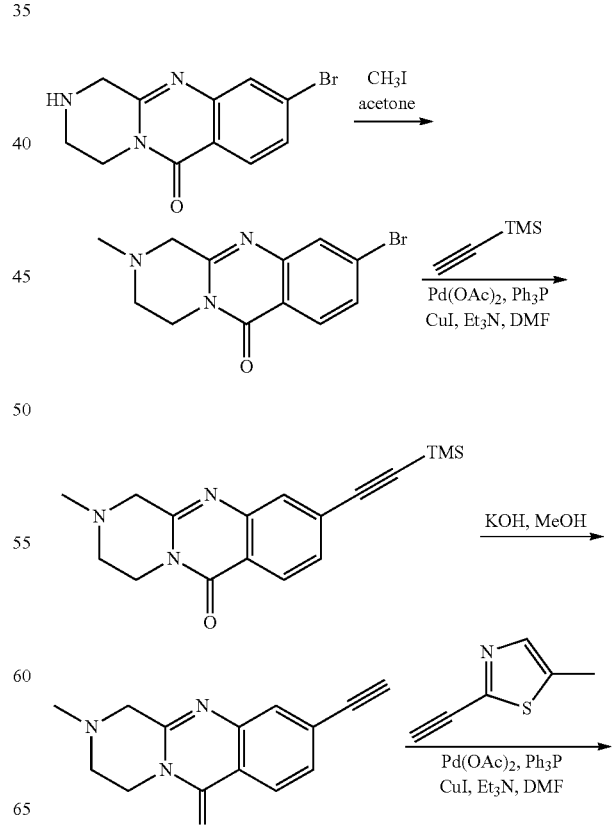

-continued

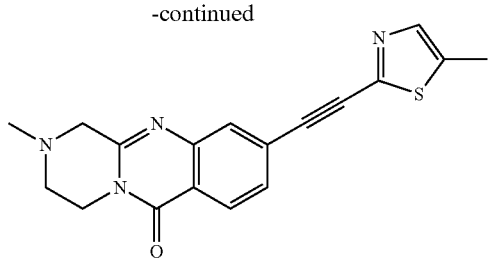

Example 5.2a. Synthesis of 9-bromo-2-methyl-3,4-dihydro-1H-pyrazino[2,1-b]quinazolin-6(2H)-one

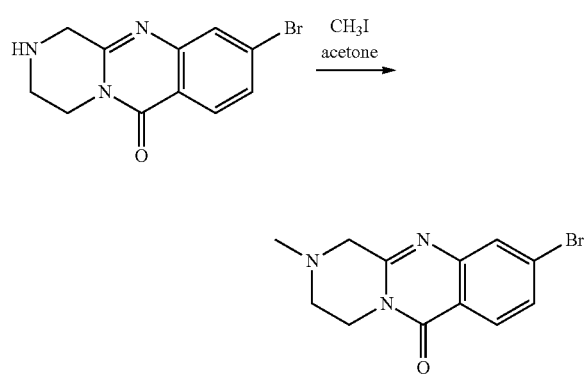

A solution of 9-bromo-3,4-dihydro-1H-pyrazino[2,1-b]quinazolin-6(2H)-one (200 mg, 0.71 mmol, 1 equiv) and MeI (101 mg, 0.71 mmol, 1 equiv) in acetone (35 mL) was stirred at room temperature for 2 h. Then the reaction mixture was then concentrated and purified by column chromatography to give 130 mg of the desired product. MS (ESI): 294/296 (MH$^+$).

Example 5.2b. Synthesis of 2-methyl-9-((trimethylsilyl)ethynyl)-3,4-dihydro-1H-pyrazino[2,1-b]quinazolin-6(2H)-one

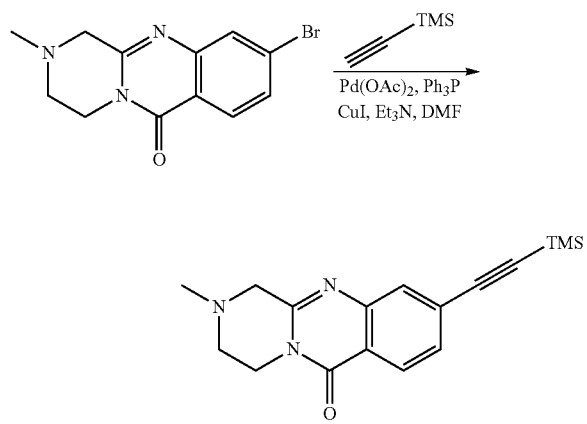

The title compound was prepared according to the experimental procedure as described in Example 5.1d. MS (ESI): 312 (MH$^+$).

Example 5.2c. Synthesis of 9-ethynyl-2-methyl-3,4-dihydro-1H-pyrazino[2,1-b]quinazolin-6(2H)-one

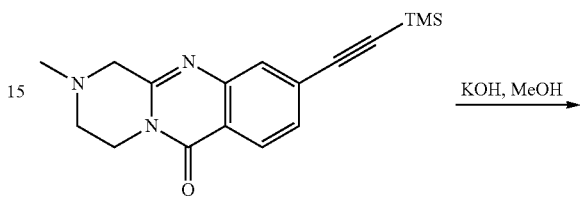

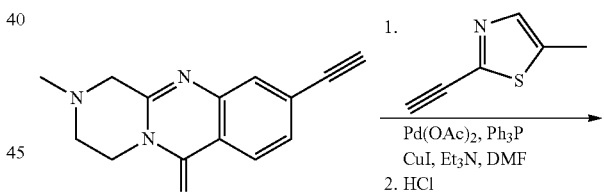

The title compound was prepared according to the experimental procedure as described in Example 5.1e. MS (ESI): 240 (MH$^+$).

Example 5.2d. Synthesis of the HCl Salt of 2-methyl-94(5-methylthiazol-2-yl)ethynyl)-3,4-dihydro-1H-pyrazino[2,1-b]quinazolin-6(2H)-one

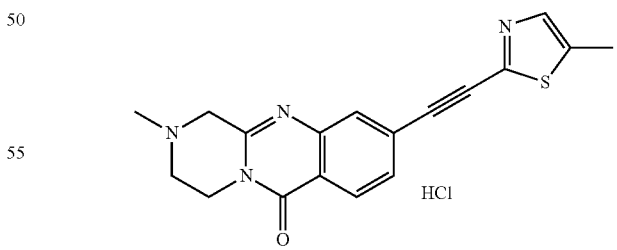

The title compound was prepared according to the experimental procedure as described in Example 5.1d. The product was then converted to the corresponding HCl salt. MS (ESI): 337 (MH$^+$); $^1$H NMR (300 MHz, CDCl$_3$) δ 8.27-8.24 (d, J=8.22 Hz, 1H), 7.81 (s, 1H), 7.61-7.56 (m, 2H), 4.11-4.07 (t, J=5.12 Hz, 2H), 3.71 (s, 2H), 2.90-2.86 (t, J=5.72 Hz, 2H), 2.55 (s, 3H), 2.50 (s, 3H).

Example 5.3. Synthesis of 9-((4-fluorophenyl)ethynyl)-2-methyl-3,4-dihydro-1H-pyrazino[2,1-b]quinazolin-6(2H)-one

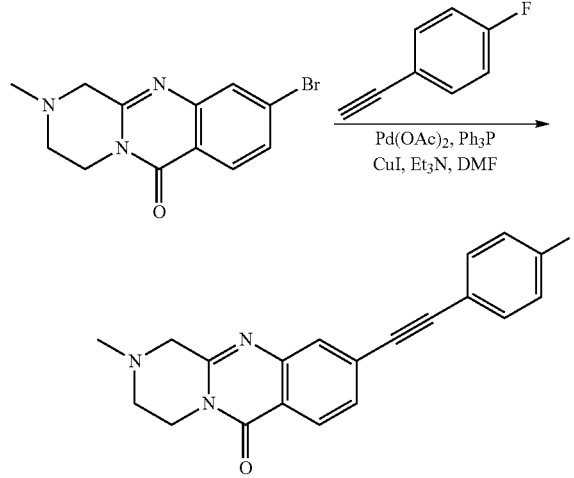

The title compound was prepared according to the experimental procedure as described in Example 1.1. MS (ESI): 334 (MH+); 1H NMR (300 MHz, CDCl3) δ 8.26-8.23 (d, J=8.28 Hz, 1H), 7.74 (s, 1H), 7.59-7.53 (m, 3H), 7.12-7.06 (t, J=8.72 Hz, 2H), 4.11-4.08 (t, J=5.73 Hz, 2H), 3.71 (s, 2H), 2.90-2.86 (t, J=5.67 Hz, 2H), 2.50 (s, 3H). mGluR5 PAM $EC_{50}$: ++++. Fold shift at 10 μM: +.

Example 5.4. Synthesis of 9-((3-fluorophenyl)ethynyl)-2-methyl-3,4-dihydro-1H-pyrazino[2,1-b]quinazolin-6(2H)-one

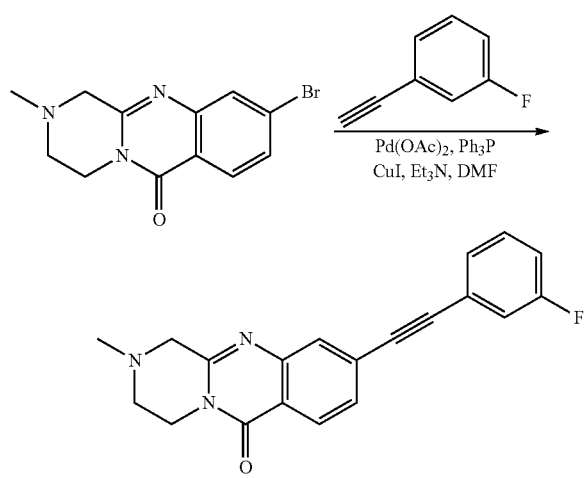

The title compound was prepared according to the experimental procedure as described in Example 1.1. MS (ESI): 334 (MH+); 1H NMR (300 MHz, CDCl3) δ 8.27-8.24 (d, J=8.28 Hz, 1H), 7.76 (s, 1H), 7.58-7.54 (dd, J=8.24, J=1.49 Hz, 1H), 7.38-7.35 (m, 2H), 7.29-7.26 (m, 1H), 7.14-7.08 (m, 1H), 4.12-4.08 (t, J=5.79 Hz, 2H), 3.71 (s, 2H), 2.90-2.86 (t, J=5.79 Hz, 2H), 2.50 (s, 3H). mGluR5 PAM $EC_{50}$: +++++.

Example 5.5. Synthesis of the HCl Salt of 2-methyl-9-(pyridin-2-ylethynyl)-3,4-dihydro-1H-pyrazino[2,1-b]quinazolin-6(2H)-one

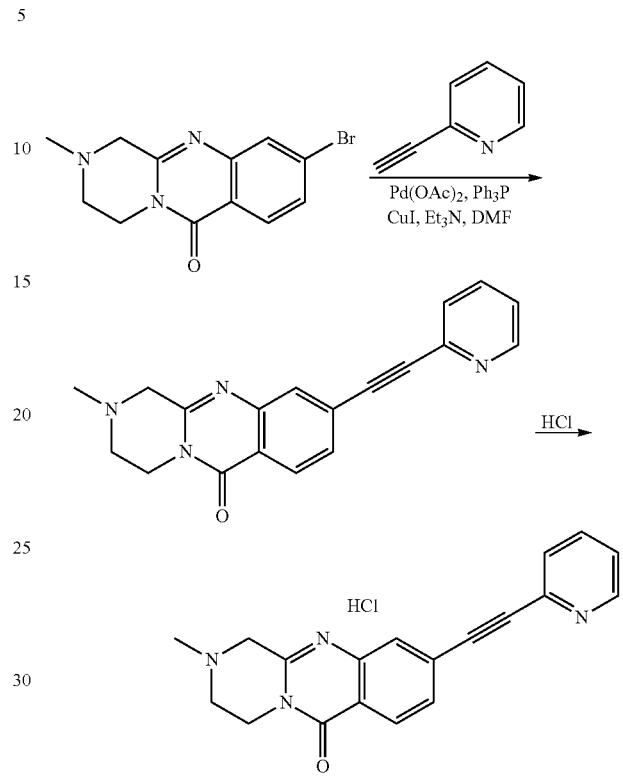

The title compound was prepared according to the experimental procedure as described in Example 1.1. The product was then converted to the corresponding HCl salt. MS (ESI): 317 (MH+); 1H NMR (300 MHz, CD3OD) δ 8.89-8.87 (d, J=5.64 Hz, 1H), 8.61-8.55 (t, J=7.95 Hz, 1H), 8.38-8.35 (d, J=8.4 Hz, 1H), 8.27-8.25 (d, J=8.28 Hz, 1H), 8.06-8.01 (m, 2H), 7.86-7.83 (dd, J=8.24, 1.46 Hz, 1H), 4.65 (s, 2H), 4.38 (s, 2H), 4.38 (t, J=5.8 Hz, 2H), 3.90 (t, J=5.8 Hz, 2H), 3.20 (s, 3H). mGluR5 PAM $EC_{50}$: ++.

Example 5.6. Synthesis of the HCl Salt of 2-(sec-butyl)-9-((3-fluorophenyl)ethynyl)-3,4-dihydro-1H-pyrazino[2,1-b]quinazolin-6(2H)-one

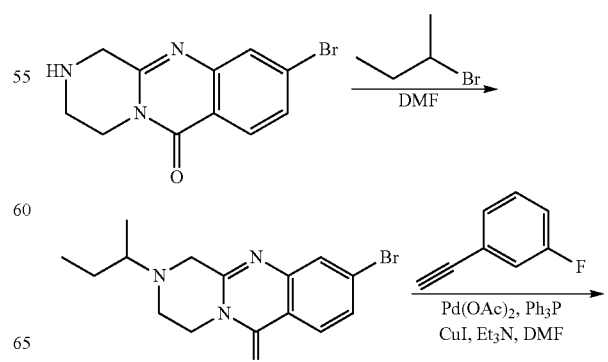

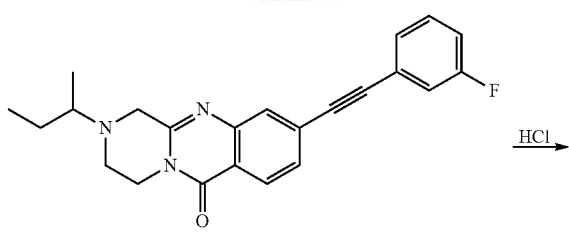

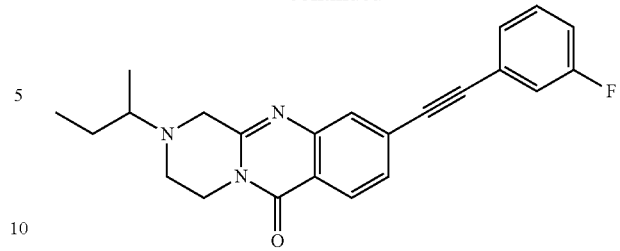

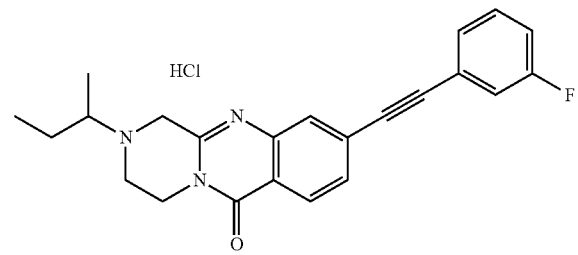

Example 5.6a. Synthesis of 9-bromo-2-sec-butyl-3,4-dihydro-1H-pyrazino[2,1-b]quinazolin-6(2H)-one

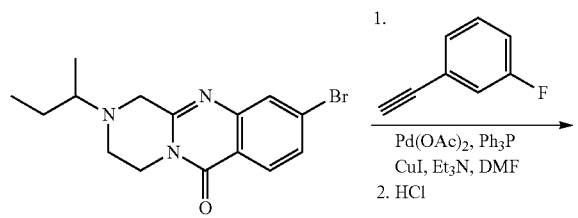

A solution of 9-bromo-3,4-dihydro-1H-pyrazino[2,1-b]quinazolin-6(2H)-one (30 mg, 0.11 mmol) and excess 2-bromobutane in DMF (5 mL) was stirred at 140° C. for 6 h. Then the reaction mixture was concentrated and purified by column chromatography to give the desired product. MS (ESI): 336, 338 (MH$^+$).

Example 5.6b. Synthesis of the HCl Salt of 2-(sec-butyl)-9-((3-fluorophenyl)ethynyl)-3,4-dihydro-1H-pyrazino[2,1-b]quinazolin-6(2H)-one The title compound was prepared according to the experimental procedure as described in Example 1.1. The compound was then converted to the corresponding HCl salt. MS (ESI): 376 (MH$^+$); $^1$H NMR (300 MHz, CDCl$_3$) δ 8.26-8.25 (d, J=8.61 Hz, 1H), 7.75 (s, 1H), 7.57-7.53 (dd, J=8.28, 1.53 Hz, 1H), 7.26-7.25 (m, 1H), 7.13-7.06 (m, 1H), 7.37-7.34 (m, 2H), 4.08-4.04 (m, 2H), 3.92-3.78 (q, 2H), 3.04-2.84 (m, 2H), 2.73-2.67 (m, 1H), 1.53-1.35 (m, 1H), 1.11-1.08 (d, J=6.57 Hz, 3H), 0.99-1.00 (q, 3H), 0.99-0.94 (m, 1H). mGluR5 PAM EC$_{50}$: ++.

Example 5.7. Synthesis of the HCl Salt of 2-allyl-9-((3-fluorophenyl)ethynyl)-3,4-dihydro-1H-pyrazino[2,1-b]quinazolin-6(2H)-one

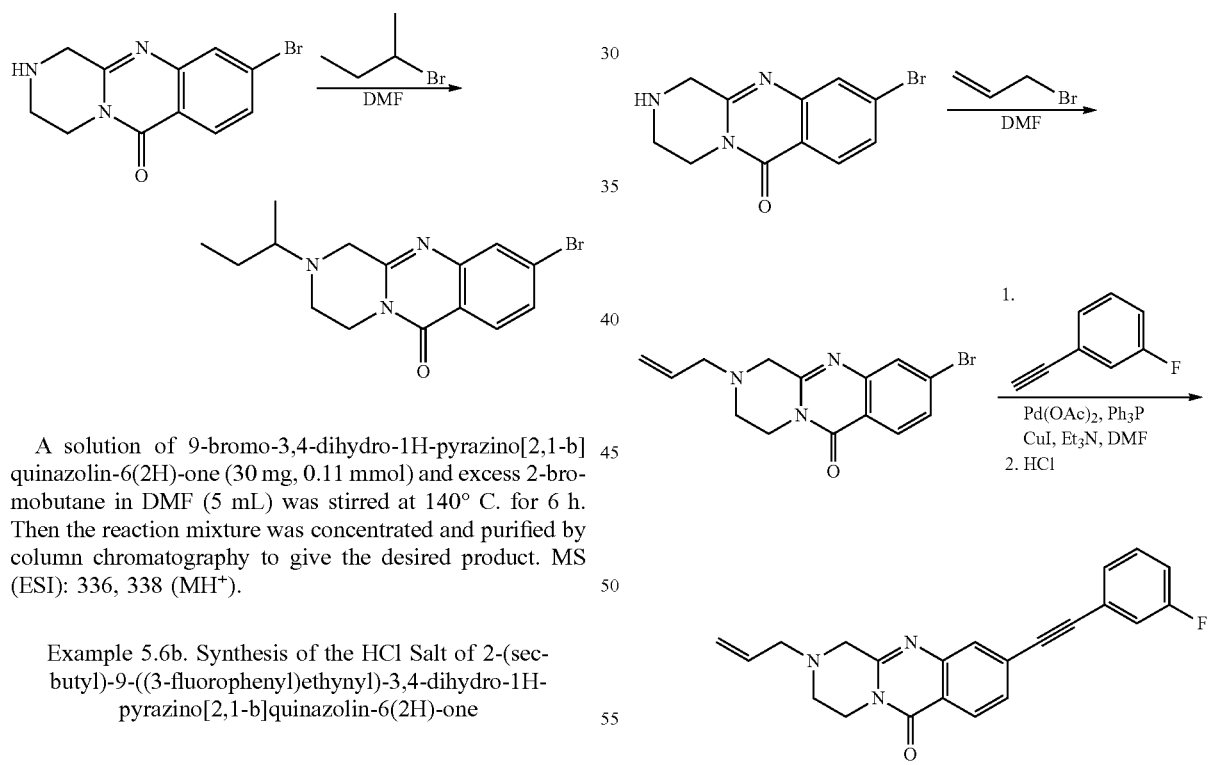

The title compound was prepared according to the experimental procedure as described in Example 5.6a and Example 1.1. The product was then converted to the corresponding HCl salt. MS (ESI): 360 (MH$^+$); $^1$H NMR (300 MHz, DMSO-d$^6$) δ 8.20-8.17 (d, J=8.28 Hz, 1H), 7.80 (s, 1H), 7.72-7.69 (d, J=7.95 Hz, 1H), 7.51-7.48 (m, 3H), 7.33-7.27 (m, 1H), 5.98-5.92 (m, 1H), 5.66-5.59 (m, 2H), 4.45 (s, 2H), 4.17-4.18 (t, J=6.17 Hz, 2H), 3.96-3.94 (d, J=6.66 Hz, 2H), 3.70-3.54 (m, 2H).

Example 5.8. Synthesis of the HCl Salt of 9-((3-fluorophenyl)ethynyl)-2-(2-hydroxyethyl)-3,4-dihydro-1H-pyrazino[2,1-b]quinazolin-6(2H)-one

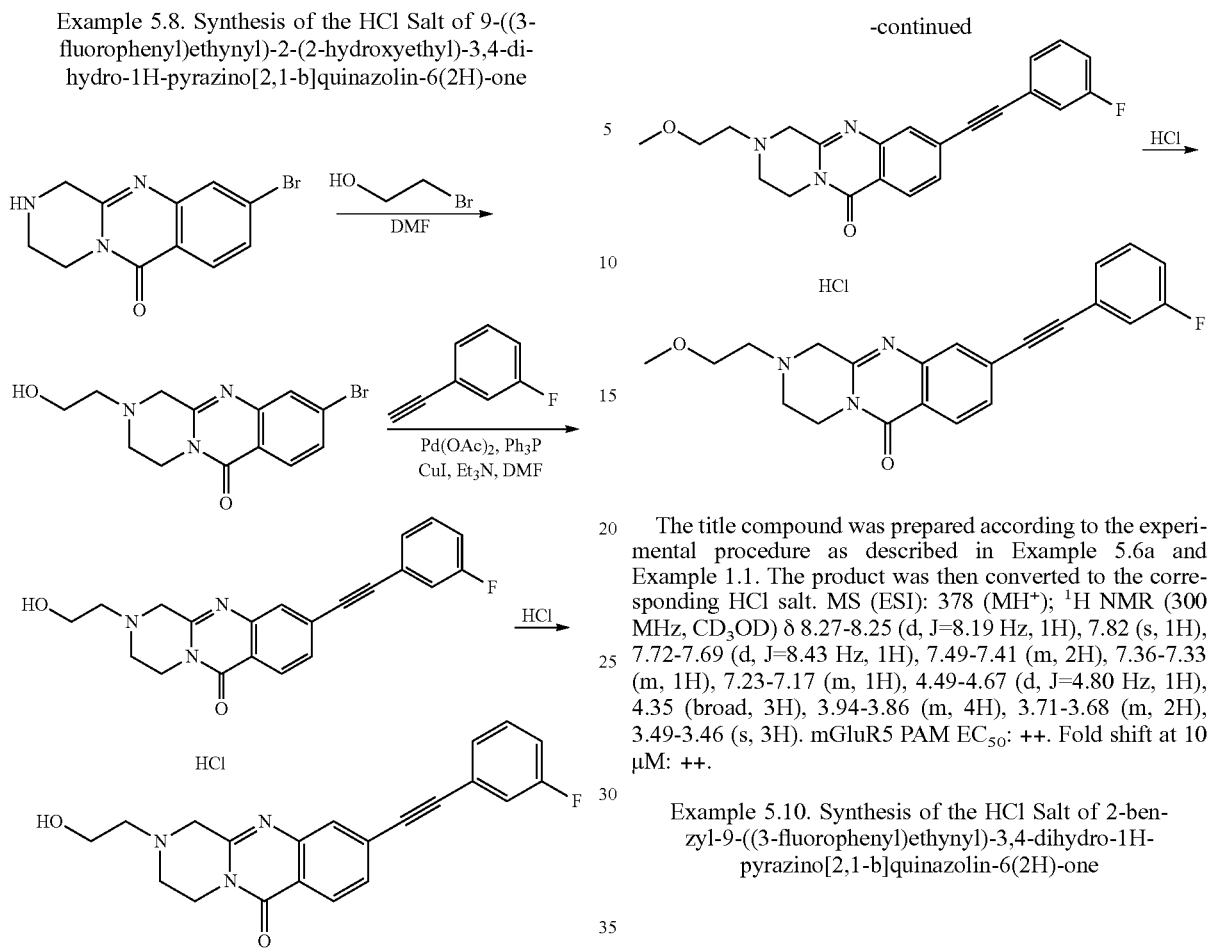

The title compound was prepared according to the experimental procedure as described in Example 5.6a and Example 1.1. The product was then converted to the corresponding HCl salt. MS (ESI): 364 (MH+); $^1$H NMR (300 MHz, DMSO-d$^6$) δ 8.21-8.18 (d, J=8.10 Hz, 1H), 7.83 (s, 1H), 7.72-7.69 (d, J=8.46 Hz, 1H), 7.54-7.47 (m, 3H), 7.38-7.35 (m, 1H), 5.17-5.06 (broad, 6H), 4.61 (broad, 2H), 3.87 (broad, 2H), 3.44 (broad, 2H). mGluR5 PAM EC$_{50}$: +++. Fold shift at 10 μM: +++.

Example 5.9. Synthesis of the HCl Salt of 9-((3-fluorophenyl)ethynyl)-2-(2-methoxyethyl)-3,4-dihydro-1H-pyrazino[2,1-b]quinazolin-6(2H)-one The title compound was prepared according to the experimental procedure as described in Example 5.6a and Example 1.1. The product was then converted to the corresponding HCl salt. MS (ESI): 378 (MH+); $^1$H NMR (300 MHz, CD$_3$OD) δ 8.27-8.25 (d, J=8.19 Hz, 1H), 7.82 (s, 1H), 7.72-7.69 (d, J=8.43 Hz, 1H), 7.49-7.41 (m, 2H), 7.36-7.33 (m, 1H), 7.23-7.17 (m, 1H), 4.49-4.67 (d, J=4.80 Hz, 1H), 4.35 (broad, 3H), 3.94-3.86 (m, 4H), 3.71-3.68 (m, 2H), 3.49-3.46 (s, 3H). mGluR5 PAM EC$_{50}$: ++. Fold shift at 10 μM: ++.

Example 5.10. Synthesis of the HCl Salt of 2-benzyl-9-((3-fluorophenyl)ethynyl)-3,4-dihydro-1H-pyrazino[2,1-b]quinazolin-6(2H)-one

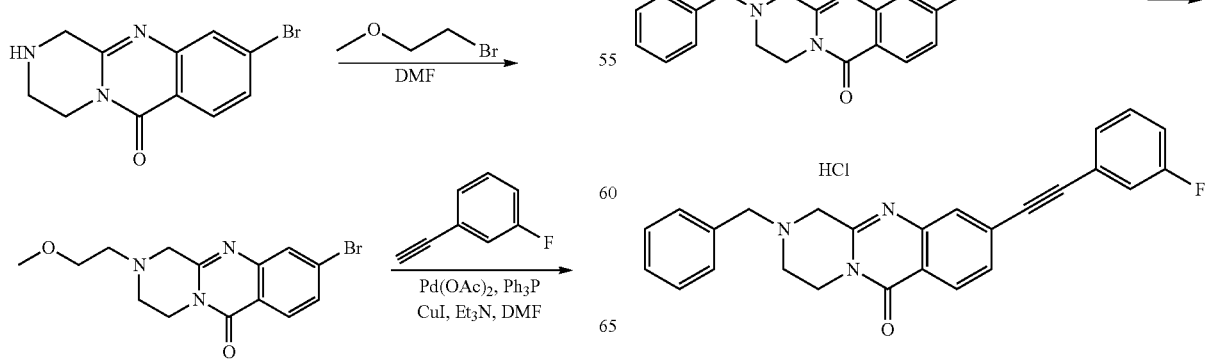

The title compound was prepared according to the experimental procedure as described in Example 5.6a and Example 1.1. The product was then converted to the corresponding HCl salt. MS (ESI): 410 (MH+); ¹H NMR (300 MHz, CD₃OD) δ 8.27-8.24 (d, J=8.31 Hz, 1H), 7.79 (s, 1H), 7.71-7.64 (m, 3H), 7.61-7.57 (m, 3H), 7.47-7.40 (m, 2H), 7.36-7.32 (m, 1H), 7.23-7.17 (m, 1H), 4.65 (s, 2H), 4.52-4.50 (m, 2H), 4.35 (m, 2H), 3.91-3.87 (m, 2H). mGluR5 PAM EC₅₀: +.

Example 5.11. Synthesis of the HCl Salt of 2-butyl-9-((3-fluorophenyl)ethynyl)-3,4-dihydro-1H-pyrazino[2,1-b]quinazolin-6(2H)-one

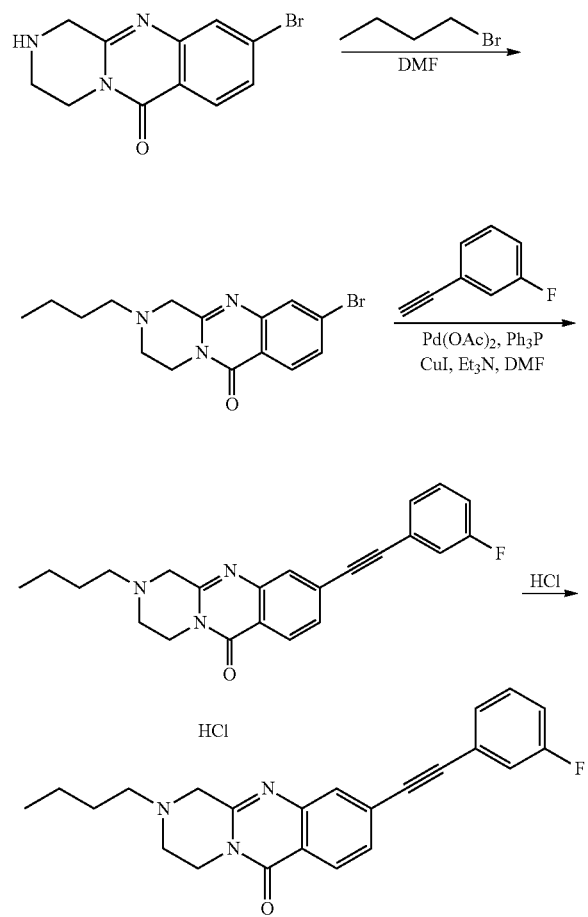

The title compound was prepared according to the experimental procedure as described in Example 5.6a and Example 1.1. The product was then converted to the corresponding HCl salt. MS (ESI): 376 (MH+); ¹H NMR (300 MHz, CDCl₃) δ 8.26-8.23 (d, J=8.28 Hz, 1H), 7.76 (s, 1H), 7.57-7.54 (dd, J=8.13, 1.53 Hz, 1H), 7.38-7.34 (m, 2H), 7.32-7.31 (m, 1H), 7.13-7.07 (m, 1H), 4.10-4.06 (t, J=5.73 Hz, 2H), 3.75 (s, 2H), 2.93-2.89 (t, J=5.70 Hz, 2H), 2.58-2.53 (t, J=7.23 Hz, 2H), 1.56-1.54 (m, 2H), 1.48-1.38 (m, 2H), 1.01-0.95 (t, J=5.7 Hz, 3H). mGluR5 PAM EC₅₀: ++. Fold shift at 10 μM: +++.

Example 5.12. Synthesis of the HCl Salt of 2-(6-oxo-9-(pyridin-2-ylethynyl)-3,4-dihydro-1H-pyrazino[2,1-b]quinazolin-2(6H)-yl)acetonitrile

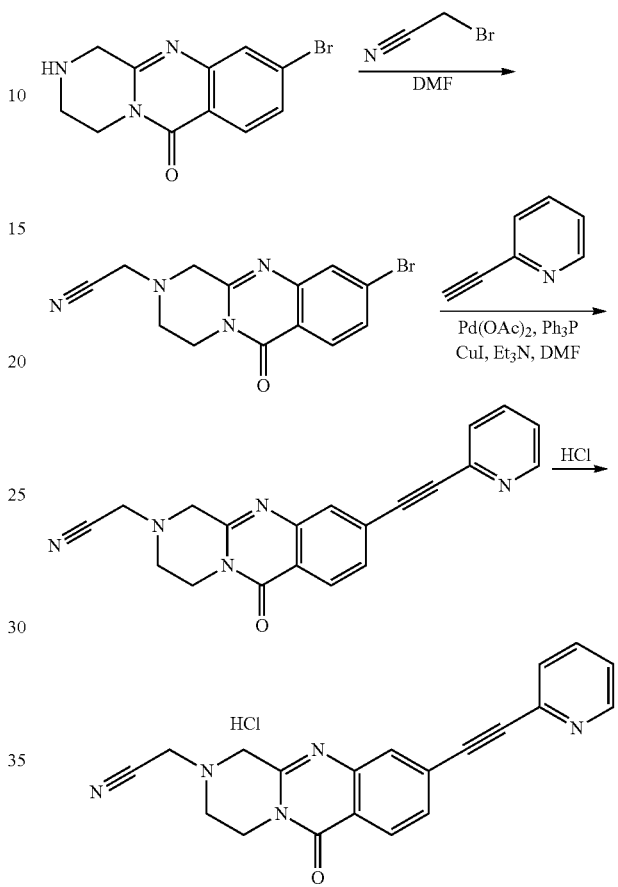

The title compound was prepared according to the experimental procedure as described in Example 5.6a and Example 1.1. The product was then converted to the corresponding HCl salt. MS (ESI): 342 (MH+); ¹H NMR (300 MHz, CD₃OD) δ 8.96-8.94 (dd, J=8.28, 1.41 Hz, 1H), 8.73-8.67 (t, J=7.98 Hz, 1H), 8.45-8.42 (d, J=8.31 Hz, 1H), 8.38-8.36 (d, J=7.98 Hz, 1H), 8.16-8.10 (m, 2H), 7.80-7.99 (dd, J=8.28, 1.41 Hz, 1H), 4.23-4.19 (m, 4H), 4.06 (s, 2H), 3.24-3.20 (t, J=5.60 Hz, 2H).

Example 5.13. Synthesis of the HCl Salt of 2-(9-((3-fluorophenyl)ethynyl)-6-oxo-3,4-dihydro-1H-pyrazino[2,1-b]quinazolin-2(6H)-yl)-N-methylacetamide

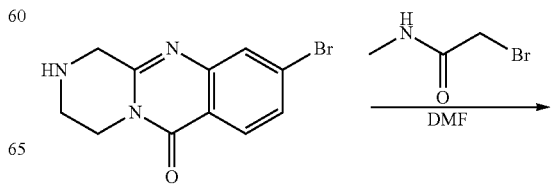

-continued

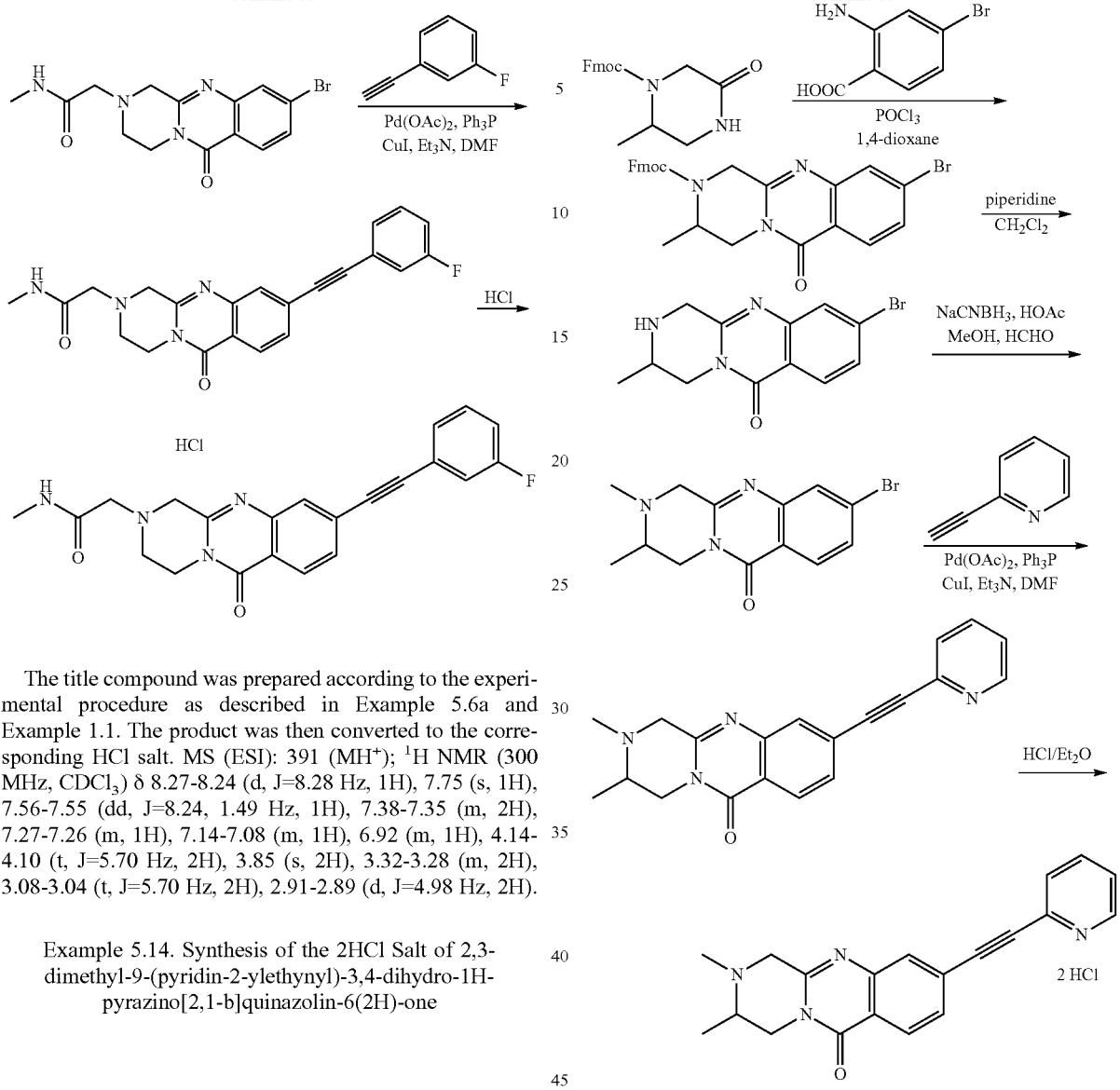

The title compound was prepared according to the experimental procedure as described in Example 5.6a and Example 1.1. The product was then converted to the corresponding HCl salt. MS (ESI): 391 (MH⁺); ¹H NMR (300 MHz, CDCl₃) δ 8.27-8.24 (d, J=8.28 Hz, 1H), 7.75 (s, 1H), 7.56-7.55 (dd, J=8.24, 1.49 Hz, 1H), 7.38-7.35 (m, 2H), 7.27-7.26 (m, 1H), 7.14-7.08 (m, 1H), 6.92 (m, 1H), 4.14-4.10 (t, J=5.70 Hz, 2H), 3.85 (s, 2H), 3.32-3.28 (m, 2H), 3.08-3.04 (t, J=5.70 Hz, 2H), 2.91-2.89 (d, J=4.98 Hz, 2H).

Example 5.14. Synthesis of the 2HCl Salt of 2,3-dimethyl-9-(pyridin-2-ylethynyl)-3,4-dihydro-1H-pyrazino[2,1-b]quinazolin-6(2H)-one Example 5.14a. Synthesis of ethyl 2-(1-aminopropan-2-ylamino)acetate and ethyl 2-(2-aminopropylamino)acetate

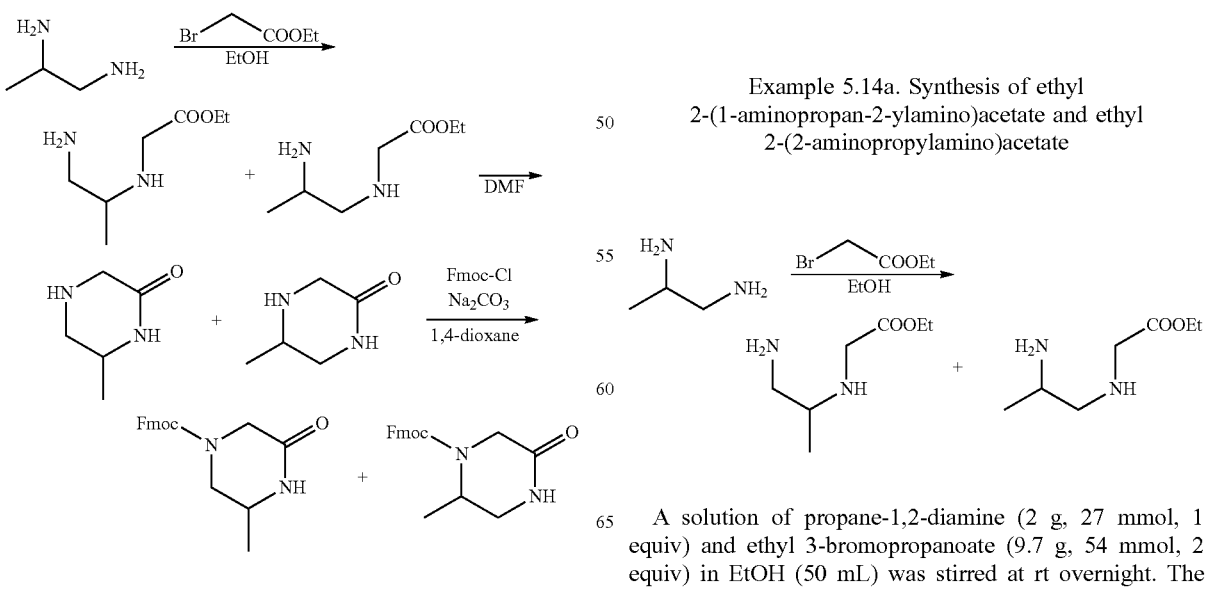

A solution of propane-1,2-diamine (2 g, 27 mmol, 1 equiv) and ethyl 3-bromopropanoate (9.7 g, 54 mmol, 2 equiv) in EtOH (50 mL) was stirred at rt overnight. The reaction mixture was then concentrated under reduce pressure to obtain the crude product, which was directly used for the next step.

Example 5.14b. Synthesis of 5-methylpiperazin-2-one and 6-methylpiperazin-2-one

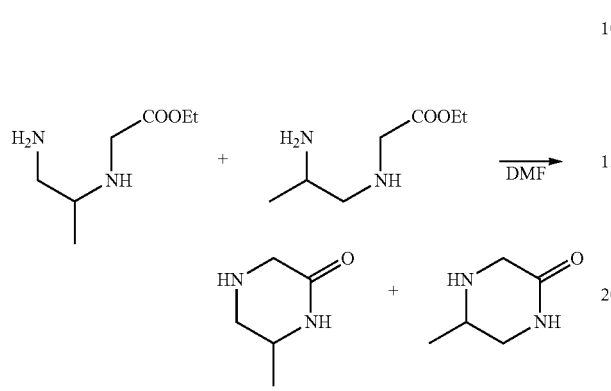

A solution of ethyl 2-(1-aminopropan-2-ylamino)acetate and ethyl 2-(2-aminopropylamino)acetate (4 g, 22.8 mmol, 1 equiv) in DMF (50 mL) was stirred at reflux for 1 hour. After it was cooled to rt, the reaction mixture was diluted with water and extracted with DCM (3×100 mL). The combined organic layers were dried over Na$_2$SO$_4$ and concentrated under reduced pressure to give the crude product, which was directly used for the next step.

Example 5.14c. Synthesis of (9H-fluoren-9-yl) methyl 2-methyl-5-oxopiperazine-1-carboxylate and (9H-fluoren-9-yl)methyl 3-methyl-5-oxopiperazine-1-carboxylate

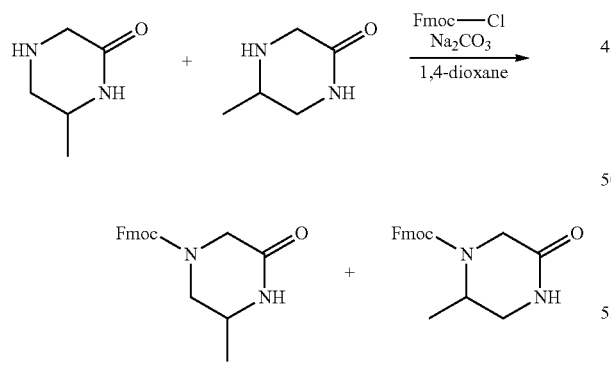

A solution of 5-methylpiperazin-2-one and 6-methylpiperazin-2-one (3 g, 26.3 mmol, 1 equiv), Na$_2$CO$_3$ (11.1 g, 105.2 mmol, 4 equiv) and Fmoc-Cl (13.6 g, 52.6 mmol, 2 equiv) in 1,4-dioxane (100 mL) and water was stirred at rt over night. The reaction mixture was diluted with water and extracted with ethyl acetate (3×100 mL). The combined organic layers were dried over Na$_2$SO$_4$. After filtration and concentration, the residue was purified by silica gel chromatography to give the desired product.

Example 5.14d. Synthesis of (9H-fluoren-9-yl) methyl 9-bromo-3-methyl-6-oxo-3,4-dihydro-1H-pyrazino[2,1-b]quinazoline-2(6H)-carboxylate

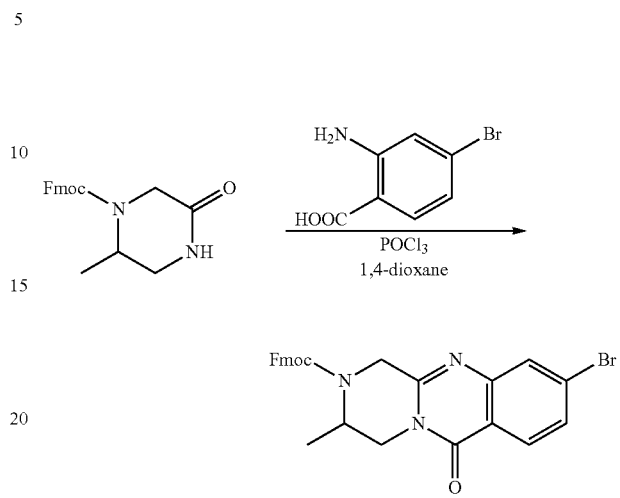

A solution of 2-amino-4-bromobenzoic acid (2.8 g, 13.1 mmol, 1.1 equiv), (9H-fluoren-9-yl)methyl 2-methyl-5-oxopiperazine-1-carboxylate (4 g, 11.9 mmol, 1 equiv), and phosphoryl trichloride (4 mL) in 1,4-dioxane (100 mL) was stirred at 80° C. for two hours. After it was cooled to room temperature, the reaction mixture was quenched with water and extracted with ethyl acetate (3×100 mL). The combined organic layers were dried over Na$_2$SO$_4$. After filtration and concentration, the residue was purified by silica gel chromatography to give the desired product.

Example 5.14e. Synthesis of 9-bromo-3-methyl-3,4-dihydro-1H-pyrazino[2,1-b]quinazolin-6(2H)-one

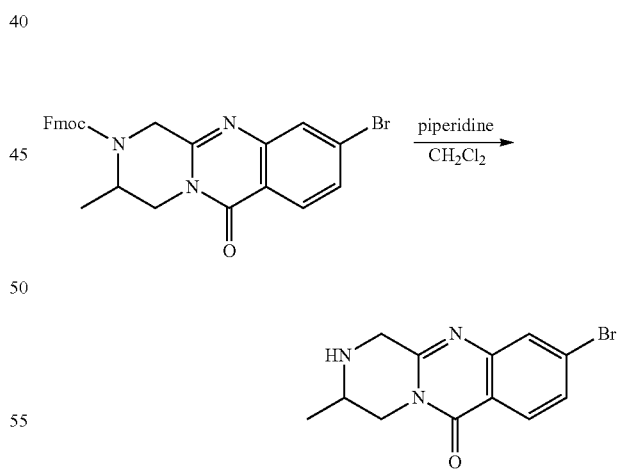

A solution of (9H-fluoren-9-yl)methyl 9-bromo-3-methyl-6-oxo-3,4-dihydro-1H-pyrazino[2,1-b]quinazoline-2(6H)-carboxylate (2 g, 3.9 mmol, 1 equiv) and piperidine (4 mL) in DCM (50 mL) was stirred at room temperature overnight. The reaction mixture was then diluted with water and extracted with ethyl acetate (3×100 mL). The combined organic layers were dried over Na$_2$SO$_4$. After filtration and concentration, the residue was purified by silica gel chromatography to give the desired product.

Example 5.14f. Synthesis of 9-bromo-2,3-dimethyl-3,4-dihydro-1H-pyrazino[2,1-b]quinazolin-6(2H)-one

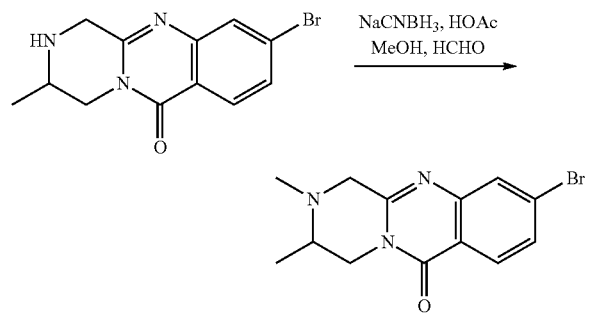

To a solution of 9-bromo-2,3-dimethyl-3,4-dihydro-1H-pyrazino[2,1-b]quinazolin-6(2H)-one (0.2 g, 0.65 mmol, 1 equiv), NaH$_3$BCN (4.1 mg, 0.065 mmol, 0.1 equiv) and HOAc (0.05 mL) in methanol (5.0 mL) was added aq. formaldehyde (39 mg, 1.3 mmol, 2 equiv) dropwise at room temperature. After stirring for a few minutes, the reaction mixture was diluted with water and extracted with ethyl acetate (3×20 mL). The combined organic layers were dried over Na$_2$SO$_4$ and concentrated under reduced pressure to give the desired product, which was purified by silica gel chromatography.

Example 5.14g. Synthesis of the 2HCl Salt of 2,3-dimethyl-9-(pyridin-2-ylethynyl)-3,4-dihydro-1H-pyrazino[2,1-b]quinazolin-6(2H)-one

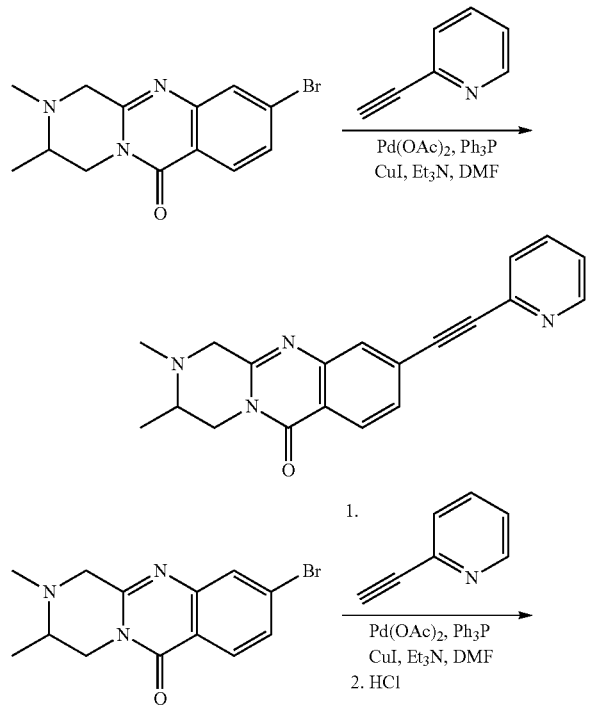

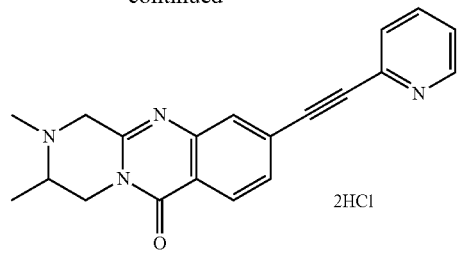

The title compound was prepared according to the experimental procedure as described in Example 1.1. The product was then converted to the corresponding 2HCl salt. MS (ESI): 331 (M+H$^+$); $^1$H NMR (300 MHz, DMSO-d$^6$+D$_2$O) δ 8.66-8.65 (d, J=4.74 Hz, 1H), 8.23-8.20 (d, J=8.25, 1H), 8.02-7.97 (t, J=7.71 Hz, 1H), 7.87 (s, 1H), 7.82-7.74 (m, 2H), 7.57-7.53 (m, 1H), 4.60 (s, 1H), 4.47-4.415 (dd, J=14.42, 3.49 Hz, 1H), 3.93-3.90 (m, 3H), 2.96 (s. 3H), 1.46-1.45 (d, J=6.27 Hz, 3H). mGluR5 PAM EC$_{50}$: +++. Fold shift at 10 μM: +++.

Example 5.15. Synthesis of the 2HCl Salt of 2,4-dimethyl-9-(pyridin-2-ylethynyl)-3,4-dihydro-1H-pyrazino[2,1-b]quinazolin-6(2H)-one

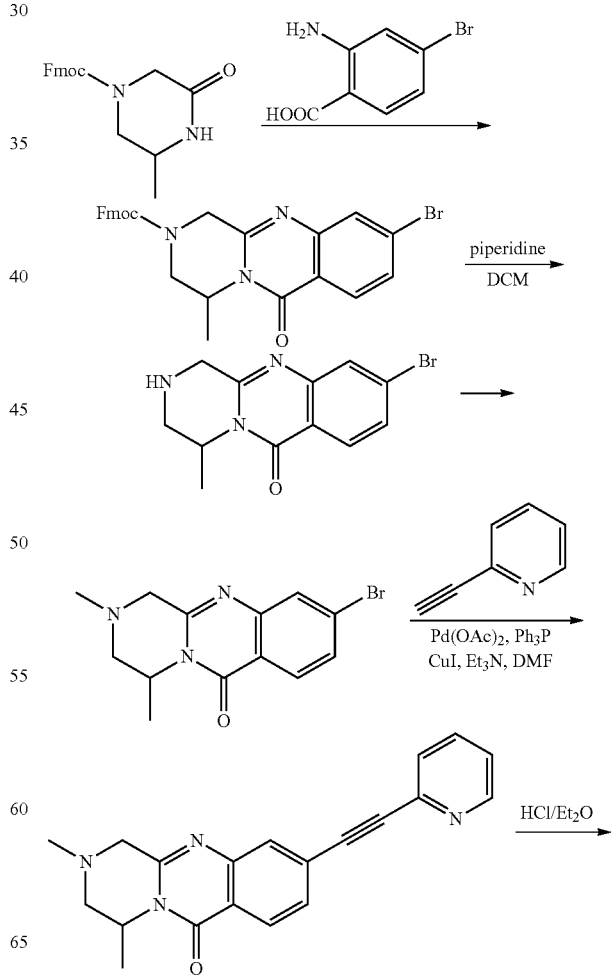

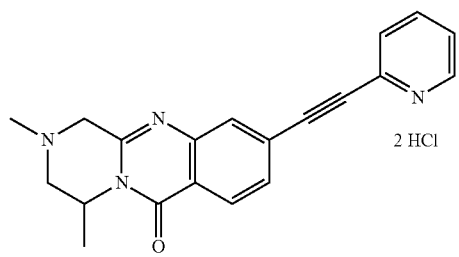 [SMILES: CC1Cn2c(nc3cc(C#Cc4ccccn4)ccc3c2=O)CN1C]

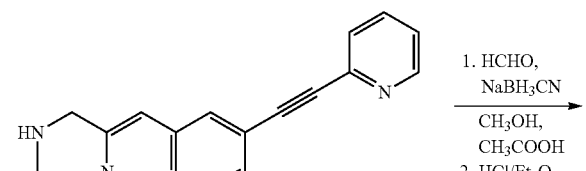

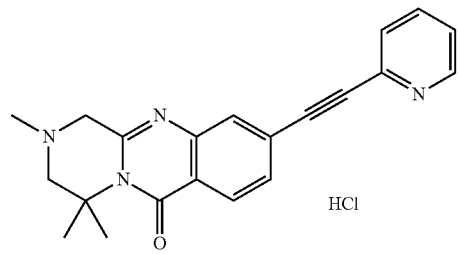

The title compound was prepared according to the experimental procedure as described in Example 5.14d, Example 5.14e, Example 5.14f, and Example 1.1. The product was then converted to the corresponding 2HCl salt. MS (ESI): 331 (M+H$^+$); $^1$H NMR (300 MHz, DMSO-d$^6$) δ 8.69-8.68 (d, J=4.47 Hz, 1H), 8.23-8.20 (d, J=8.25 Hz, 1H), 8.02-7.96 (t, J=7.8 Hz, 1H), 7.88 (s, 1H), 7.82-7.80 (d, J=7.8 Hz, 1H), 7.76-7.73 (dd, J=8.25, 1.26 Hz, 1H), 7.57-7.53 (m, 1H), 4.97 (broad, 1H), 4.61-4.56 (d, J=16.57 Hz, 1H), 4.44-4.39 (d, J=16.53 Hz, 1H), 3.81 (broad, 1H), 3.69 (broad, 1H), 2.99 (s, 3H), 1.59-1.56 (d, J=6.30 Hz, 3H). mGluR5 PAM EC$_{50}$: +++.

Example 5.16. Synthesis of the HCl Salt of 2,4,4-trimethyl-9-(pyridin-2-ylethynyl)-3,4-dihydro-1H-pyrazino[2,1-b]quinazolin-6(2H)-one The title compound was prepared according to the experimental procedure as described in Example 5.17b, Example 5.17d, Example 5.1a, Example 5.14d, Example 3.17b, Example 1.1, and Example 1.21d. The product was then converted to the corresponding HCl salt. MS (ESI): 345 (MH$^+$); $^1$H NMR (300 MHz, CD$_3$OD) δ 8.82-8.80 (m, 1H), 8.57-8.52 (td, J=7.98 Hz, 1.55 Hz, 1H), 8.24-8.20 (m, 2H), 8.01-7.87 (m, 1H), 7.73-7.72 (d, J=1.08 Hz, 1H), 7.71-7.70 (dd, J=8.27 Hz, 1.48 Hz, 1H), 4.53 (s, 2H), 3.65 (s, 2H), 3.08 (s, 3H), 1.80 (s, 6H).

Example 5.17. Synthesis of the 2HCl Salt of 3,3-dimethyl-9-(pyridin-2-ylethynyl)-3,4-dihydro-1H-pyrazino[2,1-b]quinazolin-6(2H)-one

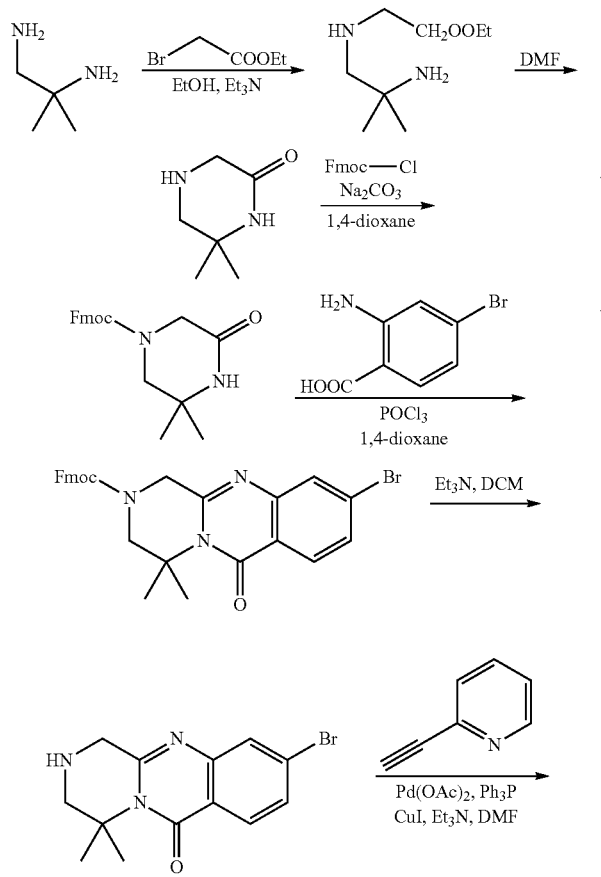

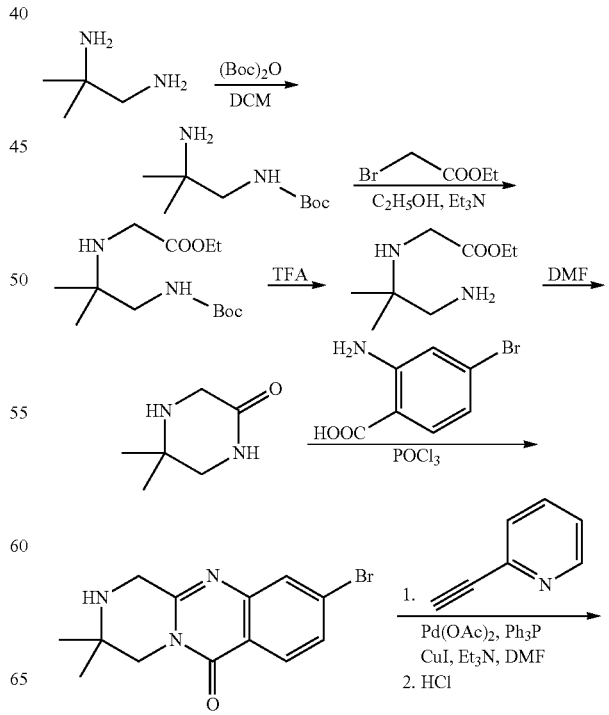

-continued

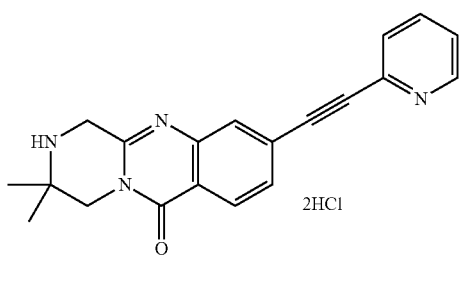

2HCl

Example 5.17a. Synthesis of tert-butyl 2-amino-2-methylpropylcarbamate

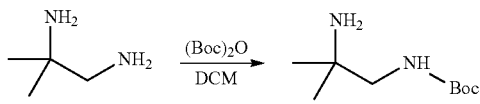

To a stirred solution of 2-methylpropane-1,2-diamine (1.0 g, 11.3 mmol) in DCM (15 mL) at −55° C. was added a solution of di-tert-butyl-dicarbonate (2.5 g, 11.3 mmol) in DCM (15 mL) while maintaining the reaction temperature below −40° C. The reaction mixture was stirred at −50° C. to −40° C. for 2 h, warmed to ambient temperature over 2.5 h, and then stirred at ambient temperature for 1 h. The solution was then extracted with aqueous citric acid solution (10 wt percent, 50 mL). The aqueous phase (pH 2-3) was made strongly alkaline (pH 14) with aqueous sodium hydroxide solution (50 wt percent, 5 mL) and extracted with DCM (5×25 mL). The combined organic layers were dried with MgSO$_4$ and concentrated under reduced pressure to give the desired product. MS (ESI): 189 (MH$^+$).

Example 5.17b. Synthesis of ethyl 2-(1-(tert-butoxycarbonyl)-2-methylpropan-2-ylamino)acetate

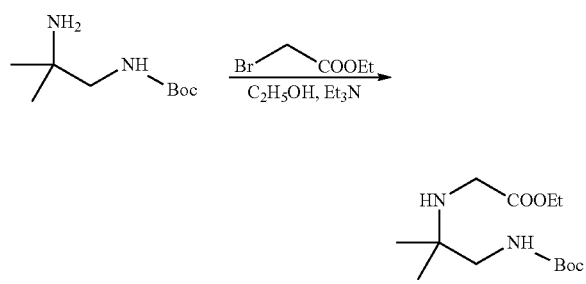

A solution of tert-butyl 2-amino-2-methylpropylcarbamate (2.2 g, 11.7 mmol) and ethyl bromoacetate (2.9 g, 17.6 mmol) in ethanol (40 mL) was stirred at 60° C. for 48 h. After it was cooled to room temperature, the mixture was concentrated and purified by column chromatography to give the desired product. MS (ESI): 275 (MH$^+$).

Example 5.17c. Synthesis of ethyl 2-(1-amino-2-methylpropan-2-ylamino)acetate

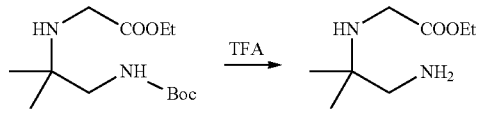 [SMILES: CCOC(=O)CNC(C)(C)CNC(=O)OC(C)(C)C ; CCOC(=O)CNC(C)(C)CN]

To a solution of ethyl 2-(1-(tert-butoxycarbonyl)-2-methylpropan-2-ylamino) acetate (1.3 g, 4.7 mmol) in DCM (30 mL) was added trifluoroacetic acid (15 mL). The mixture was stirred at room temperature for 1 h. Then the reaction mixture was concentrated to give the desired product, which was directly used for the next step. MS (ESI): 175 (MH$^+$).

Example 5.17d. Synthesis of 5,5-dimethylpiperazin-2-one

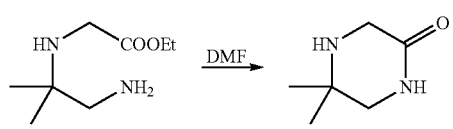

A solution of ethyl 2-(1-amino-2-methylpropan-2-ylamino) acetate (0.8 g, 4.7 mmol) in DMF (20 mL) was stirred at reflux for 1 h. After it was cooled to room temperature, the mixture was concentrated to give the crude product, which was directly used for the next step. MS (ESI): 129 (MH$^+$).

Example 5.17e. Synthesis of 9-bromo-3,3-dimethyl-1,2,3,4-tetrahydropyrazino-[2,1-b]quinazolin-6-one

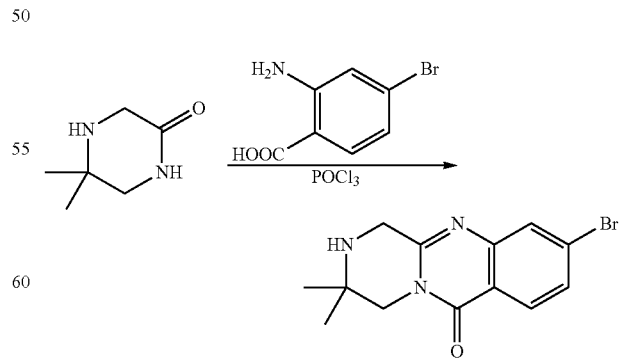

The title compound was prepared according to the experimental procedure as described in Example 5.14d. MS (ESI): 308, 310 (MH$^+$).

Example 5.17f. Synthesis of the 2HCl Salt of 3,3-dimethyl-9-(pyridin-2-ylethynyl)-3,4-dihydro-1H-pyrazino[2,1-b]quinazolin-6(2H)-one hydrochloride

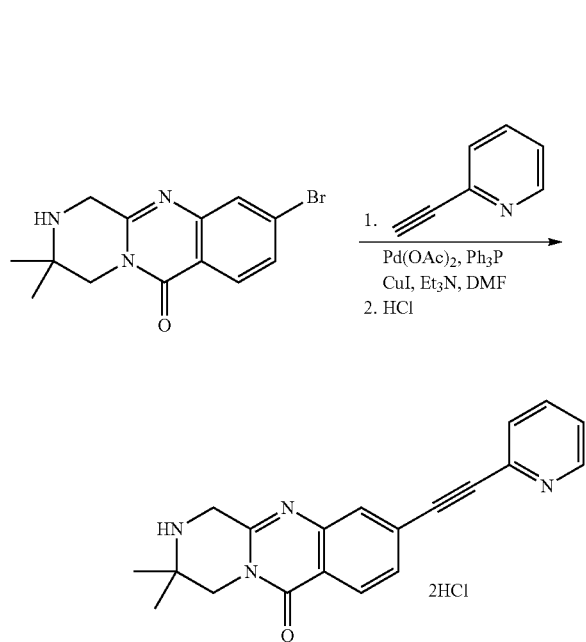

The title compound was prepared according to the experimental procedure as described in Example 1.1. The product was then converted to the corresponding 2HCl salt. MS (ESI): 331 (MH$^+$); $^1$H NMR (300 MHz, CD$_3$OD) δ 8.93-8.91 (d, J=5.78 Hz, 1H), 8.70-8.64 (t, J=7.98 Hz, 1H), 8.39-8.36 (d, J=8.22 Hz, 1H), 8.34-8.31 (d, J=7.98 Hz, 1H), 8.13-8.08 (t, J=6.40 Hz, 1H), 8.06 (s, 1H), 7.88-7.85 (dd, J=8.25, 1.50 Hz, 1H), 4.59 (s, 2H), 4.25 (s, 2H), 1.61 (s, 6H). mGluR5 PAM EC$_{50}$: ++.

Example 5.18. Synthesis of the 2HCl Salt of 2,3,3-trimethyl-9-(pyridin-2-ylethynyl)-3,4-dihydro-1H-pyrazino[2,1-b]quinazolin-6(2H)-one

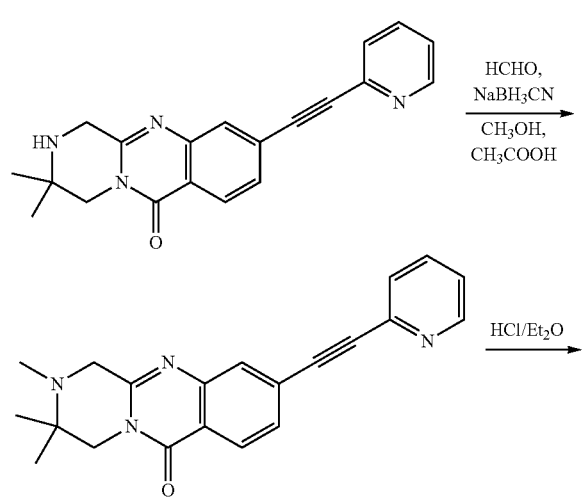

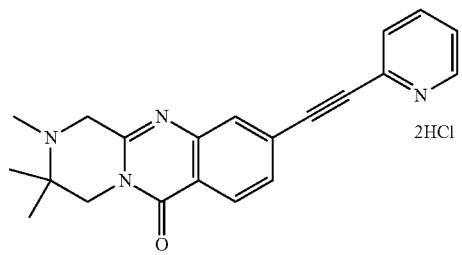

The title compound was prepared according to the experimental procedure as described in Example 5.14f. The product was then converted to the corresponding 2HCl salt. MS (ESI): 345 (MH$^+$); $^1$H NMR (300 MHz, CD$_3$OD) δ 8.92-8.90 (d, J=5.82 Hz, 1H), 8.67-8.62 (t, J=7.98 Hz, 1H), 8.38-8.35 (d, J=8.22 Hz, 1H), 8.32-8.30 (d, J=8.01 Hz, 1H), 8.11-8.06 (t, J=7.62 Hz, 1H), 8.04 (s, 1H), 7.87-7.84 (dd, J=8.25, 1.50 Hz, 1H), 4.69 (s, 2H), 4.32 (s, 2H), 3.09 (s, 3H), 1.62 (s, 6H). mGluR5 PAM EC$_{50}$: +.

Example 5.19. Synthesis of the HCl Salt of 3-((3-fluorophenyl)ethynyl)-8,9,10,11,11a,12-hexahydropyrido[1',2':4,5]pyrazino[2,1-b]quinazolin-14(6H)-one

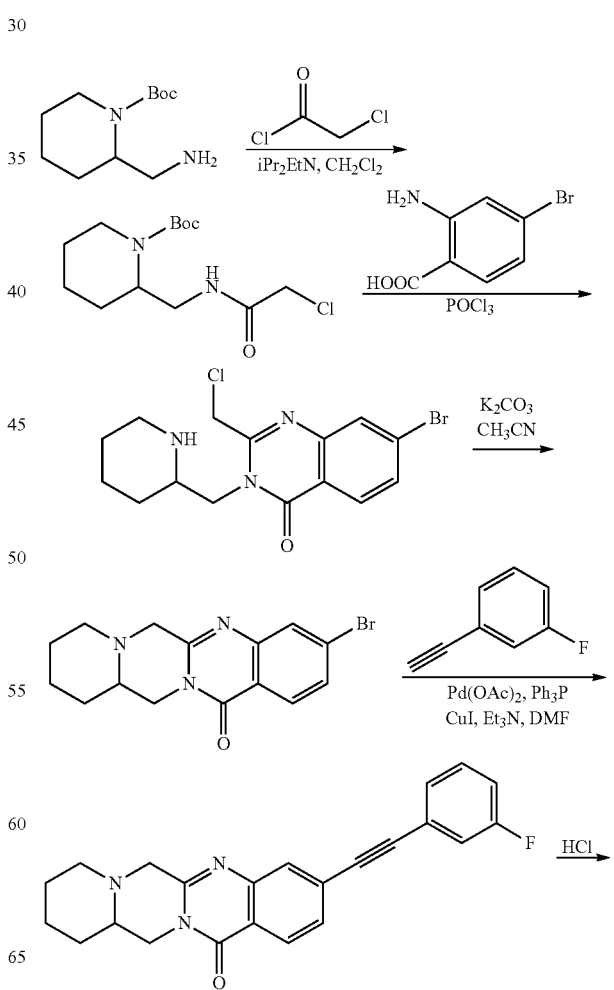

-continued

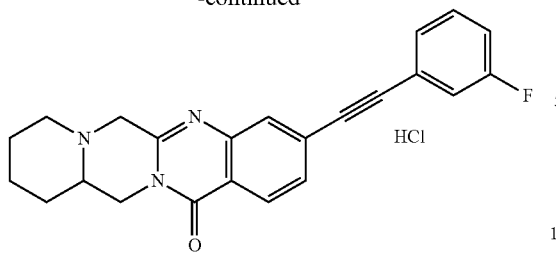

Example 5.19a. Synthesis of tert-butyl 2-((2-chloro-acetamido)methyl)piperidine-1-carboxylate

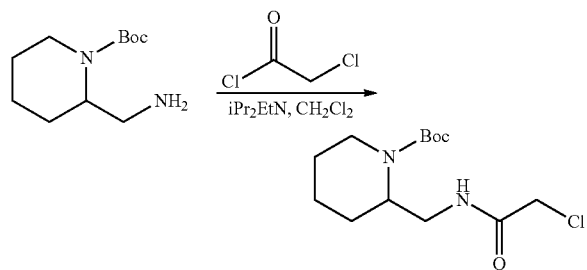

To a solution of tert-butyl 2-(aminomethyl)piperidine-1-carboxylate (2.0 g, 9.3 mmol) and diisopropylethylamine (5 mL) in DCM (30 mL) was added 2-chloroacetyl chloride (1.2 g, 10.6 mmol) dropwise at 0° C. The mixture was stirred at room temperature overnight. Then the mixture was quenched with water (30 mL) and extracted with DCM (5×100 mL). The combined organic layers were dried over $Na_2SO_4$. After filtration and concentration, the residue was used directly for the next reaction. MS (ESI): 291, 293 (MH$^+$).

Example 5.19b. Synthesis of 7-bromo-2-(chloromethyl)-3-(piperidin-2-ylmethyl)quinazolin-4(3H)-one

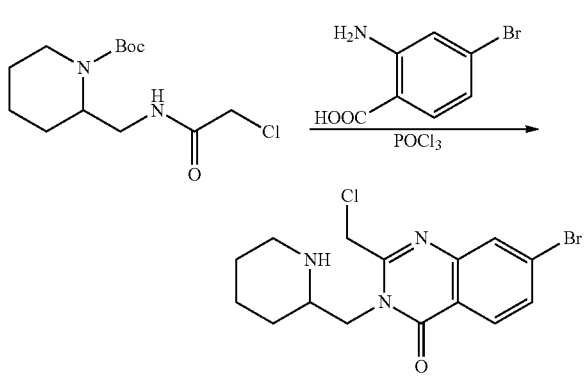

A solution of tert-butyl 2-((2-chloroacetamido)methyl) piperidine-1-carboxylate (590 mg, 2.02 mmol) and POCl$_3$ (5 mL) was stirred at room temperature for 30 min. Then 2-amino-4-bromobenzoic acid (442 mg, 1.94 mmol) was added to the mixture and stirred for another 20 min After warming slowly to 100° C., the mixture was maintained at 100° C. for 1.5 h. Then the reaction mixture was poured into ice water, adjusted pH to 8 and extracted with ethyl acetate (3×100 mL). The combined organic layers were washed with brine and dried over $Na_2SO_4$. After filtration and concentration, the crude product was directly used for the next reaction. MS (ESI): 370, 372 (MH$^+$).

Example 5.19c. Synthesis of 3-bromo-8,9,10,11,11a,12-hexahydropyrido[1',2':4,5]pyrazino[2,1-b]quinazolin-14 (6H)-one

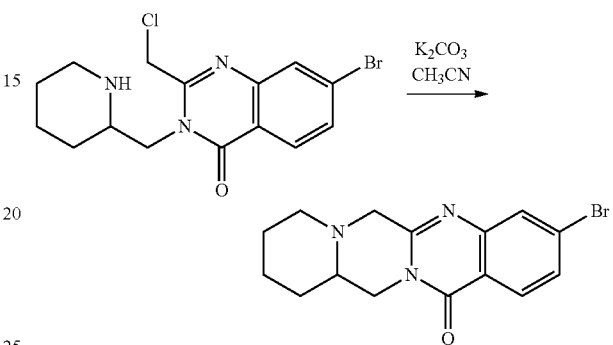

A solution of 7-bromo-2-(chloromethyl)-3-(piperidin-2-ylmethyl)quinazolin-4(3H)-one and K$_2$CO$_3$ (1 g, 7.2 mmol) in CH$_3$CN was stirred at reflux for 1.5 h. After it was cooled to room temperature, the mixture was diluted with H$_2$O (30 mL) and extracted with ethyl acetate (3×50 mL). The combined organic layers were dried over Na$_2$SO$_4$, and the crude product was purified by column chromatography to give the desired product. MS (ESI): 334, 336 (MH$^+$).

Example 5.19d. Synthesis of the HCl Salt of 3-((3-fluorophenyl)ethynyl)-8,9,10,11,11a,12-hexahydro-pyrido[1',2': 4,5]pyrazino[2,1-b]quinazolin-14 (6H)-one

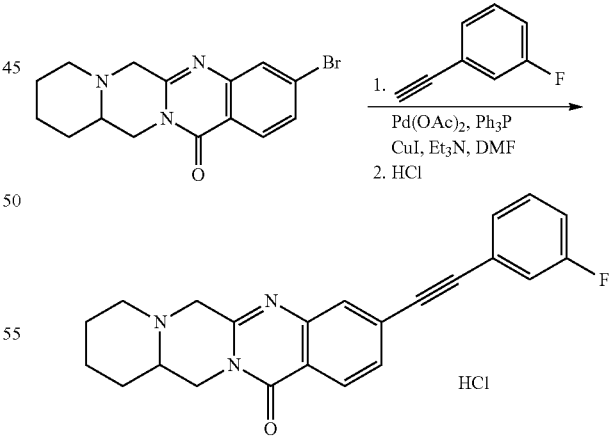

A solution of 3-bromo-8,9,10,11,11a,12-hexahydropyrido [1',2':4,5]pyrazino[2,1-b]quinazolin-14(6H)-one (105 mg, 0.31 mmol), 1-ethynyl-4-fluorobenzene (57 mg, 0.47 mmol), Pd(OAc)$_2$ (13 mg, 0.031 mmol), PPh$_3$ (39 mg, 0.15 mmol), CuI (8 mg, 0.031 mmol), and Et$_3$N (0.2 mL) in DMF (7 mL) was stirred in a sealed tube at 70° C. for 3.5 hours. After it was cooled to room temperature, the reaction mixture was diluted with H₂O and extracted with ethyl acetate (2×50 mL). The combined organic layers were washed with brine and dried over anhydrous sodium sulfate. After filtration and concentration, the crude product was purified by silica gel chromatography to produce 45 mg of the desired product. The compound was then converted to the corresponding HCl salt. MS (ESI): 374 (MH⁺); ¹H NMR (300 MHz, DMSO-d⁶) δ 8.21-8.18 (d, J=8.25 Hz, 1H), 7.82 (s, 1H), 7.74-7.68 (d, J=8.25 Hz, 1H), 7.56-7.47 (m, 3H), 7.38-7.31 (m, 1H), 4.75-4.52 (m, 2H), 3.58 (broad, 3H), 2.14-2.121 (m, 2H), 1.86-1.41 (m, 6H). mGluR5 PAM EC$_{50}$: +.

Example 5.20. Synthesis of the HCl Salt of 3-(pyridin-2-ylethynyl)-8,9,10,11,11a,12-hexahydropyrido[1',2':4,5]pyrazino[2,1-b]quinazolin-14(6H)-one Example 5.21. Synthesis of the HCl Salt of 8-((3-fluorophenyl)ethynyl)-2,3,13,13a-tetrahydro-1H-pyrrolo[1',2':4,5]pyrazino[2,1-b]quinazolin-11(5H)-one

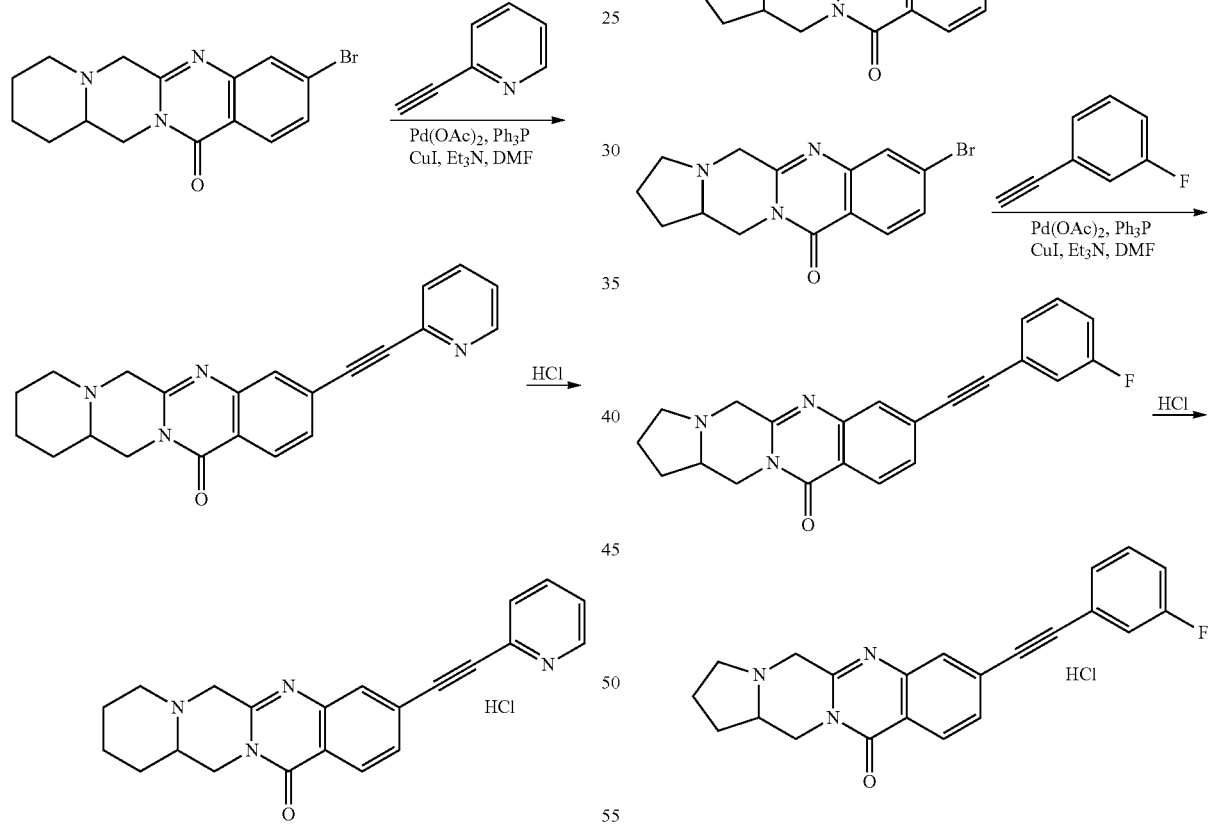
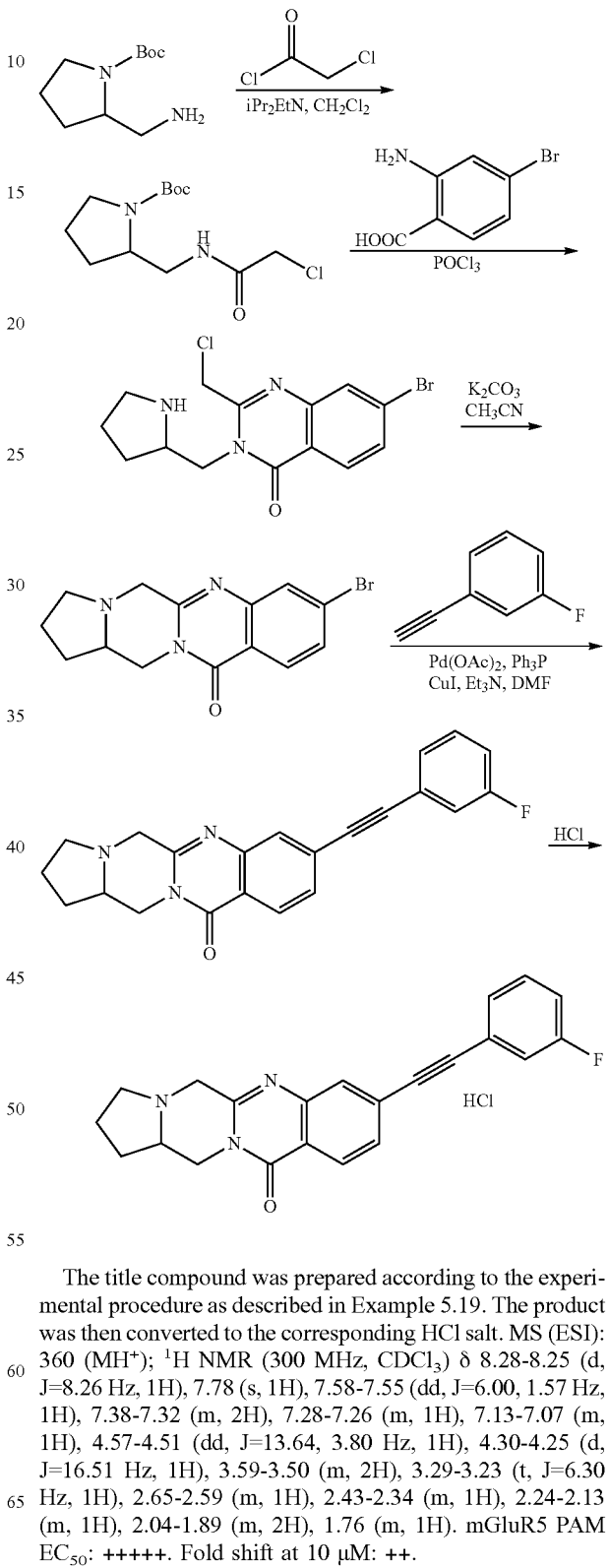

The title compound was prepared according to the experimental procedure as described in Example 5.19d. The product was then converted to the corresponding HCl salt. MS (ESI): 357 (MH⁺); δ 8.93-8.91 (d, J=5.16 Hz, 1H), 8.70-8.64 (dt, J=7.98, 1.44 Hz, 1H), 8.37-8.32 (m, 2H), 8.13-8.08 (m, 1H), 8.04-8.03 (d, J=1.08 Hz, 1H), 7.87-7.83 (m, J=8.28, 1.44 Hz, 1H), 4.80-4.54 (m, 3H), 3.82 (broad, 3H), 3.27-3.19 (m, 1H), 2.33-2.29 (m, 1H), 2.12-1.93 (m, 3H), 1.84-1.72 (m, 2H). mGluR5 PAM EC$_{50}$: +.

The title compound was prepared according to the experimental procedure as described in Example 5.19. The product was then converted to the corresponding HCl salt. MS (ESI): 360 (MH⁺); ¹H NMR (300 MHz, CDCl₃) δ 8.28-8.25 (d, J=8.26 Hz, 1H), 7.78 (s, 1H), 7.58-7.55 (dd, J=6.00, 1.57 Hz, 1H), 7.38-7.32 (m, 2H), 7.28-7.26 (m, 1H), 7.13-7.07 (m, 1H), 4.57-4.51 (dd, J=13.64, 3.80 Hz, 1H), 4.30-4.25 (d, J=16.51 Hz, 1H), 3.59-3.50 (m, 2H), 3.29-3.23 (t, J=6.30 Hz, 1H), 2.65-2.59 (m, 1H), 2.43-2.34 (m, 1H), 2.24-2.13 (m, 1H), 2.04-1.89 (m, 2H), 1.76 (m, 1H). mGluR5 PAM EC$_{50}$: +++++. Fold shift at 10 μM: ++.

Example 5.22. Synthesis of the HCl Salt of 8-(pyridin-2-ylethynyl)-2,3,13,13a-tetrahydro-1H-pyrrolo[1',2':4,5]pyrazino[2,1-b]quinazolin-11(5H)-one

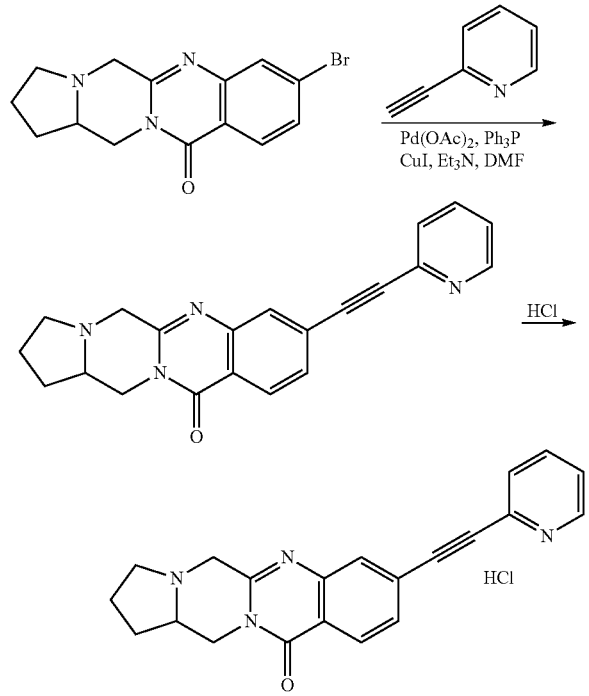

The title compound was prepared according to the experimental procedure as described in Example 5.19d. The product was then converted to the corresponding HCl salt. MS (ESI): 343 (MH$^+$); $^1$H NMR (300 MHz, CD$_3$OD) δ 8.97-8.92 (d, J=6.51 Hz, 1H), 8.71-8.63 (t, J=8.03 Hz, 1H), 8.44-8.32 (d, J=6.51 Hz, 2H), 8.14-8.03 (m, 2H), 7.92-7.89 (dd, J=8.22, 1.44 Hz, 1H), 4.86-4.80 (m, 2H), 4.76-4.71 (d, J=14.58 Hz, 1H), 4.60-4.56 (d, J=14.70 Hz, 1H), 4.33-4.29 (m, 2H), 3.92-3.91 (m, 1H), 2.49-2.43 (m, 1H), 2.30-2.22 (m, 1H), 2.13-2.1.90 (m, 2H). mGluR5 PAM EC$_{50}$: +++. Fold shift at 10 μM: +++.

Example 5.23. Synthesis of the HCl Salt of (S)-8-(pyridin-2-ylethynyl)-2,3,13,13a-tetrahydro-1H-pyrrolo[1',2':4,5]pyrazino[2,1-b]quinazolin-11(5H)-one

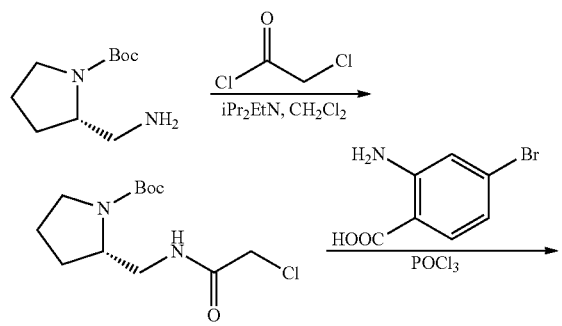

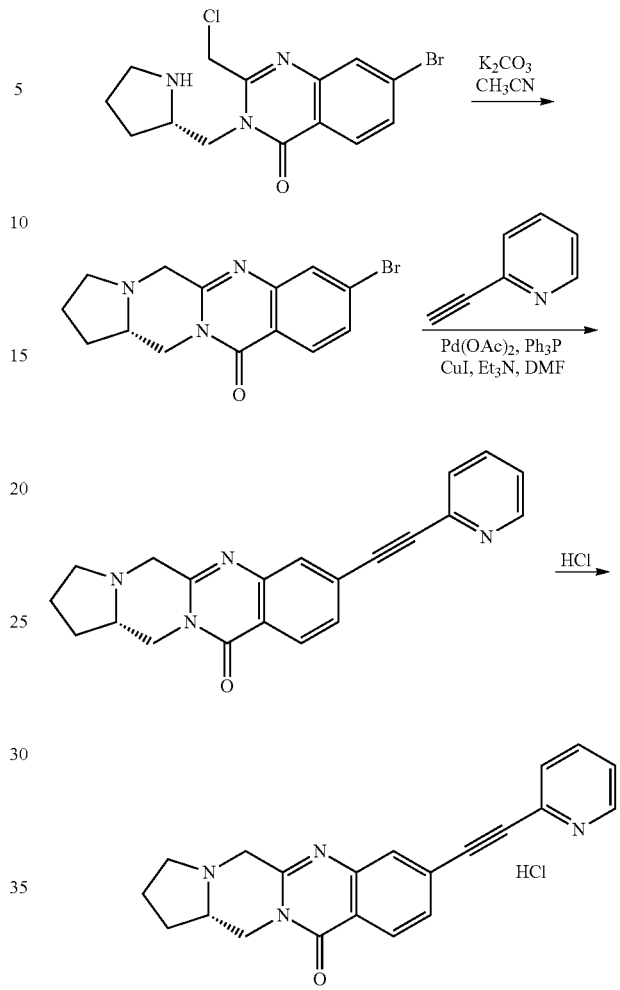

The title compound was prepared according to the experimental procedure as described in Example 5.19. The product was then converted to the corresponding HCl salt. MS (ESI): 321 (MH$^+$); $^1$H NMR (300 MHz, CD$_3$OD) δ 8.94-8.92 (dd, J=5.83, 0.76 Hz, 1H), 8.71-8.65 (t, J=7.98 Hz, 1H), 8.40-8.33 (m, 2H), 8.14-8.09 (m, 2H), 7.91-7.88 (dd, J=8.25, 1.50 Hz, 1H), 4.86-4.80 (m, 2H), 4.76-4.71 (m, 1H), 4.60-4.55 (m, 1H), 4.32-4.29 (d, J=9.45 Hz, 2H), 3.91 (s, 1H), 2.49-2.45 (m, 1H), 2.25-2.20 (m, 1H), 2.04-1.96 (m, 2H). mGluR5 PAM EC$_{50}$: +++.

Example 5.24. Synthesis of the HCl Salt of 8-(pyridin-3-ylethynyl)-2,3,13,13a-tetrahydro-1H-pyrrolo[1',2':4,5]pyrazino[2,1-b]quinazolin-11(5H)-one

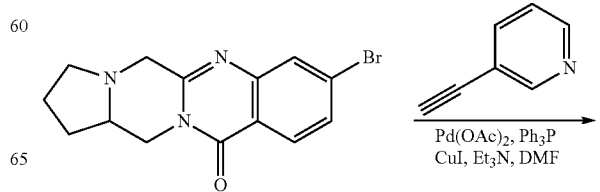

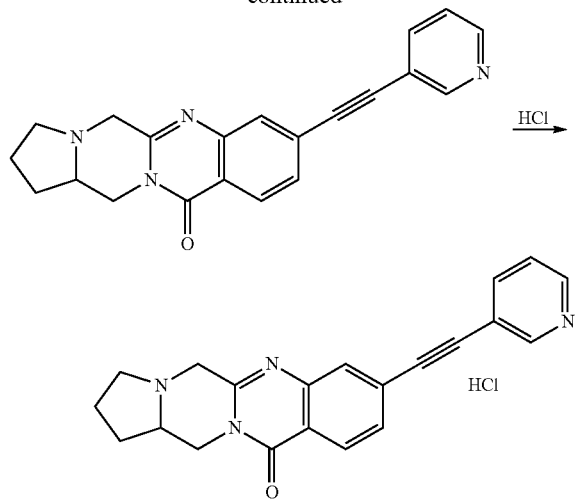

The title compound was prepared according to the experimental procedure as described in Example 5.19d. The product was then converted to the corresponding HCl salt. MS (ESI): 321 (MH$^+$); $^1$H NMR (300 MHz, CD$_3$OD) δ 9.22 (s, 1H), 8.94-8.92 (d, J=5.79 Hz, 1H), 8.87-8.84 (d, J=8.37 Hz, 1H), 8.38-8.34 (d, J=8.16 Hz, 1H), 8.22-8.17 (m, 2H), 8.03 (s, 1H), 7.85-7.82 (d, J=8.27 Hz, 1H), 4.85-4.80 (m, 2H), 4.76-4.71 (m, 1H), 4.62-4.60 (d, J=14.77 Hz, 1H), 4.37-4.29 (m, 2H), 4.39-4.38 (m, 1H), 2.49-2.41 (m, 1H), 2.28-2.22 (m, 1H), 2.10-1.96 (m, 2H). mGluR5 PAM EC$_{50}$: +++.

Example 5.25. Synthesis of the HCl Salt of 11-((3-fluorophenyl)ethynyl)-2,3,5,6-tetrahydro-1H-pyrrolo[2',1':3,4]pyrazino[2,1-b]quinazolin-8(13bH)-one

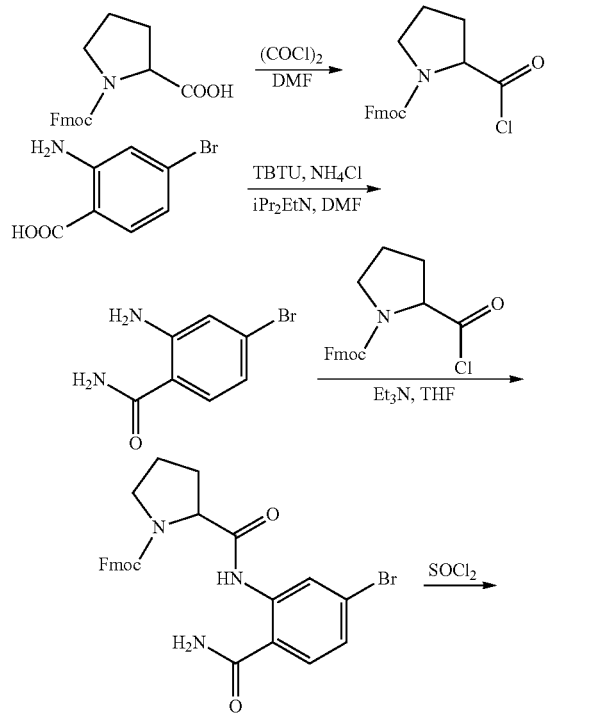

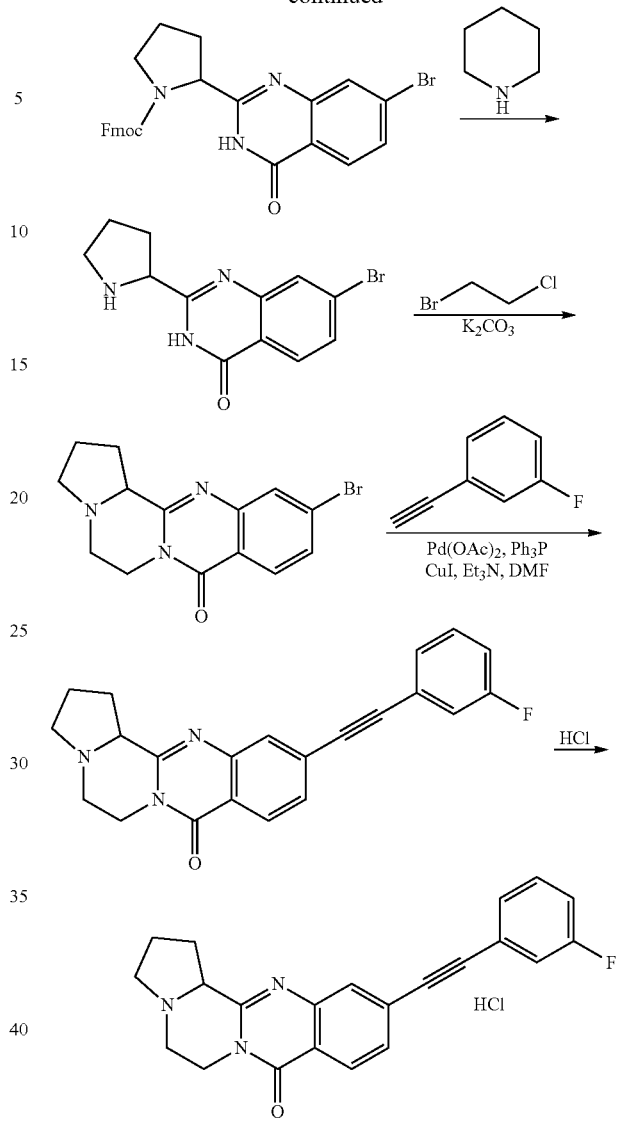

Example 5.25a. Synthesis of 2-amino-4-bromobenzamide

A solution of 2-amino-4-bromobenzoic acid (1 g, 4.63 mmol), NH$_4$Cl (1.8 g, 32.41 mmol), TBTU (1.5 g, 4.63 mmol) and diisopropylethylamine (1.2 g, 9.26 mmol) in DMF (30 mL) was stirred at room temperature overnight. Then the mixture was adjusted to pH 8.0 with saturated Na₂CO₃ and extracted with ethyl acetate (3×50 mL). The combined organic layers were dried over Na₂SO₄ and concentrated to give the desired yellow product. MS (ESI): 215, 217 (MH⁺).

Example 5.25b. Synthesis of (9H-fluoren-9-yl)methyl 2-(chlorocarbonyl)pyrrolidine-1-carboxylate

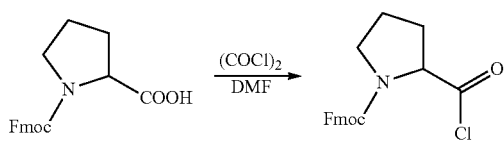

To a solution of 1-(((9H-fluoren-9-yl)methoxy)carbonyl)pyrrolidine-2-carboxylic acid (1.2 mg, 3.6 mmol) and 2 drops DMF in DCM was added oxalyl dichloride (2 g, 15.9 mmol), resulting in bubbling of the solution. After the solution stopped bubbling, the reaction solution was concentrated to give the crude product, which was directly used for the next step.

Example 5.25c. Synthesis of (9H-fluoren-9-yl) methyl 2-(5-bromo-2-carbamoylphenylcarbamoyl) pyrrolidine-1-carboxylate

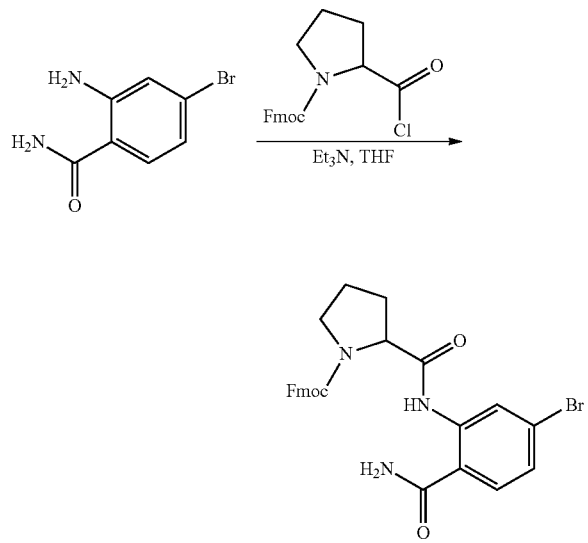

A solution of (9H-fluoren-9-yl)methyl 2-(chlorocarbonyl)pyrrolidine-1-carboxylate (600 mg, 1.8 mmol), 2-amino-4-bromobenzamide (400 mg, 1.8 mmol), and Et₃N (2 mL) in THF was stirred at room temperature. The reaction was monitored by TLC. After diluting with H₂O (50 mL), the mixture was extracted with ethyl acetate (3×100 mL). The organic layers were dried over Na₂SO₄ and concentrated to give yellow residue, which was purified by column chromatography. MS (ESI): 534, 536 (MH⁺)

Example 5.25d. Synthesis of (9H-fluoren-9-yl) methyl 2-(7-bromo-4-oxo-3,4-dihydroquinazolin-2-yl)pyrrolidine-1-carboxylate

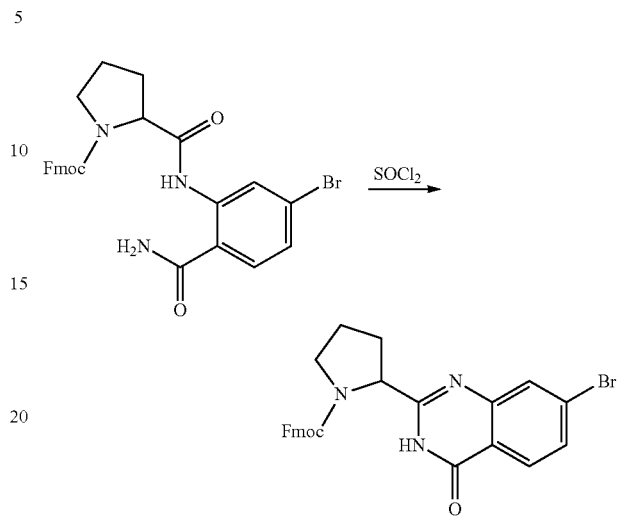

A solution of (9H-fluoren-9-yl)methyl-2-(5-bromo-2-carbamoylphenylcarbamoyl) pyrrolidine-1-carboxylate (0.55 g, 0.94 mmol) in excess SOCl₂ was stirred at room temperature. After pouring into ice water, the mixture was adjusted to pH 7.0, extracted with ethyl acetate (3×100 mL) and concentrated to give the crude product. 152 mg of the desired product was obtained by column chromatography. MS (ESI): 516, 518 (MH⁺)

Example 5.25e. Synthesis of 7-bromo-2-(pyrrolidin-2-yl)quinazolin-4(3H)-one

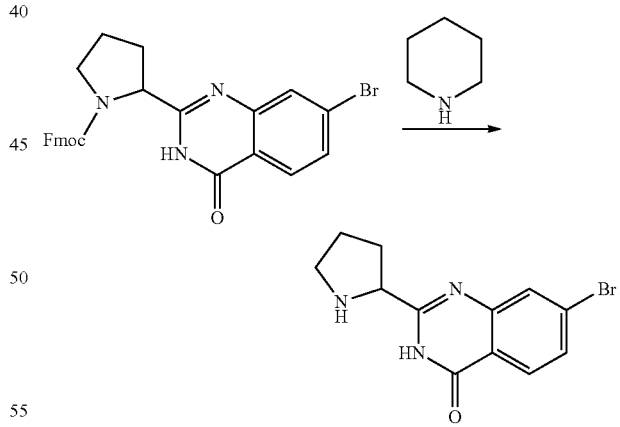

A solution of (9H-fluoren-9-yl)methyl-2-(7-bromo-4-oxo-3,4-dihydroquinazolin-2-yl) pyrrolidine-1-carboxylate (305 mg, 1.04 mmol) and piperidine (2 mL) in CH₃CN was stirred at room temperature for 2 h. The mixture was diluted with H₂O (30 mL) and extracted with ethyl acetate (3×100 mL). The combined organic layers were washed with brine and dried over Na₂SO₄. After filtration and concentration, the crude product was purified by column chromatography to give 162 mg of the desired product. MS (ESI): 294, 296 (MH⁺)

Example 5.25f. Synthesis of 11-bromo-2,3,5,6-tetrahydro-1H-pyrrolo[2',1':3,4]pyrazino[2,1-b]quinazolin-8(13bH)-one

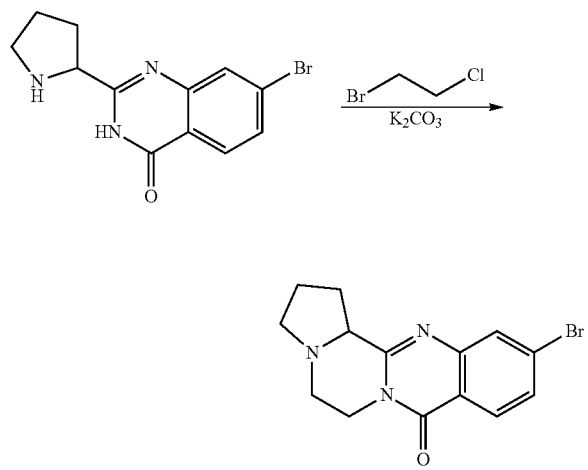

A solution of 7-bromo-2-(pyrrolidin-2-yl)quinazolin-4(3H)-one (158 mg, 0.49 mmol), K₂CO₃ (0.5 g, 3.6 mmol), a catalytic amount of NaI, and 1-bromo-2-chloroethane (70 mg, 0.49 mmol) in CH₃CN was stirred at 80° C. overnight. After dilution with H₂O (30 mL), the mixture was extracted with ethyl acetate (3×100 mL). Then the combined organic layers were dried over Na₂SO₄ and concentrated to give crude product. After purified by column chromatography, 46 mg of the desired product was obtained. MS (ESI): 320, 322 (MH⁺)

Example 5.25g. Synthesis of the HCl Salt of 11-((3-fluorophenyl)ethynyl)-2,3,5,6-tetrahydro-1H-pyrrolo[2',1':3,4]pyrazino[2,1-b]quinazolin-8(13bH)-one

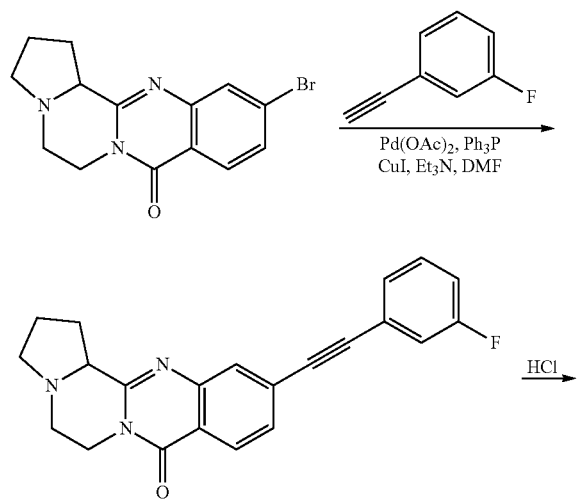

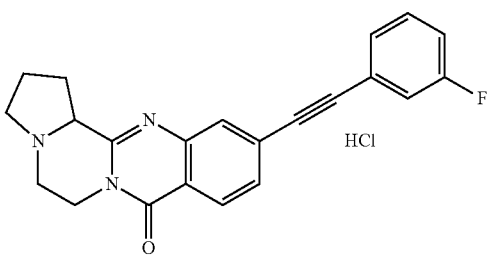

The title compound was prepared according to the experimental procedure as described in Example 1.1. The product was then converted to the corresponding HCl salt. MS (ESI): 360 (MH⁺); ¹H NMR (300 MHz, CD₃OD) δ 7.92-7.89 (d, J=8.01 Hz, 1H), 7.83-7.82 (d, J=1.44 Hz, 1H), 7.76-7.73 (dd, J=8.07, 1.50 Hz, 1H), 7.50-7.39 (m, 2H), 7.35-7.31 (m, 1H), 7.25-7.18 (m, 1H) 4.69-4.64 (t, J=8.58 Hz, 1H), 4.24-4.06 (m, 2H), 4.02-3.84 (m, 2H), 3.81-3.74 (m, 1H), 3.64-3.55 (m, 1H), 2.69-2.60 (m, 1H), 2.57-2.50 (m, 1H), 2.35-2.28 (m, 1H), 2.22-2.12 (m, 1H).

Example 5.26. Synthesis of 3,3-dimethyl-9-(pyridin-2-ylethynyl)-3,4-dihydro-1H-pyrimido[2,1-b]quinazolin-6(2H)-one

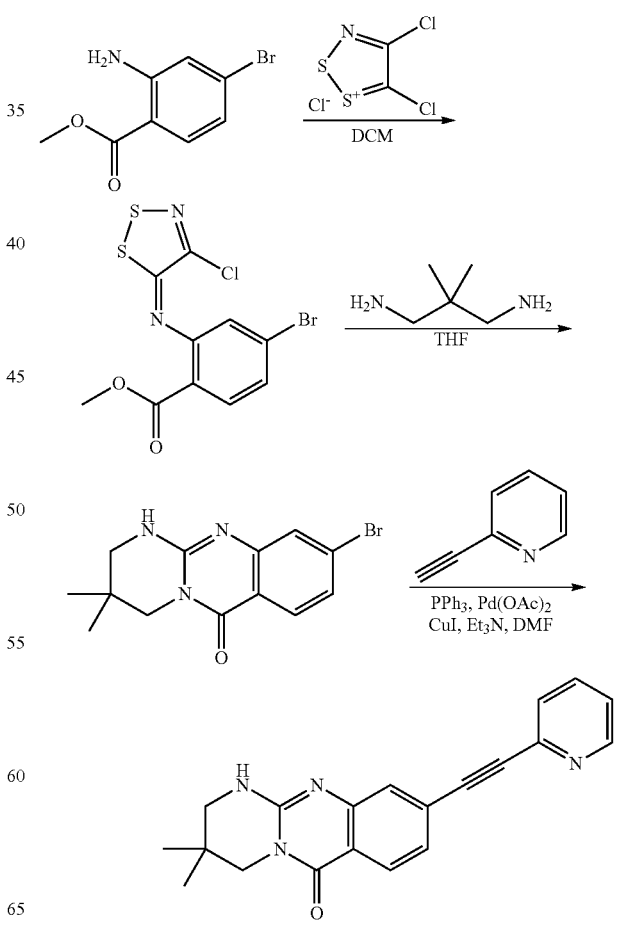

Example 5.26a. Synthesis of (E)-methyl 4-bromo-2-(4-chloro-5H-1,2,3-dithiazol-5-ylideneamino)benzoate

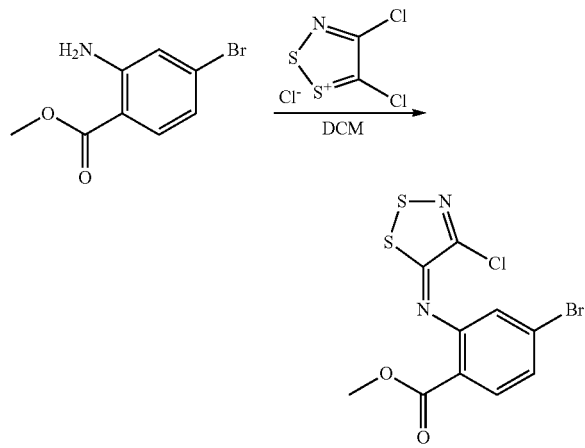

A mixture of 4,5-dichloro-1,2,3-dithiazol-1-ium chloride (1.9 g, 9.1 mmol) and methyl 2-amino-4-bromobenzoate (1.0 g, 4.3 mmol) in DCM (10 mL) was stirred for 48 h at room temperature. The solvent was evaporated to give the crude compound, which was purified by column chromatography on silica gel to give 350 mg of the desired product. MS (ESI): 367 (MH$^+$).

Example 5.26b. Synthesis of 9-bromo-3,3-dimethyl-3,4-dihydro-1H-pyrimido[2,1-b]quinazolin-6(2H)-one

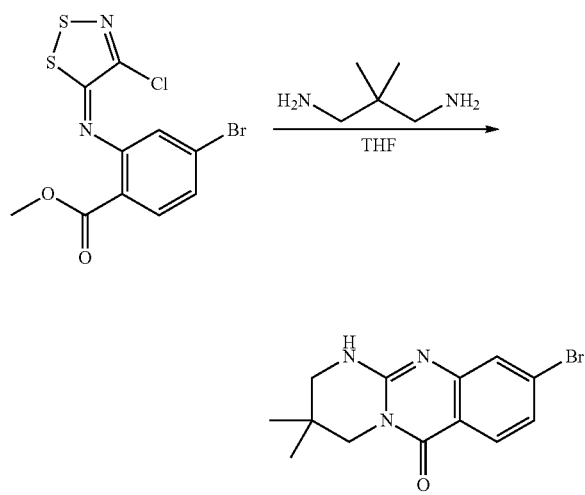

A mixture of (E)-methyl-4-bromo-2-(4-chloro-5H-1,2,3-dithiazol-5-ylideneamino)benzoate (0.1 g, 0.27 mmol) and 2,2-dimethylpropane-1,3-diamine (28 mg, 0.27 mmol) in dry THF was stirred for 2 h at room temperature, then the solvent was evaporated to give the crude product, which was purified by column chromatography to give 80 mg of the title compound. MS (ESI): 308, 310 (MH$^+$).

Example 5.26c. Synthesis of 3,3-dimethyl-9-(pyridin-2-ylethynyl)-3,4-dihydro-1H-pyrimido[2,1-b]quinazolin-6(2H)-one

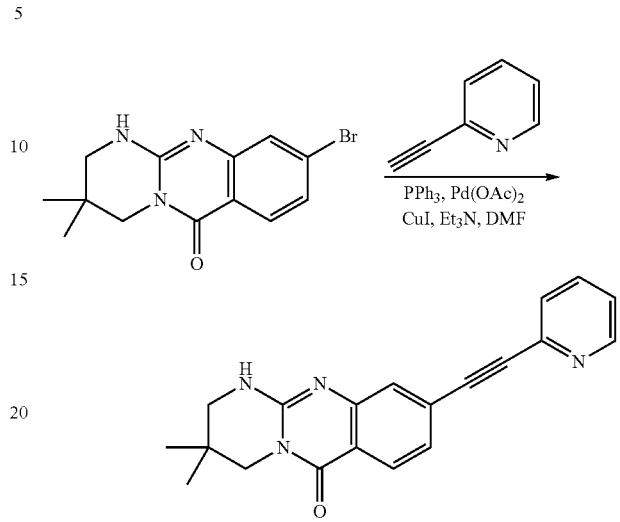

The title compound was prepared according to the experimental procedure described in Example 1.1. MS (ESI): 331 (MH$^+$); $^1$H NMR (300 MHz, CDCl$_3$) δ 8.67-8.65 (d, J=4.2 Hz, 1H), 8.11-8.08 (d, J=8.2 Hz, 1H), 7.75-7.69 (td, J=7.5, 1.5 Hz, 1H), 7.62-7.57 (d, J=7.8 Hz, 1H), 7.48 (s, 1H), 7.34-7.31 (m, 2H), 3.81 (s, 2H), 3.19 (s, 2H), 1.16 (s, 6H). mGluR5 PAM EC$_{50}$: +++++. Fold shift at 10 μM: +++.

Example 5.27. Synthesis of 1,3,3-trimethyl-9-(pyridin-2-ylethynyl)-3,4-dihydro-1H-pyrimido[2,1-b]quinazolin-6(2H)-one

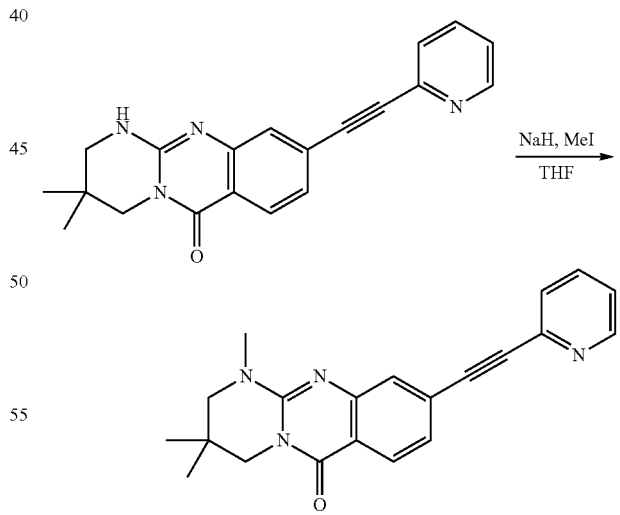

A mixture of 3,3-dimethyl-9-(pyridin-2-ylethynyl)-3,4-dihydro-1H-pyrimido[2,1-b]quinazolin-6(2H)-one (30 mg, 0.09 mmol), NaH (14 mg, 0.36 mmol) and MeI (28 mg, 0.2 mmol) in dry THF was stirred for 24 h at room temperature. Then the solvent was evaporated to give the crude product, which was purified by column chromatography to give 3 mg of the title compound. MS (ESI): 345 (MH$^+$). $^1$H NMR (300

MHz, CDCl₃) δ 8.66-8.65 (d, J=4.8 Hz, 1H), 8.08-8.05 (d, J=8.2 Hz, 1H), 7.75-7.69 (td, J=7.8, 1.8 Hz, 1H), 7.60-7.55 (m, 2H), 7.31-7.30 (m, 2H), 3.82 (s, 2H), 3.28 (s, 3H), 3.18 (s, 2H), 1.13 (s, 6H).

Example 6.1. Synthesis of 8-((4-fluorophenyl)ethynyl)-4,5-dihydro-1H-[1,4]oxazepino[5,4-b]quinazolin-11(2H)-one

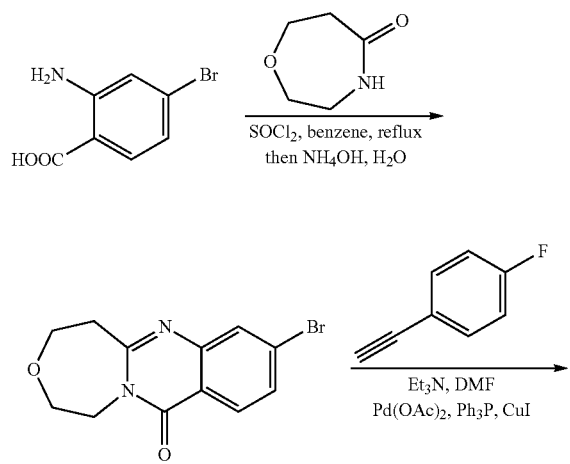

The title compound was prepared according to the experimental procedure as described in Example 2.2a and Example 1.1. MS (ESI): 335 (MH⁺); ¹H NMR (300 MHz, CDCl₃) δ 8.25-8.22 (d, J=8.2 Hz, 1H), 7.76 (s, 1H), 7.59-7.55 (m, 3H), 7.13-7.06 (d, J=7.8 Hz, 2H), 4.60-4.58 (m, 2H), 4.01-3.98 (m, 2H), 3.92-3.89 (m, 2H), 3.32-3.29 (m, 2H). mGluR5 PAM EC₅₀: +++++. Fold shift at 10 μM: ++.

Example 6.2. Synthesis of the HCl Salt of 8-(pyridin-2-ylethynyl)-4,5-dihydro-1H-[1,4]oxazepino[5,4-b]quinazolin-11(2H)-one

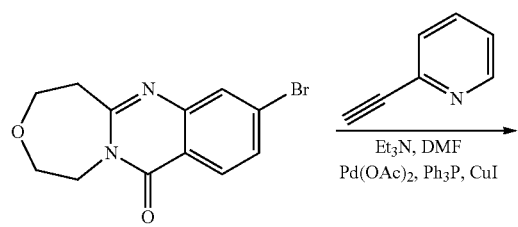

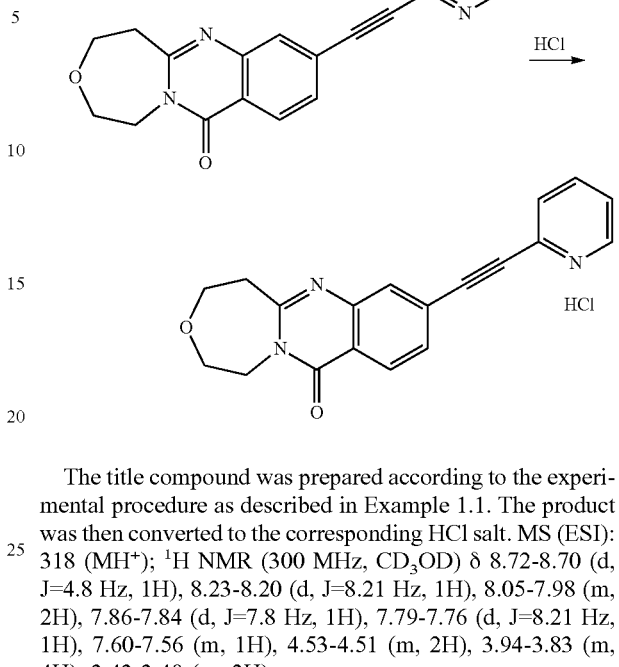

The title compound was prepared according to the experimental procedure as described in Example 1.1. The product was then converted to the corresponding HCl salt. MS (ESI): 318 (MH⁺); ¹H NMR (300 MHz, CD₃OD) δ 8.72-8.70 (d, J=4.8 Hz, 1H), 8.23-8.20 (d, J=8.21 Hz, 1H), 8.05-7.98 (m, 2H), 7.86-7.84 (d, J=7.8 Hz, 1H), 7.79-7.76 (d, J=8.21 Hz, 1H), 7.60-7.56 (m, 1H), 4.53-4.51 (m, 2H), 3.94-3.83 (m, 4H), 3.43-3.40 (m, 2H).

Example 6.3. Synthesis of 3-((4-ethylphenyl)ethynyl)-7,8,9,10-tetrahydroazepino[2,1-b]quinazolin-12(6H)-one

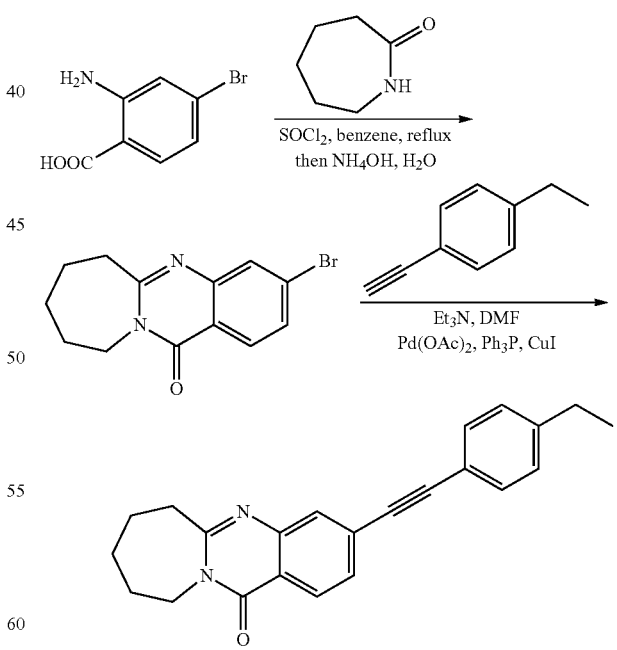

The title compound was prepared according to the experimental procedure as described in Example 2.2a and Example 1.1. MS (ESI): 343 (MH⁺); ¹H NMR (300 MHz, CDCl₃) δ 8.11-8.09 (d, J=8.22 Hz, 1H), 7.69 (s, 1H), 7.59-7.52 (m, 3H), 7.32-7.29 (d, J=8.16 Hz, 2H), 4.34-4.31

(m, 2H), 3.05 (broad, 2H), 2.69-2.62 (m, 2H), 1.75-1.72 (m, 6H), 1.22-1.17 (t, J=7.56 Hz, 3H). mGluR5 PAM EC$_{50}$: ++.

Example 6.4. Synthesis of 3-(phenylethynyl)-7,8,9,10-tetrahydroazepino[2,1-b]quinazolin-12(6H)-one

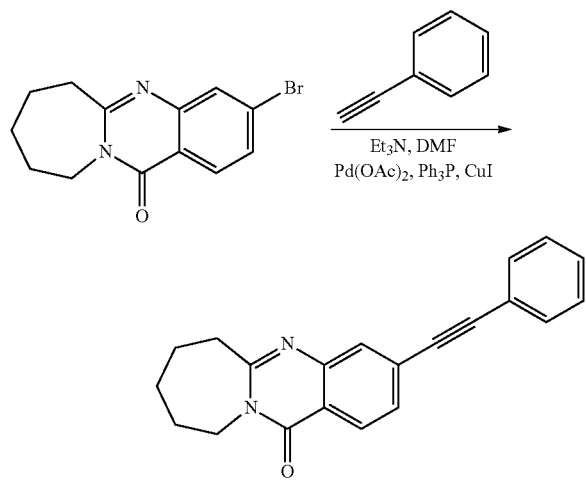

The title compound was prepared according to the experimental procedure as described in Example 1.1. MS (ESI): 315 (MH$^+$). $^1$H NMR (300 MHz, CDCl$_3$) δ 8.24-8.22 (d, J=8.4 Hz, 1H), 7.80 (s, 1H), 7.62-7.56 (m, 3H), 7.46-7.38 (m, 3H), 4.42-4.39 (m, 2H), 3.11-3.07 (m, 2H), 1.89-1.85 (m, 6H). mGluR5 PAM EC$_{50}$: +++++. Fold shift at 10 μM: ++.

Example 6.5. Synthesis of the HCl Salt of 3-(pyridin-2-ylethynyl)-7,8,9,10-tetrahydroazepino[2,1-b]quinazolin-12(6H)-one

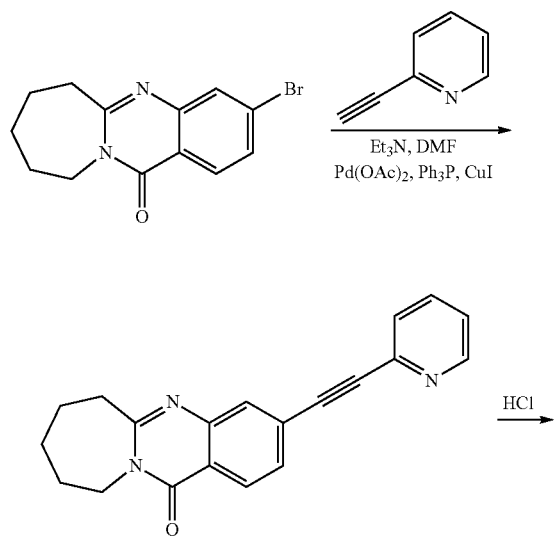

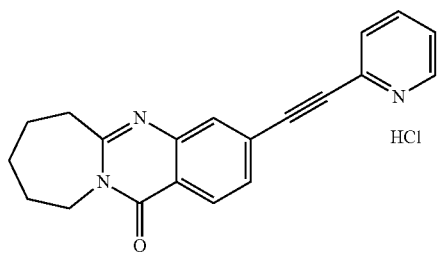

The title compound was prepared according to the experimental procedure as described in Example 1.1. The product was then converted to the corresponding HCl salt. MS (ESI): 316 (MH$^+$); $^1$H NMR (300 MHz, CD$_3$OD) δ 8.95-8.93 (d, J=5.61 Hz, 1H), 8.69-8.63 (t, J=7.98 Hz, 1H), 8.47-8.44 (d, J=8.28 Hz, 1H), 8.36-8.33 (d, J=8.01 Hz, 1H), 8.14-8.09 (m, 2H), 8.05-8.02 (d, J=8.30 Hz, 1H), 4.59-4.56 (m, 2H), 3.44-3.40 (m, 2H), 2.06-1.90 (m, 6H). mGluR5 PAM EC$_{50}$: +++++. Fold shift at 10 μM: ++.

Example 6.6. Synthesis of 3-((4-fluorophenyl)ethynyl)-8-methyl-7,8,9,10-tetrahydroazepino[2,1-b]quinazolin-12(6H)-one

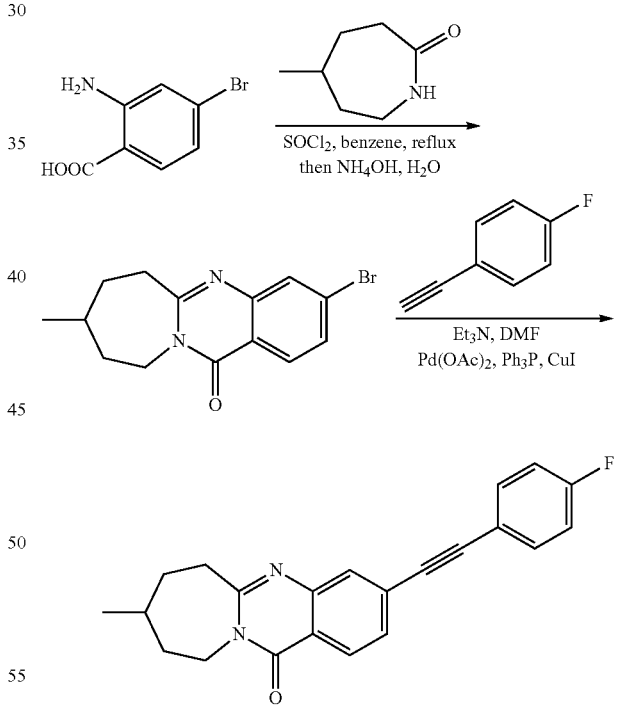

The title compound was prepared according to the experimental procedure as described in Example 2.2a and Example 1.1. MS (ESI): 347 (MH$^+$); $^1$H NMR (300 MHz, CDCl$_3$) δ 8.24-8.214 (d, J=8.22 Hz, 1H), 7.76 (s, 1H), 7.59-7.52 (m, 3H), 7.12-7.06 (t, J=8.7 Hz, 2H), 5.21-5.15 (m, 1H), 3.64-3.55 (m, 1H), 3.15-3.00 (m, 2H), 2.13-2.08 (m, 2H), 1.95-1.81 (m, 1H), 1.46-1.20 (m, 2H), 1.02-1.00 (d, J=6.57 Hz, 3H). mGluR5 PAM EC$_{50}$: +++++. Fold shift at 10 μM: ++.

Example 6.7. Synthesis of 3-((3-fluorophenyl)ethynyl)-8-methyl-7,8,9,10-tetrahydroazepino[2,1-b]quinazolin-12(6H)-one

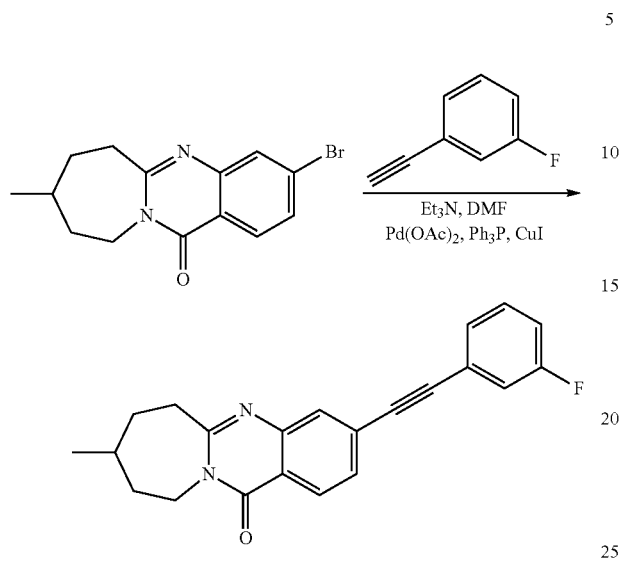

The title compound was prepared according to the experimental as described in Example 1.1. MS (ESI): 347 (MH+); ¹H NMR (300 MHz, CDCl₃) δ 8.29-8.24 (d, J=8.22 Hz, 1H), 7.76 (s, 1H), 7.55-7.53 (d, J=8.21 Hz, 1H), 7.36-7.25 (m, 3H), 7.12-7.06 (m, 1H), 5.21-5.19 (m, 1H), 3.64-3.55 (m, 1H), 3.15-3.00 (m, 2H), 2.13-2.08 (m, 2H), 1.95-1.81 (m, 1H), 1.46-1.20 (m, 2H), 1.02-1.00 (d, J=6.57 Hz, 3H). mGluR5 PAM EC₅₀: +++++. Fold shift at 10 μM: ++.

Example 6.8. Synthesis of 8-methyl-3-((5-methylthiazol-2-yl)ethynyl)-7,8,9,10-tetrahydroazepino[2,1-b]quinazolin-12(6H)-one

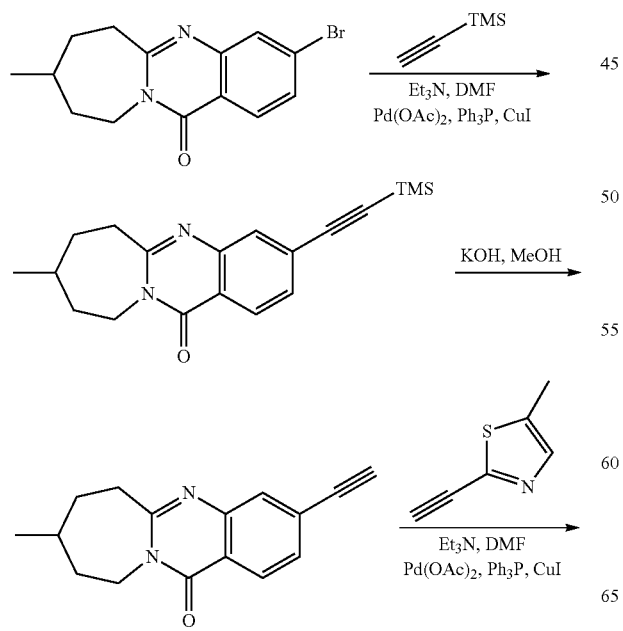

Example 6.8a. Synthesis of 8-methyl-3-((trimethylsilyl)ethynyl)-7,8,9,10-tetrahydroazepino[2,1-b]quinazolin-12(6H)-one

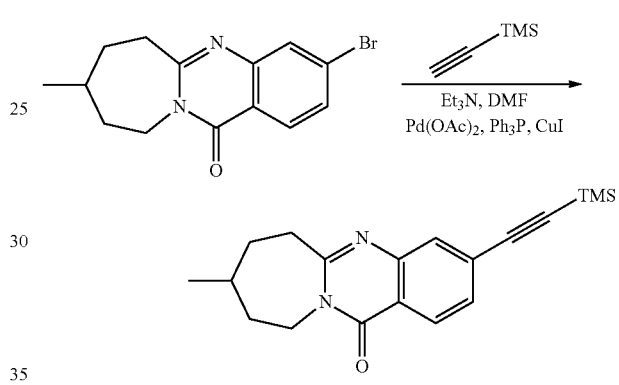

The title compound was prepared according to the experimental procedure as described in Example 5.1d.

Example 6.8b. Synthesis of 3-ethynyl-8-methyl-7,8,9,10-tetrahydroazepino[2,1-b]quinazolin-12(6H)-one

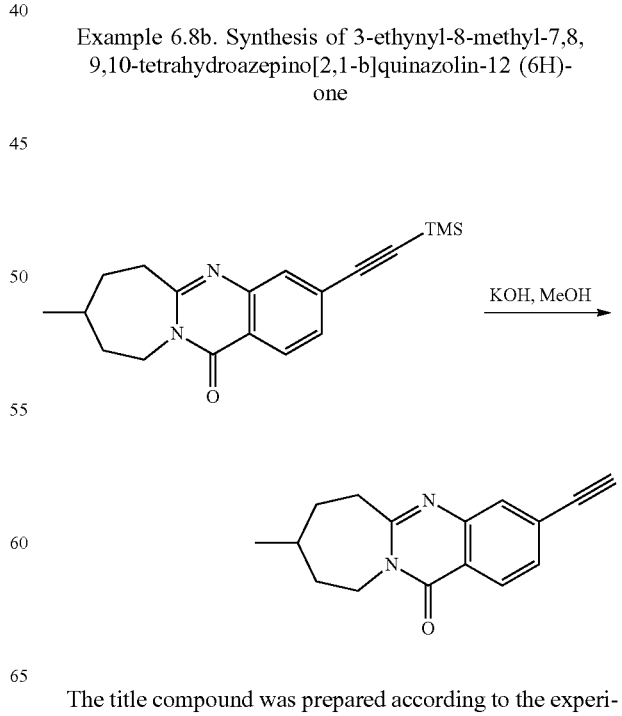

The title compound was prepared according to the experimental procedure as described in Example 5.1e.

Example 6.8c. Synthesis of 8-methyl-3-((5-methyl-thiazol-2-yl)ethynyl)-7,8,9,10-tetrahydroazepino[2,1-b]quinazolin-12(6H)-one

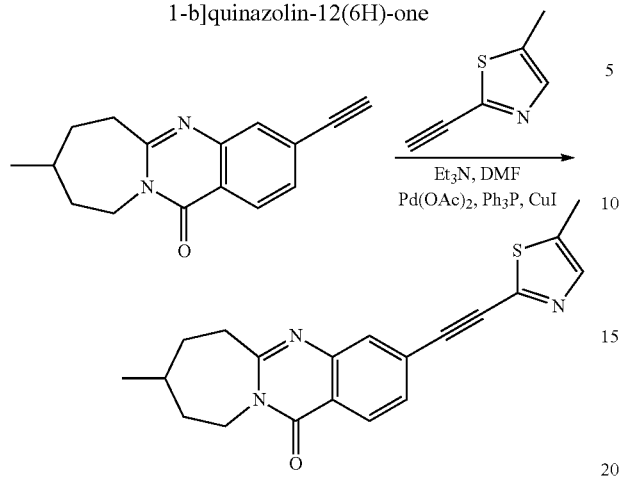

The title compound was prepared according to the experimental procedure as described in Example 1.1. MS (ESI): 350 (MH+); $^1$H NMR (300 MHz, CDCl$_3$) δ 8.26-8.23 (d, J=8.1 Hz, 1H), 7.81 (s, 1H), 7.62-7.56 (m, 2H), 5.22-5.15 (m, 1H), 3.65-3.56 (m, 1H), 3.16-3.00 (m, 2H), 2.55 (s, 3H), 2.14-2.08 (m, 2H), 1.96-1.86 (m, 1H), 1.47-1.33 (m, 1H), 1.29-1.23 (m, 1H), 1.02-1.00 (d, J=6.6 Hz, 3H). mGluR5 PAM EC$_{50}$: ++++. Fold shift at 10 μM: ++.

Example 6.9. Synthesis of the HCl Salt of 8-methyl-3-(pyridin-2-ylethynyl)-7,8,9,10-tetrahydroazepino[2,1-b]quinazolin-12(6H)-one

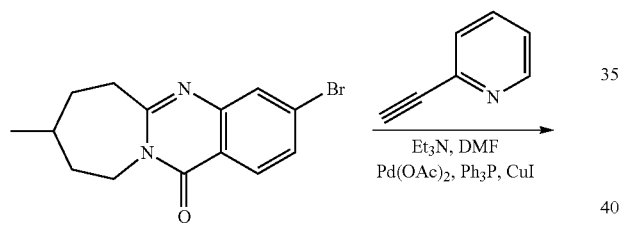

The title compound was prepared according to the experimental procedure as described in Example 1.1. The product was then converted to the corresponding HCl salt. MS (ESI): 330 (MH+); $^1$H NMR (300 MHz, CD$_3$OD) δ 8.69-8.67 (d, J=4.3 Hz, 1H), 8.22-8.19 (d, J=8.2 Hz, 1H), 7.99-7.94 (m, 2H), 7.82-7.76 (m, 2H), 7.56-7.51 (m, 1H), 4.95-4.88 (dd, J=14.40, 6.9 Hz, 1H), 3.84-3.76 (m, 1H), 3.28-3.24 (m, 2H), 1.98-1.91 (m, 3H), 1.41-1.21 (m, 2H), 0.93-0.91 (d, J=6.3 Hz, 3H). mGluR5 PAM EC$_{50}$: +++++. Fold shift at 10 μM: +++.

Example 6.10 and Example 6.11. Separation of (S)-8-methyl-3-(pyridin-2-ylethynyl)-7,8,9,10-tetrahydroazepino[2,1-b]quinazolin-12(6H)-one and (R)-8-methyl-3-(pyridin-2-ylethynyl)-7,8,9,10-tetrahydroazepino[2,1-b]quinazolin-12(6H)-one

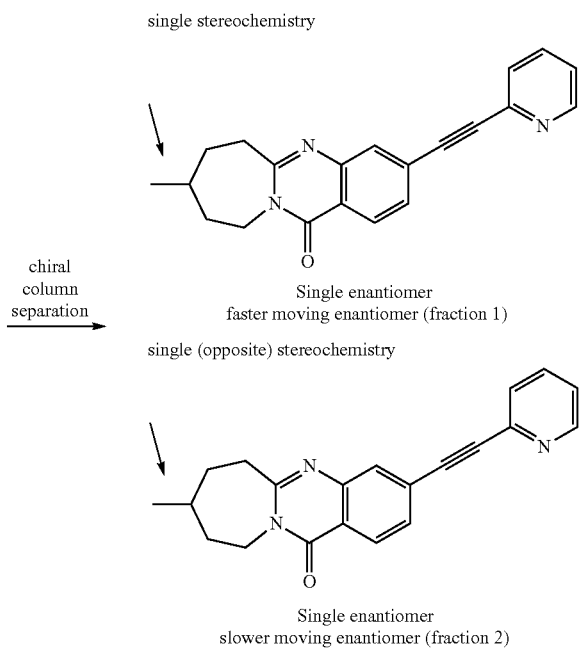

Racemic 8-methyl-3-(pyridin-2-ylethynyl)-7,8,9,10-tetrahydroazepino[2,1-b]quinazolin-12(6H)-one was separated into the corresponding two single enantiomer compounds (S)-8-methyl-3-(pyridin-2-ylethynyl)-7,8,9,10-tetrahydroazepino[2,1-b]quinazolin-12(6H)-one and (R)-8-methyl-3-(pyridin-2-ylethynyl)-7,8,9,10-tetrahydroazepino[2,1-b]quinazolin-12(6H)-one using chiral chromatography with an isocratic SFC method. The column used was a 3.0×25.0 cm RegisPack from Regis Technologies (Morton Grove, Ill.). The $CO_2$ co-solvent was methanol:isopropanol (1:1) with 1% isopropylamine. Isocratic Method: 45% Co-solvent at 80 mL/min System Pressure: 100 bar. Column Temperature 25° C.

Faster moving enantiomer (fraction 1): Retention time=1.9 min 98.2% ee. mGluR5 PAM $EC_{50}$: +++++. Fold shift at 10 µM: +++.

Slower moving enantiomer (fraction 2): Retention time=3.5 min. 99.8% ee. mGluR5 PAM $EC_{50}$: +++++. Fold shift at 10 µM: +++.

Example 6.12. Synthesis of 8-ethyl-3-((4-fluorophenyl)ethynyl)-7,8,9,10-tetrahydroazepino[2,1-b]quinazolin-12(6H)-one

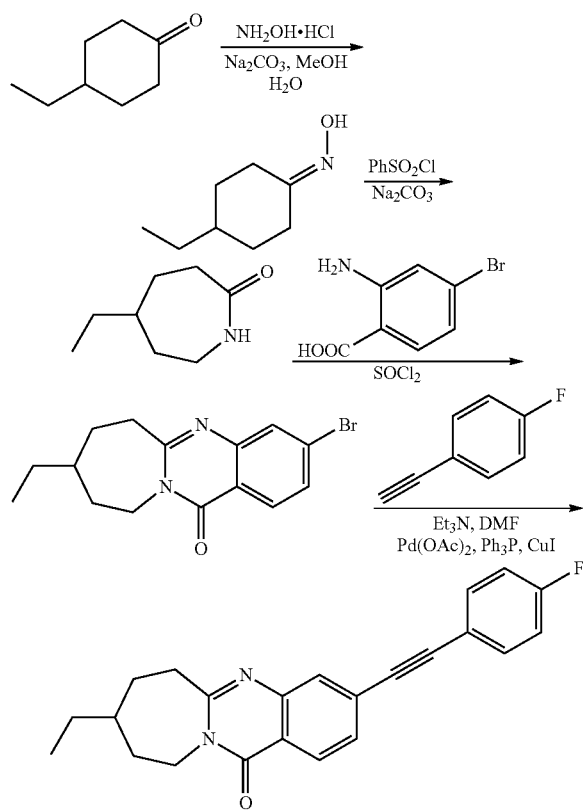

The title compound was prepared according to the experimental procedure as described in Example 4.11a, Example 4.11b, Example 2.2a, and Example 1.1. MS (ESI): 361 (M+H$^+$); $^1$H NMR (300 MHz, CDCl$_3$) δ 8.24-8.21 (d, J=8.10 Hz, 1H), 7.75 (s, 1H), 7.59-7.52 (m, 3H), 7.12-7.06 (m, 2H), 5.24-5.16 (dd, J=14.40, 6.60 Hz, 1H), 3.64-3.55 (t, J=14.70 Hz, 1H), 3.13-3.03 (m, 2H), 2.21-2.13 (m, 2H), 1.70-1.60 (m, 1H), 1.44-1.19 (m, 4H), 0.97-0.92 (t, J=7.43 Hz, 3H). mGluR5 PAM $EC_{50}$: +++++. Fold shift at 10 µM: ++.

Example 6.13. Synthesis of 3-((4-fluorophenyl)ethynyl)-8-propyl-7,8,9,10-tetrahydroazepino[2,1-b]quinazolin-12(6H)-one

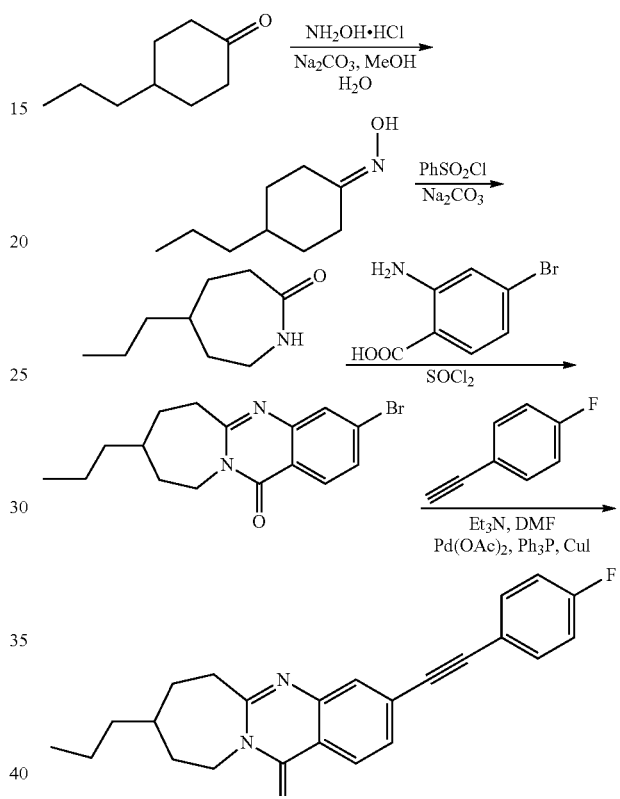

The title compound was prepared according to the experimental procedure as described in Example 4.11a, Example 4.11b, Example 2.2a, and Example 1.1. MS (ESI): 375 (M+H$^+$); $^1$H NMR (300 MHz, CDCl$_3$) δ 8.24-8.21 (d, J=8.28 Hz, 1H), 7.75 (s, 1H), 7.59-7.52 (m, 3H), 7.18-7.06 (m, 2H), 5.23-5.15 (m, 1H), 3.64-3.56 (m, 1H), 3.17-2.99 (m, 2H), 2.20-2.12 (m, 2H), 1.78-1.71 (m, 1H), 1.44-1.22 (m, 6H), 0.95-0.88 (t, J=7.04 Hz, 3H). mGluR5 PAM $EC_{50}$: +++. Fold shift at 10 µM: +.

Example 6.14. Synthesis of 3-((3-fluorophenyl)ethynyl)-6,7,9,10-tetrahydroazepino[2,1-b]quinazoline-8,12-dione

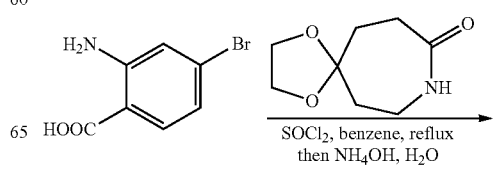

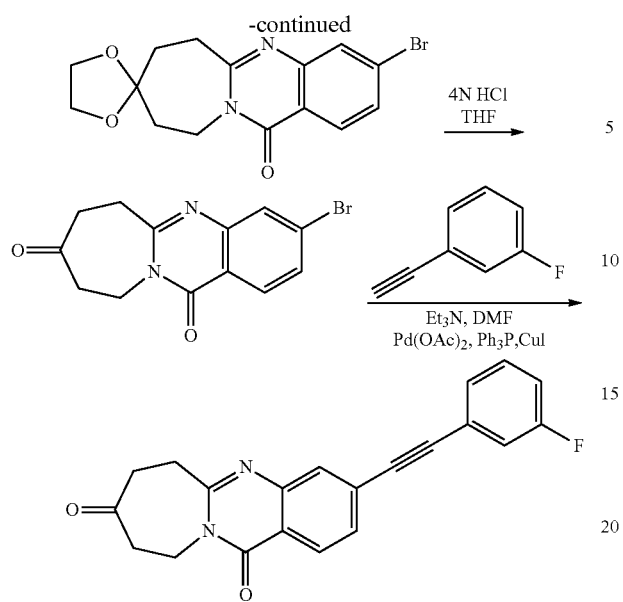

Example 6.14a. Synthesis of 3-bromo-9,10-dihydro-6H-spiro[azepino[2,1-b]quinazoline-8,2'-[1,3]dioxolan]-12(7H)-one

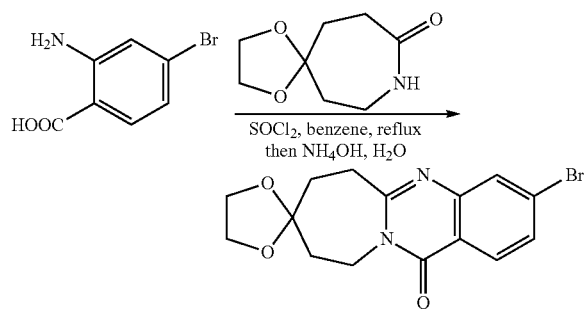

The title compound was prepared according to the experimental as described in Example 2.2a.

Example 6.14b. Synthesis of 3-bromo-6,7,9,10-tetrahydroazepino[2,1-b]quinazoline-8,12-dione

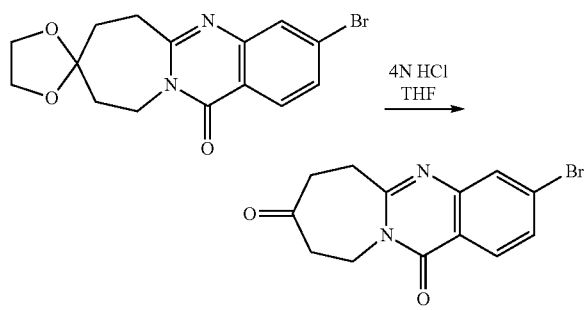

A solution of 3-bromo-9,10-dihydro-6H-spiro[azepino[2,1-b]quinazoline-8,2'-[1,3]dioxolan]-12(7H)-one (0.5 g, 1.43 mmol) and 4N HCl (4 mL) in THF (20 mL) was heated at reflux for 4 h. After it was cooled to rt, the reaction mixture was quenched with aq. Na$_2$CO$_3$ and extracted with ethyl acetate (3×50 mL). The combined organic layers were dried over Na$_2$SO$_4$. After filtration and concentration, the residue was purified by silica gel chromatography to give the desired product.

Example 6.14c. Synthesis of 3-((3-fluorophenyl)ethynyl)-6,7,9,10-tetrahydroazepino[2,1-b]quinazoline-8,12-dione

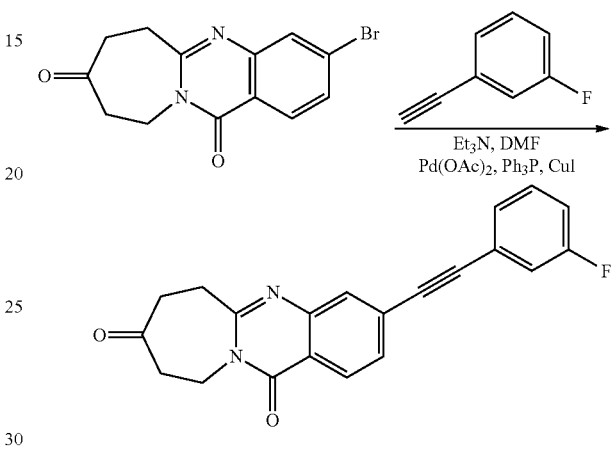

The title compound was prepared according to the experimental procedure as described in Example 1.1. MS (ESI): 347 (M+H$^+$); $^1$H NMR (300 MHz, CDCl$_3$) δ 8.28-8.26 (d, J=8.19 Hz, 1H), 7.80 (s, 1H) 7.63-7.60 (dd, J=8.24, 1.55 Hz, 1H), 7.39-7.35 (m, 2H), 7.31-7.30 (m, 1H), 7.15-7.09 (m, 1H), 4.60-4.56 (m, 2H), 3.30-3.26 (m, 2H), 2.89-2.79 (m, 4H). mGluR5 PAM EC$_{50}$: ++++. Fold shift at 10 μM: +++.

Example 6.15. Synthesis of 3-((3-fluorophenyl)ethynyl)-8-hydroxy-7,8,9,10-tetrahydroazepino[2,1-b]quinazolin-12(6H)-one

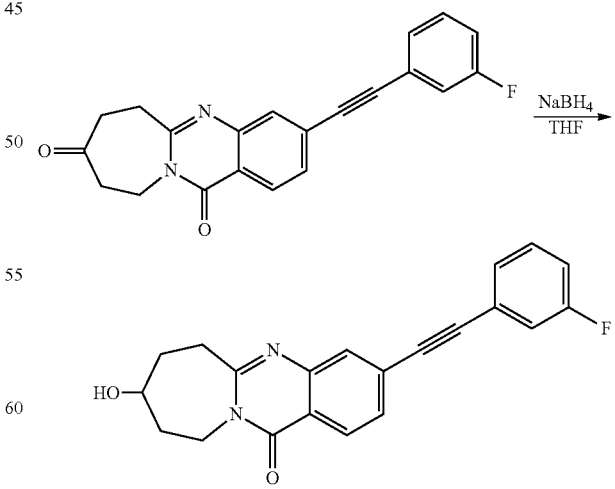

The title compound was prepared according to the experimental procedure as described in Example 4.23. MS (ESI): 349 (M+H$^+$); $^1$H NMR (300 MHz, CDCl$_3$) δ 8.25-8.22 (d, J=8.25 Hz, 1H), 7.76 (s, 1H) 7.58-7.55 (dd, J=8.24, 1.52 Hz, 1H), 7.38-7.35 (m, 2H), 7.30-7.29 (m, 1H), 7.14-7.07 (m, 1H), 4.49-4.48 (m, 2H), 4.24-4.20 (m, 1H), 3.50-3.41 (m, 1H), 2.94-2.86 (m, 1H), 2.09-2.06 (m, 4H). mGluR5 PAM EC$_{50}$: +++++. Fold shift at 10 μM: ++.

Example 6.16. Synthesis of the HCl Salt of 8-hydroxy-3-(pyridin-2-ylethynyl)-7,8,9,10-tetrahydroazepino[2,1-b]quinazolin-12(6H)-one

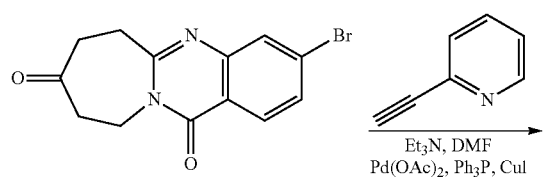

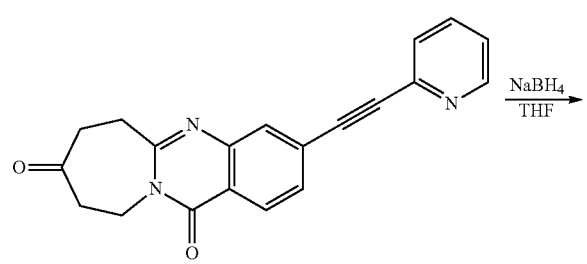

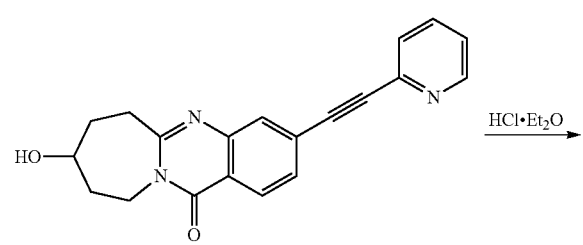

The title compound was prepared according to the experimental procedure as described in Example 1.1 and Example 4.23. The product was then converted to the corresponding HCl salt. MS (ESI): 332 (M+H$^+$); $^1$H NMR (300 MHz, DMSO-d$^6$) δ 8.69-8.67 (d, J=4.71 Hz, 1H), 8.21-8.18 (d, J=8.25 Hz, 1H), 7.99-7.93 (m, 2H), 7.81-7.74 (m, 2H), 7.55-7.50 (m, 1H), 4.51-4.38 (m, 2H), 3.95-3.90 (m, 1H), 3.43-3.35 (m, 1H), 3.06-2.98 (m, 1H), 2.04-1.68 (m, 4H). mGluR5 PAM EC$_{50}$: +++.

Example 6.17. Synthesis of the HCl Salt of 8-hydroxy-3-(pyridin-3-ylethynyl)-7,8,9,10-tetrahydroazepino[2,1-b]quinazolin-12(6H)-one

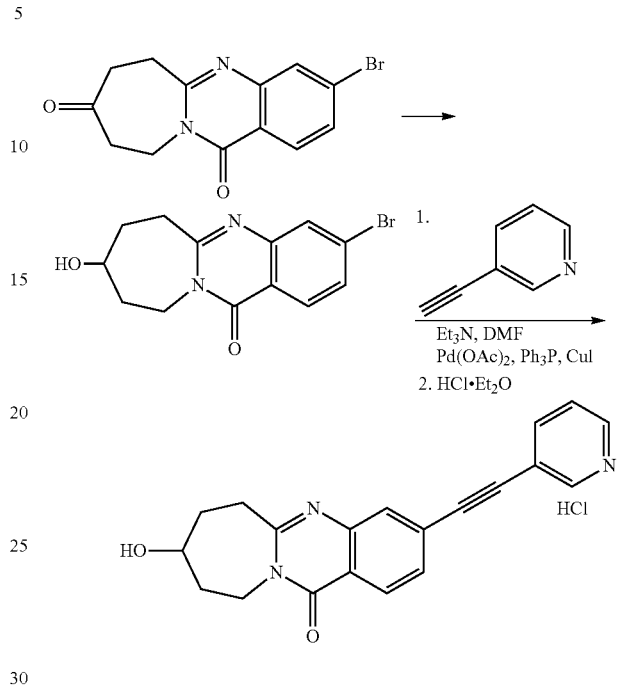

The title compound was prepared according to the experimental procedure as described in Example 4.23 and Example 1.1. The product was then converted to the corresponding HCl salt. MS (ESI): 332 (M+H$^+$); $^1$H NMR (300 MHz, DMSO-d$^6$) δ 8.92 (s, 1H), 8.70-8.68 (m, 1H), 8.21-8.16 (m, 2H), 7.87 (s, 1H), 7.72-7.69 (dd, J=8.24, 1.52 Hz, 1H), 7.63-7.58 (m, 1H), 4.52-4.38 (m, 1H), 4.32-4.14 (m, 2H), 3.38-3.29 (m, 1H), 2.99-2.91 (m, 1H), 2.02-1.66 (m, 4H). mGluR5 PAM EC$_{50}$: ++.

Example 6.18. Synthesis of 3-((3-fluorophenyl)ethynyl)-8-methoxy-7,8,9,10-tetrahydroazepino[2,1-b]quinazolin-12(6H)-one

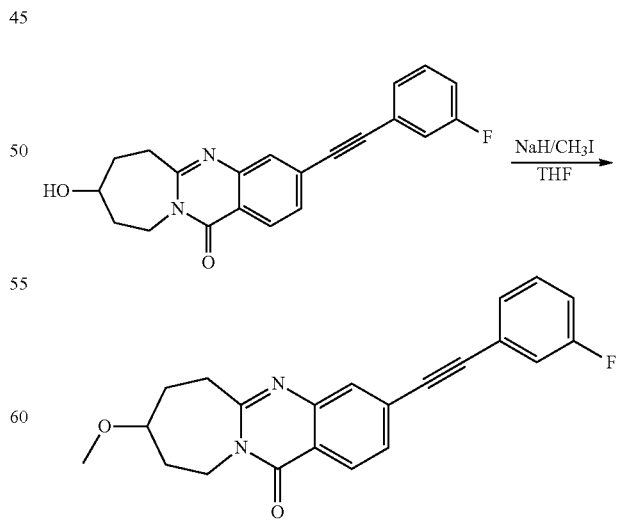

The title compound was prepared according to the experimental procedure as described in Example 4.25. MS (ESI):

363 (M+H⁺); $^1$H NMR (300 MHz, CDCl$_3$) δ 8.25-8.22 (d, J=8.25 Hz, 1H), 7.76 (s, 1H) 7.57-7.54 (d, J=8.07 Hz, 1H), 7.40-7.32 (m, 2H), 7.28-7.26 (m, 1H), 7.13-7.06 (m, 1H), 4.68-4.64 (m, 1H), 4.27-4.19 (m, 1H), 3.65-3.64 (m, 1H), 3.50-3.36 (m, 4H), 2.89-2.81 (m, 1H), 2.26-2.10 (m, 2H), 1.97-1.78 (m, 2H). mGluR5 PAM EC$_{50}$: +++++. Fold shift at 10 μM: ++.

Example 6.19. Synthesis of the HCl Salt of 8-amino-3-((3-fluorophenyl)ethynyl)-7,8,9,10-tetrahydroazepino[2,1-b]quinazolin-12(6H)-one

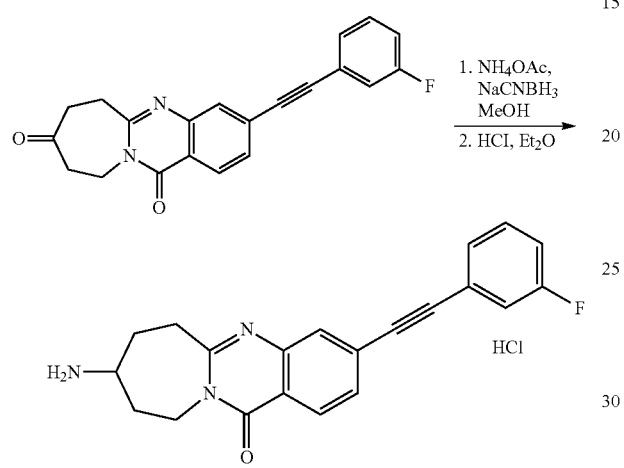

A solution of 3-((3-fluorophenyl)ethynyl)-6,7,9,10-tetrahydroazepino[2,1-b]-quinazoline-8,12-dione (0.2 g, 0.58 mmol, 1 equiv) and NaCNBH$_3$ (3.6 mg, 0.058 mmol, 0.1 equiv) in methanol (15 mL) was heated at reflux overnight. After it was cooled to rt, the reaction mixture was quenched with water and extracted with ethyl acetate (3×20 mL). The combined organic layers were dried over Na$_2$SO$_4$ and concentrated under reduced pressure to give the desired product, which was purified by silica gel chromatography. The product was then converted to the corresponding HCl salt. MS (ESI): 348 (M+H⁺); $^1$H NMR (300 MHz, CD$_3$OD) δ 8.36-8.33 (d, J=8.52 Hz, 1H), 7.87-7.82 (m, 2H), 7.52-7.44 (m, 2H), 7.41-7.36 (m, 1H), 7.28-7.24 (m, 1H), 5.36-5.29 (m, 1H), 3.97-3.85 (m, 1H), 3.77-3.69 (m, 1H), 3.58-3.48 (m, 1H), 3.44-3.36 (m, 1H), 2.55-2.45 (m, 2H), 2.05-1.92 (m, 1H), 1.87-1.75 (m, 1H).

Example 6.20. Synthesis of the HCl Salt of 3-((3-fluorophenyl)ethynyl)-8-(methylamino)-7,8,9,10-tetrahydroazepino[2,1-b]quinazolin-12(6H)-one

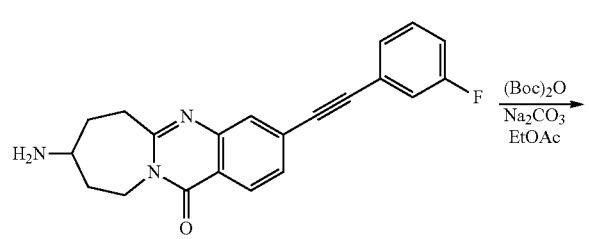

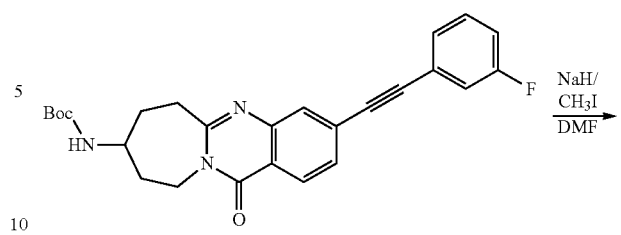

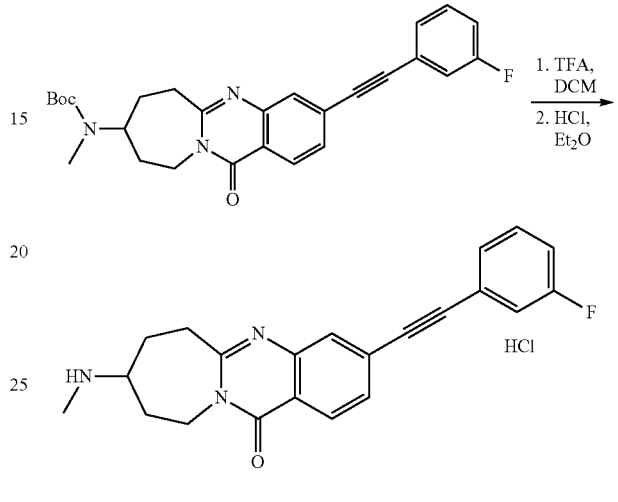

Example 6.20a. Synthesis of tert-butyl 3-((3-fluorophenyl)ethynyl)-12-oxo-6,7,8,9,10,12-hexahydroazepino[2,1-b]quinazolin-8-ylcarbamate

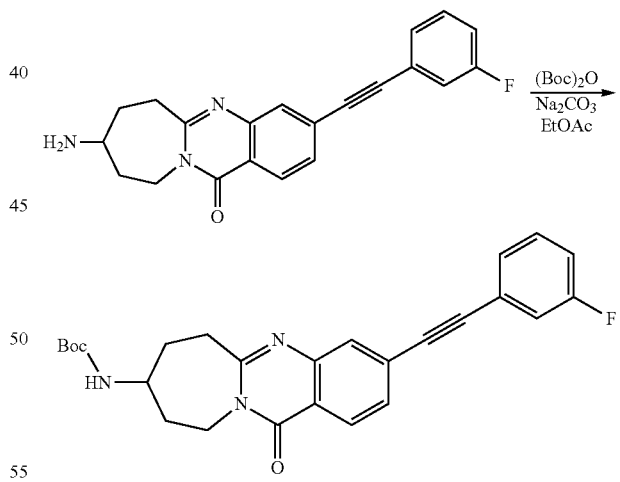

A solution of 8-amino-3((3-fluorophenyl)ethynyl)-7,8,9,10-tetrahydroazepino[2,1-b]quinazolin-12(6H)-one (0.2 g, 0.58 mmol, 1 equiv), aq. Na$_2$CO$_3$ (1 mL) and (Boc)$_2$O (250.1 mg, 1.16 mmol, 2 equiv) in ethyl acetate (15 mL) was stirred at rt overnight. Then the reaction mixture was quenched with water and extracted with ethyl acetate (3×20 mL). The combined organic layers were dried over Na$_2$SO$_4$ and concentrated under reduced pressure to give the desired product, which was purified by silica gel chromatography. MS (ESI): 448 (MH⁺).

Example 6.20b. Synthesis of tert-butyl 3-((3-fluorophenyl)ethynyl)-12-oxo-6,7,8,9,10,12-hexahydroazepino[2,1-b]quinazolin-8-yl(methyl)carbamate

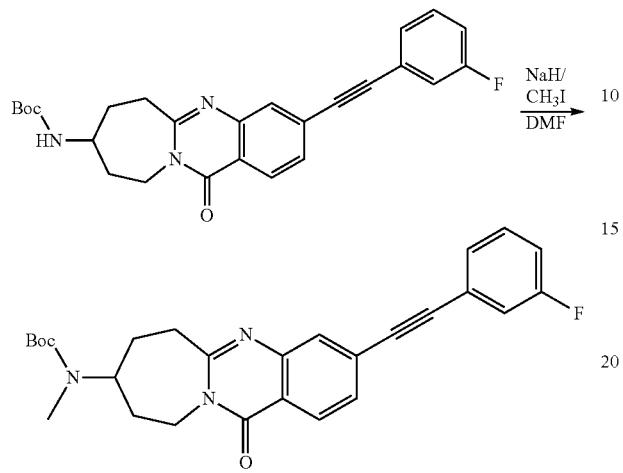

To a stirred mixture of tert-butyl-3-((3-fluorophenyl)ethynyl)-12-oxo-6,7,8,9,10,12-hexahydroazepino[2,1-b]quinazolin-8-ylcarbamate (0.3 g, 0.67 mmol, 1 equiv) and NaH (64.3 mg, 2.68 mmol, 4 equiv) in DMF (15 mL) was added $CH_3I$ dropwise. After stirring at rt for 2 hours, the reaction mixture was quenched with water and extracted with ethyl acetate (3×20 mL). The combined organic layers were dried over $Na_2SO_4$ and concentrated under reduced pressure to give the desired product, which was purified by silica gel chromatography. MS (ESI): 462 (MH+).

Example 6.20c. Synthesis of the HCl Salt of 3-((3-fluorophenyl)ethynyl)-8-(methylamino)-7,8,9,10-tetrahydroazepino[2,1-b]quinazolin-12(6H)-one

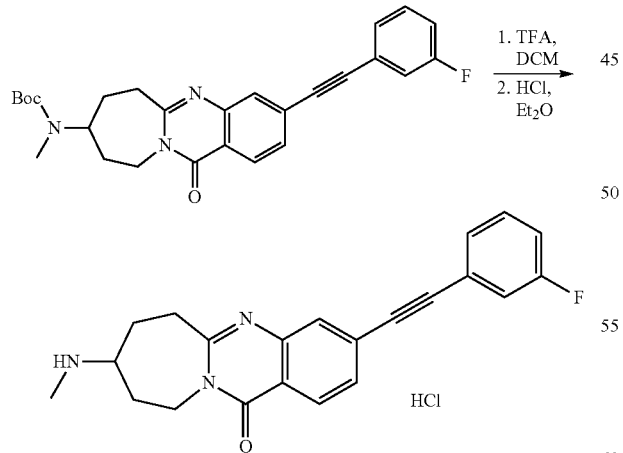

A solution of tert-butyl-3-((3-fluorophenyl)ethynyl)-12-oxo-6,7,8,9,10,12-hexahydroazepino[2,1-b]quinazolin-8-yl(methyl)carbamate (0.2 g, 0.43 mmol, 1 equiv) and TFA (2 mL) in DCM (10 mL) was stirred at rt for 2 hours. The reaction mixture was quenched with water and extracted with DCM (3×20 mL). The combined organic layers were dried over $Na_2SO_4$ and concentrated under reduced pressure to give the desired product, which was purified by silica gel chromatography. MS (ESI): 362 (MH+). The product was then converted to the corresponding HCl salt. MS (ESI): 362 (MH+); $^1$H NMR (300 MHz, $CD_3OD$) δ 8.37-8.34 (d, J=8.19 Hz, 1H), 7.89-7.86 (m, 2H), 7.52-7.44 (m, 2H), 7.41-7.37 (m, 1H), 7.28-7.21 (m, 1H), 5.39-5.32 (m, 1H), 3.94-3.86 (m, 1H), 3.71-3.64 (m, 1H), 3.59-3.40 (m, 2H), 2.79 (s, 3H), 2.61-2.55 (m, 2H), 2.11-2.04 (m, 1H), 1.93-1.81 (m, 1H).

Example 6.21. Synthesis of the HCl Salt of 8-(dimethylamino)-3-((3-fluorophenyl)ethynyl)-7,8,9,10-tetrahydroazepino[2,1-b]quinazolin-12(6H)-one

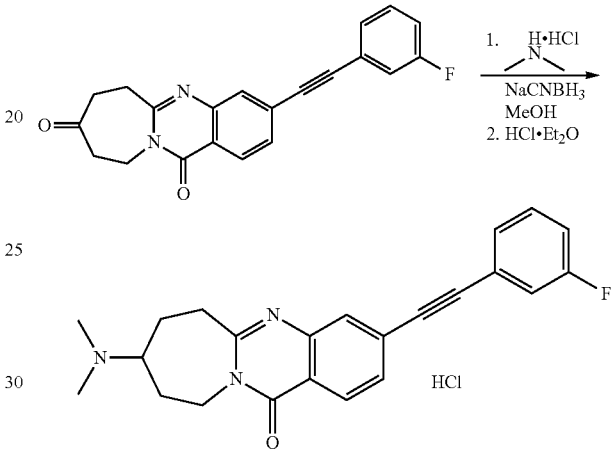

The title compound was prepared according to the experimental procedure as described in Example 1.21d. The product was then converted to the corresponding HCl salt. MS (ESI): 376 (M+H+); $^1$H NMR (300 MHz, $CD_3OD$) δ 8.36-8.34 (d, J=8.16 Hz, 1H), 7.88-7.85 (m, 2H), 7.52-7.43 (m, 2H), 7.40-7.34 (m, 1H), 7.28-7.19 (m, 1H), 5.44-5.39 (m, 1H), 3.86-3.74 (m, 2H), 3.57-3.43 (m, 2H), 2.90 (s, 6H), 2.63-2.53 (m, 2H), 2.24-2.14 (m, 1H), 2.03-1.95 (m, 1H).

Example 6.22. Synthesis of 3-((3-fluorophenyl)ethynyl)-8-methylene-7,8,9,10-tetrahydroazepino[2,1-b]quinazolin-12(6H)-one

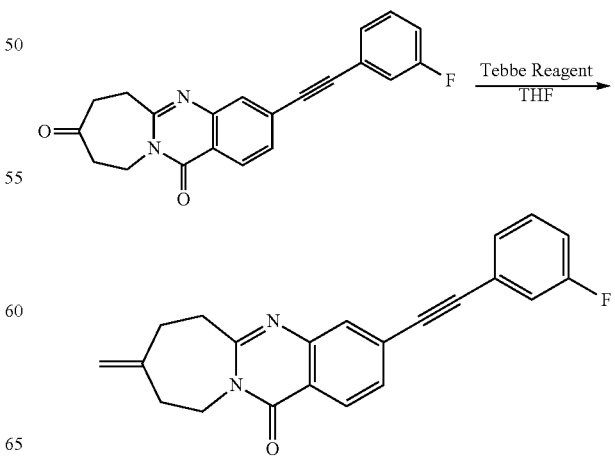

A solution of 3-((3-fluorophenyl)ethynyl)-6,7,9,10-tetrahydroazepino[2,1-b]-quinazoline-8,12-dione (0.1 g, 0.29 mmol, 1 equiv) and Tebbe Reagent in THF (5 mL) was stirred at rt for half an hour. Then the reaction mixture was quenched with NaOH aqueous and extracted with ethyl acetate (3×20 mL). The combined organic layers were dried over Na$_2$SO$_4$ and concentrated under reduced pressure to give the desired product, which was purified by silica gel chromatography. MS (ESI): 345 (M+H$^+$); $^1$H NMR (300 MHz, CDCl$_3$) δ 8.26-8.23 (d, J=8.19 Hz, 1H), 7.78 (s, 1H) 7.58-7.55 (dd, J=8.24, 1.52 Hz, 1H), 7.38-7.32 (m, 2H), 7.28-7.26 (m, 1H), 7.13-7.06 (m, 1H), 4.88-4.86 (d, J=7.50 Hz, 2H), 4.42-4.39 (m, 2H), 3.14-3.10 (m, 2H), 2.61-2.51 (m, 4H). mGluR5 PAM EC$_{50}$: +++++. Fold shift at 10 µM: ++.

Example 6.23. Synthesis of 3-((3-fluorophenyl)ethynyl)-8-(hydroxyimino)-7,8,9,10-tetrahydroazepino[2,1-b]quinazolin-12(6H)-one

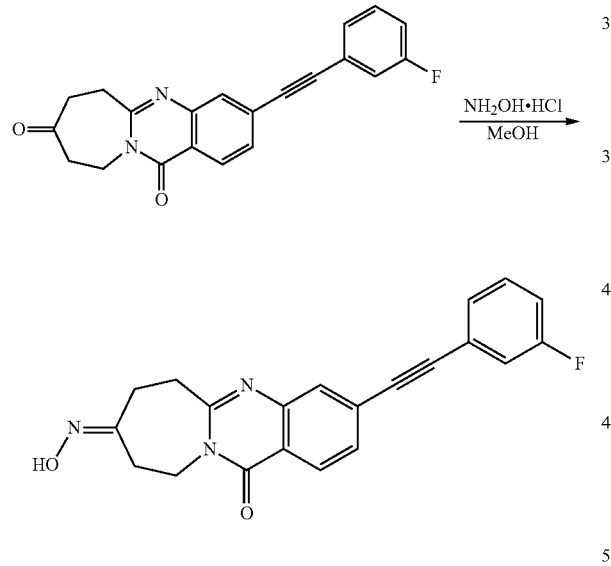

3-((3-fluorophenyl)ethynyl)-6,7,9,10-tetrahydroazepino[2,1-b]quinazoline-8,12-dione (0.1, 0.29 mmol, 1 equiv) was combined with hydroxylamine hydrochloride (40 mg, 0.58 mmol, 2 equiv) and aqueous Na$_2$CO$_3$ (0.5 mL) in a mixture of MeOH (10 mL) and water (1 mL). The mixture was stirred overnight. Then the reaction mixture was diluted with water and extracted with ethyl acetate (3×20 mL). The combined organic layers were dried over Na$_2$SO$_4$ and concentrated under reduced pressure to give the desired product, which was purified by silica gel chromatography. MS (ESI): 362 (MH$^+$); $^1$H NMR (300 MHz, DMSO-d$^6$) δ 8.15-8.13 (d, J=7.80 Hz, 1H), 7.76 (s, 1H) 7.64-7.59 (d, J=8.10 Hz, 1H), 7.52-7.48 (m, 3H), 7.36-7.33 (m, 1H), 4.46-4.35 (m, 2H), 3.15-3.08 (m, 2H), 2.84-2.73 (m, 2H), 2.59-2.55 (m, 2H). mGluR5 PAM EC$_{50}$: +++. Fold shift at 10 µM: ++.

Example 6.24. Synthesis of 3-((3-fluorophenyl)ethynyl)-8-(methoxymethyl)-7,8,9,10-tetrahydroazepino[2,1-b]quinazolin-12(6H)-one

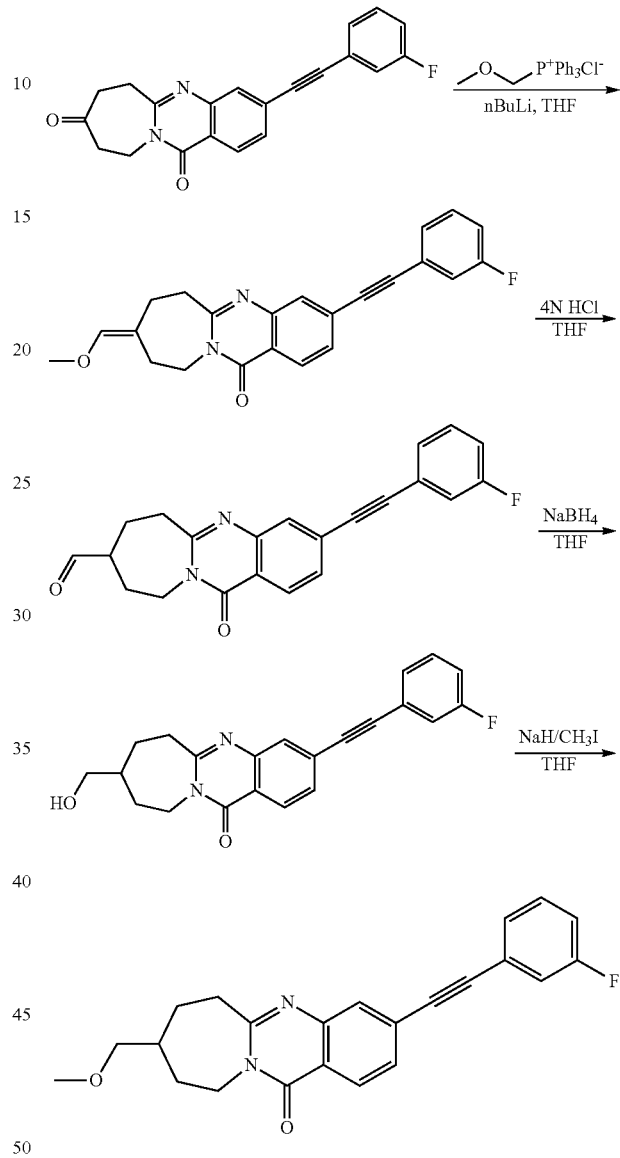

Example 6.24a. Synthesis of (Z)-3((3-fluorophenyl)ethynyl)-8-(methoxymethylene)-7,8,9,10-tetrahydroazepino[2,1-b]quinazolin-12(6H)-one

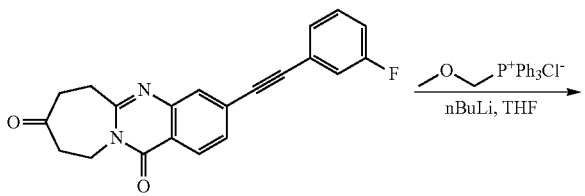

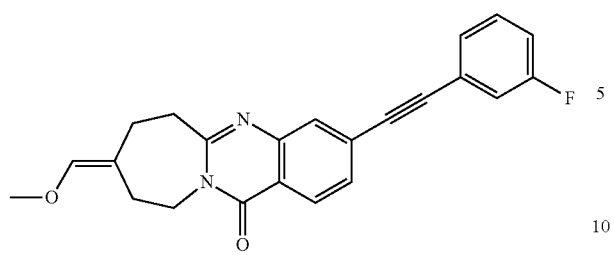

To a solution of (methoxymethyl)triphenylphosphonium chloride (171 mg, 0.5 mmol, 1 equiv) in 5 mL THF at −78° C. was added n-BuLi (0.2 mL, 0.5 mmol, 1 equiv) dropwise and stirred at the same temperature for half an hour. A solution of 3-((3-fluorophenyl)ethynyl)-6,7,9,10-tetrahydroazepino[2,1-b]quinazoline-8,12-dione (173 mg, 0.5 mmol, 1 equiv) in THF was then added to the mixture dropwise at the same temperature and stirred for 2 hours. Then the reaction mixture was quenched with water and extracted with ethyl acetate (3×20 mL). The combined organic layers were dried over Na$_2$SO$_4$ and concentrated under reduced pressure to give the desired product, which was purified by silica gel chromatography. MS (ESI): 375 (MH$^+$).

Example 6.24b. Synthesis of 3-((3-fluorophenyl)ethynyl)-12-oxo-6,7,8,9,10,11,12-hexahydropazepino[2,1-b]quinazoline-8-carbaldehyde A solution of (Z)-3-((3-fluorophenyl)ethynyl)-8-(methoxymethylene)-7,8,9,10-tetrahydroazepino[2,1-b]quinazolin-12(6H)-one (0.1 g, 0.8 mmol, 1 equiv) and 4N HCl (4 mL) in THF (20 mL) was heated at reflux for 4 h. After it was cooled to rt, the reaction mixture was quenched with Na$_2$CO$_3$ aqueous and extracted with ethyl acetate (3×50 mL). The combined organic layers were dried over Na$_2$SO$_4$. After filtration and concentration, the residue was purified by silica gel chromatography to give the desired product. MS (ESI): 361 (MH$^+$).

Example 6.24c. Synthesis of 3-((3-fluorophenyl)ethynyl)-8-(hydroxymethyl)-7,8,9,10-tetrahydroazepino[2,1-b]quinazolin-12(6H)-one

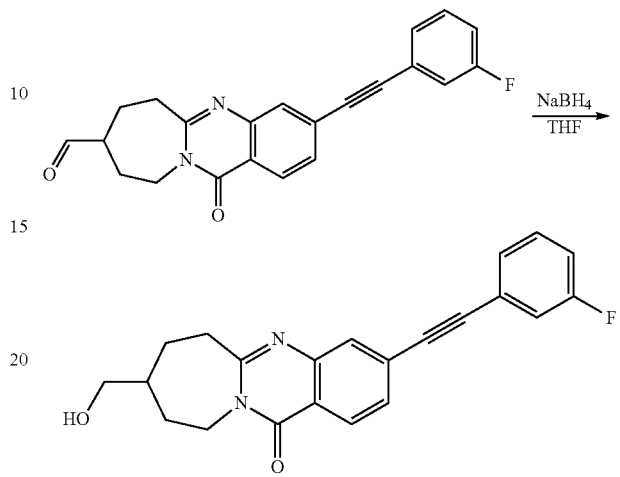

The title compound was prepared according to the experimental procedure as described in Example 4.23. MS (ESI): 363 (MH$^+$).

Example 6.24d. Synthesis of 3-((3-fluorophenyl)ethynyl)-8-(methoxymethyl)-7,8,9,10-tetrahydroazepino[2,1-b]quinazolin-12(6H)-one

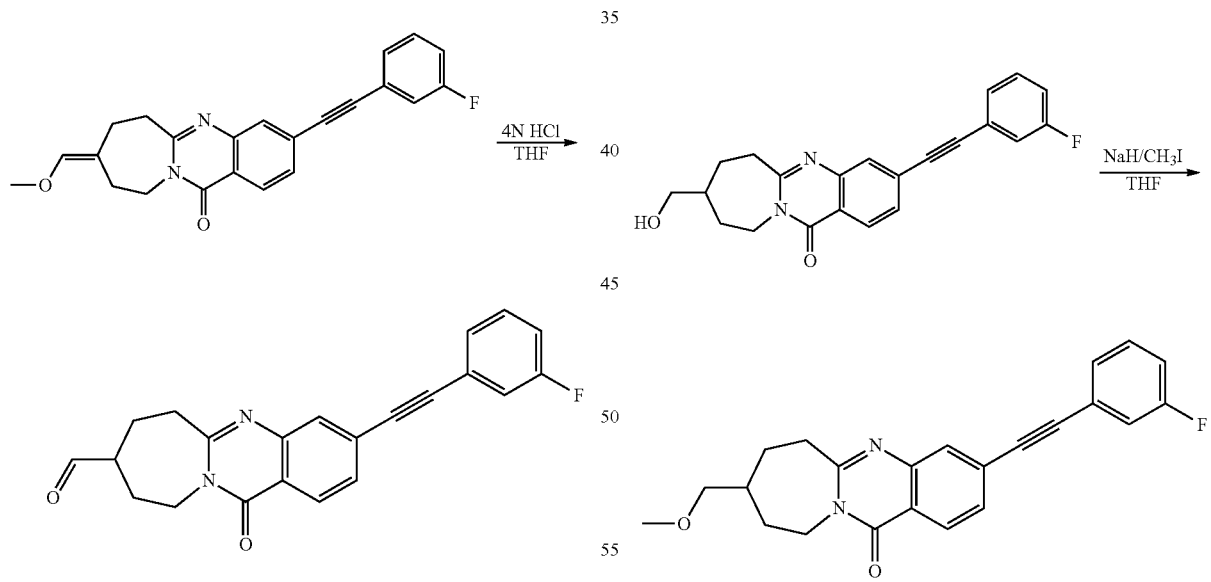

The title compound was prepared according to the experimental procedure as described in Example 4.25. MS (ESI): 377 (MH$^+$); $^1$H NMR (300 MHz, CDCl$_3$) δ 8.17-8.14 (d, J=8.67 Hz, 1H), 7.75 (s, 1H), 7.64-7.61 (d, J=8.52 Hz, 1H), 7.56-7.53 (d, J=8.5 Hz, 1H), 7.36-7.32 (m, 1H), 7.27-7.26 (m, 1H), 7.13-7.07 (m, 1H), 5.29-5.22 (m, 1H), 3.64-3.55 (m, 1H), 3.35 (s, 3H), 3.27-3.00 (m, 4H), 2.26-2.21 (m, 4H), 1.52-1.43 (m, 1H). mGluR5 PAM EC$_{50}$: ++++. Fold shift at 10 μM: ++.

Example 6.25. Synthesis of the HCl Salt of 8-((dimethylamino)methyl)-3-((3-fluorophenyl)ethynyl)-7,8,9,10-tetrahydroazepino[2,1-b]quinazolin-12(6H)-one

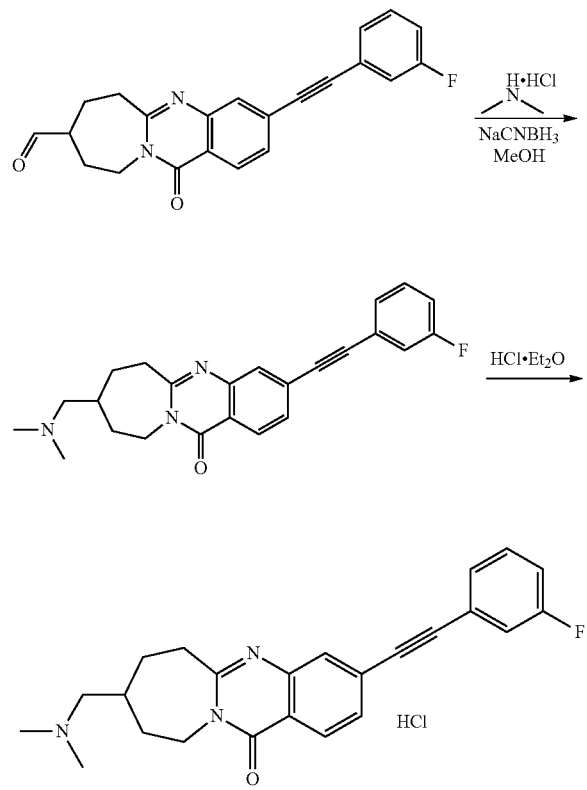

The title compound was prepared according to the experimental procedure as described in Example 1.21d. The product was then converted to the corresponding HCl salt. MS (ESI): 390 (M+H$^+$); $^1$H NMR (300 MHz, CD$_3$OD) δ 8.37-8.35 (d, J=8.73 Hz, 1H), 7.90-7.87 (m, 2H), 7.50-7.44 (m, 2H), 7.41-7.40 (m, 1H), 7.28-7.22 (m, 1H), 5.31-5.24 (m, 1H), 4.01-3.92 (m, 1H), 3.60-3.54 (m, 1H), 3.14-3.12 (d, J=6.87 Hz, 2H), 2.79 (s, 6H), 2.52-2.51 (m, 1H), 2.35-2.23 (m, 2H), 1.73-7.69 (m, 1H), 1.54-1.50 (m, 1H), 1.22-1.17 (m, 1H).

Example 6.26. Synthesis of 3-((3-fluorophenyl)ethynyl)-4',5',9,10-tetrahydro-3'H,6H-spiro[azepino[2,1-b]quinazoline-8,2'-furan]-12(7H)-one

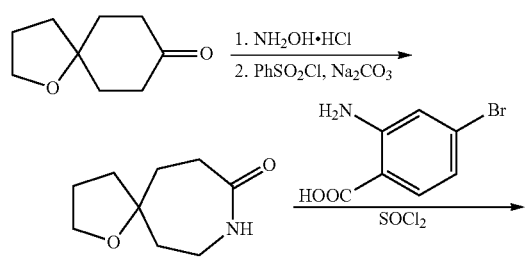

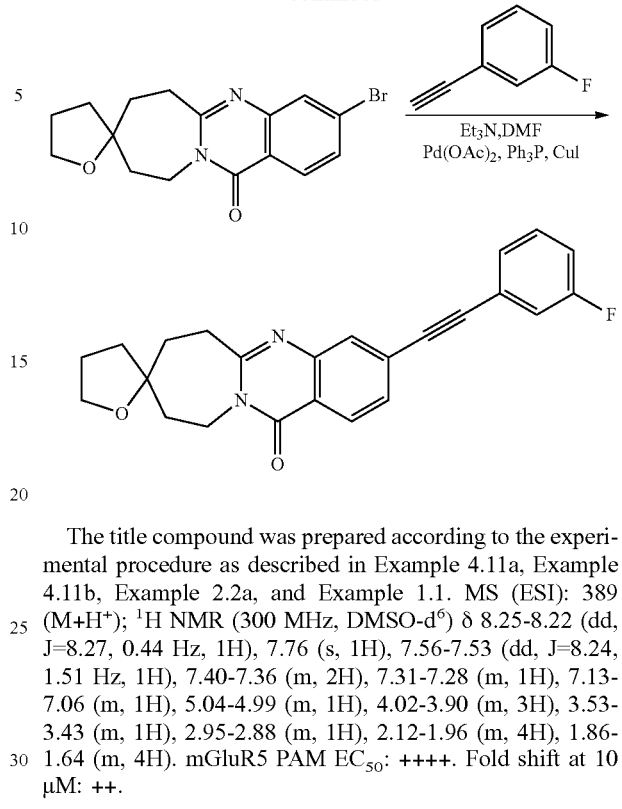

The title compound was prepared according to the experimental procedure as described in Example 4.11a, Example 4.11b, Example 2.2a, and Example 1.1. MS (ESI): 389 (M+H$^+$); $^1$H NMR (300 MHz, DMSO-d$^6$) δ 8.25-8.22 (dd, J=8.27, 0.44 Hz, 1H), 7.76 (s, 1H), 7.56-7.53 (dd, J=8.24, 1.51 Hz, 1H), 7.40-7.36 (m, 2H), 7.31-7.28 (m, 1H), 7.13-7.06 (m, 1H), 5.04-4.99 (m, 1H), 4.02-3.90 (m, 3H), 3.53-3.43 (m, 1H), 2.95-2.88 (m, 1H), 2.12-1.96 (m, 4H), 1.86-1.64 (m, 4H). mGluR5 PAM EC$_{50}$: ++++. Fold shift at 10 µM: ++.

Example 6.27. Synthesis of the HCl Salt of 3-(pyridin-2-ylethynyl)-4',5',9,10-tetrahydro-3'H,6H-spiro[azepino[2,1-b]quinazoline-8,2'-furan]-12(7H)-one

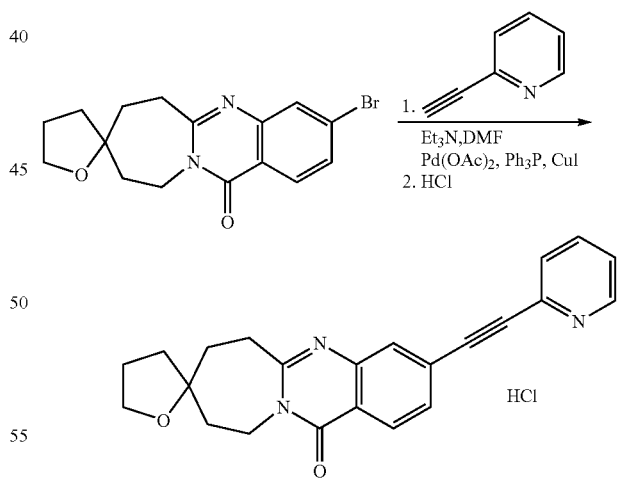

The title compound was prepared according to the experimental procedure as described in Example 2.2a. The product was then converted to the corresponding HCl salt. MS (ESI): 372 (M+H$^+$); $^1$H NMR (300 MHz, DMSO-d$^6$) δ 8.706-8.691 (d, J=4.50 Hz, 1H), 8.240-8.213 (d, J=8.25 Hz, 1H), 8.022-7.975 (m, 2H), 7.853-7.793 (m, 2H), 7.579-7.539 (m, 1H), 4.687 (s, 1H), 4.020-3.991 (m, 1H), 3.825-3.781 (m, 2H), 3.465-3.384 (m, 1H), 3.184-3.135 (m, 1H), 2.005-1.656 (m, 8H). mGluR5 PAM EC$_{50}$: +++. Fold shift at 10 µM: +++.

Example 6.28. Synthesis of 3-((3-fluorophenyl)
ethynyl)-9,10-dihydro-6H-spiro[azepino[2,1-b]qui-
nazoline-8,2'-pyrrolidine]-5',12(7H)-dione

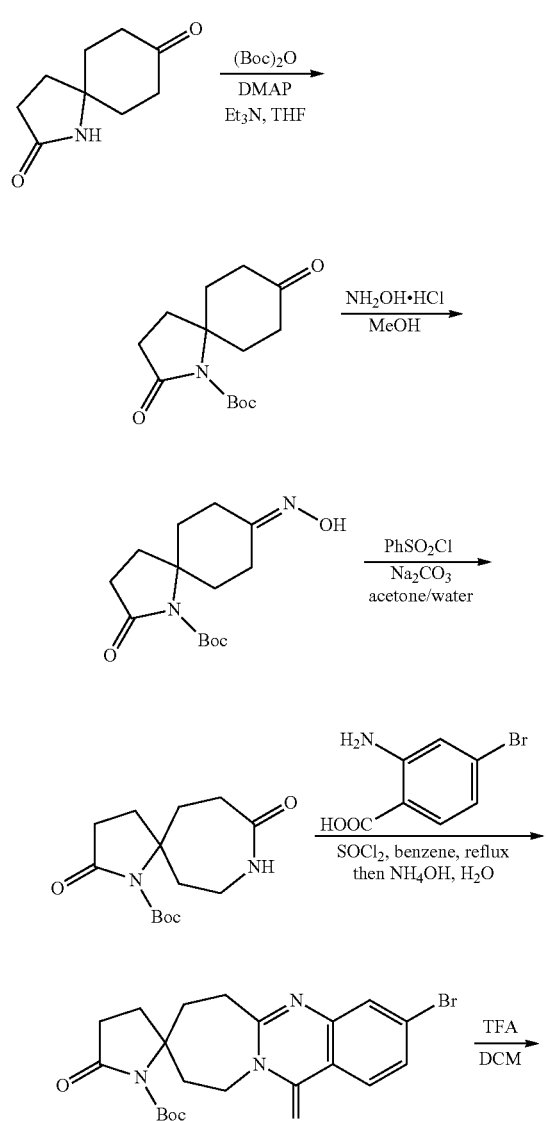

Example 6.28a. Synthesis of tert-butyl 2,8-dioxo-1-
azaspiro[4.5]decane-1-carboxylate

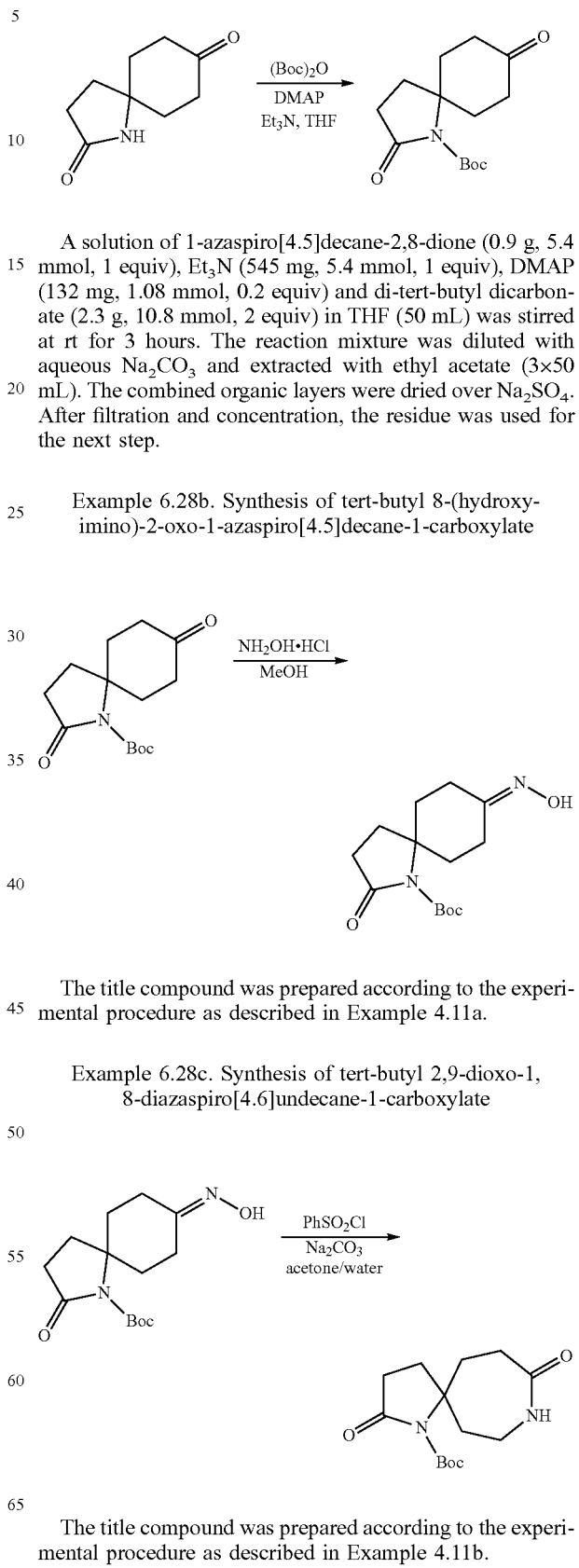

A solution of 1-azaspiro[4.5]decane-2,8-dione (0.9 g, 5.4 mmol, 1 equiv), Et$_3$N (545 mg, 5.4 mmol, 1 equiv), DMAP (132 mg, 1.08 mmol, 0.2 equiv) and di-tert-butyl dicarbonate (2.3 g, 10.8 mmol, 2 equiv) in THF (50 mL) was stirred at rt for 3 hours. The reaction mixture was diluted with aqueous Na$_2$CO$_3$ and extracted with ethyl acetate (3×50 mL). The combined organic layers were dried over Na$_2$SO$_4$. After filtration and concentration, the residue was used for the next step.

Example 6.28b. Synthesis of tert-butyl 8-(hydroxy-
imino)-2-oxo-1-azaspiro[4.5]decane-1-carboxylate The title compound was prepared according to the experimental procedure as described in Example 4.11a.

Example 6.28c. Synthesis of tert-butyl 2,9-dioxo-1,
8-diazaspiro[4.6]undecane-1-carboxylate The title compound was prepared according to the experimental procedure as described in Example 4.11b.

301

Example 6.28d. Synthesis of tert-butyl 3-bromo-5', 12-dioxo-7,9,10,12-tetra hydro-6H-spiro[azepino[2,1-b]quinazoline-8,2'-pyrrolidine]-1'-carboxylate

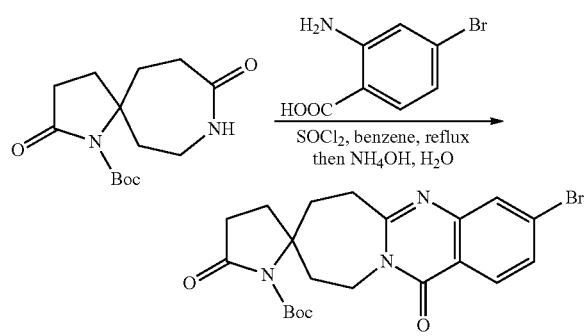

The title compound was prepared according to the experimental procedure as described in Example 2.2a.

Example 6.28e. Synthesis of 3-bromo-9,10-dihydro-6H-spiro[azepino[2,1-b]quinazoline-8,2'-pyrrolidine]-5',12(7H)-dione

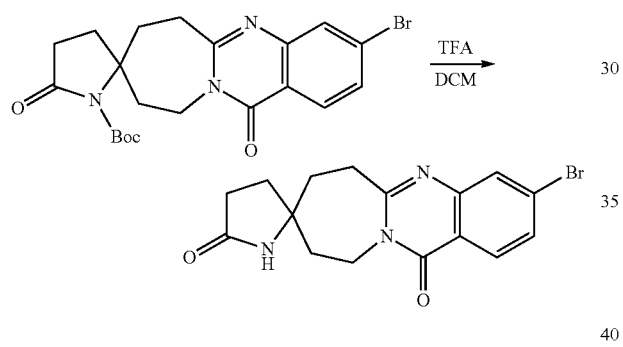

The title compound was prepared according to the experimental procedure as described in Example 1.21c.

Example 6.28f. Synthesis of 3-bromo-9,10-dihydro-6H-spiro[azepino[2,1-b]quinazoline-8,2'-pyrrolidine]-5',12(7H)-dione

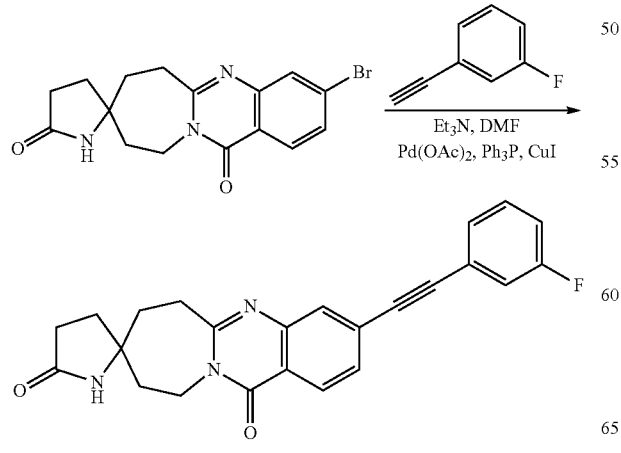

302

The title compound was prepared according to the experimental procedure as described in Example 1.1. MS (ESI): 402 (M+H$^+$); $^1$H NMR (300 MHz, DMSO-d$^6$) δ 8.29-8.28 (m, 1H), 8.14-8.12 (d, J=7.75 Hz, 1H), 7.75 (s, 1H), 7.64-7.60 (m, 1H), 7.55-7.46 (m, 3H), 7.36-7.31 (m, 1H), 4.50-4.19 (m, 2H), 3.18-3.17 (m, 1H), 3.10-3.00 (m, 1H), 2.28-2.23 (m, 2H), 1.99-1.77 (m, 6H).

Example 6.29. Synthesis of the HCl Salt of 3-((3-fluorophenyl)ethynyl)-9,10-dihydro-6H-spiro[azepino[2,1-b]quinazoline-8,2'-pyrrolidin]-12(7H)-one

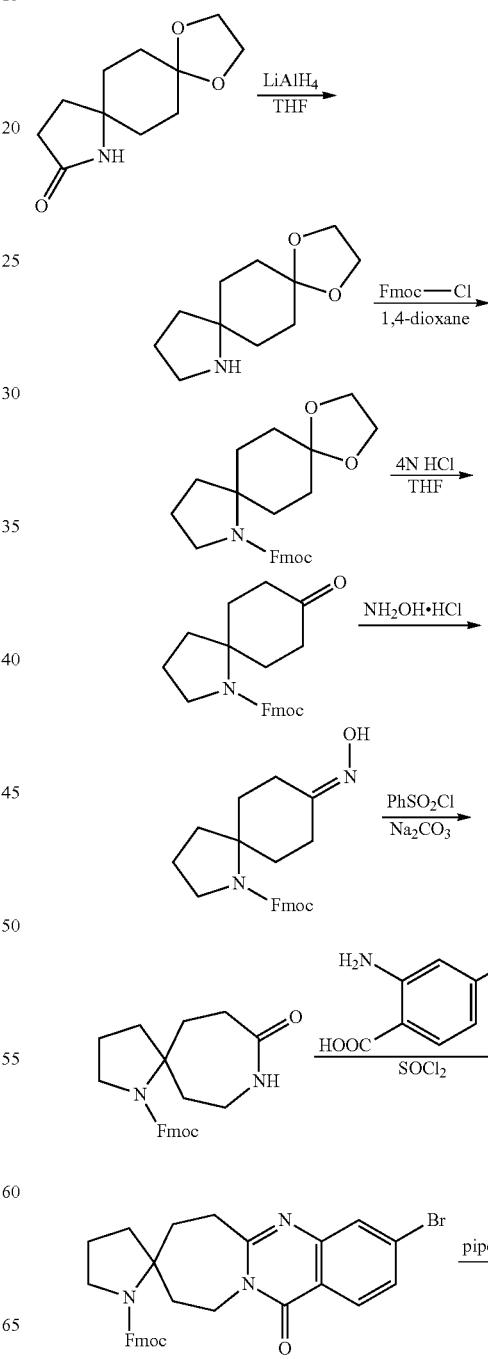

-continued

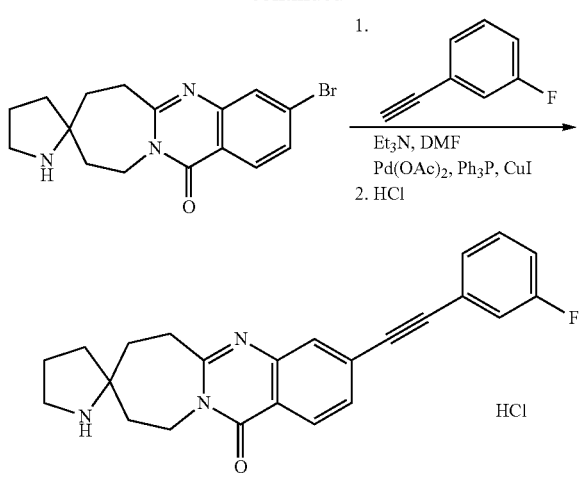

Example 6.29a. Synthesis of 1,4-dioxa-9-azadispiro[4.2.4⁸.2⁵]tetradecane

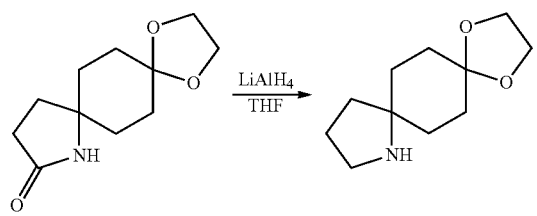

To a solution of 1,4-dioxa-9-azadispiro[4.2.4⁸.2⁵]tetradecan-10-one (1.5 g, 7.1 mmol, 1 equiv) in dry THF (100 mL) was added LiAlH₄ (3 g, 78.9 mmol, 11 equiv) in portions and heated at reflux overnight. After it was cooled to rt, the reaction mixture was quenched with 1 N NaOH and extracted with DCM (3×100 mL). The combined organic layers were dried over Na₂SO₄ and concentrated under reduced pressure to give the desired product for the next step.

Example 6.29b. Synthesis of 9H-fluoren-9-ylmethyl-1,4-dioxa-9-azadispiro[4.2.4⁸.2⁵]tetradecane-9-carboxylate

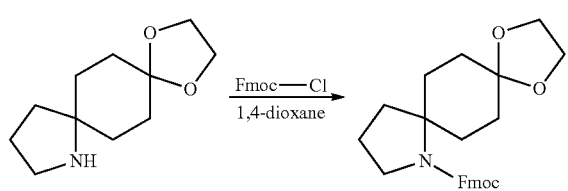

The title compound was prepared according to the experimental procedure as described in Example 5.1a.

Example 6.29c. Synthesis of (9H-fluoren-9-yl)methyl 8-oxo-1-azaspiro[4.5]decane-1-carboxylate

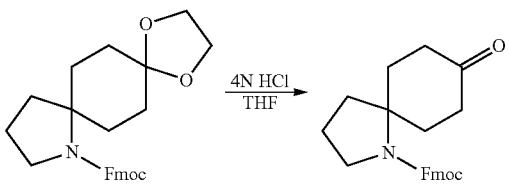

The title compound was prepared according to the experimental procedure as described in Example 6.14b.

Example 6.29d. Synthesis of (9H-fluoren-9-yl)methyl 8-(hydroxyimino)-1-azaspiro[4.5]decane-1-carboxylate

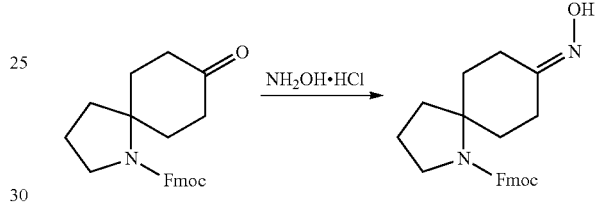

The title compound was prepared according to the experimental procedure as described in Example 4.11a.

Example 6.29e. Synthesis of (9H-fluoren-9-yl)methyl 9-oxo-1,8-diazaspiro[4.6]undecane-1-carboxylate

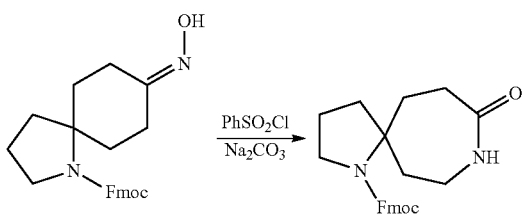

The title compound was prepared according to the experimental procedure as described in Example 4.11b.

Example 6.29f. Synthesis of (9H-fluoren-9-yl)methyl 3-bromo-12-oxo-7,9,10,12-tetrahydro-6H-spiro[azepino[2,1-b]quinazoline-8,2'-pyrrolidine]-1'-carboxylate

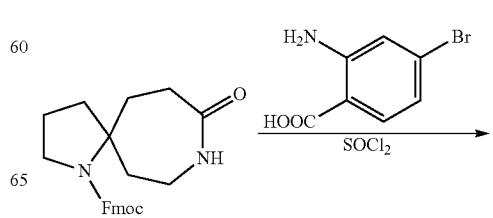

-continued

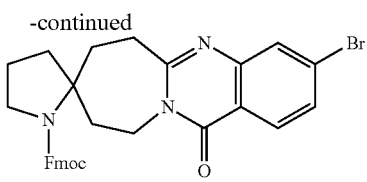

The title compound was prepared according to the experimental procedure as described in Example 2.2a.

Example 6.29g. Synthesis of 3-bromo-9,10-dihydro-6H-spiro[azepino[2,1-b]quinazoline-8,2'-pyrrolidin]-12(7H)-one

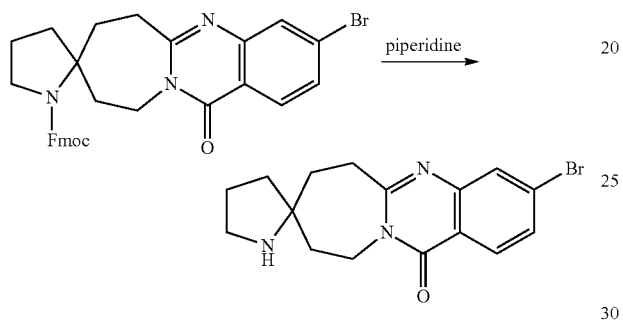

The title compound was prepared according to the experimental procedure as described in Example 3.17b.

Example 6.29h. Synthesis of the HCl Salt of 3-((3-fluorophenyl)ethynyl)-9,10-dihydro-6H-spiro[azepino[2,1-b]quinazoline-8,2'-pyrrolidin]-12(7H)-one

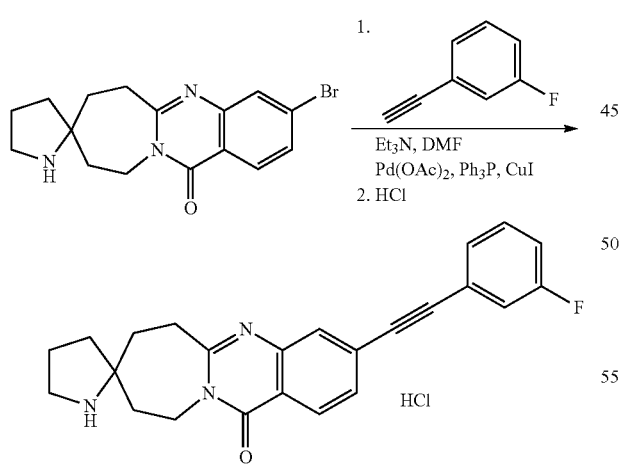

The title compound was prepared according to the experimental procedure as described in Example 1.1. The product was then converted to the corresponding HCl salt. MS (ESI): 388 (M+H$^+$); $^1$H NMR (300 MHz, CD$_3$OD) δ 8.35-8.32 (d, J=9.00 Hz, 1H), 7.86-7.82 (m, 2H), 7.49-7.48 (m, 2H), 7.39-7.36 (m, 1H), 7.27-7.21 (m, 1H), 4.91-4.90 (m, 1H), 4.15-4.08 (m, 1H), 3.50-3.31 (m, 4H), 2.40-2.10 (m, 8H).

Example 6.30. Synthesis of the HCl Salt of ((3-fluorophenyl)ethynyl)-1'-methyl-9,10-dihydro-6H-spiro[azepino[2,1-b]quinazoline-8,2'-pyrrolidin]-12(7H)-one

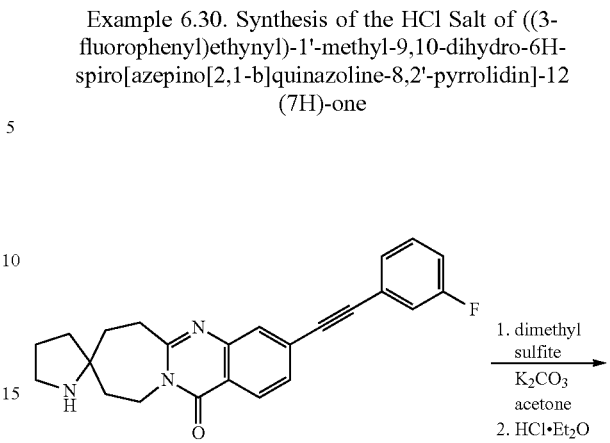

To a solution of 3-((3-fluorophenyl)ethynyl)-9,10-dihydro-6H-spiro[azepino[2,1-b]-quinazoline-8,2'-pyrrolidin]-12(7H)-one (80 mg, 0.21 mmol, 1 eq) and K$_2$CO$_3$ (116 mg, 0.82 mmol, 4 eq) in acetone (20 mL) was added dimethyl sulfite (25.4 mg, 0.23 mmol, 1.1 equiv). After stirring at rt for 1 h, the mixture was quenched with water and extracted with ethyl acetate (3×20 mL). The combined organic layers were dried over Na$_2$SO$_4$ and concentrated under reduced pressure to give the desired product, which was purified by silica gel chromatography. The product was then converted to the corresponding HCl salt. MS (ESI): 402 (M+H$^+$); $^1$H NMR (300 MHz, CD$_3$OD) δ 8.32-8.29 (d, J=8.31 Hz, 1H), 7.83-7.76 (m, 2H), 7.51-7.42 (m, 2H), 7.38-7.33 (m, 1H), 7.26-7.19 (m, 1H), 5.42-5.31 (m, 1H), 3.84-3.63 (m, 5H), 2.80 (s, 3H), 2.70-2.65 (m, 1H), 2.40-2.09 (m, 7H).

Example 6.31 and Example 6.32. Synthesis of 3-((3-fluorophenyl)ethynyl)-6-isobutyl-7,8,9,10-tetrahydroazepino[2,1-b]quinazolin-12(6H)-one and 3-((4-fluorophenyl)ethynyl)-10-isobutyl-7,8,9,10-tetrahydroazepino[2,1-b]quinazolin-12(6H)-one

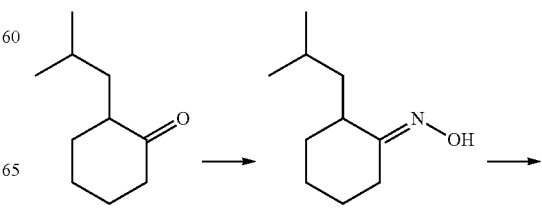

307
-continued

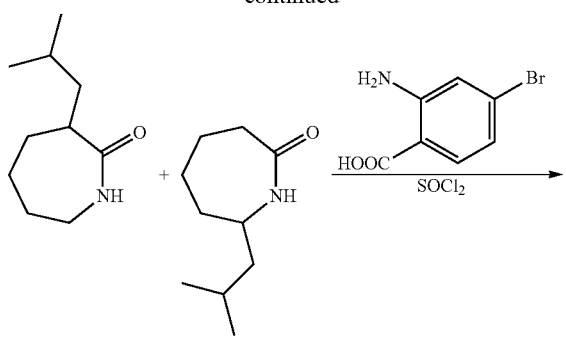

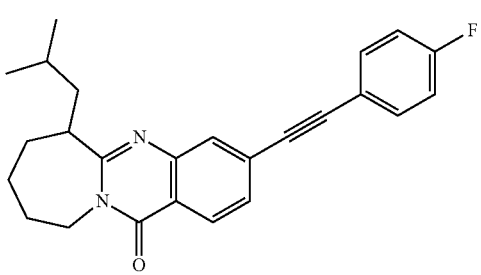 [SMILES: CC(C)CC1CCCCn2c1nc1cc(C#Cc3ccc(F)cc3)ccc1c2=O]

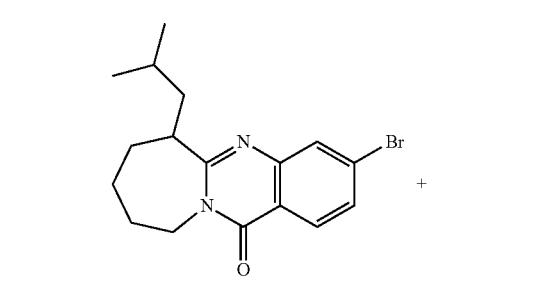

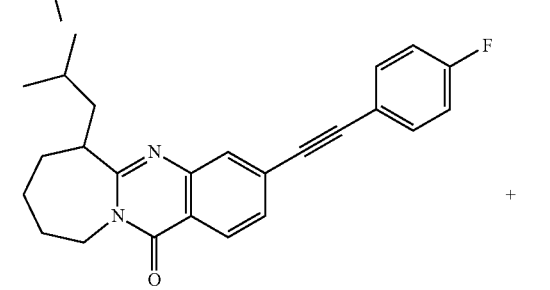

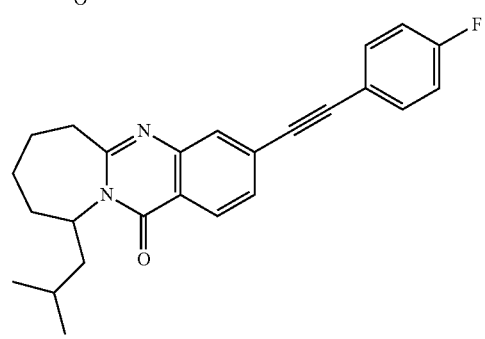

The title compounds were prepared according to the experimental procedure as described in Example 4.11b, Example 2.2a, and Example 1.1.

308

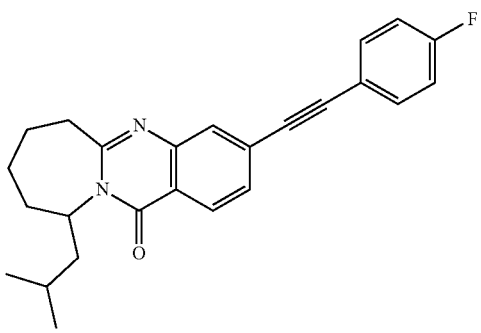 [SMILES: CC(C)CC1CCCCc2nc3cc(C#Cc4ccc(F)cc4)ccc3c(=O)n21]

3-((3-fluorophenyl)ethynyl)-6-isobutyl-7,8,9,10-tetrahydroazepino[2,1-b]quinazolin-12(6H)-one MS (ESI): 389 (M+H$^+$); $^1$H NMR (300 MHz, CDCl$_3$) δ 8.24-8.21 (dd, J=8.25, 0.48 Hz, 1H), 7.82 (s, 1H), 7.62-7.52 (m, 3H), 7.13-7.05 (m, 2H), 5.19-5.14 (m, 1H), 3.79-3.68 (m, 1H), 3.14-3.06 (m, 1H), 2.18-2.11 (m, 1H), 2.06-1.80 (m, 4H), 1.80-1.70 (m, 2H), 1.50-1.44 (m, 2H), 1.02-0.98 (m, 6H).

3-((4-fluorophenyl)ethynyl)-10-isobutyl-7,8,9,10-tetrahydroazepino[2,1-b]quinazolin-12(6H)-one MS (ESI): 389 (MH$^+$). mGluR5 PAM EC$_{50}$: ++. Fold shift at 10 μM: +.

Example 6.33. Synthesis of 10-allyl-3-((4-fluorophenyl)ethynyl)-7,8,9,10-tetrahydroazepino[2,1-b]quinazolin-12(6H)-one

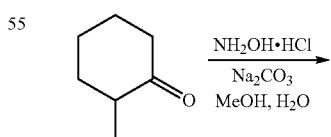

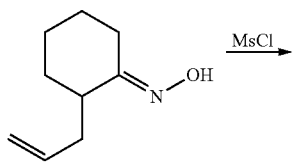

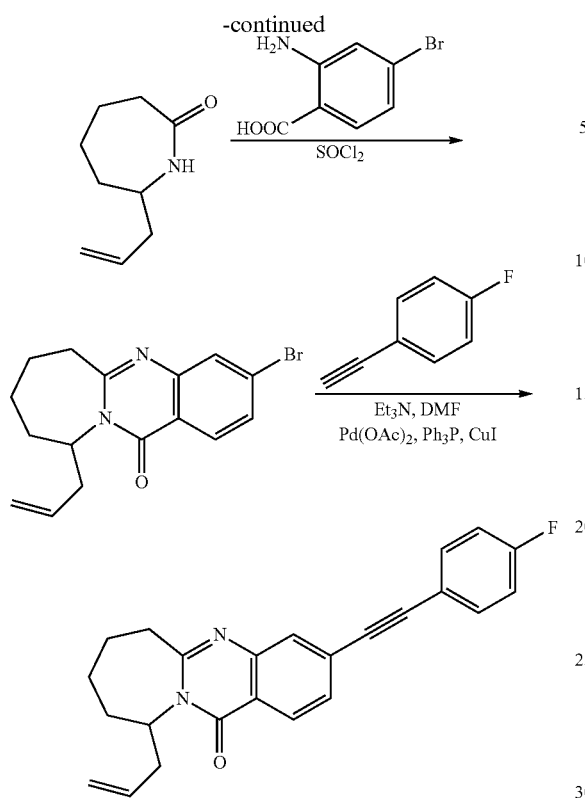

The title compound was prepared according to the experimental procedure as described in Example 4.11a, Example 4.11b, Example 2.2a, and Example 1.1. MS (ESI): 373 (M+H⁺); ¹H NMR (300 MHz, CDCl₃) δ 8.23-8.20 (d, J=8.25 Hz, 1H), 7.72 (s, 1H), 7.59-7.52 (m, 3H), 7.12-7.05 (t, J=8.69 Hz, 2H), 5.92-5.74 (m, 2H), 5.15-5.03 (m, 2H), 3.18-3.14 (m, 2H), 2.74-2.69 (t, J=7.52 Hz, 2H), 2.21-2.07 (m, 2H), 1.94-1.74 (m, 3H), 1.71-1.62 (m, 1H). mGluR5 PAM EC$_{50}$: ++++.

Example 6.34. Synthesis of 3-((3-fluorophenyl)ethynyl)-9,10-dihydro-6H-spiro[azepino[2,1-b]quinazoline-8,2'-[1,3]dioxolan]-12(7H)-one

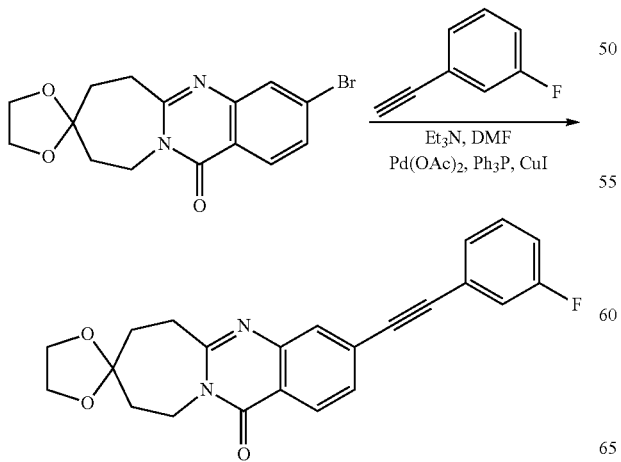

The title compound was prepared according to the experimental procedure as described in Example 1.1. MS (ESI): 391 (M+H⁺); ¹H NMR (300 MHz, CDCl₃) δ 8.26-8.23 (d, J=8.25 Hz, 1H), 7.77 (s, 1H), 7.58-7.55 (dd, J=8.21, 1.52 Hz, 1H), 7.38-7.34 (m, 2H), 7.30-7.29 (m, 1H), 7.14-7.07 (m, 1H), 4.47-4.46 (m, 2H), 4.05 (s, 4H), 3.17-3.13 (m, 2H), 2.06-2.03 (m, 2H), 1.99-1.96 (m, 2H). mGluR5 PAM EC$_{50}$: ++++. Fold shift at 10 μM: +++.

Example 6.35. Synthesis of 6-methyl-3-(pyridin-2-ylethynyl)-7,8,9,10-tetrahydroazepino[2,1-b]quinazolin-12(6H)-one

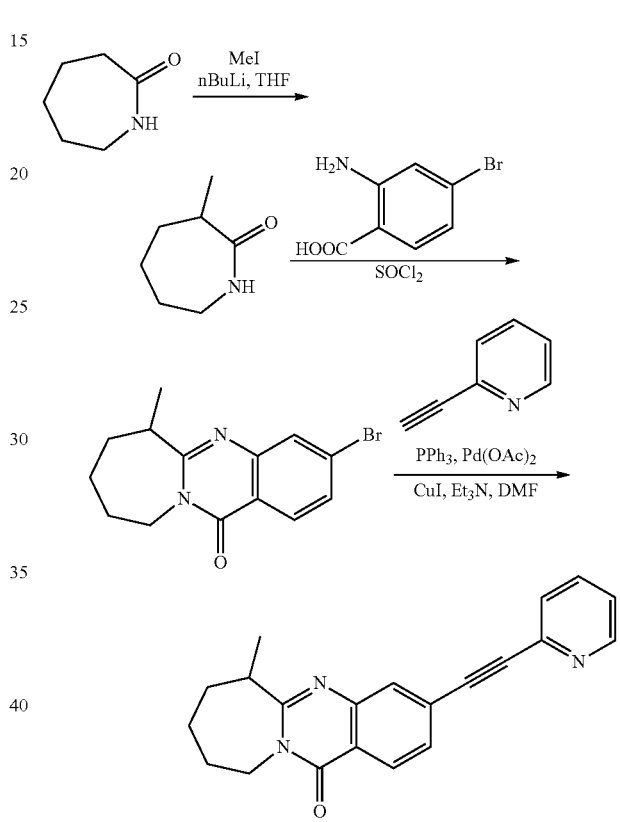

Example 6.35a. Synthesis of 3-methylazepan-2-one

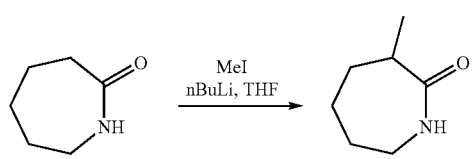

To a solution of azepan-2-one (0.5 g, 4.42 mmol, 1 equiv) in anhydrous THF (20 mL) under nitrogen, was added n-BuLi (4.4 mL, 2.5 M in n-hexane, 11.06 mmol) dropwise at 0° C. The reaction mixture was kept at 0° C. for 2 h, then MeI (0.3 mL, 4.86 mmol) was added. After stirring for 1 h, the mixture was quenched with water and extracted with DCM (2×50 mL). The combined organic layers were dried over anhydrous Na₂SO₄. After filtration and concentration, the crude product was directly used for the next step without further purification. MS (ESI): 128 (MH⁺).

Example 6.35b. Synthesis of 3-bromo-6-methyl-7,8,9,10-tetrahydroazepino[2,1-b]quinazolin-12(6H)-one

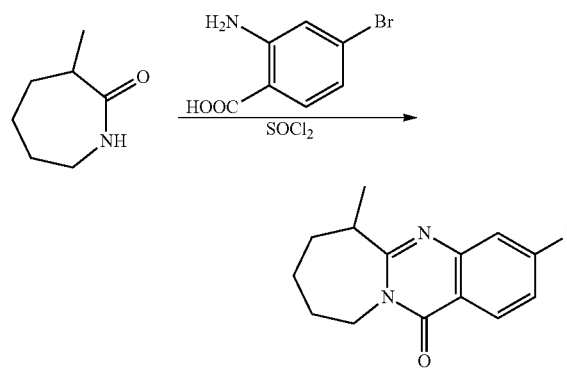

The title compound was prepared according to the experimental procedure as described in Example 2.2a. MS (ESI): 307, 309 (MH+).

Example 6.35c. Synthesis of 6-methyl-3-(pyridin-2-ylethynyl)-7,8,9,10-tetrahydroazepino[2,1-b]quinazolin-12(6H)-one

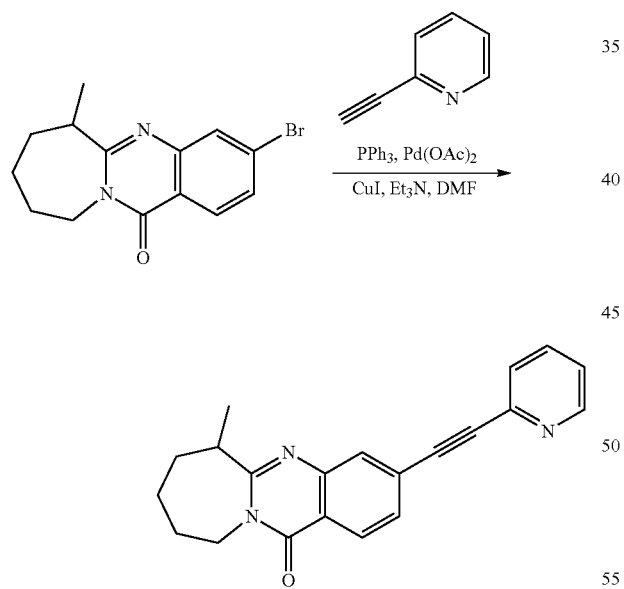

The title compound was prepared according to the experimental procedure as described in Example 1.1. MS (ESI): 330 (MH+); $^1$H NMR (300 MHz, CD$_3$OD) δ 8.92-8.90 (d, J=5.67 Hz, 1H), 8.64-8.58 (m, 1H), 8.41-8.38 (d, J=8.28 Hz, 1H), 8.31-8.28 (d, J=8.10 Hz, 1H), 8.24 (s, 1H), 8.09-8.05 (m, 1H), 7.95-7.92 (dd, J=8.28, 1.26 Hz, 1H), 5.00-4.99 (m, 1H), 4.19-4.12 (m, 1H), 3.69-3.64 (m, 1H), 2.03-1.92 (m, 4H), 1.83-1.65 (m, 2H), 1.61-1.59 (d, J=6.90 Hz, 3H). mGluR5 PAM EC$_{50}$: ++++. Fold shift at 10 μM: ++.

Example 6.36 and Example 6.42. Synthesis of 7-methyl-3-(pyridin-2-ylethynyl)-7,8,9,10-tetrahydroazepino[2,1-b]quinazolin-12(6H)-one and 9-methyl-3-(pyridin-2-ylethynyl)-7,8,9,10-tetrahydroazepino[2,1-b]quinazolin-12 (6H)-one

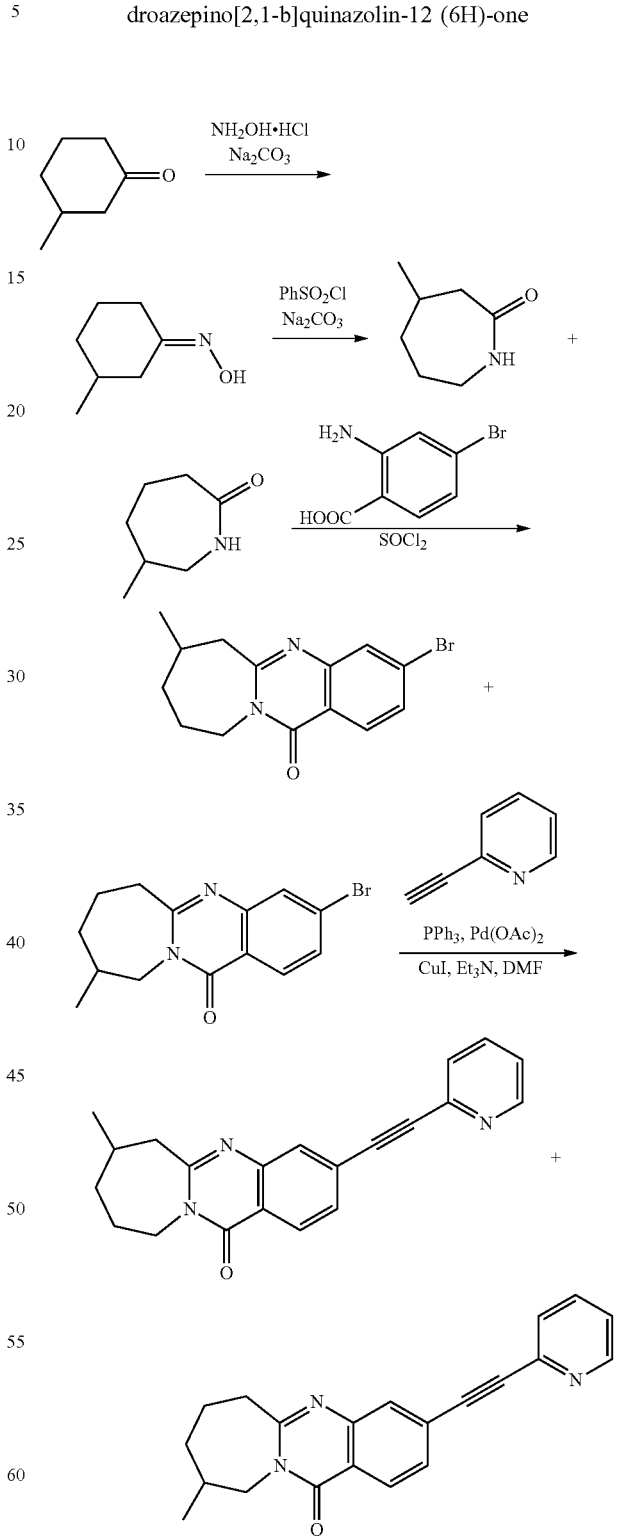

The title compounds were prepared according to the experimental procedure as described in Example 4.11a, Example 4.11b, Example 2.2a, and Example 1.1.

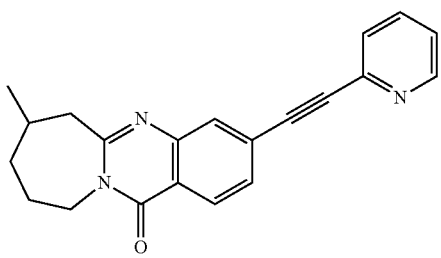 [SMILES: CC1CCCn2c(nc3cc(C#Cc4ccccn4)ccc3c2=O)C1]

7-methyl-3-(pyridin-2-ylethynyl)-7,8,9,10-tetrahydroazepino[2,1-b]quinazolin-12(6H)-one MS (ESI): 330 (MH$^+$); $^1$H NMR (300 MHz, CD$_3$OD) δ 8.88-8.86 (d, J=5.01 Hz, 1H), 8.53-8.47 (t, J=7.94 Hz, 1H), 8.44-8.42 (d, J=8.31 Hz, 1H), 8.22-8.20 (d, J=8.04 Hz, 1H), 8.05 (s, 1H), 8.01-7.95 (m, 2H), 5.10-5.03 (m, 1H), 4.07-3.99 (m, 1H), 3.42-3.31 (m, 1H), 3.20-3.15 (d, J=14.44 Hz, 1H), 2.13-2.04 (m, 3H), 1.75-1.69 (m, 2H), 1.23-1.21 (d, J=6.75 Hz, 3H). mGluR5 PAM EC$_{50}$: ++++. Fold shift at 10 μM: ++.

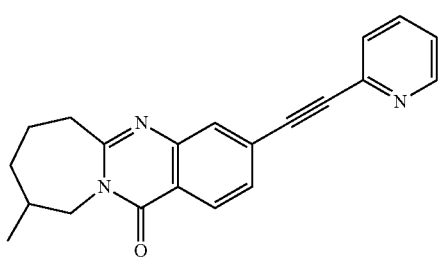 [SMILES: CC1CCCc2nc3cc(C#Cc4ccccn4)ccc3c(=O)n2C1]

9-methyl-3-(pyridin-2-ylethynyl)-7,8,9,10-tetrahydroazepino[2,1-b]quinazolin-12(6H)-one MS (ESI): 330 (MH$^+$); $^1$H NMR (300 MHz, CDCl$_3$) δ 8.92-8.90 (d, J=5.3 Hz, 1H), 8.61-8.55 (t, 7.92 Hz, 1H), 8.46-8.43 (d, J=8.25 Hz, 1H), 8.29-8.26 (d, J=8.01 Hz, 1H), 8.09-8.00 (m, 3H), 4.91-4.84 (d, J=14.29 Hz, 1H), 4.04-3.96 (m, 1H), 3.54-3.31 (m, 2H), 2.21 (m, 1H), 2.09-1.92 (m, 3H), 1.71-1.65 (m, 1H), 1.13-1.11 (d, J=6.90 Hz, 3H). mGluR5 PAM EC$_{50}$: +++++. Fold shift at 10 μM: +++.

Example 6.36a and Example 6.36b. Separation of 7-methyl-3-(pyridin-2-ylethynyl)-7,8,9,10-tetrahydroazepino[2,1-b]quinazolin-12(6H)-one into (S)-7-methyl-3-(pyridin-2-ylethynyl)-7,8,9,10-tetrahydroazepino[2,1-b]quinazolin-12(6H)-one and (R)-7-methyl-3-(pyridin-2-ylethynyl)-7,8,9,10-tetrahydroazepino[2,1-b]quinazolin-12(6H)-one -continued single stereochemistry

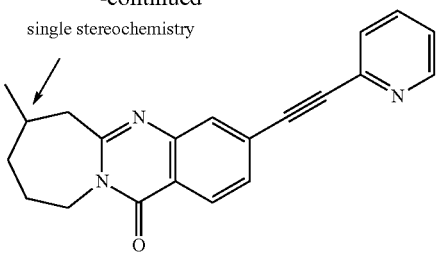

Single enantiomer
faster moving enantiomer (fraction 1)

single (opposite) stereochemistry

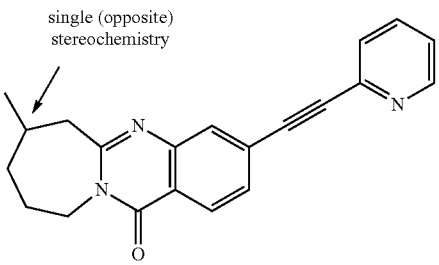

Single enantiomer
slower moving enantiomer (fraction 2)

Racemic 7-methyl-3-(pyridin-2-ylethynyl)-7,8,9,10-tetrahydroazepino[2,1-b]quinazolin-12(6H)-one was separated into the corresponding two single enantiomer compounds (S)-7-methyl-3-(pyridin-2-ylethynyl)-7,8,9,10-tetrahydroazepino[2,1-b]quinazolin-12(6H)-one and (R)-7-methyl-3-(pyridin-2-ylethynyl)-7,8,9,10-tetrahydroazepino[2,1-b]quinazolin-12(6H)-one using chiral chromatography with an isocratic SFC method. The column used was a 4.6×100 mm RegisPack from Regis Technologies (Morton Grove, Ill.). The CO$_2$ co-solvent was methanol:isopropanol (3:1) with 0.1% isopropylamine. Isocratic Method: 45% Co-solvent at 4 mL/min System Pressure: 100 bar. Column Temperature 25° C.

Faster moving enantiomer of 7-methyl-3-(pyridin-2-ylethynyl)-7,8,9,10-tetrahydroazepino[2,1-b]quinazolin-12(6H)-one (fraction 1): Retention time=2.4 min 99% ee.

Slower moving enantiomer of 7-methyl-3-(pyridin-2-ylethynyl)-7,8,9,10-tetrahydroazepino[2,1-b]quinazolin-12 (6H)-one (fraction 2): Retention time=## min. ##% ee.

Example 6.42a and Example 6.42b. Separation of 9-methyl-3-(pyridin-2-ylethynyl)-7,8,9,10-tetrahydroazepino[2,1-b]quinazolin-12(6H)-one (S)-9-methyl-3-(pyridin-2-ylethynyl)-7,8,9,10-tetrahydroazepino[2,1-b]quinazolin-12(6H)-one and (R)-9-methyl-3-(pyridin-2-ylethynyl)-7,8,9,10-tetrahydroazepino[2,1-b]quinazolin-12(6H)-one

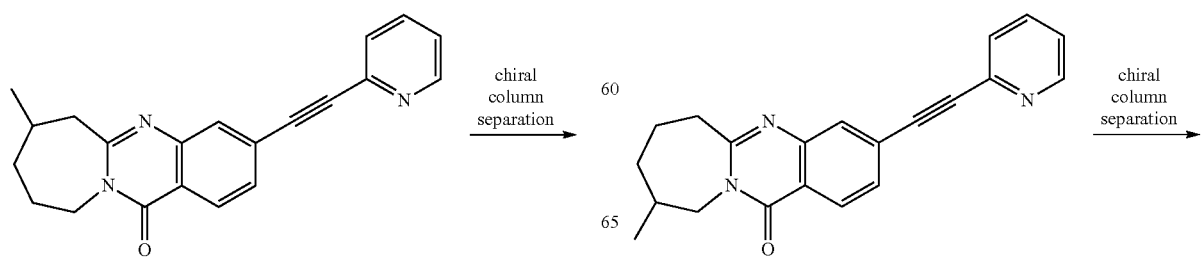

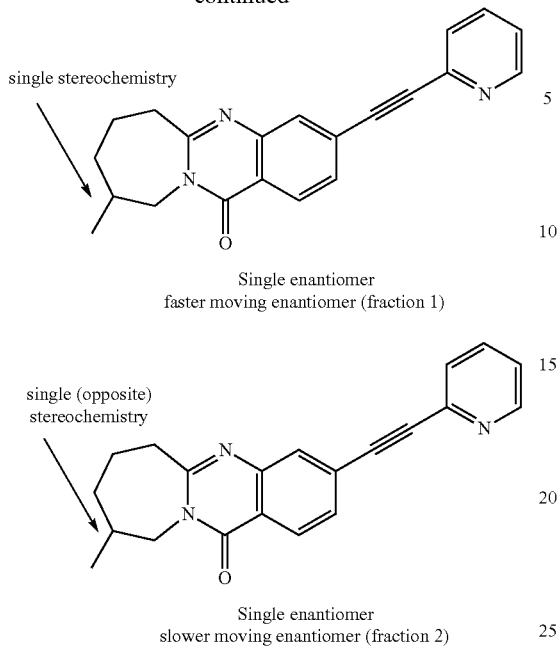

Single enantiomer
faster moving enantiomer (fraction 1)

Single enantiomer
slower moving enantiomer (fraction 2)

Racemic 9-methyl-3-(pyridin-2-ylethynyl)-7,8,9,10-tetrahydroazepino[2,1-b]quinazolin-12(6H)-one was separated into the corresponding two single enantiomer compounds (S)-9-methyl-3-(pyridin-2-ylethynyl)-7,8,9,10-tetrahydroazepino[2,1-b]quinazolin-12(6H)-one and (R)-9-methyl-3-(pyridin-2-ylethynyl)-7,8,9,10-tetrahydroazepino[2,1-b]quinazolin-12(6H)-one using chiral chromatography with an isocratic SFC method. The column used was a 4.6×100 mm RegisPack from Regis Technologies (Morton Grove, Ill.). The $CO_2$ co-solvent was methanol:isopropanol (2:1) with 0.1% isopropylamine. System Pressure: 100 bar. Column Temperature 25° C.

Faster moving enantiomer of 9-methyl-3-(pyridin-2-ylethynyl)-7,8,9,10-tetrahydroazepino[2,1-b]quinazolin-12(6H)-one (fraction 1): Retention time=3.0 min.

Slower moving enantiomer of 9-methyl-3-(pyridin-2-ylethynyl)-7,8,9,10-tetrahydroazepino[2,1-b]quinazolin-12 (6H)-one (fraction 2): Retention time=3.9 min.

Example 6.37 and Example 6.43. Synthesis of 7,7-dimethyl-3-(pyridin-2-ylethynyl)-7,8,9,10-tetrahydroazepino[2,1-b]quinazolin-12(6H)-one and Synthesis of 9,9-dimethyl-3-(pyridin-2-ylethynyl)-7,8,9,10-tetrahydroazepino[2,1-b]quinazolin-12 (6H)-one

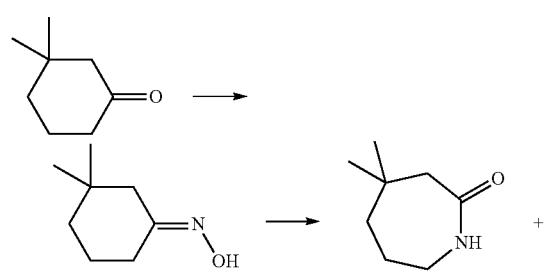

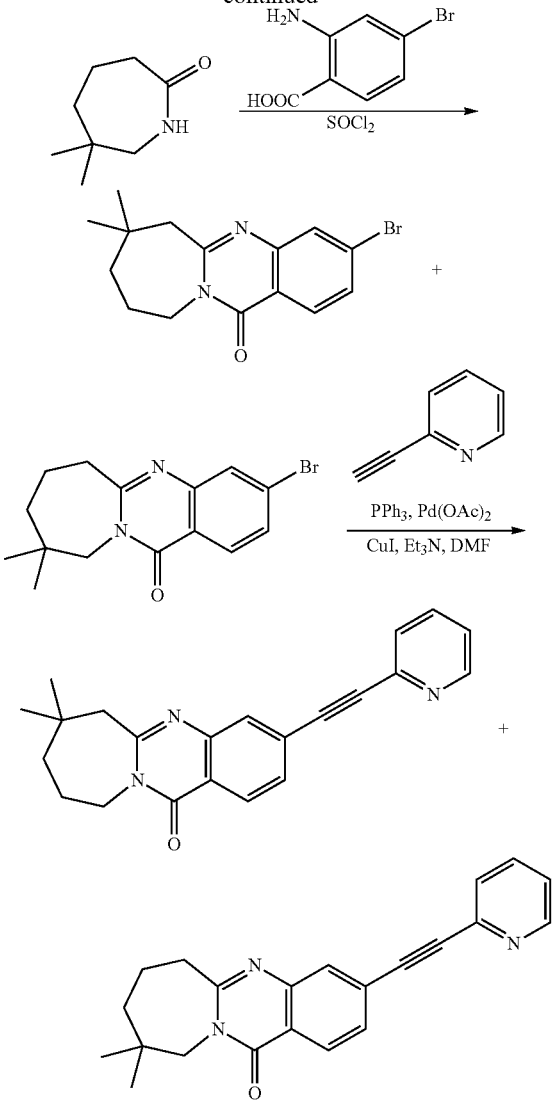

The title compounds were prepared according to the experimental procedures as described in Example 4.11a, Example 4.11b, Example 2.2a, and Example 1.1. The title compounds were separated after the last step.

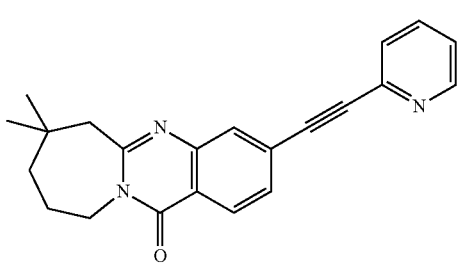 [SMILES: CC1(C)CCCn2c(nc3cc(C#Cc4ccccn4)ccc3c2=O)C1]

7,7-dimethyl-3-(pyridin-2-ylethynyl)-7,8,9,10-tetrahydroazepino[2,1-b]quinazolin-12(6H)-one MS (ESI): 344 (MH$^+$); $^1$H NMR (300 MHz, CD$_3$OD) δ 8.98-8.96 (d, J=5.37 Hz, 1H), 8.75-8.69 (t, J=7.98 Hz, 1H), 8.47-8.45 (d, J=8.16 Hz, 1H), 8.41-8.38 (d, J=8.16 Hz, 1H), 8.23 (s, 1H), 8.20-8.14 (m, 1H), 8.08-8.05 (dd, J=8.28, 1.23 Hz, 1H), 4.85-4.32 (m, 2H), 3.39 (s, 2H), 2.00-1.90 (m, 2H), 1.86-1.82 (m, 2H), 1.18 (s, 6H). mGluR5 PAM EC$_{50}$: +++++.

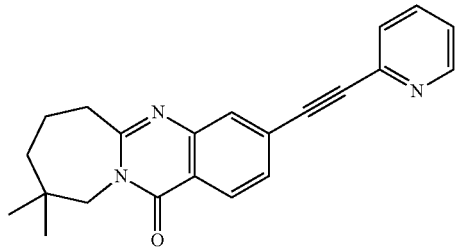 [SMILES: CC1(C)CCCc2nc3cc(C#Cc4ccccn4)ccc3c(=O)n2C1]

9,9-dimethyl-3-(pyridin-2-ylethynyl)-7,8,9,10-tetrahydroazepino[2,1-b]quinazolin-12(6H)-one MS (ESI): 344 (MH$^+$); $^1$H NMR (300 MHz, CD$_3$OD) δ 8.91 (s, H), 8.58-8.53 (t, J=7.46 Hz, 1H), 8.44-8.41 (d, J=8.28 Hz, 1H), 8.28-8.25 (d, J=8.01 Hz, 1H), 8.11 (s, 1H), 8.05-7.99 (m, 2H), 4.65-4.01 (broad s, 2H), 3.32 (s, 2H), 2.05 (broad s, 2H), 1.78-1.74 (t, J=11.77 Hz, 2H), 1.19-1.05 (s, 6H). mGluR5 PAM EC$_{50}$: ++++. Fold shift at 10 μM: +++.

Example 6.38. Synthesis of 3-(pyridin-2-ylethynyl)-8-(trifluoromethyl)-7,8,9,10-tetrahydroazepino[2,1-b]quinazolin-12(6H)-one

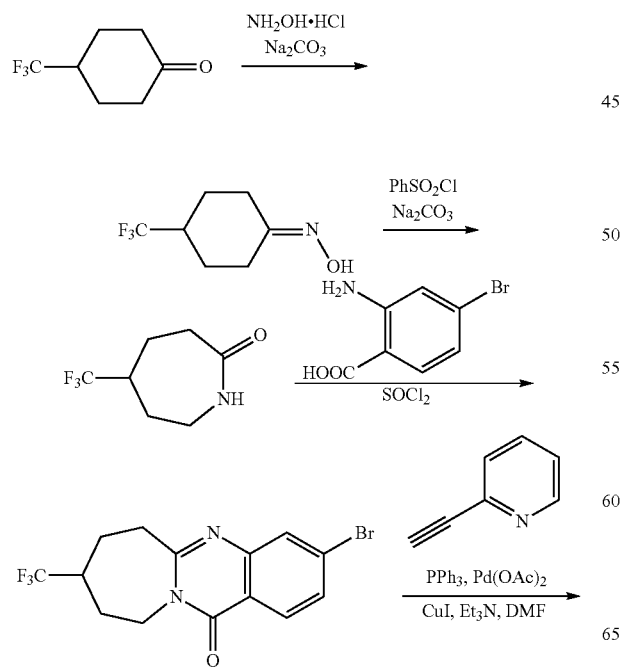

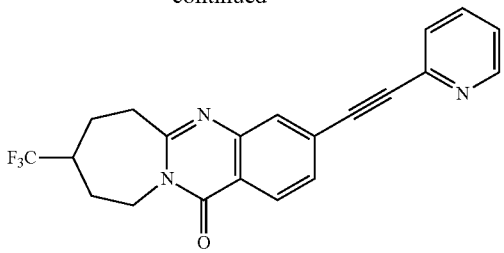

The title compound was prepared according to the experimental procedure as described in Example 4.11a, Example 4.11b, Example 2.2a and Example 1.1. MS (ESI): 384 (MH$^+$); $^1$H NMR (300 MHz, CD$_3$OD) δ 8.93-8.91 (d, J=5.04 Hz, 1H), 8.64-8.58 (t, J=6.6 Hz, 1H), 8.46-8.43 (d, J=8.31 Hz, 1H), 8.32-8.29 (d, J=8.04 Hz, 1H), 8.10-7.99 (m, 3H), 5.40-5.32 (dd, J=15.0, 5.0 Hz, 1H), 3.95-3.87 (dd, J=15.0, 11.1 Hz, 1H), 3.54-3.31 (m, 2H), 2.94-2.83 (m, 1H), 2.42-2.41 (m, 2H), 1.99-1.86 (m, 1H), 1.81-1.69 (m, 1H). mGluR5 PAM EC$_{50}$: +++. Fold shift at 10 μM: +++.

Example 6.38a and Example 6.38b. Separation of 3-(pyridin-2-ylethynyl)-8-(trifluoromethyl)-7,8,9,10-tetrahydroazepino[2,1-b]quinazolin-12(6H)-one into (S)-3-(pyridin-2-ylethynyl)-8-(trifluoromethyl)-7,8,9,10-tetrahydroazepino[2,1-b]quinazolin-12(6H)-one and (R)-3-(pyridin-2-ylethynyl)-8-(trifluoromethyl)-7,8,9,10-tetrahydroazepino[2,1-b]quinazolin-12(6H)-one

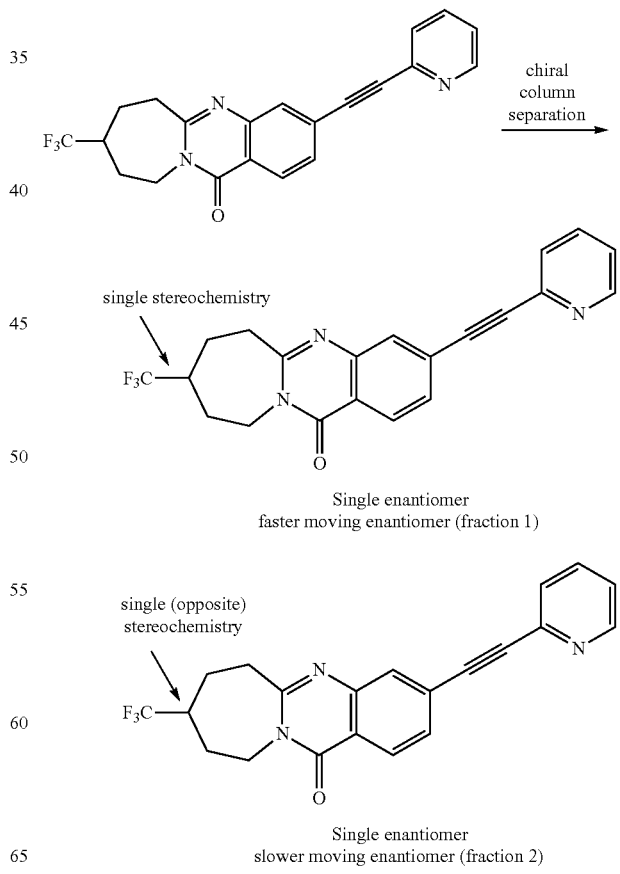

Racemic 3-(pyridin-2-ylethynyl)-8-(trifluoromethyl)-7,8,9,10-tetrahydroazepino[2,1-b]quinazolin-12(6H)-one was separated into the corresponding two single enantiomer compounds (S)-3-(pyridin-2-ylethynyl)-8-(trifluoromethyl)-7,8,9,10-tetrahydroazepino[2,1-b]quinazolin-12(6H)-one and (R)-(pyridin-2-ylethynyl)-8-(trifluoromethyl)-7,8,9,10-tetrahydroazepino[2,1-b]quinazolin-12(6H)-one using chiral chromatography with an isocratic SFC method. The column used was a 4.6×100 mm RegisPack from Regis Technologies (Morton Grove, Ill.). The $CO_2$ co-solvent was methanol:isopropanol (1:3) with 0.1% isopropylamine. Isocratic Method: 40% Co-solvent at 4 mL/min. System Pressure: 100 bar. Column Temperature 25° C.

Faster moving enantiomer of 3-(pyridin-2-ylethynyl)-8-(trifluoromethyl)-7,8,9,10-tetrahydroazepino[2,1-b]quinazolin-12(6H)-one (fraction 1): Retention time=1.4 min 100% ee.

Slower moving enantiomer of 3-(pyridin-2-ylethynyl)-8-(trifluoromethyl)-7,8,9,10-tetrahydroazepino[2,1-b]quinazolin-12(6H)-one (fraction 2): Retention time=2.5 min 99.1% ee.

Example 6.39. Synthesis of the HCl Salt of 12-oxo-3-(pyridin-2-ylethynyl)-6,7,8,9,10,12-hexahydroazepino[2,1-b]quinazoline-8-carbonitrile Example 6.39a. Synthesis of 3-bromo-12-oxo-6,7,8,9,10,12-hexahydroazepino[2,1-b]quinazolin-8-yl methanesulfonate

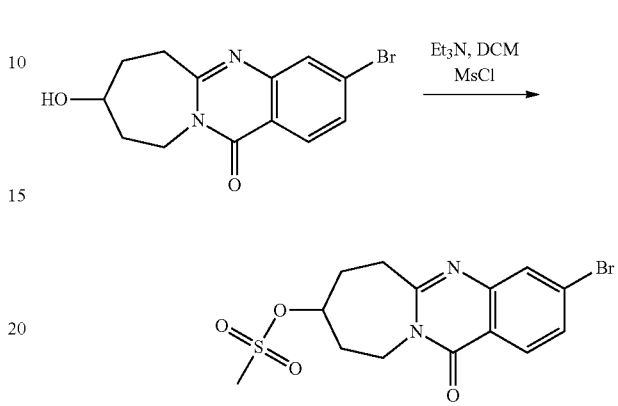

To a stirred solution of 3-bromo-8-hydroxy-7,8,9,10-tetrahydroazepino[2,1-b]quinazolin-12(6H)-one (290 mg, 0.938 mmol) and excess $Et_3N$ in DCM (10 mL) was added Ms-Cl (0.76 mL). The mixture was stirred for 1.5 h at room temperature. Then the reaction mixture was diluted with water and extracted with EtOAc (3×50 mL). The combined organic layers were dried over $Na_2SO_4$. After filtration and concentration, the crude product was directly used for the next step. MS (ESI): 387, 389 ($MH^+$).

Example 6.39b. Synthesis of 3-bromo-12-oxo-6,7,8,9,10,12-hexahydroazepino[2,1-b]quinazoline-8-carbonitrile

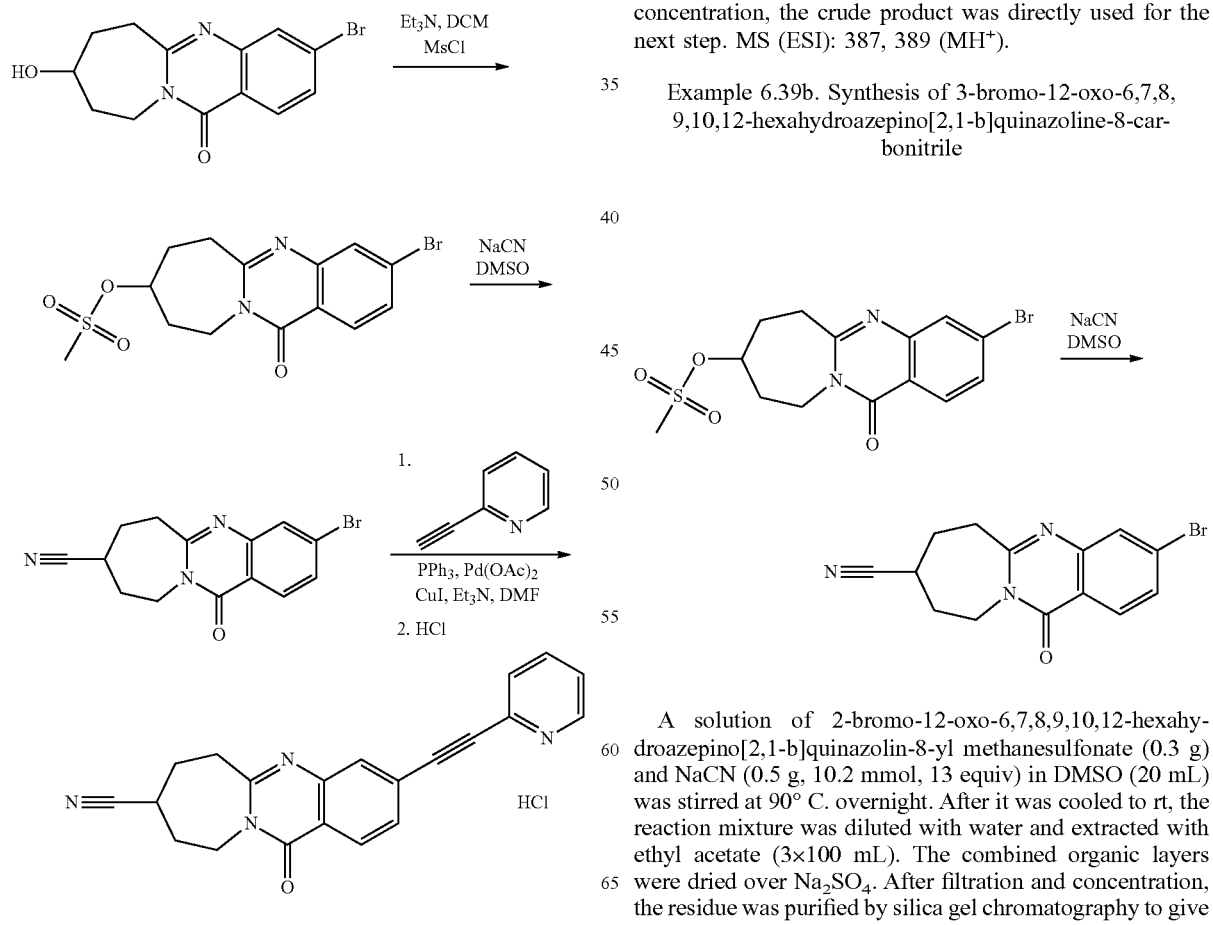

A solution of 2-bromo-12-oxo-6,7,8,9,10,12-hexahydroazepino[2,1-b]quinazolin-8-yl methanesulfonate (0.3 g) and NaCN (0.5 g, 10.2 mmol, 13 equiv) in DMSO (20 mL) was stirred at 90° C. overnight. After it was cooled to rt, the reaction mixture was diluted with water and extracted with ethyl acetate (3×100 mL). The combined organic layers were dried over $Na_2SO_4$. After filtration and concentration, the residue was purified by silica gel chromatography to give 36 mg of the desired product.

Example 6.39c. Synthesis of the HCl Salt of 12-oxo-3-(pyridin-2-ylethynyl)-6,7,8,9,10,12-hexahydroazepino[2,1-b]quinazoline-8-carbonitrile

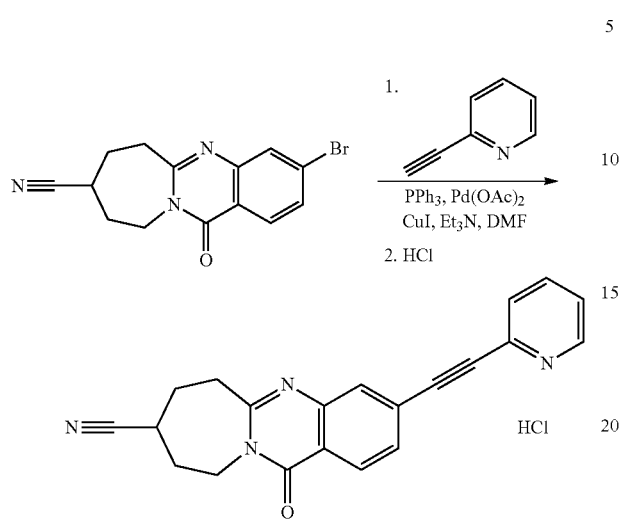

The title compound was prepared according to the experimental procedure as described in Example 1.1. The product was then converted to the corresponding HCl salt. MS (ESI): 341 (MH+); $^1$H NMR (300 MHz, CDCl$_3$) δ 8.68-8.67 (d, J=4.83 Hz, 1H), 8.26-8.23 (d, J=8.25 Hz, 1H), 7.84 (s, 1H), 7.77-7.75 (t, J=7.8 Hz, 1H), 7.67-7.64 (d, J=8.22 Hz, 1H), 7.61-7.58 (d, J=7.8 Hz, 1H), 7.34-7.28 (m, 1H), 4.71 (br s, 1H), 4.37 (br s, 1H), 3.41-3.33 (m, 1H), 3.19-3.09 (m, 2H), 2.30-2.20 (m, 3H), 2.17-2.07 (m, 1H). mGluR5 PAM EC$_{50}$: ++.

Example 6.40. Synthesis of 8,8-dimethyl-3-(pyridin-2-ylethynyl)-7,8,9,10-tetrahydroazepino[2,1-b]quinazolin-12(6H)-one

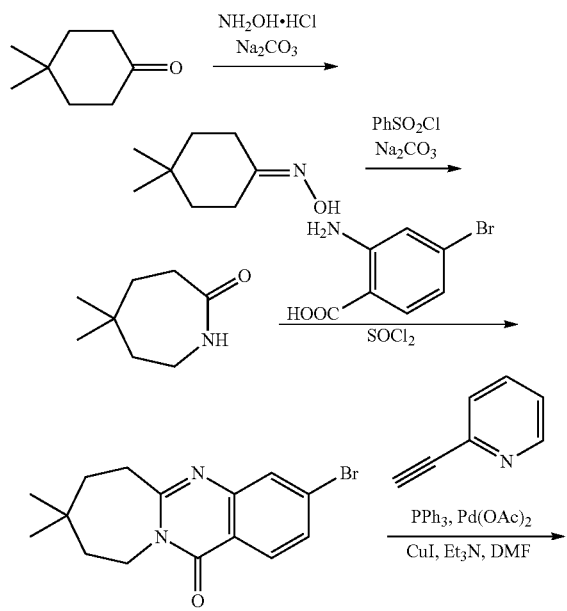

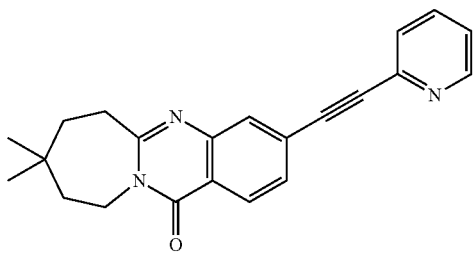

The title compound was prepared according to the experimental procedure as described in Example 4.11a, Example 4.11b, Example 2.2a and Example 1.1. MS (ESI): 344 (MH+); $^1$H NMR (300 MHz, CD$_3$OD) δ 8.97-8.95 (d, J=5.79 Hz, 1H), 8.70-8.66 (t, J=7.99 Hz, 1H), 8.47-8.44 (d, J=8.28 Hz, 1H), 8.39-8.36 (d, J=8.01 Hz, 1H), 8.15-8.11 (m, 2H), 8.06-8.03 (dd, J=8.30, 1.31 Hz, 1H), 4.52 (broad, 2H), 3.39-3.31 (m, 2H), 1.89-1.86 (d, J=11.4 Hz, 2H), 1.73-1.70 (t, J=5.1 Hz, 2H), 1.14 (s, 6H). mGluR5 PAM EC$_{50}$: +++++. Fold shift at 10 μM: +++.

Example 6.41. Synthesis of 8,8-difluoro-3-(pyridin-2-ylethynyl)-7,8,9,10-tetrahydroazepino[2,1-b]quinazolin-12(6H)-one

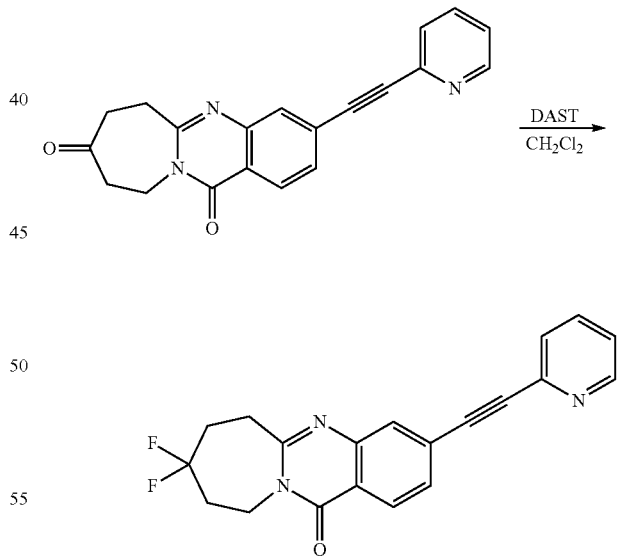

The title compound was prepared according to the experimental procedure as described in Example 4.41. MS (ESI): 352 (MH+); $^1$H NMR (300 MHz, CD$_3$OD) δ 8.93-8.91 (d, J=5.70 Hz, 1H), 8.65-8.59 (t, J=7.91 Hz, 1H), 8.44-8.41 (d, J=8.25 Hz, 1H), 8.32-8.29 (d, J=8.01 Hz, 1H), 8.29-8.10 (m, 2H), 8.07-7.96 (d, J=8.31 Hz, 1H), 4.59-4.58 (m, 2H), 3.41-3.36 (m, 2H), 2.56-2.38 (m, 4H). mGluR5 PAM EC$_{50}$: ++++. Fold shift at 10 μM: +++.

Example 6.44. Synthesis of 10-methyl-3-(pyridin-2-ylethynyl)-7,8,9,10-tetrahydroazepino[2,1-b]quinazolin-12(6H)-one

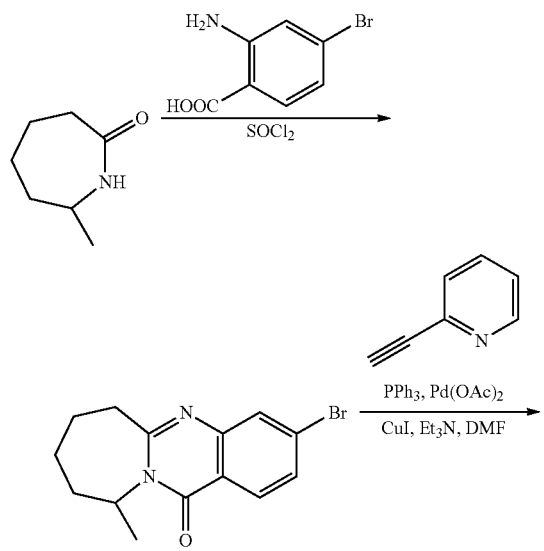

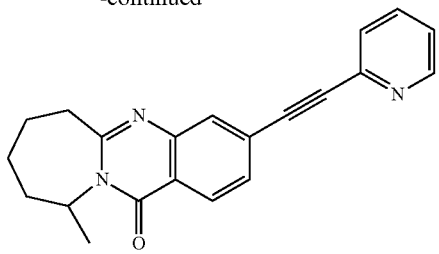

The title compound was prepared according to the experimental procedure as described in Example 2.2a and Example 1.1. MS (ESI): 330 (MH+); ¹H NMR (300 MHz, CD₃OD) δ 8.86-8.85 (d, J=5.34 Hz, 1H), 8.49-8.42 (m, 2H), 8.19-8.17 (d, J=7.80 Hz, 1H), 8.03-7.92 (m, 3H), 5.93-5.91 (m, 1H), 3.60-3.49 (m, 2H), 2.25-2.18 (m, 1H), 2.13-2.08 (m, 2H), 2.00-1.84 (m, 3H), 1.63-1.61 (d, J=7.35 Hz, 3H). mGluR5 PAM EC₅₀: +++++. Fold shift at 10 μM: ++.

Example 6.44a and Example 6.44b. Separation of 10-methyl-3-(pyridin-2-ylethynyl)-7,8,9,10-tetrahydroazepino[2,1-b]quinazolin-12(6H)-one into (S)-10-methyl-3-(pyridin-2-ylethynyl)-7,8,9,10-tetrahydroazepino[2,1-b]quinazolin-12(6H)-one and (R)-10-methyl-3-(pyridin-2-ylethynyl)-7,8,9,10-tetrahydroazepino[2,1-b]quinazolin-12(6H)-one

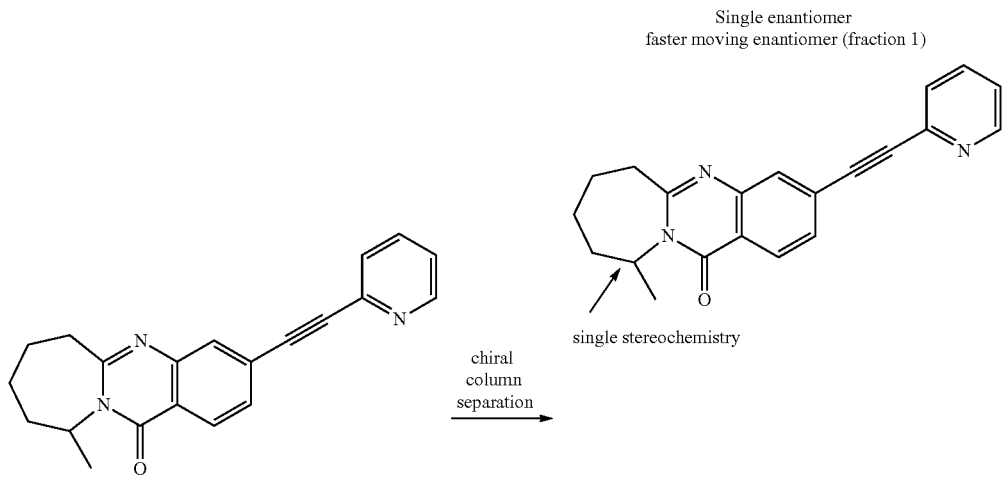

Single enantiomer
faster moving enantiomer (fraction 1)

single stereochemistry

Single enantiomer
slower moving enantiomer (fraction 2)

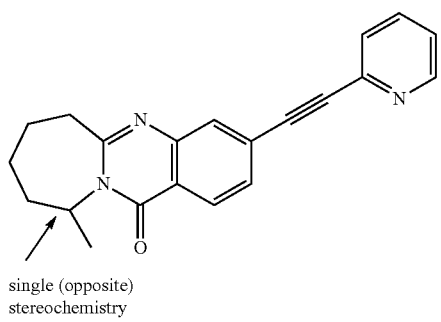

single (opposite) stereochemistry

Racemic 10-methyl-3-(pyridin-2-ylethynyl)-7,8,9,10-tetrahydroazepino[2,1-b]quinazolin-12(6H)-one was separated into the corresponding two single enantiomer compounds (S)-10-methyl-3-(pyridin-2-ylethynyl)-7,8,9,10-tetrahydroazepino[2,1-b]quinazolin-12(6H)-one and (R)-10-methyl-3-(pyridin-2-ylethynyl)-7,8,9,10-tetrahydroazepino[2,1-b]quinazolin-12(6H)-one using chiral chromatography with an isocratic SFC method. The column used was a 4.6×100 mm RegisPack from Regis Technologies (Morton Grove, Ill.). The $CO_2$ co-solvent was methanol:isopropanol (2:1) with 0.1% isopropylamine. Isocratic Method: 55% Co-solvent at 4 mL/min System Pressure: 100 bar. Column Temperature 25° C.

Faster moving enantiomer of 10-methyl-3-(pyridin-2-ylethynyl)-7,8,9,10-tetrahydroazepino[2,1-b]quinazolin-12(6H)-one (fraction 1): Retention time=1.3 min 99.3% ee. Slower moving enantiomer of 10-methyl-3-(pyridin-2-ylethynyl)-7,8,9,10-tetrahydroazepino[2,1-b]quinazolin-12(6H)-one (fraction 2): Retention time=1.9 min 99.4% ee.

Example 6.45. Synthesis of the HCl Salt of 6-((12-oxo-6,7,8,9,10,12-hexahydroazepino[2,1-b]quinazolin-3-yl)ethenyl)picolinonitrile

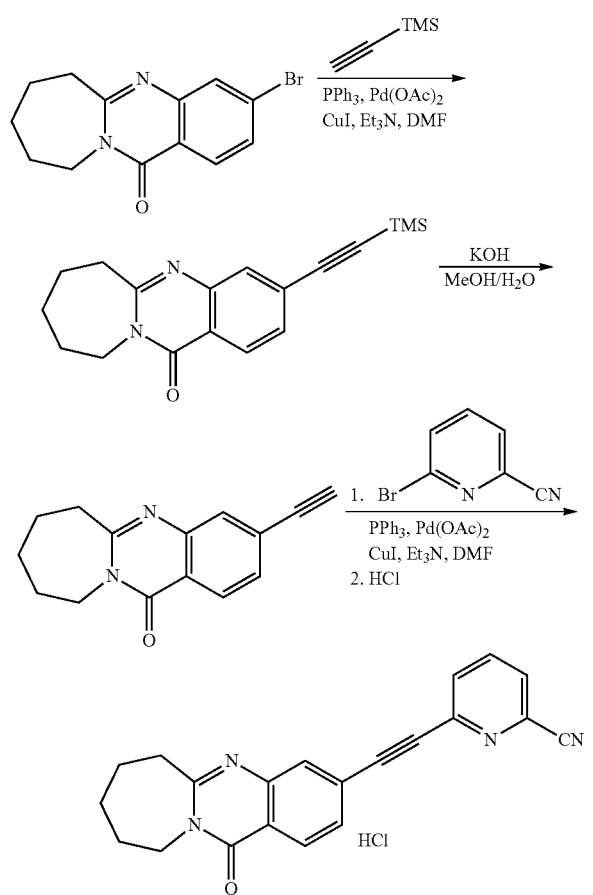

The title compound was prepared according to the experimental procedure as described in Example 5.1d, Example 5.1e, and Example 1.1. The product was then converted to the corresponding HCl salt. MS (ESI): 341 (MH$^+$); $^1$H NMR (300 MHz, CD$_3$OD) δ 8.40-8.37 (d, J=8.2 Hz, 1H), 8.14-8.09 (t, J=7.8 Hz, 1H), 7.99-7.92 (m, 4H), 4.57-4.54 (m, 2H), 3.55-3.40 (m, 2H), 2.04-1.89 (m, 6H). mGluR5 PAM EC$_{50}$: ++++. Fold shift at 10 μM: +++.

Example 6.46. Synthesis of 8-fluoro-3-(pyridin-2-ylethynyl)-7,8,9,10-tetrahydroazepino[2,1-b]quinazolin-12(6H)-one

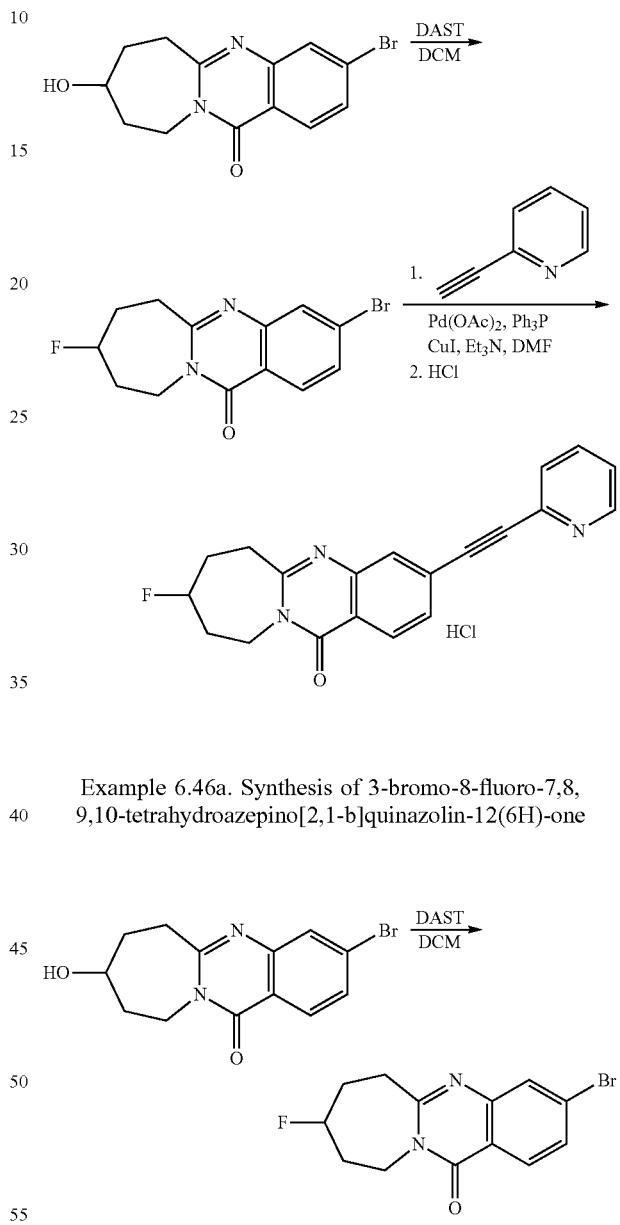

Example 6.46a. Synthesis of 3-bromo-8-fluoro-7,8,9,10-tetrahydroazepino[2,1-b]quinazolin-12(6H)-one To a stirred solution of 3-bromo-8-hydroxy-7,8,9,10-tetrahydroazepino[2,1-b]-quinazolin-12(6H)-one (200 mg, 0.64 mmol, 1 equiv) in DCM was added excess DAST under N$_2$ at −78° C. After that, the resulting mixture was stirred at −78° C. for 3 h. The reaction mixture was quenched with water (20 mL) and extracted with ethyl acetate (3×20 mL). The combined organic extract was dried over Na$_2$SO$_4$. After filtration and concentration, the crude product was purified by silica gel chromatography to give 200 mg of the desired product. MS (ESI): 311, 313 (MH$^+$).

Example 6.46b. Synthesis of the HCl Salt of 8-fluoro-3-(pyridin-2-ylethynyl)-7,8,9,10-tetrahydroazepino[2,1-b]quinazolin-12(6H)-one

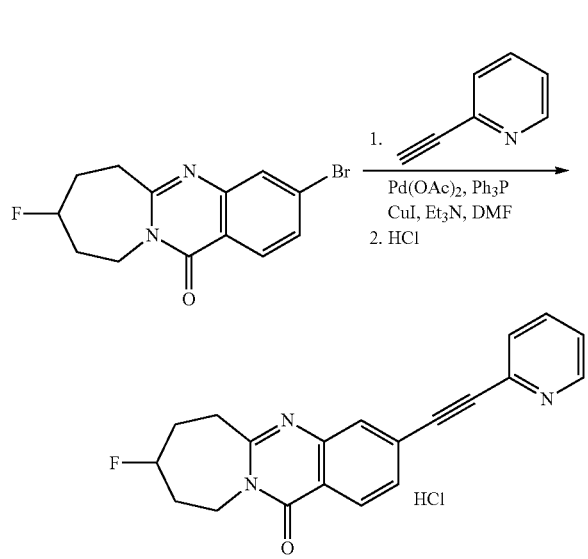

The title compound was prepared according to the experimental procedure as described in Example 1.1. The product was then converted to the corresponding HCl salt. MS (ESI): 334 (MH+); ¹H NMR (300 MHz, CD₃OD) δ 8.89-8.88 (d, J=5.25 Hz, 1H), 8.54-8.51 (t, J=8.10 Hz, 1H), 8.44-8.42 (d, J=8.25 Hz, 1H), 8.25-8.22 (d, J=7.98 Hz, 1H), 8.03-7.97 (m, 3H), 4.91-4.85 (m, 1H), 4.47-4.34 (t, J=18.60 Hz, 1H), 3.77-3.64 (t, J=18.70 Hz, 1H), 3.19-3.17 (m, 1H), 2.54-2.22 (m, 3H), 2.21-1.95 (m, 2H). mGluR5 PAM EC$_{50}$: +++++. Fold shift at 10 μM: ++.

Example 6.47. Synthesis of the HCl Salt of 6-((8-methyl-12-oxo-6,7,8,9,10,12-hexahydroazepino[2,1-b]quinazolin-3-yl)ethynyl)picolinonitrile

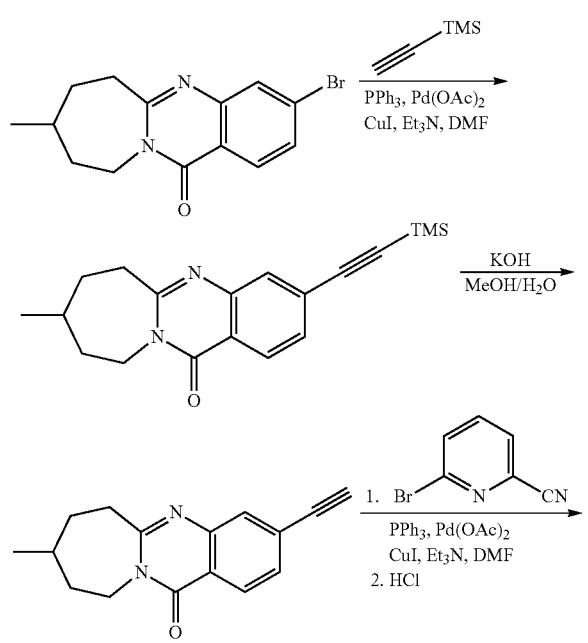

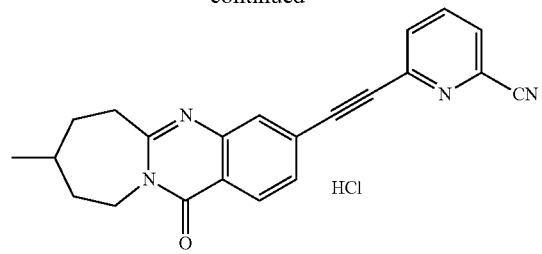

The title compound was prepared according to the experimental procedure as described in Example 5.1d, Example 5.1e, and Example 1.1. The product was then converted to the corresponding HCl salt. MS (ESI): 355 (MH+); ¹H NMR (300 MHz, CD₃OD) δ 8.40-8.37 (d, J=8.1 Hz, 1H), 8.14-8.09 (t, J=7.8 Hz, 1H), 7.99-7.92 (m, 4H), 5.20-5.18 (m, 1H), 3.93-3.88 (m, 1H), 3.45-3.40 (m, 1H), 3.26-3.23 (m, 1H), 2.16-2.09 (m, 3H), 1.64-1.56 (m, 1H), 1.40-1.30 (m, 1H), 1.07-1.04 (d, J=6.5 Hz, 3H). mGluR5 PAM EC$_{50}$: +++. Fold shift at 10 μM: +++.

Example 6.48. Synthesis of the HCl Salt of 8-fluoro-8-methyl-3-(pyridin-2-ylethynyl)-7,8,9,10-tetrahydroazepino[2,1-b]quinazolin-12(6H)-one

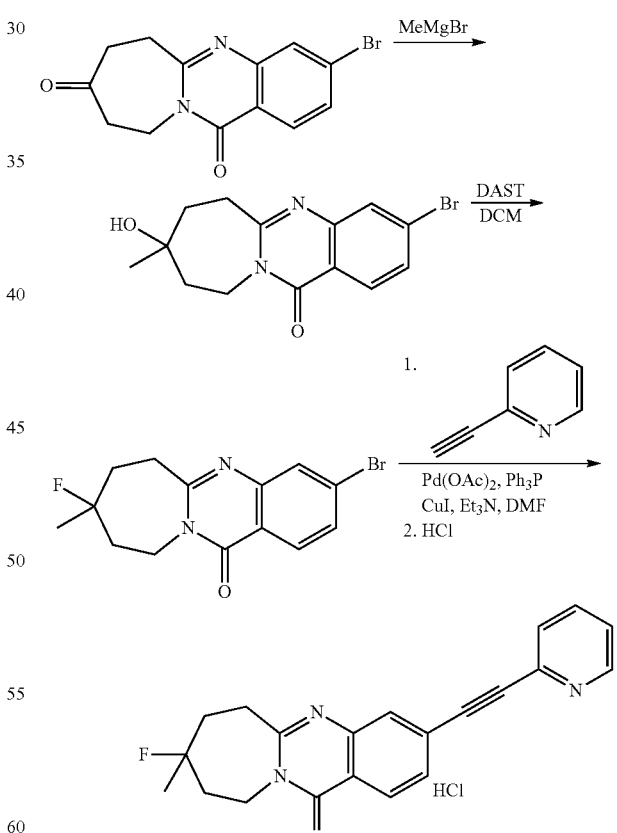

The title compound was prepared according to the experimental procedure as described in Example 4.45, Example 6.46, and Example 1.1. The product was then converted to the corresponding HCl salt. MS (ESI): 348 (MH+); ¹H NMR (300 MHz, DMSO-d⁶) δ 8.68-8.67 (d, J=4.23 Hz, 1H), 8.20-8.18 (d, J=8.22 Hz, 1H), 7.99-7.93 (td, J=7.80, 1.80 Hz, 1H), 7.90 (s, 1H), 7.81-7.78 (d, J=7.80 Hz, 1H), 7.74-7.71 (dd, J=8.22, 1.38 Hz, 1H), 7.55-7.50 (t, J=6.00 Hz, 1H), 4.84-4.77 (dd, J=14.70, 5.10 Hz, 1H), 3.99-3.90 (dd, J=12.00, 14.70 Hz, 1H), 3.43-3.39 (d, J=13.20 Hz, 1H), 2.97-2.90 (dd, J=6.30, 14.40 Hz, 1H), 2.21-2.16 (m, 2H), 1.97-1.75 (m, 2H), 1.39-1.32 (d, J=21.60 Hz, 3H). mGluR5 PAM EC$_{50}$: +++++. Fold shift at 10 μM: +++.

Example 6.48a and Example 6.48b. Separation of 8-fluoro-8-methyl-3-(pyridin-2-ylethynyl)-7,8,9,10-tetrahydroazepino[2,1-b]quinazolin-12(6H)-one into (S)-8-fluoro-8-methyl-3-(pyridin-2-ylethynyl)-7,8,9,10-tetrahydroazepino[2,1-b]quinazolin-12(6H)-one and (R)-8-fluoro-8-methyl-3-(pyridin-2-ylethynyl)-7,8,9,10-tetrahydroazepino[2,1-b]quinazolin-12(6H)-one

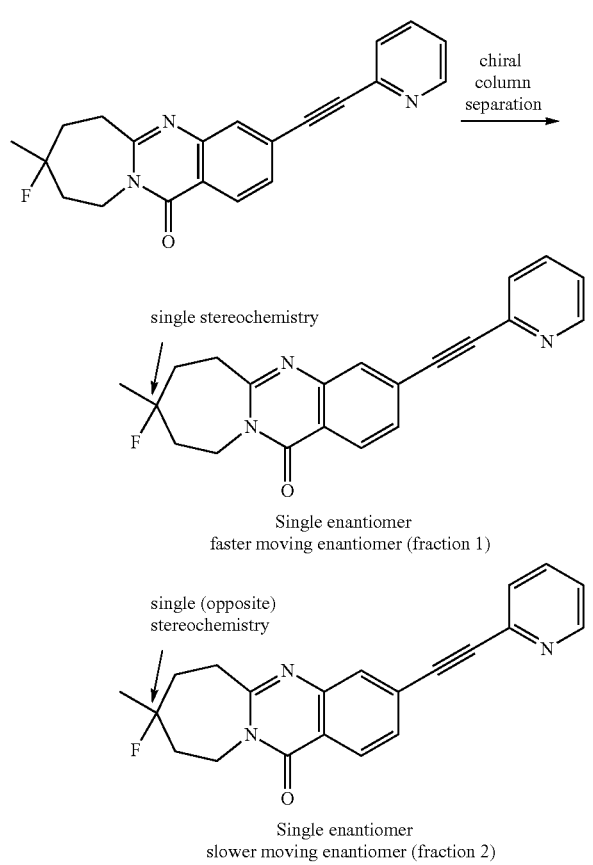

Racemic 8-fluoro-8-methyl-3-(pyridin-2-ylethynyl)-7,8,9,10-tetrahydroazepino[2,1-b]quinazolin-12(6H)-one was separated into the corresponding two single enantiomer compounds (S)-8-fluoro-8-methyl-3-(pyridin-2-ylethynyl)-7,8,9,10-tetrahydroazepino[2,1-b]quinazolin-12(6H)-one and (R)-8-fluoro-8-methyl-3-(pyridin-2-ylethynyl)-7,8,9,10-tetrahydroazepino[2,1-b]quinazolin-12(6H)-one using chiral chromatography with an isocratic SFC method. The column used was a 4.6×100 mm RegisPack from Regis Technologies (Morton Grove, Ill.). The CO$_2$ co-solvent was methanol:isopropanol (1:3) with 0.1% isopropylamine. Isocratic Method: 50% Co-solvent at 4 mL/min. System Pressure: 100 bar. Column Temperature 25° C.

Faster moving enantiomer of 8-fluoro-8-methyl-3-(pyridin-2-ylethynyl)-7,8,9,10-tetrahydroazepino[2,1-b]quinazolin-12(6H)-one (fraction 1): Retention time=1.0 min 96.4% ee. mGluR5 PAM EC$_{50}$: +++++. Fold shift at 10 μM: +++.

Slower moving enantiomer of 8-fluoro-8-methyl-3-(pyridin-2-ylethynyl)-7,8,9,10-tetrahydroazepino[2,1-b]quinazolin-12(6H)-one (fraction 2): Retention time=2.2 min 96.0% ee. mGluR5 PAM EC$_{50}$: +++++. Fold shift at 10 μM: ++.

Example 6.49. Synthesis of the HCl Salt of 8-hydroxy-8-methyl-3-(pyridin-2-ylethynyl)-7,8,9,10-tetrahydroazepino[2,1-b]quinazolin-12(6H)-one

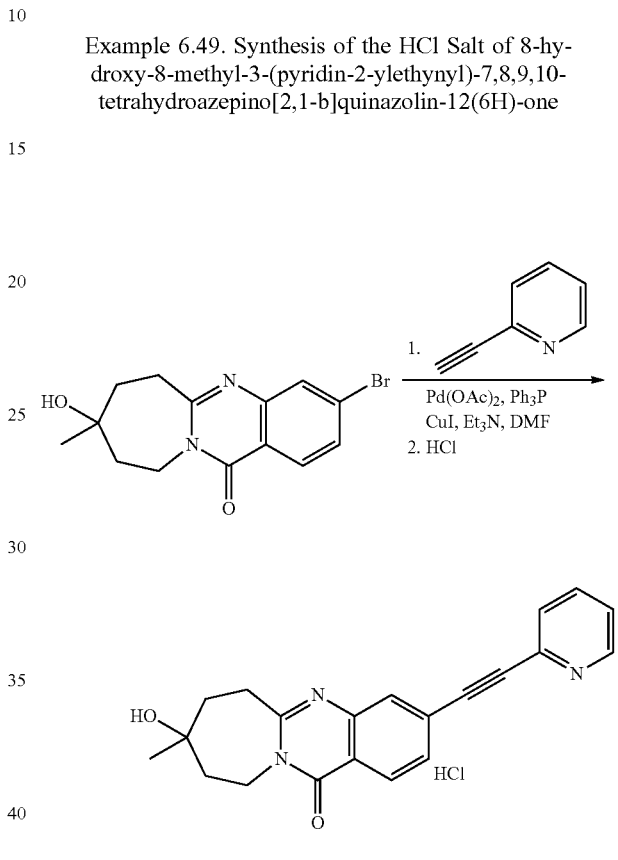

The title compound was prepared according to the experimental procedure as described in Example 1.1. The product was then converted to the corresponding HCl salt. MS (ESI): 346 (MH+); $^1$H NMR (300 MHz, DMSO-d$^6$) δ 8.68-8.67 (d, J=4.50 Hz, 1H), 8.21-8.18 (d, J=8.25 Hz, 1H), 7.94-7.81 (m, 2H), 7.81-7.74 (dd, J=7.80, 12.30 Hz, 2H), 7.54-7.50 (m, 1H), 4.74-4.69 (t, J=8.10 Hz, 1H), 4.03-3.94 (t, J=10.80 Hz, 1H), 3.54-3.45 (t, J=13.20 Hz, 1H), 2.97-2.89 (dd, J=14.40, 6.95 Hz, 1H), 1.84-1.78 (m, 3H), 1.65-1.57 (m, 1H), 1.15 (s, 3H). mGluR5 PAM EC$_{50}$: ++ Fold shift at 10 μM: +++.

Example 6.50. Synthesis of the HCl Salt of 8-methoxy-8-methyl-3-(pyridin-2-ylethynyl)-7,8,9,10-tetrahydroazepino[2,1-b]quinazolin-12(6H)-one

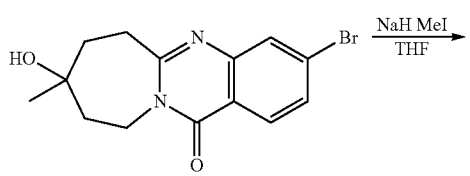

-continued

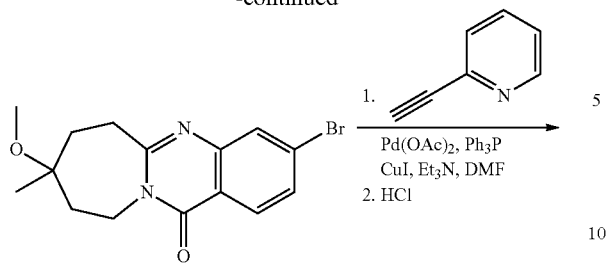

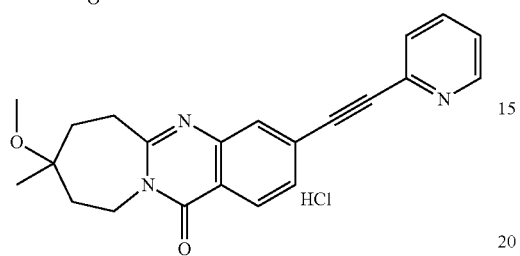

The title compound was prepared according to the experimental procedure as described in Example 4.46, and Example 1.1. The product was then converted to the corresponding HCl salt. MS (ESI): 360 (MH+). MS (ESI): 360 (MH+); $^1$H NMR (300 MHz, DMSO-d$^6$) δ 8.69-8.68 (d, J=4.62 Hz, 1H), 8.22-8.19 (d, J=8.25 Hz, 1H), 7.99-7.95 (m, 2H), 7.83-7.76 (dd, J=11.40, 8.10 Hz, 2H), 7.56-7.52 (m, 1H), 4.78-4.76 (m, 1H), 3.91-3.82 (t, J=11.70 Hz, 1H), 3.41-3.32 (t, J=13.80 Hz, 1H), 3.18 (s, 3H), 3.02-2.94 (dd, J=13.50, 6.90 Hz, 1H), 2.16-2.02 (m, 2H), 1.80-1.71 (t, J=13.50 Hz, 1H), 1.65-1.56 (t, J=12.90 Hz, 1H), 1.11 (s, 3H). mGluR5 PAM EC$_{50}$: +++. Fold shift at 10 μM: ++.

Example 6.50a and Example 6.50b. Separation of 8-methoxy-8-methyl-3-(pyridin-2-ylethynyl)-7,8,9,10-tetrahydroazepino[2,1-b]quinazolin-12(6H)-one into (S)-8-methoxy-8-methyl-3-(pyridin-2-ylethynyl)-7,8,9,10-tetrahydroazepino[2,1-b]quinazolin-12(6H)-one and (R)-8-methoxy-8-methyl-3-(pyridin-2-ylethynyl)-7,8,9,10-tetrahydroazepino[2,1-b]quinazolin-12(6H)-one -continued

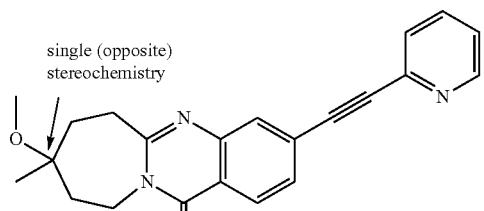

Racemic 8-methoxy-8-methyl-3-(pyridin-2-ylethynyl)-7,8,9,10-tetrahydroazepino[2,1-b]quinazolin-12(6H)-one was separated into the corresponding two single enantiomer compounds (S)-8-methoxy-8-methyl-3-(pyridin-2-ylethynyl)-7,8,9,10-tetrahydroazepino[2,1-b]quinazolin-12(6H)-one and (R)-8-methoxy-8-methyl-3-(pyridin-2-ylethynyl)-7,8,9,10-tetrahydroazepino[2,1-b]quinazolin-12(6H)-one using chiral chromatography with an isocratic SFC method. The column used was a 4.6×100 mm RegisPack from Regis Technologies (Morton Grove, Ill.). The CO$_2$ co-solvent was methanol:isopropanol (1:1) with 0.1% isopropylamine. Isocratic Method: 45% Co-solvent at 4 mL/min. System Pressure: 100 bar. Column Temperature 25° C.

Faster moving enantiomer of 8-methoxy-8-methyl-3-(pyridin-2-ylethynyl)-7,8,9,10-tetrahydroazepino[2,1-b]quinazolin-12(6H)-one (fraction 1): Retention time=2.1 min 96.5% ee. mGluR5 PAM EC$_{50}$: +++. Fold shift at 10 μM: +++.

Slower moving enantiomer of 8-methoxy-8-methyl-3-(pyridin-2-ylethynyl)-7,8,9,10-tetrahydroazepino[2,1-b]quinazolin-12(6H)-one (fraction 2): Retention time=2.8 min 98.8% ee. mGluR5 PAM EC$_{50}$: ++++. Fold shift at 10 μM: ++.

Example 6.51. Synthesis of the HCl Salt of 3-(pyridin-2-ylethynyl)-9,10-dihydro-6H-spiro[azepino[2,1-b]quinazoline-8,1'-cyclopropan]-12(7H)-one

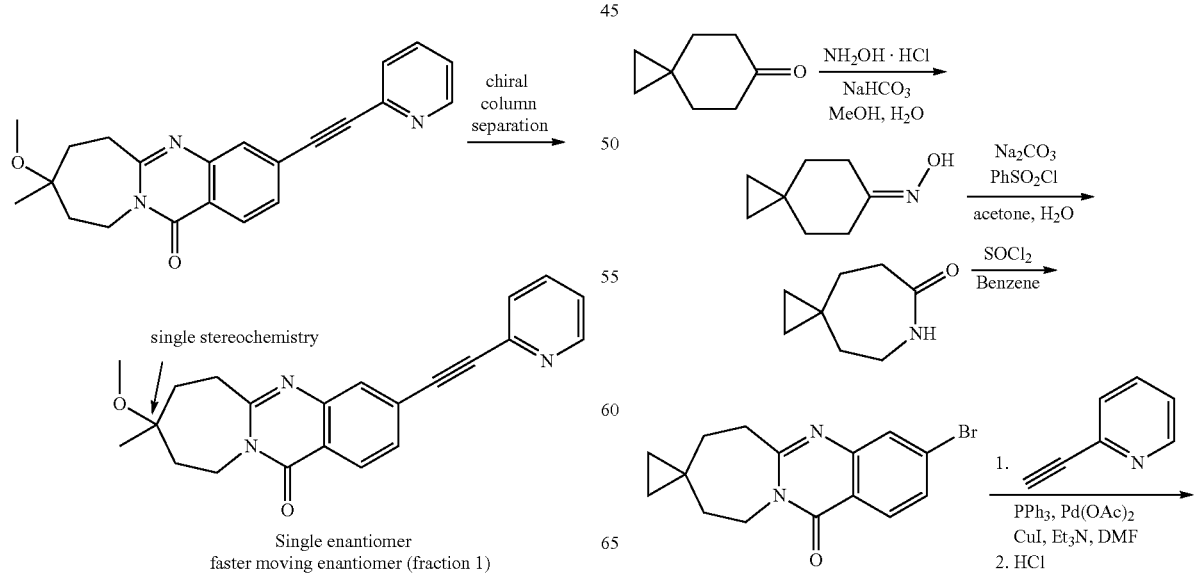

333

-continued

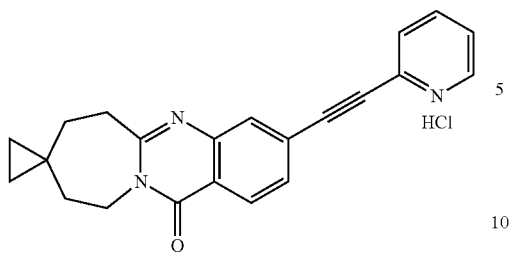

The title compound was prepared according to the experimental procedure as described in Example 4.11a, Example 4.11b, Example 2.2a, and Example 1.1. The product was then converted to the corresponding HCl salt. MS (ESI): 342 (MH⁺); ¹H NMR (300 MHz, CD₃OD) δ 8.91-8.89 (d, J=5.6 Hz, 1H), 8.61-8.53 (t, J=7.8 Hz, 1H), 8.46-8.44 (d, J=8.3 Hz, 1H), 8.28-8.25 (d, J=8.0 Hz, 1H), 8.09 (s, 1H), 8.05-8.00 (m, 2H), 4.75-4.50 (m, 2H), 3.47-3.43 (m, 2H), 1.89-1.86 (m, 2H), 1.81-1.63 (m, 2H), 0.58 (s, 4H). mGluR5 PAM EC₅₀: +++++. Fold shift at 10 μM: +++.

Example 6.52. Synthesis of 10-methyl-3-(pyridin-2-ylethynyl)-7,8,9,10-tetrahydroazepino[2,1-b]quinazolin-12(6H)-one

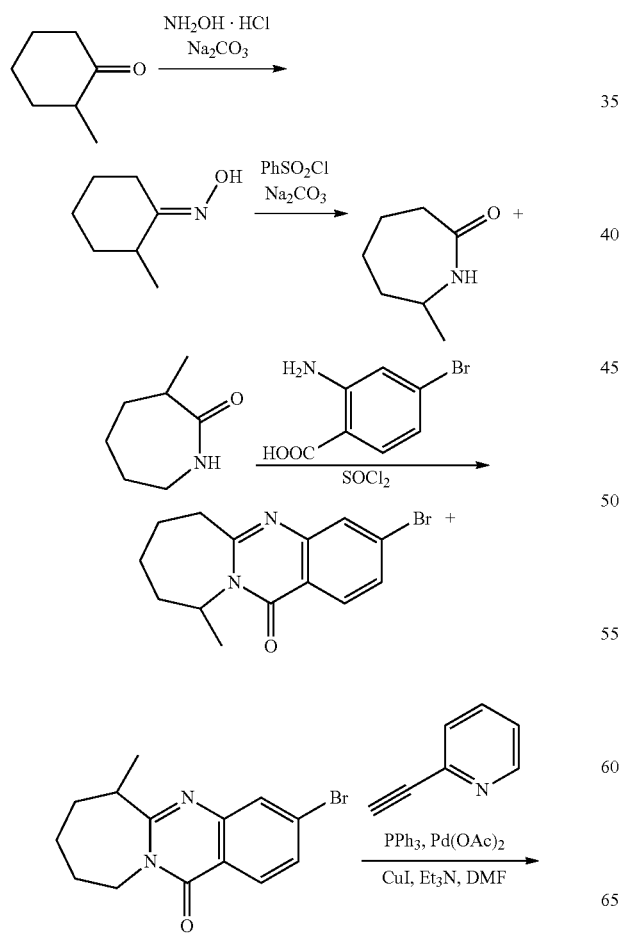

334

-continued

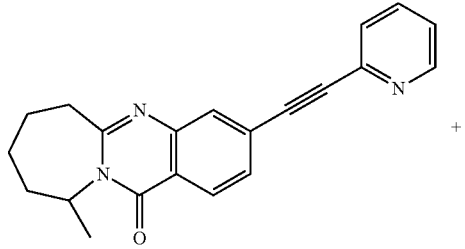

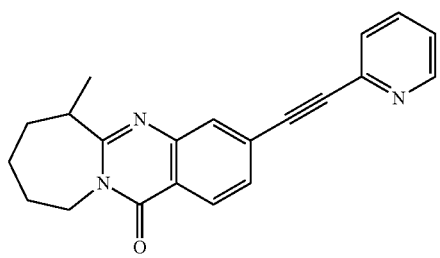

The title compound was prepared according to the experimental procedure as described in Example 4.11a, Example 4.11b, Example 2.2a and Example 1.1. The title compound was separated from 6-methyl-3-(pyridin-2-ylethynyl)-7,8,9,10-tetrahydroazepino[2,1-b]quinazolin-12(6H)-one. Data for the title compound: MS (ESI): 330 (MH⁺); ¹H NMR (300 MHz, CD₃OD) δ 8.86-8.85 (d, J=5.34 Hz, 1H), 8.49-8.42 (m, 2H), 8.19-8.17 (d, J=7.80 Hz, 1H), 8.03-7.92 (m, 3H), 5.93-5.91 (m, 1H), 3.60-3.49 (m, 2H), 2.25-2.18 (m, 1H), 2.13-2.08 (m, 2H), 2.00-1.84 (m, 3H), 1.63-1.61 (d, J=7.35 Hz, 3H).

Example 6.53. Synthesis of 1-fluoro-8-methyl-3-(pyridin-2-ylethynyl)-7,8,9,10-tetrahydroazepino[2,1-b]quinazolin-12(6H)-one

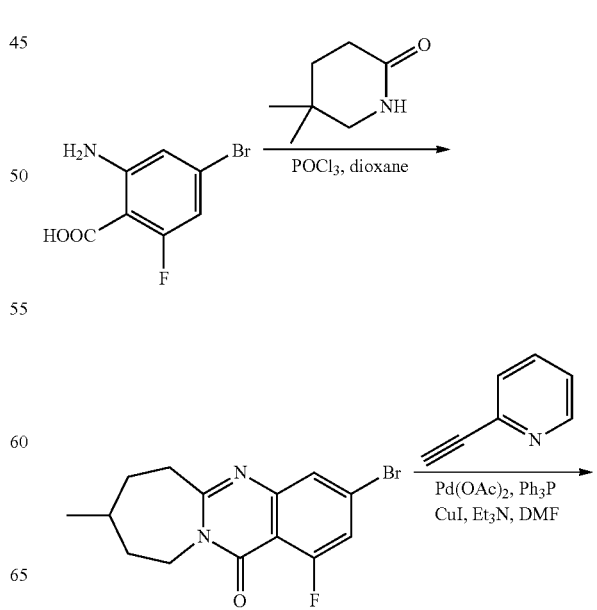

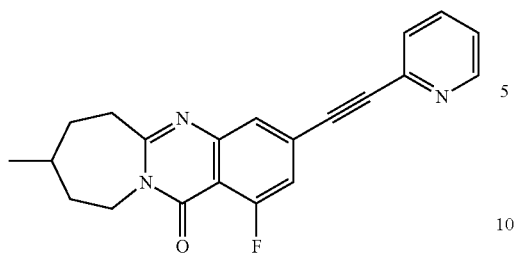

The title compound was prepared according to the experimental procedures described in Example 4.27b and Example 1.1. MS (ESI): 348 (MH⁺).

Example 6.54. Synthesis of 1-chloro-8-methyl-3-(pyridin-2-ylethynyl)-7,8,9,10-tetrahydroazepino[2,1-b]quinazolin-12(6H)-one

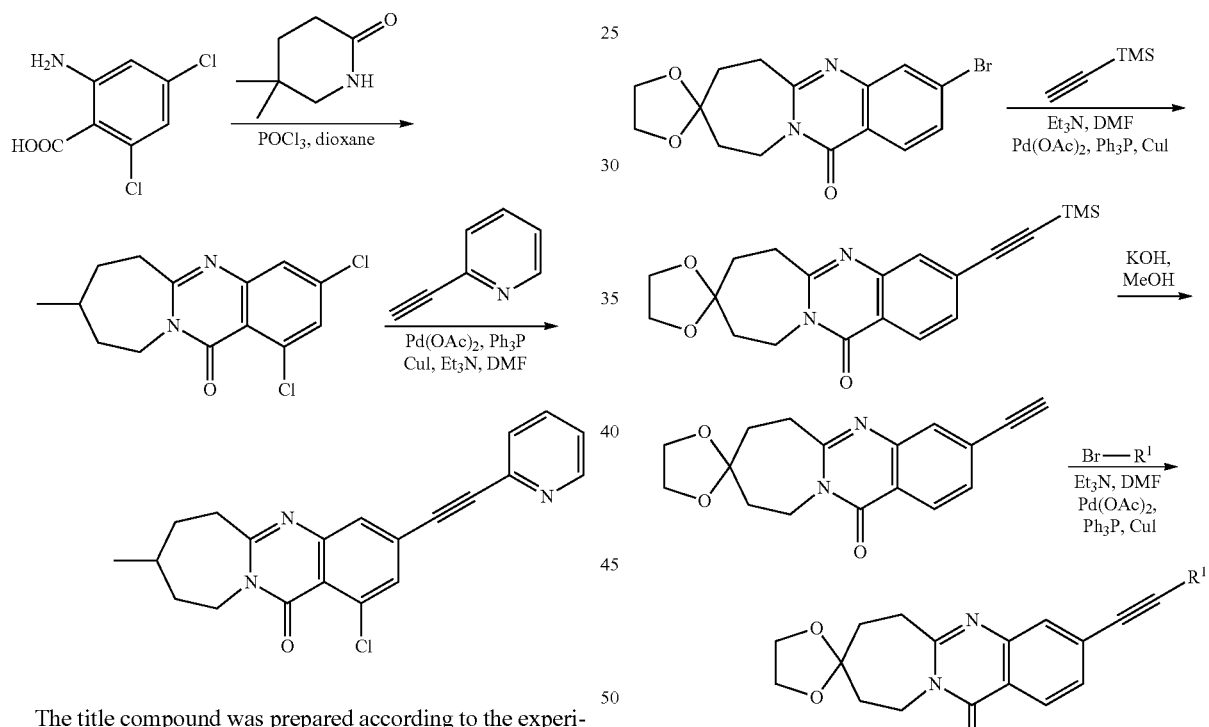

The title compound was prepared according to the experimental procedures described in Example 4.27b and Example 1.1. MS (ESI): 348 (MH⁺).

Example 7.1 Through Example 7.69

Method A:

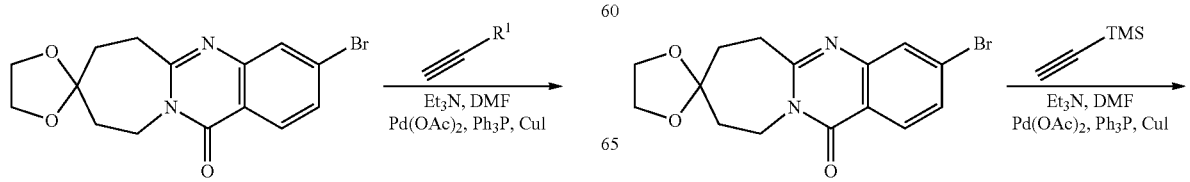

A solution of 3-bromo-9,10-dihydro-6H-spiro[azepino[2,1-b]quinazoline-8,2'-[1,3]-dioxolan]-12(7H)-one (0.1 g, 0.28 mmol, 1 equiv), the required ethyne (0.56 mmol, 2 equiv), Pd(OAc)₂ (6.3 mg, 0.028 mmol, 0.1 equiv), PPh₃ (66 mg, 0.252 mmol, 0.9 equiv), CuI (5.3 mg, 0.028 mmol, 0.1 equiv) and Et₃N (0.5 mL) in DMF (8 mL) was stirred in a sealed tube at 70° C. for 3.5 hours. After it was cooled to room temperature, the reaction mixture was diluted with H₂O and extracted with ethyl acetate (3×50 mL). The combined organic layers were washed with brine and dried over anhydrous sodium sulfate, then concentrated under reduced pressure to give the desired product, which was purified by silica gel chromatography.

Method B:

Example 7.1a. Synthesis of 3-((trimethylsilyl)ethynyl)-9,10-dihydro-6H-spiro[azepino[2,1-b]quinazoline-8,2'-[1,3]dioxolan]-12(7H)-one -continued

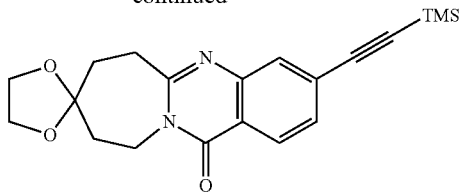

A solution of 3-bromo-9,10-dihydro-6H-spiro[azepino[2,1-b]quinazoline-8,2'-[1,3]dioxolan]-12(7H)-one (1.74 g, 4.96 mmol, 1 equiv), ethynyltrimethylsilane (972 mg, 9.92 mmol, 2 equiv), Pd(OAc)$_2$ (223.2 mg, 0.992 mmol, 0.2 equiv), PPh$_3$ (1.04 g, 3.96 mmol, 0.8 equiv), CuI (189 mg, 0.992 mmol, 0.2 equiv) and Et$_3$N (1.3 mL) in DMF (50 mL) was stirred in a sealed tube at 70° C. for 3.5 hours. After it was cooled to room temperature, the reaction mixture was diluted with H$_2$O and extracted with ethyl acetate (3×100 mL). The combined organic layers were washed with brine and dried over anhydrous sodium sulfate, then concentrated under reduced pressure. The product was obtained by silica gel chromatography purification.

Example 7.1b. Synthesis of 3-ethynyl-9,10-dihydro-6H-spiro[azepino[2,1-b]quinazoline-8,2'-[1,3]dioxolan]-12(7H)-one

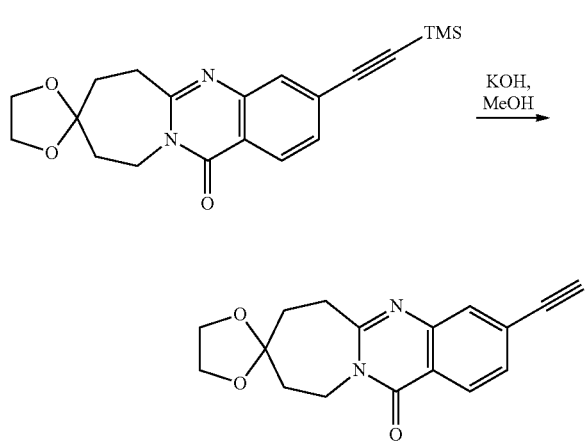

A solution of 3-((trimethylsilyl)ethynyl)-9,10-dihydro-6H-spiro[azepino[2,1-b]quinazoline-8,2'-[1,3]dioxolan]-12(7H)-one (1.5 g, 4.1 mmol, 1 equiv) and 1 N aq. KOH in methanol was stirred at rt for half an hour. The reaction mixture was quenched with water and extracted with ethyl acetate (3×100 mL). The combined organic layers were washed with brine and dried over anhydrous sodium sulfate, then concentrated under reduced pressure. The product was obtained by silica gel chromatography purification.

Example 7.1c. Synthesis of Substituted 3-ethynyl-9,10-dihydro-6H-spiro[azepino[2,1-b]quinazoline-8,2'-[1,3]dioxolan]-12(7H)-ones

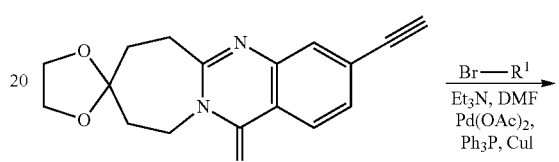

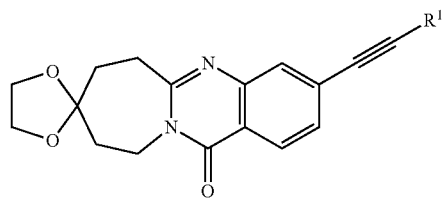

A solution of 3-ethynyl-9,10-dihydro-6H-spiro[azepino[2,1-b]quinazoline-8,2'-[1,3]-dioxolan]-12(7H)-one (0.1 g, 0.34 mmol, 1 equiv), the required R$^1$—Br (0.68 mmol, 2 equiv), Pd(OAc)$_2$ (7.6 mg, 0.034 mmol, 0.1 equiv), PPh$_3$ (80.2 mg, 0.031 mmol, 0.9 equiv), CuI (6.5 mg, 0.034 mmol, 0.1 equiv) and Et$_3$N (0.5 mL) in DMF (8 mL) was stirred in a sealed tube at 70° C. for 3.5 hours. After it was cooled to room temperature, the reaction mixture was diluted with H$_2$O and extracted with ethyl acetate (3×50 mL). The combined organic layers were washed with brine and dried over anhydrous sodium sulfate, then concentrated under reduced pressure. The product was obtained by silica gel chromatography purification.

| Example | Structure/Compound # | Method & Data |
|---|---|---|
| Example 7.1 | 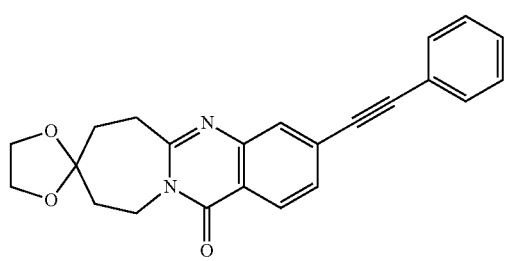 [SMILES: O=c1c2ccc(C#Cc3ccccc3)cc2nc2n1CCC1(CC2)OCCO1] | Method A; MS (ESI): 373 (MH$^+$); $^1$H NMR (300 MHz, CDCl$_3$) δ 8.25-8.22 (d, J = 8.19 Hz, 1H), 7.77 (s, 1H), 7.60-7.56 (m, 3H), 7.40-7.38 (m, 3H), 4.47-4.45 (m, 2H), 4.05 (s, 4H), 3.17-3.13 (m, 2H), 2.06-1.96 (m, 4H). mGluR5 PAM EC$_{50}$: ++++. Fold shift at 10 μM: +. |

| Example | Structure/Compound # | Method & Data |
|---|---|---|
| Example 7.2 | 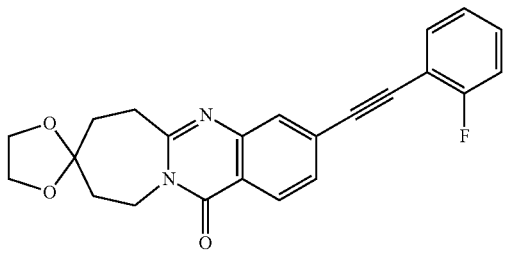 | Method A; MS (ESI): 391; $^1$H NMR (300 MHz, CDCl$_3$) δ 8.26-8.23 (dd, J = 8.28, 0.48 Hz, 1H), 7.81 (s, 1H), 7.61-7.54 (m, 2H), 7.41-7.34 (m, 1H), 7.20-7.11 (m, 2H), 4.46-4.45 (m, 2H), 4.05 (s, 4H), 3.17-3.13 (m, 2H), 2.06-1.96 (m, 4H). mGluR5 PAM EC$_{50}$: +++. Fold shift at 10 μM: ++. |
| Example 7.3 | 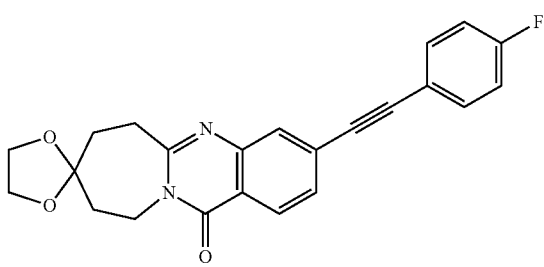 [SMILES: O=c1c2ccc(C#Cc3ccc(F)cc3)cc2nc2n1CCC1(CC2)OCCO1] | Method A; MS (ESI): 391; $^1$H NMR (300 MHz, CDCl$_3$) δ 8.25-8.22 (d, J = 8.28 Hz, 1H), 7.75 (s, 1H), 7.59-7.54 (m, 3H), 7.13-7.06 (t, J = 8.72 Hz, 2H), 4.46-4.45 (m, 2H), 4.05 (s, 4H), 3.17-3.13 (m, 2H), 2.06-1.95 (m, 4H). mGluR5 PAM EC$_{50}$: +++. |
| Example 7.4 | 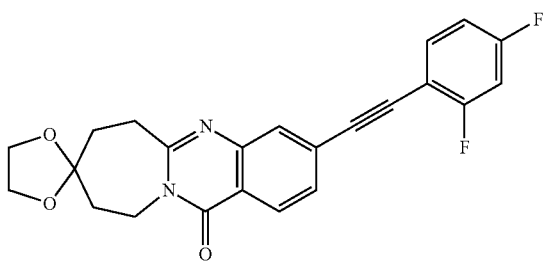 | Method A; MS (ESI): 409; $^1$H NMR (300 MHz, CDCl$_3$) δ 8.26-8.23 (d, J = 8.16 Hz, 1H), 7.90 (s, 1H), 7.59-7.28 (m, 2H), 6.95-6.88 (m, 2H), 4.46-4.45 (m, 2H), 4.05 (s, 4H), 3.17-3.13 (m, 2H), 2.06-1.96 (m, 4H). |
| Example 7.5 | 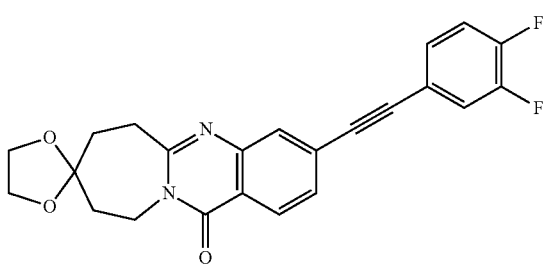 [SMILES: O=c1c2ccc(C#Cc3ccc(F)c(F)c3)cc2nc2n1CCC1(CC2)OCCO1] | Method B; MS (ESI): 409; $^1$H NMR (300 MHz, CDCl$_3$) δ 8.25-8.23 (d, J = 8.24 Hz, 1H), 7.75 (s, 1H), 7.56-7.53 (dd, J = 8.22, 1.53 Hz, 1H), 7.43-7.28 (m, 2H), 7.23-7.14 (m, 1H), 4.51-4.40 (m, 2H), 4.05 (s, 4H), 3.17-3.13 (m, 2H), 2.06-1.96 (m, 4H). mGluR5 PAM EC$_{50}$: ++. Fold shift at 10 μM: +++. |
| Example 7.6 | 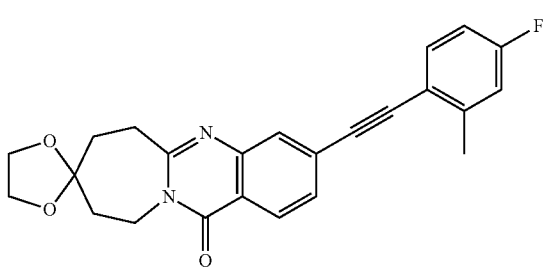 [SMILES: Cc1cc(F)ccc1C#Cc1ccc2c(=O)n3c(nc2c1)CCC1(CC3)OCCO1] | Method B; MS (ESI): 405; $^1$H NMR (300 MHz, CDCl$_3$) δ 8.25-8.22 (d, J = 8.3 Hz, 1H), 7.77 (s, 1H), 7.57-7.49 (m, 2H), 7.01-6.88 (m, 2H), 4.46 (m, 2H), 4.05 (s, 4H), 3.17-3.13 (m, 2H), 2.54 (s, 3H), 2.06-1.96 (m, 4H). mGluR5 PAM EC$_{50}$: +. |
| Example 7.7 | 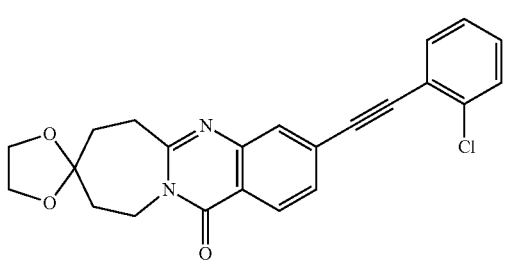 [SMILES: O=c1c2ccc(C#Cc3ccccc3Cl)cc2nc2n1CCC1(CC2)OCCO1] | Method A; MS (ESI): 407; $^1$H NMR (300 MHz, CDCl$_3$) δ 8.26-8.24 (d, J = 8.58 Hz, 1H), 7.83 (s, 1H), 7.63-7.59 (m, 2H), 7.49-7.46 (m, 1H), 7.35-7.30 (m, 2H), 4.47-4.46 (m, 2H), 4.05 (s, 4H), 3.17-3.13 (m, 2H), 2.06-1.96 (m, 4H). |

-continued

| Example Structure/Compound # | Method & Data |
|---|---|
| Example 7.8 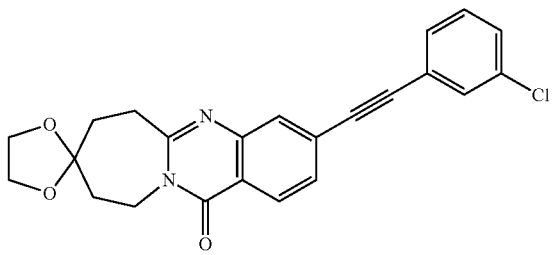 [SMILES: O=c1c2ccc(C#Cc3cccc(Cl)c3)cc2nc2n1CCC1(CC2)OCCO1] | Method A; MS (ESI): 407; $^1$H NMR (300 MHz, CDCl$_3$) δ 8.26-8.23 (d, J = 8.31 Hz, 1H), 7.76 (s, 1H), 7.57-7.54 (m, 2H), 7.48-7.45 (m, 1H), 7.39-7.32 (m, 2H), 4.47-4.46 (m, 2H), 4.05 (s, 4H), 3.17-3.13 (m, 2H), 2.06-1.96 (m, 4H). mGluR5 PAM EC$_{50}$: +. |
| Example 7.09 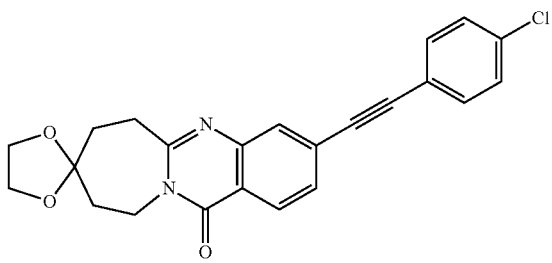 [SMILES: O=c1c2ccc(C#Cc3ccc(Cl)cc3)cc2nc2n1CCC1(CC2)OCCO1] | Method A; MS (ESI): 407; $^1$H NMR (300 MHz, CDCl$_3$) δ 8.25-8.22 (d, J = 8.28 Hz, 1H), 7.76 (s, 1H), 7.57-7.49 (m, 3H), 7.39-7.35 (m, 2H), 4.47-4.46 (m, 2H), 4.05 (s, 4H), 3.17-3.13 (m, 2H), 2.06-1.96 (m, 4H). mGluR5 PAM EC$_{50}$: +. |
| Example 7.10 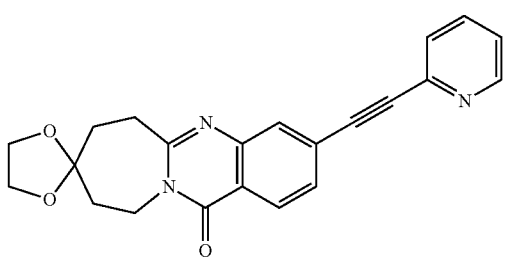 [SMILES: O=c1c2ccc(C#Cc3ccccn3)cc2nc2n1CCC1(CC2)OCCO1] | Method A; MS (ESI): 374; $^1$H NMR (300 MHz, DMSO-d$^6$) δ 8.71-8.69 (d, J = 4.4 Hz, 1H), 8.24-8.21 (d, J = 8.3 Hz, 1H), 8.02-7.97 (m, 2H), 7.85-7.77 (m, 2H), 7.58-7.54 (m, 1H), 4.33-4.32 (m, 2H), 3.96 (s, 4H), 3.24-3.17 (m, 2H), 2.02-1.93 (m, 4H). mGluR5 PAM EC$_{50}$: +++. Fold shift at 10 µM: +++. |
| Example 7.11 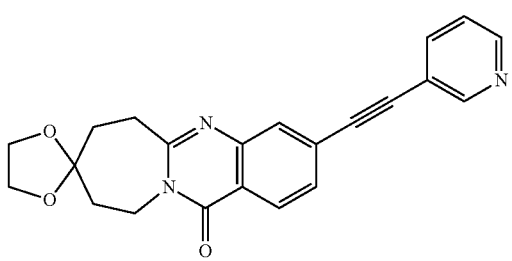 [SMILES: O=c1c2ccc(C#Cc3cccnc3)cc2nc2n1CCC1(CC2)OCCO1] | Method A; MS (ESI): 374; $^1$H NMR (300 MHz, CDCl$_3$) δ 8.82 (s, 1H), 8.61-8.60 (m, 1H), 8.27-8.24 (d, J = 8.61 Hz, 1H), 7.88-7.85 (m, 1H), 7.79 (s, 1H), 7.60-7.56 (dd, J = 8.24, 1.52 Hz, 1H), 7.36-7.31 (m, 1H), 4.45-4.44 (m, 2H), 4.05 (s, 4H), 3.17-3.14 (m, 2H), 2.06-1.96 (m, 4H). mGluR5 PAM EC$_{50}$: +. |
| Example 7.12 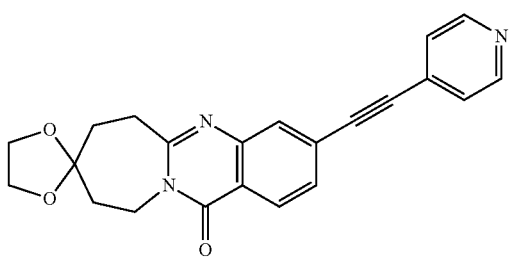 [SMILES: O=c1c2ccc(C#Cc3ccncc3)cc2nc2n1CCC1(CC2)OCCO1] | Method A; MS (ESI): 374; $^1$H NMR (300 MHz, CDCl$_3$) δ 8.67-8.65 (d, J = 6.03 Hz, 2H), 8.28-8.25 (d, J = 8.25 Hz, 1H), 7.80 (s, 1H), 7.60-7.57 (dd, J = 8.25, 1.47 Hz, 1H), 7.45-7.28 (d, J = 6.06 Hz, 2H), 4.47-4.46 (s, 2H), 4.05 (s, 4H), 3.18-3.14 (m, 2H), 2.06-1.96 (m, 4H). mGluR5 PAM EC$_{50}$: ++++. Fold shift at 10 µM: ++. |
| Example 7.13 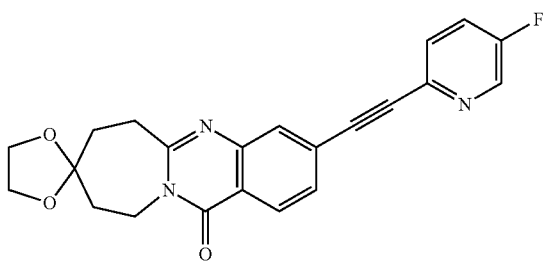 [SMILES: O=c1c2ccc(C#Cc3ccc(F)cn3)cc2nc2n1CCC1(CC2)OCCO1] | Method B; MS (ESI): 392; $^1$H NMR (300 MHz, CDCl$_3$) δ 8.53-8.52 (d, J = 6.03 Hz, 1H), 8.27-8.24 (d, J = 8.25 Hz, 1H), 7.83 (s, 1H), 7.63-7.59 (m, 2H), 7.49-7.28 (m, 1H), 4.46-4.44 (m, 2H), 4.05 (s, 4H), 3.18-3.14 (m, 2H), 2.06-1.95 (m, 4H). mGluR5 PAM EC$_{50}$: +++. |

| Example Structure/Compound # | Method & Data |
|---|---|
| Example 7.14 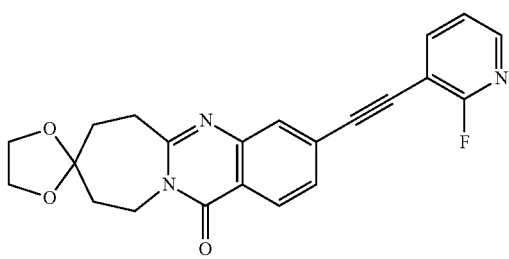 | Method B; MS (ESI): 392; $^1$H NMR (300 MHz, CDCl$_3$) δ 8.25-8.23 (d, J = 8.61 Hz, 2H), 8.00-7.94 (m, 1H), 7.81 (s, 1H), 7.61-7.58 (dd, J = 8.24, 1.52 Hz, 1H), 7.28-7.24 (m, 1H), 4.46-4.44 (m, 2H), 4.05 (s, 4H), 3.17-3.14 (m, 2H), 2.06-1.96 (m, 4H). mGluR5 PAM EC$_{50}$: ++. |
| Example 7.15 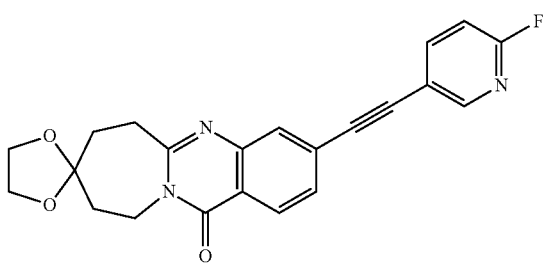 [SMILES: O=c1c2ccc(C#Cc3ccc(F)nc3)cc2nc2n1CCC1(CC2)OCCO1] | Method B; MS (ESI): 392; $^1$H NMR (300 MHz, CDCl$_3$) δ 8.45 (s, 1H), 8.27-8.24 (d, J = 8.19 Hz, 1H), 8.00-7.93 (m, 1H), 7.78 (s, 1H), 7.58-7.54 (dd, J = 8.22, 1.50 Hz, 1H), 7.01-6.97 (m, 1H), 4.46-4.43 (m, 2H), 4.05 (s, 4H), 3.17-3.14 (m, 2H), 2.06-1.96 (m, 4H). mGluR5 PAM EC$_{50}$: +++. Fold shift at 10 μM: +++. |
| Example 7.16 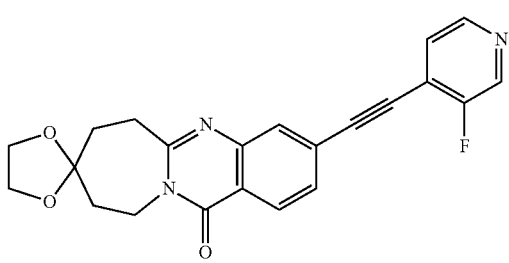 | Method B; MS (ESI): 392; $^1$H NMR (300 MHz, CDCl$_3$) δ 8.52 (s, 1H), 8.27-8.24 (d, J = 8.22 Hz, 1H), 7.83 (s, 1H), 7.70-7.59 (m, 2H), 7.51-7.42 (m, 1H), 4.47-4.46 (m, 2H), 4.05 (s, 4H), 3.17-3.14 (m, 2H), 2.06-1.95 (m, 4H). mGluR5 PAM EC$_{50}$: ++. |
| Example 7.17 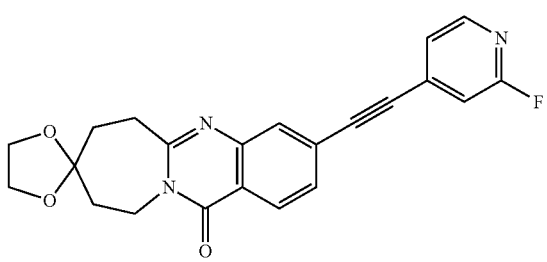 [SMILES: O=c1c2ccc(C#Cc3ccnc(F)c3)cc2nc2n1CCC1(CC2)OCCO1] | Method B; MS (ESI): 392; $^1$H NMR (300 MHz, CDCl$_3$) δ 8.29-8.25 (m, 2H), 7.80 (s, 1H), 7.80-7.56 (dd, J = 8.21, 1.55 Hz, 1H), 7.34-7.28 (m, 1H), 7.09 (s, 1H), 4.47-4.46 (m, 2H), 4.05 (s, 4H), 3.18-3.14 (m, 2H), 2.06-1.95 (m, 4H). mGluR5 PAM EC$_{50}$: +++. Fold shift at 10 μM: ++. |
| Example 7.18 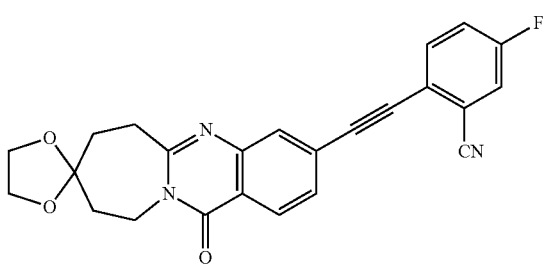 [SMILES: N#Cc1cc(F)ccc1C#Cc1ccc2c(=O)n3c(nc2c1)CCC1(CC3)OCCO1] | Method B; MS (ESI): 416; $^1$H NMR (300 MHz, CDCl$_3$) δ 8.27-8.25 (d, J = 6.00 Hz, 1H), 7.89 (s, 1H), 7.85-7.62 (m, 2H), 7.44-7.25 (m, 2H), 4.55-4.31 (m, 2H), 4.05 (s, 4H), 3.17-3.14 (m, 2H), 2.06-1.97 (m, 4H). |
| Example 7.19 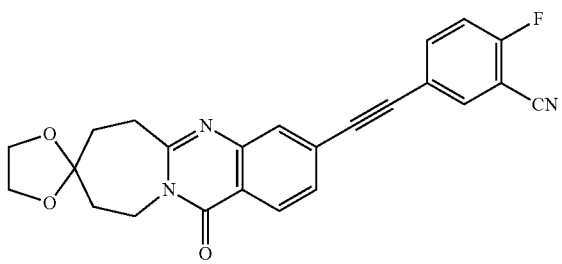 [SMILES: N#Cc1cc(C#Cc2ccc3c(=O)n4c(nc3c2)CCC2(CC4)OCCO2)ccc1F] | Method B; MS (ESI): 416; $^1$H NMR (300 MHz, CDCl$_3$) δ 8.27-8.25 (d, J = 8.16 Hz, 1H), 7.86-7.76 (m, 3H), 7.57-7.54 (dd, J = 8.22 Hz, 1H), 7.27-7.24 (m, 1H), 4.48-4.44 (m, 2H), 4.05 (s, 4H), 3.17-3.14 (m, 2H), 2.07-1.96 (m, 4H). mGluR5 PAM EC$_{50}$: +. |

| Example Structure/Compound # | Method & Data |
|---|---|
| Example 7.20 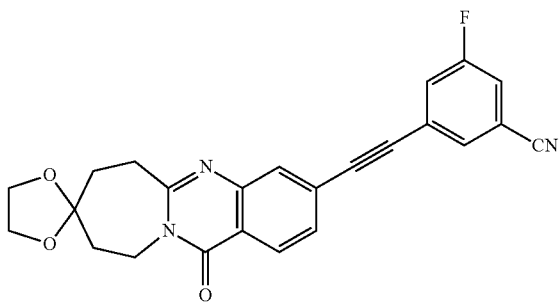 [SMILES: N#Cc1cc(F)cc(C#Cc2ccc3c(=O)n4c(nc3c2)CCC2(CC4)OCCO2)c1] | Method B; MS (ESI): 416; $^1$H NMR (300 MHz, CDCl$_3$) δ 8.28-8.26 (d, J = 7.83 Hz, 1H), 7.78 (s, 1H), 7.67 (s, 1H), 7.57-7.50 (m, 2H), 7.39-7.37 (m, 1H), 4.45-4.46 (m, 2H), 4.05 (s, 4H), 3.17-3.14 (m, 2H), 2.06-1.96 (m, 4H). |
| Example 7.21 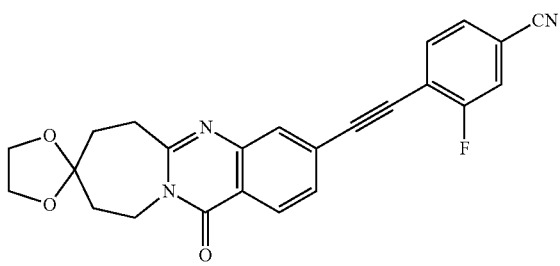 [SMILES: N#Cc1ccc(C#Cc2ccc3c(=O)n4c(nc3c2)CCC2(CC4)OCCO2)c(F)c1] | Method B; MS (ESI): 416; $^1$H NMR (300 MHz, CDCl$_3$) δ 8.28-8.26 (d, J = 8.28 Hz, 1H), 7.83 (s, 1H), 7.70-7.67 (m, 1H), 7.61-7.57 (m, 1H), 7.50-7.43 (m, 2H), 4.46-4.45 (m, 2H), 4.05 (s, 4H), 3.17-3.14 (m, 2H), 2.06-1.98 (m, 4H). |
| Example 7.22 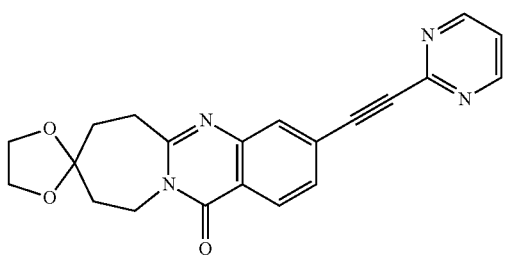 [SMILES: O=c1c2ccc(C#Cc3ncccn3)cc2nc2n1CCC1(CC2)OCCO1] | Method B; MS (ESI): 375; $^1$H NMR (300 MHz, CDCl$_3$) δ 8.82-8.80 (d, J = 4.93 Hz, 2H), 8.28-8.86 (d, J = 8.34 Hz, 1H), 7.91 (s, 1H), 7.78-7.67 (d, J = 8.24 Hz, 1H), 7.33-7.29 (m, 1H), 4.46-4.40 (m, 2H), 4.05 (s, 4H), 3.28-3.13 (m, 2H), 2.06-1.96 (m, 4H). |
| Example 7.23 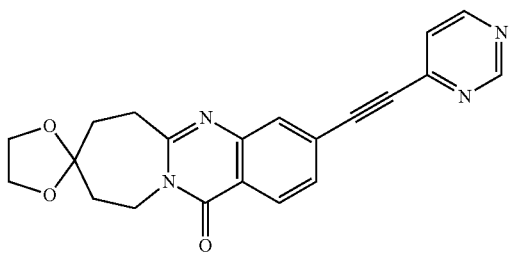 [SMILES: O=c1c2ccc(C#Cc3ccncn3)cc2nc2n1CCC1(CC2)OCCO1] | Method B; MS (ESI): 375; $^1$H NMR (300 MHz, CDCl$_3$) δ 9.27 (s, 1H), 8.80-8.79 (d, J = 5.13 Hz, 1H), 8.29-8.26 (d, J = 8.22 Hz, 1H), 7.86 (s, 1H), 7.65-7.62 (dd, J = 8.25, 1.50 Hz, 1H), 7.54-7.52 (dd, J = 5.15, 1.40 Hz, 4H), 4.46-4.45 (m, 2H), 4.05 (s, 4H), 3.17-3.13 (m, 2H), 2.06-1.67 (m, 4H). |
| Example 7.24 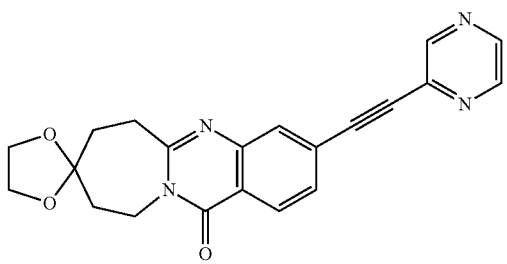 [SMILES: O=c1c2ccc(C#Cc3cnccn3)cc2nc2n1CCC1(CC2)OCCO1] | Method B; MS (ESI): 375; $^1$H NMR (300 MHz, CDCl$_3$) δ 8.83 (s, 1H), 8.64 (s, 1H), 8.56 (s, 1H), 8.56-8.27 (d, J = 8.25 Hz, 1H), 7.87 (s, 1H), 7.66-7.63 (dd, J = 8.24, 1.55 Hz, 1H), 4.46-4.45 (m, 2H), 4.05 (s, 4H), 3.18-3.14 (m, 2H), 2.06-1.66 (m, 4H). |

| Example Structure/Compound # | Method & Data |
|---|---|
| Example 7.25 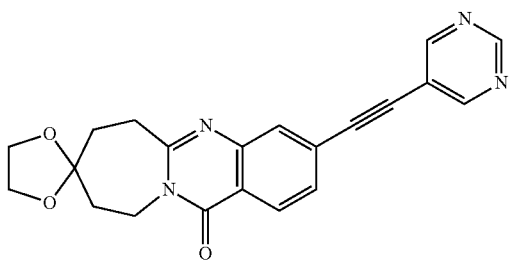 [SMILES: O=c1c2ccc(C#Cc3cncnc3)cc2nc2n1CCC1(CC2)OCCO1] | Method B; MS (ESI): 375; $^1$H NMR (300 MHz, CDCl$_3$) δ 9.20 (s, 1H), 8.92 (s, 2H), 8.29-8.26 (d, J = 8.24 Hz, 1H), 7.68 (s, 1H), 7.60-7.57 (dd, J = 8.24, 1.54 Hz, 1H), 4.48-4.46 (m, 2H), 4.05 (s, 4H), 3.18-3.14 (m, 2H), 2.06-1.96 (m, 4H). |
| Example 7.26 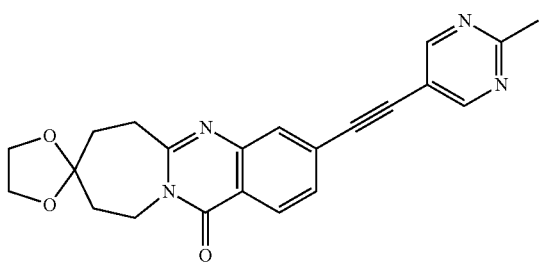 [SMILES: Cc1ncc(C#Cc2ccc3c(=O)n4c(nc3c2)CCC2(CC4)OCCO2)cn1] | Method B; MS (ESI): 389; $^1$H NMR (300 MHz, CDCl$_3$) δ 8.82 (s, 2H), 8.28-8.25 (d, J = 7.83 Hz, 1H), 7.79 (s, 1H), 7.59-7.56 (dd, J = 8.25, 1.53 Hz, 1H), 4.46-4.44 (m, 2H), 4.05 (s, 4H), 3.17-3.13 (m, 2H), 2.80 (s, 3H), 2.06-1.96 (m, 4H). |
| Example 7.27 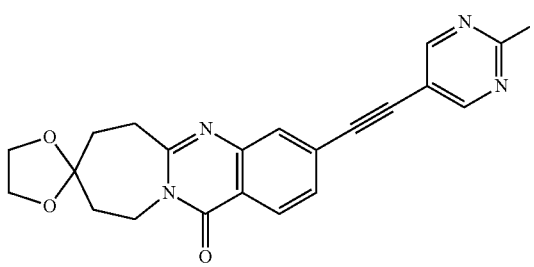 | Method B; MS (ESI): 421; $^1$H NMR (300 MHz, CDCl$_3$) δ 8.66 (s, 2H), 8.27-8.24 (dd, J = 8.25, 0.45 Hz, 1H), 7.77 (s, 1H), 7.58-7.55 (dd, J = 8.24, 1.55 Hz, 1H), 4.48-4.46 (m, 2H), 4.05 (s, 4H), 2.62 (s, 3H), 3.17-3.13 (m, 2H), 2.06-1.96 (m, 4H). |
| Example 7.28 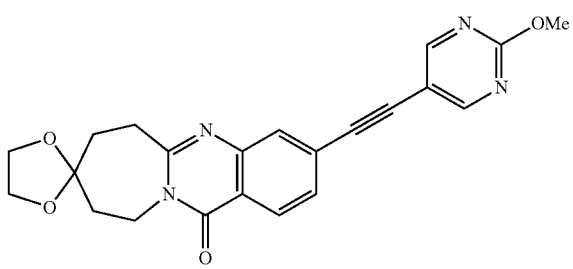 [SMILES: COc1ncc(C#Cc2ccc3c(=O)n4c(nc3c2)CCC2(CC4)OCCO2)cn1] | Method B; MS (ESI): 405; $^1$H NMR (300 MHz, CDCl$_3$) δ 8.71 (s, 2H), 8.27-8.24 (dd, J = 7.78, 0.48 Hz, 1H), 7.67 (s, 1H), 7.58-7.54 (dd, J = 8.22, 1.56 Hz, 1H), 4.45-4.41 (m, 2H), 4.08 (s, 3H), 4.05 (s, 4H), 3.17-3.13 (m, 2H), 2.06-1.96 (m, 4H). |
| Example 7.29 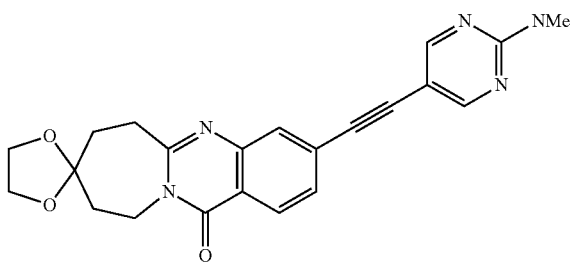 | Method B; MS (ESI): 418; $^1$H NMR (300 MHz, CDCl$_3$) δ 8.49 (s, 2H), 8.24-8.21 (d, J = 8.25 Hz, 1H), 7.72 (s, 1H), 7.55-7.52 (dd, J = 8.25, 1.54 Hz, 1H), 4.46-4.45 (m, 2H), 4.05 (s, 4H), 3.25 (s, 6H), 3.17-3.13 (m, 2H), 2.06-1.96 (m, 4H). |
| Example 7.30 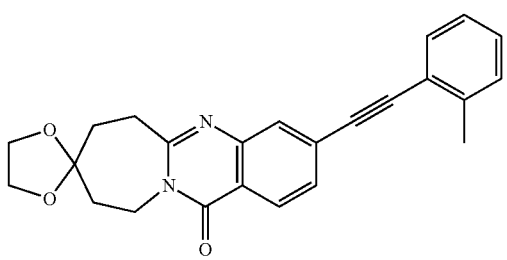 [SMILES: Cc1ccccc1C#Cc1ccc2c(=O)n3c(nc2c1)CCC1(CC3)OCCO1] | Method A; MS (ESI): 387; $^1$H NMR (300 MHz, CDCl$_3$) δ 8.25-8.23 (d, J = 8.28 Hz, 1H), 7.79 (s, 1H), 7.59-7.53 (t, J = 8.15 Hz, 2H), 7.29-7.28 (m, 1H), 7.26-7.25 (m, 1H), 7.23-7.19 (m, 1H), 4.47-4.46 (m, 2H), 4.05 (s, 4H), 3.17-3.13 (m, 2H), 2.55 (s, 3H), 2.06-1.96 (m, 4H). |

| Example Structure/Compound # | Method & Data |
|---|---|
| Example 7.31 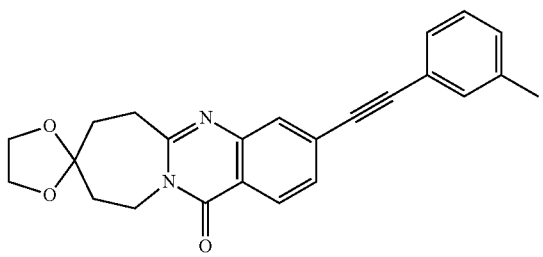 | Method A; MS (ESI): 387; $^1$H NMR (300 MHz, CDCl$_3$) δ 8.24-8.22 (d, J = 8.25 Hz, 1H), 7.76 (s, 1H), 7.57-7.55 (dd, J = 8.25, 1.50 Hz, 1H), 7.41-7.38 (m, 2H), 7.28-7.25 (m, 1H), 7.21-7.19 (m, 1H), 4.45-4.46 (m, 2H), 4.05 (s, 4H), 3.17-3.13 (m, 2H), 2.39 (s, 3H), 2.39-1.96 (m, 4H). mGluR5 PAM EC$_{50}$: ++. Fold shift at 10 μM: +++. |
| Example 7.32 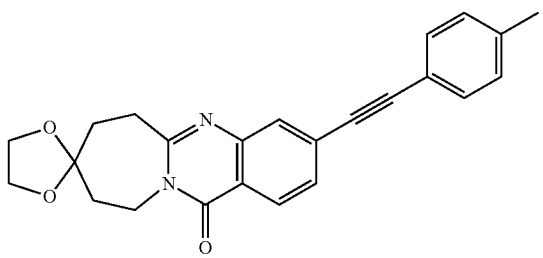 | Method A; MS (ESI): 387; $^1$H NMR (300 MHz, CDCl$_3$) δ 8.24-8.13 (d, J = 8.31 Hz, 1H), 7.88 (s, 1H), 7.57-7.54 (dd, J = 8.27, 1.55 Hz, 1H), 7.49-7.46 (m, 2H), 7.21-7.19 (d, J = 7.98 Hz, 2H), 4.49-4.45 (m, 2H), 4.05 (s, 4H), 3.17-3.13 (m, 2H), 2.46 (s, 3H), 2.06-2.02 (m, 2H), 1.99-1.96 (m, 2H). mGluR5 PAM EC$_{50}$: +. |
| Example 7.33 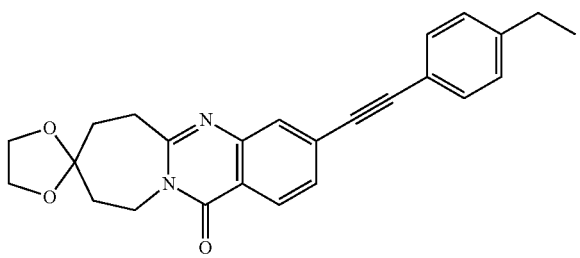 [SMILES: CCc1ccc(C#Cc2ccc3c(=O)n4c(nc3c2)CCC2(CC4)OCCO2)cc1] | Method A; MS (ESI): 401; $^1$H NMR (300 MHz, CDCl$_3$) δ 8.24-8.21 (d, J = 8.10 Hz, 1H), 7.76 (s, 1H), 7.58-7.54 (dd, J = 8.27, 1.52 Hz, 1H), 7.52-7.49 (d, J = 8.16 Hz, 2H), 7.24-7.21 (d, J = 8.22 Hz, 2H), 4.45-4.44 (m, 2H), 4.05 (s, 4H), 3.17-3.13 (m, 2H), 2.73-2.66 (m, 2H), 2.06-1.96 (m, 4H), 1.30-1.24 (t, J = 7.59 Hz, 3H). |
| Example 7.34 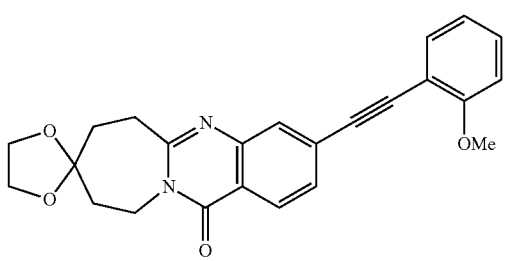 [SMILES: COc1ccccc1C#Cc1ccc2c(=O)n3c(nc2c1)CCC1(CC3)OCCO1] | Method A; MS (ESI): 403; $^1$H NMR (300 MHz, CDCl$_3$) δ 8.24-8.21 (d, J = 8.28 Hz, 1H), 7.80 (s, 1H), 7.61-7.58 (d, J = 7.85 Hz, 1H), 7.55-7.52 (d, J = 7.85 Hz, 1H), 7.39-7.33 (t, J = 8.22 Hz, 1H), 7.00-6.93 (m, 2H), 4.48-4.46 (m, 2H), 4.05 (s, 4H), 3.95 (s, 3H), 3.17-3.13 (m, 2H), 2.06-1.96 (m, 4H). |
| Example 7.35 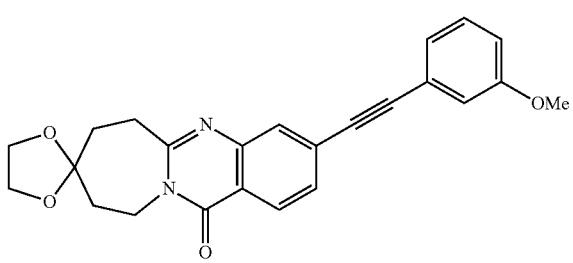 [SMILES: COc1cccc(C#Cc2ccc3c(=O)n4c(nc3c2)CCC2(CC4)OCCO2)c1] | Method A; MS (ESI): 403; $^1$H NMR (300 MHz, CDCl$_3$) δ 8.25-8.22 (d, J = 8.28 Hz, 1H), 7.78 (s, 1H), 7.59-7.55 (d, J = 8.22 Hz, 1H), 7.33-7.30 (m, 1H), 7.19-7.17 (dd, J = 8.10, 1.86 Hz, 1H), 7.10 (s, 1H), 6.97-6.93 (m, 1H), 4.46-4.45 (m, 2H), 4.05 (s, 4H), 3.86 (s, 3H), 3.17-3.13 (m, 2H), 2.06-1.96 (m, 4H). |
| Example 7.36 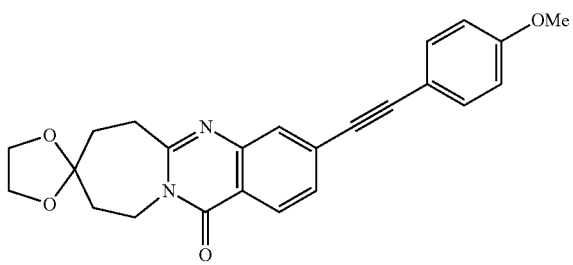 [SMILES: COc1ccc(C#Cc2ccc3c(=O)n4c(nc3c2)CCC2(CC4)OCCO2)cc1] | Method A; MS (ESI): 403; $^1$H NMR (300 MHz, CDCl$_3$) δ 8.25-8.20 (d, J = 8.25 Hz, 1H), 7.75 (s, 1H), 7.56-7.53 (dd, J = 8.35, 1.53 Hz, 1H), 7.38-7.36 (d, J = 4.38 Hz, 2H), 6.94-6.91 (m, 2H), 4.47-4.46 (m, 2H), 4.05 (s, 4H), 3.86 (s, 3H), 3.17-3.13 (m, 2H), 2.06-1.95 (m, 4H). |

| Example Structure/Compound # | Method & Data |
|---|---|
| Example 7.37 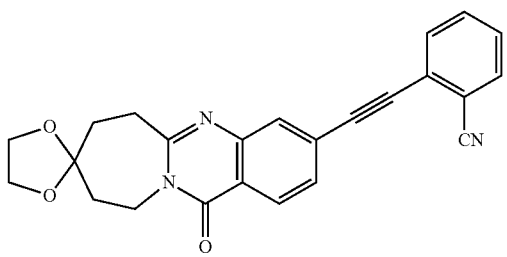 [SMILES: N#Cc1ccccc1C#Cc1ccc2c(=O)n3c(nc2c1)CCC1(CC3)OCCO1] | Method A; MS (ESI): 398; $^1$H NMR (300 MHz, CDCl$_3$) δ 8.28-8.25 (d, J = 7.80 Hz, 1H), 7.87 (s, 1H), 7.74-7.68 (m, 2H), 7.67-7.59 (m, 2H), 7.51-7.45 (m, 1H), 4.46-4.41 (m, 2H), 4.05 (s, 4H), 3.17-3.14 (m, 2H), 2.06-1.96 (m, 4H). |
| Example 7.38 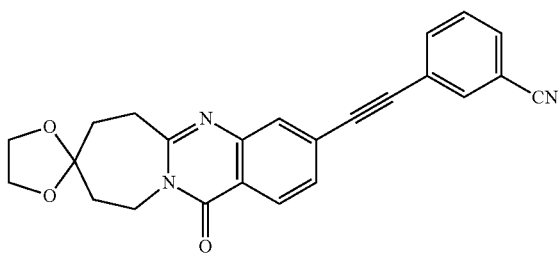 [SMILES: N#Cc1cccc(C#Cc2ccc3c(=O)n4c(nc3c2)CCC2(CC4)OCCO2)c1] | Method B; MS (ESI): 398; $^1$H NMR (300 MHz, CDCl$_3$) δ 8.28-8.25 (d, J = 8.25 Hz, 1H), 7.86 (s, 1H), 7.81-7.80 (m, 2H), 7.78-7.65 (m, 1H), 7.58-7.28 (m, 2H), 4.49-4.46 (m, 2H), 4.05 (s, 4H), 3.18-3.14 (m, 2H), 2.06-1.96 (m, 4H). mGluR5 PAM EC$_{50}$: +++. Fold shift at 10 µM: ++. |
| Example 7.39 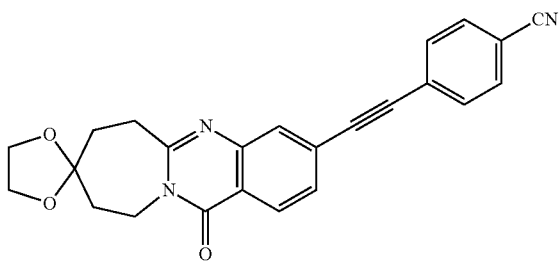 [SMILES: N#Cc1ccc(C#Cc2ccc3c(=O)n4c(nc3c2)CCC2(CC4)OCCO2)cc1] | MS (ESI): 398; $^1$H NMR (300 MHz, CDCl$_3$) δ 8.27-8.25 (d, J = 8.16 Hz, 1H), 7.82 (s, 1H), 7.67 (broad, 4H), 7.58-7.28 (m, 1H), 4.46-4.45 (m, 2H), 4.05 (s, 4H), 3.53-3.46 (m, 2H), 2.06-1.90 (m, 4H). mGluR5 PAM EC$_{50}$: +. |
| Example 7.40 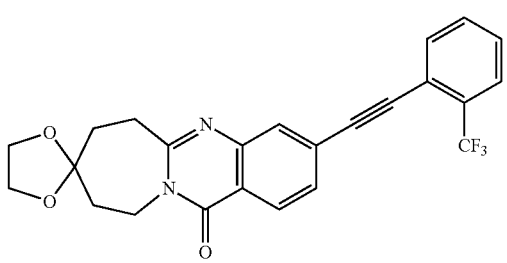 | Method A; MS (ESI): 441; $^1$H NMR (300 MHz, CDCl$_3$) δ 8.27-8.24 (d, J = 8.25 Hz, 1H), 7.82 (s, 1H), 7.74-7.71 (d, J = 8.70 Hz, 2H), 7.60-7.55 (dd, J = 8.22, 1.47 Hz, 2H), 7.55-7.50 (d, J = 11.89 Hz, 1H), 4.46-4.41 (m, 2H), 4.05 (s, 4H), 3.18-3.14 (m, 2H), 2.06-1.96 (m, 4H). mGluR5 PAM EC$_{50}$: ++. |
| Example 7.41 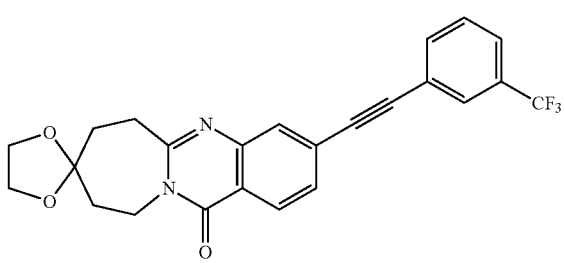 [SMILES: O=c1c2ccc(C#Cc3cccc(C(F)(F)F)c3)cc2nc2n1CCC1(CC2)OCCO1] | Method A; MS (ESI): 441; $^1$H NMR (300 MHz, CDCl$_3$) δ 8.27-8.24 (d, J = 8.28 Hz, 1H), 7.85 (s, 1H), 7.78-7.74 (m, 2H), 7.65-7.50 (m, 3H), 4.46-4.45 (m, 2H), 4.05 (s, 4H), 3.17-3.14 (m, 2H), 2.06-1.96 (m, 4H). |
| Example 7.42 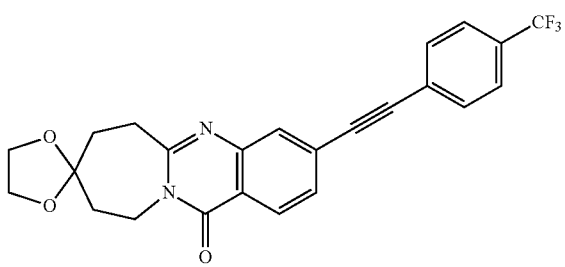 [SMILES: O=c1c2ccc(C#Cc3ccc(C(F)(F)F)cc3)cc2nc2n1CCC1(CC2)OCCO1] | Method A; MS (ESI): 441; $^1$H NMR (300 MHz, CDCl$_3$) δ 8.27-8.24 (d, J = 8.31 Hz, 1H), 7.79 (s, 1H), 7.71-7.63 (m, 4H), 7.60-7.56 (dd, J = 8.25, 1.44 Hz, 1H), 4.46-4.41 (m, 2H), 4.05 (s, 4H), 3.17-3.14 (m, 2H), 2.06-1.96 (m, 4H). |

| Example Structure/Compound # | Method & Data |
|---|---|
| Example 7.43 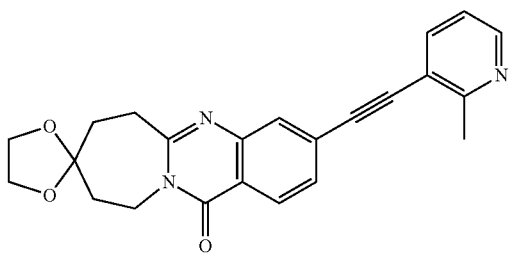 [SMILES: Cc1ncccc1C#Cc1ccc2c(=O)n3c(nc2c1)CCC1(CC3)OCCO1] | Method B; MS (ESI): 388; $^1$H NMR (300 MHz, CDCl$_3$) δ 8.24-8.23 (m, 1H), 8.22-8.20 (d, J = 8.25 Hz, 1H), 7.80-7.75 (m, 2H), 7.56-7.53 (dd, J = 7.59, 2.70 Hz, 1H), 7.18-7.13 (m, 1H), 4.44-4.43 (m, 2H), 4.03 (s, 4H), 3.15-3.11 (m, 2H), 2.77 (s, 3H), 2.10-1.94 (m, 4H). |
| Example 7.44 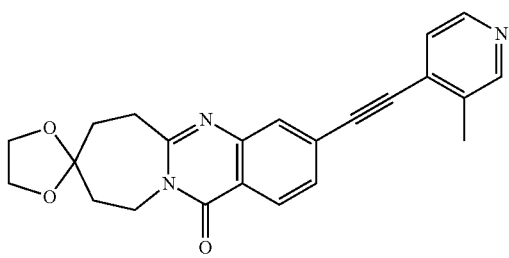 [SMILES: Cc1cnccc1C#Cc1ccc2c(=O)n3c(nc2c1)CCC1(CC3)OCCO1] | Method B; MS (ESI): 388; $^1$H NMR (300 MHz, CDCl$_3$) δ 8.55 (s, 1H), 8.48-8.46 (d, J = 5.10 Hz, 1H), 8.28-8.26 (d, J = 8.22 Hz, 1H), 7.81 (s, 1H), 7.60-7.57 (d, J = 8.24 Hz, 1H), 7.39-7.38 (d, J = 4.98 Hz, 1H), 4.46 (s, 2H), 4.05 (s, 4H), 3.18-3.14 (m, 2H), 2.51 (s, 3H), 2.06-1.96 (m, 4H). |
| Example 7.45 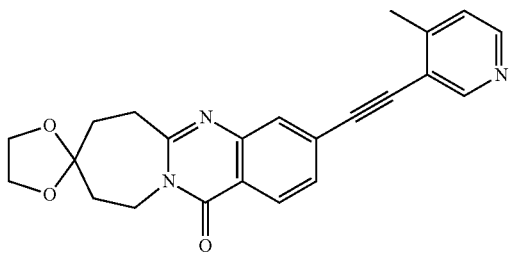 [SMILES: Cc1ccncc1C#Cc1ccc2c(=O)n3c(nc2c1)CCC1(CC3)OCCO1] | Method B; MS (ESI): 388; $^1$H NMR (300 MHz, CDCl$_3$) δ 8.72 (s, 1H), 8.46-8.44 (m, 1H), 8.26-8.24 (d, J = 6.00 Hz, 1H), 7.80 (s, 1H), 7.59-7.55 (d, J = 12.00 Hz, 1H), 7.28-7.19 (m, 1H), 4.46-4.45 (m, 2H), 4.04 (s, 4H), 3.17-3.13 (m, 2H), 2.54 (s, 3H), 2.11-1.95 (m, 4H). |
| Example 7.46 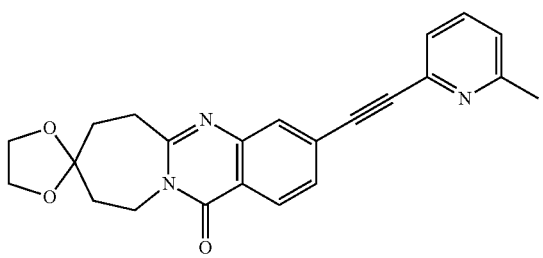 [SMILES: Cc1cccc(C#Cc2ccc3c(=O)n4c(nc3c2)CCC2(CC4)OCCO2)n1] | Method B; MS (ESI): 388; (300 MHz, CDCl$_3$) δ 8.25-8.23 (dd, J = 8.24, 0.41 Hz, 1H), 7.84 (s, 1H), 7.65-7.59 (m, 2H), 7.43-7.40 (d, J = 7.68 Hz, 1H), 7.18-7.16 (d, J = 7.32 Hz, 1H), 4.45-4.44 (m, 2H), 4.04 (s, 4H), 3.17-3.13 (m, 2H), 2.62 (s, 3H), 2.06-1.95 (m, 4H). mGluR5 PAM EC$_{50}$: ++. |
| Example 7.47 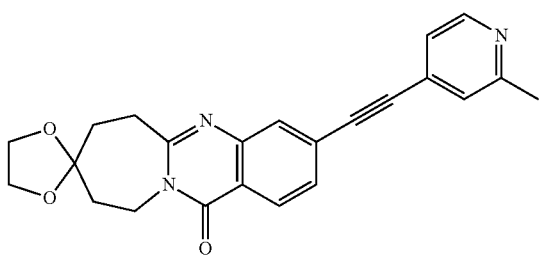 [SMILES: Cc1cc(C#Cc2ccc3c(=O)n4c(nc3c2)CCC2(CC4)OCCO2)ccn1] | Method B; MS (ESI): 388; $^1$H NMR (300 MHz, CDCl$_3$) δ 8.53-8.51 (d, J = 5.10 Hz, 1H), 8.26-8.23 (d, J = 8.22 Hz, 1H), 7.78 (s, 1H), 7.57-7.54 (dd, J = 8.24, 1.46 Hz, 1H), 7.31-7.28 (d, J = 9.33 Hz, 1H), 7.25-7.23 (d, J = 5.10 Hz, 1H), 4.45-4.44 (m, 2H), 4.04 (s, 4H), 3.16-3.12 (m, 2H), 2.59 (s, 3H), 2.06-1.95 (m, 4H). mGluR5 PAM EC$_{50}$: ++++. Fold shift at 10 μM: +++. |
| Example 7.48 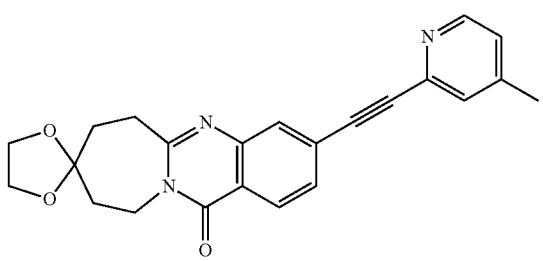 [SMILES: Cc1ccnc(C#Cc2ccc3c(=O)n4c(nc3c2)CCC2(CC4)OCCO2)c1] | Method B; MS (ESI): 388; $^1$H NMR (300 MHz, CDCl$_3$) δ 8.52-8.50 (d, J = 5.04 Hz, 1H), 8.26-8.23 (d, J = 8.25 Hz, 1H), 7.82 (s, 1H), 7.64-7.60 (dd, J = 8.24, 1.43 Hz, 1H), 7.43 (s, 1H), 7.11 (m, 1H), 4.45-4.44 (m, 2H), 4.04 (s, 4H), 3.17-3.13 (m, 2H), 2.40 (s, 3H), 2.12-1.95 (m, 4H). mGluR5 PAM EC$_{50}$: +++. Fold shift at 10 μM: +++. |

| Example Structure/Compound # | | Method & Data |
|---|---|---|
| Example 7.49 | 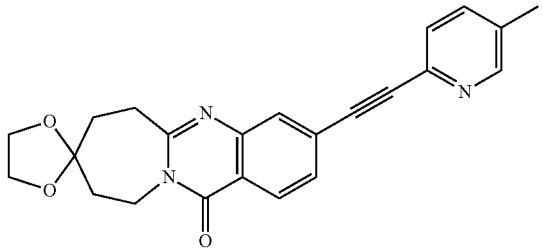 | Method B; MS (ESI): 399; $^1$H NMR (300 MHz, CDCl$_3$) δ 8.86-8.85 (dd, J = 4.92, 1.77 Hz, 1H), 8.30-8.27 (d, J = 8.22 Hz, 1H), 8.05-8.01 (dd, J = 7.98, 1.71 Hz, 1H), 7.96 (s, 1H), 7.89-7.82 (m, 1H), 7.73-7.66 (dd, J = 7.97, 4.94 Hz, 2H), 7.44-7.40 (m, 1H), 7.38-7.31 (m, 2H), 7.22-7.17 (m, 1H), 4.47-4.46 (m, 2H), 4.05 (s, 4H), 3.17-3.13 (m, 2H), 2.06-1.96 (m, 4H). mGluR5 PAM EC$_{50}$: +. |
| Example 7.50 | 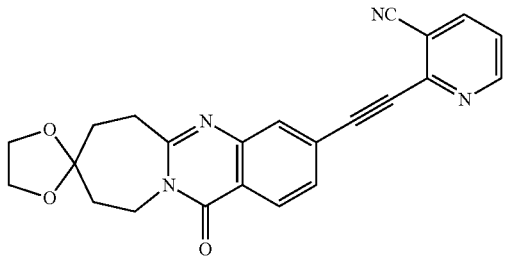 [SMILES: N#Cc1cccnc1C#Cc1ccc2c(=O)n3c(nc2c1)CCC1(CC3)OCCO1] | Method B; MS (ESI): 399; $^1$H NMR (300 MHz, CDCl$_3$) δ 8.86-8.85 (dd, J = 4.92, 1.77 Hz, 1H), 8.30-8.27 (d, J = 8.22 Hz, 1H), 8.05-8.01 (dd, J = 7.98, 1.71 Hz, 1H), 7.96 (s, 1H), 7.89-7.82 (m, 1H), 7.73-7.66 (dd, J = 7.97, 4.94 Hz, 2H), 7.44-7.40 (m, 1H), 7.38-7.31 (m, 2H), 7.22-7.17 (m, 1H), 4.47-4.46 (m, 2H), 4.05 (s, 4H), 3.17-3.13 (m, 2H), 2.06-1.96 (m, 4H) |
| Example 7.51 | 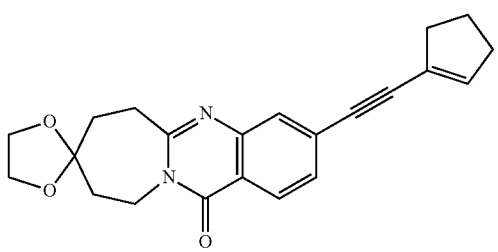 [SMILES: O=c1c2ccc(C#CC3=CCCC3)cc2nc2n1CCC1(CC2)OCCO1] | Method B; MS (ESI): 363; $^1$H NMR (300 MHz, CDCl$_3$) δ 8.20-8.17 (d, J = 8.3 Hz, 1H), 7.67-7.66 (d, J = 1.0 Hz, 1H), 7.49-7.46 (dd, J = 8.3, 1.4 Hz, 1H), 6.25-6.24 (t, J = 2.1 Hz, 1H), 4.44 (broad, 2H), 4.04 (s, 4H), 3.15-3.11 (t, J = 5.4 Hz, 2H), 2.62-2.49 (m, 4H), 2.05-1.94 (m, 6H). mGluR5 PAM EC$_{50}$: ++. |
| Example 7.52 | 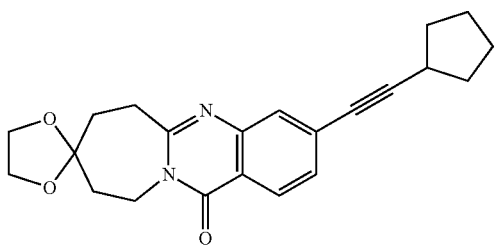 [SMILES: O=c1c2ccc(C#CC3CCCC3)cc2nc2n1CCC1(CC2)OCCO1] | Method A; MS (ESI): 365; $^1$H NMR (300 MHz, CDCl$_3$) δ 8.17-8.14 (d, J = 8.2 Hz, 1H), 7.61 (s, 1H), 7.44-7.41 (dd, J = 8.2, 1.5 Hz, 1H), 4.43 (broad, 2H), 4.06 (s, 4H), 3.14-3.11 (t, J = 5.7 Hz, 2H), 2.90-2.86 (m, 1H), 2.04-1.94 (m, 6H), 1.83-1.74 (m, 4H), 1.67-1.61 (m, 2H). mGluR5 PAM EC$_{50}$: +. |
| Example 7.53 | 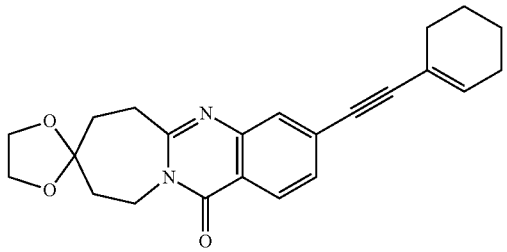 [SMILES: O=c1c2ccc(C#CC3=CCCCC3)cc2nc2n1CCC1(CC2)OCCO1] | Method B; MS (ESI): 377; $^1$H NMR (300 MHz, CDCl$_3$) δ 8.19-8.16 (d, J = 8.2 Hz, 1H), 7.65 (s, 1H), 7.47-7.44 (dd, J = 8.2, 1.5 Hz, 1H), 6.32-6.29 (m, 1H), 4.43 (broad, 2H), 4.07 (s, 4H), 3.15-3.11 (t, J = 5.7 Hz, 2H), 2.26-2.18 (m, 4H), 2.05-1.94 (m, 4H), 1.73-1.61 (m, 4H). mGluR5 PAM EC$_{50}$: +. Fold shift at 10 μM: ++. |
| Example 7.54 | 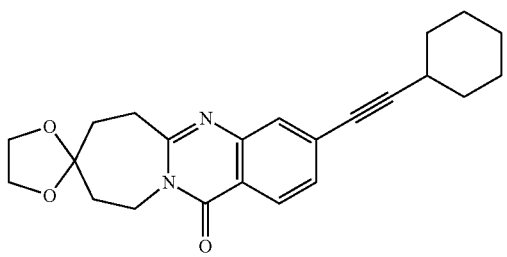 [SMILES: O=c1c2ccc(C#CC3CCCCC3)cc2nc2n1CCC1(CC2)OCCO1] | Method A; MS (ESI): 379; $^1$H NMR (300 MHz, CDCl$_3$) δ 8.17-8.11 (d, J = 8.2 Hz, 1H), 7.81 (s, 1H), 7.45-7.42 (dd, J = 8.2, 1.5 Hz, 1H), 4.43 (broad, 2H), 4.04 (s, 4H), 3.15-3.11 (t, J = 5.7 Hz, 2H), 2.70-2.61 (m, 1H), 2.08-1.88 (m, 6H), 1.81-1.76 (m, 2H) 1.58-1.53 (m, 2H), 1.38-1.35 (m, 2H). mGluR5 PAM EC$_{50}$: +. |

| Example Structure/Compound # | Method & Data |
|---|---|
| Example 7.55 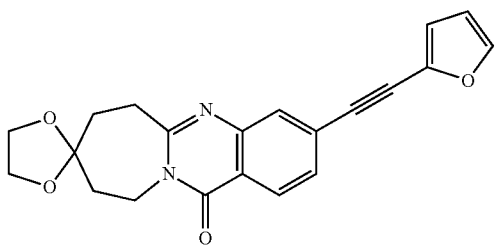 | Method B; MS (ESI): 363; ¹H NMR (300 MHz, CDCl$_3$) δ 8.26-8.22 (d, J = 8.2 Hz, 1H), 7.75-7.74 (d, J = 1.1 Hz, 1H), 7.57-7.54 (dd, J = 8.2, 1.5 Hz, 1H), 7.49-7.48 (d, J = 1.3 Hz, 1H), 6.77-6.76 (d, 3.2 Hz, 1H), 6.49-6.47 (dd, J = 3.4 Hz, 1.9 Hz, 1H), 4.45 (broad, 2H), 4.050 (s, 4H), 3.16-3.12 (t, J = 5.7 Hz, 2H), 2.06-2.03 (t, J = 5.4 Hz, 2H), 1.98-1.95 (t, J = 5.1 Hz, 2H). mGluR5 PAM EC$_{50}$: +++. Fold shift at 10 μM: +++. |
| Example 7.56 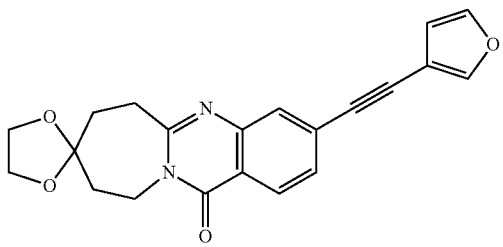 [SMILES: O=c1c2ccc(C#Cc3ccoc3)cc2nc2n1CCC1(CC2)OCCO1] | Method B; MS (ESI): 363; ¹H NMR (300 MHz, CDCl$_3$) δ 8.23-8.21 (d, J = 8.1 Hz, 1H), 7.76-7.72 (d, J = 12.7 Hz, 2H), 7.54-7.51 (dd, J = 8.2, 1.3 Hz, 1H), 7.45-7.44 (d, J = 1.5 Hz, 1H), 6.58-6.57 (d, J = 1.3 Hz, 1H), 4.45 (s, 2H), 4.05 (s, 4H), 3.16-3.12 (t, J = 5.7 Hz, 2H), 2.05-2.02 (t, J = 5.4 Hz, 2H), 1.98-1.95 (t, J = 5.1 Hz, 2H). mGluR5 PAM EC$_{50}$: +++. |
| Example 7.57 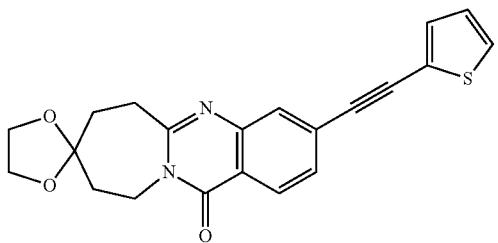 [SMILES: O=c1c2ccc(C#Cc3cccs3)cc2nc2n1CCC1(CC2)OCCO1] | Method A; MS (ESI): 379; ¹H NMR (300 MHz, CDCl$_3$) δ 8.25-8.22 (d, J = 8.2 Hz, 1H), 7.74-7.73 (d, J = 1.2 Hz, 1H), 7.56-7.53 (dd, J = 8.3, 1.5 Hz, 1H), 7.38-7.36 (d, J = 4.4 Hz, 2H), 7.07-7.05 (m, 1H), 4.46 (broad, 2H), 4.05 (s, 4H), 3.17-3.13 (t, J = 5.7 Hz, 2H), 2.06-2.02 (t, J = 5.4 Hz, 2H), 1.99-1.95 (t, J = 5.1 Hz, 2H). mGluR5 PAM EC$_{50}$: +++. Fold shift at 10 μM: ++. |
| Example 7.58 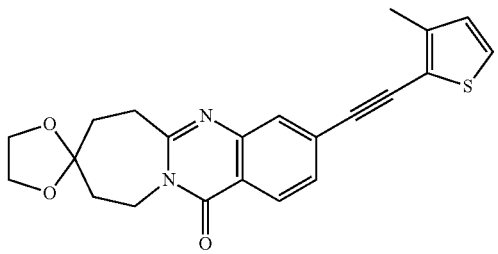 [SMILES: Cc1ccsc1C#Cc1ccc2c(=O)n3c(nc2c1)CCC1(CC3)OCCO1] | Method B; MS (ESI): 393; ¹H NMR (300 MHz, CDCl$_3$) δ 8.24-8.20 (d, J = 8.2 Hz, 1H), 7.75 (s, 1H), 7.56-7.50 (dd, J = 8.2, 1.5 Hz, 1H), 7.26-7.24 (d, J = 5.1 Hz, 1H), 6.92-6.91 (d, J = 5.1 Hz, 1H), 4.51 (broad, 2H), 4.05 (s, 4H), 3.17-3.13 (t, J = 5.7 Hz, 2H), 2.42 (s, 3H), 2.06-2.02 (t, J = 5.4 Hz, 2H), 1.99-1.95 (t, J = 5.1 Hz, 2H). mGluR5 PAM EC$_{50}$: +. |
| Example 7.59 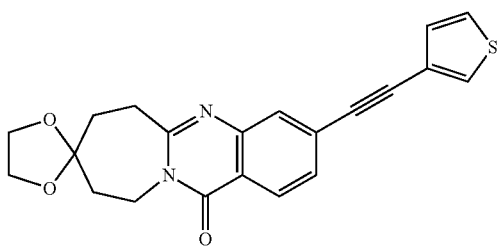 [SMILES: O=c1c2ccc(C#Cc3ccsc3)cc2nc2n1CCC1(CC2)OCCO1] | Method A; MS (ESI): 379; ¹H NMR (300 MHz, CDCl$_3$) δ 8.24-8.21 (d, J = 8.2 Hz, 1H), 7.74 (s, 1H), 7.62-7.61 (dd, J = 3.0, 1.1 Hz, 1H), 7.56-7.53 (dd, J = 8.2, 1.5 Hz, 1H), 7.36-7.33 (m, 1H), 7.28-7.24 (m, 1H), 4.46 (broad, 2H), 4.05 (s, 4H), 3.17-3.13 (t, J = 5.7 Hz, 2H), 2.06-2.02 (t, J = 5.4 Hz, 2H), 1.99-1.95 (t, J = 5.1 Hz, 2H). mGluR5 PAM EC$_{50}$: ++++. Fold shift at 10 μM: ++. |
| Example 7.60 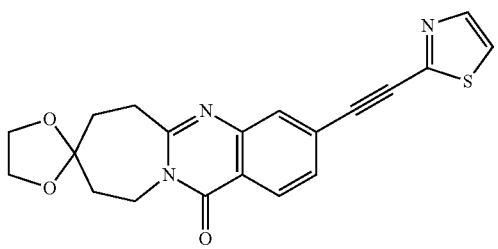 [SMILES: O=c1c2ccc(C#Cc3nccs3)cc2nc2n1CCC1(CC2)OCCO1] | Method B; MS (ESI): 380; ¹H NMR (300 MHz, CDCl$_3$) δ 8.28-8.25 (d, J = 8.4 Hz, 1H), 7.93 (d, J = 3.3 Hz, 1H), 7.84 (s, 1H), 7.64-7.61 (dd, J = 8.2, 1.6 Hz, 1H), 7.46-7.45 (d, J = 3.3 Hz, 1H), 4.45 (broad, 2H), 4.05 (s, 4H), 3.17-3.13 (t, J = 5.7 Hz, 2H), 2.06-2.02 (t, J = 5.4 Hz, 2H), 1.99-1.95 (t, J = 5.1 Hz, 2H). mGluR5 PAM EC$_{50}$: +. |

| Example Structure/Compound # | | Method & Data |
|---|---|---|
| Example 7.61 | 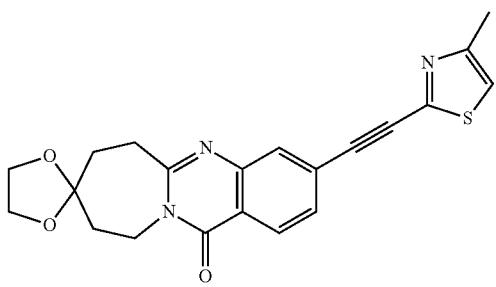 [SMILES: Cc1csc(C#Cc2ccc3c(=O)n4c(nc3c2)CCC2(CC4)OCCO2)n1] | Method B; MS (ESI): 394; $^1$H NMR (300 MHz, CDCl$_3$) δ 8.27-8.24 (d, J = 8.3 Hz, 1H), 7.82 (s, 1H), 7.62-7.59 (dd, J = 8.3, 1.4 Hz, 1H), 7.01 (s, 1H), 4.45 (broad, 2H), 4.04 (s, 4H), 3.17-3.13 (t, J = 5.7 Hz, 2H), 2.53 (s, 3H), 2.06-2.02 (t, J = 5.4 Hz, 2H), 1.99-1.95 (t, J = 5.1 Hz, 2H). mGluR5 PAM EC$_{50}$: +++. Fold shift at 10 μM: +++. |
| Example 7.62 | 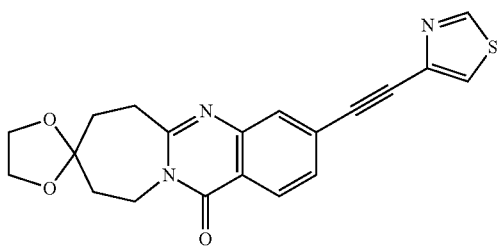 [SMILES: O=c1c2ccc(C#Cc3cscn3)cc2nc2n1CCC1(CC2)OCCO1] | Method B; MS (ESI): 380; $^1$H NMR (300 MHz, CDCl$_3$) δ 8.60 (s, 1H), 8.26-8.23 (d, J = 8.1 Hz, 1H), 7.81 (s, 1H), 7.68 (s, 1H), 7.62-7.60 (dd, J = 8.3, 1.4 Hz, 1H), 4.45 (broad, 2H), 4.05 (s, 4H), 3.17-3.13 (t, J = 5.7 Hz, 2H), 2.06-2.02 (t, J = 5.4 Hz, 2H), 1.99-1.95 (t, J = 5.1 Hz, 2H). mGluR5 PAM EC$_{50}$: +. |
| Example 7.63 | 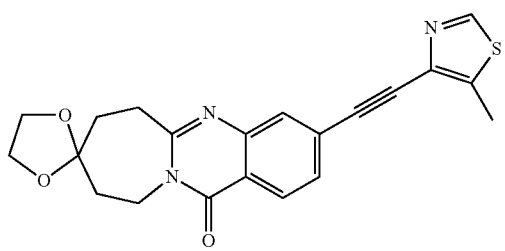 [SMILES: Cc1scnc1C#Cc1ccc2c(=O)n3c(nc2c1)CCC1(CC3)OCCO1] | Method B; MS (ESI): 394; $^1$H NMR (300 MHz, CDCl$_3$) δ 8.69 (s, 1H), 8.26-8.23 (d, J = 8.2 Hz, 1H), 7.76 (d, J = 1.2 Hz, 1H), 7.56-7.52 (dd, J = 8.3, 1.5 Hz, 1H), 4.45 (broad, 2H), 4.03 (s, 4H), 3.15-3.11 (t, J = 5.7 Hz, 2H), 2.63 (s, 3H), 2.06-2.02 (t, J = 5.4 Hz, 2H), 1.99-1.95 (t, J = 5.1 Hz, 2H). mGluR5 PAM EC$_{50}$: +. |
| Example 7.64 | 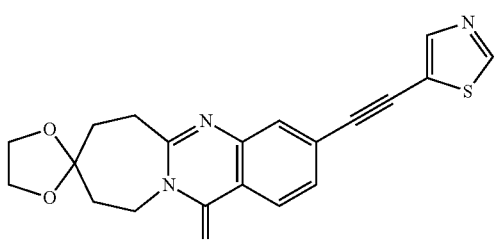 | Method B; MS (ESI): 380; $^1$H NMR (300 MHz, CDCl$_3$) δ 8.81 (s, 1H), 8.27-8.24 (d, J = 8.3 Hz, 1H), 8.13 (s, 1H), 7.76 (s, 1H), 7.57-7.54 (dd, J = 7.7, 2.4 Hz, 1H), 4.45 (broad, 2H), 4.05 (s, 4H), 3.17-3.13 (t, J = 5.7 Hz, 2H), 2.06-2.02 (t, J = 5.4 Hz, 2H), 1.99-1.95 (t, J = 5.1 Hz, 2H). |
| Example 7.65 | 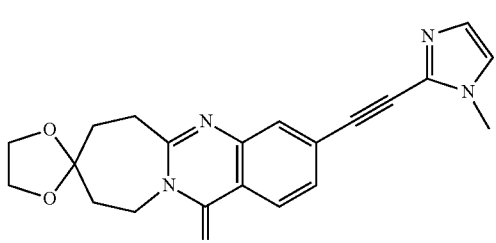 | Method B; MS (ESI): 377; $^1$H NMR (300 MHz, CDCl$_3$) δ 8.24-8.21 (d, J = 8.2 Hz, 1H), 7.78 (s, 1H), 7.59-7.56 (dd, J = 8.2, 1.4 Hz, 1H), 7.15-7.08 (broad, 1H), 6.98 (s, 1H), 4.43 (broad, 2H), 4.03 (s, 4H), 3.82 (s, 3H), 3.15-3.11 (t, J = 5.7 Hz, 2H), 2.04-2.00 (t, J = 5.4 Hz, 2H), 1.97-1.93 (t, J = 5.1 Hz, 2H). |
| Example 7.66 | 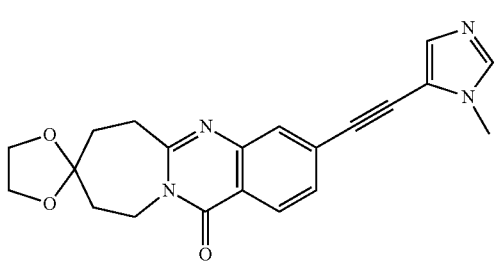 [SMILES: Cn1cncc1C#Cc1ccc2c(=O)n3c(nc2c1)CCC1(CC3)OCCO1] | Method A; MS (ESI): 377; $^1$H NMR (300 MHz, CDCl$_3$) δ 8.26-8.23 (d, J = 8.2 Hz, 1H), 7.74 (s, 1H), 7.54-7.50 (m, 2H), 7.45-7.42 (m, 1H), 4.45 (broad, 2H), 4.05 (s, 4H), 3.78 (s, 3H), 3.17-3.13 (t, J = 5.7 Hz, 2H), 2.06-2.02 (t, J = 5.4 Hz, 2H), 1.99-1.95 (t, J = 5.1 Hz, 2H). |

| Example Structure/Compound # | Method & Data |
|---|---|
| Example 7.67 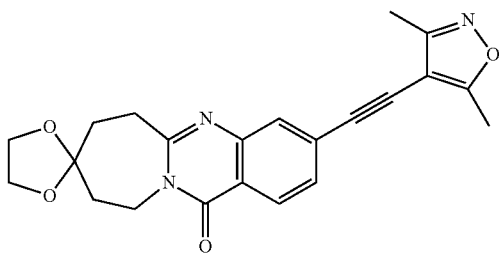 [SMILES: Cc1noc(C)c1C#Cc1ccc2c(=O)n3c(nc2c1)CCC1(CC3)OCCO1] | Method A; MS (ESI): 392; ¹H NMR (300 MHz, CDCl$_3$) δ 8.25-8.22 (d, J = 8.3 Hz, 1H), 7.74-7.74 (d, J = 1.3 Hz, 1H), 7.54-7.51 (dd, J = 8.2, 1.4 Hz, 1H), 4.45 (broad, 2H), 4.05 (s, 4H), 3.17-3.13 (t, J = 5.7 Hz, 2H), 2.55 (s, 3H), 2.38 (s, 3H), 2.06-2.02 (t, J = 5.4 Hz, 2H), 1.99-1.95 (t, J = 5.1 Hz, 2H). mGluR5 PAM EC$_{50}$: ++++. |
| Example 7.68 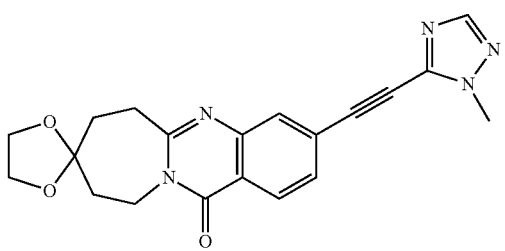 [SMILES: Cn1ncnc1C#Cc1ccc2c(=O)n3c(nc2c1)CCC1(CC3)OCCO1] | Method B; MS (ESI): 378; ¹H NMR (300 MHz, CDCl3) δ 8.28-8.27 (d, J = 8.3 Hz, 1H), 7.97 (s, 1H), 7.85 (s, 1H), 7.63-7.60 (d, J = 8.2 Hz, 1H), 4.48 (broad, 2H), 4.06-4.05 (d, 7H), 3.17-3.13 (t, J = 5.7 Hz, 2H), 2.06-2.02 (t, J = 5.4 Hz, 2H), 1.99-1.95 (t, J = 5.1 Hz, 2H). |
| Example 7.69 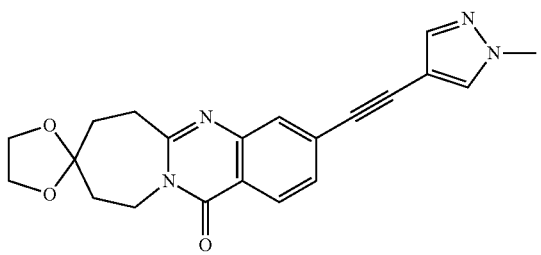 [SMILES: Cn1cc(C#Cc2ccc3c(=O)n4c(nc3c2)CCC2(CC4)OCCO2)cn1] | Method B; MS (ESI): 377; ¹H NMR (300 MHz, CDCl$_3$) δ 8.22-8.19 (d, J = 8.3 Hz, 1H), 7.70 (s, 2H), 7.62 (s, 1H), 7.53-7.49 (dd, J = 8.2, 1.4 Hz, 1H), 4.44 (broad, 2H), 4.05 (s, 4H), 3.95 (s, 3H), 3.16-3.12 (t, J = 5.7 Hz, 2H), 2.05-2.01 (t, J = 5.4 Hz, 2H), 1.98-1.94 (t, J = 5.1 Hz, 2H). mGluR5 PAM EC$_{50}$: ++. |

Example 8.1. Synthesis of 8-((4-fluorophenyl)ethynyl)-3-methyl-2,3,4,5-tetrahydro-[1,4]diazepino[7,1-b]quinazolin-11(1H)-one

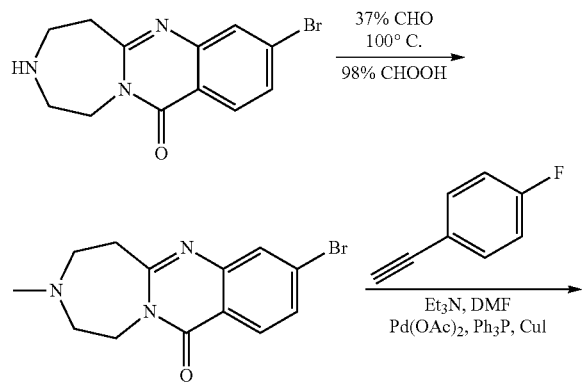

Example 8.1a. Synthesis of 8-bromo-3-methyl-2,3,4,5-tetrahydro-[1,4]diazepino[7,1-b]quinazolin-11(1H)-one

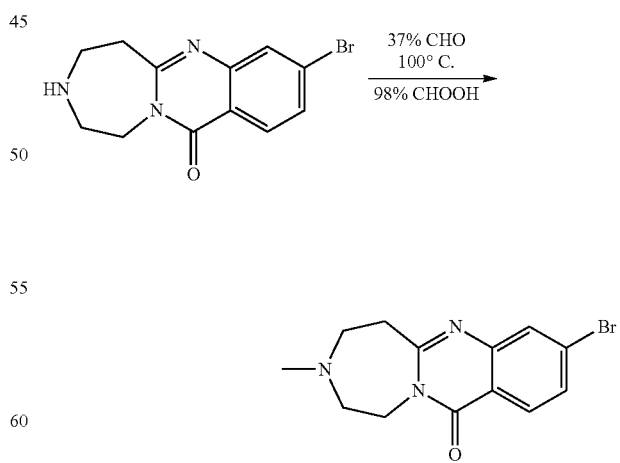

The title compound was prepared according to the experimental procedure as described in Example 1.21d.

Example 8.1b. Synthesis of 8-((4-fluorophenyl)ethynyl)-3-methyl-2,3,4,5-tetrahydro-[1,4]diazepino[7,1-b]quinazolin-11(1H)-one

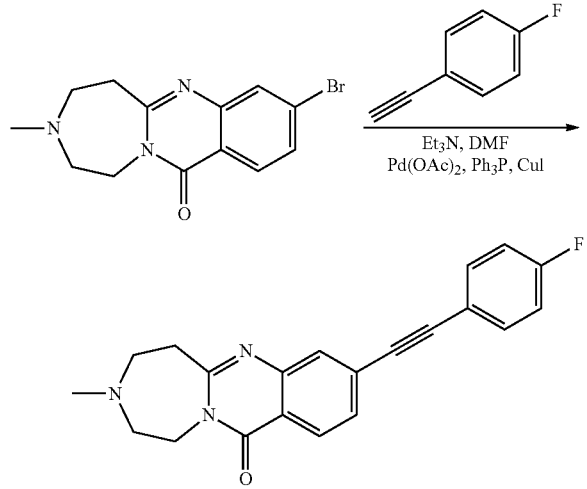

The title compound was prepared according to the experimental procedure as described in Example 1.1. MS (ESI): 348 (MH$^+$); $^1$H NMR (300 MHz, CDCl$_3$) δ 8.24-8.20 (d, J=6.54 Hz, 1H), 7.75 (s, 1H), 7.56 (m, 3H), 7.08 (m, 2H), 4.56 (m, 2H), 3.22 (m, 2H), 2.78-2.72 (m, 4H), 2.40 (s, 3H). mGluR5 PAM EC$_{50}$: ++. Fold shift at 10 μM: ++.

Example 8.2. Synthesis of 3-ethyl-8-((4-fluorophenyl)ethynyl)-2,3,4,5-tetrahydro-[1,4]diazepino[7,1-b]quinazolin-11(1H)-one

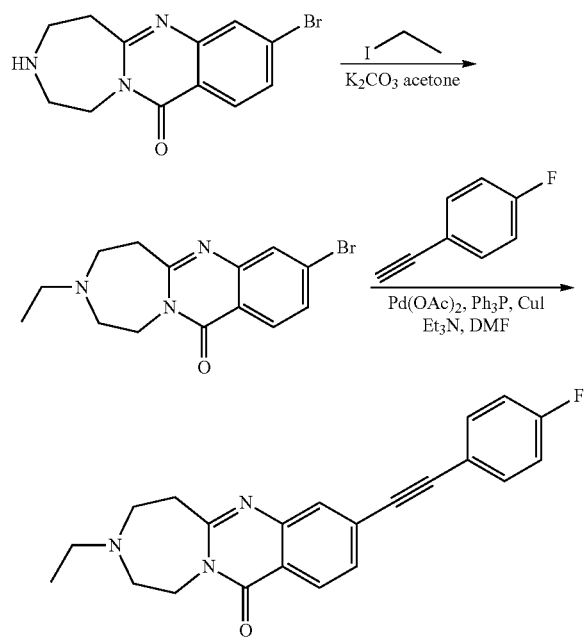

Example 8.2a. Synthesis of 8-bromo-3-ethyl-2,3,4,5-tetrahydro-[1,4]diazepino-[7,1-b]quinazolin-11(1H)-one

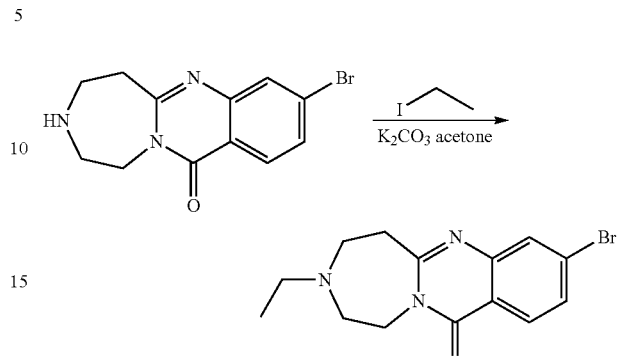

A solution of 8-bromo-2,3,4,5-tetrahydro-[1,4]diazepino[7,1-b]quinazolin-11(1H)-one (100 mg, 0.34 mmol), K$_2$CO$_3$ (188 mg, 1.36 mmol) and excess iodoethane in acetone (20 mL) was stirred at room temperature overnight. Then the reaction mixture was diluted with water (80 mL) and extracted with ethyl acetate (3×70 mL). The combined organic layers were dried over Na$_2$SO$_4$. After filtration and concentration, the residue was purified by silica gel chromatography to give 100 mg of the desired product. MS (ESI): 322, 324 (MH$^+$).

Example 8.2b. Synthesis of 3-ethyl-8-((4-fluorophenyl)ethynyl)-2,3,4,5-tetrahydro-[1,4]diazepino[7,1-b]quinazolin-11(1H)-one

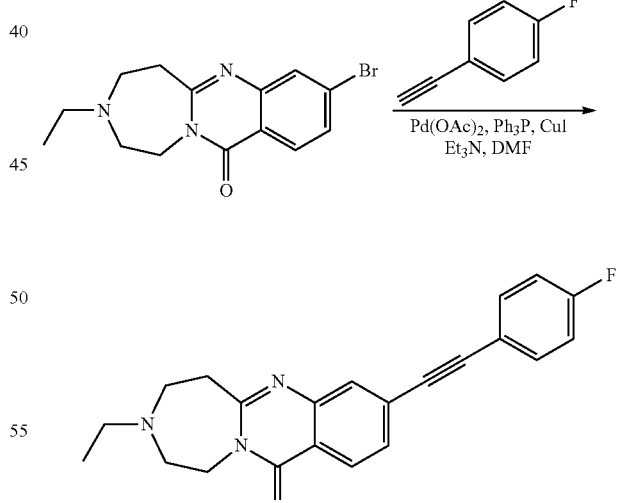

The title compound was prepared according to the experimental procedure as described in Example 1.1. MS (ESI): 362 (MH$^+$); $^1$H NMR (300 MHz, CDCl$_3$) δ 8.25-8.22 (d, J=8.25 Hz, 1H), 7.76 (s, 1H), 7.60-7.54 (m, 3H), 7.12-7.06 (d, J=8.72 Hz, 2H), 4.53-4.51 (m, 2H), 3.25-3.22 (m, 2H), 2.84-2.77 (m, 4H), 2.62-2.55 (q, J=7.2 Hz, 2H), 1.15-1.10 (t, J=7.1 Hz, 3H). mGluR5 PAM EC$_{50}$: ++.

Example 8.3. Synthesis of 8-((4-fluorophenyl)ethynyl)-3-isopropyl-2,3,4,5-tetrahydro-[1,4]diazepino[7,1-b]quinazolin-11(1H)-one

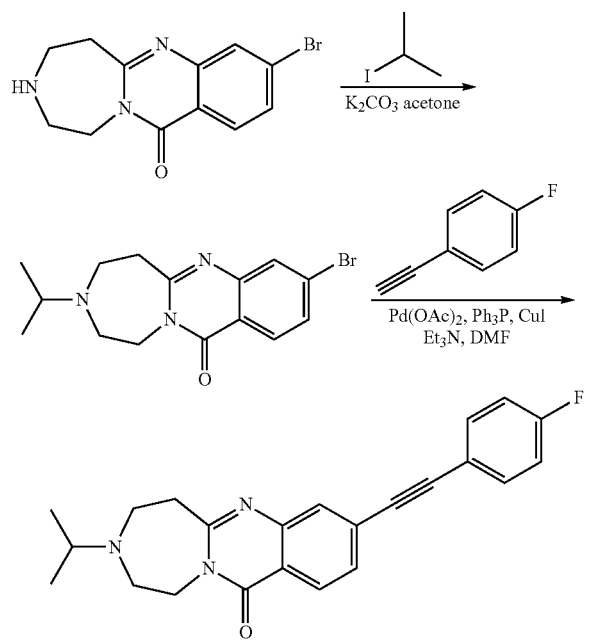

The title compound was prepared according to the experimental procedure as described in Example 8.2a and Example 1.1. MS (ESI): 376 (MH⁺); ¹H NMR (300 MHz, CD₃OD) δ 8.25-8.22 (d, J=8.28 Hz, 1H), 7.75 (s, 1H), 7.59-7.54 (m, 3H), 7.12-7.07 (t, J=8.72 Hz, 2H), 4.51-4.49 (m, 2H), 3.23-3.19 (m, 2H), 3.03-2.94 (m, 1H), 2.88-2.79 (m, 4H), 1.06-1.04 (d, J=6.66 Hz, 6H). mGluR5 PAM EC$_{50}$: ++.

Example 8.4. Synthesis of 8-((4-fluorophenyl)ethynyl)-3,3-dimethyl-11-oxo-1,2,3,4,5,11-hexahydro-[1,4]diazepino[7,1-b]quinazolin-3-ium

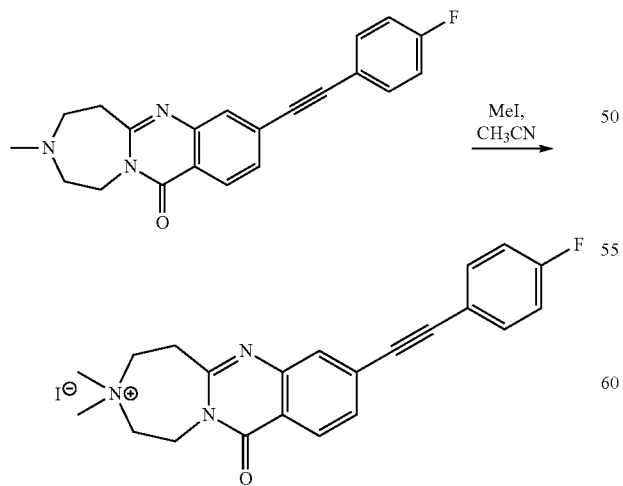

To a solution of 8-((4-fluorophenyl)ethynyl)-3-methyl-2,3,4,5-tetrahydro-[1,4]diazepino[7,1-b]quinazolin-11(1H)-one (6.2 mg, 0.018 mmol) in CH₃CN (1 mL) at room temperature was added MeI (20 μL). The resulting mixture was stirred overnight. LC-Mass analysis indicated the reaction was complete. Solvent and excess methyl iodide was removed by evaporation. MS (ESI): 362.4 (MH⁺).

Example 8.5. Synthesis of tert-butyl 8-((3-fluorophenyl)ethynyl)-11-oxo-1,2,4,5-tetrahydro-[1,4]diazepino[7,1-b]quinazoline-3(11H)-carboxylate

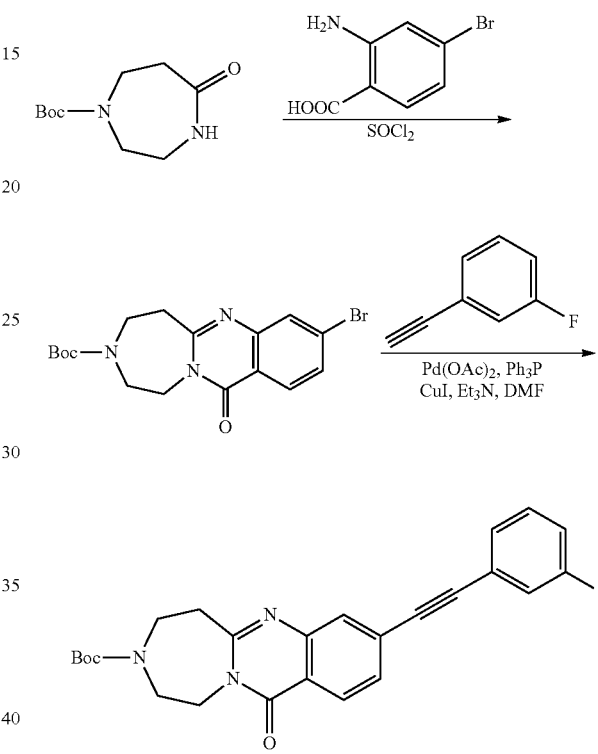

The title compound was prepared according to the experimental procedure as described in Example 2.2a and Example 1.1. MS (ESI): 434 (MH⁺); ¹H NMR (300 MHz, CDCl₃) δ 8.26-8.23 (d, J=8.2 Hz, 1H), 7.78 (s, 1H), 7.60-7.56 (dd, J=8.3, 1.5 Hz, 1H), 7.38-7.35 (m, 2H), 7.29-7.28 (m, 1H), 7.13-7.08 (m, 1H), 4.50-4.48 (t, J=4.2 Hz, 2H), 3.83-3.80 (t, J=4.5 Hz, 2H), 3.76-3.74 (t, J=3.9 Hz, 2H), 3.22-3.19 (t, J=5.1 Hz, 2H), 1.51 (s, 9H).

Example 8.6. Synthesis of 8-((3-fluorophenyl)ethynyl)-2,3,4,5-tetrahydro-[1,4]diazepino[7,1-b]quinazolin-11(1H)-one

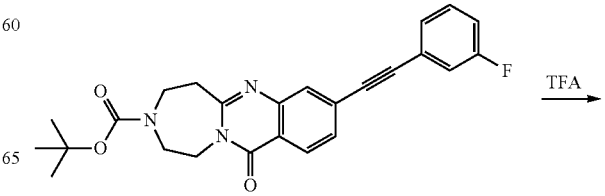

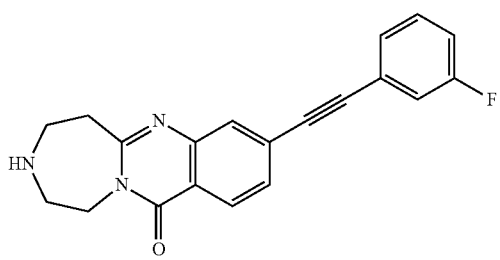

To a solution of tert-butyl-8-(2-(3-fluorophenyl)ethynyl)-11-oxo-1,2,4,5-tetrahydro-[1,4]diazepino[7,1-b]quinazoline-3(11H)-carboxylate (1.3 g, 3.0 mmol) in DCM (30 mL) was added trifluoroacetic acid (15 mL). The mixture was stirred for 1 h at room temperature. Then the reaction mixture was concentrated and purified by silica gel chromatography to give the desired product. MS (ESI): 334 (MH$^+$); $^1$H NMR (300 MHz, CDCl$_3$) δ 8.26-8.23 (d, J=8.2 Hz, 1H), 7.77 (s, 1H), 7.59-7.55 (d, J=8.3 Hz, 1.5 Hz, 1H), 7.38-7.34 (m, 2H), 7.29-7.26 (m, 1H), 7.14-7.09 (m, 1H), 4.53-4.50 (t, J=3.6 Hz, 2H), 3.24-3.17 (m, 4H), 3.11-3.10 (t, J=4.5 Hz, 2H). mGluR5 PAM EC$_{50}$: ++.

Example 8.7. Synthesis of 8-((3-fluorophenyl)ethynyl)-3-methyl-2,3,4,5-tetrahydro-[1,4]diazepino[7,1-b]quinazolin-11(1H)-one

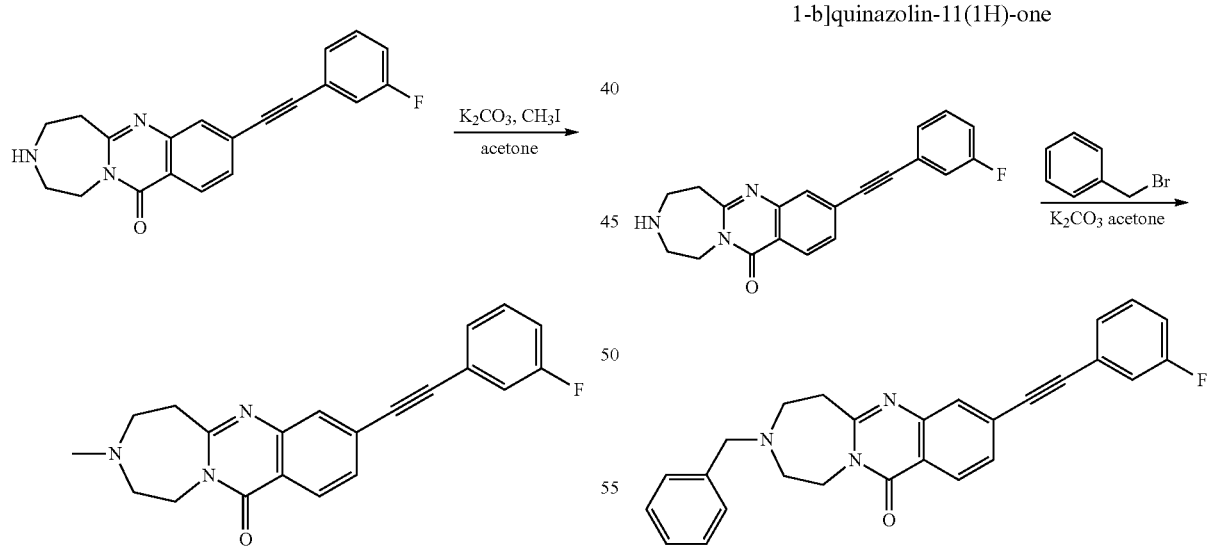

The title compound was prepared according to the experimental procedure as described in Example 8.2a. MS (ESI): 348 (MH$^+$); $^1$H NMR (300 MHz, CDCl$_3$) δ 8.25-8.22 (d, J=8.16 Hz, 1H), 7.77 (s, 1H), 7.58-7.55 (dd, J=8.22, J=1.41 Hz, 1H), 7.37-7.34 (m, 2H), 7.32-7.28 (m, 1H), 7.14-7.07 (m, 1H), 4.52 (m, 2H), 3.30-3.22 (m, 2H), 2.80-2.72 (m, 4H), 2.41 (s, 3H). mGluR5 PAM EC$_{50}$: +++. Fold shift at 10 μM: +++.

Example 8.8. Synthesis of 8-((3-fluorophenyl)ethynyl)-3-propyl-2,3,4,5-tetrahydro-[1,4]diazepino[7,1-b]quinazolin-11(1H)-one

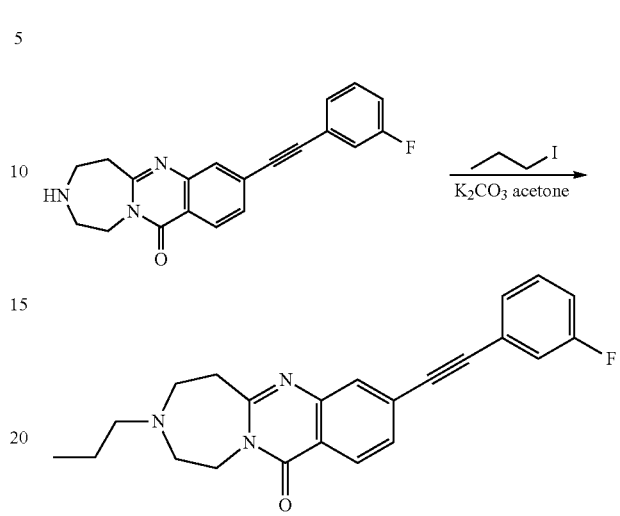

The title compound was prepared according to the experimental procedure as described in Example 8.2a. MS (ESI): 376 MH$^+$); $^1$H NMR (300 MHz, CDCl$_3$) δ 8.26-8.23 (d, J=8.25 Hz, 1H), 7.77 (s, 1H), 7.59-7.55 (d, J=8.25 Hz, 1.51 Hz, 1H), 7.38-7.35 (m, 2H), 7.29-7.28 (m, 1H), 7.12-7.08 (m, 1H), 4.53-4.52 (m, 2H), 3.25-3.21 (m, 2H), 2.84-2.75 (m, 4H), 2.48-2.43 (t, J=7.35 Hz, 2H), 1.62-1.51 (m, 2H), 0.96-0.91 (t, J=7.34 Hz, 3H). mGluR5 PAM EC$_{50}$: ++.

Example 8.9. Synthesis of 3-benzyl-8-((3-fluorophenyl)ethynyl)-2,3,4,5-tetrahydro-[1,4]diazepino[7,1-b]quinazolin-11(1H)-one The title compound was prepared according to the experimental procedure as described in Example 8.2a. MS (ESI): 424(MH$^+$); $^1$H NMR (300 MHz, CDCl$_3$) δ 8.25-8.22 (d, J=8.22 Hz, 1H), 7.76 (s, 1H), 7.58-7.55 (dd, J=8.22, 1.35 Hz, 1H), 7.40-7.32 (m, 7H), 7.28-7.26 (m, 1H), 7.13-7.07 (m, 1H), 4.52-4.51 (m, 2H), 3.65 (s, 2H), 3.24-3.21 (m, 2H), 2.84-2.77 (m, 4H). mGluR5 PAM EC$_{50}$: ++++. Fold shift at 10 μM: ++.

Example 8.10. Synthesis of 8-((3-fluorophenyl)ethynyl)-3-(2-methoxyethyl)-2,3,4,5-tetrahydro-[1,4]diazepino[7,1-b]quinazolin-11(1H)-one

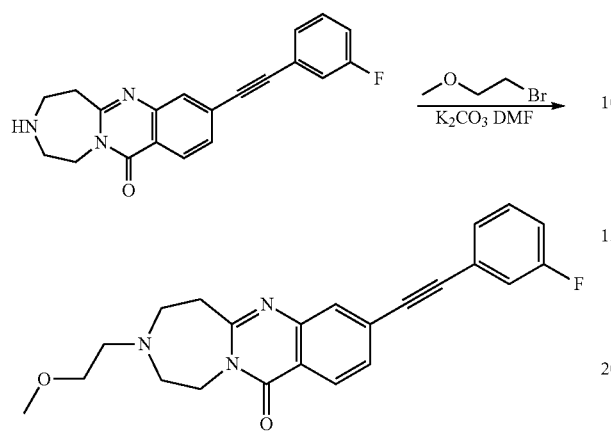

The title compound was prepared according to the experimental procedure as described in Example 8.2a. DMF was used as the solvent. MS (ESI): 392 (MH+); ¹H NMR (300 MHz, CDCl₃) δ 8.26-8.23 (d, J=8.3 Hz, 1H), 7.77 (s, 1H), 7.59-7.55 (d, J=8.3 Hz, 1.5 Hz, 1H), 7.38-7.34 (m, 2H), 7.30-7.26 (m, 1H), 7.12-7.08 (m, 1H), 4.55-4.52 (m, 2H), 3.57-3.51 (t, J=5.4 Hz, 2H), 3.39 (s, 3H), 3.25-3.19 (m, 2H), 2.92-2.83 (m, 4H), 2.76-2.73 (t, J=5.4 Hz, 2H). mGluR5 PAM EC₅₀: ++. Fold shift at 10 μM: ++.

Example 8.11. Synthesis of 3-cyclobutyl-8-((3-fluorophenyl)ethynyl)-2,3,4,5-tetrahydro-[1,4]diazepino[7,1-b]quinazolin-11(1H)-one

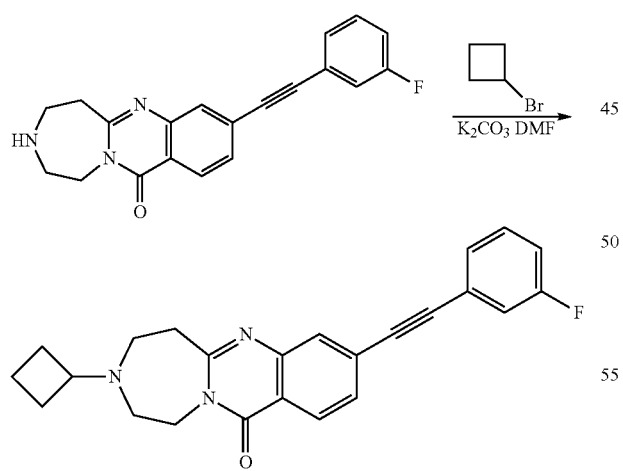

The title compound was prepared according to the experimental procedure as described in Example 8.2a. DMF was used as the solvent. MS (ESI): 388 (MH+); ¹H NMR (300 MHz, CDCl₃) δ 8.34-8.32 (d, J=8.16 Hz, 1H), 7.89-7.82 (m 2H), 7.59-7.45 (m, 2H), 7.38-7.35 (d, J=8.10 Hz, 1H), 7.31-7.19 (m, 1H), 5.60-5.36 (m, 1H), 4.50-4.32 (m, 1H), 4.22-3.90 (m, 3H), 3.85-3.70 (m, 1H), 3.66-3.59 (m, 2H), 3.24-3.22 (d, J=7.14 Hz, 1H), 2.53-2.42 (m, 2H), 2.10-1.77 (m, 1H), 1.30 (s, 1H), 0.88-0.83 (m, 1H), 0.55-0.53 (m, 1H). mGluR5 PAM EC₅₀: +.

Example 8.12. Synthesis of 3-allyl-8-((3-fluorophenyl)ethynyl)-2,3,4,5-tetrahydro-[1,4]diazepino[7,1-b]quinazolin-11(1H)-one

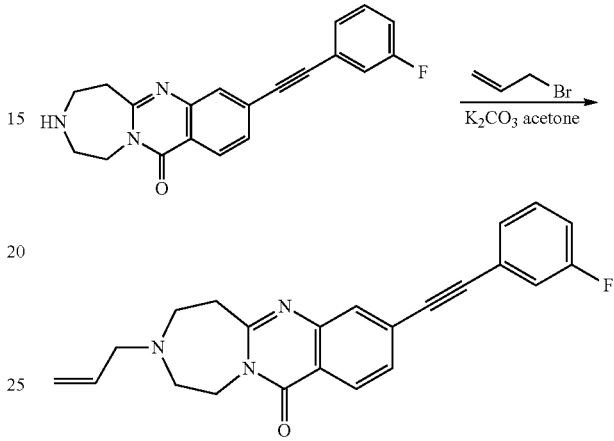

The title compound was prepared according to the experimental procedure as described in Example 8.2a. MS (ESI): 374(MH+); ¹H NMR (300 MHz, CDCl₃) δ 8.25-8.22 (d, J=8.25 Hz, 1H), 7.77 (s, 1H), 7.62-7.56 (dd, J=8.26, 1.55 Hz, 1H), 7.41-7.35 (m, 2H), 7.28-7.27 (m, 1H), 7.16-7.07 (m, 1H), 6.04-5.88 (m, 1H), 5.34-5.24 (m, 2H), 4.72-4.46 (m, 2H), 3.42-3.12 (m, 4H), 3.05-2.65 (m, 4H). mGluR5 PAM EC₅₀: ++++. Fold shift at 10 μM: ++.

Example 8.13. Synthesis of 8-((3-fluorophenyl)ethynyl)-3-(tetrahydrofuran-3-yl)-2,3,4,5-tetrahydro-[1,4]diazepino[7,1-b]quinazolin-11(1H)-one acetonitrile

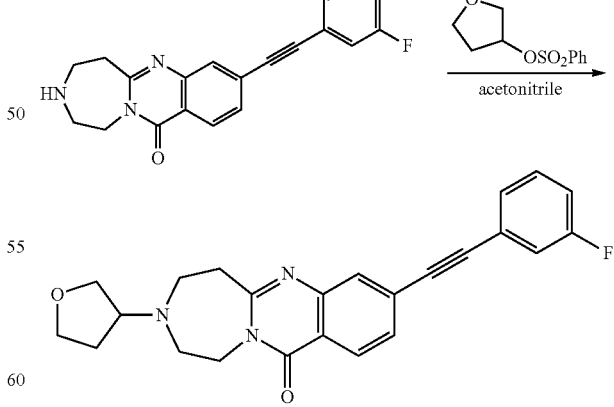

A solution of 8-((3-fluorophenyl)ethynyl)-2,3,4,5-tetrahydro-[1,4]diazepino[7,1-b]quinazolin-11(1H)-one (100 mg, 0.3 mmol) and tetrahydrofuran-3-yl-benzenesulfonate (137 mg, 0.6 mmol) in acetonitrile (20 mL) was stirred at room temperature overnight. The mixture was diluted with H₂O (50 mL) and extracted with ethyl acetate (3×50 mL), the combined organic layers were washed with brine, dried over Na₂SO₄. After filtration and concentration, the residue was purified by silica gel chromatography to give the desired product. MS (ESI): 404(MH⁺); ¹H NMR (300 MHz, CDCl₃) δ 8.25-8.22 (d, J=8.25 Hz, 1H), 7.77 (s, 1H), 7.58-7.55 (dd, J=8.25, 1.38 Hz, 1H), 7.40-7.34 (m, 2H), 7.28-7.26 (m, 1H), 7.13-7.06 (m, 1H), 4.61-4.32 (m, 2H), 4.02-3.95 (m, 1H), 3.90-3.70 (m, 3H), 3.25-3.22 (m, 3H), 2.89-2.74 (m, 4H), 2.09-1.86 (m, 2H). mGluR5 PAM EC₅₀: ++.

Example 8.14. Synthesis of the HCl Salt of 2-(8-((3-fluorophenyl)ethynyl)-11-oxo-1,2,4,5-tetrahyrdro-[1,4]diazepino[7,1-b]quinazolin-3(11H)-yl)acetonitrile

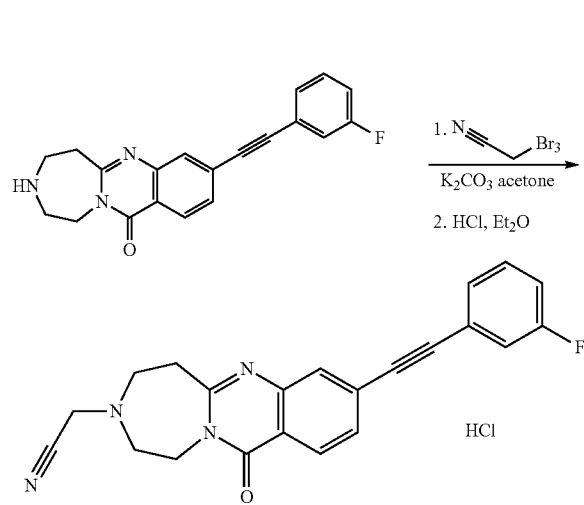

The title compound was prepared according to the experimental procedure as described in Example 8.2a. The product was then converted to the corresponding HCl salt. MS (ESI): 373 (MH⁺); ¹H NMR (300 MHz, DMSO-d⁶) δ 8.18-8.15 (d, J=8.25 Hz, 1H), 7.82 (s, 1H), 7.70-7.66 (dd, J=8.24, 1.52 Hz, 1H), 7.53-7.41 (m, 3H), 7.37-7.31 (m, 1H), 4.51-4.49 (m, 2H), 3.97 (s, 2H), 3.34-3.31 (m, 2H), 2.51-2.49 (m, 4H). mGluR5 PAM EC₅₀: ++++. Fold shift at 10 μM: +++.

Example 8.15. Synthesis of 2-(8-((3-fluorophenyl)ethynyl)-11-oxo-1,2,4,5-tetrahydro-[1,4]diazepino[7,1-b]quinazolin-3(11H)-yl)-N-methylacetamide

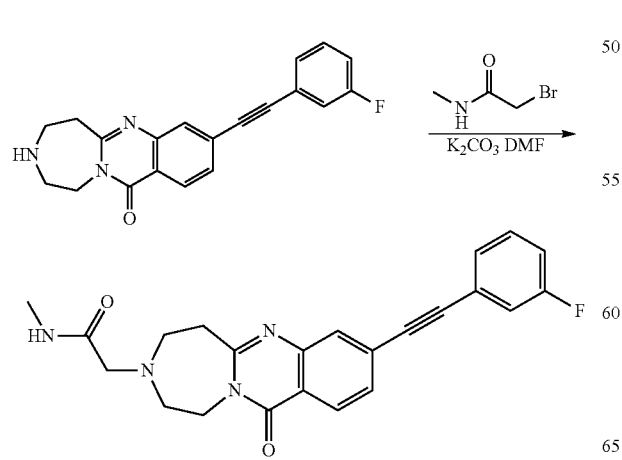

The title compound was prepared according to the experimental procedure as described in Example 8.2a. DMF was used as the solvent. MS (ESI): 405 (MH⁺); ¹H NMR (300 MHz, DMSO-d⁶+D₂O) δ 8.17-8.14 (d, J=8.16 Hz, 1H), 7.78 (s, 1H), 7.69-7.65 (dd, J=8.21, 1.54 Hz, 1H), 7.54-7.45 (m, 3H), 7.38-7.27 (m, 1H), 4.83-4.42 (s, 2H), 3.92 (s, 2H), 3.69-3.50 (m, 4H), 3.50-3.45 (m, 2H), 2.68 (s, 3H). mGluR5 PAM EC₅₀: ++. Fold shift at 10 μM: ++.

Example 8.16. Synthesis of 8-((3-fluorophenyl)ethynyl)-3-((tetrahydrofuran-2-yl)methyl)-2,3,4,5-tetrahydro-[1,4]diazepino[7,1-b]quinazolin-11(1H)-one

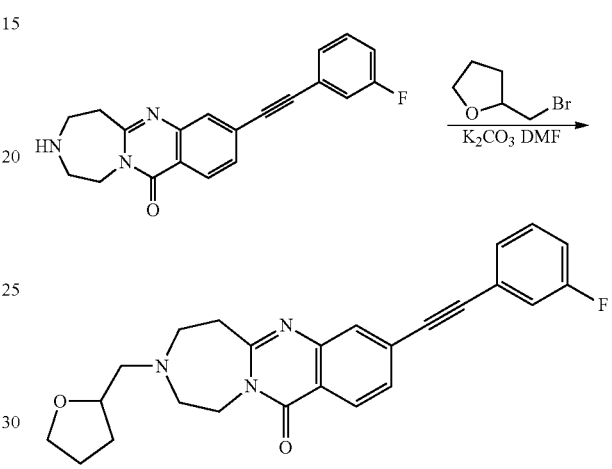

The title compound was prepared according to the experimental procedure as described in Example 8.2a. DMF was used as the solvent. MS (ESI): 418 (MH⁺); ¹H NMR (300 MHz, DMSO-d⁶+D₂O) δ 8.17-8.14 (d, J=8.16 Hz, 1H), 7.78 (s, 1H), 7.69-7.66 (d, J=8.19 Hz, 1H), 7.58-7.47 (m, 3H), 7.34-7.28 (m, 1H), 5.22-4.97 (s, 1H), 4.30-4.12 (m, 2H), 3.93-3.73 (m, 4H), 3.52-3.12 (m, 6H), 2.08-2.02 (m, 2H), 1.89-1.82 (m, 2H), 1.54-1.48 (m, 1H). mGluR5 PAM EC₅₀: ++.

Example 8.17. Synthesis of 3-acetyl-8-((3-fluorophenyl)ethynyl)-2,3,4,5-tetrahydro-[1,4]diazepino[7,1-b]quinazolin-11(1H)-one

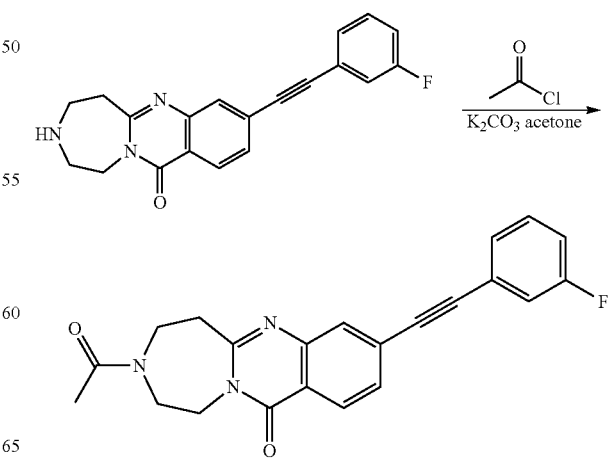

The title compound was prepared according to the experimental procedure as described in Example 8.20. MS (ESI): 376 (MH+); 1H NMR (300 MHz, CDCl3) δ 8.27-8.23 (dd, J=8.36, 3.83 Hz, 1H), 7.89 (s, 1H), 7.62-7.58 (dd, J=8.25, 1.50 Hz, 1H), 7.38-7.30 (m, 2H), 7.29-7.28 (m, 1H), 7.14-7.08 (m, 1H), 4.56-4.48 (m, 2H), 4.00-3.92 (m, 2H), 3.84-3.75 (m, 2H), 3.28-3.19 (m, 2H), 2.25-2.23 (d, J=7.83 Hz, 3H). mGluR5 PAM EC50: ++. Fold shift at 10 μM: +++.

Example 8.18. Synthesis of 8-((3-fluorophenyl)ethynyl)-11-oxo-1,2,4,5-tetrahydro-[1,4]diazepino[7,1-b]quinazoline-3(11H)-carbaldehyde

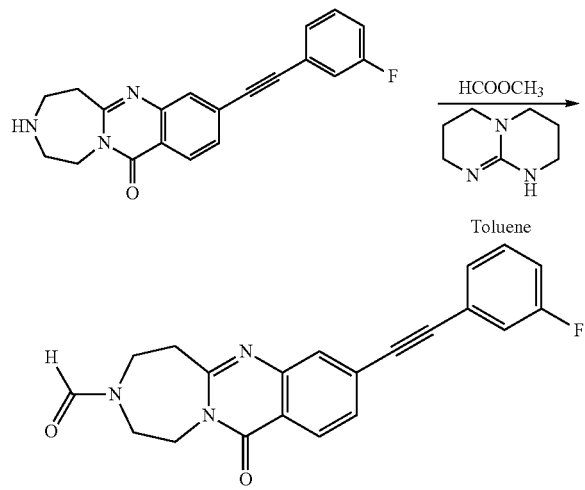

A solution of 8-((3-fluorophenyl)ethynyl)-2,3,4,5-tetrahydro-[1,4]diazepino[7,1-b]quinazolin-11(1H)-one (0.1 g, 0.3 mmol), methyl formate (22 mg, 1.2 mmol), and 2,3,4,6,7,8-hexahydro-1H-pyrimido[1,2-a]pyrimidine (2.1 mg, 0.015 mmol) in toluene (3 mL) was stirred at room temperature for 12 h. The reaction mixture was quenched with saturated potassium bisulfate (5 mL). The solution was extracted with ethyl acetate (3×20 mL) and the combined organic layers were washed with brine, dried over Na2SO4. After filtration and concentration, the residue was purified by silica gel chromatography to give the desired product. MS (ESI): 362 (M+H+); 1H NMR (300 MHz, CDCl3) δ 8.27-8.23 (m, 1H), 8.20-8.18 (d, J=6.24 Hz, 1H), 7.79-7.78 (m, 1H), 7.62-7.59 (m, 1H), 7.38-7.32 (m, 2H), 7.29-7.26 (m, 1H), 7.14-7.07 (m, 1H), 4.57-4.49 (m, 2H), 3.94-3.84 (m, 2H), 3.75-3.65 (m, 2H), 3.28-3.19 (m, 2H). mGluR5 PAM EC50: +++. Fold shift at 10 μM: ++.

Example 8.19. Synthesis of the HCl Salt of 11-oxo-8-(pyridin-2-ylethynyl)-1,2,4,5-tetrahydro-[1,4]diazepino[7,1-b]quinazoline-3(11H)-carbaldehyde

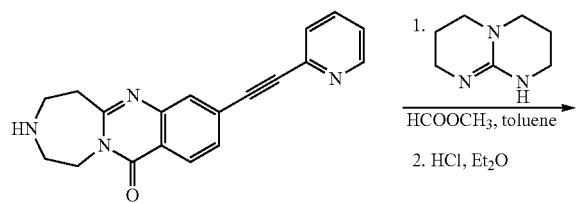

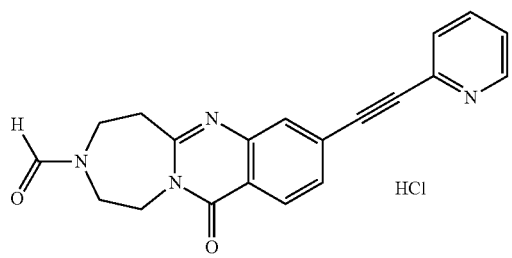

The title compound was prepared according to the experimental procedure as described in Example 8.18. The product was then converted to the corresponding HCl salt. MS (ESI): 345 (MH+); 1H NMR (300 MHz, CD3OD) δ 8.76-8.74 (d, J=7.20 Hz, 1H), 8.46-8.42 (m, 1H), 8.42-8.28 (d, J=8.41 Hz, 1H), 8.18-8.05 (m, 2H), 7.98-7.85 (m, 2H), 7.82-7.75 (m, 1H), 4.61-4.45 (m, 2H), 3.90-3.67 (m, 4H), 3.52-3.24 (m, 2H).

Example 8.20. Synthesis of the HCl Salt of 3-acetyl-8-(pyridin-2-ylethynyl)-2,3,4,5-tetrahydro-[1,4]diazepino[7,1-b]quinazolin-11(1H)-one

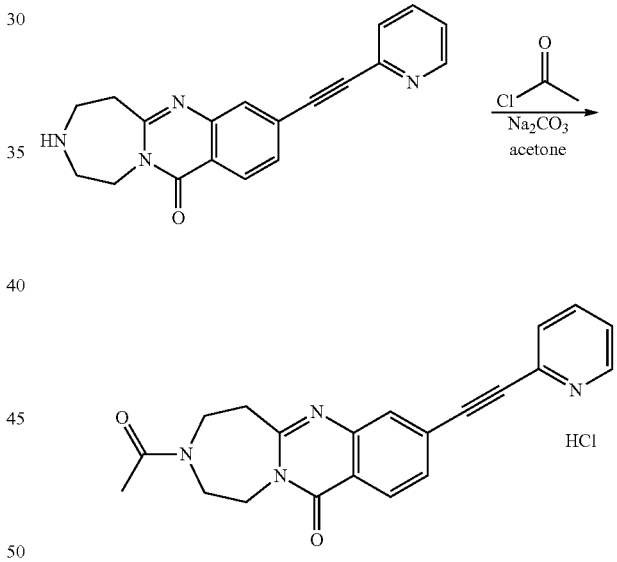

To a solution of 8-(pyridin-2-ylethynyl)-2,3,4,5-tetrahydro-[1,4]diazepino[7,1-b]quinazolin-11(1H)-one (120 mg, 0.38 mmol) and Na2CO3 (200 mg, 1.89 mmol) in acetone (20 mL) was added acetyl chloride (0.8 mL) dropwise. After stirring for 2 h, the reaction mixture was concentrated and diluted with water. The aqueous mixture was extracted with EtOAc (3×50 mL). The combined organic layers were concentrated and purified by column chromatography to give 70 mg of the desired product. MS (ESI): 359 (MH+); 1H NMR (300 MHz, CD3OD) δ 8.92-8.90 (d, J=5.64 Hz, 1H), 8.63-8.58 (m, 1H), 8.43-8.39 (dd, J=8.27 Hz, 3.02 Hz, 1H), 8.31-8.28 (d, J=8.01 Hz, 1H), 8.08-8.01 (m, 2H), 7.97-7.93 (m, 1H), 4.75 (d, 1H), 4.65 (d, 1H), 4.07-3.91 (m, 4H), 3.56-3.53 (m, 1H), 3.46-3.42 (m, 1H), 2.2 (d, J=9.6 Hz, 3H).

Example 8.21. Synthesis of the 2HCl Salt of 8-(pyridin-2-ylethynyl)-3-(3,3,3-trifluoropropyl)-2,3,4,5-tetrahydro-[1,4]diazepino[7,1-b]quinazolin-11(1H)-one

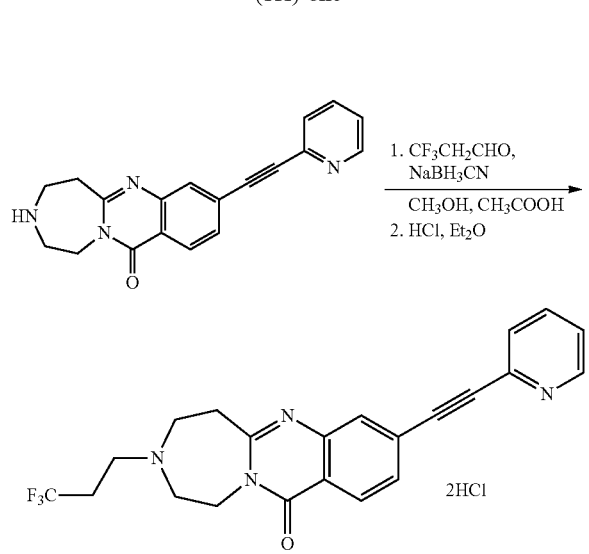

To a solution of 8-(2-(pyridin-2-yl)ethynyl)-2,3,4,5-tetrahydro-[1,4]diazepino[7,1-b]quinazolin-11(1H)-one (150 mg, 0.48 mmol), 3,3,3-trifluoropropanal (80 mg, 0.72 mmol), and sodium cyanoborohydride (60 mg, 0.96 mmol) in MeOH (10 mL) was added acetic acid (29 mg, 0.48 mmol). The mixture was stirred for 1 h at room temperature. The reaction mixture was quenched with saturated sodium carbonate solution (30 mL) and extracted with ethyl acetate (3×50 mL). The combined organic layers were washed with brine, dried over $Na_2SO_4$. After filtration and concentration, the crude product was purified by column chromatography to give the desired product. The product was then converted to the corresponding 2HCl salt. MS (ESI): 413 (MH$^+$); $^1$H NMR (300 MHz, CD$_3$OD) δ 8.94-8.92 (d, J=5.82 Hz, 1H), 8.72-8.66 (t, J=7.98 Hz, 1H), 8.39-8.34 (t, J=9.00 Hz, 2H), 8.15-8.10 (t, J=7.83 Hz, 1H), 8.07 (s, 1H), 7.91-7.88 (d, J=8.22 Hz, 1H), 4.84-4.80 (m, 3H), 3.81-3.71 (m, 5H), 3.66-3.54 (m, 2H), 3.03-2.94 (m, 2H). mGluR5 PAM EC$_{50}$: ++. Fold shift at 10 μM: +++.

Example 8.22. Synthesis of the HCl Salt of 3-(prop-2-yn-1-yl)-8-(pyridin-2-ylethynyl)-2,3,4,5-tetrahydro-[1,4]diazepino[7,1-b]quinazolin-11(1H)-one

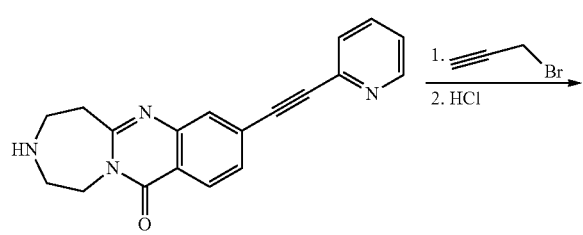

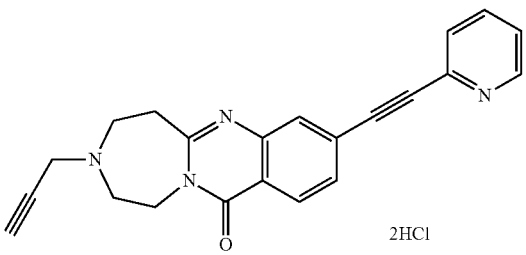

The title compound was prepared according to the experimental procedure as described in Example 2.29b. The product was then converted to the corresponding HCl salt. MS (ESI): 355 (MH$^+$); $^1$H NMR (300 MHz, CD$_3$OD) δ 8.70-8.66 (dd, J=5.88, 0.75 Hz, 1H), 8.72-8.66 (t, J=7.98 Hz, 1H), 8.40-8.34 (t, J=8.60 Hz, 2H), 8.15-8.10 (m, 1H), 8.08-8.07 (d, J=1.08 Hz, 1H), 7.92-7.89 (dd, J=8.27 Hz, 1.46 Hz, 1H), 4.83-4.81 (m, 2H), 4.28-4.27 (d, J=2.40 Hz, 2H), 3.86-3.70 (m, 6H), 3.48-3.46 (t, J=2.46 Hz, 1H). mGluR5 PAM EC$_{50}$: +++. Fold shift at 10 μM: +++.

Example 8.23. Synthesis of the 2HCl Salt of 2-(11-oxo-8-(pyridin-2-ylethynyl)-1,2,4,5-tetrahydro-[1,4]diazepino[7,1-b]quinazolin-3(11H)-yl)acetonitrile

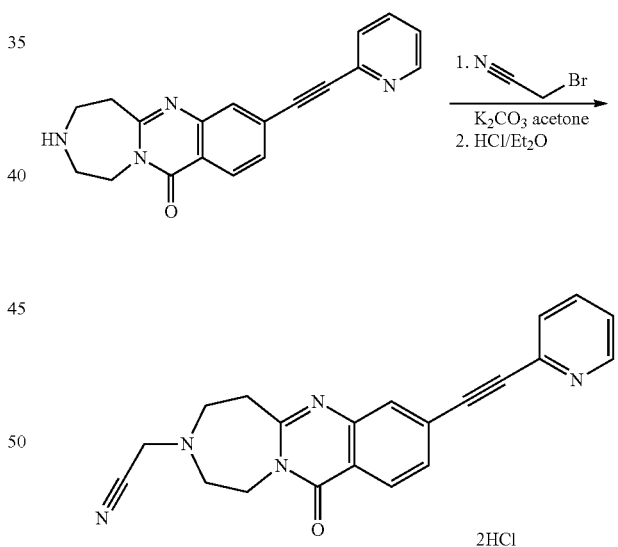

The title compound was prepared according to the experimental procedure as described in Example 2.29. The product was then converted to the corresponding 2HCl salt. MS (ESI): 356 (MH$^+$); $^1$H NMR (300 MHz, CD$_3$OD) δ 8.85-8.83 (d, J=8.84 Hz, 1H), 8.61-8.55 (t, J=7.95 Hz, 1H), 8.39-8.33 (d, J=8.28 Hz, 1H), 8.29-8.24 (d, J=8.10 Hz, 1H), 8.09-7.96 (m, 2H), 7.93-7.89 (dd, J=8.28, 1.32 Hz, 1H), 4.64-4.62 (m, 2H), 3.89 (s, 2H), 3.53-3.49 (m, 2H), 3.16-3.12 (m, 2H), 3.06-3.03 (m, 2H). mGluR5 PAM EC$_{50}$: +++. Fold shift at 10 μM: +++.

Example 8.24. Synthesis of the 2HCl Salt of 2-(11-oxo-8-(pyridin-2-ylethynyl)-1,2,4,5-tetrahydro-[1,4]diazepino[7,1-b]quinazolin-3(11H)-yl)propanenitrile

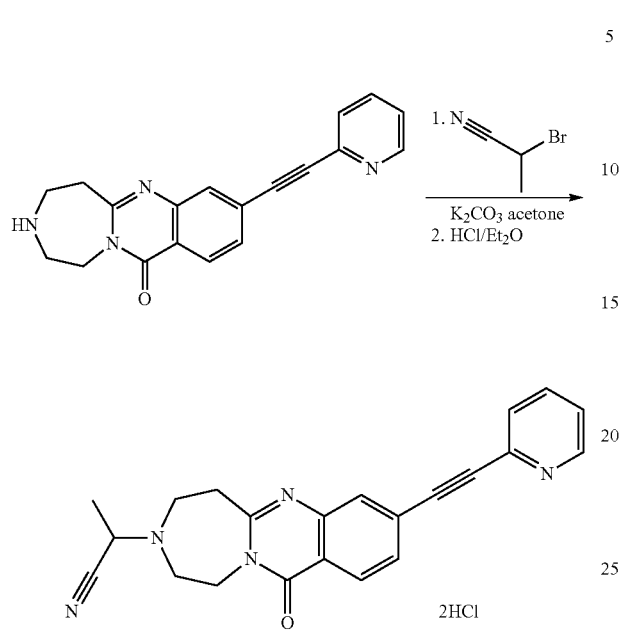

The title compound was prepared according to the experimental procedure as described in Example 2.29. The product was then converted to the corresponding 2HCl salt. MS (ESI): 370 (MH⁺); ¹H NMR (300 MHz, CD₃OD) δ 8.95-8.93 (d, J=5.70 Hz, 1H), 8.70-8.65 (t, J=8.00 Hz, 1H), 8.46-8.43 (d, J=8.25 Hz, 1H), 8.36-8.34 (d, J=8.01 Hz, 1H), 8.16-8.06 (m, 2H), 8.03-8.00 (d, J=8.01 Hz, 1H), 4.96-4.68 (m, 2H), 4.19-4.14 (m, 1H), 3.66-3.52 (m, 2H), 3.28-2.94 (m, 4H), 1.58-1.56 (d, J=7.17 Hz, 3H). mGluR5 PAM EC₅₀: +.

Example 8.25. Synthesis of 10-(pyridin-2-ylethynyl)-2,3,4,5-tetrahydro-[1,3]diazepino[2,1-b]quinazolin-7(1H)-one

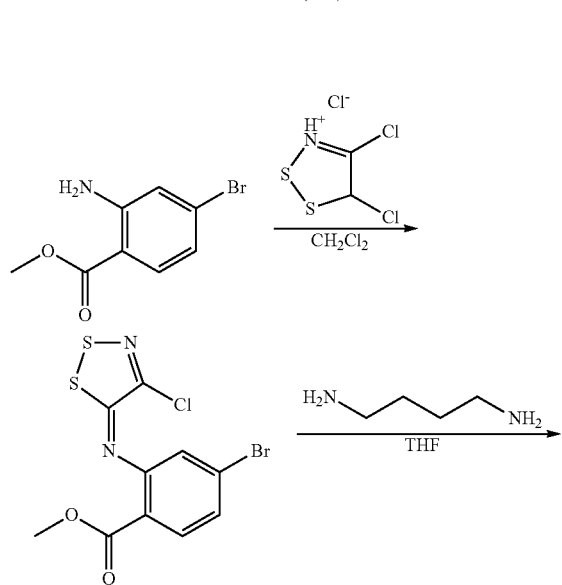

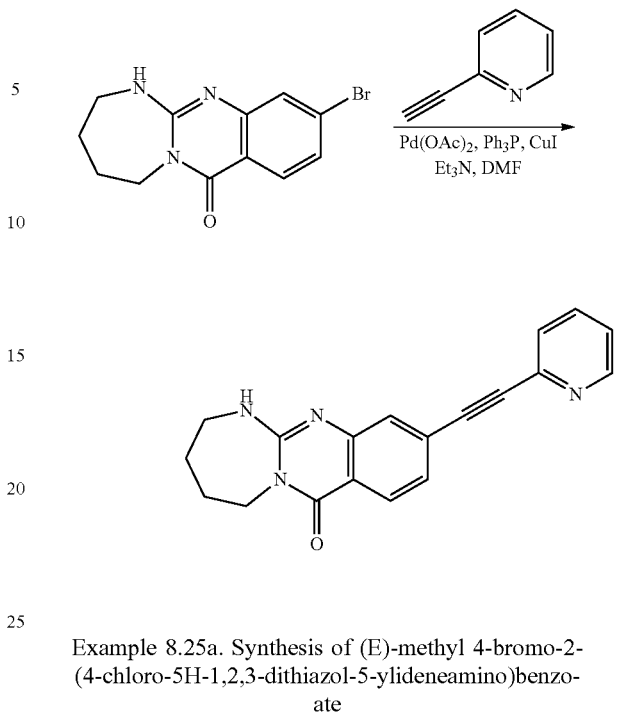

Example 8.25a. Synthesis of (E)-methyl 4-bromo-2-(4-chloro-5H-1,2,3-dithiazol-5-ylideneamino)benzoate

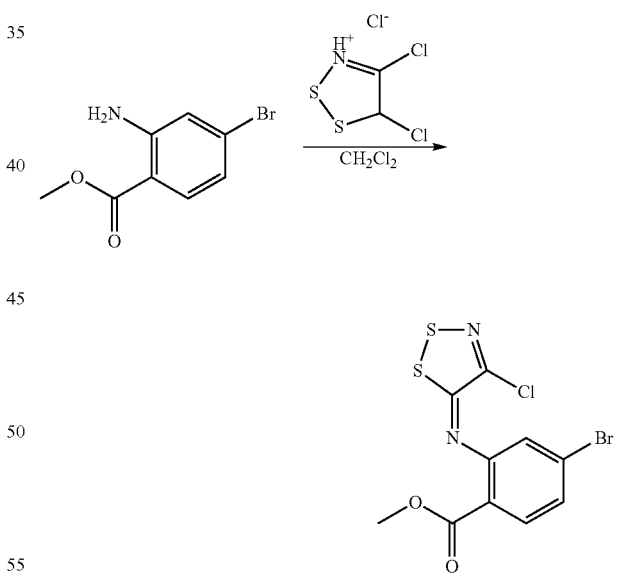

A solution of methyl 2-amino-4-bromobenzoate (1.0 g, 4.34 mmol, 1 eq) and 4,5-dichloro-1,2,3-dithiazolium chloride (2.0 g, 9.6 mmol, 2.2 eq) in DCM (20 mL) was stirred at rt under N₂ for 5 days. The reaction mixture was quenched with water and filtered. The filtrate was extracted with ethyl acetate (3×100 mL). The combined organic layers were dried over Na₂SO₄. After filtration and concentration, the residue was purified by silica gel chromatography to give the desired product. MS (ESI): 365, 367 (MH⁺).

Example 8.25b. Synthesis of 10-bromo-2,3,4,5-tetrahydro-[1,3]diazepino[2,1-b]quinazolin-7(1H)-one

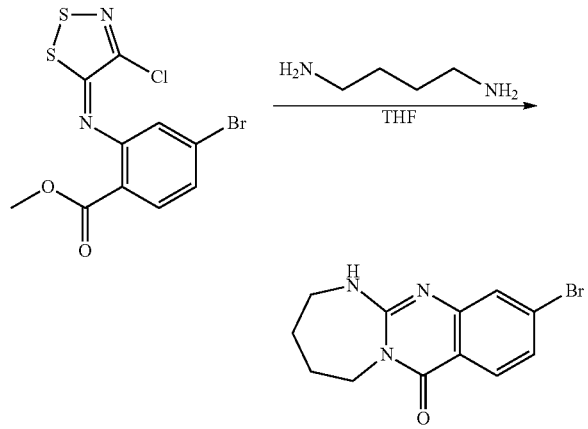

To a stirred solution of (E)-methyl 4-bromo-2-(4-chloro-5H-1,2,3-dithiazol-5-ylideneamino)benzoate (100 mg, 0.27 mmol, 1 eq) in THF was added butane-1,4-diamine (0.027 mL, 0.27 mmol, 1 eq) dropwise under N₂ and the reaction was heated at reflux for 3 hours. After it was cooled to rt, the reaction mixture was diluted with water (20 mL) and extracted with ethyl acetate (3×20 mL). The combined organic layers were dried over Na₂SO₄ and concentrated under reduced pressure to give the desired product, which was purified by silica gel chromatography. MS (ESI): 294, 296 (MH⁺).

Example 8.25c. Synthesis of 10-(pyridin-2-ylethynyl)-2,3,4,5-tetrahydro-[1,3]diazepino[2,1-b]quinazolin-7(1H)-one

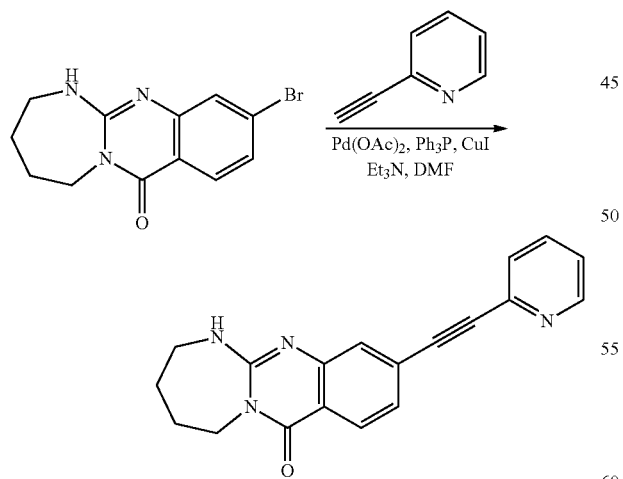

The title compound was prepared according to the experimental procedure as described in Example 1.1. MS (ESI): 317 (MH⁺); ¹H NMR (300 MHz, CD₃OD) δ 8.94-8.92 (d, J=5.73 Hz, 1H), 8.69-8.64 (t, J=7.98 Hz, 1H), 8.34-8.31 (d, J=8.07 Hz, 1H), 8.28-8.25 (d, J=8.19 Hz, 1H), 8.13-8.09 (t, J=6.9 Hz, 1H), 7.81 (s, 1H), 7.76-7.73 (dd, J=8.21, 1.19 Hz, 1H), 4.47-4.43 (t, J=6.3 Hz, 2H), 3.81-3.78 (t, J=3.9 Hz, 2H), 2.19-2.10 (m, 4H). mGluR5 PAM EC₅₀: ++++. Fold shift at 10 μM: ++.

Example 8.26. Synthesis of 10-(pyridin-2-ylethynyl)-2,3,4,5-tetrahydro-[1,3]diazepino[2,1-b]quinazolin-7(1H)-one

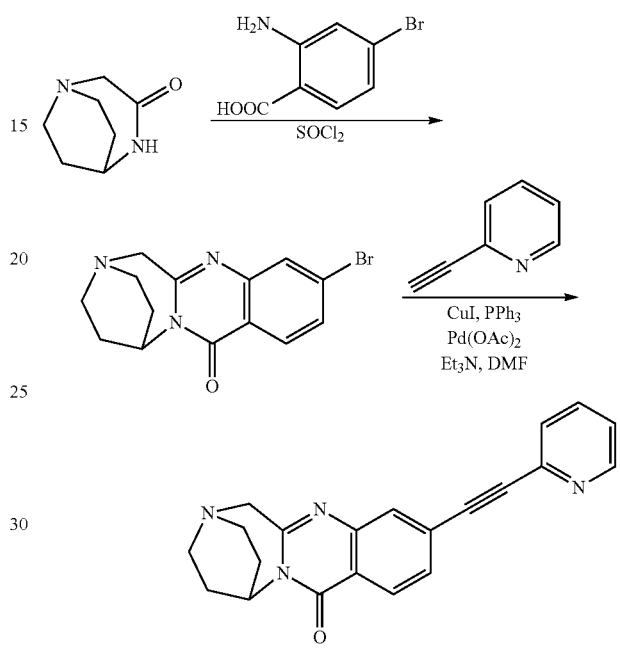

The title compound was prepared according to the experimental procedure as described in Example 2.2a and Example 1.1. MS (ESI): 343 (MH⁺); ¹H NMR (300 MHz, CD₃OD) δ 8.91-8.90 (d, J=5.4 Hz, 1H), 8.67-8.61 (t, J=7.9 Hz, 1H), 8.38-8.35 (d, 8.10 Hz, 1H), 8.32-8.29 (d, J=8.10 Hz, 1H), 8.10-8.06 (t, J=6.68 Hz, 1H), 8.02 (s, 1H), 7.86-7.83 (d, J=8.07 Hz, 1H), 5.86 (broad, 1H), 4.97 (s, 2H), 3.77-3.58 (m, 4H), 2.59-2.38 (m, 4H). mGluR5 PAM EC₅₀: ++.

Example 8.27. Synthesis of 4-methyl-8-(pyridin-2-ylethynyl)-2,3,4,5-tetrahydro-[1,4]diazepino[7,1-b]quinazolin-11(1H)-one

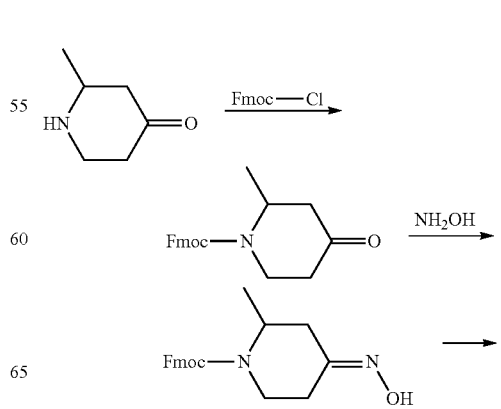

-continued

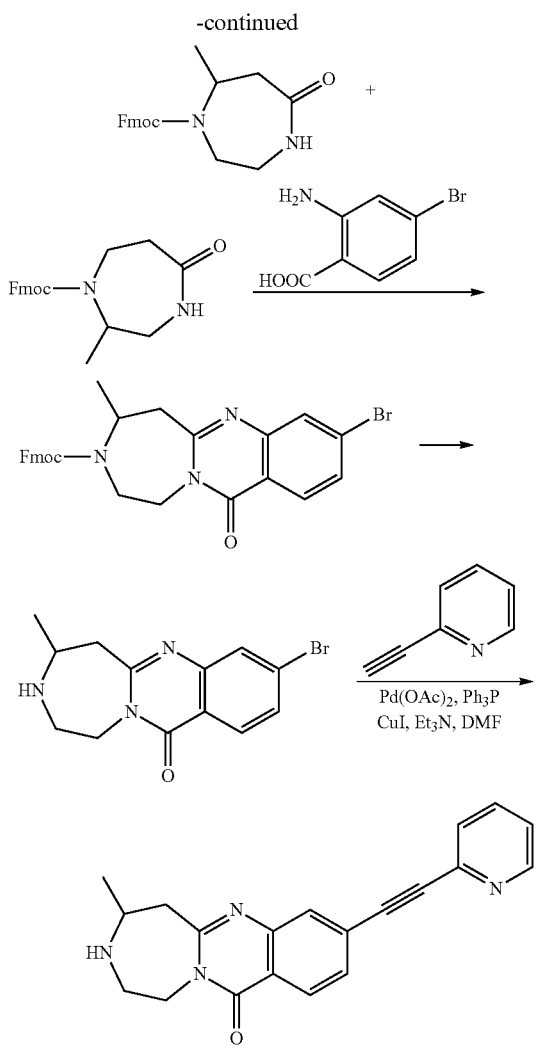

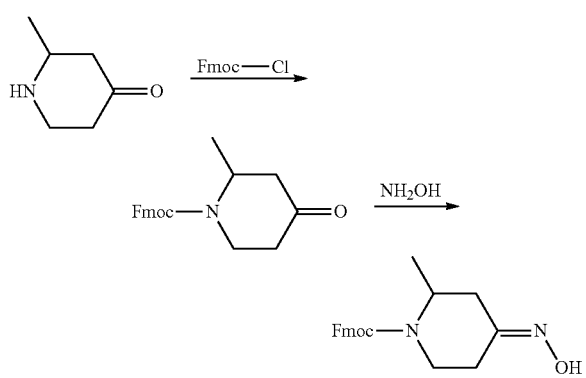

Example 8.27a. Synthesis of (E)-(9H-fluoren-9-yl) methyl 4-(hydroxyimino)-2-methylpiperidine-1-carboxylate The title compound was prepared according to the experimental procedure as described in Example 5.1a and Example 4.11a.

Example 8.27b. Synthesis of (9H-fluoren-9-yl) methyl 7-methyl-5-oxo-1,4-diazepane-1-carboxylate and (9H-fluoren-9-yl)methyl 2-methyl-5-oxo-1,4-diazepane-1-carboxylate

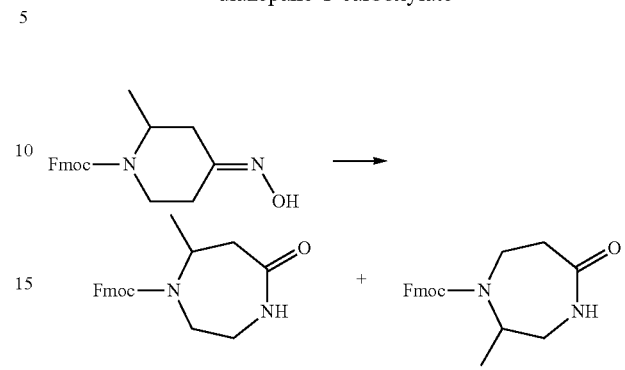

The title compound was prepared according to the experimental procedure as described in Example 4.11b. The two intermediates were separated in this step.

Example 8.27c. Synthesis of (9H-fluoren-9-yl) methyl 8-bromo-4-methyl-11-oxo-1,2,4,5-tetrahydro-[1,4]diazepino[7,1-b]quinazoline-3(11H)-carboxylate

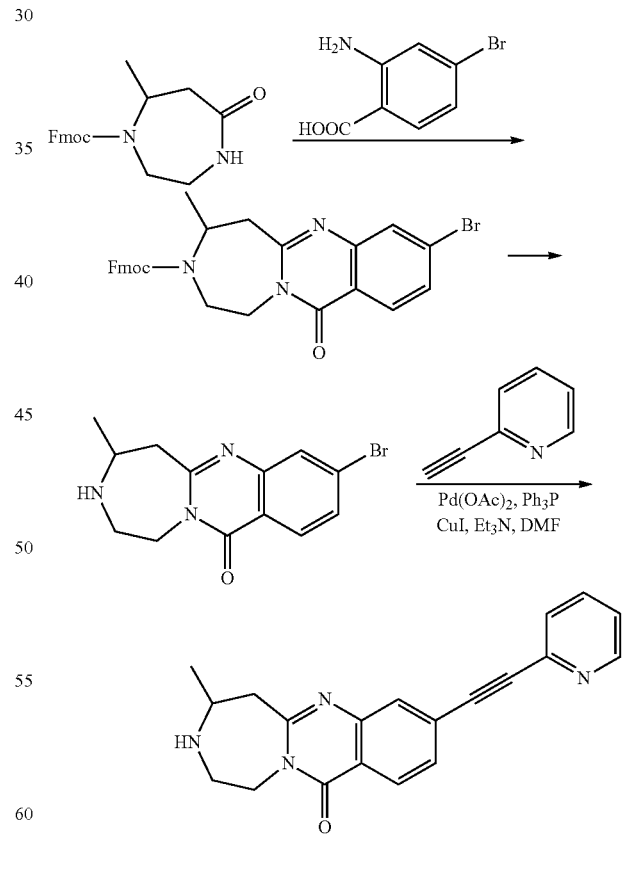

The title compound was prepared according to the experimental procedure as described in Example 2.2a, Example 3.17b, and Example 1.1. MS (ESI): 331 (MH$^+$); $^1$H NMR (300 MHz, DMSO-d$^6$) δ 10.00 (broad, 1H), 9.85 (broad, 1H), 8.71-8.69 (d, J=4.2 Hz, 1H), 8.21-8.18 (d, J=8.25 Hz, 1H), 8.05-8.00 (t, J=7.8 Hz, 1H), 7.86-7.83 (m, 2H), 7.75-7.73 (d, J=7.80 Hz, 1H), 7.60-7.56 (t, J=4.8 Hz, 1H), 4.97-4.78 (m, 1H), 4.42-4.34 (m, 1H), 3.68-3.56 (m, 3H), 3.31-3.21 (m, 2H), 1.41-1.39 (d, J=4.8 Hz, 3H).

Example 8.28. Synthesis of 3,4-dimethyl-8-(pyridin-2-ylethynyl)-2,3,4,5-tetrahydro-[1,4]diazepino[7,1-b]quinazolin-11(1H)-one

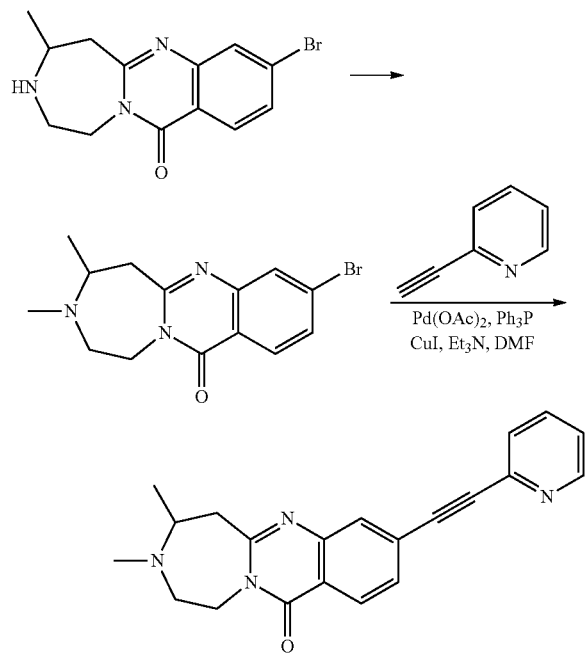

The title compound was prepared according to the experimental procedure as described in Example 5.2a and Example 1.1. MS (ESI): 345 (MH+); ¹H NMR (300 MHz, CDCl₃) δ 8.66 (m, 1H), 8.25-8.22 (d, J=8.25 Hz, 1H), 7.85 (s, 1H), 7.79-7.70 (m, 1H), 7.64-7.57 (m, 2H), 7.32-7.57 (m, 1H), 4.64-4.57 (m, 1H), 4.42-4.35 (m, 1H), 3.34-3.29 (d, J=14.08 Hz, 1H), 3.18-3.10 (m, 1H), 3.07-2.94 (m, 2H), 2.76-2.65 (m, 1H), 2.43 (s, 3H), 1.12-1.09 (d, J=6.39 Hz, 3H). mGluR5 PAM EC₅₀: +.

Example 8.29. Synthesis of the 2HCl Salt of 2-methyl-8-(pyridin-2-ylethynyl)-2,3,4,5-tetrahydro-[1,4]diazepino[7,1-b]quinazolin-11(1H)-one

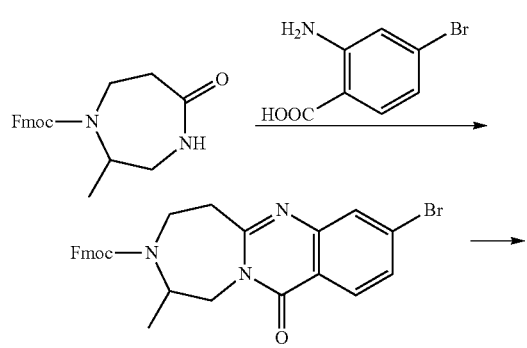

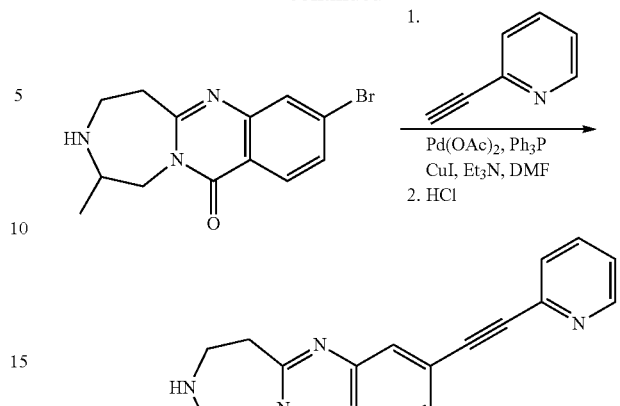

The title compound was prepared according to the experimental procedure as described in Example 2.2a, Example 3.17b, and Example 1.1. The product was then converted to the corresponding 2HCl salt. MS (ESI): 331 (MH+); ¹H NMR (300 MHz, DMSO-d⁶) δ 9.88-9.81 (m, 2H), 8.69-8.68 (d, J=4.71 Hz, 1H), 8.19-8.17 (d, J=8.22 Hz, 1H), 8.01-7.95 (m, 1H), 7.86 (s, 1H), 7.82-7.79 (d, J=7.74 Hz, 1H), 7.74-7.71 (dd, J=8.18, 1.40 Hz, 1H), 7.56-7.52 (m, 1H), 4.74-4.68 (d, J=15.88 Hz, 1H), 4.44-4.41 (m, 1H), 3.68-3.51 (m, 3H), 3.39-3.26 (m, 2H), 1.34-1.32 (d, J=6.75 Hz, 3H).

Example 8.30. Synthesis of 2,3-dimethyl-8-(pyridin-2-ylethynyl)-2,3,4,5-tetrahydro-[1,4]diazepino[7,1-b]quinazolin-11(1H)-one

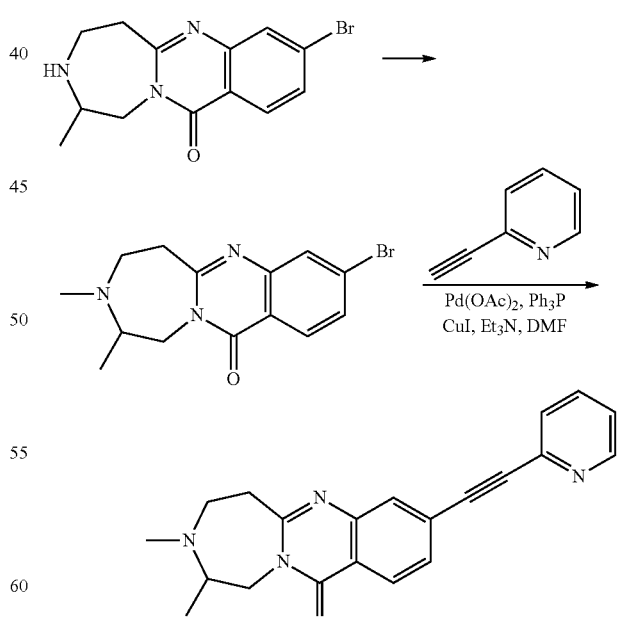

The title compound was prepared according to the experimental procedure as described in Example 5.2a and Example 1.1. MS (ESI): 345 (MH+); ¹H NMR (300 MHz, CDCl₃) δ 8.68-8.66 (d, J=4.74 Hz, 1H), 8.28-8.23 (d, J=8.25

Hz, 1H), 7.84 (s, 1H), 7.77-7.71 (t, J=7.8 Hz, 1H), 7.65-7.58 (m, 2H), 7.32-7.28 (m, 1H), 4.72-4.71 (broad, 1H), 4.30-4.26 (m, 1H), 3.27-3.25 (m, 1H), 3.19-2.97 (m, 3H), 2.85 (broad, 1H), 2.45 (s, 3H), 1.03-1.00 (d, J=6.54 Hz, 3H). mGluR5 PAM EC$_{50}$: ++.

Example 8.31. Synthesis of 1-methyl-10-(pyridin-2-ylethynyl)-2,3,4,5-tetrahydro-[1,3]diazepino[2,1-b]quinazolin-7(1H)-one

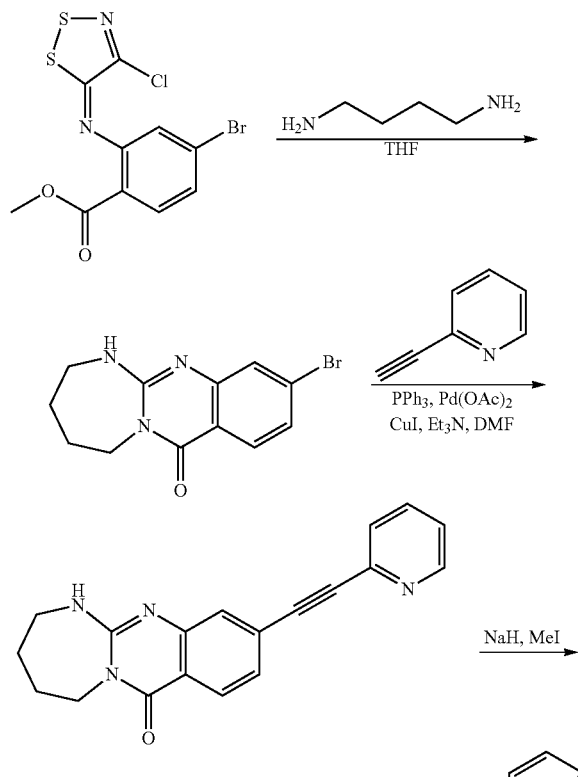

The title compound was prepared according to the experimental procedure as described in Example 5.26b, Example 1.1 and Example 5.27. MS (ESI): 331 (MH$^+$).

Example 8.32. Synthesis of the 2HCl Salt of 3-(tert-butyl)-8-(pyridin-2-ylethynyl)-2,3,4,5-tetrahydro-[1,4]diazepino[7,1-b]quinazolin-11(1H)-one

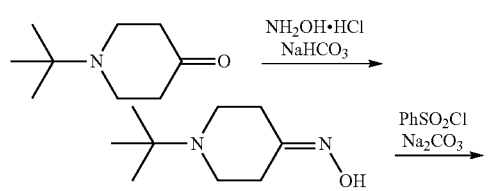

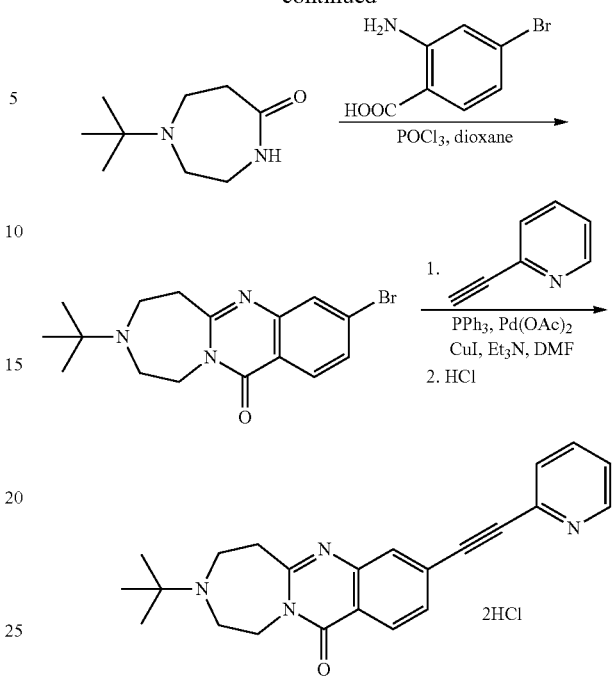

The title compound was prepared according to the experimental procedure as described in Example 4.11a, Example 4.11b, Example 2.2a, and Example 1.1. The product was then converted to the corresponding 2HCl salt. MS (ESI): 373 (MH$^+$); $^1$H NMR (300 MHz, CD$_3$OD) δ 9.00-8.94 (s, 1H), 8.70-8.65 (t, J=7.5 Hz, 1H), 8.39-8.33 (m, 2H), 8.13-8.09 (t, J=6.6 Hz, 1H), 8.05 (s, 1H), 7.90-7.87 (dd, J=8.2, 1.2 Hz, 1H), 5.60-5.52 (dd, J=16.9, 5.7 Hz, 1H), 4.29-4.12 (m, 3H), 3.98-3.89 (m, 1H), 3.51-3.33 (m, 3H), 1.53 (s, 9H).

Example 9.1. Synthesis of 3-((3-fluorophenyl)ethynyl)-14-methyl-8,9,10,11-tetrahydro-6H-7,10-epiminoazocino[2,1-b]quinazolin-13(7H)-one

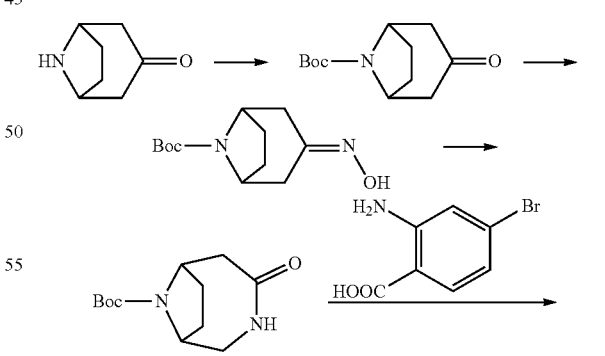

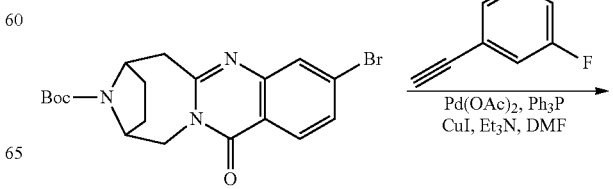

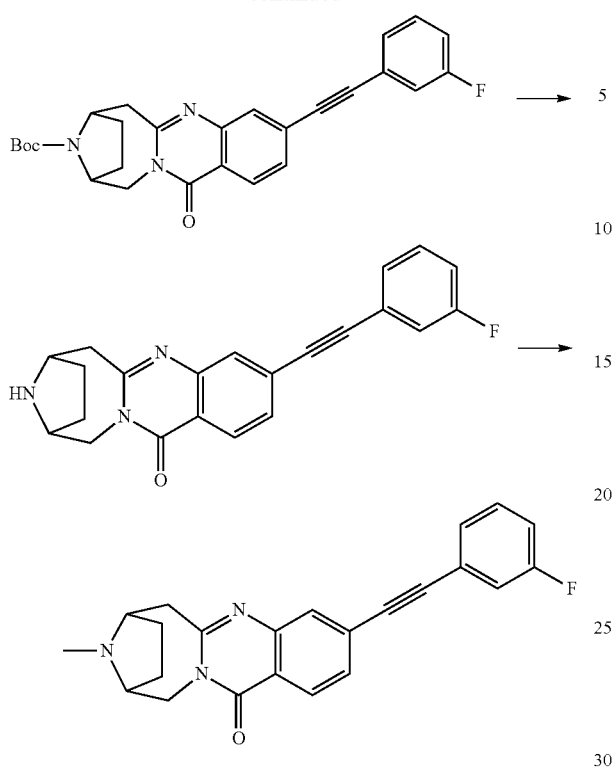

The title compound was prepared according to the experimental procedure as described in Example 6.20a, Example 4.11a, Example 4.11b, Example 2.2a, Example 1.1, Example 1.21c, and Example 1.21d. MS (ESI): 374 (MH+); $^1$H NMR (300 MHz, CD$_3$OD) δ 8.32-8.30 (d, J=7.80 Hz, 1H), 7.92 (s, 1H), 7.85-7.82 (m, 1H), 7.51-7.44 (m, 2H), 7.38-7.35 (d, J=7.80 Hz, 1H), 7.25-7.20 (m, 1H), 5.68-5.64 (m, 1H), 4.52-4.43 (m, 1H), 4.27-4.21 (m, 1H), 4.11-4.06 (m, 1H), 3.89-3.80 (m, 1H), 3.03 (s, 3H), 2.50-2.39 (m, 2H), 2.03-2.00 (m, 1H), 1.41-1.25 (m, 1H), 1.22-1.16 (m, 1H). mGluR5 PAM EC$_{50}$: +.

Example 9.2 and Example 9.3. Synthesis of the HCl Salt of 3-(pyridin-2-ylethynyl)-9,10,11,12,12a,13-hexahydro-6H-pyrido[2',1':3,4][1,4]diazepino[7,1-b]quinazolin-15(7H)-one and HCl Salt of 12-(pyridin-2-ylethynyl)-3,4,6,7,15,15a-hexahydro-1H-pyrido[1',2':4,5][1,4]diazepino[7,1-b]quinazolin-9(2H)-one

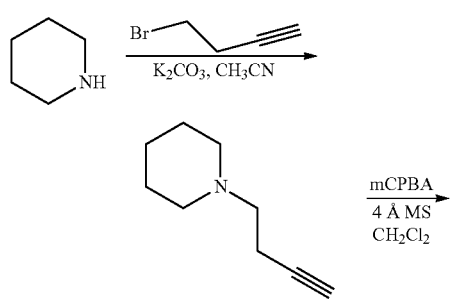

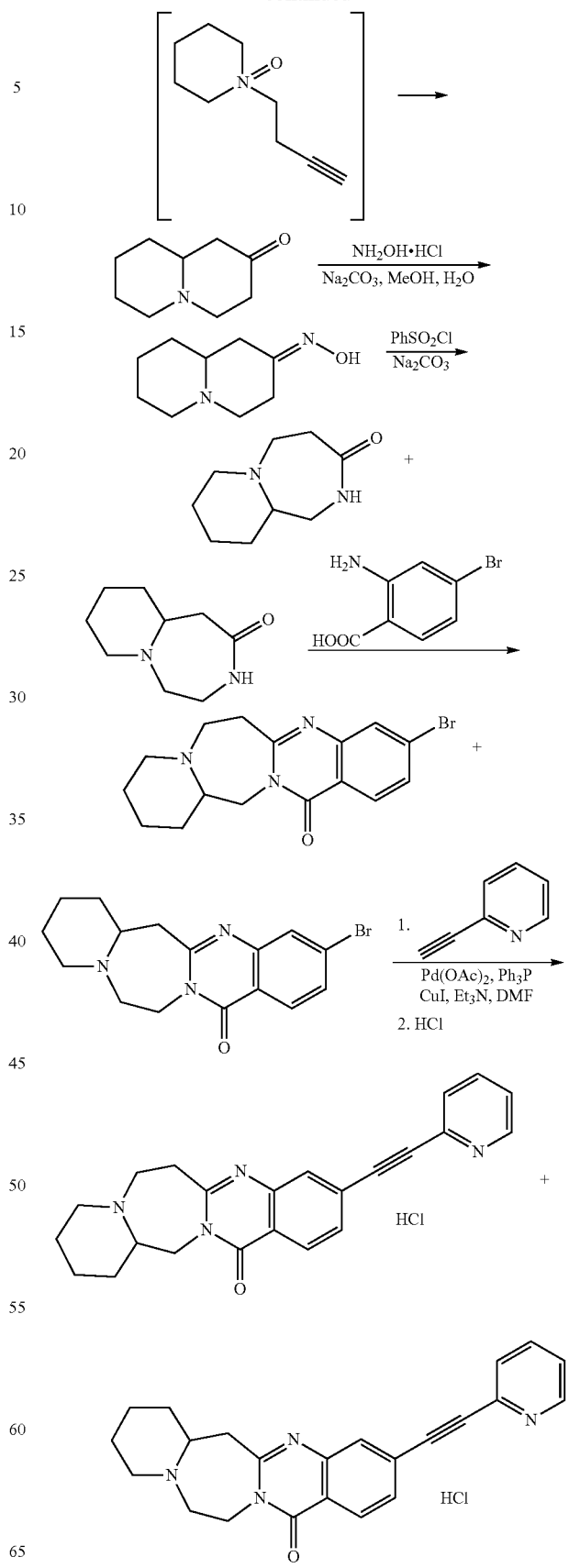

Example 9.2a. 1-(but-3-ynyl)piperidine

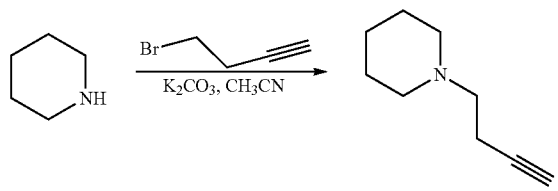

A solution of piperidine (2.9 g, 33.8 mmol), 4-bromobut-1-yne (5 g, 37.6 mmol) and K₂CO₃ (3 g, 2.2 mmol) in CH₃CN was stirred at 80° C. for 2 h. After it was cooled to room temperature, the solution was diluted with H₂O and extracted with ethyl acetate (3×200 mL). Then the combined organic layers were dried over Na₂SO₄ and concentrated to give 2 g of the crude product, which was directly used for the next step without further purification. MS (ESI): 138 (MH⁺).

Example 9.2b. Synthesis of hexahydro-1H-quinolizin-2(6H)-one

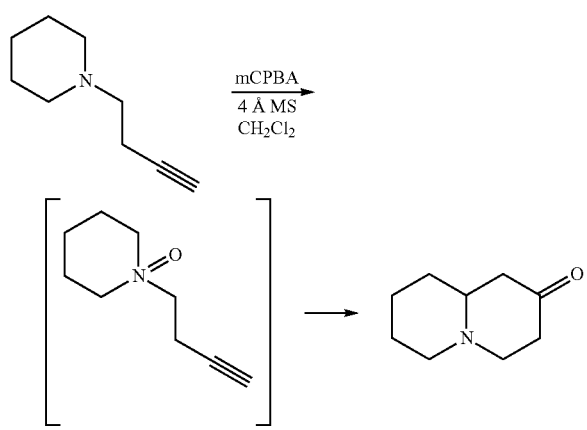

m-CPBA (600 mg, 3.65 mmol) was added into a solution of 1-(but-3-ynyl)piperidine (500 mg, 3.65 mmol and 4 Å MS (5×weight of m-CPBA) in DCM under N₂ at 0° C. The N-oxide formation was monitored by TLC. After completion, Ph₃PAuNTf₂ (134 mg, 0.18 mmol) was added to the reaction at 0° C. Upon completion, the mixture was diluted with DCM and the molecular sieves were filtered off. The filtrate was washed with 5% aqueous Na₂CO₃, dried over Na₂SO₄ and concentrated under vacuum. The residue was used for the next reaction without further purification. MS (ESI): 154 (MH⁺).

Example 9.2c. Synthesis of hexahydro-1H-quinolizin-2(6H)-one oxime

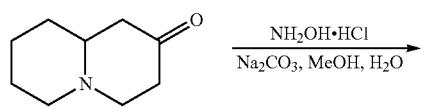

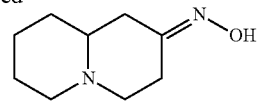

The title compound was prepared according to the experimental procedure as described in Example 4.11a. MS (ESI): 169 (MH⁺).

Example 9.2d and Example 9.3d. Synthesis of octahydropyrido[1,2-d][1,4]diazepin-2(1H)-one and octahydropyrido[1,2-a][1,4]diazepin-3(7H)-one

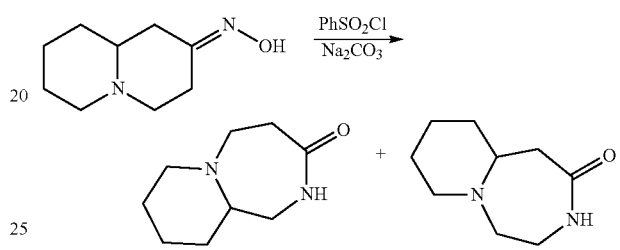

The title compound was prepared according to the experimental procedure as described in Example 4.11b. MS (ESI): 169 (MH⁺).

Example 9.2e and Example 9.3e. Synthesis of 3-bromo-9,10,11,12,12a,13-hexahydro-6H-pyrido[2',1':3,4][1,4]diazepino[7,1-b]quinazolin-15(7H)-one and 12-bromo-3,4,6,7,15,15a-hexahydro-1H-pyrido[1',2':4,5][1,4]diazepino[7,1-b]quinazolin-9(2H)-one

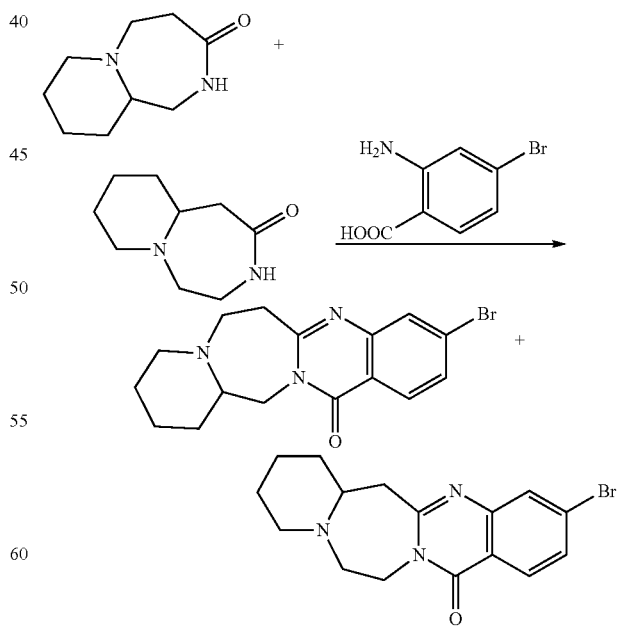

The title compound was prepared according to the experimental procedure as described in Example 2.2a. MS (ESI): 348-350 (MH⁺)

Example 9.2f and Example 9.3f. Synthesis of the HCl Salt of 3-(pyridin-2-ylethynyl)-9,10,11,12,12a,13-hexahydro-6H-pyrido[2',1':3,4][1,4]diazepino[7,1-b]quinazolin-15(7H)-one and the HCl Salt of 12-(pyridin-2-ylethynyl)-3,4,6,7,15,15a-hexahydro-1H-pyrido[1',2':4,5][1,4]diazepino[7,1-b]quinazolin-9(2H)-one

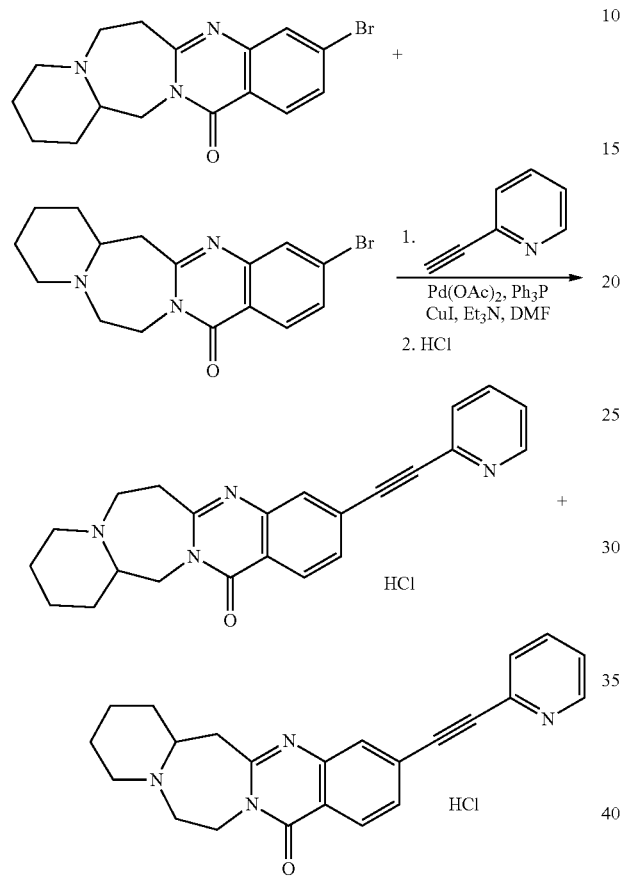

The title compounds were prepared according to the experimental procedure as described in Example 1.1. The products were then converted to the corresponding HCl salt. MS (ESI): 371 (MH+);

3-(pyridin-2-ylethynyl)-9,10,11,12,12a,13-hexahydro-6H-pyrido[2',1':3,4][1,4]diazepino[7,1-b]quinazolin-15(7H)-one MS (ESI): 371 (MH+); $^1$H NMR (300 MHz, CD$_3$OD): δ 8.92-8.90 (d, J=5.82 Hz, 1H), 8.68-8.63 (d, J=7.99 Hz, 1H), 8.37-8.30 (m, 2H), 8.11-8.07 (t, J=6.48 Hz, 1H), 8.03 (s, 1H), 7.87-7.84 (d, J=8.25 Hz, 1H), 5.21-5.15 (d, J=16.78 Hz, 1H), 4.19-4.11 (m, 1H), 3.97-3.84 (m, 2H), 3.63-3.42 (m, 3H), 3.09-3.06 (m, 1H), 2.27-2.20 (m, 1H), 2.15-3.39 (m, 1H), 2.03-1.89 (m, 4H), 1.68-1.64 (m, 2H). mGluR5 PAM EC$_{50}$: ++. Fold shift at 10 μM: +++.

12-(pyridin-2-ylethynyl)-3,4,6,7,15,15a-hexahydro-1H-pyrido[1',2':4,5][1,4]diazepino[7,1-b]quinazolin-9(2H)-one MS (ESI): 371 (MH+); $^1$H NMR (300 MHz, CD$_3$OD): δ 8.93-8.91 (d, J=5.85 Hz, 1H), 8.70-8.64 (d, J=7.98 Hz, 1H), 8.38-8.32 (m, 2H), 8.13-8.08 (t, J=7.17 Hz, 1H), 8.03 (s, 1H), 7.88-7.85 (d, J=8.24 Hz, 1H), 5.54-5.57 (m, 1H), 4.30-4.211 (m, 1H), 3.94-3.82 (m, 2H), 3.63-3.59 (m, 2H), 3.47-3.39 (m, 1H), 3.20-3.15 (d, J=16.15 Hz, 1H), 3.10-3.00 (m, 1H), 2.15-3.39 (m, 1H), 2.00-1.88 (m, 3H), 1.73-1.64 (m, 2H).

Example 9.4 and Example 9.5. Synthesis of the HCl Salt of 9-(pyridin-2-ylethynyl)-2,3,5,6,14,14a-hexahydropyrrolo[2',1':3,4][1,4]diazepino[7,1-b]quinazolin-12(1H)-one and the HCl Salt of 11-(pyridin-2-ylethynyl)-2,3,5,6,14,14a-hexahydropyrrolo[1',2':4,5][1,4]diazepino[7,1-b]quinazolin-8(1H)-one

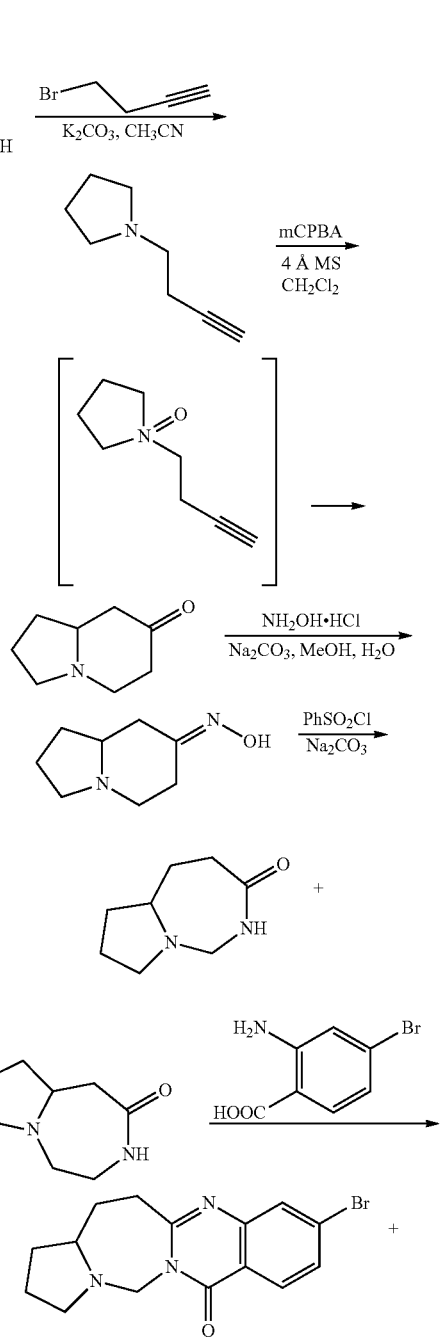

393
-continued

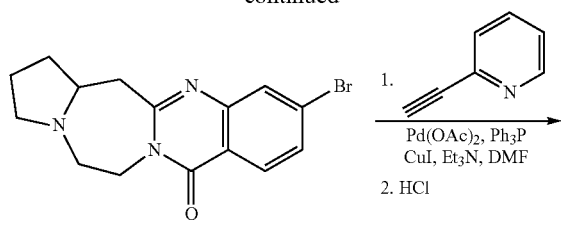

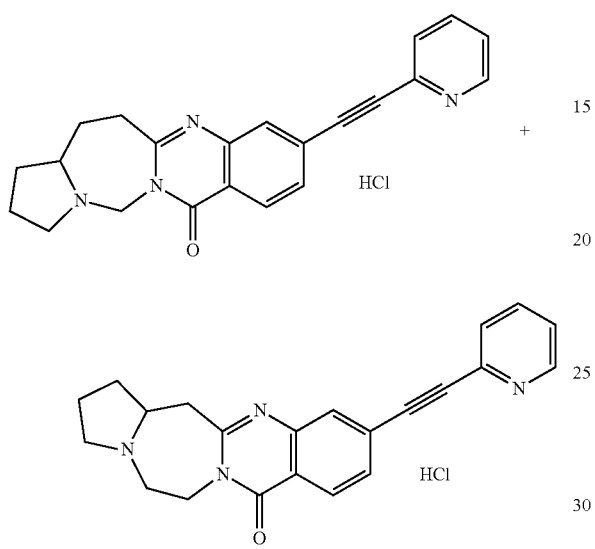

The title compounds were prepared according to the experimental procedure as described in Example 9.2a, Example 9.2b, Example 4.11a, Example 4.11b, Example 2.2a, and Example 1.1. The products were then converted to the corresponding HCl salt.

9-(Pyridin-2-ylethynyl)-2,3,5,6,14,14a-hexahydropyrrolo[2',1':3,4][1,4]diazepino[7,1-b]quinazolin-12(1H)-one MS (ESI): 357 (MH$^+$); $^1$H NMR (300 MHz, CD$_3$OD) δ 8.93-8.92 (d, J=3.00 Hz, 1H), 8.72-8.66 (dt, J=7.97, 1.48 mHz, 1H), 8.40-8.34 (t, J=8.74 Hz, 2H), 8.15-8.10 (dt, J=13.71, 1.02 Hz, 1H), 8.08 (s 1H), 7.93-7.90 (dd, J=8.25, 1.32 Hz, 1H), 5.64-5.58 (d, J=10.8 Hz, 1H), 4.24-4.16 (m, 1H), 4.07-4.04 (m, 1H), 3.88-3.84 (m, 2H), 3.66-3.48 (m, 3H), 3.28-3.21 (m, 1H), 2.52-2.49 (m, 1H), 2.29-2.21 (m, 3H). mGluR5 PAM EC$_{50}$: +++. Fold shift at 10 μM: +++.

11-(pyridin-2-ylethynyl)-2,3,5,6,14,14a-hexahydropyrrolo[1',2':4,5][1,4]diazepino[7,1-b]quinazolin-8(1H)-one MS (ESI): 357 (M+H$^+$); $^1$H NMR (300 MHz, CD$_3$OD) δ 8.91-8.91 (d, J=5.04 Hz, 1H), 8.71-8.65 (dt, J=7.99, 1.53 Hz, 1H), 8.38-8.32 (m, 2H), 8.14-8.09 (m, 1H), 8.05-8.04 (d, J=1.14 Hz, 1H), 7.89-7.86 (dd, J=8.20, 1.45 Hz, 1H), 5.59-5.55 (m, 1H), 4.12-4.07 (m, 2H), 3.86-3.81 (m, 2H), 3.75-3.69 (m, 1H), 3.51-3.45 (m, 2H), 3.28-3.19 (m, 1H), 2.59-2.50 (m, 1H), 2.21-2.00 (m, 3H). mGluR5 PAM EC$_{50}$: ++.

394

Example 9.4a and Example 9.4b. Separation of Enantiomers of 9-(pyridin-2-ylethynyl)-2,3,5,6,14,14a-hexahydropyrrolo[2',1':3,4][1,4]diazepino[7,1-b]quinazolin-12(1H)-one into (S)-9-(pyridin-2-ylethynyl)-2,3,5,6,14,14a-hexahydropyrrolo[2',1':3,4][1,4]diazepino[7,1-b]quinazolin-12(1H)-one and (R)-9-(pyridin-2-ylethynyl)-2,3,5,6,14,14a-hexahydropyrrolo[2',1':3,4][1,4]diazepino[7,1-b]quinazolin-12(1H)-one

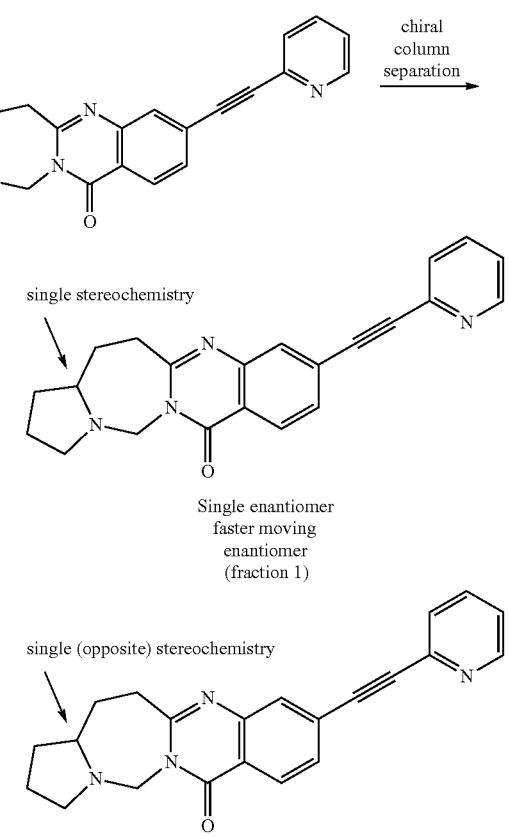

Racemic 9-(pyridin-2-ylethynyl)-2,3,5,6,14,14a-hexahydropyrrolo[2',1':3,4][1,4]diazepino[7,1-b]quinazolin-12(1H)-one was separated into the corresponding two single enantiomer compounds (S)-9-(pyridin-2-ylethynyl)-2,3,5,6,14,14a-hexahydropyrrolo[2',1':3,4][1,4]diazepino[7,1-b]quinazolin-12(1H)-one and (R)-9-(pyridin-2-ylethynyl)-2,3,5,6,14,14a-hexahydropyrrolo[2',1':3,4][1,4]diazepino[7,1-b]quinazolin-12(1H)-one using chiral chromatography with an isocratic SFC method. The column used was a 4.6×100 mm RegisPack from Regis Technologies (Morton Grove, Ill.). The CO$_2$ co-solvent was methanol:isopropanol)1:1) with 0.1% isopropylamine. Isocratic Method: 50% Co-solvent at 4 mL/min System Pressure: 100 bar. Column Temperature 25° C.

Faster moving enantiomer (fraction 1): Retention time=1.8 min 99.6% ee. mGluR5 PAM EC$_{50}$: +++.

Slower moving enantiomer (fraction 2): Retention time=2.5 min. 99.2% ee. mGluR5 PAM EC$_{50}$: ++.

Example 10.1 and Example 10.2. Synthesis of the HCl Salt of 11-((4-fluorophenyl)ethynyl)-3-methyl-3,4,5,6-tetrahydro-1H-[1,5]diazocino[2,1-b]quinazolin-8(2H)-one and the HCl Salt of 9-((4-fluorophenyl)ethynyl)-3-methyl-3,4,5,6-tetrahydro-1H-[1,4]diazocino[8,1-b]quinazolin-12(2H)-one

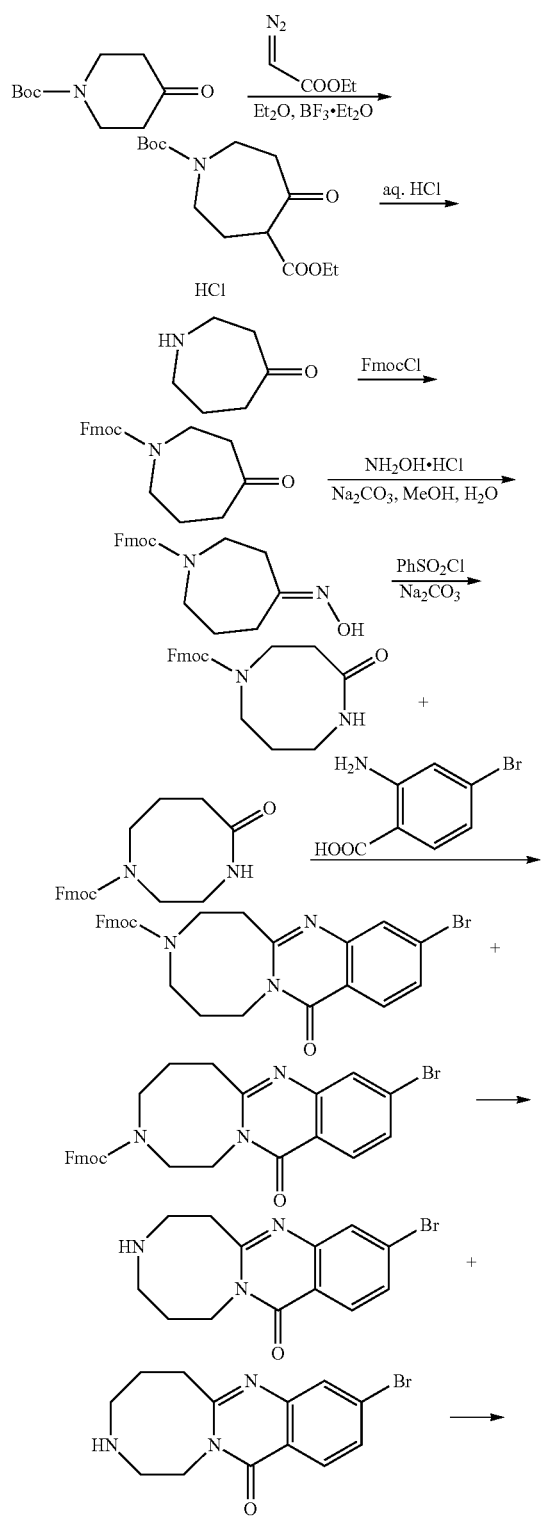

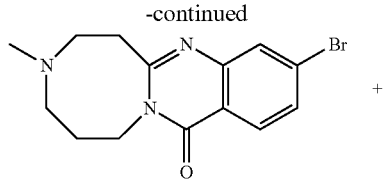

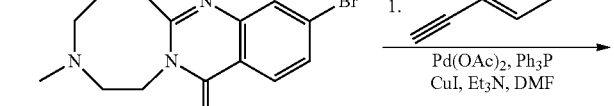

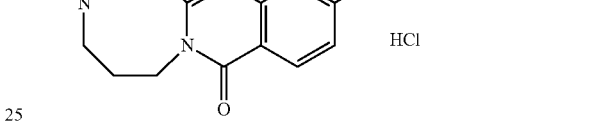

Example 10.1a. Synthesis of 1-tert-butyl 4-ethyl 5-oxoazepane-1,4-dicarboxylate

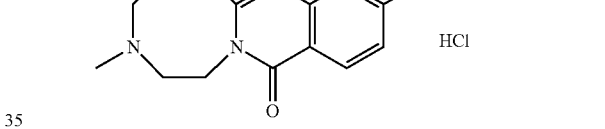

To a solution of tert-butyl 4-oxopiperidine-1-carboxylate (3.2 g, 16 mmol, 1.0 equiv) in Et$_2$O (20 mL) at −50° C. were added BF$_3$.Et$_2$O (2.3 g, 16 mmol, 1.0 equiv) in dropwise. After completion of addition of BF$_3$.Et$_2$O, ethyl 2-diazoacetate (2 g, 17.6 mmol, 1.1 equiv) was added dropwise. The reaction was then stirred at −50° C. for an hour and kept at room temperature overnight. Then the reaction mixture was poured into water (100 mL), extracted with ethyl acetate (3×100 mL), combined of the organic layers and dried over Na$_2$SO$_4$. The solvent was removed under reduced pressure to give the desired product (4 g), which was purified by silica gel chromatography. MS (ESI): 286 (MH$^+$).

Example 10.1b. Synthesis of azepan-4-one hydrochloride

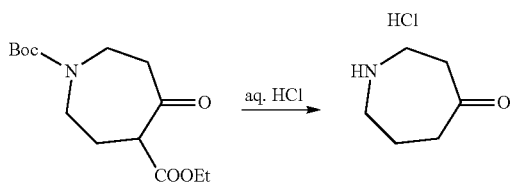 [SMILES: Cl ; CCOC(=O)C1CCN(C(=O)OC(C)(C)C)CCC1=O ; O=C1CCCNCC1]

A solution of 1-tert-butyl 4-ethyl 5-oxoazepane-1,4-dicarboxylate (0.9 g, 3.16 mmol, 1 equiv) in aq. HCl (30 mL, 4N) was stirred at reflux for 7 h. The reaction mixture was then concentrated to give the desired product, which was directly used for the next step without further purification. MS (ESI): 114 (MH$^+$).

Example 10.1c. Synthesis of (E,Z)-(9H-fluoren-9-yl)methyl 4-(hydroxyimino)azepane-1-carboxylate

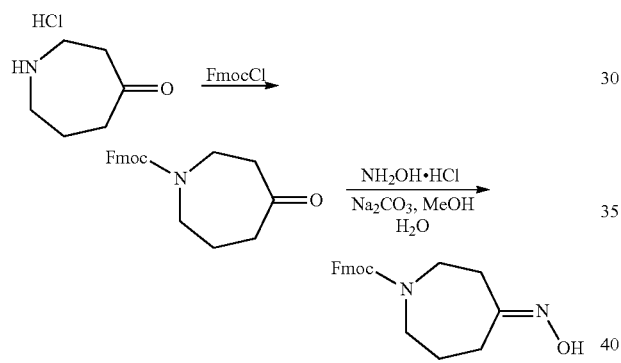

The title compound was prepared according to the experimental procedure as described in Example 5.1a, Example 4.11a. MS (ESI): 351 (MH$^+$).

Example 10.1d and Example 10.2d. Synthesis of (9H-fluoren-9-yl)methyl 4-oxo-1,5-diazocane-1-carboxylate and (9H-fluoren-9-yl)methyl 5-oxo-1,4-diazocane-1-carboxylate

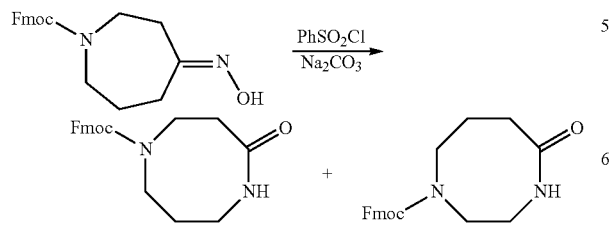

The title compound was prepared according to the experimental procedure as described in Example 4.11b. MS (ESI): 351 (MH$^+$).

Example 10.1e and Example 10.2e. Synthesis of (9H-fluoren-9-yl)methyl 9-bromo-12-oxo-4,5,6,12-tetrahydro-1H-[1,4]diazocino[8,1-b]quinazoline-3 (2H)-carboxylate and (9H-fluoren-9-yl)methyl 11-bromo-8-oxo-4,5,6,8-tetrahydro-1H-[1,5]diazocino[2,1-b]quinazoline-3(2H)-carboxylate

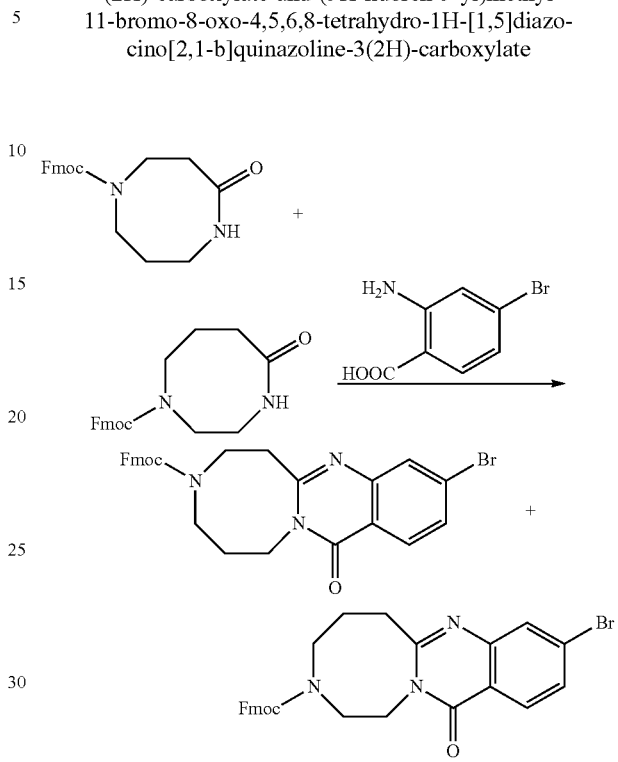

The title compounds were prepared according to the experimental procedure as described in Example 2.2a. MS (ESI): 530, 532 (MH$^+$).

Example 10.1f and Example 10.2f. Synthesis of 9-bromo-3,4,5,6-tetrahydro-1H-[1,4]diazocino[8,1-b]quinazolin-12 (2H)-one and 11-bromo-3,4,5,6-tetrahydro-1H-[1,5]diazocino[2,1-b]quinazolin-8 (2H)-one

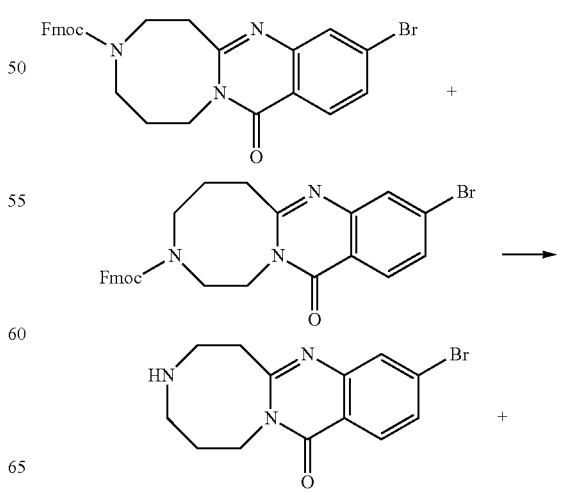

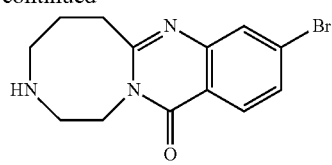

The title compounds were prepared according to the experimental procedure as described in Example 3.17b. MS (ESI): 308, 310 (MH+).

Example 10.1g and Example 10.2g. Synthesis of 9-bromo-3-methyl-3,4,5,6-tetrahydro-1H-[1,4]diazocino[8,1-b]quinazolin-12(2H)-one and 11-bromo-3-methyl-3,4,5,6-tetrahydro-1H-[1,5]diazocino[2,1-b]quinazolin-8(2H)-one

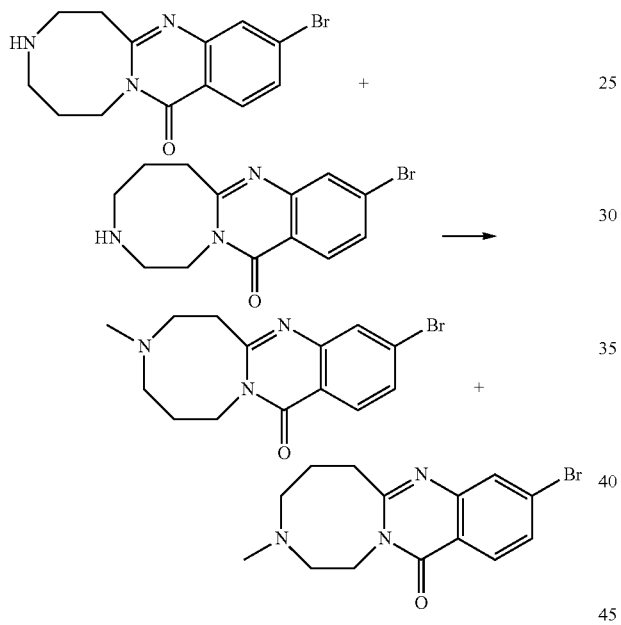

The title compounds were prepared according to the experimental procedure as described in Example 5.2a. MS (ESI): 322, 324 (MH+).

Example 10.1h and Example 10.2h. Synthesis of the HCl Salt of 11-((4-fluorophenyl)ethynyl)-3-methyl-3,4,5,6-tetrahydro-1H-[1,5]diazocino[2,1-b]quinazolin-8(2H)-one and the HCl Salt of 9-((4-fluorophenyl)ethynyl)-3-methyl-3,4,5,6-tetrahydro-1H-[1,4]diazocino[8,1-b]quinazolin-12(2H)-one

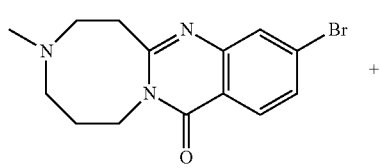

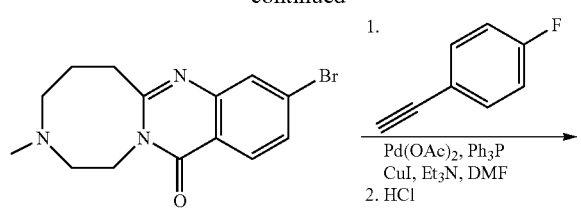

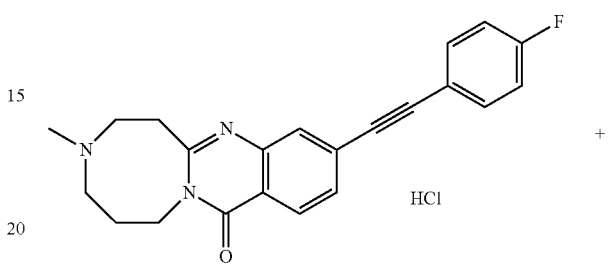

The title compounds were prepared according to the experimental procedure as described in Example 1.1. The products were then converted to the corresponding HCl salt. MS (ESI): 362 (MH+).

11-((4-fluorophenyl)ethynyl)-3-methyl-3,4,5,6-tetrahydro-1H-[1,5]diazocino[2,1-b]quinazolin-8(2H)-one MS (ESI): 362 (MH+); $^1$H NMR (300 MHz, CDCl$_3$) δ 8.24-8.21 (d, J=8.25 Hz, 1H), 7.77 (s, 1H), 7.72-7.52 (m, 3H), 7.12-7.05 (m, 2H), 4.42 (broad, 2H), 3.05-3.00 (t, J=6.12 Hz, 2H), 2.80-2.78 (m, 2H), 2.63-2.60 (t, J=5.46 Hz, 2H), 2.34 (s, 3H), 2.06-2.00 (m, 2H). mGluR5 PAM EC$_{50}$: ++++.

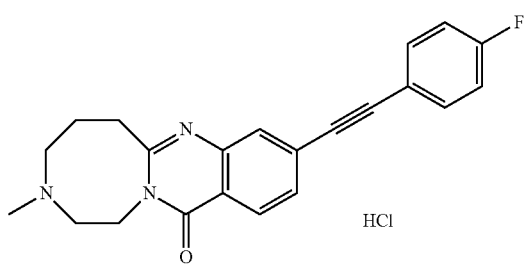 [SMILES: CN1CCCc2nc3cc(C#Cc4ccc(F)cc4)ccc3c(=O)n2CC1 ; Cl]

9-((4-fluorophenyl)ethynyl)-3-methyl-3,4,5,6-tetra-hydro-1H-[1,4]diazocino[8,1-b]quinazolin-12(2H)-one MS (ESI): 362 (MH+); $^1$H NMR (300 MHz, CDCl$_3$) δ 8.24-8.21 (d, J=8.25 Hz, 1H), 7.77 (s, 1H), 7.72-7.52 (m, 3H), 7.12-7.05 (m, 2H), 4.40 (broad, 2H), 3.05-3.00 (t, J=6.12 Hz, 2H), 2.80-2.78 (m, 2H), 2.63-2.60 (t, J=5.46 Hz, 2H), 2.34 (s, 3H), 2.06-2.00 (m, 2H). mGluR5 PAM EC$_{50}$: +++. Fold shift at 10 μM: ++.

Example 10.3 and Example 10.4. Synthesis of the HCl Salt of 11-((3-fluorophenyl)ethynyl)-3-methyl-3,4,5,6-tetrahydro-1H-[1,5]diazocino[2,1-b]quinazolin-8(2H)-one and the HCl Salt of 9-((3-fluorophenyl)ethynyl)-3-methyl-3,4,5,6-tetrahydro-1H-[1,4]diazocino[8,1-b]quinazolin-12(2H)-one

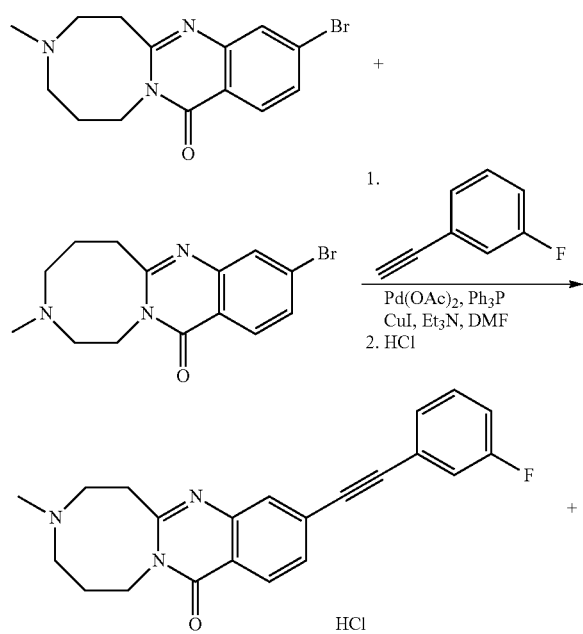

The title compounds were prepared according to the experimental procedure as described in Example 1.1. The products were then converted to the corresponding HCl salt. MS (ESI): 362 (MH+).

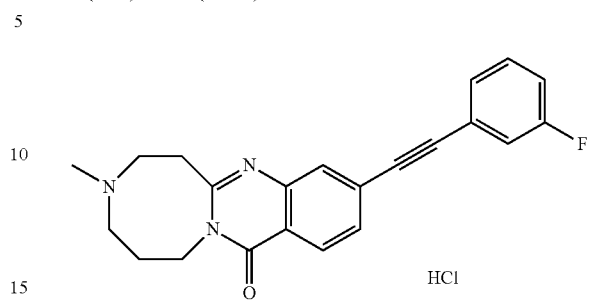

11-((3-fluorophenyl)ethynyl)-3-methyl-3,4,5,6-tetra-hydro-1H-[1,5]diazocino[2,1-b]quinazolin-8(2H)-one $^1$H NMR (300 MHz, CDCl$_3$) δ 8.25-8.23 (d, J=7.80 Hz, 1H), 7.79 (s, 1H), 7.57-7.54 (d, J=8.22 Hz, 1H), 7.38-7.35 (m, 2H), 7.26-7.25 (m, 1H), 7.14-7.17 (m, 1H), 4.44-4.42 (m, 2H), 3.16-3.13 (m, 2H), 3.01-2.97 (m, 2H), 2.47 (m, 2H), 2.45 (s, 3H), 1.94-1.87 (m, 2H). mGluR5 PAM EC$_{50}$: ++++. Fold shift at 10 μM: ++.

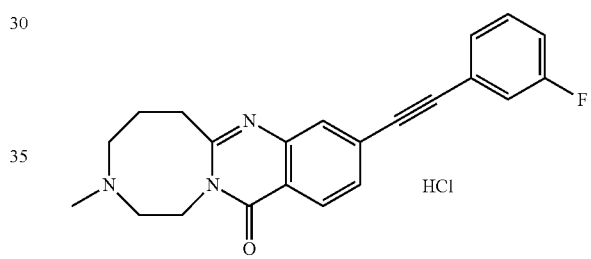

9((3-fluorophenyl)ethynyl)-3-methyl-3,4,5,6-tetra-hydro-1H-[1,4]diazocino[8,1-b]quinazolin-12(2H)-one $^1$H NMR (300 MHz, CDCl$_3$) δ 8.25-8.22 (d, J=8.25 Hz, 1H), 7.79 (s, 1H), 7.56-7.53 (d, J=8.30 Hz, 1H), 7.37-7.34 (m, 2H), 7.26-7.25 (m, 1H), 7.13-7.06 (m, 1H), 4.42-4.32 (m, 2H), 3.03-3.00 (t, J=6.09 Hz, 2H), 2.80 (s, 2H), 2.63-2.60 (t, J=5.16 Hz, 2H), 2.34 (s, 3H), 2.04-2.00 (m, 2H). mGluR5 PAM EC$_{50}$: +++. Fold shift at 10 μM: ++.

Example 10.5 and Example 10.6. Synthesis of 9-((3-fluorophenyl)ethynyl)-2,3,5,6-tetrahydro-1H-[1,4]diazocino[8,1-b]quinazoline-4,12-dione and of 11-((3-fluorophenyl)ethynyl)-2,3,5,6-tetrahydro-1H-[1,5]diazocino[2,1-b]quinazoline-4,8-dione

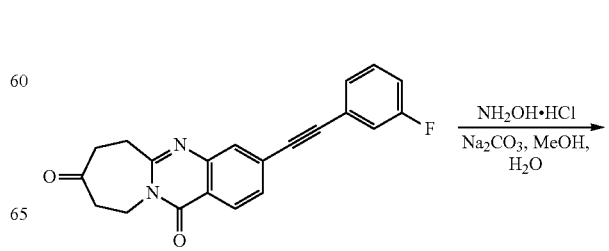

-continued

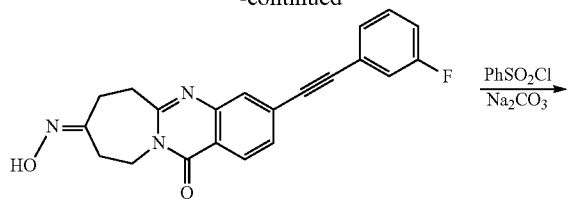

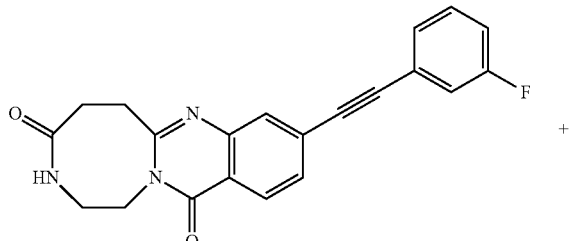

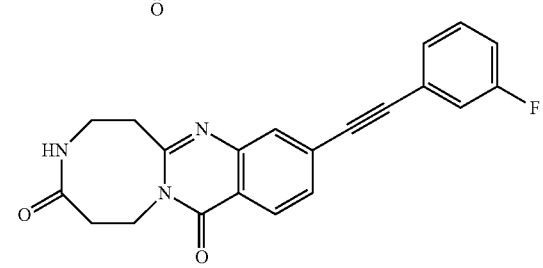

The title compounds were prepared according to the experimental procedure as described in Example 4.11a and Example 4.11b. MS (ESI): 362 (MH+).

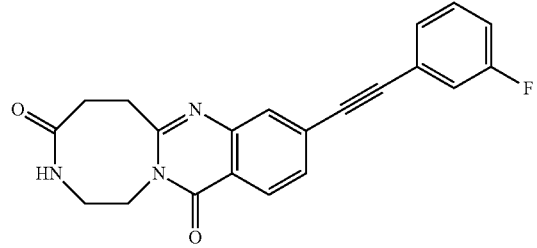 [SMILES: O=C1CCc2nc3cc(C#Cc4cccc(F)c4)ccc3c(=O)n2CCN1]

9-((3-fluorophenyl)ethynyl)-2,3,5,6-tetrahydro-1H-[1,4]diazocino[8,1-b]quinazoline-4,12-dione $^1$H NMR (300 MHz, DMSO-d$^6$) δ 8.15-8.12 (d, J=8.25 Hz, 1H), 7.77-7.76 (d, J=1.02 Hz, 1H), 7.69-7.63 (m, 2H), 7.53-7.46 (m, 3H), 7.36-7.33 (m, 1H), 4.41 (m, 2H), 3.65 (m, 2H), 3.34 (m, 2H), 2.91-2.89 (m, 2H). mGluR5 PAM EC$_{50}$: +++.

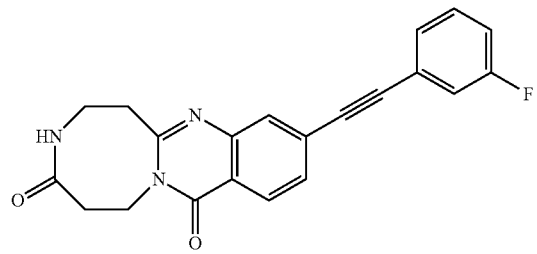 [SMILES: O=C1CCn2c(nc3cc(C#Cc4cccc(F)c4)ccc3c2=O)CCN1]

11-((3-fluorophenyl)ethynyl)-2,3,5,6-tetrahydro-1H-[1,5]diazocino[2,1-b]quinazoline-4,8-dione $^1$H NMR (300 MHz, CD$_3$OD) δ 8.22-8.20 (d, J=8.40 Hz, 1H), 7.76 (s, 1H), 7.66-7.63 (dd, J=8.28, 1.5 Hz, 1H), 7.49-7.41 (m, 2H), 7.37-7.34 (m, 1H), 7.23-7.16 (m, 1H), 4.63-4.58 (m, 2H), 3.66-3.62 (t, J=6.47 Hz, 2H), 3.55 (m, 1H), 3.47-3.42 (m, 2H), 3.11-3.06 (m, 1H), 2.94-2.86 (t, J=7.41 Hz, 1H). mGluR5 PAM EC$_{50}$: +++.

Example 11.1. Synthesis of the HCl Salt of 7-((3-fluorophenyl)ethynyl)-3-(2-methoxyethyl)pyrido[3,2-d]pyrimidin-4(3H)-one

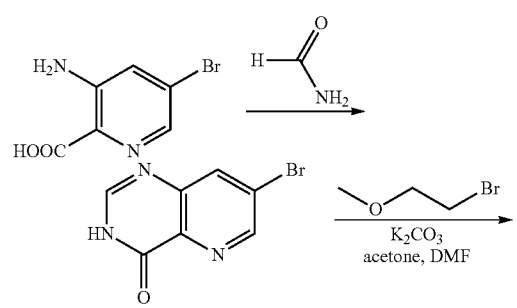

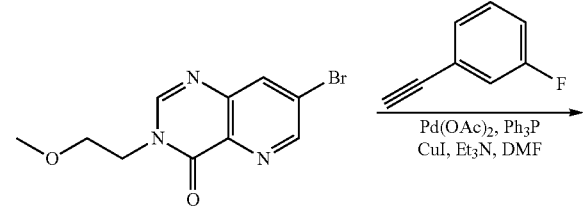

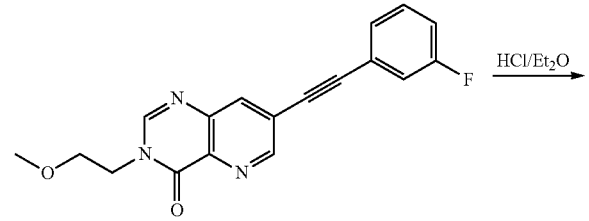

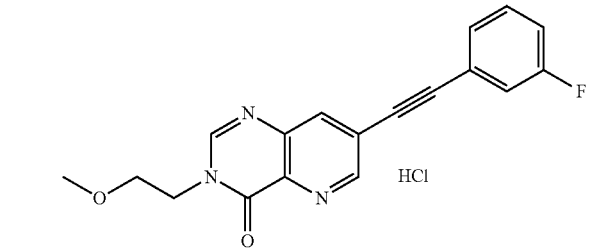

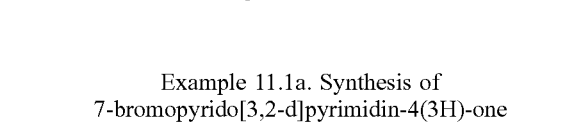

Example 11.1a. Synthesis of 7-bromopyrido[3,2-d]pyrimidin-4(3H)-one

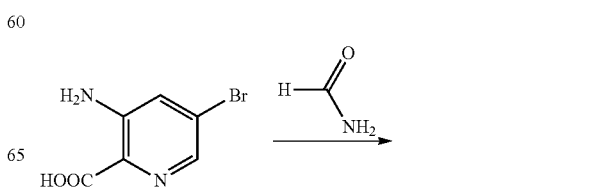

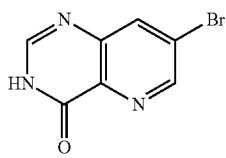

A solution of 3-amino-5-bromopicolinic acid (1.0 g, 4.6 mmol) in formamide (1.1 g, 25 mmol) was stirred at 150° C. for 4 h. After it was cooled to room temperature, the reaction mixture was poured into water (50 mL). A suspension was formed and filtered. The cake was washed with water and dried to give the desired product. MS (ESI): 226, 228 (MH$^+$).

Example 11.1b. Synthesis of 7-bromo-3-(2-methoxyethyl)pyrido[3,2-d]pyrimidin-4(3H)-one

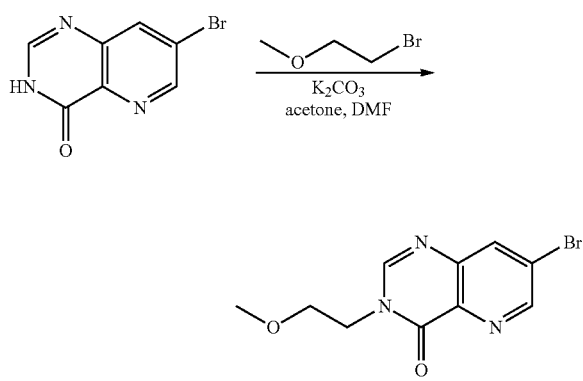

A solution of 7-bromopyrido[3,2-d]pyrimidin-4(3H)-one (200 mg, 0.89 mmol), 1-bromo-2-methoxyethane (148 mg, 1.06 mmol) and K$_2$CO$_3$ (184 mg, 1.3 mmol) in acetone (10 mL) and DMF (3 mL) was stirred at room temperature for 4 h. Then the mixture was diluted with H$_2$O (50 mL) and extracted with ethyl acetate (3×50 mL), the combined organic layers were washed with brine, dried over Na$_2$SO$_4$. After filtration and concentration, the residue was purified by silica gel chromatography to give the desired product. MS (ESI): 284, 286 (MH$^+$).

Example 11.1c. Synthesis of HCl Salt of 7-((3-fluorophenyl)ethynyl)-3-(2-methoxyethyl) pyrido[3,2-d]pyrimidin-4(3H)-one

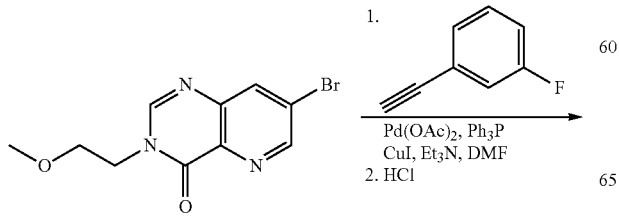

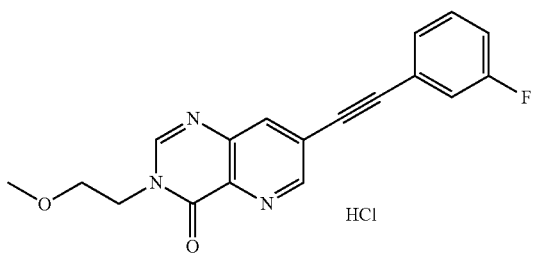

The title compound was prepared according to the experimental procedure as described in Example 1.1. The product was then converted to the corresponding HCl salt. MS (ESI): 324 (MH$^+$). MS (ESI): 324 (MH$^+$); $^1$H NMR (300 MHz, CD$_3$OD) δ 8.61 (m, 1H), 8.37 (s, 1H), 7.50-7.40 (m, 3H), 7.28-7.21 (m, 1H), 4.35-4.32 (t, J=9.57 Hz, 2H), 3.76-3.73 (t, J=9.21 Hz, 2H), 3.37 (s, 3H). mGluR5 PAM EC$_{50}$: +++. Fold shift at 10 μM: +++.

Example 11.2. Synthesis of 2-(1-methoxyethyl)-3-methyl-7-(pyridin-2-ylethynyl)pyrido[3,2-d]pyrimidin-4(3H)-one

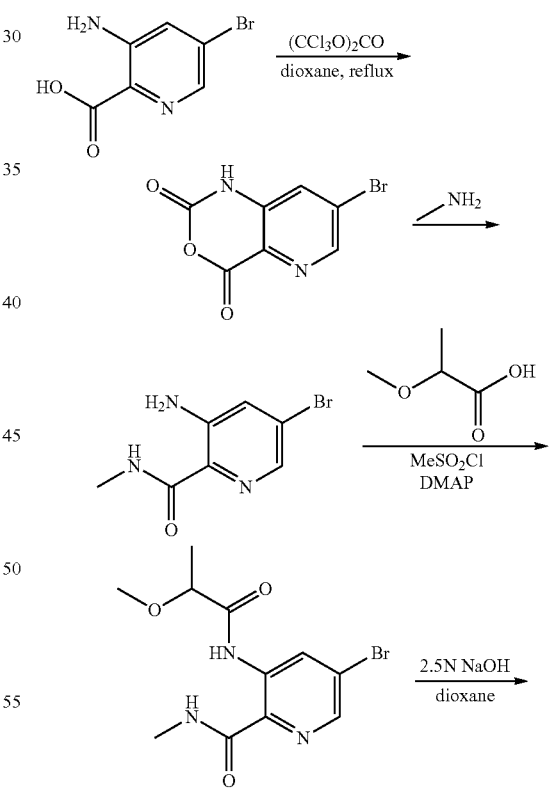

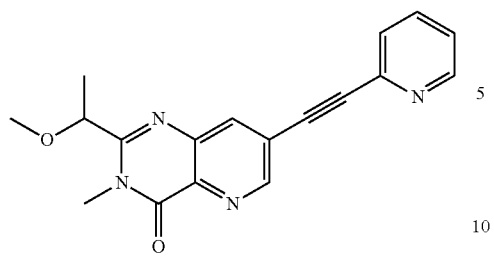

The title compound was prepared according to the experimental procedure as described in Example 2.1a, Example 2.1b, Example 2.1c, and Example 1.1. MS (ESI): 321 (MH+); 1H NMR (300 MHz, CDCl3) δ 9.01 (s, 1H), 8.71-8.69 (m, 1H), 8.22-8.21 (d, J=1.5 Hz, 1H), 7.80-7.74 (dt, J=7.80, 1.8 Hz, 1H), 7.65-7.62 (d, J=7.8 Hz, 1H), 7.37-7.32 (m, 1H), 4.68-4.64 (q, J=6.6 Hz, 1H), 3.82 (s, 3H), 3.43 (s, 3H), 1.67-1.65 (d, J=6.6 Hz, 3H).

Example 11.3. Synthesis of the 2HCl Salt of 8-(hydroxymethyl)-3-(pyridin-2-ylethynyl)-7,8-dihydropyrido[3,2-d]pyrrolo[1,2-a]pyrimidin-10(6H)-one

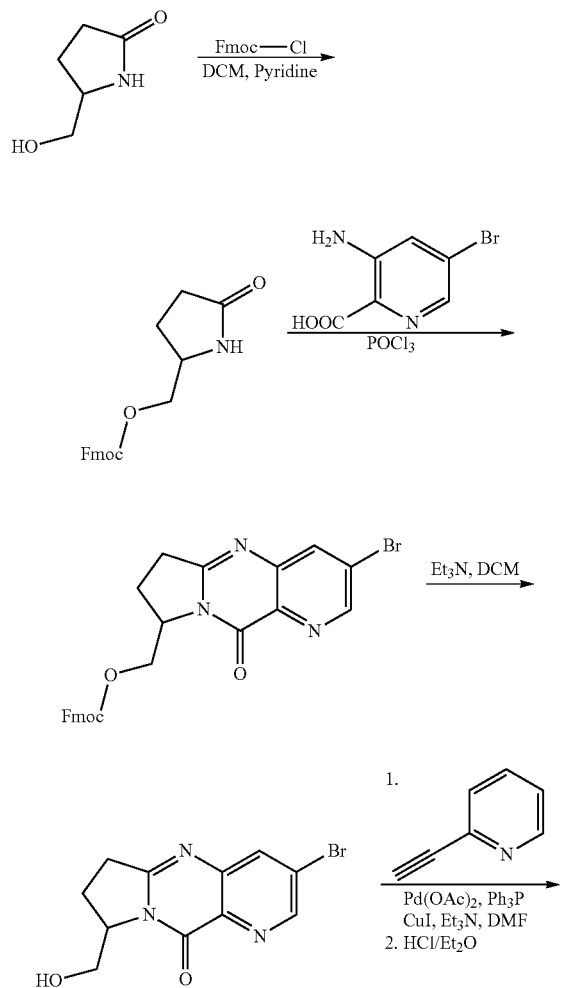

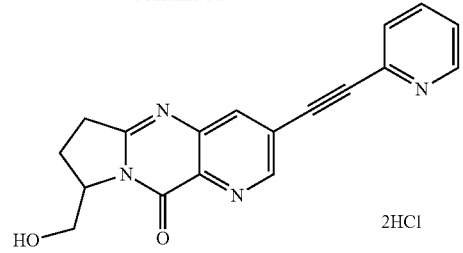

Example 11.3a. Synthesis of (9H-fluoren-9-yl)methyl (5-oxopyrrolidin-2-yl)methyl carbonate

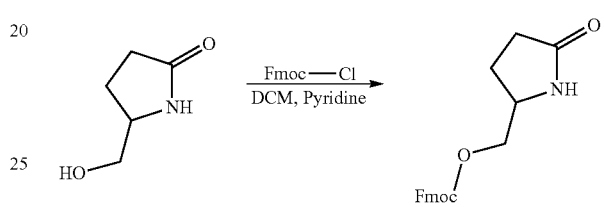

To a solution of 5-(hydroxymethyl)pyrrolidin-2-one (3 g, 26 mmol) in DCM (150 mL) was added Fmoc-Cl (8.1 g, 31 mmol) and pyridine (2 mL). The mixture was stirred for 2 h at room temperature. Then the reaction mixture was diluted with water (150 mL) and extracted with DCM (3×150 mL). The combined organic layers were washed with brine, dried over Na2SO4. After filtration and concentration, the crude product was purified by column chromatography to give 4.2 g of the desired product. MS (ESI): 338 (MH+).

Example 11.3b. Synthesis of (9H-fluoren-9-yl) methyl (3-bromo-10-oxo-6,7,8,10-tetrahydropyrido[3,2-d]pyrrolo[1,2-a]pyrimidin-8-yl)methyl carbonate

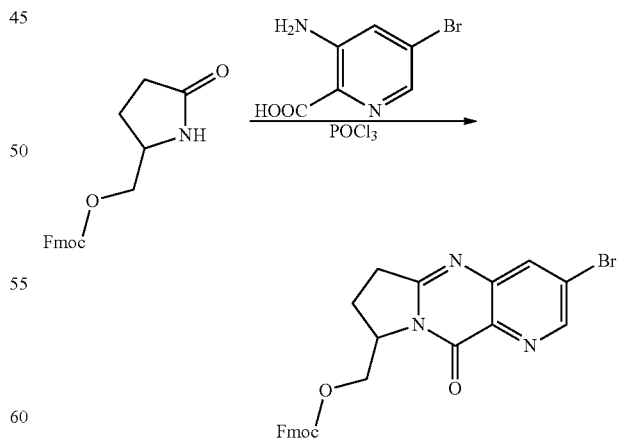

To a solution of (9H-fluoren-9-yl)methyl (5-oxopyrrolidin-2-yl)methyl carbonate (1.2 g, 3.57 mmol) and 3-amino-5-bromopicolinic acid (0.77 g, 3.57 mmol) in 1,4-dioxane (50 mL) was added POCl3 (6 mL). The mixture was stirred for 2 h at 85° C. After the reaction mixture was cooled to room temperature, it was diluted with saturated sodium carbonate solution (200 mL) and extracted with EtOAc (3×200 mL). The combined organic layers were washed with brine and dried over Na$_2$SO$_4$. After filtration and concentration, the crude product was purified by column chromatography to give 1.4 g of the desired product. MS (ESI): 518 (MH$^+$).

Example 11.3c. Synthesis of 8-(hydroxymethyl)-3-bromo-7,8-dihydropyrido[3,2-d]pyrrolo[1,2-a]pyrimidin-10(6H)-one

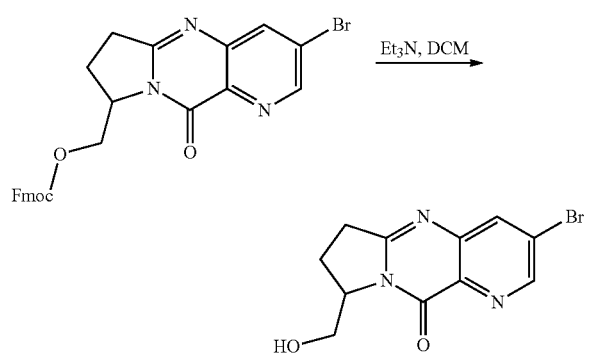

To a solution of (9H-fluoren-9-yl)methyl (3-bromo-10-oxo-6,7,8,10-tetrahydropyrido[3,2-d]pyrrolo[1,2-a]pyrimidin-8-yl)methyl carbonate (1.4 g, 4.7 mmol) in DCM (50 mL) was added Et$_3$N (4 mL). The mixture was stirred for 5 h at room temperature. The reaction mixture was then concentrated and purified by column chromatography to give 0.6 g of the desired product. MS (ESI): 296, 298 (MH$^+$).

Example 11.3d. Synthesis of the 2HCl Salt of 8-(hydroxymethyl)-3-(pyridin-2-ylethynyl)-7,8-dihydropyrido[3,2-d]pyrrolo[1,2-a]pyrimidin-10(6H)-one

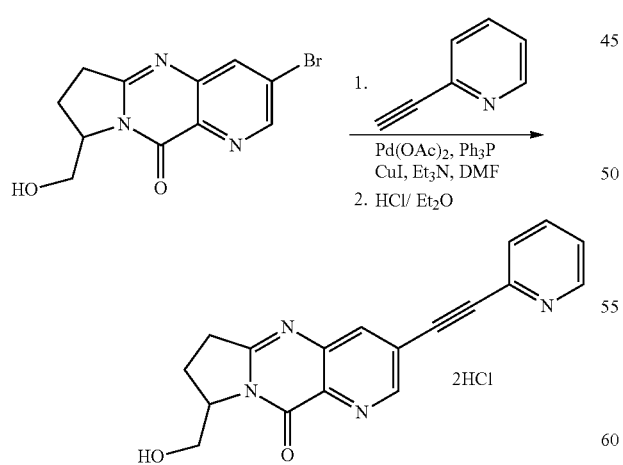

The title compound was prepared according to the experimental procedure as described in Example 1.1. The product was then converted to the corresponding 2HCl salt. MS (ESI): 319 (MH$^+$); $^1$H NMR (300 MHz, D$_2$O) δ 8.86 (s, 1H), 8.74-8.72 (d, J=5.82 Hz, 1H), 8.53-8.47 (t, J=8.00 Hz, 1H), 8.28 (s, 1H), 8.15-8.13 (d, J=8.10 Hz, 1H), 7.98-7.94 (m, 1H), 4.85-4.39 (m, 1H), 4.10-4.04 (dd, J=12.20, 3.77 Hz, 1H), 3.84-3.79 (dd, J=12.24 Hz, 2.61 Hz, 1H), 3.36-3.27 (m, 1H), 3.11-3.02 (m, 1H), 2.50-2.43 (m, 1H), 2.29-2.21 (m, 1H). mGluR5 PAM EC$_{50}$: +.

Example 11.4. Synthesis of 2HCl Salt of 3-(pyridin-2-ylethynyl)-8,9-dihydro-6H-dipyrido[1,2-a:3',2'-d]pyrimidin-11(7H)-one

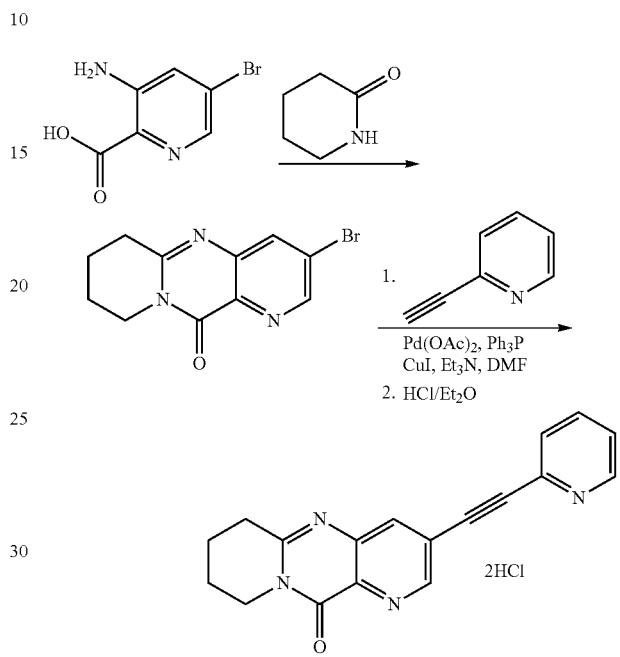

The title compound was prepared according to the experimental procedure as described in Example 2.2a and Example 1.1. The product was then converted to the corresponding 2HCl salt. MS (ESI): 303 (MH$^+$); $^1$H NMR (300 MHz, CD$_3$OD) δ 9.02 (s, 1H), 8.82-8.80 (d, J=4.80 Hz, 1H), 8.42-8.36 (m, 2H), 8.14-8.12 (d, J=7.92 Hz, 1H), 7.92-7.87 (t, J=7.74 Hz, 1H), 4.18-4.14 (m, 2H), 3.20-3.15 (m, 2H), 2.15-1.98 (m, 4H).

Example 11.5. Synthesis of the 2HCl Salt of 8,8-dimethyl-3-(pyridin-2-ylethynyl)-8,9-dihydro-6H-dipyrido[1,2-a:3',2'-d]pyrimidin-11(7H)-one

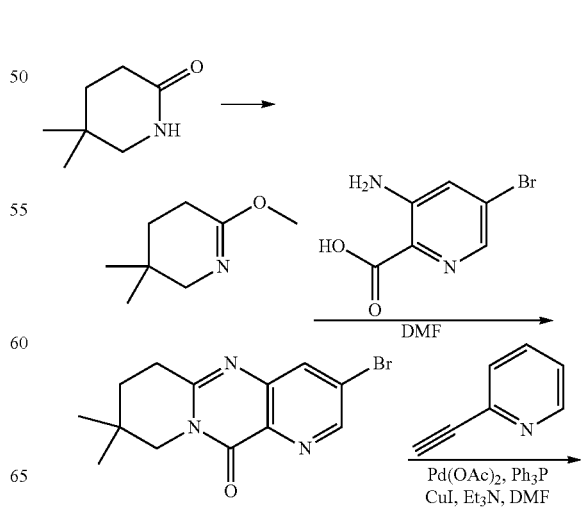

-continued

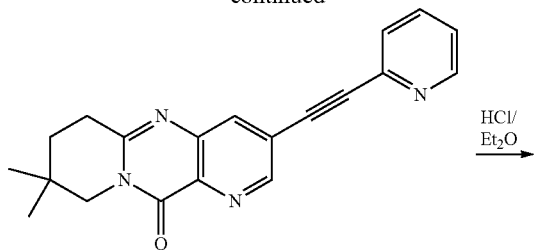

The title compound was prepared according to the experimental procedure as described in Example 11.7a, Example 11.7b, and Example 1.1. The product was then converted to the corresponding 2HCl salt. MS (ESI): 331(MH+); $^1$H NMR (300 MHz, CD$_3$OD) δ 9.15 (s, 1H), 8.98-8.96 (dd, J=5.72, 0.735 Hz, 1H), 8.69-8.64 (dt, J=7.98, 1.49 Hz, 1H), 8.53-8.52 (d, J=1.53 Hz, 1H), 8.38-8.36 (d, J=7.98 Hz, 1H), 8.15-8.10 (m, 1H), 3.94 (s, 2H), 3.37-3.31 (t, J=6.8 Hz, 2H), 1.91-1.86 (t, J=6.8 Hz, 2H), 1.20 (s, 6H). mGluR5 PAM EC$_{50}$: ++. Fold shift at 10 μM: ++.

Example 11.6. Synthesis of 3-(pyridin-2-ylethynyl)-9,10,10a,11-tetrahydro-6H-pyrido[3,2-d]pyrrolo[1',2':4,5]pyrazino[1,2-a]pyrimidin-13(8H)-one

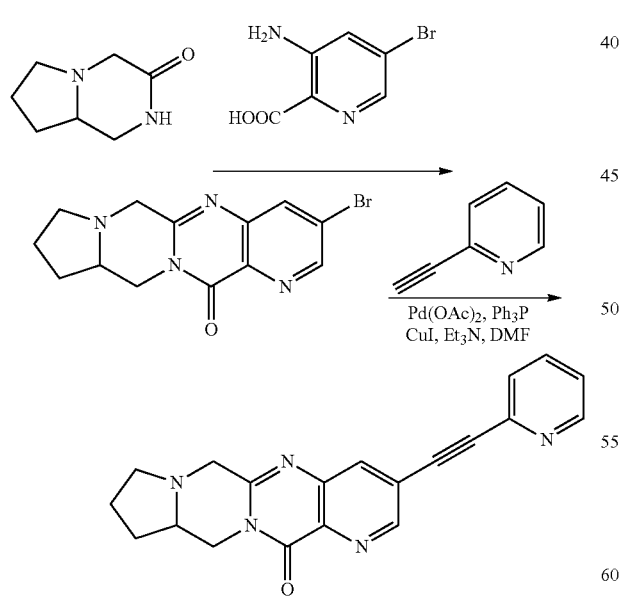

The title compound was prepared according to the experimental procedure as described in Example 2.2a and Example 1.1. MS (ESI): 344 (MH+); $^1$H NMR (300 MHz, CD$_3$OD) δ 9.09 (s, 1H), 8.96-8.94 (d, J=5.13 Hz, 1H), 8.699-8.64 (m, 1H), 8.54-8.53 (d, J=1.62 Hz, 1H), 8.37-8.34 (d, J=7.92 Hz, 1H), 8.14-8.10 (m, 1H), 4.95-4.89 (m, 2H), 4.80-4.75 (m, 1H), 4.64-4.59 (m, 1H), 4.38-4.34 (m, 2H), 3.91 (m, 1H), 2.49-2.47 (m, 1H), 2.26-2.22 (m, 1H), 2.04-1.97 (m, 2H). mGluR5 PAM EC$_{50}$: +.

Example 11.7. Synthesis of the HCl Salt of 3-((3-fluorophenyl)ethynyl)-7,8,9,10-tetrahydropyrido[3',2':4,5]pyrimido[1,2-a]azepin-12(6H)-one

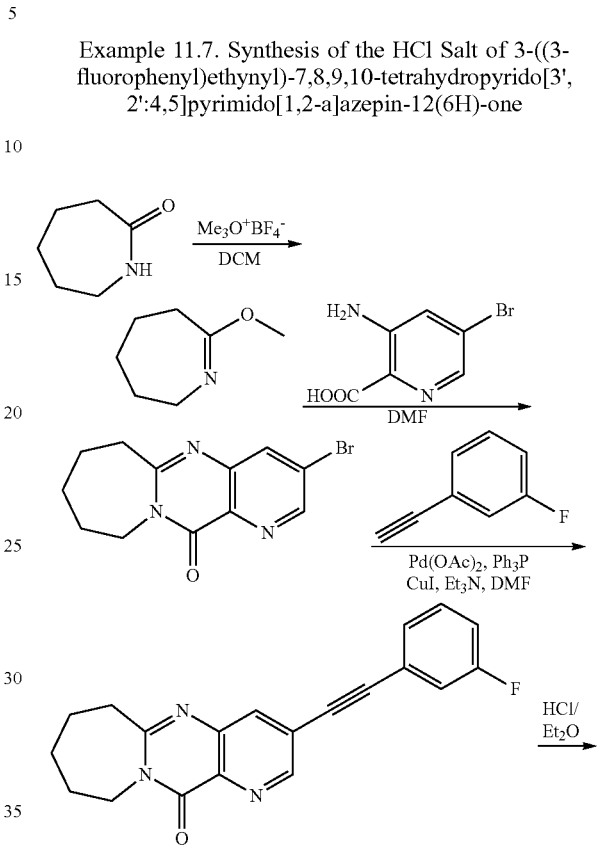

Example 11.7a. Synthesis of (E)-7-methoxy-3,4,5,6-tetrahydro-2H-azepine

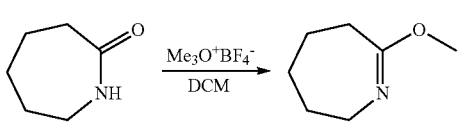

A solution of azepan-2-one (5.0 g, 44 mmol) and trimethyloxonium tetrafluoroborate (7.8 g, 53 mmol) in DCM (30 mL) was stirred at room temperature for 12 h. Then the reaction mixture was quenched with saturated sodium carbonate (50 mL) and extracted with DCM (3×100 mL). The combined organic layers were washed with brine, dried over Na$_2$SO$_4$ and concentrated to give the desired product. MS (ESI): 128 (MH+).

Example 11.7b. Synthesis of 3-bromo-7,8,9,10-tetrahydropyrido[3',2':4,5]pyrimido[1,2-a]azepin-12(6H)-one

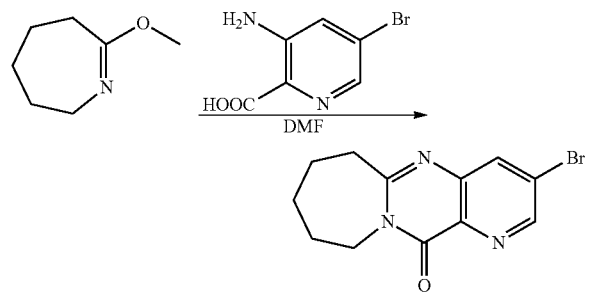

A solution of 7-methoxy-3,4,5,6-tetrahydro-2H-azepine (1.0 g, 8.8 mmol) and 3-amino-5-bromopicolinic acid (1.9 g, 8.8 mmol) in DMF (70 mL) was stirred at 130° C. for 48 h. The reaction mixture was diluted with $H_2O$ (300 mL) and extracted with DCM (3×300 mL). The combined organic layers were washed with saturated sodium carbonate and brine, dried over $Na_2SO_4$. After filtration and concentration, the residue was purified by silica gel chromatography to give the desired product. MS (ESI): 294, 296 ($MH^+$).

Example 11.7c. Synthesis of HCl Salt of 3-bromo-7,8,9,10-tetrahydropyrido[3',2':4,5]pyrimido[1,2-a]azepin-12(6H)-one

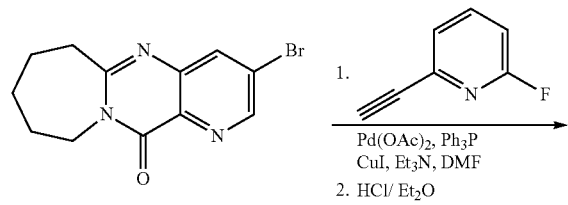

The title compound was prepared according to the experimental procedure as described in Example 1.1. The product was then converted to the corresponding HCl salt. MS (ESI): 334 ($MH^+$). MS (ESI): 334($MH^+$); $^1H$ NMR (300 MHz, DMSO-$d^6$) δ 8.89 (s, 1H), 8.20 (s, 1H), 7.56-7.51 (m, 3H), 7.40-7.33 (m, 1H), 4.37-4.35 (m, 2H), 3.12 (s, 2H), 1.77 (s, 6H). mGluR5 PAM $EC_{50}$: +++++. Fold shift at 10 μM: +.

Example 11.8. Synthesis of the 2HCl Salt of 3-(pyridin-2-ylethynyl)-7,8,9,10-tetrahydropyrido[3',2':4,5]pyrimido[1,2-a]pyrimido[1,2-a]azepin-12(6H)-one

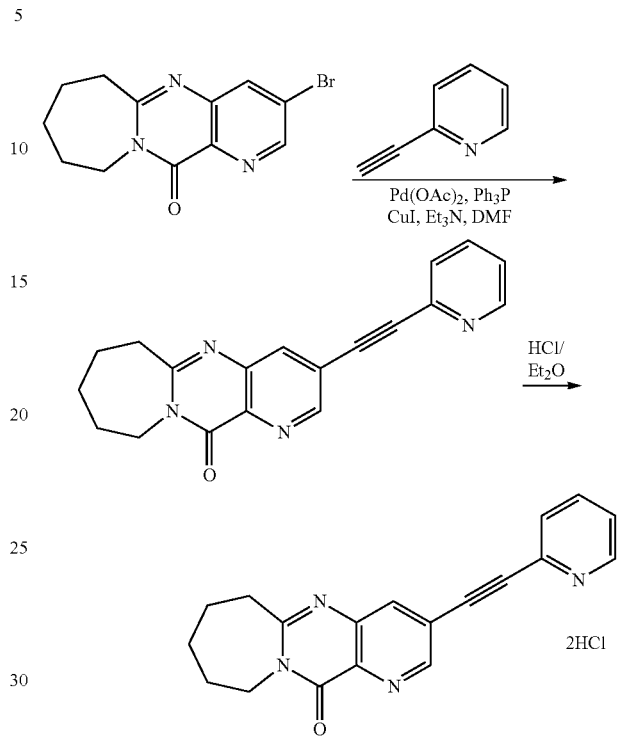

The title compound was prepared according to the experimental procedure as described in Example 1.1. The product was then converted to the corresponding 2HCl salt. MS (ESI): 317 ($MH^+$); $^1H$ NMR (300 MHz, $CD_3OD$) δ 9.16 (s, 1H), 8.99-8.97 (d, J=5.07 Hz, 1H), 8.72-8.66 (m, 1H), 8.57 (s, 1H), 8.40-8.38 (d, J=8.01 Hz, 1H), 8.17-8.12 (m, 1H), 4.60-4.57 (m, 2H), 3.41-3.38 (m, 2H), 2.03-1.92 (m, 6H). mGluR5 PAM $EC_{50}$: ++.

Example 11.9. Synthesis of the 2HCl Salt of 8-methyl-3-(pyridin-2-ylethynyl)-7,8,9,10-tetrahydropyrido[3',2':4,5]pyrimido[1,2-a]azepin-12(6H)-one

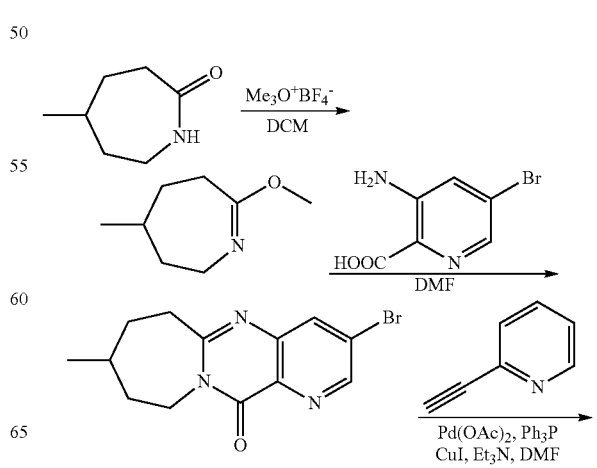

-continued

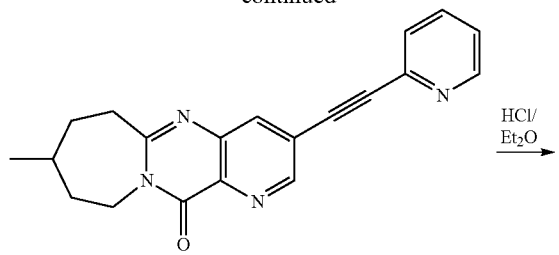

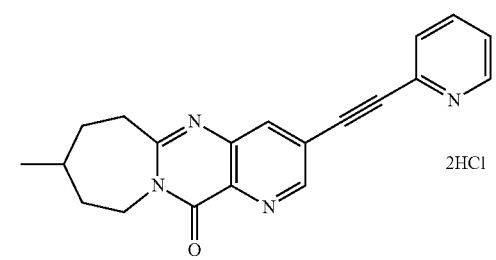

The title compound was prepared according to the experimental procedure as described in Example 11.7a, Example 11.7b, and Example 1.1. The product was then converted to the corresponding 2HCl salt. MS (ESI): 331 (MH+); $^1$H NMR (300 MHz, DMSO-d$^6$) δ 8.96-8.95 (d, J=1.89 Hz, 1H), 8.71-8.69 (d, J=4.89 Hz, 1H), 8.32-8.31 (d, J=1.92 Hz, 1H), 8.02-7.97 (t, J=7.62 Hz, 1H), 7.85-7.83 (d, J=7.80 Hz, 1H), 7.58-7.54 (t, J=7.62 Hz, 1H), 4.95-4.88 (m, 1H), 3.84-3.75 (m, 1H), 3.29-3.20 (m, 1H), 3.10-3.03 (m, 1H), 2.02-1.88 (m, 3H), 1.39-1.16 (m, 2H), 0.93-0.91 (d, J=6.42 Hz, 3H). mGluR5 PAM EC$_{50}$: ++++. Fold shift at 10 μM: +++.

Example 11.9a and Example 11.9b. Separation of Enantiomers of 8-methyl-3-(pyridin-2-ylethynyl)-7,8,9,10-tetrahydropyrido[3',2':4,5]pyrimido[1,2-a]azepin-12(6H)-one into (S)-8-methyl-3-(pyridin-2-ylethynyl)-7,8,9,10-tetrahydropyrido[3',2':4,5]pyrimido[1,2-a]azepin-12(6H)-one and (R)-8-methyl-3-(pyridin-2-ylethynyl)-7,8,9,10-tetrahydropyrido[3',2':4,5]pyrimido[1,2-a]azepin-12(6H)-one Racemic 8-methyl-3-(pyridin-2-ylethynyl)-7,8,9,10-tetrahydropyrido[3',2':4,5]pyrimido[1,2-a]azepin-12(6H)-one was separated into the corresponding two single enantiomer compounds (S)-8-methyl-3-(pyridin-2-ylethynyl)-7,8,9,10-tetrahydropyrido[3',2':4,5]pyrimido[1,2-a]azepin-12(6H)-one and (R)-8-methyl-3-(pyridin-2-ylethynyl)-7,8,9,10-tetrahydropyrido[3',2':4,5]pyrimido[1,2-a]azepin-12(6H)-one using chiral chromatography with an isocratic SFC method. The column used was a 4.6×100 mm RegisPack from Regis Technologies (Morton Grove, Ill.). The CO$_2$ co-solvent was isopropanol with 0.1% isopropylamine. Isocratic Method: 50% Co-solvent at 4 mL/min System Pressure: 100 bar. Column Temperature 25° C.

Faster moving enantiomer of 8-methyl-3-(pyridin-2-ylethynyl)-7,8,9,10-tetrahydropyrido[3',2': 4,5]pyrimido[1,2-a]azepin-12(6H)-one (fraction 1): Retention time=3.3 min 100% ee. mGluR5 PAM EC$_{50}$: +++. Fold shift at 10 μM: ++.

Slower moving enantiomer of 8-methyl-3-(pyridin-2-ylethynyl)-7,8,9,10-tetrahydropyrido[3',2':4,5]pyrimido[1,2-a]azepin-12(6H)-one (fraction 2): Retention time=3.9 min 99.7% ee. mGluR5 PAM EC$_{50}$: ++++. Fold shift at 10 μM: +++.

Example 11.10. Synthesis of 7,7-dimethyl-3-(pyridin-2-ylethynyl)-7,8-dihydropyrido[3,2-d]pyrrolo[1,2-a]pyrimidin-10(6H)-one

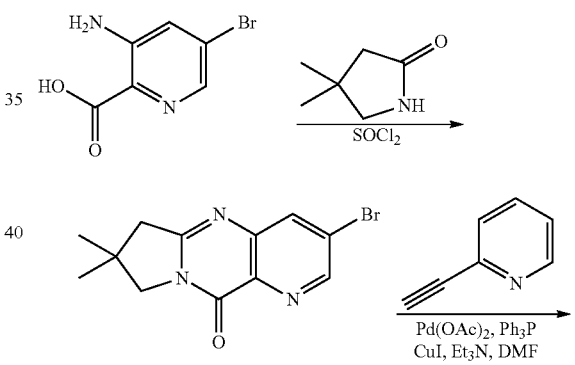

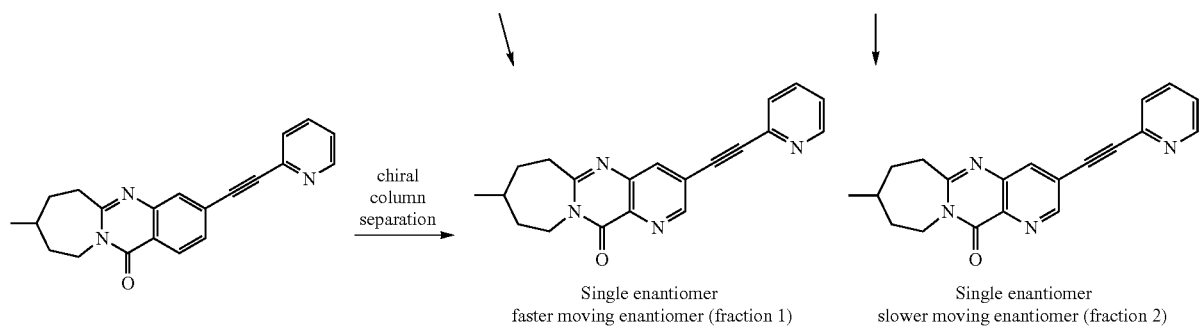

-continued

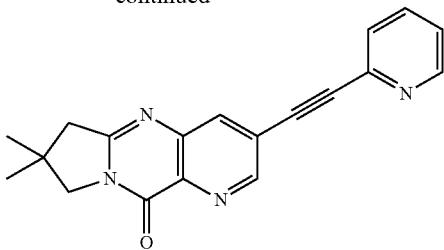

The title compound was prepared according to the experimental procedure as described in Example 2.2a and Example 1.1. MS (ESI): 317 (MH$^+$); $^1$H NMR (300 MHz, CD$_3$OD) δ 9.05 (broad, 1H), 8.98-8.96 (d, J=5.46 Hz, 1H), 8.72-8.70 (t, J=7.97 Hz, 1H), 8.67 (s, 1H), 8.46-8.39 (d, J=7.95 Hz, 1H), 8.16-8.12 (t, J=6.9 Hz, 1H), 4.06 (s, 2H), 3.15 (s, 2H), 1.34 (s, 6H). mGluR5 PAM EC$_{50}$: +++. Fold shift at 10 μM: +++.

Example 11.12. Synthesis of 8-(methoxymethyl)-3-(pyridin-2-ylethynyl)-7,8-dihydropyrido[3,2-d]pyrrolo[1,2-a]pyrimidin-10(6H)-one

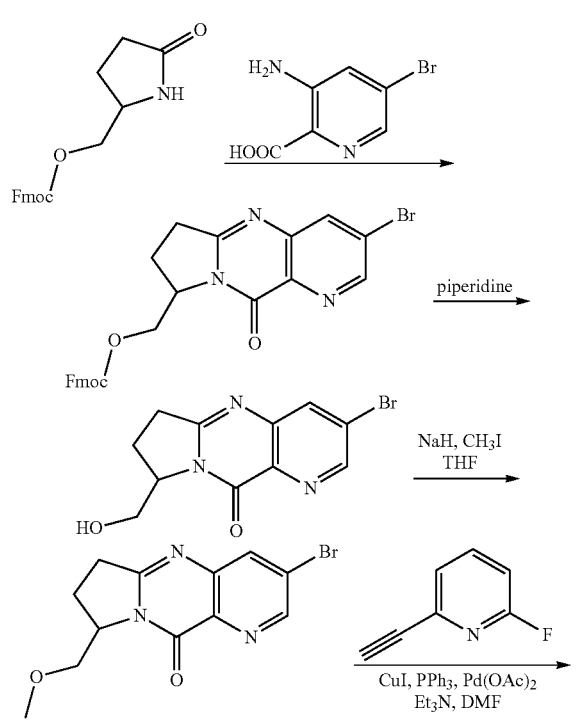

The title compound was prepared according to the experimental procedure as described in Example 2.2a, Example 3.17b, Example 4.25, and Example 1.1. MS (ESI): 333 (MH$^+$); $^1$H NMR (300 MHz, CDCl$_3$) δ 8.97 (s, 1H), 8.70-8.68 (d, J=1.80 Hz, 1H), 8.16 (s, 1H), 7.79-7.71 (m, 1H), 7.66-7.63 (d, J=7.80 Hz, 1H), 7.37-7.28 (m, 1H), 5.00-4.96 (m, 1H), 4.09-4.04 (dd, J=9.96, 3.27 Hz, 1H), 3.67-3.63 (dd, J=9.96, 2.34 Hz, 1H), 3.50-3.37 (m, 1H), 3.31 (s, 3H), 3.08-2.98 (m, 1H), 2.47-2.23 (m, 2H).

Example 11.13. Synthesis of the 2HCl Salt of 7-methyl-3-(pyridin-2-ylethynyl)-7,8-dihydropyrido[3,2-d]pyrrolo[1,2-a]pyrimidin-10(6H)-one

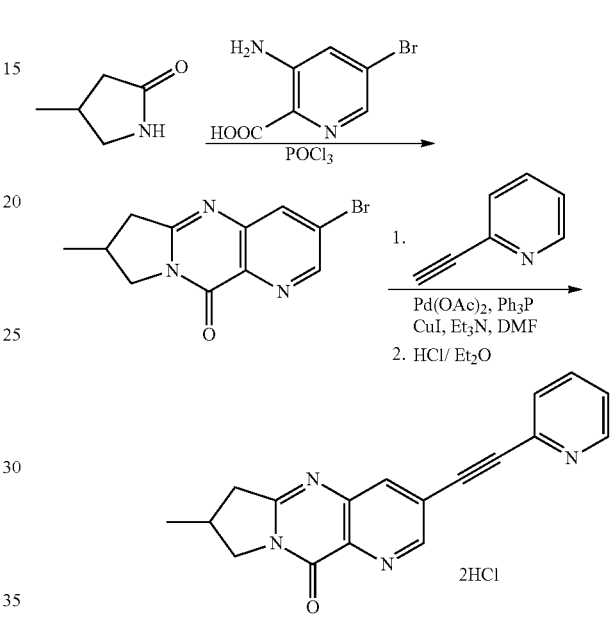

The title compound was prepared according to the experimental procedure as described in Example 2.2a and Example 1.1. The product was then converted to the corresponding 2HCl salt. MS (ESI): 303 (MH$^+$); $^1$H NMR (300 MHz, CD$_3$OD) δ 9.07 (s, 1H), 8.98-8.96 (d, J=5.6 Hz, 1H), 8.72-8.67 (t, J=8.0 Hz, 1H), 8.47 (s, 1H), 8.39-8.37 (d, J=8.0 Hz, 1H), 8.16-8.12 (t, J=6.8 Hz, 1H), 4.52-4.45 (dd, J=12.3, 7.8 Hz, 1H), 3.90-3.84 (dd, J=12.3, 7.2 Hz, 1H), 3.52-3.44 (dd, J=17.4, 7.8 Hz, 1H), 3.07-3.00 (dd, J=17.4, 7.5 Hz, 1H), 2.98-2.86 (m, 1H), 1.33-1.30 (d, J=6.7 Hz, 3H). mGluR5 PAM EC$_{50}$: +.

Example 12.1. Synthesis of 2-(1-methoxyethyl)-3-methyl-7-(pyridin-2-ylethynyl)pyrido[2,3-d]pyrimidin-4(3H)-one

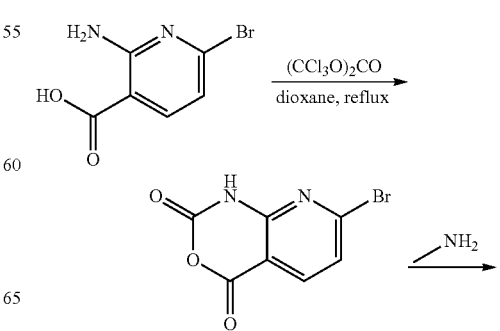

-continued

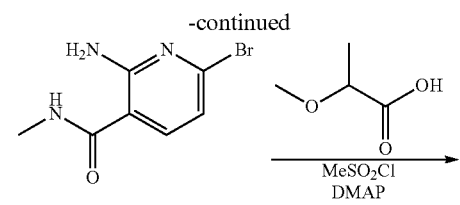

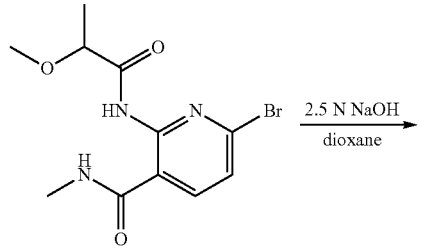

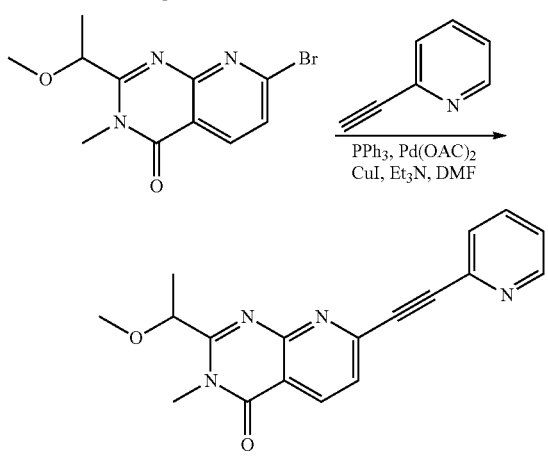

The title compound was prepared according to the experimental procedure as described in Example 2.1a, Example 2.1b, Example 2.1c, and Example 1.1. MS (ESI): 321 (MH+); ¹H NMR (300 MHz, CDCl₃) δ 8.69-8.64 (m, 2H), 7.98-7.92 (m, 1H), 7.85-7.80 (m, 2H), 7.55-7.50 (m, 1H), 4.82-4.80 (q, J=6.57 Hz, 1H), 3.75 (s, 3H), 3.45 (s, 3H), 1.67-1.65 (d, J=6.57 Hz, 3H).

Example 12.2 and Example 12.3. Synthesis of 9,9-dimethyl-2-(pyridin-2-ylethynyl)-7,8,9,10-tetrahydro-5H-dipyrido[1,2-a:2',3'-d]pyrimidin-5-one and 8,8-dimethyl-2-(pyridin-2-ylethynyl)-7,8,9,10-tetrahydro-5H-dipyrido[1,2-a:2',3'-d]pyrimidin-5-one -continued

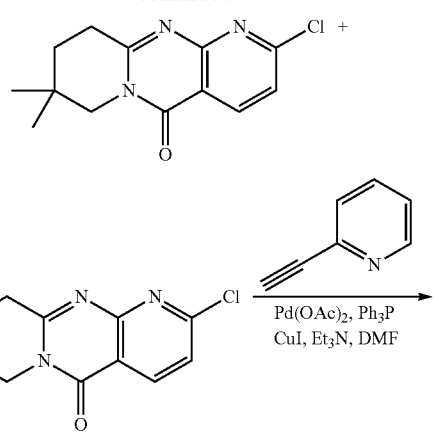

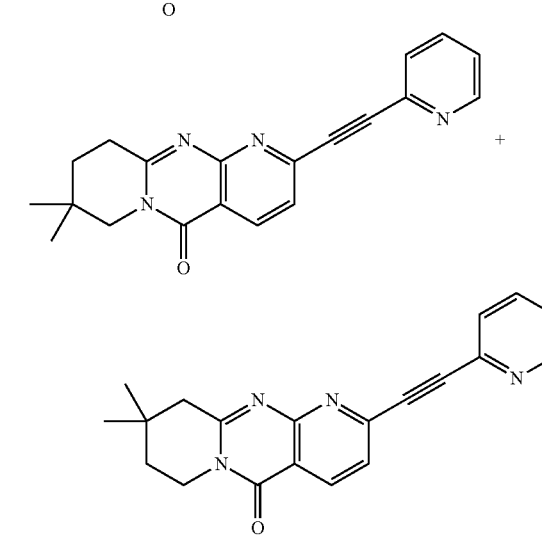

Example 12.2a and Example 12.3a. Synthesis of 9,9-dimethyl-2-chloro-7,8,9,10-tetrahydro-5H-dipyrido[1,2-a:2',3'-d]pyrimidin-5-one and 8,8-dimethyl-2-chloro-7,8,9,10-tetrahydro-5H-dipyrido[1,2-a:2',3'-d]pyrimidin-5-one

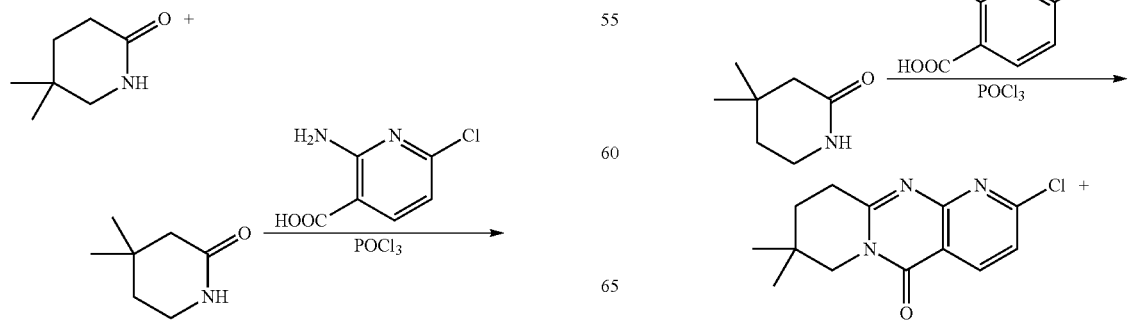

-continued

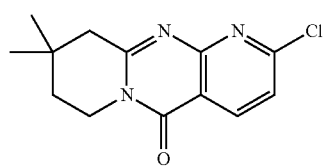

The title compounds were prepared according to the experimental procedure as described in Example 2.2a.

Example 12.2b and Example 12.3b. Synthesis of 9,9-dimethyl-2-(pyridin-2-ylethynyl)-7,8,9,10-tetrahydro-5H-dipyrido[1,2-a:2',3'-d]pyrimidin-5-one and 8,8-dimethyl-2-(pyridin-2-ylethynyl)-7,8,9,10-tetrahydro-5H-dipyrido[1,2-a:2',3'-d]pyrimidin-5-one

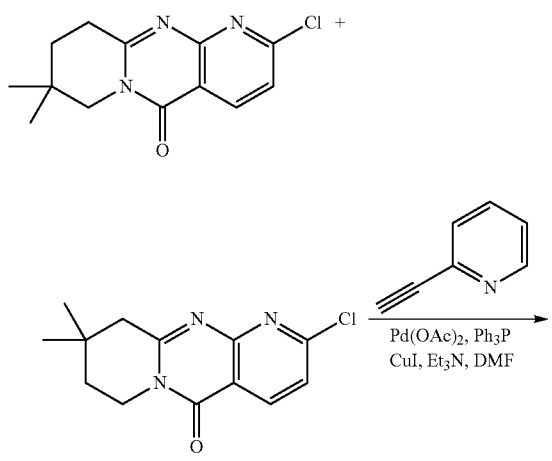

9,9-dimethyl-2-(pyridin-2-ylethynyl)-7,8,9,10-tetrahydro-5H-dipyrido[1,2-a:2',3'-d]pyrimidin-5-one MS (ESI): 331 (MH$^+$); $^1$H NMR (300 MHz, CDCl$_3$) δ 8.68-8.67 (d, J=3.63 Hz, 1H), 8.60-8.57 (d, J=7.98 Hz, 1H), 7.77-7.64 (m, 3H), 7.35-7.28 (m, 1H), 4.11-4.01 (t, J=6.45 Hz, 2H), 2.88 (m, 2H), 1.89-1.84 (m, 2H), 1.26 (s, 6H). mGluR5 PAM EC$_{50}$: +++. Fold shift at 10 μM: +++.

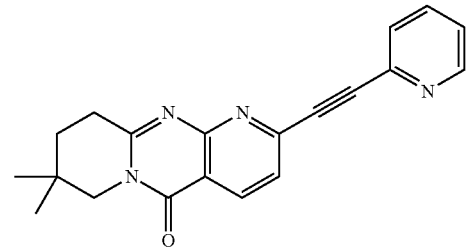 [SMILES: CC1(C)CCc2nc3nc(C#Cc4ccccn4)ccc3c(=O)n2C1]

8,8-dimethyl-2-(pyridin-2-ylethynyl)-7,8,9,10-tetrahydro-5H-dipyrido[1,2-a:2',3'-d]pyrimidin-5-one MS (ESI): 331 (MH$^+$); $^1$H NMR (300 MHz, CDCl$_3$) δ 8.69-8.68 (d, J=4.38 Hz, 1H), 8.60-8.57 (d, J=8.07 Hz, 1H), 7.78-7.72 (d, J=7.64 Hz, J=1.70 Hz, 1H), 7.67-7.64 (d, J=8.07 Hz, 2H), 7.36-7.31 (m, 1H), 3.82 (m, 2H), 3.16-3.11 (t, J=7.11 Hz, 2H), 1.81-1.76 (t, J=7.10 Hz, 2H), 1.13 (s, 6H). mGluR5 PAM EC$_{50}$: +++. Fold shift at 10 μM: +++.

Example 12.4. Synthesis of 2-(pyridin-2-ylethynyl)-7,7a,8,9,10,12-hexahydro-5H-pyrido[2,3-d]pyrrolo[1',2':4,5]pyrazino[1,2-a]pyrimidin-5-one

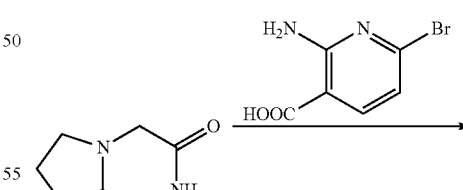

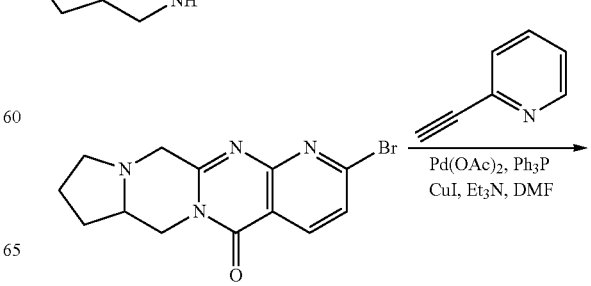

The title compounds were prepared according to the experimental procedure as described in Example 1.1.

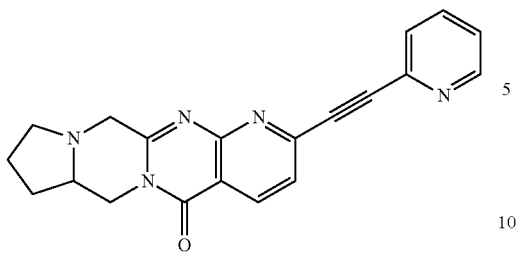

The title compound was prepared according to the experimental procedure as described in Example 2.2a and Example 1.1. MS (ESI): 344 (MH+); 1H NMR (300 MHz, CDCl3) δ 8.69-8.68 (d, J=4.56 Hz, 1H), 8.61-8.59 (d, J=8.10 Hz, 1H), 7.78-7.72 (t, J=7.64 Hz, 1H), 7.69-7.64 (t, J=5.6 Hz, 2H), 7.36-7.32 (m, 1H), 4.55-4.49 (dd, J=13.36, 3.87 Hz, 1H), 4.40-4.35 (d, J=17.16 Hz, 1H), 3.64-3.49 (m, 2H), 3.35-3.26 (m, 1H), 2.65-2.55 (m, 1H), 2.46-2.37 (m, 1H), 2.28-2.10 (m, 1H), 2.06-1.94 (m, 2H), 1.72-1.65 (m, 1H).

Example 12.5. Synthesis of 2-(pyridin-2-ylethynyl)-8,9,10,11-tetrahydropyrido[2',3':4,5]pyrimido[1,2-a]azepin-5(7H)-one

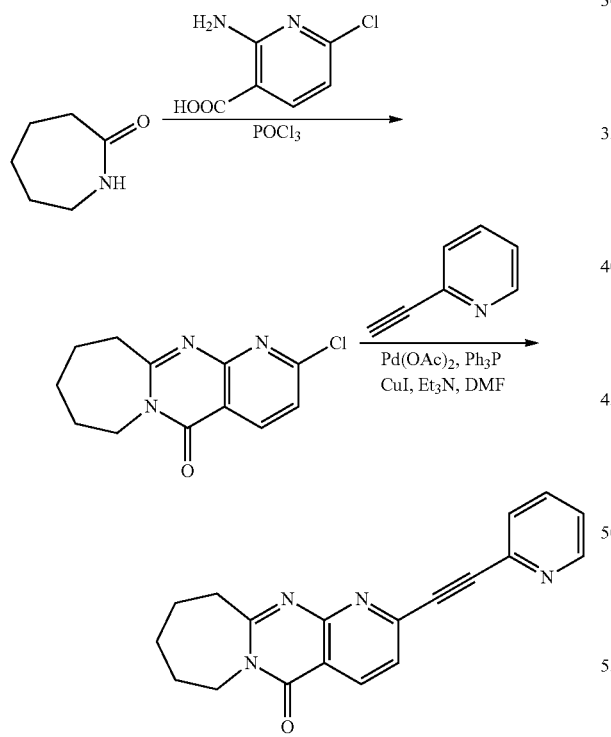

The title compound was prepared according to the experimental procedure as described in Example 2.2a and Example 1.1. MS (ESI): 317 (MH+); 1H NMR (300 MHz, CDCl3) δ 8.69-8.68 (m, 1H), 8.57-8.56 (d, J=8.07 Hz, 1H), 7.79-7.72 (m, 1H), 7.68-7.65 (m, 2H), 7.36-7.32 (m, 1H), 4.41-4.38 (m, 2H), 3.19-3.16 (m, 2H), 1.91-1.84 (m, 6H). mGluR5 PAM EC50: +.

Example 13.1. Synthesis of 8-((3-fluorophenyl)ethynyl)-3-(1-hydroxyethyl)-4H-pyrido[1,2-a]pyrimidin-4-one

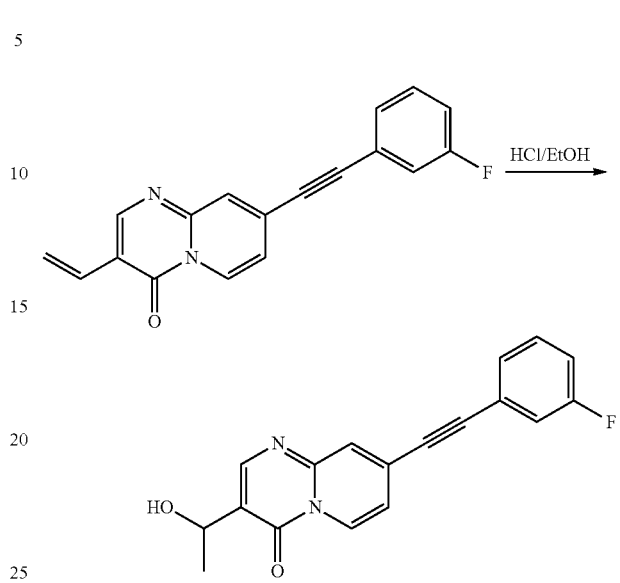

8-((3-fluorophenyl)ethynyl)-3-vinyl-4H-pyrido[1,2-a]pyrimidin-4-one (30 mg, 0.1 mmol) was added into a saturated HO/ethanol (5 mL) solution. After stirring at ambient temperature for 3 h, the solution was adjusted to pH=8 and extracted with ethyl acetate (3×50 mL). The combined organic layers were dried over Na2SO4 and concentrated to give the crude product, which was purified by column chromatography. MS (ESI): 309 (MH+); 1H NMR (300 MHz, CDCl3) δ 9.01-8.99 (d, J=7.44 Hz, 1H), 8.38 (s, 1H), 7.77 (s, 1H), 7.45-7.39 (m, 2H), 7.33-7.28 (m, 1H), 7.20 (m, 1H), 7.17 (m, 1H), 5.11-5.02 (m, 1H), 3.54-3.52 (d, J=6.03 Hz, 1H), 2.62-2.57 (d, J=6.6 Hz, 3H). mGluR5 PAM EC50: ++. Fold shift at 10 μM: +.

Example 13.2. Synthesis of 3-(1-ethoxyethyl)-8-((3-fluorophenyl)ethynyl)-4H-pyrido[1,2-a]pyrimidin-4-one

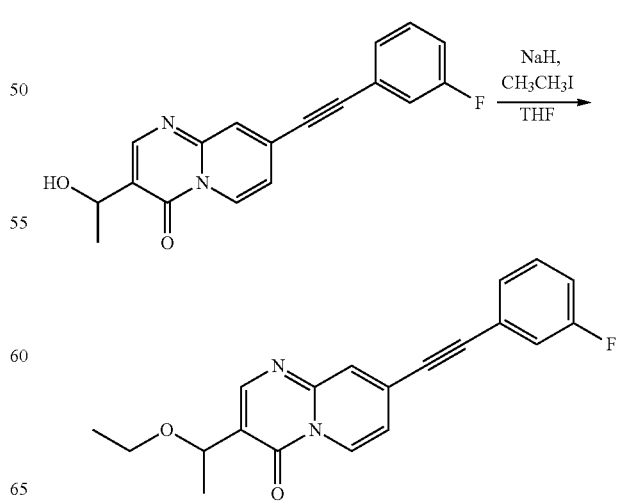

The title compound was prepared according to the experimental procedure as described in Example 4.25. MS (ESI): 337 (M+H⁺); ¹H NMR (300 MHz, CDCl₃) δ 9.02-9.00 (d, J=7.44 Hz, 1H), 8.49 (s, 1H), 7.77 (s, 1H), 7.42-7.38 (m, 2H), 7.32-7.29 (m, 1H), 7.20-7.13 (m, 2H), 4.89-4.83 (q, J=6.45 Hz, 1H), 3.56-3.49 (t, J=7.01 Hz, 2H), 1.52-1.50 (d, J=6.45 Hz, 3H) 1.30-1.23 (t, J=7.01 Hz, 3H). mGluR5 PAM EC$_{50}$: +++++. Fold shift at 10 μM: ++.

Example 13.3. Synthesis of 8-((3-fluorophenyl)ethynyl)-3-Vinyl-4H-pyrido[1,2-a]pyrimidin-4-one

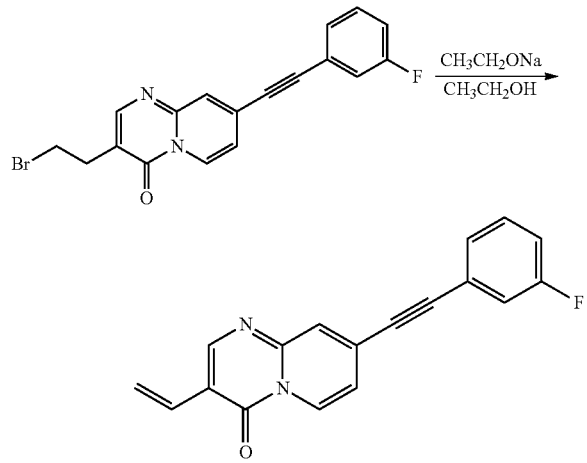

A solution of 3-(2-bromoethyl)-8-((3-fluorophenyl)ethynyl)-4H-pyrido[1,2-a]pyrimidin-4-one (289 mg, 0.78 mmol) and EtONa (208 mg, 3.05 mmol) in EtOH (absolute) was stirred at 50° C. for 3 hr. After the suspension was diluted with water (30 mL) and extracted with ethyl acetate (3×50 mL), the combined organic layers were dried over Na₂SO₄ and concentrated to give the desired product, which was purified by column chromatography. MS (ESI): 291 (MH⁺); ¹H NMR (300 MHz, CDCl₃) δ 9.10-9.07 (d, J=7.44 Hz, 1H), 8.44 (s, 1H), 7.76 (s, 1H), 7.42-7.39 (m, 2H), 7.32-7.31 (m, 1H), 7.20-7.17 (m, 2H), 6.86-6.76 (m, 1H), 6.36-6.29 (dd, J=17.65, 1.38 Hz, 1H), 5.50-5.46 (dd, J=11.41, 1.32 Hz, 1H).

Example 13.4. Synthesis of methyl 8-((3-fluorophenyl)ethynyl)-4-oxo-4H-pyrido[1,2-a]pyrimidine-3-carboxylate

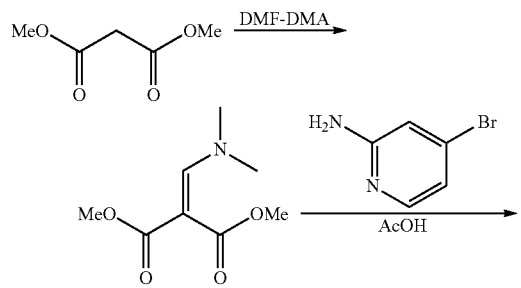

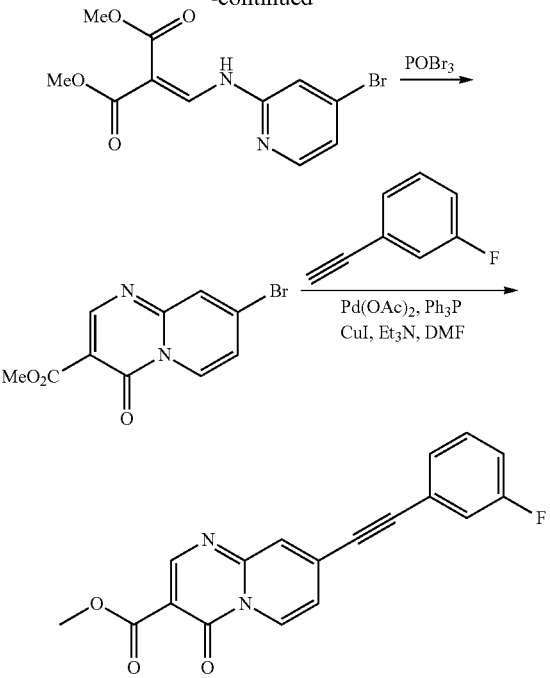

Example 13.4a. Synthesis of dimethyl 2-((dimethylamino)methylene)malonate

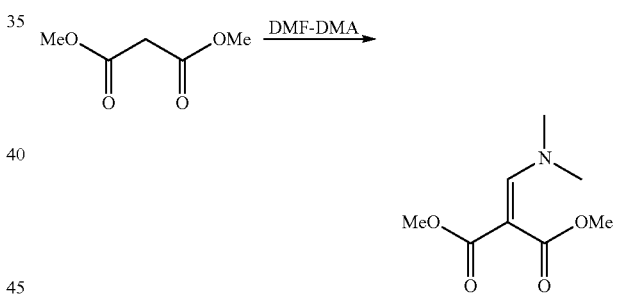

A solution of dimethyl malonate (5 g, 37.9 mmol, 1 equiv) in DMF-DMA (11.3 g, 94.8 mmol, 2.5 equiv) was stirred at room temperature overnight. Then the reaction mixture was concentrated to give 7 g of the desired product, which was directly used for the next step without further purification. MS (ESI): 188 (MH⁺).

Example 13.4b. Synthesis of dimethyl 2-((4-bromopyridin-2-ylamino)methylene)malonate

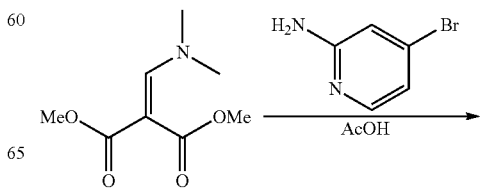

A solution of dimethyl 2-((dimethylamino)methylene) malonate (11.5 g, 65 mmol, 2.2 equiv) and 4-bromopyridin-2-amine (5 g, 28.9 mmol, 1 equiv) in AcOH (40 mL) was stirred at room temperature for 24 h. Then the reaction mixture was diluted with water, filtered, the filter cake was dried to give 4.8 g of the desired product. MS (ESI): 315, 317 (MH+).

Example 13.4c. Synthesis of methyl 8-bromo-4-oxo-4H-pyrido[1,2-a]pyrimidine-3-carboxylate

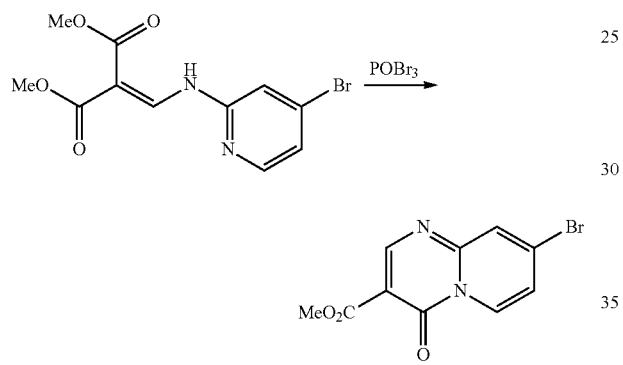

A mixture of dimethyl 2-((4-bromopyridin-2-ylamino)methylene)malonate (4.8 g, 15.2 mmol, 1 equiv) and POBr₃ (16.1 g, 56.1 mmol, 3.7 equiv) was stirred at 80° C. for 2 h. After it was cooled to room temperature, the reaction mixture was poured into water carefully. Then the solution was adjusted pH to 8 with aq. Na₂CO₃ and extracted with DCM (3×200 mL). The combined organic layers were dried over Na₂SO₄ and concentrated to give 3.4 g of the desired product. MS (ESI): 283, 285 (MH+).

Example 13.4d. Synthesis of methyl 8-((3-fluorophenyl)ethynyl)-4-oxo-4H-pyrido[1,2-a]pyrimidine-3-carboxylate

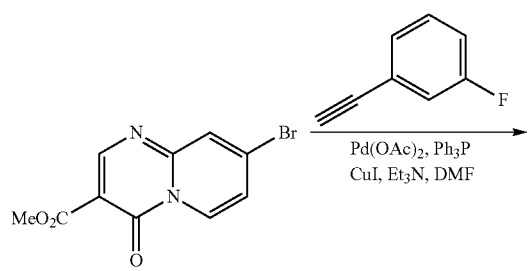

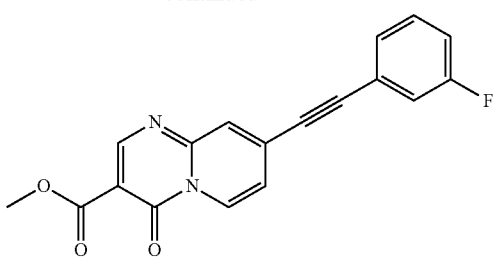

The title compound was prepared according to the experimental procedure as described in Example 1.1. MS (ESI): 323 (MH+).

Example 13.5. Synthesis of N-ethyl-8-((3-fluorophenyl)ethynyl)-4-oxo-4H-pyrido[1,2-a]pyrimidine-3-carboxamide

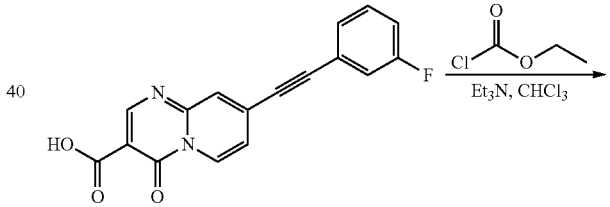

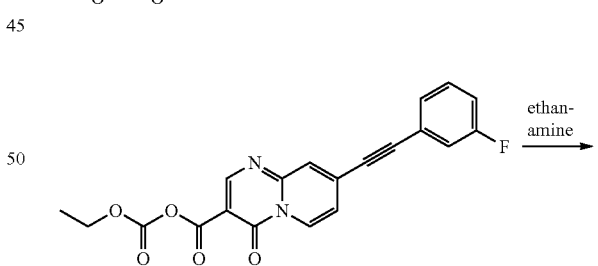

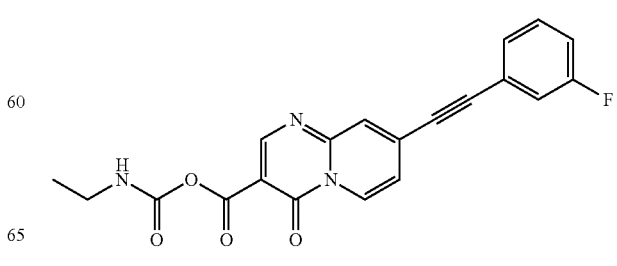

Example 13.5a. Synthesis of 8-((3-fluorophenyl)ethynyl)-4-oxo-4H-pyrido[1,2-a]pyrimidine-3-carboxylic acid

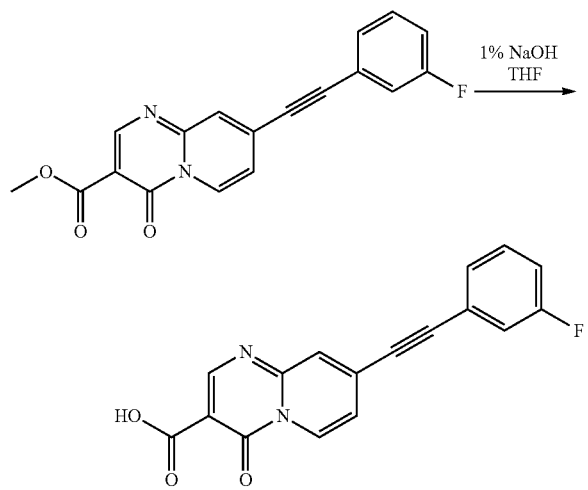

A solution of methyl 8((3-fluorophenyl)ethynyl)-4-oxo-4H-pyrido[1,2-a]pyrimidine-3 carboxylate (100 mg, 0.3 mmol, 1 equiv) in 1% NaOH (2.4 mL, 0.6 mmol, 2 equiv) and THF was stirred at room temperature overnight. Then the reaction mixture was adjusted pH to 3 with 10% aq. HCl and filtered to give 40 mg of the desired product. MS (ESI): 309 (MH$^+$).

Example 13.5b. Synthesis of N-ethyl-8-((3-fluorophenyl)ethynyl)-4-oxo-4H-pyrido[1,2-a]pyrimidine-3-carboxamide

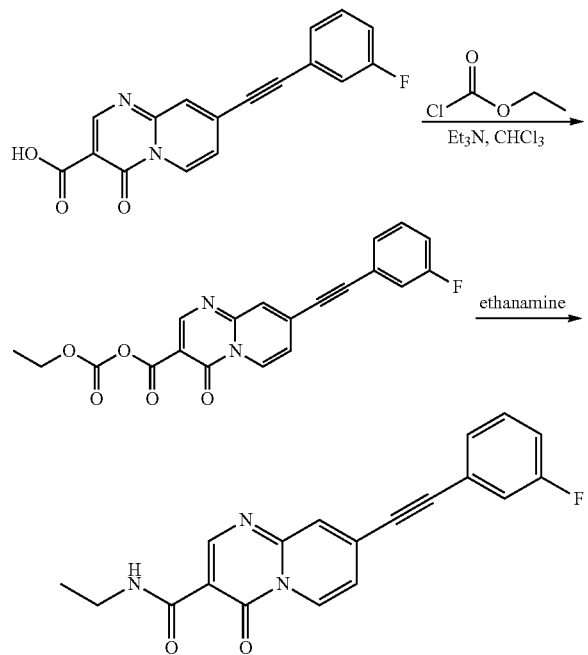

To a solution of 8-((3-fluorophenyl)ethynyl)-4-oxo-4H-pyrido[1,2-a]pyrimidine-3-carboxylic acid (50 mg, 0.62 mmol, 1 equiv) and Et$_3$N (0.5 mL) in CHCl$_3$ (20 mL) at 0° C. was added ethyl chloroformate (0.4 mL) dropwise. After the reaction mixture was stirred for 10 min, aq. ethanamine (3 mL) was added. Then the mixture was stirred for 10 min and extracted with CHCl$_3$ (3×30 mL), dried over Na$_2$SO$_4$ and concentrated to give the desired product (30 mg). MS (ESI): 336 (MH$^+$); $^1$H NMR (300 MHz, CDCl$_3$) δ 9.37 (s, 1H), 9.17-9.14 (d, J=7.32 Hz, 1H), 8.96-8.95 (m, 1H), 7.91 (s, 1H), 7.44-7.40 (m, 2H), 7.37-7.31 (m, 2H), 7.23-7.18 (m, 1H), 3.60-3.50 (m, 2H), 1.32-1.27 (t, J=7.2 Hz, 3H). mGluR5 PAM EC$_{50}$: ++++.

Example 13.6. Synthesis of 8-((3-fluorophenyl)ethynyl)-3-(hydroxymethyl)-4H-pyrido[1,2-a]pyrimidin-4-one

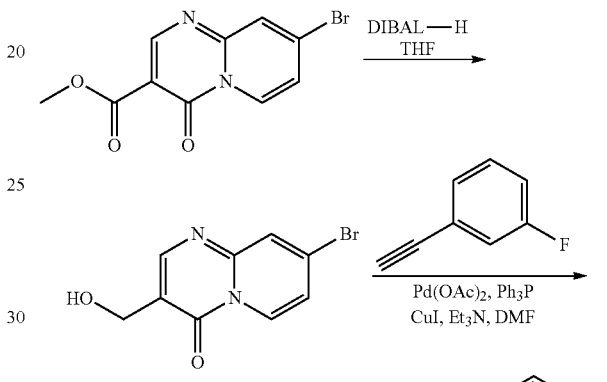

Example 13.6a. Synthesis of 8-bromo-3-(hydroxymethyl)-4H-pyrido[1,2-a]pyrimidin-4-one

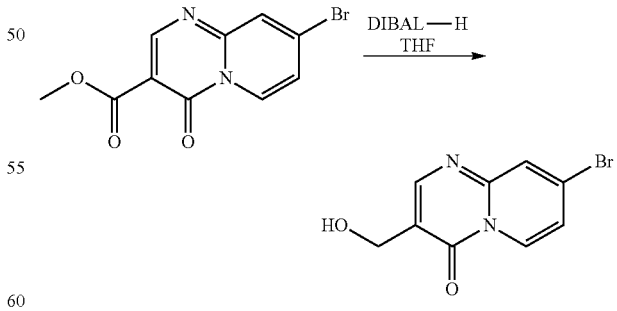

To a solution of methyl 8-bromo-4-oxo-4H-pyrido[1,2-a]pyrimidine-3-carboxylate (1 g, 3.5 mmol, 1 equiv) in anhydrous THF (25 mL) was added DIBAL-H (5 mL) at 0° C. dropwise. After stirring for 1 h, the reaction mixture was quenched with saturated NH$_4$Cl. The solution was extracted with ethyl acetate (3×150 mL). The combined organic layers were dried over Na$_2$SO$_4$ and concentrated to give the crude product. The crude was purified by column chromatography to give 145 mg of the desired product. MS (ESI): 255, 257 (MH$^+$).

Example 13.6b. Synthesis of 8-((3-fluorophenyl)ethynyl)-3-(hydroxymethyl)-4H-pyrido[1,2-a]pyrimidin-4-one

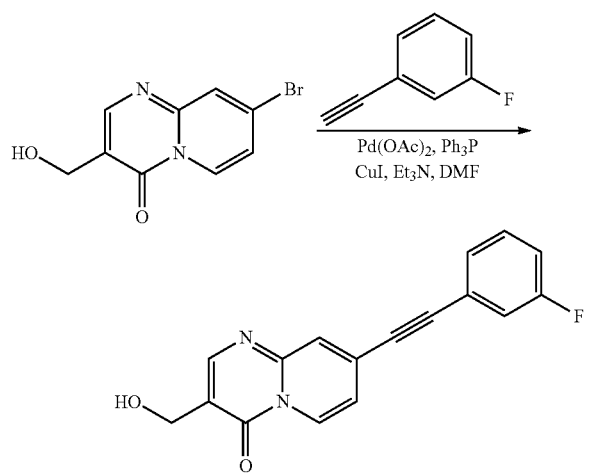

The title compound was prepared according to the experimental procedure as described in Example 1.1. MS (ESI): 295 (MH$^+$); $^1$H NMR (300 MHz, CD$_3$OD) δ 9.03-9.01 (d, J=7.47 Hz, 1H), 8.42 (s, 1H), 7.79 (s, 1H), 7.50-7.46 (m, 2H), 7.41-7.35 (m, 2H), 7.28-7.23 (m, 1H), 4.67 (s, 2H). mGluR5 PAM EC$_{50}$: +.

Example 13.7. Synthesis of 8-((3-fluorophenyl)ethynyl)-3-(methoxymethyl)-4H-pyrido[1,2-a]pyrimidin-4-one

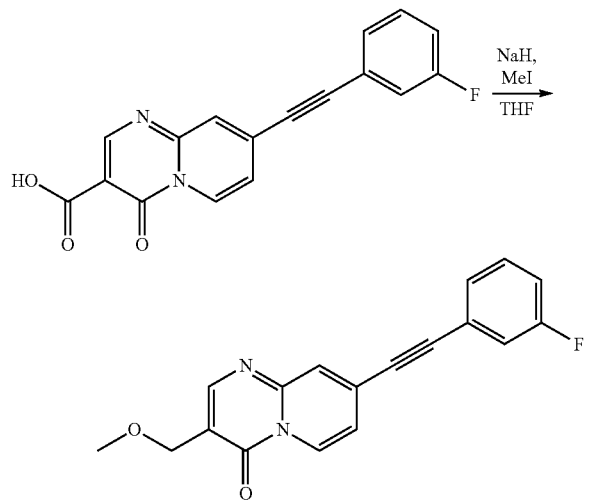

To a solution of 8-((3-fluorophenyl)ethynyl)-3-(hydroxymethyl)-4H-pyrido[1,2-a]pyrimidin-4-one (16 mg) in anhydrous THF (5 mL) was added NaH (16 mg, 60% in oil) in portions. After the reaction mixture was stirred for 15 min, MeI (0.05 mL) was added. The solution was stirred for 30 min. Then the reaction mixture was quenched with saturated NH$_4$Cl and extracted with ethyl acetate (3×50 mL). The combined organic layers were dried over Na$_2$SO$_4$ and concentrated to give the desired product (11 mg), which was purified by preparative HPLC. MS (ESI): 309 (MH$^+$); $^1$H NMR (300 MHz, CD$_3$OD) δ 9.07-9.05 (d, J=6.81 Hz, 1H), 8.42 (s, 1H), 7.83 (s, 1H), 7.51-7.48 (m, 2H), 7.44-7.39 (m, 2H), 7.29-7.27 (m, 1H), 4.53 (s, 2H), 3.54-3.50 (d, J=7.02 Hz, 3H). mGluR5 PAM EC$_{50}$: +++.

Example 13.8. Synthesis of 3-(ethoxymethyl)-8-((3-fluorophenyl)ethynyl)-4H-pyrido[1,2-a]pyrimidin-4-one

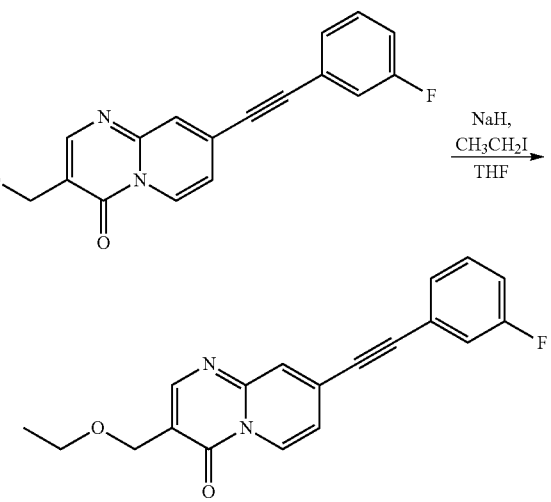

The title compound was prepared according to the experimental procedure as described in Example 13.7. MS (ESI): 323 (MH$^+$); $^1$H NMR (300 MHz, CD$_3$OD) δ 9.06-9.03 (d, J=7.50 Hz, 1H), 8.42 (s, 1H), 7.82 (s, 1H), 7.54-7.48 (m, 2H), 7.44-7.38 (m, 2H), 7.30-7.23 (m, 1H), 4.57 (s, 2H), 3.70-3.63 (q, 2H), 1.30-1.17 (t, 3H). mGluR5 PAM EC$_{50}$: +++. Fold shift at 10 μM: ++.

Example 13.9. Synthesis of 8-((3-fluorophenyl)ethynyl)-3-(2-hydroxyethyl)-4H-pyrido[1,2-a]pyrimidin-4-one

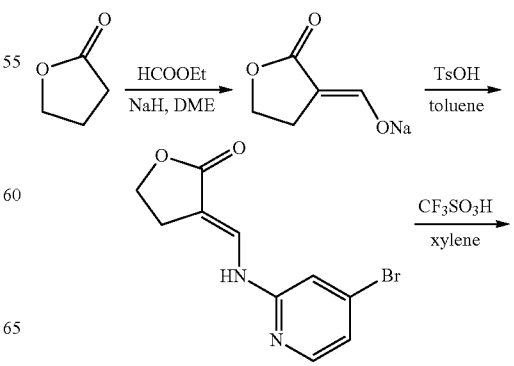

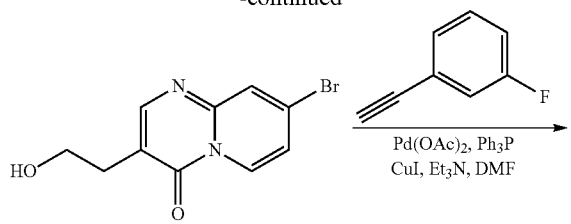

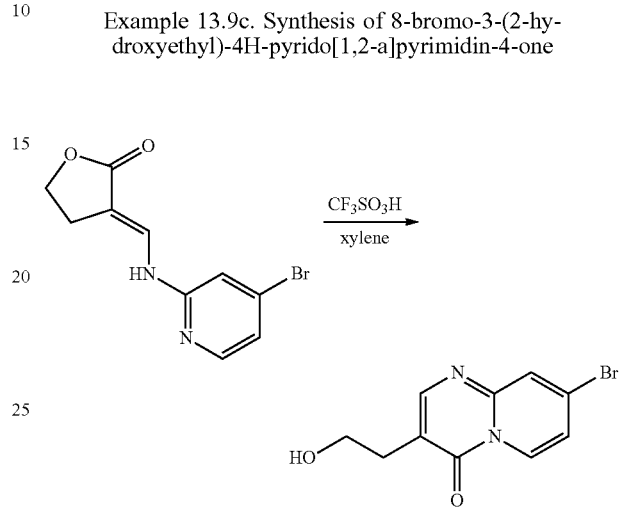

Example 13.9a. Synthesis of Sodium (2-oxodihydrofuran-3(2H)-ylidene)methanolate

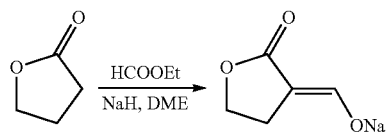

Three-neck, round-bottomed flask equipped with mechanical stirrer, addition funnel, and reflux condenser was placed in a hood behind a shield. The condenser was fitted with a drying tube which was connected to a mineral oil bubble chamber so hydrogen evolution could be monitored. After NaH (4.4 g of 60% oil dispersion, 0.11 mol) was washed with n-$C_6H_{14}$ (2×50 mL), filtered with brief suction drying, and transferred to the flask, sufficient $Et_2O$ was added to cover the resulting solid. A catalytic amount of $C_2H_5OH$ (ca. 2 drops) was added directly to the $Et_2O$—NaH suspension and dropwise addition without stirring of a solution of dihydrofuran-2(3H)-one (8.61 g, 0.1 mol) and ethyl formate (7.41 g, 0.1 mol) in $Et_2O$ (10 mL) was started. As soon as the $Et_2O$ began to reflux, additional $Et_2O$ (50-60 mL) was rapidly added through the reflux condenser and stirring was started. Lactone-formate addition was complete in 1 hr, and stirring was continued for an additional 22 h. Filtration, washing with $Et_2O$, and vacuum drying gave desired product (14.0 g) as a fine powdery solid.

Example 13.9b. Synthesis of 3-((4-bromopyridin-2-ylamino)methylene)dihydrofuran-2(3H)-one

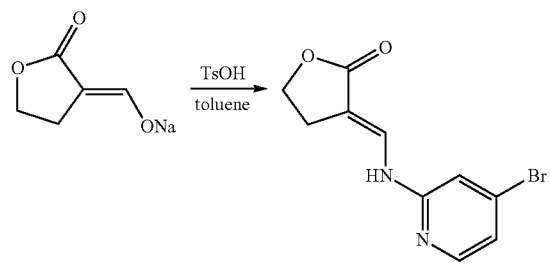

A solution of sodium (2-oxodihydrofuran-3(2H)-ylidene)methano-late (134 mg, 1 mmol), 4-bromopyridin-2-amine (173 mg, 1.0 mmol) and 4-methylbenzenesulfonic acid (50 mg, 0.29 mmol) in toluene was stirred at 150° C. for 1 hr. After the suspension was diluted with water, the solution was adjusted to pH 8 and extracted with ethyl acetate. Then, the organic layers were dried over $Na_2SO_4$ and concentrated to give crude product, which was used for then next reaction without further purification. MS (ESI): 269, 271 (MH$^+$).

Example 13.9c. Synthesis of 8-bromo-3-(2-hydroxyethyl)-4H-pyrido[1,2-a]pyrimidin-4-one

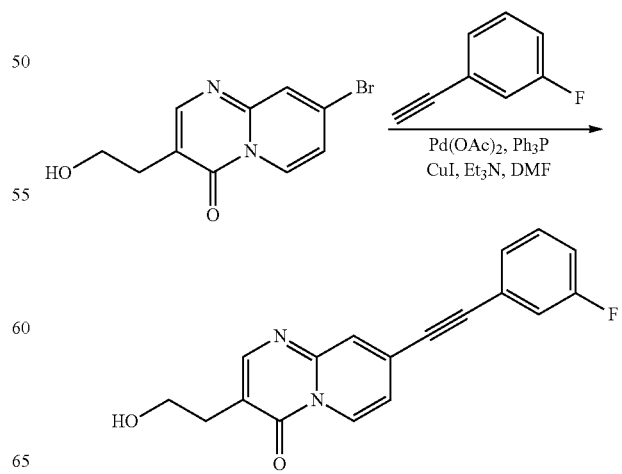

In a small flask, 3-((4-bromopyridin-2-ylamino)methylene)dihydrofuran-2(3H)-one (250 mg, 0.93 mmol) and $CF_3COOH$ (8 drops) was added into a solution of xylene. The suspension was warmed to 85° C. and maintained at that temperature for 30 min. After the upper layer of suspension was poured out, the residue was diluted with water (30 mL) and adjusted to pH 8. Then the mixture was extracted with ethyl acetate (3×50 mL). The organic layer was dried over $Na_2SO_4$ and concentrated to give the crude product, which was purified by column chromatography. MS (ESI): 269, 271 (MH$^+$).

Example 13.9d. Synthesis of 8-((3-fluorophenyl)ethynyl)-3-(2-hydroxyethyl)-4H-pyrido[1,2-a]pyrimidin-4-one The title compound was prepared according to the experimental procedure as described in Example 1.1. MS (ESI): 309 (MH⁺); $^1$H NMR (300 MHz, CDCl$_3$+D$_2$O) δ 9.02-8.99 (d, J=7.41 Hz, 1H), 8.31 (s, 1H), 7.76 (s, 1H), 7.42-7.40 (m, 2H), 7.32-7.28 (m, 1H), 7.20-7.14 (m, 2H), 3.99-3.93 (t, J=5.70 Hz, 2H), 2.99-2.94 (t, J=5.70 Hz, 2H).

Example 13.10. Synthesis of 8-((3-fluorophenyl)ethynyl)-3-(2-methoxyethyl)-4H-pyrido[1,2-a]pyrimidin-4-one

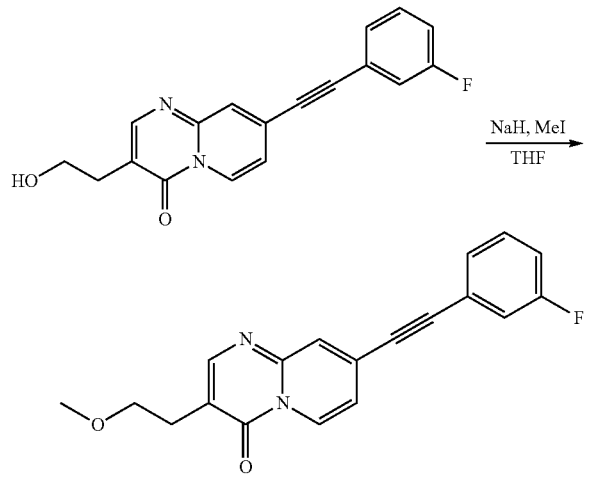

The title compound was prepared according to the experimental procedure as described in Example 13.7. MS (ESI): 323 (MH⁺); $^1$H NMR (300 MHz, DMSO-d$^6$) δ 9.0-8.98 (d, J=7.47 Hz, 1H), 8.31 (s, 1H), 7.73 (s, 1H), 7.41-7.39 (m, 2H), 7.31 (s, 1H), 7.18-7.12 (m, 2H), 3.72-3.68 (t, J=6.35 Hz, 2H), 3.38 (s, 3H), 2.97-2.93 (t, J=6.38 Hz, 2H). mGluR5 PAM EC$_{50}$: ++++. Fold shift at 10 μM: ++.

Example 13.11. Synthesis of 8-((4-fluorophenyl)ethynyl)-3-(2-methoxyethyl)-4H-pyrido[1,2-a]pyrimidin-4-one

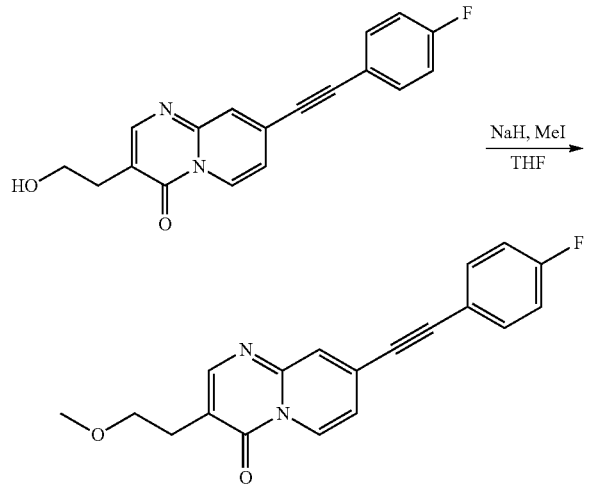

The title compound was prepared according to the experimental procedure as described in Example 13.7. MS (ESI): 323 (MH⁺); $^1$H NMR (300 MHz, DMSO-d$^6$) δ 9.0-8.97 (d, J=7.48 Hz, 1H), 8.30 (s, 1H), 7.71 (s, 1H), 7.62-7.58 (m, 2H), 7.15-7.09 (m, 3H), 3.72-3.68 (t, J=6.36 Hz, 2H), 3.38 (s, 3H), 2.97-2.93 (t, J=6.35 Hz, 2H). mGluR5 PAM EC$_{50}$: ++++. Fold shift at 10 μM: ++.

Example 13.12. Synthesis of 3-(2-methoxyethyl)-8-(pyridin-2-ylethynyl)-4H-pyrido[1,2-a]pyrimidin-4-one

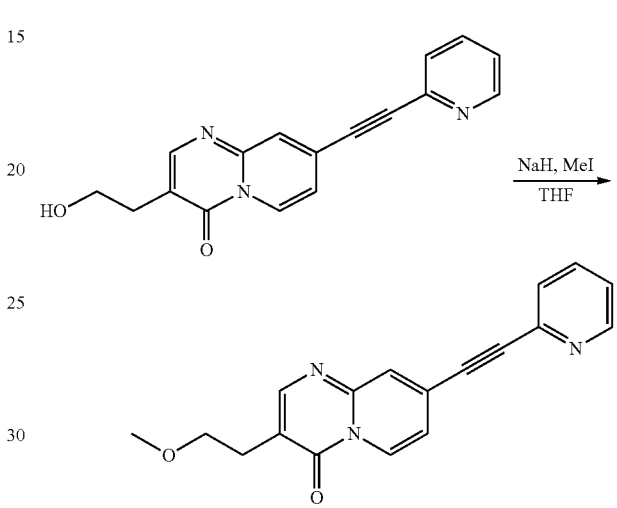

The title compound was prepared according to the experimental procedure as described in Example 13.7. MS (ESI): 306 (MH⁺); $^1$H NMR (300 MHz, CD$_3$OD) δ 9.29-9.27 (d, J=7.47 Hz, 1H), 8.78-8.77 (d, J=4.92 Hz, 1H), 8.44 (s, 1H), 8.33-8.31 (d, J=7.02 Hz, 2H), 8.23-8.18 (t, J=7.74 Hz, 1H), 8.15-8.10 (t, J=7.32 Hz, 1H), 7.68-7.63 (t, J=6.36 Hz, 1H), 3.75-3.71 (t, J=6.09 Hz, 1H), 3.38 (s, 3H), 2.98-2.94 (t, J=7.08 Hz, 2H).

Example 13.13. Synthesis of 3-(2-ethoxyethyl)-8-((3-fluorophenyl)ethynyl)-4H-pyrido[1,2-a]pyrimidin-4-one

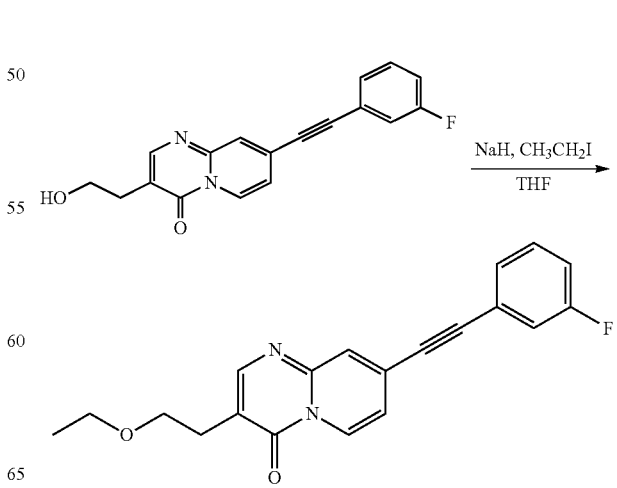

The title compound was prepared according to the experimental procedure as described in Example 13.7. MS (ESI): 337 (MH+); ¹H NMR (300 MHz, DMSO-d⁶) δ 9.0-8.98 (d, J=7.44 Hz, 1H), 8.32 (s, 1H), 7.73 (s, 1H), 7.41-7.38 (m, 2H), 7.33-7.28 (m, 1H), 7.18-7.11 (m, 2H), 3.76-3.71 (t, J=6.35 Hz, 2H), 3.57-3.50 (q, 2H), 2.98-2.93 (t, J=7.00 Hz, 2H), 1.23-1.18 (t, 3H). mGluR5 PAM EC$_{50}$: +++. Fold shift at 10 µM: ++.

Example 13.14. Synthesis of the HCl Salt of 3-(2-(dimethylamino)ethyl)-8-((3-fluorophenyl)ethynyl)-4H-pyrido[1,2-a]pyrimidin-4-one

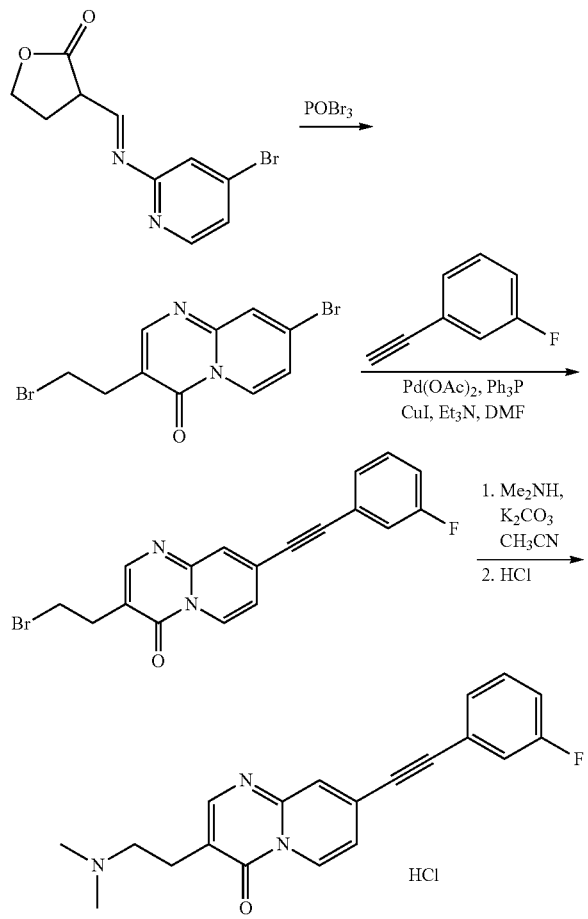

Example 13.14a. Synthesis of 8-bromo-3-(2-bromoethyl)-4H-pyrido[1,2-a]pyrimidin-4-one

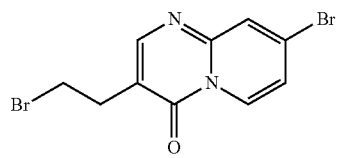

3-((4-bromopyridin-2-ylimino)methyl)dihydrofuran-2(3H)-one (800 mg, 2.97 mmol) and POBr₃ (4 g, 13.9 mmol) was stirred at 80° C. for 1.5 hr. After the suspension was poured into ice water, the solution was adjusted to pH 8 and extracted with DCM (3×100 mL). The combined organic layers were washed with brine and concentrated to give 850 mg crude product, which was directly used for the next step without further purification. MS (ESI): 330, 332, 334 (MH+).

Example 13.14b. Synthesis of 3-(2-bromoethyl)-8-((3-fluorophenyl)ethynyl)-4H-pyrido[1,2-a]pyrimidin-4-one

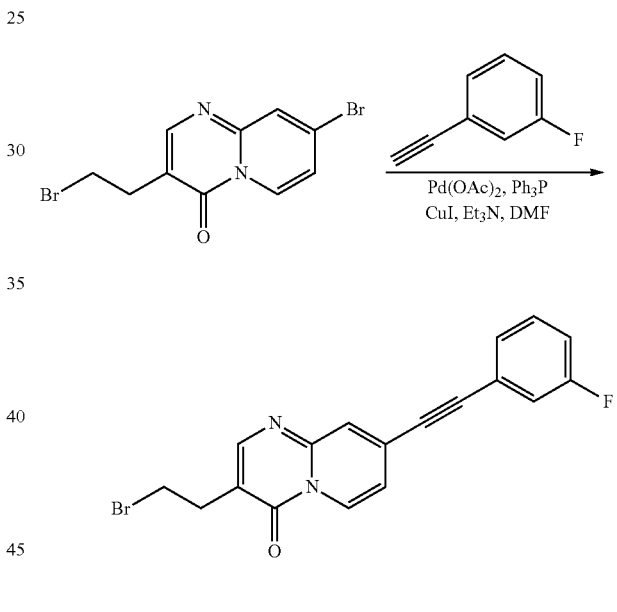

The title compound was prepared according to the experimental procedure as described in Example 1.1. MS (ESI): 371, 373 (MH+).

Example 13.14c. Synthesis of the HCl Salt of 3-(2-(dimethylamino)ethyl)-8-((3-fluorophenyl)ethynyl)-4H-pyrido[1,2-a]pyrimidin-4-one

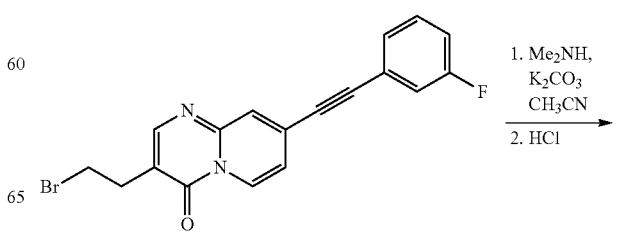

-continued

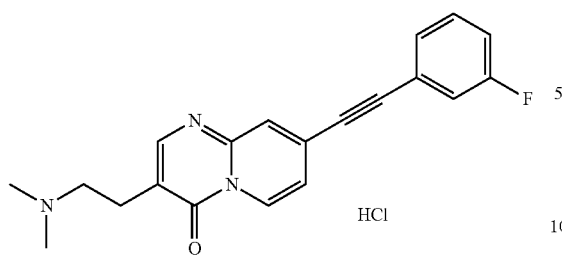

A solution of 3-(2-bromoethyl)-8-((3-fluorophenyl)ethynyl)-4H-pyrido-[1,2-a]pyrimidin-4-one (240 mg, 0.65 mmol), 30% aq. dimethylamine (0.3 mL) and K$_2$CO$_3$ (0.5 g, 3.6 mmol) in CH$_3$CN was stirred at room temperature for 3 hr. The solution was diluted with water (30 mL) and extracted with ethyl acetate (3×50 mL). Then the combined organic layers were concentrated to give the desired product, which was purified by column chromatography. The product was then converted to the corresponding HCl salt. MS (ESI): 336 (MH$^+$). $^1$H NMR (300 MHz, CDCl$_3$) δ 9.0-8.97 (d, J=7.47 Hz, 1H), 8.29 (s, 1H), 7.72 (s, 1H), 7.41-7.38 (m, 2H), 7.31-7.28 (m, 1H), 7.19-7.11 (m, 2H), 2.88-2.83 (m, 2H), 2.67-2.62 (m, 2H), 2.33 (s, 6H).

Example 13.15. Synthesis of 8-((3-fluorophenyl)ethynyl-3-(2-pyrrolidin-1-yl)-4H-pyrido[1,2-a]pyrimidin-4-one

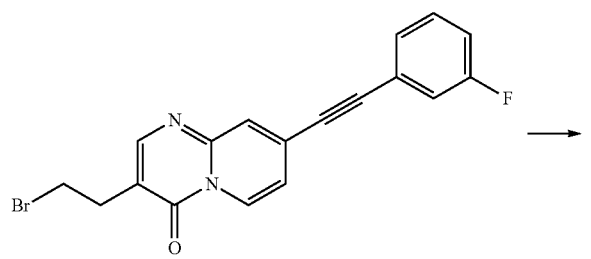

The title compound was prepared according to the experimental procedure as described in Example 13.14b. MS (ESI): 362 (MH$^+$); $^1$H NMR (300 MHz, CDCl$_3$) δ 9.00-8.98 (d, J=7.41, Hz, 1H), 8.30 (s, 1H), 7.72 (s, 1H), 7.41-7.38 (m, 2H), 7.3-7.28 (m, 1H), 7.19-7.11 (m, 2H), 2.93-2.87 (m, 2H), 2.83-2.77 (m, 2H), 2 2.62 (broad, 4H), 1.84-1.79 (m, 4H).

Example 13.16. Synthesis of 8-((3-fluorophenyl)ethynyl)-3-(2-morpholinoethyl)-4H-pyrido[1,2-a]pyrimidin-4-one

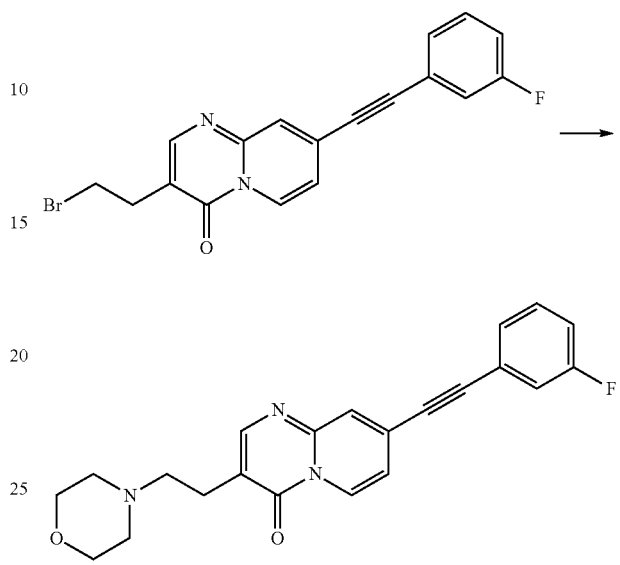

The title compound was prepared according to the experimental procedure as described in Example 13.14b. MS (ESI): 378 (MH$^+$); $^1$H NMR (300 MHz, CDCl$_3$) δ 9.0-8.98 (d, J=7.44 Hz, 1H), 8.30 (s, 1H), 7.73 (s, 1H), 7.42-7.38 (m, 2H), 7.32-7.29 (m, 1H), 7.20-7.12 (m, 2H), 3.75 (broad, 4H), 2.90-2.85 (m, 2H), 2.72-2.68 (m, 2H), 2.62-2.57 (m, 4H).

Example 13.17. Synthesis of 8-((3-fluorophenyl)ethynyl-3-(3-methyl-1,2,4-oxadiazol-5-yl)-4H-pyrido[1,2-a]pyrimidin-4-one

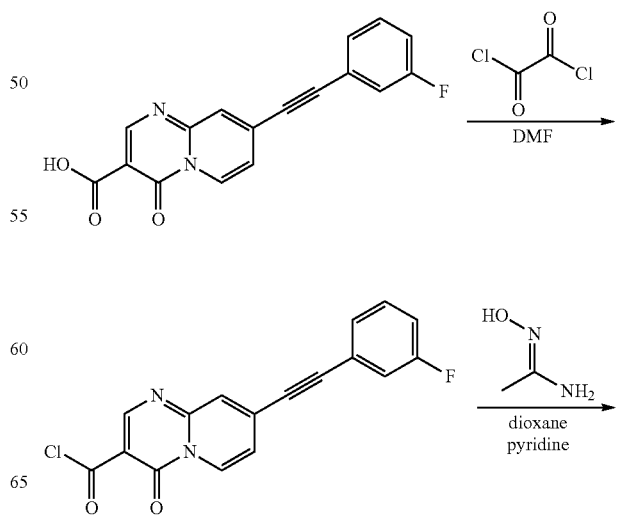

-continued

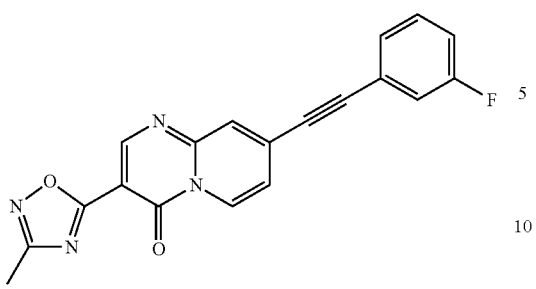

Example 13.17a. Synthesis of 8-((3-fluorophenyl)ethynyl)-4-oxo-4H-pyrido[1,2-a]pyrimidine-3-carbonyl chloride

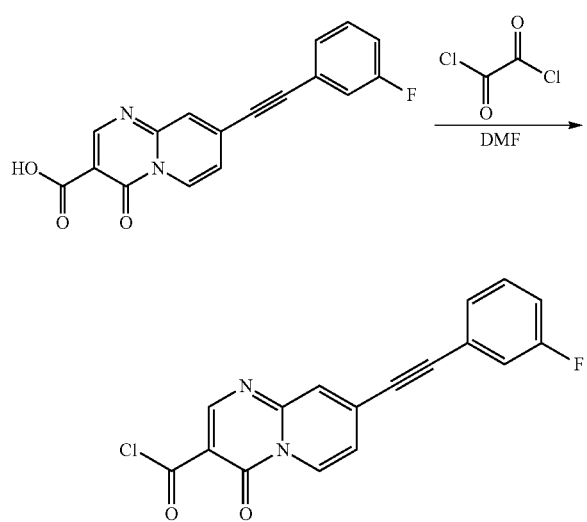

To a mixture of 8-((3-fluorophenyl)ethynyl)-4-oxo-4H-pyrido[1,2-a]pyrimidine-3-carboxylic acid (50 mg, 0.162 mmol, 1 equiv) and 1 drop DMF in dichloromethane was added oxalyl dichloride (1 mL) dropwise. The reaction mixture was stirred at room temperature for 3 h and concentrated to give the desired product, which was directly used for the next step.

Example 13.17b. Synthesis of 8-((3-fluorophenyl)ethynyl)-3-(3-methyl-1,2,4-oxadiazol-5-yl)-4H-pyrido[1,2-a]pyrimidin-4-one

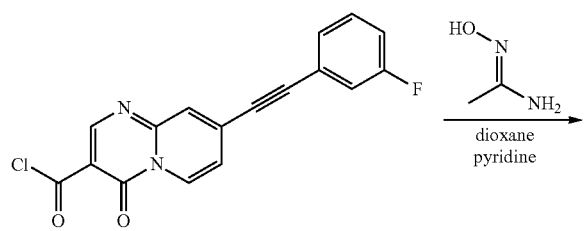

-continued

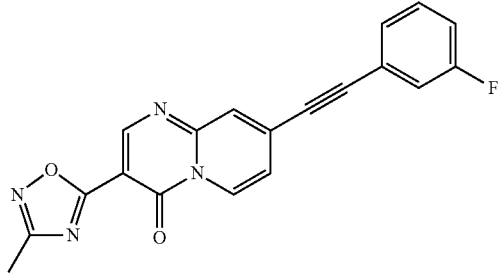

8-((3-fluorophenyl)ethynyl)-4-oxo-4H-pyrido[1,2-a]pyrimidine-3-carbonyl chloride was dissolved in 1,4-dioxane (3 mL). To the solution was added acetamidine hydrochloride (18 mg, 0.162 mmol, 1 equiv) and pyridine (2 mL). The reaction mixture was then heated at 70° C. overnight. After it was cooled to room temperature, the reaction mixture was diluted with water and extracted with ethyl acetate (3×50 mL). The combined organic layers were dried over $Na_2SO_4$. After filtration and concentration, the residue was purified by preparative TLC to give 2.2 mg of the desired product. MS (ESI): 347 ($MH^+$).

Example 13.18. Synthesis of 8-((3-fluorophenyl)ethynyl)-3-(2-hydroxypropan-2-yl)-4H-pyrido[1,2-a]pyrimidin-4-one

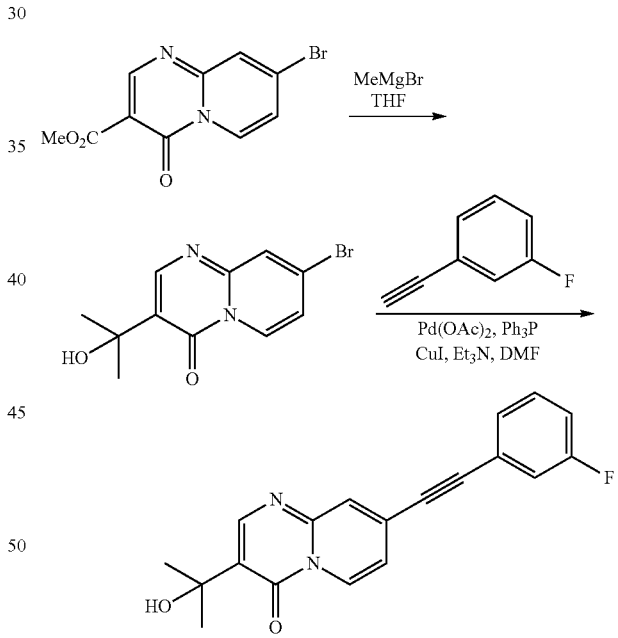

Example 13.18a. Synthesis of 8-bromo-3-(2-hydroxypropan-2-yl)-4H-pyrido[1,2-a]pyrimidin-4-one

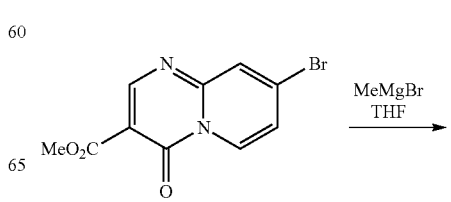

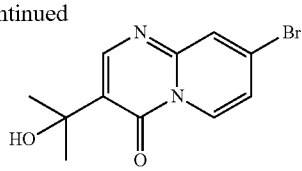

To a solution of methyl 8-bromo-4-oxo-4H-pyrido[1,2-a]pyrimidine-3-carboxylate (200 mg, 0.71 mmol, 1 equiv) in THF (10 mL) was added methylmagnesium bromide (0.78 mL, 1 M, 0.77 mmol, 2.2 equiv) at 0° C. dropwise. After the reaction mixture was stirred for 0.5 h, it was quenched with 10% HCl and extracted with ethyl acetate (3×50 mL). The combined organic layers were dried over Na$_2$SO$_4$. After filtration and concentration, the residue was purified by preparative HPLC to give 35 mg of the desired product. MS (ESI): 283, 285 (MH$^+$).

Example 13.18b. Synthesis of 8-((3-fluorophenyl)ethynyl)-3-(2-hydroxypropan-2-yl)-4H-pyrido[1,2-a]pyrimidin-4-one

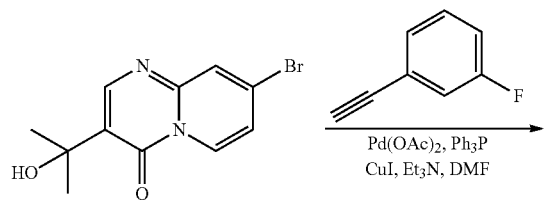

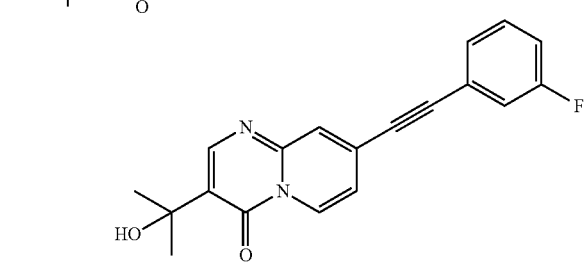

The title compound was prepared according to the experimental procedure as described in Example 1.1. MS (ESI): 265 (MH$^+$); $^1$H NMR (300 MHz, CDCl$_3$) δ 8.50-8.47 (d, J=6.84 Hz, 1H), 8.41 (m, 1H), 8.02 (s, 1H), 7.46-7.41 (m, 2H), 7.34-7.31 (m, 2H), 7.22-7.16 (m, 1H), 1.70 (s, 6H). mGluR5 PAM EC$_{50}$: ++. Fold shift at 10 μM: +.

Example 14.1. Synthesis of 6-(pyridin-2-ylethynyl)-2,3-dihydrocyclopenta[d]pyrido[1,2-a]pyrimidin-10(1H)-one

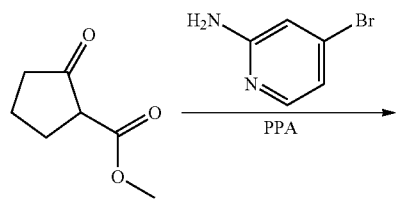

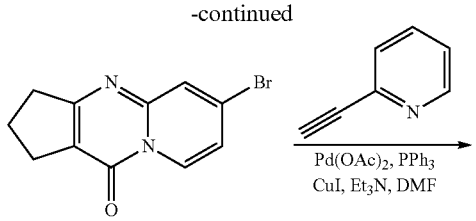

The title compound was prepared according to the experimental procedure as described in Example 16.1. MS (ESI): 288 (MH$^+$); $^1$H NMR (300 MHz, CDCl$_3$) δ 9.06-9.04 (d, J=7.41 Hz, 1H), 8.71-8.69 (d, J=3.30 Hz, 1H), 7.80-7.75 (m, 2H), 7.64-7.62 (d, J=7.80 Hz, 1H), 7.38-7.34 (m, 1H), 7.19-7.17 (dd, J=7.41, 1.80 Hz, 1H), 3.09-3.01 (m, 4H), 2.24-2.06 (m, 2H).

Example 15.1. Synthesis of 7-(pyridin-2-ylethynyl)-3,4-dihydro-1H-pyrido[2,1-b]quinazolin-11(2H)-one The title compound was prepared according to the experimental procedure as described in Example 16.1. MS (ESI): 302 (MH$^+$); $^1$H NMR (300 MHz, CDCl$_3$) δ 8.92-8.90 (d, J=7.47 Hz, 1H), 8.70-8.68 (d, J=4.86 Hz, 1H), 7.79-7.74 (t, J=7.74 Hz, 1H), 7.70 (s, 1H), 7.63-7.60 (d, J=7.80 Hz, 1H), 7.37-7.32 (m, 1H), 7.11-7.07 (d, J=7.44 Hz, 1H), 2.85-2.81 (m, 2H), 2.77-2.73 (m, 2H), 1.94-1.84 (m, 4H). mGluR5 PAM EC$_{50}$: +++.

Example 15.2. Synthesis of 3-methyl-7-(pyridin-2-ylethynyl)-3,4-dihydro-1H-pyrido[2,1-b]quinazolin-11(2H)-one

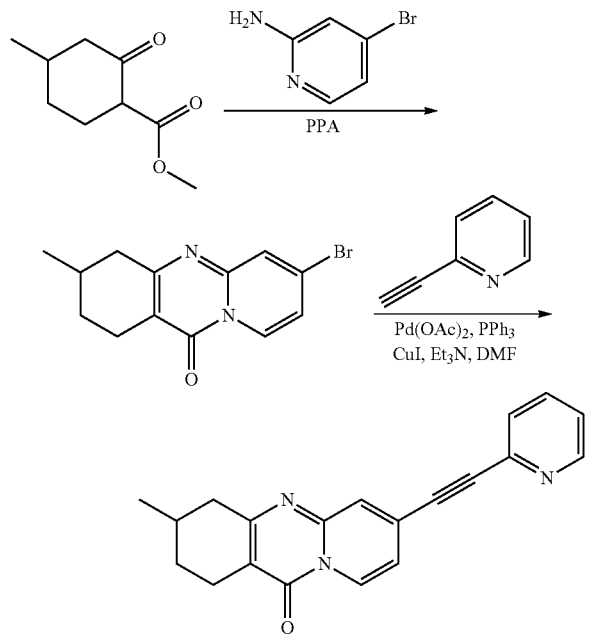

The title compound was prepared according to the experimental procedure as described in Example 16.1. MS (ESI): 316 (MH+); $^1$H NMR (300 MHz, CDCl$_3$) δ 8.92-8.89 (d, J=7.44 Hz, 1H), 8.69-8.68 (d, J=4.32 Hz, 1H), 7.78-7.73 (t, J=7.74 Hz, 1H), 7.69 (s, 1H), 7.62-7.59 (d, J=7.80 Hz, 1H), 7.36-7.32 (t, J=7.58 Hz, 1H), 7.10-7.07 (d, J=7.46 Hz, 1H), 2.96-2.85 (m, 2H), 2.69-2.57 (m, 1H), 2.50-2.41 (m, 1H), 2.01-1.95 (m, 2H), 1.47-1.33 (m, 1H), 1.13-1.11 (d, J=6.48 Hz, 3H). mGluR5 PAM EC$_{50}$: +++++. Fold shift at 10 μM: +++.

Example 15.3. Synthesis of 3,3-dimethyl-7-(pyridin-2-ylethynyl)-3,4-dihydro-1H-pyrido[2,1-b]quinazolin-11(2H)-one

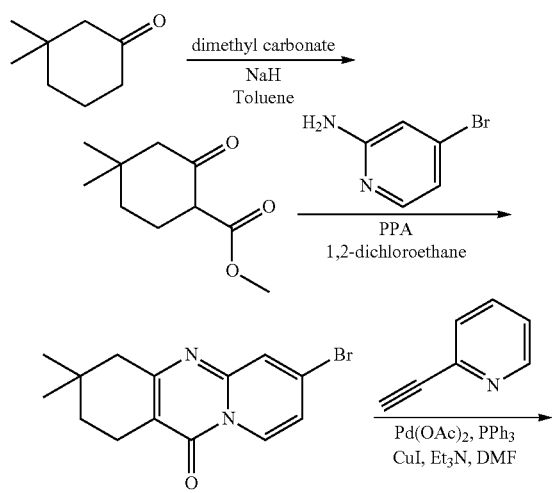

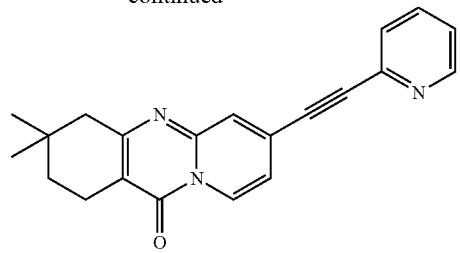

Example 15.3a. Synthesis of methyl 4,4-dimethyl-2-oxocyclohexane carboxylate

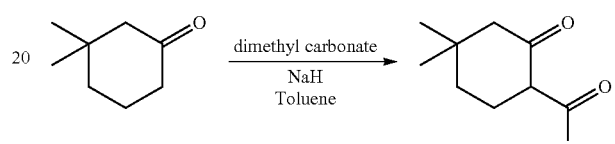

A solution of 3,3-dimethylcyclohexanone (0.5 g, 3.97 mmol, 1 equiv) and sodium hydride in toluene was stirred at rt for half an hour. To the mixture was added dimethyl carbonate and heated at reflux for 5 h. After the reaction was cooled to rt, the reaction mixture was quenched with water and extracted with ethyl acetate (3×50 mL). The combined organic layers were washed with brine and dried over anhydrous sodium sulfate, then concentrated under reduced pressure to give the crude product, which was directly used for the next step.

Example 15.3b. Synthesis of 7-bromo-3,3-dimethyl-3,4-dihydro-1H-pyrido[2,1-b]quinazolin-11(2H)-one

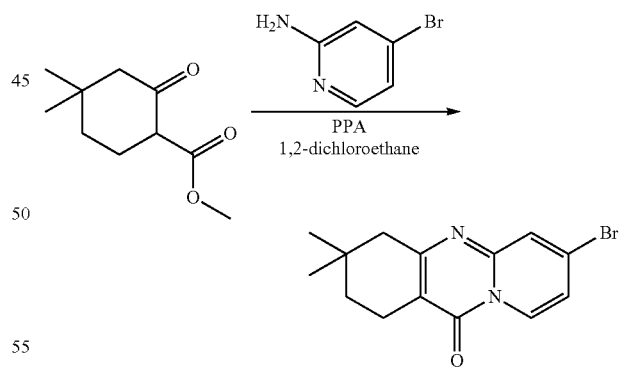

A solution of methyl 4,4-dimethyl-2-oxocyclohexanecarboxylate (0.5 g, 2.7 mmol, 1 eq), 4-bromopyridin-2-amine (0.51 g, 2.97 mmol, 1.1 eq) and PPA in 1,2-dichloroethane was stirred at 80° C. for 4 hours. After it was cooled to rt, the reaction mixture was quenched with saturated Na$_2$CO$_3$ and extracted with ethyl acetate (3×50 mL). The combined organic layers were washed with brine and dried over anhydrous sodium sulfate. After filtration and concentration, the residue was purified by silica gel chromatography to give the desired product.

Example 15.3c. Synthesis of 3,3-dimethyl-7-(pyridin-2-ylethynyl)-3,4-dihydro-1H-pyrido[2,1-b]quinazolin-11(2H)-one

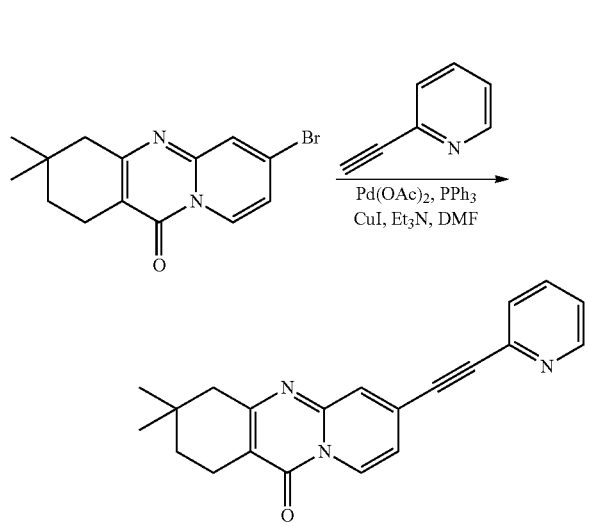

The title compound was prepared according to the experimental procedure as described in Example 1.1. MS (ESI): 330 (M+H$^+$); $^1$H NMR (300 MHz, CDCl$_3$) δ 8.93-8.91 (d, J=7.44 Hz, 1H), 8.70-8.68 (d, J=4.65 Hz, 1H), 7.79-7.74 (t, J=7.74 Hz, 1H), 7.70 (s, 1H), 7.63-7.60 (d, J=7.80 Hz, 1H), 7.37-7.33 (t, J=6.62 Hz, 1H), 7.09-7.08 (d, J=7.44 Hz, 1H), 2.80-2.62 (m, 2H), 2.62 (s, 2H), 1.69-1.61 (m, 2H), 1.05 (s, 6H). mGluR5 PAM EC$_{50}$: +++++. Fold shift at 10 μM: +++.

Example 15.4. Synthesis of 2,2-dimethyl-7-(pyridin-2-ylethynyl)-3,4-dihydro-1H-Pyrido[2,1-b]quinazolin-11(2H)-one

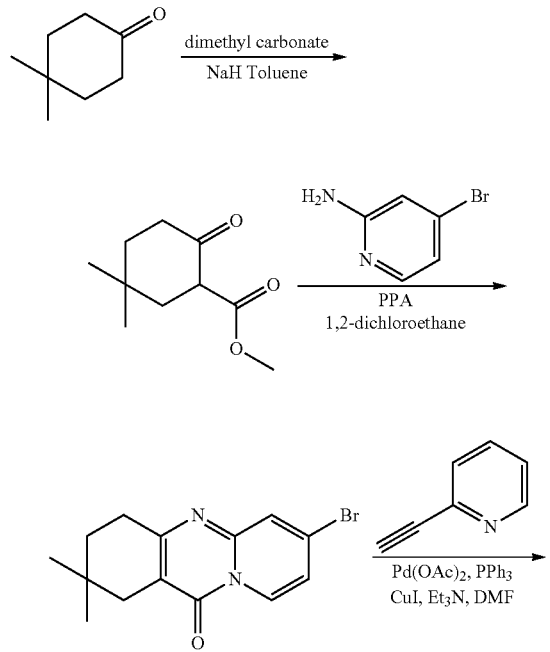

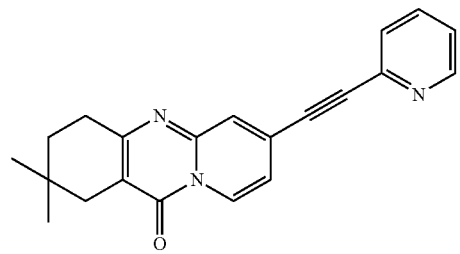

The title compound was prepared according to the experimental procedure as described in Example 15.3a, Example 15.3b, and Example 1.1. MS (ESI): 330 (M+H$^+$); $^1$H NMR (300 MHz, CDCl$_3$) δ 8.93-8.90 (d, J=7.44 Hz, 1H), 8.70-8.69 (d, J=4.71 Hz, 1H), 7.79-7.74 (t, J=7.77 Hz, 1H), 7.70 (s, 1H), 7.63-7.60 (d, J=7.83 Hz, 1H), 7.37-7.33 (t, J=6.77 Hz, 1H), 7.11-7.08 (dd, J=7.44, 1.65 Hz, 1H), 2.89-2.85 (t, J=6.62 Hz, 2H), 2.55 (s, 2H), 1.70-1.65 (t, J=6.62 Hz, 2H) 1.06 (s, 6H). mGluR5 PAM EC$_{50}$: +++++. Fold shift at 10 μM: +.

Example 15.5. Synthesis of 8-(pyridin-2-ylethynyl)-2,3,13,13a-tetrahydro-1H-pyrido[1',2':1,2]pyrimido[4,5-f]indolizin-12(5H)-one

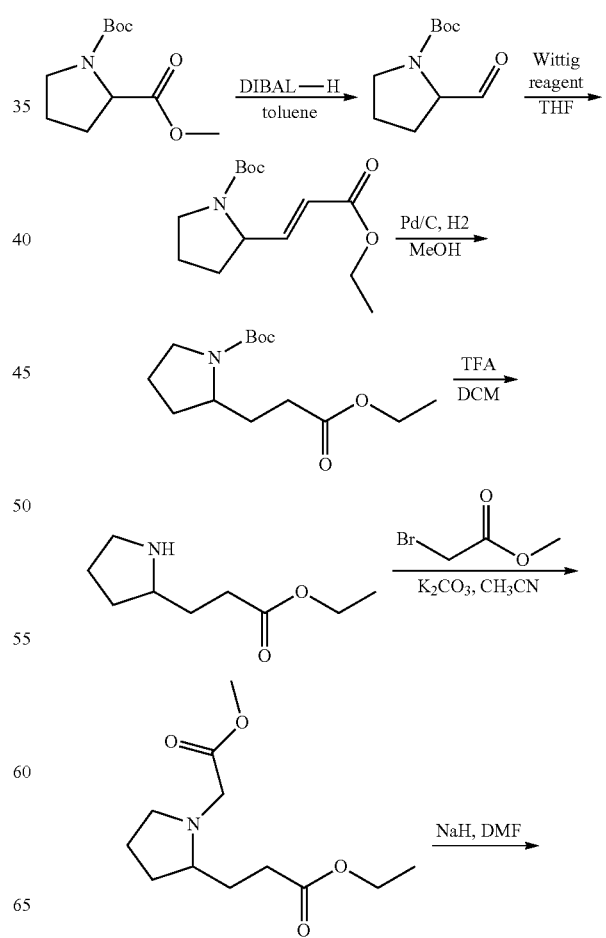

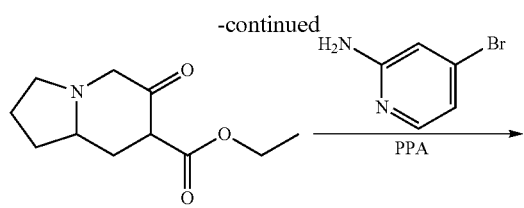

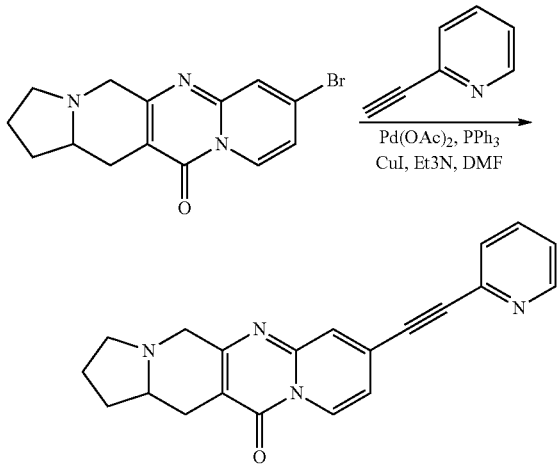

Example 15.5a. Synthesis of tert-butyl 2-formylpyrrolidine-1-carboxylate

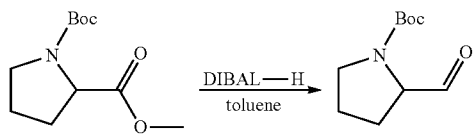

To a solution of 1-tert-butyl 2-methyl pyrrolidine-1,2-dicarboxylate (3.5 g, 15.3 mmol) in toluene at −78° C. was added DIBAL-H (17.6 mL, 30 mmol, 1.7 M) dropwise while maintaining the reaction temperature below −65° C. The reaction was stirred at −78° C. for 2 h and then quenched with methanol (10 mL). The mixture was then diluted with ethyl acetate (50 mL), saturated NH₄Cl was added, and the mixture was stirred vigorously for 20 min at room temperature. The two phases were then separated and the aqueous layer was extracted with DCM (2×50 mL). The combined organics were then washed with brine, dried over Na₂SO₄, concentrated under reduced pressure and purified by column chromatography to give 3 g of the desired product. MS (ESI): 200 (MH⁺).

Example 15.5b. Synthesis of tert-butyl 2-(3-ethoxy-3-oxoprop-1-enyl)pyrrolidine-1-carboxylate

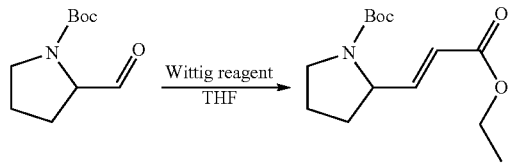 [SMILES: CC(C)(C)OC(=O)N1CCCC1C=O ; CCOC(=O)/C=C/C1CCCN1C(=O)OC(C)(C)C ; "THF"]

A solution of tert-butyl 2-formylpyrrolidine-1-carboxylate (4 g, 20 mmol) and (carbethoxymethylene)triphenylphosphorane (7 g, 20 mmol) in THF was stirred at room temperature for 2 hr. Then the mixture was concentrated and purified by column chromatography to give 4 g of desired product. MS (ESI): 270 (MH⁺).

Example 15.5c. Synthesis of tert-butyl 2-(3-ethoxy-3-oxopropyl)pyrrolidine-1-carboxylate

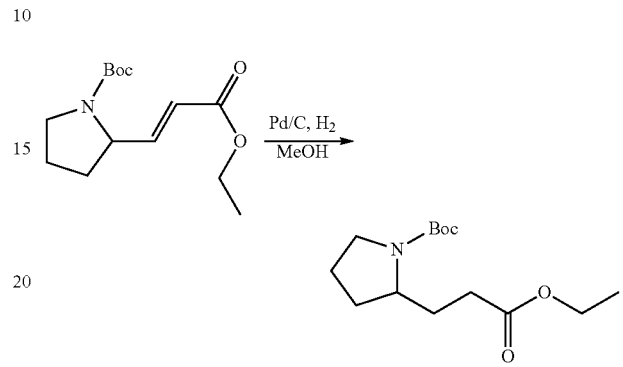

A solution of tert-butyl 2-(3-ethoxy-3-oxoprop-1-enyl)pyrrolidine-1-carboxylate (4 g, 14.9 mmol) and Pd/C (1 g, 10% weight) in MeOH was stirred at room temperature. Hydrogen from a balloon was ventilated to the suspension continuously and the completion of the reaction was monitored by TLC. After the suspension was filtered, the organic phases was concentrated to give the desired product, which was directly used for the next step without further purification. MS (ESI): 272 (MH⁺).

Example 15.5d. Synthesis of ethyl-3-(pyrrolidin-2-yl)propanoate

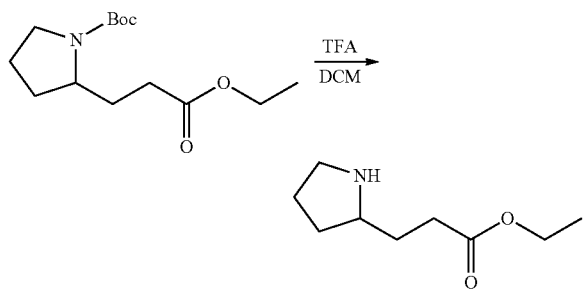

The title compound was prepared according to the experimental procedure as described in Example 1.21c. MS (ESI): 172 (MH⁺).

Example 15.5e. Synthesis of ethyl 3-(1-(2-methoxy-2-oxoethyl)pyrrolidin-2-yl)propanoate

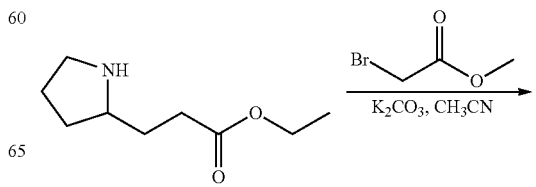

-continued

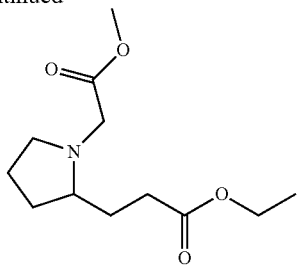

A solution of ethyl 3-(pyrrolidin-2-yl) propanoate (3 g, 17.5 mmol), methyl 2-bromoacetate (3 g, 18 mmol) and K₂CO₃ (3 g, 21.7 mmol) in CH₃CN was stirred at 80° C. overnight. The completion of the reaction was monitored by TLC. After the suspension was diluted with water (50 mL) and extracted with ethyl acetate (3×50 mL), the combined organic layers were concentrated to give the crude product, which was directly used for the next step without further purification. MS (ESI): 244 (MH$^+$).

Example 15.5f. Synthesis of ethyl 6-oxooctahydroindolizine-7-carboxylate

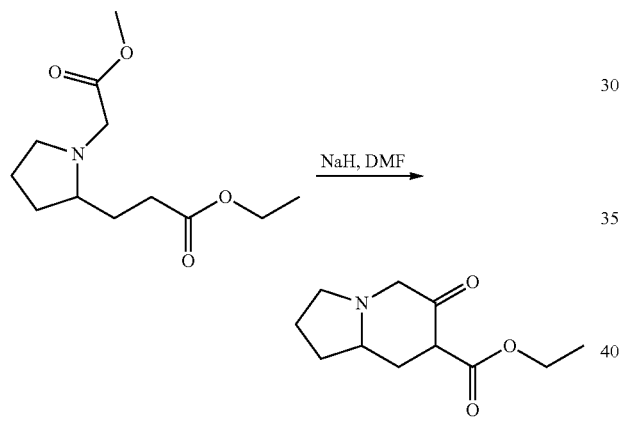

A solution of ethyl 3-(1-(2-methoxy-2-oxoethyl)pyrrolidin-2-yl)propanoate (2 g) and NaH (2 g, 60% weight) in DMF was stirred at 40° C. for 10 mins. The completion of reaction was monitored by TLC. After the suspension was quenched with water (30 mL), the solution was extracted with ethyl acetate (3×100 mL) and the combined organic layer was washed with brine, dried over Na₂SO₄. The desired product (230 mg) was obtained by column chromatography. MS (ESI): 212 (MH$^+$).

Example 15.5g. Synthesis of 8-bromo-2,3,13,13a-tetrahydro-1H-pyrido[1',2':1,2]pyrimido[4,5-f]indolizin-12(5H)-one

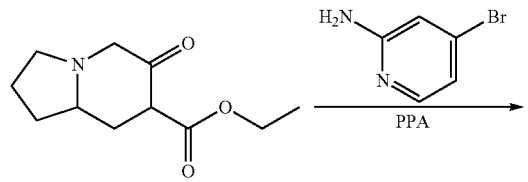

-continued

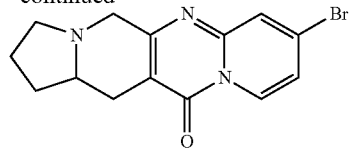

A solution of ethyl 6-oxooctahydroindolizine-7-carboxylate (230 mg, 1.1 mmol), 4-bromopyridin-2-amine (188 mg, 1.1 mmol) and excess PPA (2 g) in 1,2-dichloroethane was stirred at 80° C. overnight. After the suspension was diluted with water (20 mL) and adjusted to pH 8. The mixture was extracted with ethyl acetate (3×50 mL) and the combined organic layers were concentrated to give the crude product. 70 mg of the desired product was obtained after column chromatography. MS (ESI): 320, 322 (MH$^+$).

Example 15.5h. Synthesis of 8-(pyridin-2-ylethynyl)-2,3,13,13a-tetrahydro-1H-pyrido[1',2':1,2]pyrimido[4,5-f]indolizin-12(5H)-one

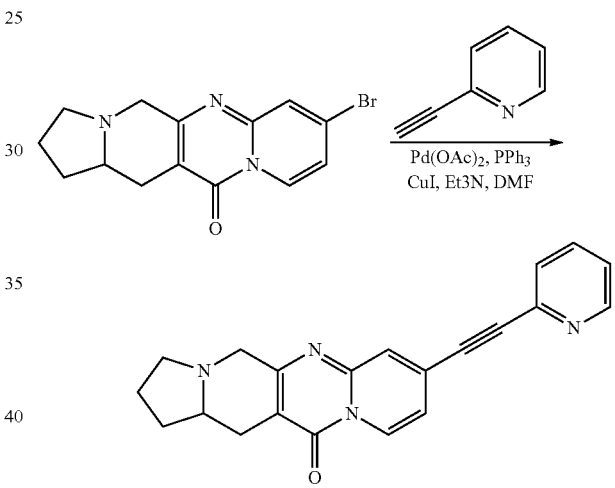

The title compound was prepared according to the experimental procedure as described in Example 1.1. MS (ESI): 343 (MH$^+$); $^1$H NMR (300 MHz, CDCl₃) δ 8.78-8.76 (d, J=7.53 Hz, 1H), 8.68-8.66 (d, J=4.77 Hz, 1H), 7.77-7.71 (t, J=7.76 Hz, 1H), 7.62-7.57 (m, 2H), 7.34-7.29 (m, 1H), 6.98-6.95 (d, J=7.58 Hz, 1H), 4.38 (m, 1H), 3.66-3.43 (m, 3H), 2.99-2.90 (m, 2H), 2.26-2.20 (m, 1H), 2.12-2.06 (m, 1H), 2.02-1.95 (m, 2H), 1.16-1.15 (m, 1H).

Example 15.6. Synthesis of 2-(11-oxo-7-(pyridin-2-ylethynyl)-3,4-dihydro-1H-dipyrido[1,2-a:4',3'-d]pyrimidin-2(11H)-yl)acetonitrile

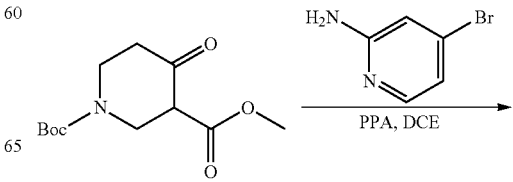

-continued

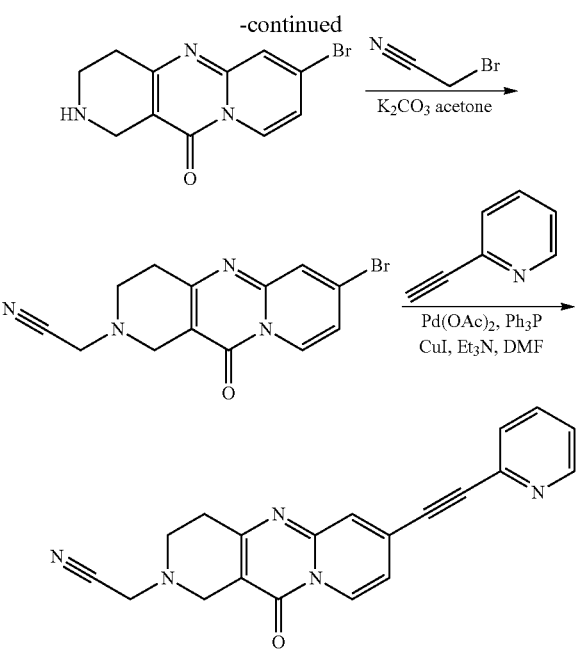

Example 15.6a. Synthesis of 7-bromo-3,4-dihydro-1H-dipyrido[1,2-a:4',3'-d]pyrimidin-11(2H)-one

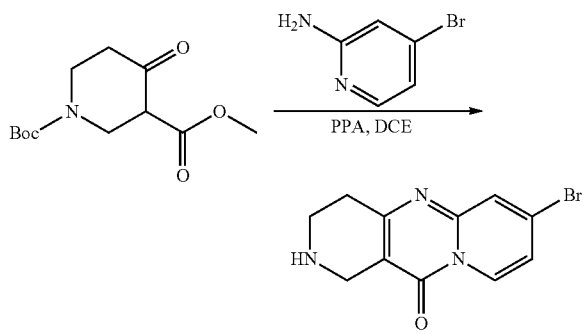

The title compound was prepared according to the experimental procedure as described in Example 16.1a.

Example 15.6b. Synthesis of 2-(11-oxo-7-bromo-3,4-dihydro-1H-dipyrido[1,2-a:4',3'-d]pyrimidin-2(11H)-yl)acetonitrile

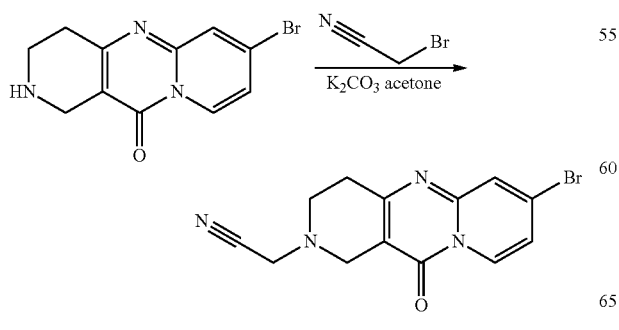

The title compound was prepared according to the experimental procedure as described in Example 5.6a.

Example 15.6c. Synthesis of 2-(11-oxo-7-(pyridin-2-ylethynyl)-3,4-dihydro-1H-dipyrido[1,2-a:4',3'-d]pyrimidin-2(11H)-yl)acetonitrile

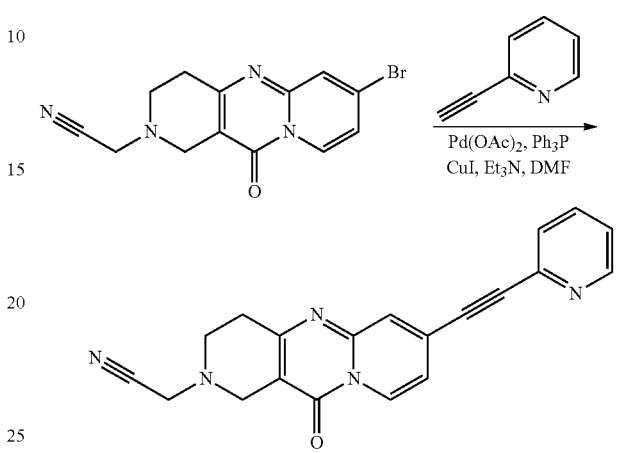

The title compound was prepared according to the experimental procedure as described in Example 1.1. MS (ESI): 315 (MH$^+$); $^1$H NMR (300 MHz, CDCl$_3$) δ 8.94-8.92 (d, J=7.41 Hz, 1H), 8.71-8.69 (d, J=3.93 Hz, 1H), 7.80-7.74 (m, 2H), 7.64-7.61 (d, J=7.65 Hz, 1H), 7.38-7.34 (t, J=4.92 Hz, 1H), 7.17-7.15 (d, J=7.38 Hz, 1H), 3.81-3.78 (d, J=3.39 Hz, 4H), 3.03-2.99 (m, 4H). mGluR5 PAM EC$_{50}$: +.

Example 15.7 and Example 15.8. Synthesis of (S)-10-(pyridin-2-ylethynyl)-2,3,13,13a-tetrahydro-1H-pyrido[1',2':1,2]pyrimido[5,4-f]indolizin-6(5H)-one and (S)-9-(pyridin-2-ylethynyl)-2,3,5,6-tetrahydro-1H-pyrido[1',2':1,2]pyrimido[4,5-g]indolizin-13(13bH)-one

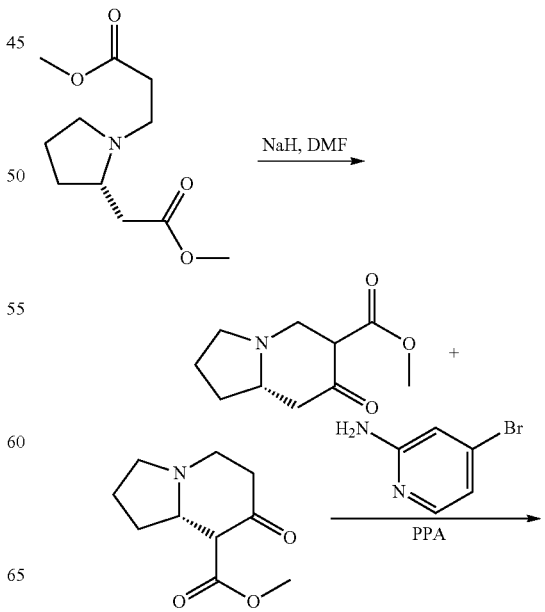

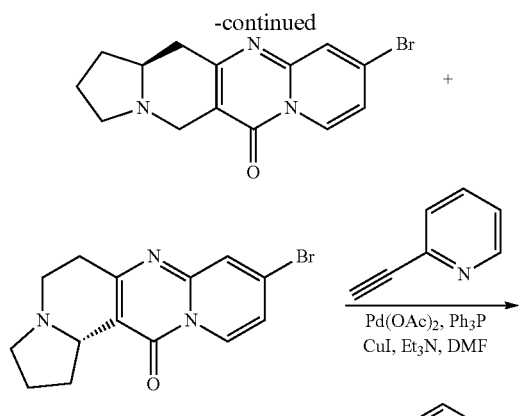

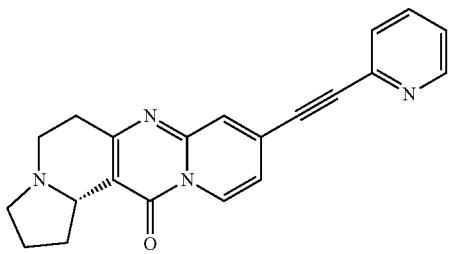 [SMILES: O=c1c2c(nc3cc(C#Cc4ccccn4)ccn13)CCN1CCC[C@@H]21]

(S)-9-(pyridin-2-ylethynyl)-2,3,5,6-tetrahydro-1H-pyrido[1',2': 1,2]pyrimido[4,5-g]indolizin-13(13bH)-one $^1$H NMR (300 MHz, CDCl$_3$) δ 8.93-8.91 (d, J=7.47 Hz, 1H), 8.71-8.69 (d, J=4.47 Hz, 1H), 7.80-7.74 (m, 2H), 7.64-7.61 (d, J=7.77 Hz, 1H), 7.38-7.34 (t, J=6.69 Hz, 1H), 7.17-7.14 (d, J=7.46 Hz, 1H), 4.18 (broad, 1H), 3.57 (broad, 1H), 3.16-3.05 (m, 4H), 2.85-2.74 (m, 1H), 2.06-1.96 (m, 2H), 1.82-1.69 (m, 2H).

Example 16.1. Synthesis of 3-((4-fluorophenyl)ethynyl)-7,8,9,10-tetrahydrocyclohepta[d]pyrido[1,2-a]pyrimidin-11(6H)-one

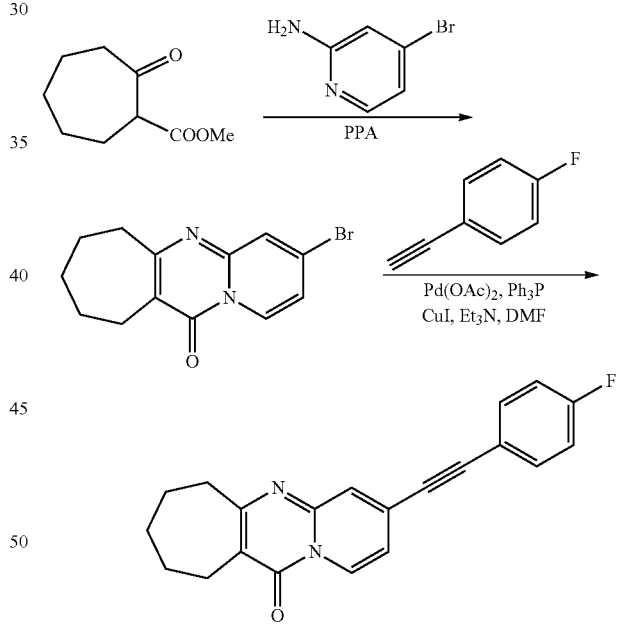

The title compounds were prepared according to the experimental procedure as described in Example 15.5f, Example 15.5g, and Example 1.1. MS (ESI): 343 (MH$^+$).

(S)-10-(pyridin-2-ylethynyl)-2,3,13,13a-tetrahydro-1H-pyrido[1',2':1,2]pyrimido[5,4-f]indolizin-6(5H)-one $^1$H NMR (300 MHz, CDCl$_3$) δ 8.95-8.93 (d, J=7.50 Hz, 1H), 8.70-8.69 (d, J=4.80 Hz, 1H), 7.80-7.74 (m, 2H), 7.63-7.61 (d, J=7.80 Hz, 1H), 7.38-7.33 (m, 1H), 7.15-7.12 (dd, J=7.44, 1.47 Hz, 1H), 4.36-4.31 (d, J=16.2 Hz, 1H), 3.40-3.33 (t, J=8.65 Hz, 1H), 3.29-3.24 (d, J=16.2 Hz, 1H), 3.07-3.01 (dd, J=16.2, 2.87 Hz, 1H), 2.85-2.76 (m, 1H), 2.48-2.43 (m, 1H), 2.40-2.34 (m, 1H), 2.19-2.14 (m, 1H), 2.00-1.88 (m, 2H), 1.59-1.58 (m, 1H). mGluR5 PAM EC$_{50}$: +.

Example 16.1a. Synthesis of 3-bromo-7,8,9,10-tetrahydrocyclohepta[d]pyrido[1,2-a]pyrimidin-11(6H)-one

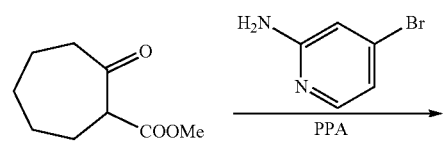

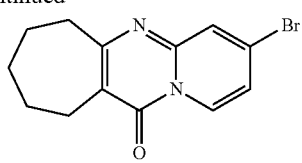

A mixture of methyl 2-oxocycloheptanecarboxylate (2 g, 11.8 mmol) and 4-bromopyridin-2-amine (2.04 g, 11.8 mmol), and PPA (5 mL) in 1,2-dichloroethane (10 mL) was stirred at 85° C. for 5 h. The reaction mixture was cooled to ambient temperature. A chilled saturated sodium carbonate solution was added to adjust pH to 8. The resulting mixture was extracted with ethyl acetate (2×100 mL). The combined organic layers were washed with brine and dried over anhydrous sodium sulfate. After filtration and concentration, the crude product was purified by silica gel chromatography to produce 2.4 g of the desired product. MS (ESI): 293 (MH+).

Example 16.1b. Synthesis of 3-(4-fluoro-phenyl-ethynyl)-7,8,9,10-tetrahydrocyclohepta[d]pyrido[1,2-a]pyrimidin-11(6H)-one

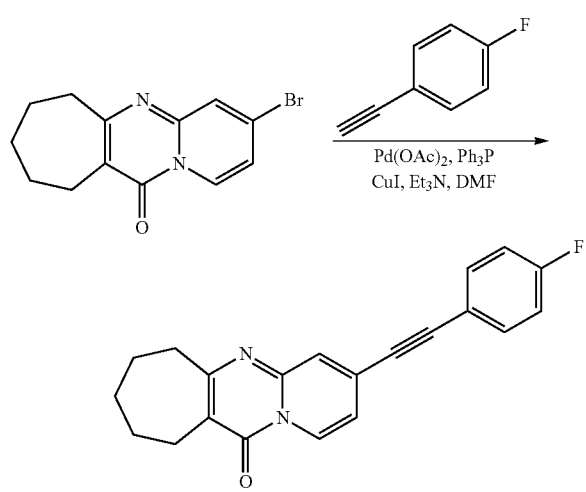

A solution of 3-bromo-7,8,9,10-tetrahydrocyclohepta[d]pyrido[1,2-a]pyrimidin-11(6H)-one (250 mg, 0.85 mmol), 1-ethynyl-4-fluorobenzene (255 mg, 2.12 mmol), Pd(OAc)$_2$ (38.2 mg, 0.17 mmol), PPh$_3$ (200 mg, 0.76 mmol), CuI (16.2 mg, 0.085 mmol), and Et$_3$N (0.7 mL) in DMF (8 mL) was stirred in a sealed tube at 70° C. for 3.5 hours. After it was cooled to room temperature, the reaction mixture was diluted with H$_2$O and extracted with ethyl acetate (2×50 mL). The combined organic layers were washed with brine and dried over anhydrous sodium sulfate. After filtration and concentration, the crude product was purified by silica gel to produce 185 mg of desired product. MS (ESI): 333 (MH+); $^1$H NMR (300 MHz, CDCl$_3$) δ 8.97-8.94 (dd, J=7.44, 0.66 Hz, 1H), 7.65-7.56 (m, 3H), 7.15-7.06 (m, 3H), 3.00-2.97 (m, 4H), 1.94-1.88 (m, 2H), 1.80-1.64 (m, 4H). mGluR5 PAM EC$_{50}$: +++++. Fold shift at 10 μM: +.

Example 16.2. Synthesis of 3-(phenylethynyl)-7,8,9,10-tetrahydrocyclohepta[d]pyrido[1,2-a]pyrimidin-11(6H)-one

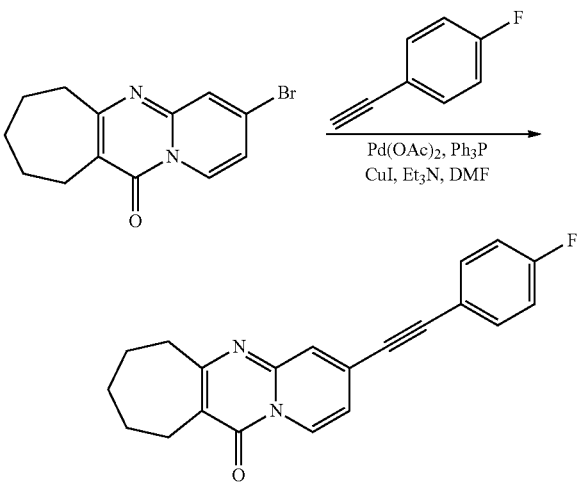

The title compound was prepared according to the experimental as described in Example 16.1b. MS (ESI): 315 (MH+); $^1$H NMR (300 MHz, CDCl$_3$) δ 8.97-8.95 (d, J=7.50 Hz, 1H), 7.67-7.66 (d, J=1.05 Hz, 1H), 7.62-7.58 (m, 2H), 7.45-7.39 (m, 2H), 7.12-7.09 (dd, J=7.44 Hz, 1.80 Hz, 1H), 3.00-2.70 (m, 4H), 1.79-1.74 (m, 2H), 1.72-1.64 (m, 4H). mGluR5 PAM EC$_{50}$: +++++. Fold shift at 10 μM: +.

Example 16.3. Synthesis of 3-(pyridin-2-ylethynyl)-7,8,9,10-tetrahydrocyclohepta[d]pyrido[1,2-a]pyrimidin-11(6H)-one

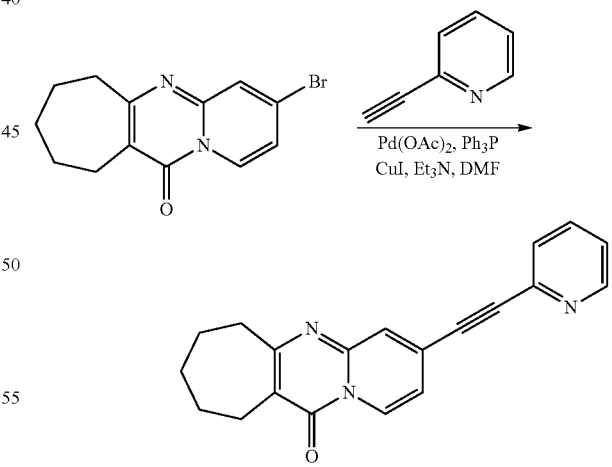

The title compound was prepared according to the experimental procedure as described in Example 16.1b. MS (ESI): 316 (MH+); $^1$H NMR (300 MHz, CDCl$_3$) δ 9.00-8.92 (d, J=7.29 Hz, 1H), 8.75-8.69 (m, 1H), 7.82-7.74 (m, 2H), 7.63-7.61 (d, J=7.56 Hz, 1H), 7.46-7.33 (m, 1H), 7.16-7.13 (d, J=8.25 Hz, 1H), 3.05-2.87 (m, 4H), 1.91-1.90 (m, 2H), 1.77-1.66 (m, 4H). mGluR5 PAM EC$_{50}$: +++++. Fold shift at 10 μM: +.

Example 16.4. Synthesis of 3-(pyridin-3-ylethynyl)-7,8,9,10-tetrahydrocyclohepta[d]pyrido[1,2-a]pyrimidin-11(6H)-one

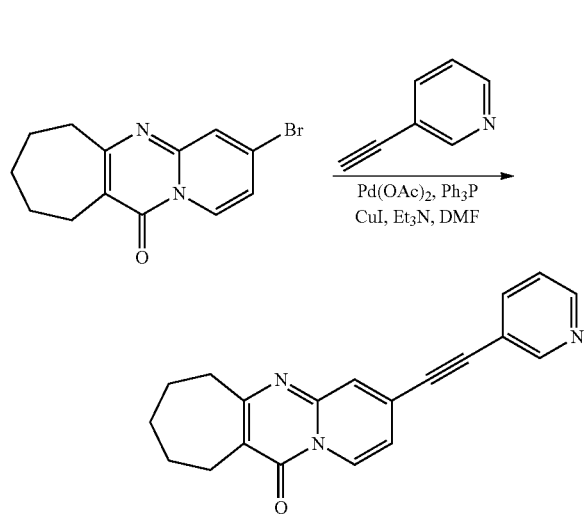

The title compound was prepared according to the experimental procedure as described in Example 16.1b. MS (ESI): 316 (MH+); 1H NMR (300 MHz, CDCl3) δ 8.99-8.96 (d, J=7.41 Hz, 1H), 8.83 (s, 1H), 8.69-8.61 (m, 1H), 7.91-7.83 (d, J=7.89 Hz, 1H), 7.69 (s, 1H), 7.43-7.34 (m, 1H), 7.11-7.09 (d, J=6.87 Hz, 1H), 3.01-2.97 (m, 4H), 1.92-1.90 (m, 2H), 1.78-1.68 (m, 4H). mGluR5 PAM EC$_{50}$: +++++. Fold shift at 10 μM: ++.

Example 16.5. Synthesis of 3-(pyridin-4-ylethynyl)-7,8,9,10-tetrahydrocyclohepta[d]pyrido[1,2-a]pyrimidin-11(6H)-one

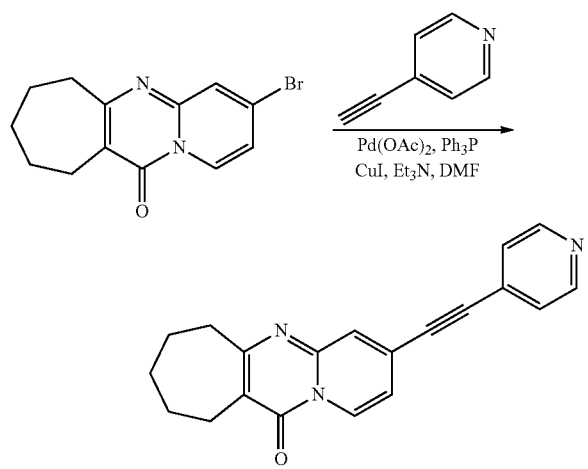

The title compound was prepared according to the experimental procedure as described in Example 16.1b. MS (ESI): 316 (MH+); 1H NMR (300 MHz, CDCl3) δ 8.99-8.96 (d, J=7.47 Hz, 1H), 8.70-8.68 (d, J=6.00 Hz, 2H), 7.70 (s, 1H), 7.45-7.43 (d, J=6.03 Hz, 2H), 7.10-7.07 (dd, J=7.44, 1.77 Hz, 1H), 3.01-2.97 (m, 4H), 1.96-1.88 (m, 2H), 1.79-1.68 (m, 4H). mGluR5 PAM EC$_{50}$: +++++. Fold shift at 10 μM: ++.

Example 16.6. Synthesis of 8-methyl-3-(pyridin-2-ylethynyl)-7,8,9,10-tetrahydrocyclohepta[d]pyrido[1,2-a]pyrimidin-11(6H)-one

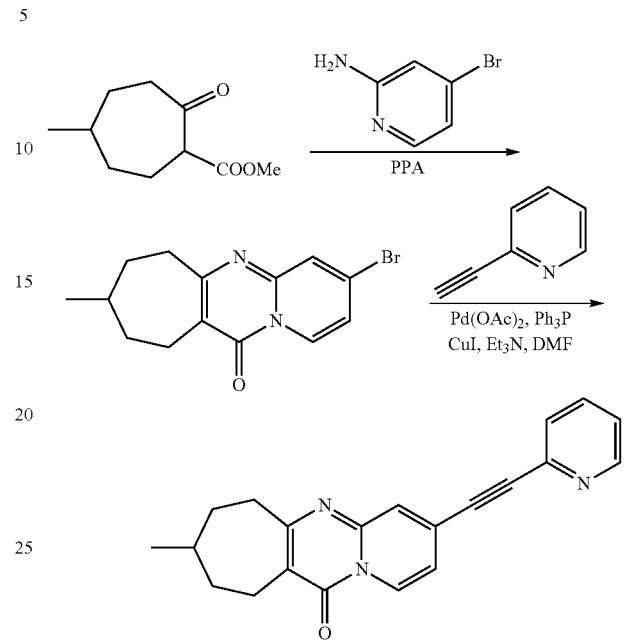

The title compound was prepared according to the experimental procedures as described in Example 16.1a and Example 16.1b. MS (ESI): 330 (MH+); 1H NMR (300 MHz, CDCl3) δ 8.98-8.96 (d, J=7.35 Hz, 1H), 8.71-8.69 (d, J=5.01 Hz, 1H), 7.80-7.74 (m, 2H), 7.63-7.61 (d, J=7.77 Hz, 1H), 7.37-7.30 (m, 1H), 7.16-7.13 (d, J=7.44 Hz, 1H), 3.51-3.44 (m, 1H), 3.06-2.94 (m, 2H), 2.51-2.42 (t, J=5.8 Hz, 1H), 2.01-1.94 (m, 2H), 1.89-1.85 (m, 1H), 1.29-1.20 (m, 1H), 1.09-1.06 (m, 1H), 1.00-0.98 (d, J=6.60 Hz, 3H). mGluR5 PAM EC$_{50}$: +++++. Fold shift at 10 μM: +++.

Example 16.7. Synthesis of 4-fluoro-N-(13-oxo-7,8,9,10,11,13-hexahydro-6H-azocino[2,1-b]quinazolin-3-yl)benzamide

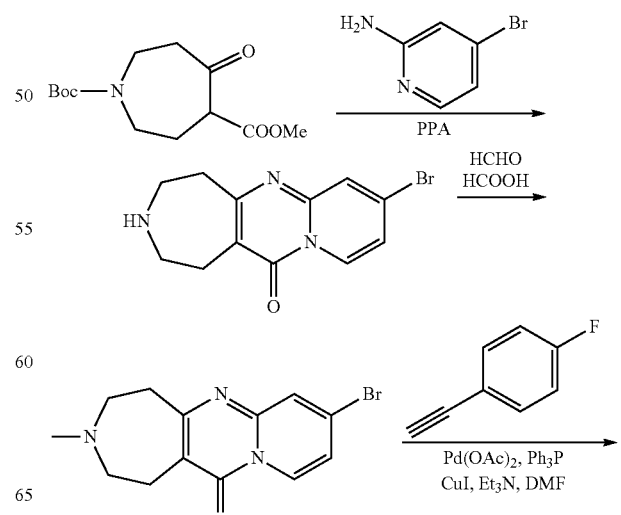

-continued

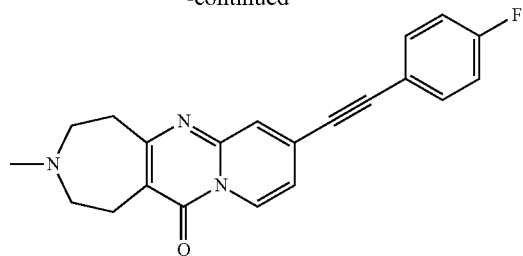

Example 16.7a. Synthesis of 2-bromo-5,7,8,9,10,11-hexahydroazepino[1,2-b]isoquinoline

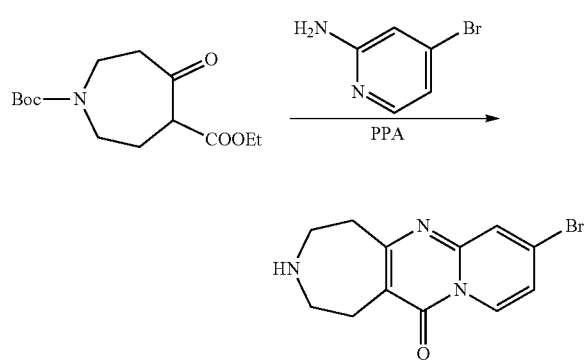

The title compound was prepared according to the experimental procedure as described in Example 16.1a. MS (ESI): 294, 296 (MH+).

Example 16.7b. Synthesis of 8-bromo-3-methyl-2,3,4,5-tetrahydropyrido[1',2':1,2]pyrimido[4,5-d]azepin-12(1H)-one

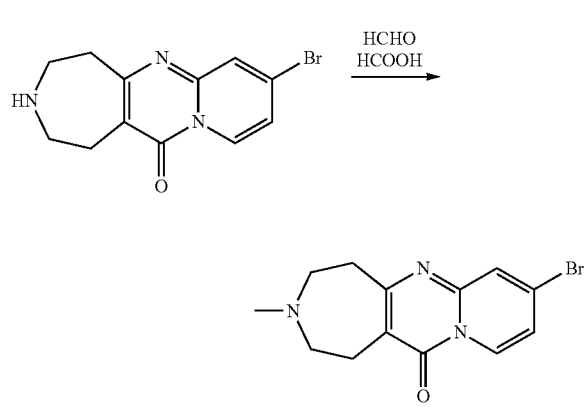

The title compound was prepared according to the experimental procedure as described in Example 1.21d. MS (ESI): 308, 310 (MH+).

Example 16.7c. Synthesis of 8-((4-fluorophenyl)ethynyl)-3-methyl-2,3,4,5-tetrahydropyrido[1',2':1,2]pyrimido[4,5-d]azepin-12(1H)-one

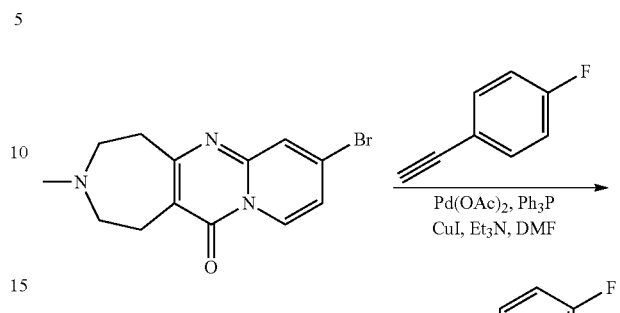

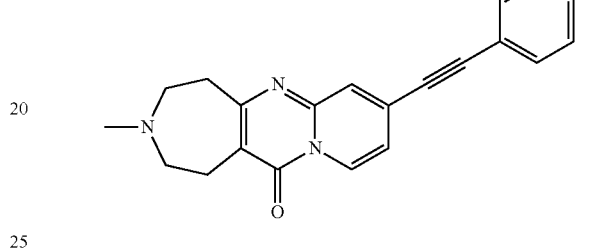

The title compound was prepared according to the experimental procedure as described in Example 1.1. MS (ESI): 348 (MH+); $^1$H NMR (300 MHz, CDCl$_3$) δ 8.97-8.95 (d, J=7.41 Hz, 1H), 7.66 (s, 1H), 7.61-7.57 (m, 2H), 7.15-7.09 (t, J=8.78 Hz, 3H), 3.14-3.11 (m, 4H), 2.70-2.60 (m, 4H), 2.42 (s, 3H). mGluR5 PAM EC$_{50}$: +. Fold shift at 10 μM: +++.

Example 17.1. Synthesis of 3-(phenylethynyl)-8,9,10,11-tetrahydro-6H-cycloocta[d]pyrido[1,2-a]pyrimidin-12(7H)-one

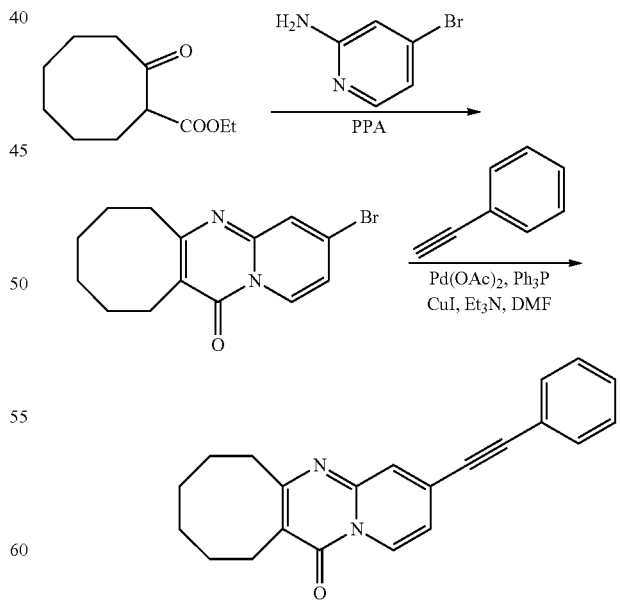

The title compound was prepared according to the experimental procedure as described in Example 16.1. MS (ESI): 329 (MH+); $^1$H NMR (300 MHz, CDCl$_3$) δ 8.95-8.93 (dd, J=7.46, 0.68 Hz, 1H), 7.68-7.67 (m, 1H), 7.62-7.58 (m, 2H), 7.45-7.38 (m, 3H), 7.09-7.06 (dd, J=7.46, 1.79 Hz, 1H), 2.95-2.90 (m, 4H), 1.88-1.78 (m, 4H), 1.52-1.44 (m, 4H). mGluR5 PAM EC$_{50}$: +++++. Fold shift at 10 μM: +.

Example 17.2. Synthesis of 3-(pyridin-2-ylethynyl)-8,9,10,11-tetrahydro-6H-cycloocta[d]pyrido[1,2-a]pyrimidin-12(7H)-one

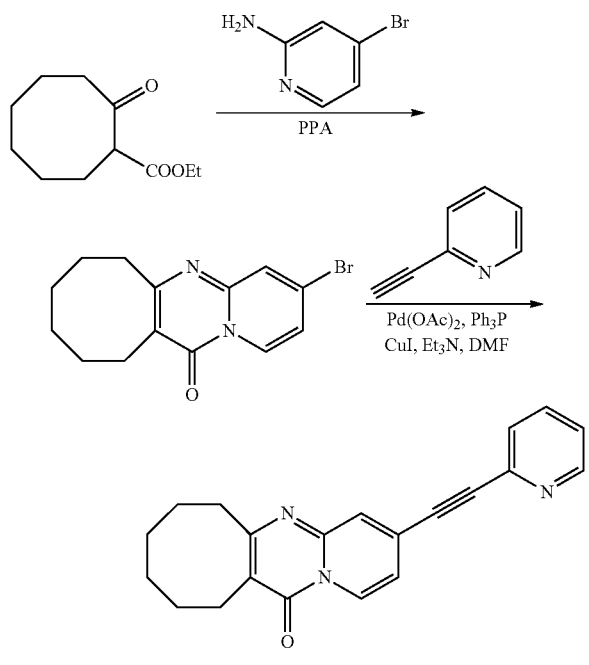

The title compound was prepared according to the experimental procedure as described in Example 16.1. MS (ESI): 330 (MH$^+$); $^1$H NMR (300 MHz, CDCl$_3$) δ 8.96-8.94 (dd, J=7.41, 0.69 Hz, 1H), 8.71-8.69 (d, J=4.35 Hz, 1H), 7.80-7.74 (m, 2H), 7.63-7.60 (d, J=7.95 Hz, 1H), 7.38-7.28 (m, 1H), 7.13-7.10 (dd, J=7.44, 1.80 Hz, 1H), 2.96-2.91 (m, 4H), 1.91-1.78 (m, 4H), 1.48 (s, 4H). mGluR5 PAM EC$_{50}$: +++++.

Example 17.3. Synthesis of 3-(pyridin-3-ylethynyl)-8,9,10,11-tetrahydro-6H-cycloocta[d]pyrido[1,2-a]pyrimidin-12(7H)-one

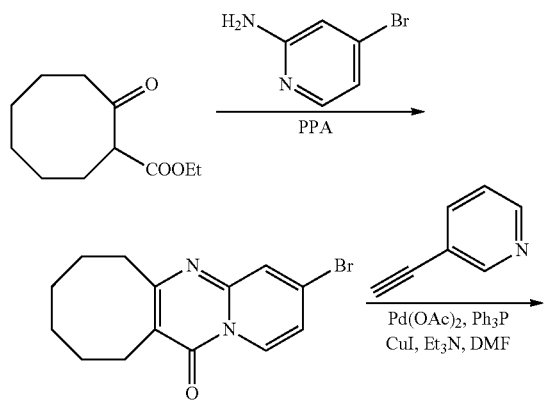

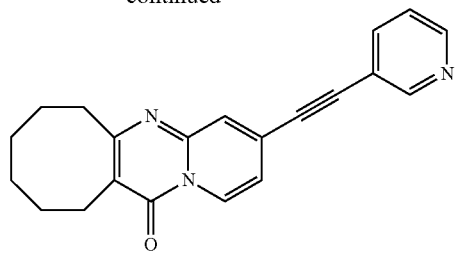

The title compound was prepared according to the experimental procedure as described in Example 16.1. MS (ESI): 330 (MH$^+$); $^1$H NMR (300 MHz, CDCl$_3$) δ 8.97-8.94 (d, J=7.14 Hz, 1H), 8.83 (s, 1H), 8.66-8.64 (m, 1H), 7.90-7.86 (m, 1H), 7.71 (s, 1H), 7.46-7.35 (m, 1H), 7.09-7.06 (dd, J=7.41, 1.71 Hz, 1H), 2.96-2.91 (m, 4H), 1.88-1.78 (m, 4H), 1.48 (m, 4H). mGluR5 PAM EC$_{50}$: +++++. Fold shift at 10 μM: ++.

Example 17.4. Synthesis of 3-(pyridin-4-ylethynyl)-8,9,10,11-tetrahydro-6H-cycloocta[d]pyrido[1,2-a]pyrimidin-12(7H)-one

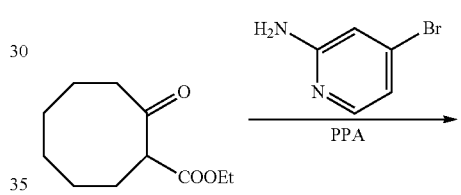

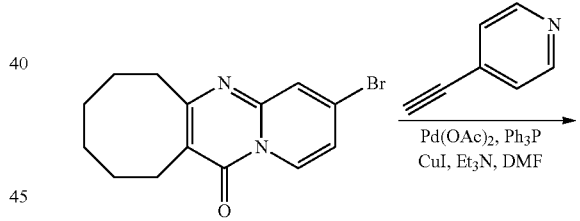

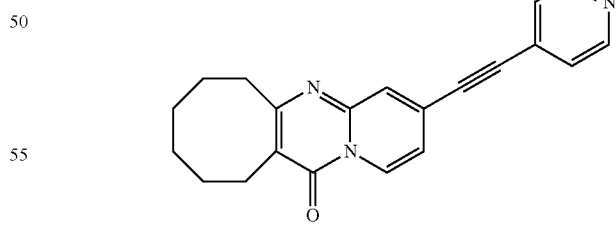

The title compound was prepared according to the experimental procedure as described in Example 16.1. MS (ESI): 330 (MH$^+$); $^1$H NMR (300 MHz, CDCl$_3$) δ 8.97-8.95 (dd, J=7.44, 0.66 Hz, 1H), 8.70-8.68 (d, J=6.03 Hz, 2H), 7.72 (s, 1H), 7.45-7.43 (d, J=6.06 Hz, 2H), 7.08-7.05 (dd, J=7.46, 1.79 Hz, 1H), 2.96-2.91 (m, 4H), 7.88-1.79 (m, 4H), 1.49-1.47 (m, 4H). mGluR5 PAM EC$_{50}$: +++++. Fold shift at 10 μM: ++.

Example 17.5. Synthesis of 3-((4-fluorophenyl)ethynyl)-8,9,10,11-tetrahydro-6H-cycloocta[d]pyrido[1,2-a]pyrimidin-12(7H)-one

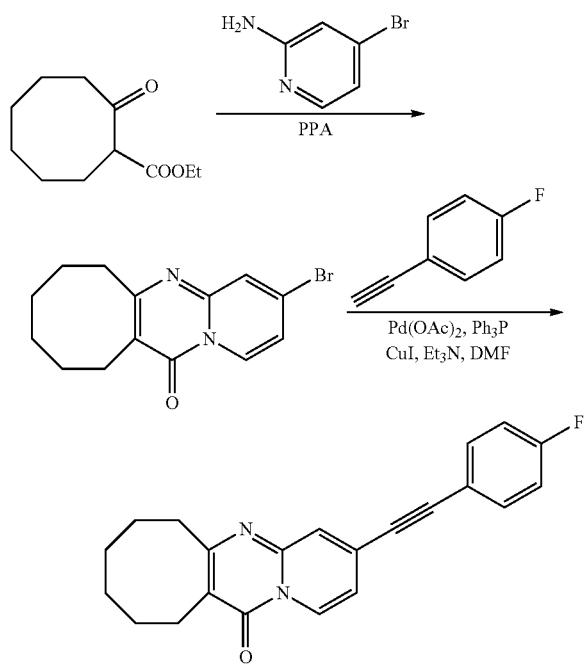

The title compound was prepared according to the experimental procedure as described in Example 16.1. MS (ESI): 347 (MH⁺); ¹H NMR (300 MHz, CDCl₃) δ 8.95-8.92 (dd, J=7.44, 0.72 Hz, 1H), 7.66 (s, 1H), 7.61-7.56 (m, 2H), 7.15-7.04 (m, 3H), 2.95-2.90 (m, 4H), 1.87-1.78 (m, 4H), 1.541.48 (m, 4H). mGluR5 PAM EC₅₀: +++++. Fold shift at 10 μM: +.

Example 18.1. Synthesis of 6-((3-fluorophenyl)ethynyl)isoquinolin-1(2H)-one

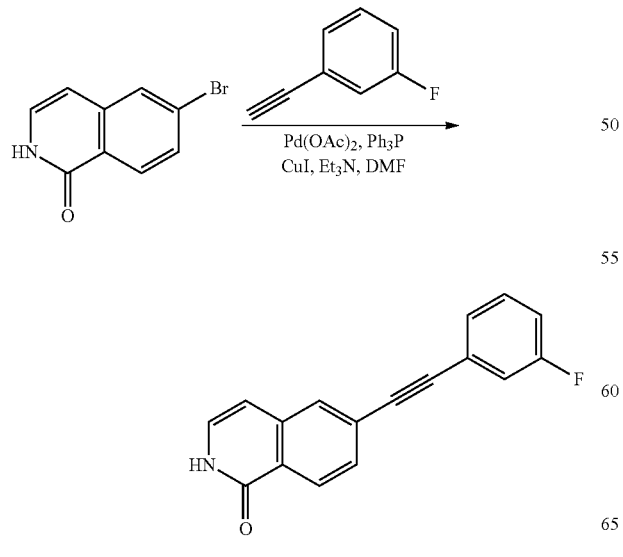

The title compound was prepared according to the experimental procedure as described in Example 1.1. MS (ESI): 264(MH⁺); ¹H NMR (300 MHz, DMSO-d⁶) δ 11.38 (s, 1H), 8.21 (d, J=8.31 Hz, 1H), 7.91 (s, 1H), 7.62-7.59 (m, 1H), 7.55-7.44 (m, 3H), 7.36-7.29 (m, 1H), 7.25 (m, 1H), 6.59-6.56 (d, J=7.20 Hz, 1H). mGluR5 PAM EC₅₀: +.

Example 18.2. Synthesis of 6-((4-fluorophenyl)ethynyl)-2-propylisoquinolin-1(2H)-one

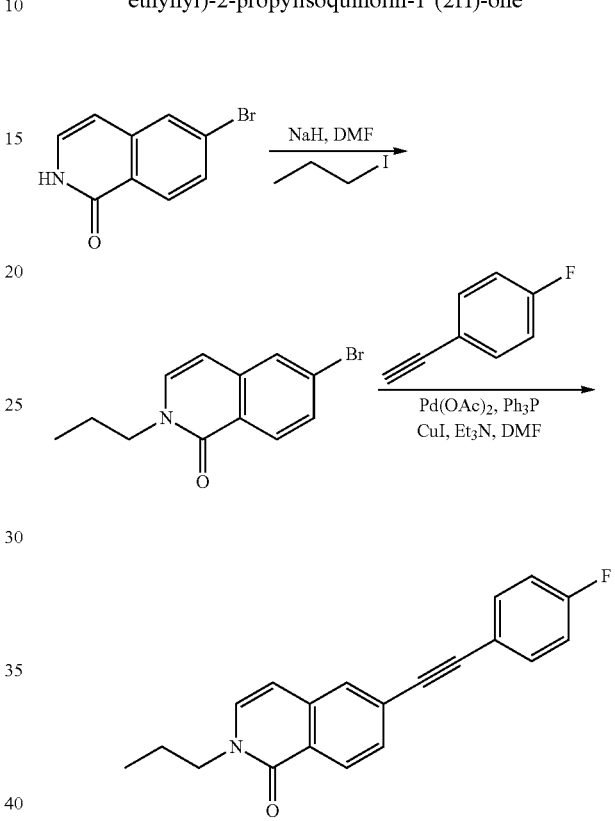

The title compound was prepared according to the experimental procedure as described in Example 1.6a and Example 1.1. MS (ESI): 306 (MH⁺); ¹H NMR (300 MHz, CDCl₃) δ 8.43-8.40 (d, J=8.43 Hz, 1H), 7.68 (s, 1H), 7.60-7.54 (m, 3H), 7.11-7.06 (m, 3H), 6.48-6.45 (d, J=7.89 Hz, 1H), 4.00-3.95 (t, J=7.50 Hz, 2H), 1.87-1.80 (m, 2H), 1.03-0.98 (t, J=7.34 Hz, 3H). mGluR5 PAM EC₅₀: +.

Example 18.3. Synthesis of the HCl Salt of 3,3-dimethyl-9-(pyridin-2-ylethynyl)-3,4-dihydro-1H-pyrido[1,2-b]isoquinolin-6(2H)-one and the HCl Salt of 2,2-dimethyl-9-(pyridin-2-ylethynyl)-3,4-dihydro-1H-pyrido[1,2-b]isoquinolin-6(2H)-one as an 85:15 Mixture

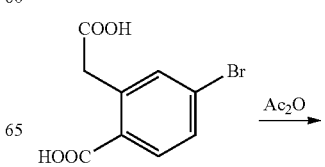

467

-continued

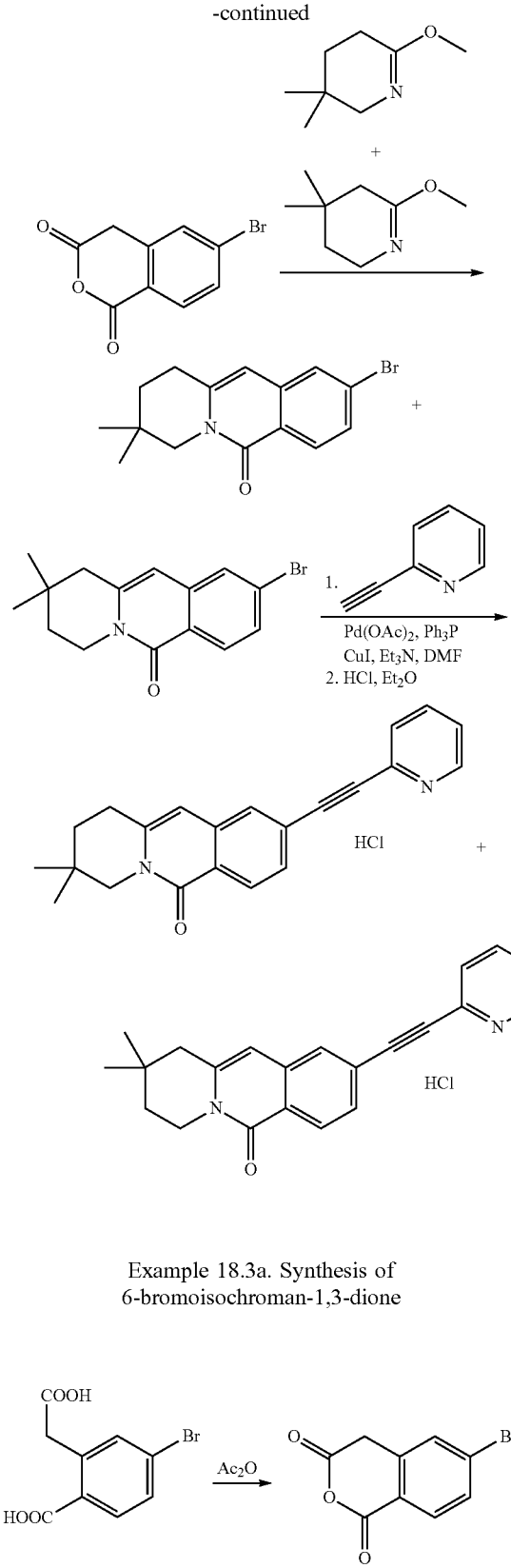

Example 18.3a. Synthesis of
6-bromoisochroman-1,3-dione

A solution of 4-bromo-2-carboxymethyl-benzoic acid (200 mg, 1.1 mmol) in 2 mL acetic anhydride was refluxed for 10 h. Then the mixture was concentrated to dryness and the crude 6-bromoisochroman-1,3-dione was used into the next step without further purification.

Example 18.3b. Synthesis of
6-methoxy-3,3-dimethyl-2,3,4,5-tetrahydropyridine
and
6-methoxy-4,4-dimethyl-2,3,4,5-tetrahydropyridine

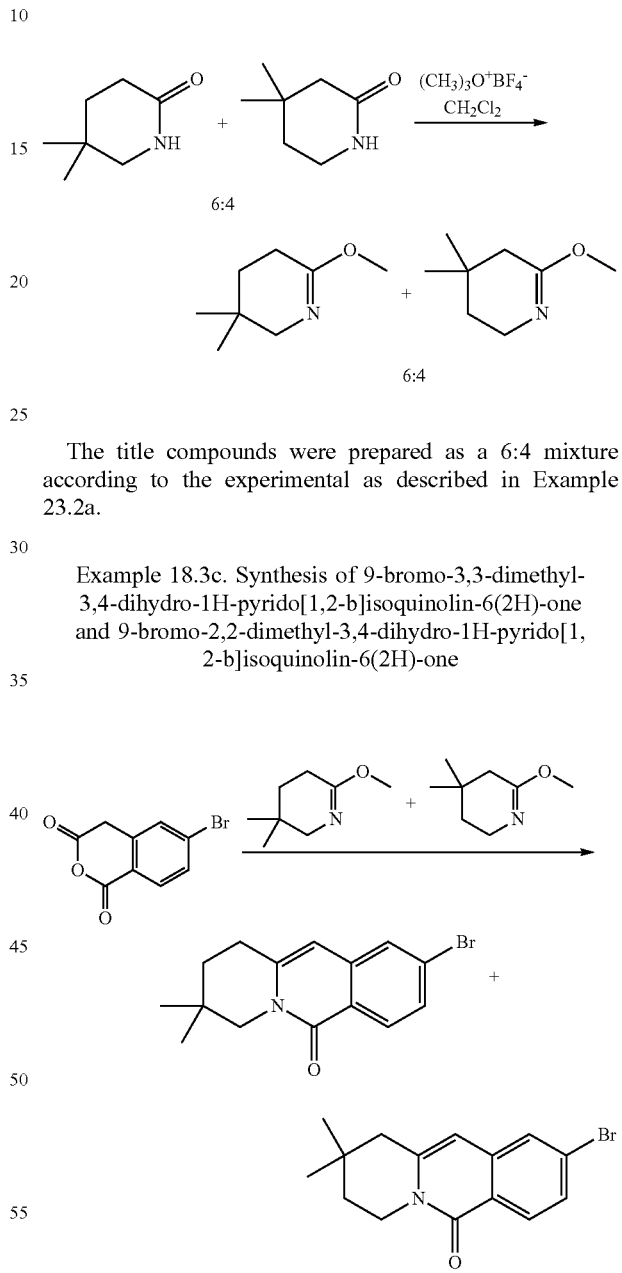

The title compounds were prepared as a 6:4 mixture according to the experimental as described in Example 23.2a.

Example 18.3c. Synthesis of 9-bromo-3,3-dimethyl-3,4-dihydro-1H-pyrido[1,2-b]isoquinolin-6(2H)-one and 9-bromo-2,2-dimethyl-3,4-dihydro-1H-pyrido[1,2-b]isoquinolin-6(2H)-one 6-bromoisochroman-1,3-dione prepared from Example 18.3a and a mixture of 6-methoxy-3,3-dimethyl-2,3,4,5-tetrahydropyridine and 6-methoxy-4,4-dimethyl-2,3,4,5-tetrahydropyridine (ratio of 6:4, respectively) (200 mg, 1.57 mmol) in 30 mL toluene was refluxed over night. After the solvent was removed, the crude product was purified by silica gel chromatography to give desired products (20 mg). MS (ESI): 306, 308 (MH$^+$).

Example 18.3d. Synthesis of HCl Salt of 3,3-dimethyl-9-(pyridin-2-ylethynyl)-3,4-dihydro-1H-pyrido[1,2-b]isoquinolin-6(2H)-one and HCl Salt of 2,2-dimethyl-9-(pyridin-2-ylethynyl)-3,4-dihydro-1H-pyrido[1,2-b]isoquinolin-6(2H)-one as an 85:15 Mixture

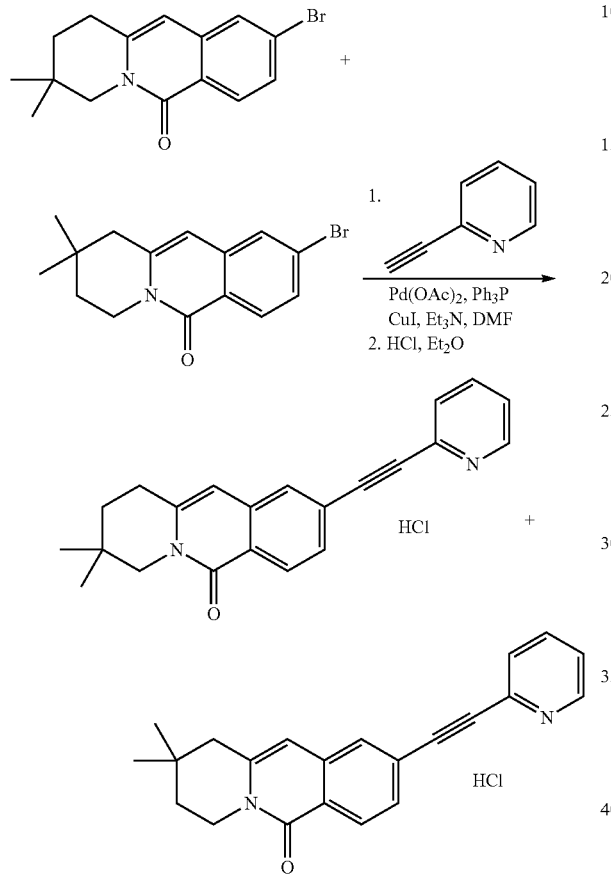

A flask was charged with a mixture of 9-bromo-3,3-dimethyl-3,4-dihydro-1H-pyrido[1,2-b]isoquinolin-6(2H)-one and 9-bromo-2,2-dimethyl-3,4-dihydro-1H-pyrido[1,2-b]isoquinolin-6(2H)-one (55 mg, 0.18 mmol, 1 equiv), 2-ethynylpyridine (0.05 mL, 0.27 mmol, 1.5 equiv), Pd(AcO)$_2$ (4.5 mg, 0.018 mmol, 0.1 equiv), PPh$_3$ (42 mg, 0.162 mmol, 0.9 equiv), CuI (4 mg, 0.018 mmol, 0.1 equiv), Et$_3$N (0.4 mL) and DMF (5 mL). A vacuum was applied and the reaction mixture was back filled with nitrogen three times. The mixture was stirred at 70° C. for 3.5 h. After the reaction mixture was cooled to room temperature, it was diluted with H$_2$O and extracted with ethyl acetate (3×50 mL). The combined organic layers were washed with brine and dried over anhydrous sodium sulfate, then concentrated under reduced pressure and purified by column chromatography to give the title compounds as a mixture. 3,3-Dimethyl-9-(pyridin-2-ylethynyl)-3,4-dihydro-1H-pyrido[1,2-b]isoquinolin-6(2H)-one and 2,2-dimethyl-9-(pyridin-2-ylethynyl)-3,4-dihydro-1H-pyrido[1,2-b]isoquinolin-6(2H)-one were obtained in an 85:15 ratio. MS (ESI): 329 (MH$^+$). The products were then converted to the corresponding HCl salts.

3,3-dimethyl-9-(pyridin-2-ylethynyl)-3,4-dihydro-1H-pyrido[1,2-b]isoquinolin-6(2H)-one: MS (ESI): 329 (MH$^+$); $^1$H NMR (300 MHz, CD$_3$OD) δ 8.87-8.85 (d, J=5.5 Hz, 1H), 8.60-8.51 (t, J=8.2 Hz, 1H), 8.39-8.36 (d, J=8.3 Hz, 1H), 8.23-8.21 (d, J=8.1 Hz, 1H), 7.99-7.97 (m, 2H), 7.72-7.68 (dd, J=8.4, 1.3 Hz, 1H), 6.66 (s, 1H), 3.94 (s, 2H), 2.95-2.91 (t, J=6.8 Hz, 2H), 1.71-1.67 (t, J=7.0 Hz, 2H), 1.06 (s, 6H).

Example 19.1. Synthesis of 3-((4-fluorophenyl)ethynyl)-6,7,8,9,10,12-hexahydroazepino[2,1-b]quinazoline

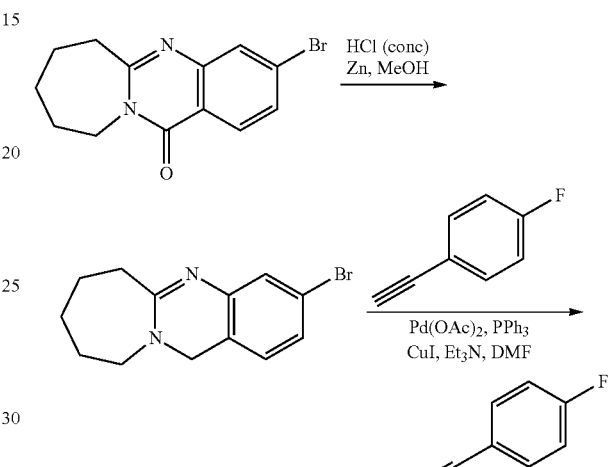

Example 19.1a. Synthesis of 3-bromo-6,7,8,9,10,12-hexahydroazepino[2,1-b]quinazoline

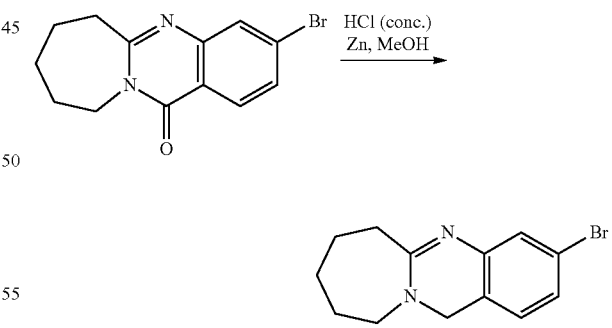

A mixture of 3-bromo-7,8,9,10-tetrahydroazepino[2,1-b]quinazolin-12(6H)-one (200 mg, 0.21 mmol, 1.0 equiv) and excess zinc powder, HCl (37%, 1 mL) in MeOH (4 mL) was stirred at 75° C. for 30 min. The reaction mixture was poured into water (50 mL) and extracted with ethyl acetate (3×20 mL). The combined organic layer was concentrated under reduced pressure. The residue was purified by silica gel chromatography to give the desired product. MS (ESI): 279, 281 (MH+).

Example 19.1b. Synthesis of 3-((4-fluorophenyl)ethynyl)-6,7,8,9,10,12-hexahydroazepino[2,1-b]quinazoline

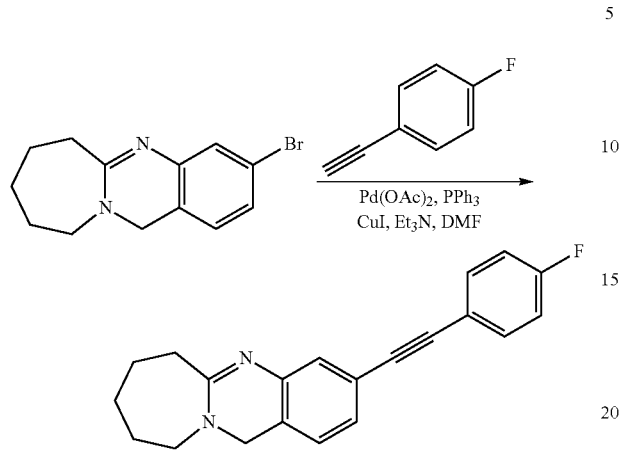

The title compound was prepared according to the experimental procedure as described in Example 1.1. MS (ESI): 319 (MH$^+$); $^1$H NMR (300 MHz, CD$_3$OD) δ 7.56-7.51 (m, 2H), 7.16-7.10 (m, 3H), 7.86-7.81 (d, J=1.41 Hz, 1H), 6.96-6.94 (t, J=7.74 Hz, 1H), 4.68 (s, 2H), 3.50-3.47 (d, J=9.09 Hz, 2H), 2.64-2.61 (m, 2H), 1.79-1.76 (m, 6H). mGluR5 PAM EC$_{50}$: +++.

Example 20.1. Synthesis of (E)-3-methyl-7-styrylquinazolin-4(3H)-one

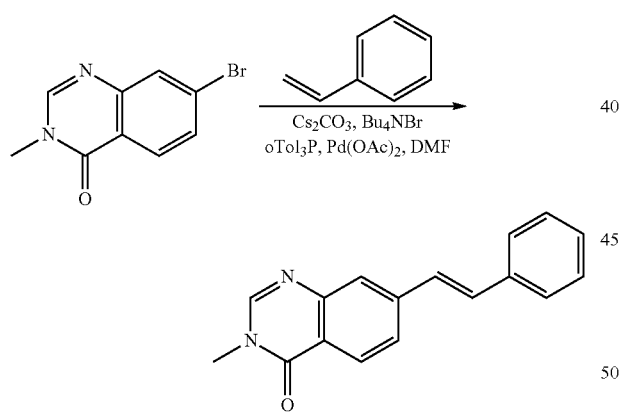

A solution of 7-bromo-3-methylquinazolin-4(3H)-one (100 mg, 0.42 mmol), styrene (109 mg, 1.05 mmol), Cs$_2$CO$_3$ (163.8 mg, 0.5 mmol), Bu$_4$NBr (135 mg, 0.42 mmol), tri(o-tolyl)phosphine (128 mg, 0.42 mmol), and Pd(OAc)$_2$ in DMF (5 mL) was stirred at 100° C. for 3 hours. After it was cooled to room temperature, the mixture was diluted with H$_2$O (30 mL) and extracted with ethyl acetate (2×30 mL). The combined organic layers were washed with brine and dried over Na$_2$SO$_4$. After filtration and concentration, the crude product was purified by column chromatography to give the desired product (37 mg). MS (ESI): 263 (MH$^+$); $^1$H NMR (300 MHz, DMSO-d$^6$) δ 8.37 (s, 1H), 8.15-8.12 (d, J=8.70 Hz, 1H), 7.85-7.82 (m, 2H), 7.69-7.67 (d, J=7.26 Hz, 2H), 7.57-7.30 (m, 5H), 3.49 (s, 3H).

Example 20.2. Synthesis of (E)-3-styryl-7,8,9,10-tetrahydroazepino[2,1-b]quinazolin-12(6H)-one

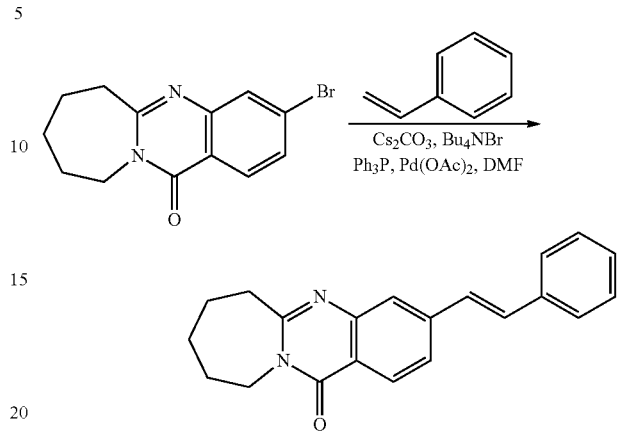

A mixture of 3-bromo-7,8,9,10-tetrahydroazepino[2,1-b]quinazolin-12(6H)-one (100 mg, 0.34 mmol), Cs$_2$CO$_3$ (132.6 mg, 0.85 mmol), Pd(OAc)$_2$ (30.6 mg, 0.14 mmol), PPh$_3$ (103 mg, 0.34 mmol), Bu$_4$NBr (109.5 mg, 0.34 mmol), and styrene (88.7 mg, 0.85 mmol) in DMF (6 mL) in a sealed tube was stirred at 120° C. for two hours. After it was cooled to room temperature, the reaction mixture was quenched with water (20 mL) and extracted with ethyl acetate (3×20 mL). The combined organic layers were dried over Na$_2$SO$_4$. After filtration and concentration, the residue was purified by silica gel chromatography to give the desired product. MS (ESI): 317 (MH$^+$); $^1$H NMR (300 MHz, CDCl$_3$) δ 8.08-8.05 (d, J=8.19 Hz, 1H), 7.78-7.74 (m, 2H), 7.68-7.66 (m, 2H), 7.54-7.30 (m, 5H), 4.34-4.31 (m, 2H), 3.05 (broad, 2H), 1.73-1.70 (m, 6H). mGluR5 PAM EC$_{50}$: +++++. Fold shift at 10 μM: ++.

Example 20.3. Synthesis of (E)-8-methyl-3-(2-(pyridin-2-yl)vinyl)-7,8,9,10-tetrahydroazepino[2,1-b]quinazolin-12(6H)-one

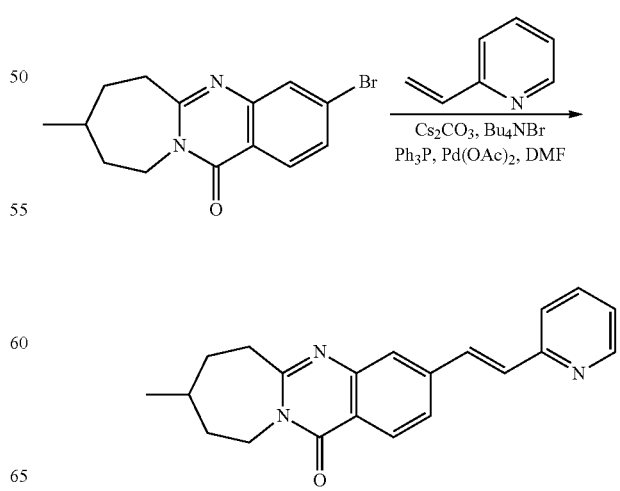

A solution of 3-bromo-8-methyl-7,8,9,10-tetrahydroazepino[2,1-b]quinazolin-12(6H)-one (100 mg, 0.42 mmol), styrene (100 mg, 0.33 mmol), Cs$_2$CO$_3$ (128 mg, 0.396 mmol), Bu$_4$NBr (106 mg, 0.33 mmol), PPh$_3$ (43.2 mg, 0.165 mmol) and Pd(OAc)$_2$ (7.4 mg, 0.033 mmol) in DMF (10 mL) was stirred at 140° C. in a sealed tube for 8 hours. After it was cooled to room temperature, the mixture was diluted with H$_2$O and extracted with EtOAc. The combined organic layers were washed with brine and dried over Na$_2$SO$_4$. Then the filtration was concentrated and purified by column chromatography to give the desired product. MS (ESI): 332 (MH$^+$); $^1$H NMR (300 MHz, CD$_3$OD) δ 8.84-8.83 (d, J=5.73 Hz, 1H), 8.68-8.62 (m, 1H), 8.53-8.51 (d, J=8.22 Hz, 1H), 8.43-8.41 (d, J=8.37 Hz, 1H), 8.20-8.10 (m, 2H), 8.06 (s, 1H), 8.03-7.98 (t, J=13.57 Hz, 1H), 7.74-7.69 (d, J=16.47 Hz, 1H), 5.24-5.17 (dd, J=14.92, 6.84 Hz, 1H), 3.95-3.86 (m, 1H), 3.51-3.37 (m, 2H), 2.24-2.01 (m, 3H), 1.64-1.52 (m, 1H), 1.45-1.33 (m, 1H), 1.07-1.05 (d, J=6.45 Hz, 3H). mGluR5 PAM EC$_{50}$: ++.

Example 20.4. Synthesis of (E)-2-methyl-6-styryl-2,3-dihydropyrrolo[2,1-b]quinazolin-9(1H)-one

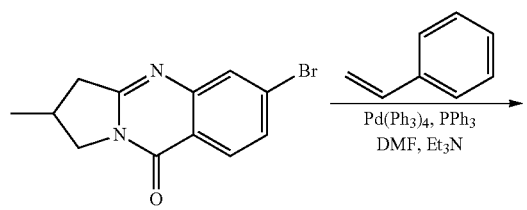

A solution of 6-bromo-2-methyl-2,3-dihydropyrrolo[2,1-b]quinazolin-9(1H)-one (100 mg, 0.36 mmol), styrene (75 mg, 0.72 mmol), Pd (PPh$_3$)$_4$ (45 mg, 0.036 mmol), PPh$_3$ (1 mg, 0.0036 mmol) and Et$_3$N (182 mg, 1.8 mmol) in DMF (10 mL) was stirred at 140° C. under N$_2$ for 8 hours. After cooled to room temperature, the mixture was diluted with H$_2$O and extracted with EtOAc. The combined organic layer was washed with brine and dried over Na$_2$SO$_4$. Then the filtrate was concentrated and purified by column chromatography to give the desired product (67 mg). MS (ESI): 303 (MH$^+$); $^1$H NMR (300 MHz, DMSO-d$^6$) δ 8.13-8.10 (d, J=8.3 Hz, 1H), 7.87-7.84 (d, J=8.4 Hz, 1H), 7.80 (s, 1H), 7.70-7.68 (d, J=7.5 Hz, 2H), 7.56-7.47 (m, 2H), 7.44-7.40 (m, 2H), 7.35-7.30 (m, 1H), 4.29-4.22 (dd, J=11.7, 7.8 Hz, 1H), 3.68-3.62 (dd, J=11.7, 6.8 Hz, 1H), 3.38-3.29 (dd, J=17.2, 8.1 Hz, 1H), 2.91-2.83 (dd, J=17.2, 7.5 Hz, 1H), 2.75-2.67 (m, 1H), 1.18-1.16 (d, J=6.7 Hz, 3H). mGluR5 PAM EC$_{50}$: +++.

Example 20.5. Synthesis of the HCl Salt of (E)-2-methyl-6-(2-(pyridin-2-yl)vinyl)-2,3-dihydropyrrolo[2,1-b]quinazolin-9(1H)-one

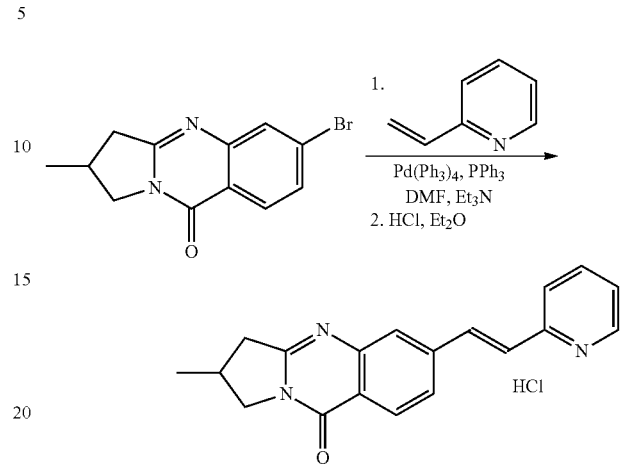

The title compound was prepared according to the experimental procedure as described in Example 20.4. The product was then converted to the corresponding HCl salt. MS (ESI): 304 (MH$^+$); $^1$H NMR (300 MHz, CD$_3$OD) δ 8.84-8.83 (d, J=5.4 Hz, 1H), 8.68-8.63 (t, J=8.1 Hz, 1H), 8.54-8.51 (d, J=8.1 Hz, 1H), 8.43-8.40 (d, J=8.3 Hz, 1H), 8.20-8.08 (m, 2H), 8.03-7.99 (m, 2H), 7.72-7.67 (d, J=16.6 Hz, 1H), 4.56-4.50 (q, 1H), 3.93-3.87 (q, 1H), 3.71-3.63 (dd, J=18.2, 8.5 Hz, 1H), 3.25-3.16 (dd, J=18.3, 7.8 Hz, 1H), 3.10-2.96 (m, 1H), 1.36-1.30 (d, J=6.2 Hz, 3H).

Example 20.6. Synthesis of (E)-3-(2-fluorostyryl)-7,7-dimethyl-8,9-dihydro-6H-pyrido[2,1-b]quinazolin-11(7H)-one

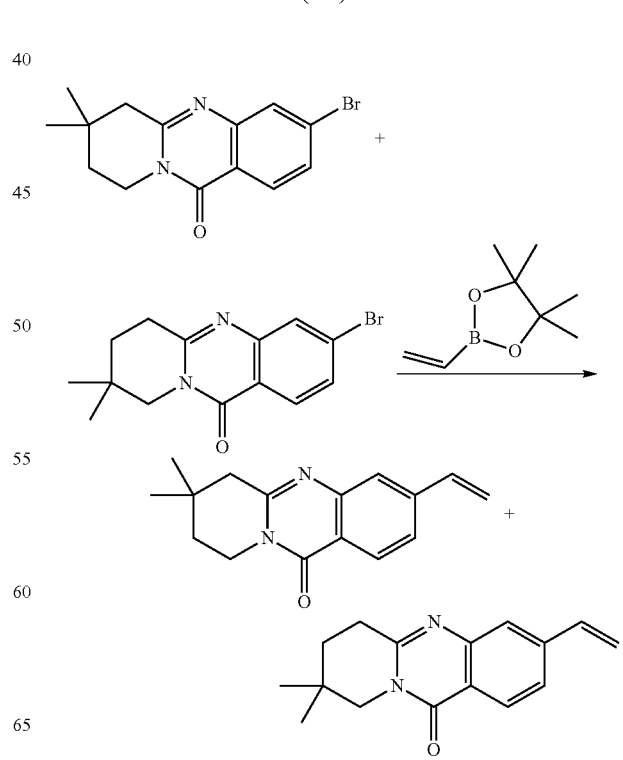

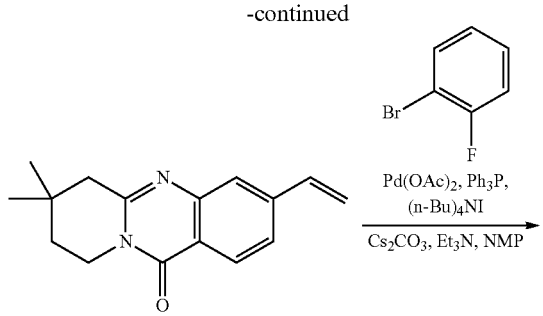

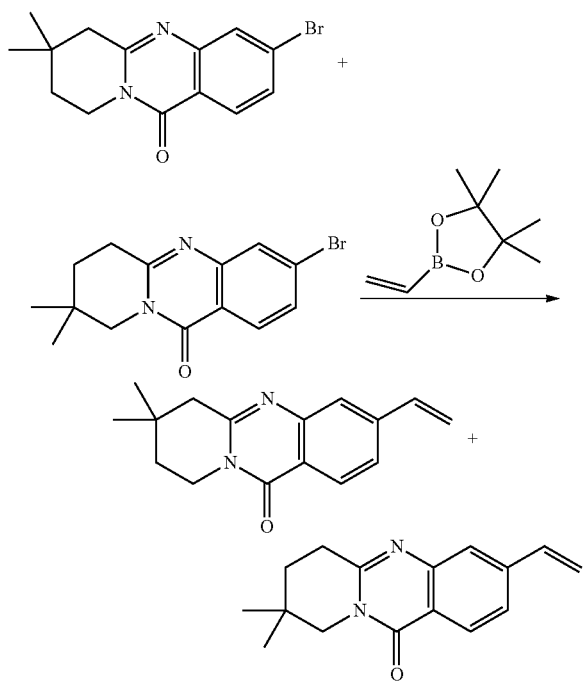

Example 20.6a. Synthesis of 7,7-dimethyl-3-vinyl-8,9-dihydro-6H-pyrido[2,1-b]quinazolin-11(7H)-one and 8,8-dimethyl-3-vinyl-8,9-dihydro-6H-pyrido[2,1-b]quinazolin-11(7H)-one A solution of 3-bromo-7,7-dimethyl-8,9-dihydro-6H-pyrido[2,1-b]quinazolin-11(7H)-one, 3-bromo-8,8-dimethyl-8,9-dihydro-6H-pyrido[2,1-b]quinazolin-11(7H)-one (2.0 g, 6.4 mmol, 1 equiv), 4,4,5,5-tetramethyl-2-vinyl-1,3,2-dioxaborolane (2.2 g, 12.8 mmol, 2 eq), $K_2CO_3$ (1.76 g, 12.8 mmol, 2 equiv), Pd(OAc)$_2$ (576 mg, 2.56 mmol, 0.4 equiv) and Ph$_3$P (1.34 g, 5.12 mmol, 0.8 equiv) in dioxane (200 mL) was stirred at 85° C. for 4 hours under N$_2$. After that, the reaction mixture was cooled to rt. The reaction was quenched with water (50 mL) and extracted with ethyl acetate (3×50 mL). The combined organic extract was dried over Na$_2$SO$_4$ and concentrated. The crude product was purified by silica gel chromatography to afford 650 mg of 7,7-dimethyl-3-vinyl-8,9-dihydro-6H-pyrido[2,1-b]quinazolin-11(7H)-one and 1.0 g of 8,8-dimethyl-3-vinyl-8,9-dihydro-6H-pyrido[2,1-b]quinazolin-11(7H)-one. MS (ESI): 255 (MH$^+$).

Example 20.6b. Synthesis of (E)-3-(2-fluorostyryl)-7,7-dimethyl-8,9-dihydro-6H-pyrido[2,1-b]quinazolin-11(7H)-one

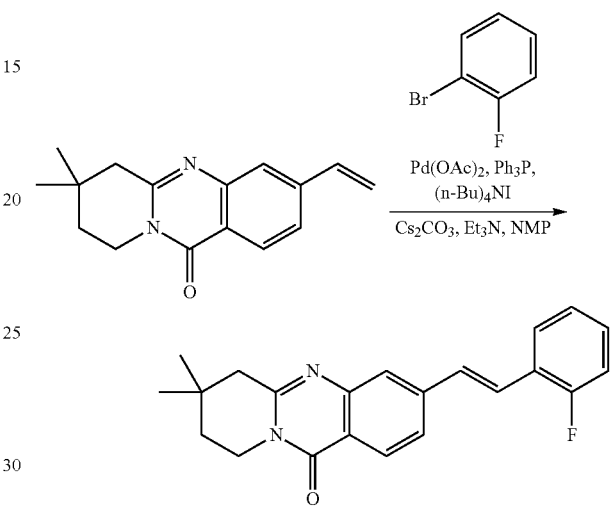

A solution of 7,7-dimethyl-3-vinyl-8,9-dihydro-6H-pyrido[2,1-b]quinazolin-11(7H)-one (116 mg, 0.4 mmol, 1 equiv), 1-bromo-2-fluorobenzene (140 mg, 0.8 mmol, 2 equiv), Cs$_2$CO$_3$ (260 mg, 0.8 mmol, 2 equiv), Pd(OAc)$_2$ (576 mg, 0.08 mmol, 0.2 equiv), Ph$_3$P (88 mg, 0.32 mmol, 0.8 equiv), Et$_3$N (80 mg, 0.8 mmol, 2 equiv) and (n-Bu)$_4$NI (256 mg, 0.8 mmol, 2 equiv) in NMP was stirred at 140° C. for 20 minutes in a microwave reactor. After that, the reaction mixture was cooled to rt. The reaction was quenched with water (20 mL) and extracted with ethyl acetate (3×20 mL). The organic combined organic layers were dried over Na$_2$SO$_4$ and concentrated. The crude was purified by silica gel chromatography to produce 53 mg desired product. MS (ESI): 349 (MH$^+$); $^1$H NMR (300 MHz, CD$_3$OD) δ 8.20-8.17 (d, J=8.12 Hz, 1H), 7.80-7.68 (m, 2H), 7.56 (s, 1H), 7.43-7.19 (m, 3H), 7.15-6.99 (m, 2H), 4.12-3.92 (t, J=13.20 Hz, 2H), 2.82 (s, 2H), 1.85-1.72 (t, J=12.84 Hz, 2H), 1.15 (s, 6H). mGluR5 PAM EC$_{50}$: +++.

Example 20.7. and Example 20.8. Synthesis of the HCl Salt of (E)-3-(2-fluorostyryl)-7,7-dimethyl-8,9-dihydro-6H-pyrido[2,1-b]quinazolin-11 (7H)-one and of HCl salt of (E)-8,8-dimethyl-3-(2-(pyridin-2-yl)vinyl)-8,9-dihydro-6H-pyrido[2,1-b]quinazolin-11 (7H)-one

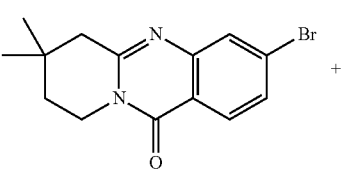

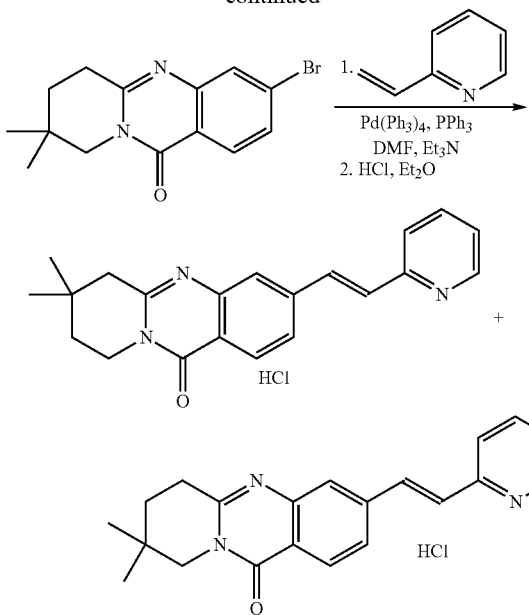

The title compounds were prepared according to the experimental procedure as described in Example 20.4. The products were then converted to the corresponding HCl salt.

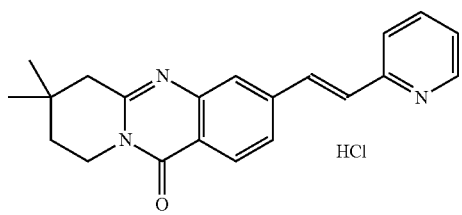 [SMILES: CC1(C)CCn2c(nc3cc(/C=C/c4ccccn4)ccc3c2=O)C1 ; Cl]

(E)-3-(2-fluorostyryl)-7,7-dimethyl-8,9-dihydro-6H-pyrido[2,1-b]quinazolin-11(7H)-one MS (ESI): 332 (MH+); $^1$H NMR (300 MHz, CD$_3$OD) δ 8.84-8.83 (d, J=5.0 Hz, 1H), 8.67-8.62 (t, J=8.1 Hz, 1H), 8.53-8.50 (d, J=9.2 Hz, 1H), 8.44-8.42 (d, J=8.4 Hz, 1H), 8.19-8.10 (m, 2H), 8.03-7.98 (m, 2H), 7.72-7.67 (d, J=16.4 Hz, 1H), 4.22-4.18 (t, J=6.4 Hz, 2H), 3.11 (s, 2H), 2.02-1.98 (t, J=6.4 Hz, 2H), 1.23 (s, 6H). mGluR5 PAM EC$_{50}$: ++++. Fold shift at 10 μM: ++.

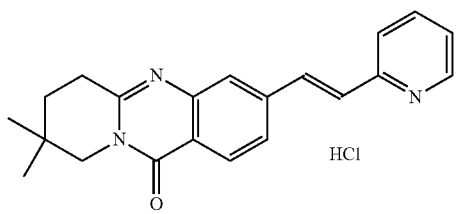 [SMILES: CC1(C)CCc2nc3cc(/C=C/c4ccccn4)ccc3c(=O)n2C1 ; Cl]

(E)-8,8-dimethyl-3-(2-(pyridin-2-yl)vinyl)-8,9-dihydro-6H-pyrido[2,1-b]quinazolin-11(7H)-one MS (ESI): 332 (MH+); $^1$H NMR (300 MHz, CD$_3$OD) δ 8.84-8.82 (d, J=5.7 Hz, 1H), 8.66-8.61 (t, J=7.9 Hz, 1H), 8.51-8.48 (d, J=8.3 Hz, 1H), 8.44-8.41 (d, J=8.4 Hz, 1H), 8.18-8.09 (m, 2H), 8.02-7.98 (m, 2H), 7.72-7.66 (d, J=16.4 Hz, 1H), 3.89 (s, 2H), 3.37-3.32 (t, J=6.7 Hz, 2H), 1.90-1.86 (t, J=6.7 Hz, 2H), 1.19 (s, 6H). Fold shift at 10 μM: +.

Example 20.9. Synthesis of the HCl Salt of (E)-6-(2-(7,7-dimethyl-11-oxo-7,8,9,11-tetrahydro-6H-pyrido[2,1-b]quinazolin-3-yl)vinyl)picolinonitrile

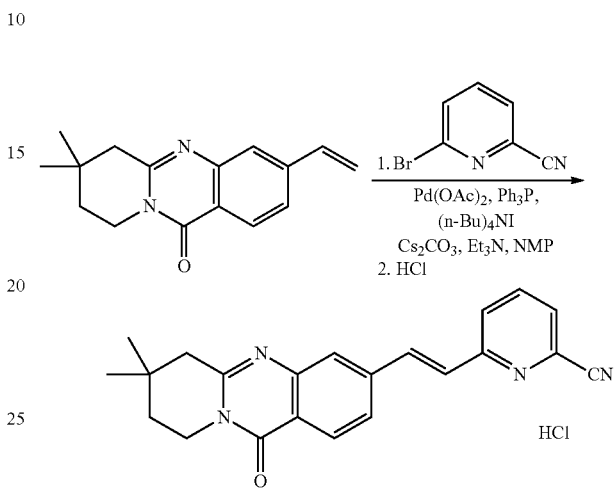

A solution of 7,7-dimethyl-3-vinyl-8,9-dihydro-6H-pyrido[2,1-b]quinazolin-11(7H)-one (50 mg, 0.2 mmol, 1 equiv), 1-bromo-2-fluorobenzene (70 mg, 0.4 mmol, 2 equiv), Cs$_2$CO$_3$ (130 mg, 0.4 mmol, 2 equiv), Pd(OAc)$_2$ (238 mg, 0.04 mmol, 0.2 equiv), Ph$_3$P (44 mg, 0.16 mmol, 0.8 equiv), Et$_3$N (40 mg, 0.4 mmol, 2 equiv), CuI (15 mg, 0.08 mmol, 0.4 equiv) and (n-Bu)$_4$NI (128 mg, 0.4 mmol, 2 equiv) in NMP was stirred at 100° C. over night under N$_2$. After that, the reaction mixture was cooled to rt. The reaction was quenched with water (20 mL) and extracted with ethyl acetate (3×20 mL). The combined organic layers were dried over Na$_2$SO$_4$ and concentrated under reduced pressure. The crude product was purified by silica gel chromatography to produce 20 mg of the desired product. MS (ESI): 357 (MH+). The product was then converted to the corresponding HCl salt. MS (ESI): 357 (MH+); $^1$H NMR (300 MHz, CD$_3$OD) δ 8.37-8.34 (d, J=8.40 Hz, 1H), 8.11-7.90 (m, 4H), 7.86 (s, 1H), 7.82-7.79 (d, J=16.11 Hz, 1H), 7.64-7.59 (d, J=7.41 Hz, 1H), 4.22-4.18 (t, J=6.38 Hz, 2H), 3.12 (s, 2H), 2.02-1.98 (t, J=6.42 Hz, 2H), 1.23 (s, 6H). mGluR5 PAM EC$_{50}$: ++.

Example 20.10. Synthesis of (E)-3-(2-(pyridin-2-yl)vinyl)-7,8,9,10-tetrahydroazepino[2,1-b]quinazolin-12(6H)-one

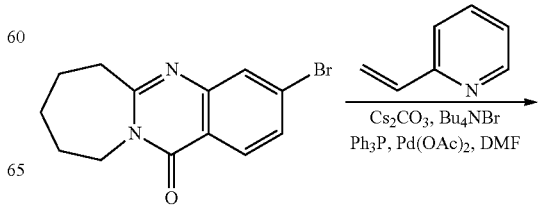

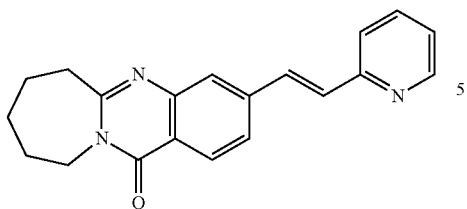

The title compound was prepared according to the experimental procedure as described in Example 20.3. MS (ESI): 318 (MH$^+$); $^1$H NMR (300 MHz, CD$_3$OD) δ 8.88-8.86 (d, J=5.6 Hz, 1H), 8.69-8.64 (t, J=7.8 Hz, 1H), 8.53-8.51 (d, J=8.2 Hz, 1H), 8.45-8.41 (d, J=8.4 Hz, 1H), 8.23-8.12 (m, 2H), 8.07-8.00 (m, 2H), 7.76-7.71 (d, J=16.5 Hz, 1H), 4.59-4.56 (m, 2H), 3.49-3.40 (m, 2H), 2.06-1.91 (m, 6H). mGluR5 PAM EC$_{50}$: +++. Fold shift at 10 μM: +.

Example 20.11. Synthesis of the HCl Salt of (E)-8-methyl-3-(2-(pyridin-2-yl)vinyl)-7,8,9,10-tetrahydroazepino[2,1-b]quinazolin-12(6H)-one

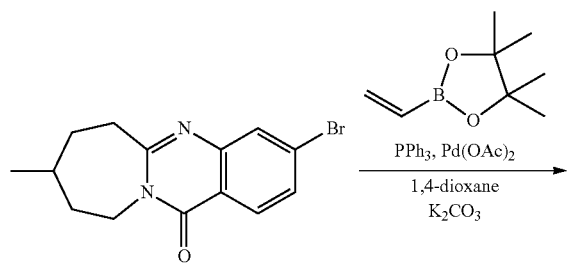

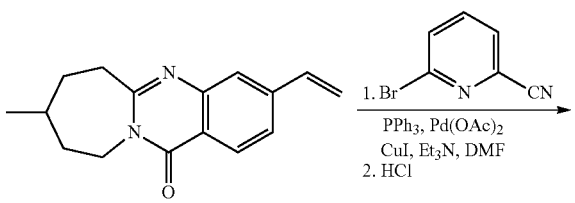

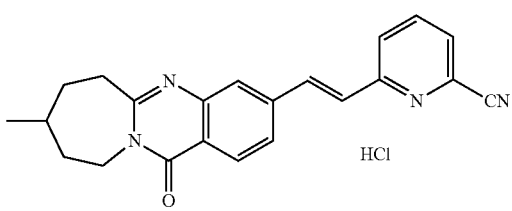

The title compound was prepared according to the experimental procedure as described in Example 20.6a and Example 20.6b. The product was then converted to the corresponding HCl salt. MS (ESI): 332 (MH$^+$).

Example 20.12. Synthesis of (E)-3-(2-fluorostyryl)-8,8-dimethyl-8,9-dihydro-6H-pyrido[2,1-b]quinazolin-11(7H)-one

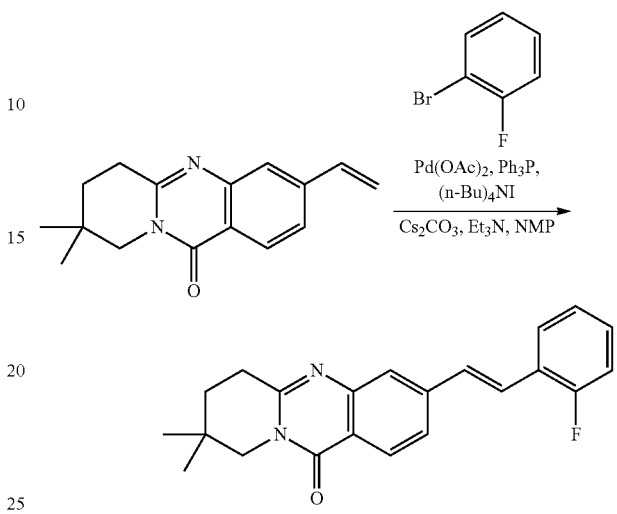

The title compound was prepared according to the experimental procedure as described in Example 20.6a. MS (ESI): 349 (MH$^+$); $^1$H NMR (300 MHz, CDCl$_3$) δ 8.27-8.25 (d, J=8.28 Hz, 1H), 7.73-7.63 (m, 3H), 7.52-7.46 (d, J=16.48 Hz, 1H), 7.30 (s, 1H), 7.24-7.08 (m, 3H), 3.84 (s, 2H), 3.07-3.02 (t, J=7.08 Hz, 2H), 1.80-1.75 (t, J=7.80 Hz, 2H), 1.13 (s, 6H). mGluR5 PAM EC$_{50}$: +++.

Example 20.13. Synthesis of the HCl Salt of (E)-6-(2-(8,8-dimethyl-11-oxo-7,8,9,11-tetrahydro-6H-pyrido[2,1-b]quinazolin-3-yl)vinyl)picolinonitrile

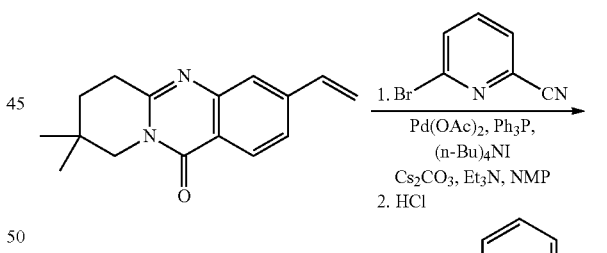

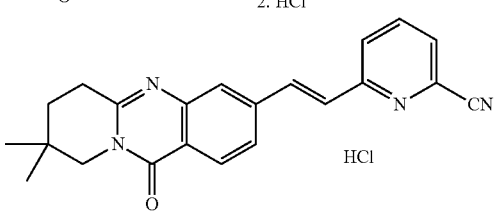

The title compound was prepared according to the experimental procedure as described in Example 20.6a. The product was then converted to the corresponding HCl salt. MS (ESI): 357 (MH$^+$); $^1$H NMR (300 MHz, CD$_3$OD) δ 8.37-8.35 (d, J=8.40 Hz, 1H), 8.11-8.08 (dd, J=8.70, 1.50 Hz, 1H), 8.04-8.01 (d, J=7.80 Hz, 1H), 7.95-7.90 (d, J=7.98 Hz, 2H), 7.84-7.80 (t, J=6.63 Hz, 2H), 7.65-7.59 (d, J=16.09 Hz, 1H), 3.88 (s, 2H), 3.38-3.35 (m, 2H), 1.91-1.86 (t, J=6.80 Hz, 2H), 1.20 (s, 6H). mGluR5 PAM EC$_{50}$: ++++.

Example 20.14. Synthesis of 6-(3-fluorostyryl)-2,3-dihydro-2-methylpyrrolo[2,1-b]quinazolin-9(1H)-one

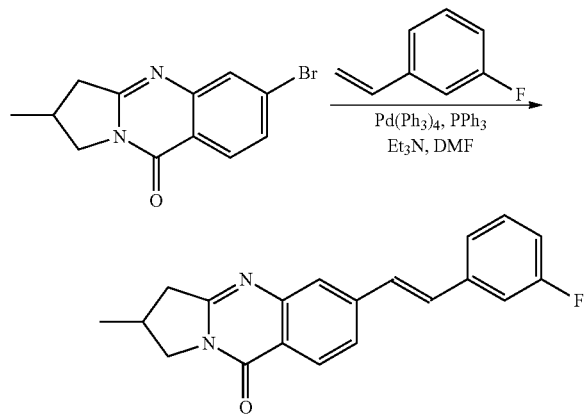

The title compound was prepared according to the experimental procedure as described in Example 20.4. MS (ESI): 321 (MH+); $^1$H NMR (300 MHz, CDCl$_3$) δ 8.29-8.26 (d, J=8.3 Hz, 1H), 7.72 (s, 1H), 7.65-7.62 (d, J=8.4 Hz, 1H), 7.38-7.34 (m, 2H), 7.31-7.28 (m, 1H), 7.24-7.22 (m, 2H), 7.05-6.99 (m, 1H), 4.40-4.34 (dd, J=12.3, 7.5 Hz, 1H), 3.79-3.73 (dd, J=12.3, 6.6 Hz, 1H), 3.35-3.73 (q, 1H), 2.88-2.74 (m, 2H), 1.30-1.28 (d, J=6.6 Hz, 3H). mGluR5 PAM EC$_{50}$: ++.

Example 21.1. Synthesis of 3-phenethyl-7,8,9,10-tetrahydroazepino[2,1-b]quinazolin-12(6H)-one

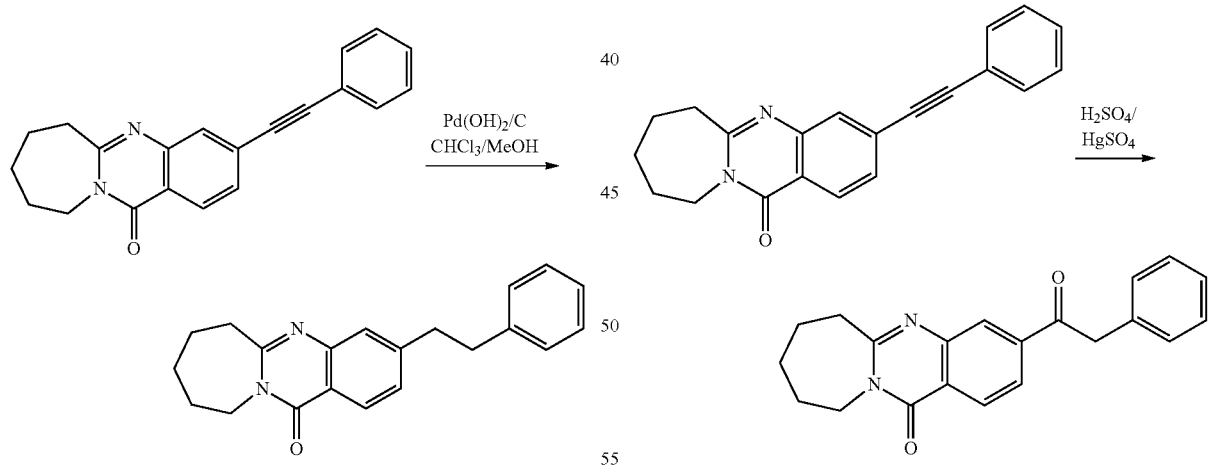

A solution of 3-(phenylethynyl)-7,8,9,10-tetrahydroazepino[2,1-b]-quinazolin-12(6H)-one (50 mg, 0.16 mmol) and Pd(OH)$_2$/C in CHCl$_3$ (10 mL) and MeOH (10 mL) was stirred under H$_2$ (1 atm) at room temperature for 8 h. The reaction mixture was filtered and the filter cake was washed with water. The combined filtrate was extracted with ethyl acetate (3×20 mL) and dried over Na$_2$SO$_4$. After filtration and concentration, the residue was purified by preparative HPLC to give 20 mg of the desired product. MS (ESI): 319 (MH+); $^1$H NMR (300 MHz, CDCl$_3$) δ 7.99-7.97 (d, J=8.10 Hz, 1H), 7.40 (s, 1H), 7.38-7.33 (d, J=8.22 Hz, 1H), 7.29-7.17 (m, 5H), 4.32-4.29 (t, J=4.98 Hz, 2H), 3.06-2.91 (m, 6H), 1.75 (broad, 4H), 1.68 (broad, 2H). mGluR5 PAM EC$_{50}$: ++.

Example 21.2. Synthesis of 8,8-dimethyl-3-(2-(pyridin-2-yl)ethyl)-8,9-dihydro-6H-pyrido[2,1-b]quinazolin-11(7H)-one

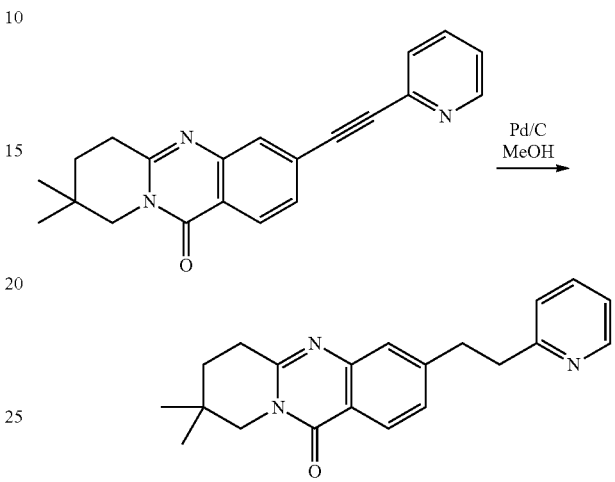

The title compound was prepared according to the experimental procedure as described in Example 21.1. MS (ESI): 334 (MH+).

Example 21.3. Synthesis of 3-(2-phenylacetyl)-7,8,9,10-tetrahydroazepino[2,1-b]quinazolin-12(6H)-one A mixture of 3-(phenylethynyl)-7,8,9,10-tetrahydroazepino[2,1-b]quinazolin-12(6H)-one (400 mg, 1.3 mmol), HgSO$_4$ (0.1 g, 0.3 mmol, 0.2 equiv) and H$_2$SO$_4$ (6 mL) was stirred at room temperature for 2 h. After quenching with water and basifying with saturated sodium carbonate, the solution was extracted with ethyl acetate (3×20 mL). The combined organic layers were concentrated. The residue was purified by silica gel chromatography to give the desired product (30 mg). MS (ESI): 333 (MH+); $^1$H NMR (300 MHz, CDCl$_3$) δ 8.22-8.19 (d, J=8.16 Hz, 1H), 8.03-7.99 (d, J=7.14 Hz, 2H), 7.59-7.43 (m, 4H), 7.37-7.34 (d, J=8.19 Hz, 1H), 4.40 (s, 2H), 4.39-4.36 (t, J=5.34 Hz, 2H), 3.06-3.03 (t, J=3.60 Hz, 2H), 1.85-1.81 (m, 6H). mGluR5 PAM EC$_{50}$: ++.

Example 21.4. Synthesis of 3-(1-hydroxy-2-phenylethyl)-7,8,9,10-tetrahydroazepino[2,1-b]quinazolin-12(6H)-one

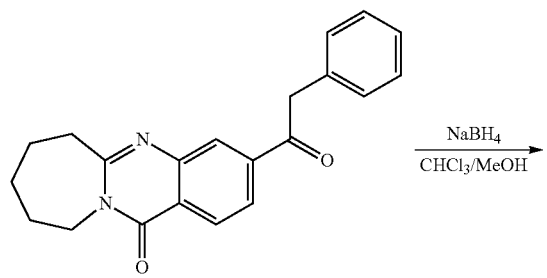

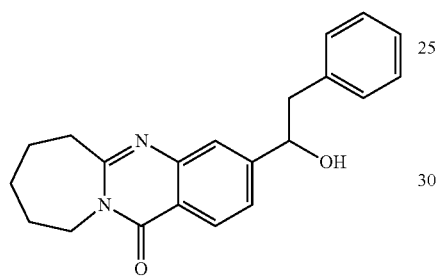

A mixture of 3-(2-phenylacetyl)-7,8,9,10-tetrahydroazepino[2,1-b]quinazolin-12(6H)-one, obtained from Example 21.3 (100 mg, 0.3 mmol) and excess NaBH$_4$ in CHCl$_3$/MeOH (10 mL, 1:1) was stirred at room temperature for 2 h. After quenching with water, the reaction solution was extracted with ethyl acetate (3×20 mL). The combined organic layers were concentrated. The residue was purified by silica gel chromatography to give the desired product. MS (ESI): 335 (MH$^+$); $^1$H NMR (300 MHz, CDCl$_3$) δ: 8.18-8.16 (d, J=8.19 Hz, 1H), 7.82 (s, 1H), 7.41-7.28 (m, 6H), 5.05-5.01 (t, J=7.65 Hz, 1H), 4.49-4.46 (t, J=5.01 Hz, 2H), 3.76 (brs, 1H), 3.36-3.33 (t, J=4.08 Hz, 2H), 3.23-3.20 (m, 2H), 2.00-1.86 (m, 6H).

Example 21.5. Synthesis of 2-methyl-6-(2-(pyridin-2-yl)ethyl)-2,3-dihydropyrrolo[2,1-b]quinazolin-9(1H)-one

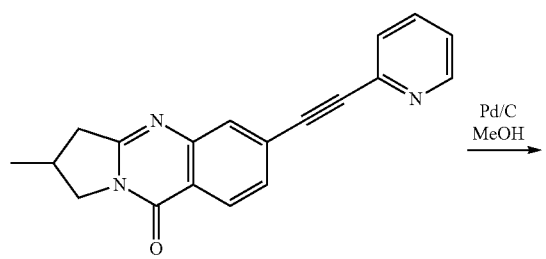

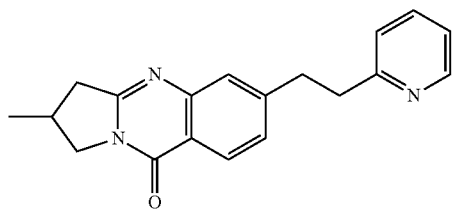

The title compound was prepared according to the experimental procedure as described in Example 21.1. MS (ESI): 306 (MH$^+$). MS (ESI): 306 (MH$^+$); $^1$H NMR (300 MHz, DMSO-d$^6$+D$_2$O) δ 8.76-8.74 (d, J=5.4 Hz, 1H), 8.50-8.45 (t, J=6.6 Hz, 1H), 8.06-7.96 (d, J=8.1 Hz, 1H), 7.96-7.94 (d, J=7.8 Hz, 1H), 7.91-7.86 (t, J=6.6 Hz, 1H), 7.47 (s, 1H), 7.43-7.41 (d, J=8.1 Hz, 1H), 4.25-4.18 (m, 1H), 3.65-3.59 (m, 1H), 3.40-3.35 (t, J=6.6 Hz, 2H), 3.30-3.20 (m, 3H), 2.84-2.76 (dd, J=16.8, 7.2 Hz, 1H), 2.70-2.63 (m, 1H), 1.14-1.11 (d, J=6.6 Hz, 3H).

Example 21.6. Synthesis of the HCl Salt of 7,7-dimethyl-3-(2-(pyridin-2-yl)ethyl)-8,9-dihydro-6H-pyrido[2,1-b]quinazolin-11(7H)-one

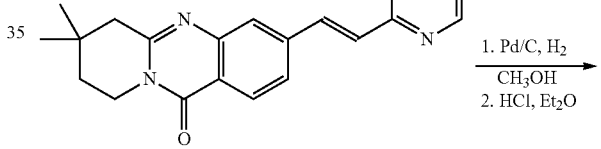

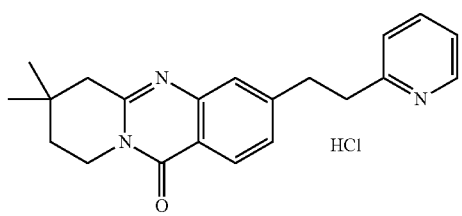

A solution of (E)-7,7-dimethyl-3-(2-(pyridin-2-yl)vinyl)-8,9-dihydro-6H-pyrido[2,1-b]quinazolin-11(7H)-one (150 mg, 0.45 mmol) and 10% Pd/C (20 mg) in CH$_3$OH (20 mL) was stirred under H$_2$ (1 atm) at room temperature for 2 h. The reaction mixture was filtered and concentrated to give 140 mg of the desired product. MS (ESI): 334 (MH$^+$). The product was then converted to the corresponding HCl salt. MS (ESI): 334 (MH$^+$); $^1$H NMR (300 MHz, CD$_3$OD) δ 8.80-8.78 (d, J=5.8 Hz, 1H), 8.61-8.55 (t, J=7.9 Hz, 1H), 8.31-8.28 (d, J=8.2 Hz, 1H), 8.08-8.05 (d, J=8.0 Hz, 1H), 7.98-7.96 (m, 1H), 7.70-7.67 (d, J=8.1 Hz, 2H), 4.20-4.15 (t, J=6.4 Hz, 2H), 3.56-3.51 (m, 2H), 3.43-3.33 (m, 2H), 3.11 (s, 2H), 2.01-1.96 (t, J=6.4 Hz, 2H), 1.21 (s, 6H). mGluR5 PAM EC$_{50}$: +. Fold shift at 10 µM: ++.

Example 21.7. Synthesis of 6-(3-fluorophenethyl)-2-methyl-2,3-dihydropyrrolo[2,1-b]quinazolin-9(1H)-one

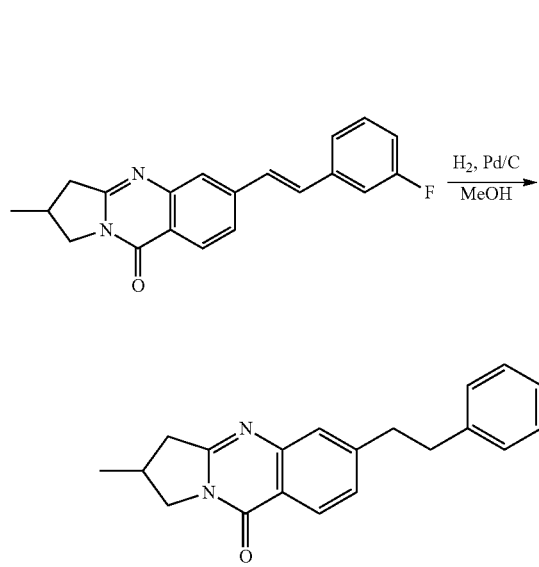

The title compound was prepared according to the experimental procedure as described in Example 21.6. MS (ESI): 323 (MH+); 1H NMR (300 MHz, MeOH) δ 8.13-8.10 (d, J=8.9 Hz, 1H), 7.39-7.36 (d, J=7.4 Hz, 2H), 7.28-7.21 (m, 1H), 7.00-6.86 (m, 3H), 4.38-4.31 (dd, J=12.0, 7.5 Hz, 1H), 3.75-3.69 (dd, J=12.0, 6.9 Hz, 1H), 3.34-3.20 (m, 1H), 3.14-3.00 (m, 4H), 2.88-2.72 (m, 2H), 1.27-1.25 (d, J=6.6 Hz, 3H). mGluR5 PAM EC$_{50}$: +.

Example 22.1. Synthesis of 3-methyl-4-oxo-N-(thiazol-2-yl)-3,4-dihydroquinazoline-7-carboxamide

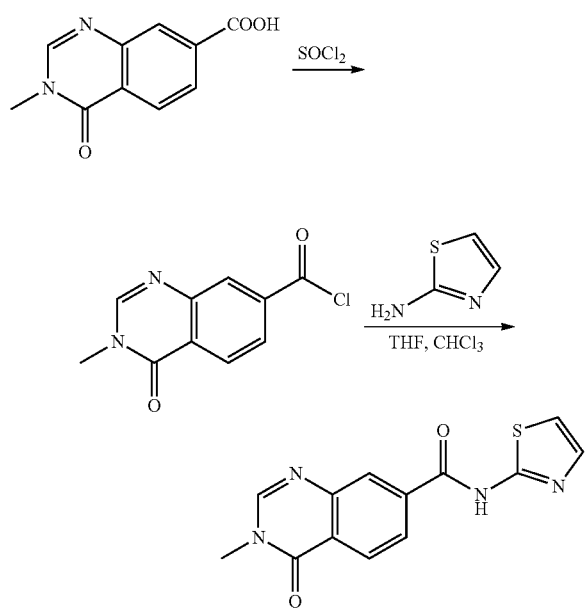

Example 22.1a. Synthesis of 3-methyl-4-oxo-3,4-dihydroquinazoline-7-carbonyl chloride

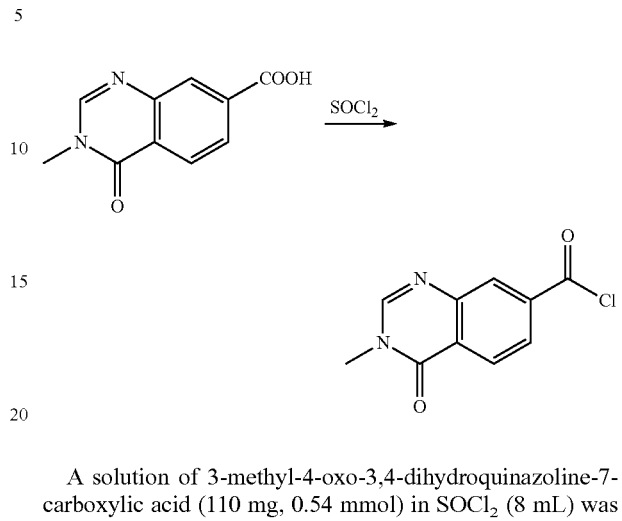

A solution of 3-methyl-4-oxo-3,4-dihydroquinazoline-7-carboxylic acid (110 mg, 0.54 mmol) in SOCl$_2$ (8 mL) was stirred at reflux for 5 h. The excess SOCl$_2$ was then removed under reduced pressure. The crude 3-methyl-4-oxo-3,4-dihydroquinazoline-7-carbonyl chloride was used without further purification for the next step.

Example 22.1b. Synthesis of 3-methyl-4-oxo-N-(thiazol-2-yl)-3,4-dihydroquinazoline-7-carboxamide

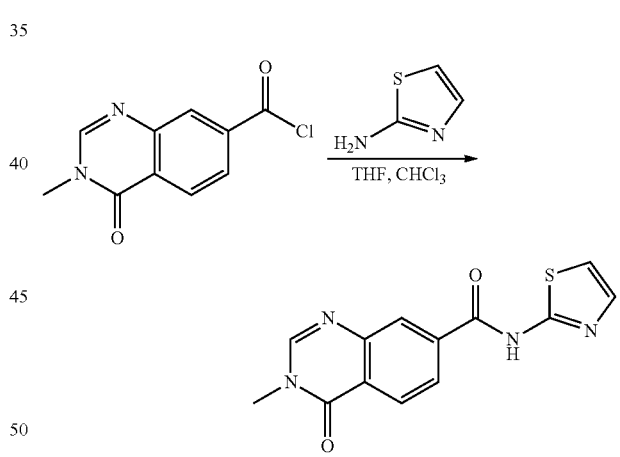

3-methyl-4-oxo-3,4-dihydroquinazoline-7-carbonyl chloride prepared as described in Example 22.1a was dissolved in anhydrous THF and added to a solution of thiazol-2-amine (81 mg, 0.81 mmol) in CHCl$_3$ (10 mL). The reaction was stirred at room temperature for 30 min and then poured into water. The mixture was extracted with ethyl acetate, and the organic layer was washed with brine, dried over anhydrous sodium sulfate. After filtration and concentration, the crude product was purified by silica gel chromatography purification to provide the desired product. MS (ESI): 287 (MH+); 1H NMR (300 MHz, DMSO-d$^6$) δ 12.95 (s, 1H), 8.46 (s, 1H), 8.38-8.37 (d, J=1.44 Hz, 1H), 8.29-8.26 (m, 1H), 8.15-8.12 (dd, J=8.36, 1.60 Hz, 1H), 7.60-7.59 (d, J=3.57 Hz, 1H), 7.33-7.32 (d, J=3.45 Hz, 1H), 3.53 (s, 3H).

Example 22.2. Synthesis of N-(4-ethylphenyl)-3-methyl-4-oxo-3,4-dihydroquinazoline-7-carboxamide

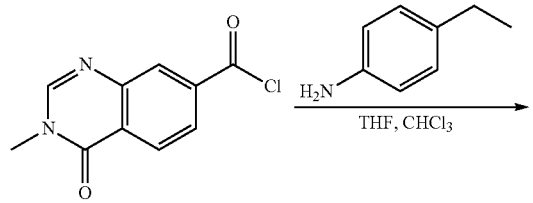

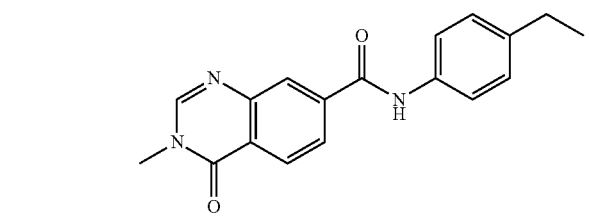

The title compound was prepared according to the experimental procedure as described in Example 22.1b. MS (ESI): 308 (MH$^+$); $^1$H NMR (300 MHz, CDCl$_3$) δ 10.47 (s, 1H), 8.47 (s, 1H), 8.28-8.25 (m, 2H), 8.04-8.01 (dd, J=8.30, 1.67 Hz, 1H), 7.72-7.70 (d, J=8.43 Hz, 2H), 7.22-7.19 (d, J=8.43 hz, 2H), 3.53 (s, 3H), 2.63-2.55 (q, J=7.58 Hz, 2H), 1.21-1.16 (t, J=7.58 Hz, 3H).

Example 22.3. Synthesis of N-(1H-benzo[d]imidazol-2-yl)-3-methyl-4-oxo-3,4-dihydroquinazoline-7-carboxamide

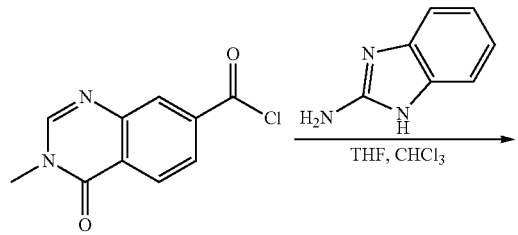

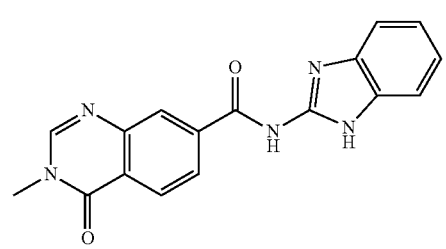

The title compound was prepared according to the experimental procedure as described in Example 22.1b. MS (ESI): 320 (MH$^+$).

Example 22.4. Synthesis of N-(4-fluorophenyl)-2-isobutyl-4-oxo-3,4-dihydroquinazoline-7-carboxamide

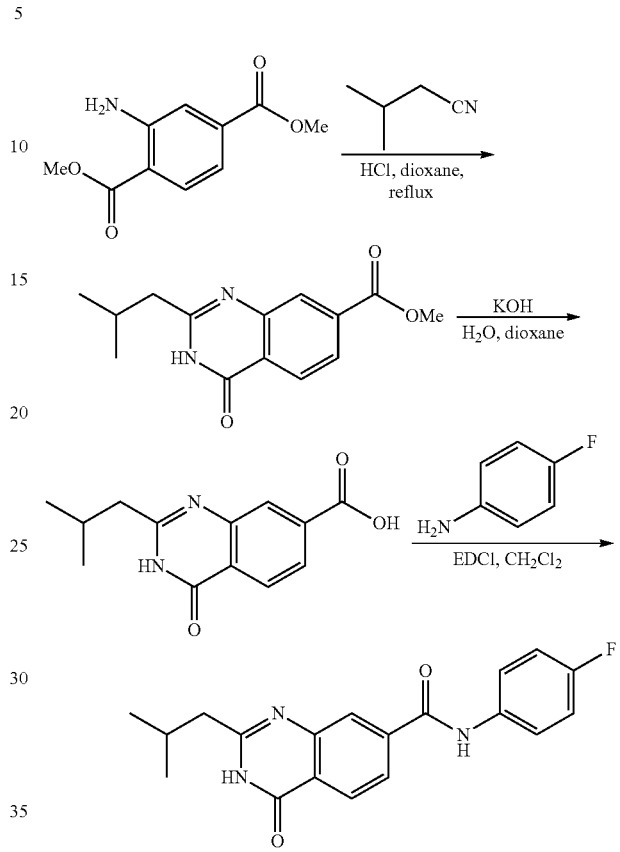

Example 22.4a. Synthesis of methyl 2-isobutyl-4-oxo-3,4-dihydroquinazoline-7-carboxylate

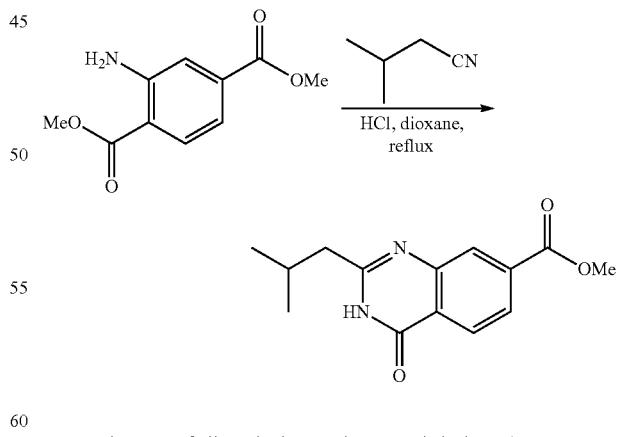

A mixture of dimethyl 2-aminoterephthalate (3.0 g, 14.4 mmol), 3-methylbutanenitrile (1.2 g, 14.4 mmol), and saturated HCl solution in dioxane (20 mL) in sealed tube was stirred at 100° C. overnight. After it was cooled to room temperature, the reaction mixture was poured into water (50 mL) and extracted with ethyl acetate (3×20 mL). The combined organic layer was concentrated and the residue was purified by silica gel chromatography give the desired product. MS (ESI): 260 (MH+).

Example 22.4b. Synthesis of 2-isobutyl-4-oxo-3,4-dihydroquinazoline-7-carboxylic Acid

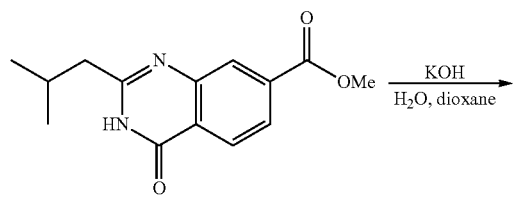

A mixture of methyl 2-isobutyl-4-oxo-3,4-dihydroquinazoline-7-carboxylate (55.8 mg, 0.21 mmol), KOH (0.3 g, 5.3 mmol) in water/dioxane (2 mL/5 mL) was stirred at room temperature for 1 h. The reaction mixture was poured into water (50 mL) and the solution was adjusted to pH to 4-5. The mixture was extracted with ethyl acetate (3×20 mL) and dried over $Na_2SO_4$. After filtration and concentration, the residue was purified by silica gel chromatography to give the desired product. MS (ESI): 246 (MH+).

Example 22.4c. Synthesis of N-(4-fluorophenyl)-2-isobutyl-4-oxo-3,4-dihydroquinazoline-7-carboxamide

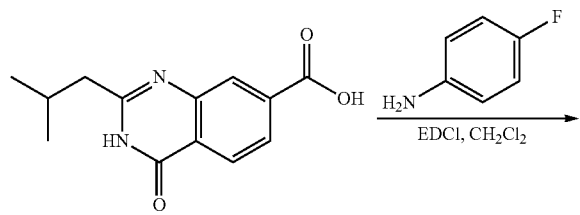

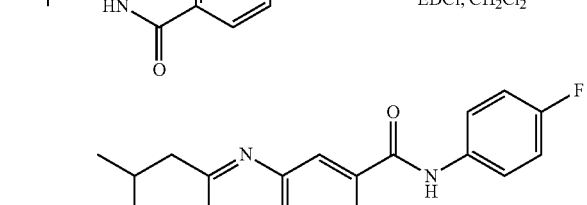

The title compound was prepared according to the experimental procedure as described in Example 28.1c. MS (ESI): 339 (MH+); $^1$H NMR (300 MHz, DMSO-d$^6$) δ 12.35 (brs, 1H), 10.55 (brs, 1H), 8.21-8.18 (m, 2H), 7.96-7.93 (dd, J=8.22, 1.74 Hz, 1H), 7.86-7.81 (dd, J=9.11, 5.15 Hz, 2H), 7.24-7.18 (t, J=8.88 Hz, 2H), 2.53 (broad, 2H), 2.27-2.20 (m, 1H), 0.97-0.95 (d, J=6.63 Hz, 6H).

Example 23.1. Synthesis of 8-methyl-N-(5-methyl-thiazol-2-yl)-12-oxo-6,7,8,9,10,12-hexahydroazepino[2,1-b]quinazoline-3-carboxamide

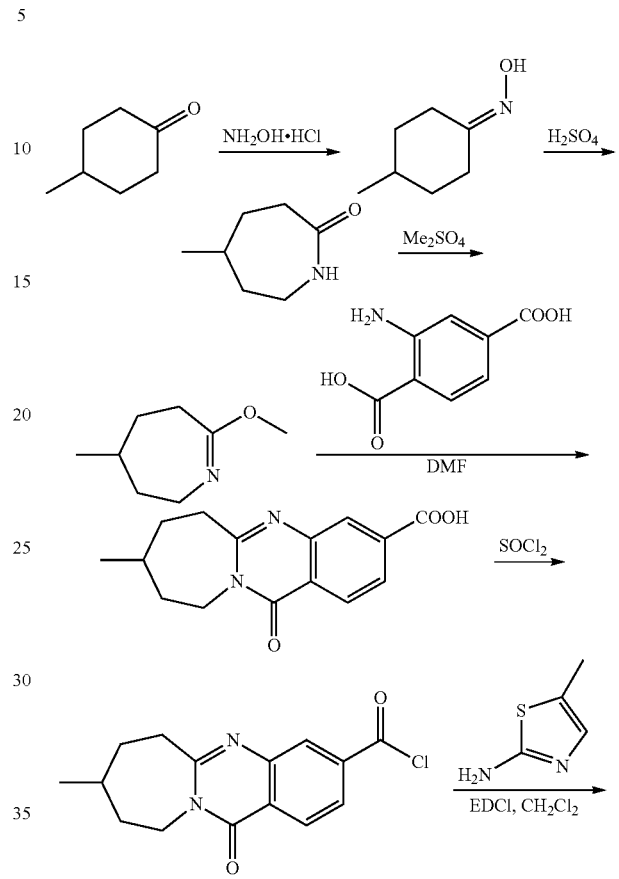

Example 23.1a. Synthesis of 4-methylcyclohexanone oxime

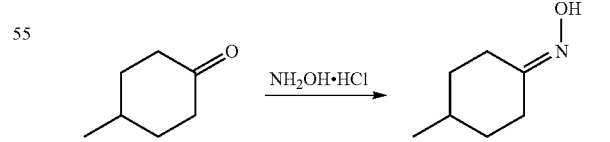

4-Methylcyclohexanone (2.0 g, 17.8 mmol) was mixed with hydroxylamine hydrochloride (1.86 g, 26.8 mmol) and sodium acetate (2.63 g, 32.0 mmol) in a mixture of EtOH (20 mL) and water (12 mL). The mixture was refluxed for 5 h. All solvent was removed under reduced pressure and the residue was partitioned between ethyl acetate and water. After separation, the organic layer was washed with brine,

Example 23.1b. Synthesis of 5-methylazepan-2-one

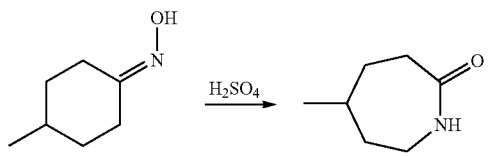

4-methylcyclohexanone oxime in 5 mL 80% H₂SO₄ was added dropwise to H₂SO₄ (80%, 5 mL) while stirring and the reaction temperature was maintained at 120° C. with an external oil bath. An exotherm was observed. After 5 min, the reaction was removed from the oil bath and allowed to cool to room temperature. The reaction mixture was diluted with water (30 mL) and adjusted to pH 6 with concentrated NH₄OH. This solution was further diluted with water (30 mL) and extracted with DCM (2×25 mL). The combined organic layer was washed with brine, dried over anhydrous sodium sulfate. After filtration and concentration, the crude product (1.6 g) was used for the next step without further purification.

Example 23.1c. Synthesis of (E)-7-methoxy-4-methyl-3,4,5,6-tetrahydro-2H-azepine

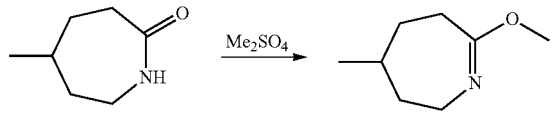

A mixture of 5-methylazepan-2-one (1.6 g) and dimethyl sulfate (2 g, 15.9 mmol) was stirred at 120° C. for 4 h. After it was cooled to room temperature, the reaction mixture was diluted with 10 mL ether and adjusted to pH 6 with aqueous KOH. The mixture was extracted with ether (2×50 mL). The organic layer was washed with brine and dried over anhydrous sodium sulfate. After filtration and concentration, the crude (E)-7-methoxy-4-methyl-3,4,5,6-tetrahydro-2H-azepine (1.2 g) was used for the next step without further purification.

Example 23.1d. Synthesis of 8-methyl-12-oxo-6,7,8,9,10,12-hexahydroazepino[2,1-b]quinazoline-3-carboxylic Acid

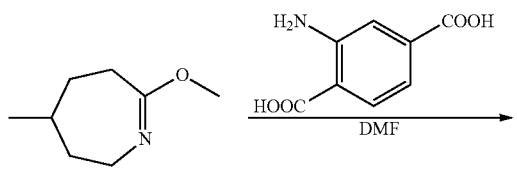

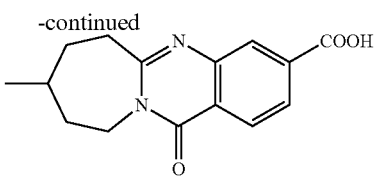

A solution of (E)-7-methoxy-4-methyl-3,4,5,6-tetrahydro-2H-azepine (1.1 g) and 2-aminoterephthalic acid (1.4 g, 7.7 mmol) in DMF (30 mL) was stirred at 100° C. for 4 h. After it was cooled to room temperature, the reaction was diluted with water (80 mL) and extracted with ethyl acetate (2×60 mL). The combined organic layers were washed with brine and dried over anhydrous sodium sulfate. After filtration and concentration, the crude product was purified by silica gel chromatography to give 47 mg of desired product.

Example 23.1e. Synthesis of 8-methyl-N-(5-methylthiazol-2-yl)-12-oxo-6,7,8,9,10,12-hexahydroazepino[2,1-b]quinazoline-3-carboxamide

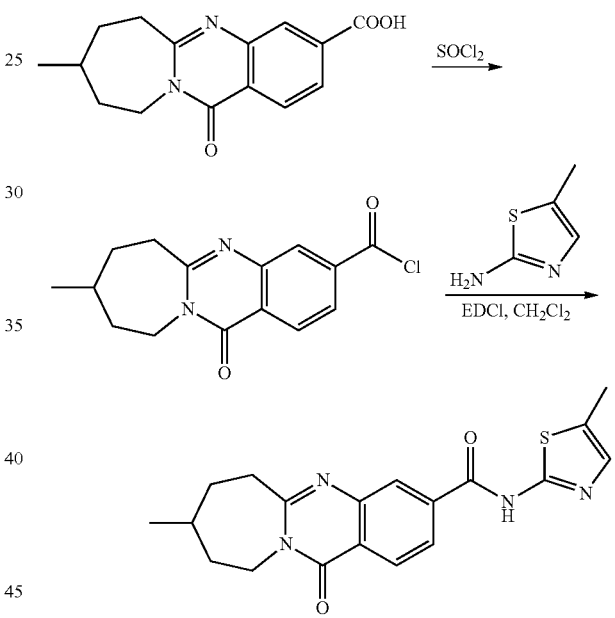

The title compound was prepared according to the experimental procedures as described in Example 22.1. MS (ESI): 369 (MH⁺); ¹H NMR (300 MHz, CDCl₃) δ 11.44 (broad, 1H), 8.38-8.36 (d, J=8.28 Hz, 1H), 8.18-8.17 (d, J=1.38 Hz, 1H), 7.99-7.95 (dd, J=8.31, 1.53 Hz, 1H), 6.91 (s, 1H), 5.22-5.15 (dd, J=14.7, 6.9 Hz, 1H), 3.67-3.59 (m, 1H), 3.17-3.06 (m, 2H), 2.39 (s, 3H), 2.25-2.10 (m, 3H), 2.04-1.89 (m, 2H), 1.03-1.01 (d, J=6.60 Hz, 3H). mGluR5 PAM EC₅₀: ++. Fold shift at 10 μM: ++.

Example 23.2. Synthesis of N-(5-methylthiazol-2-yl)-11-oxo-2,4,5,11-tetrahyrdo-1H-[1,4]oxazepino[5,4-b]quinazoline-8-carboxamide

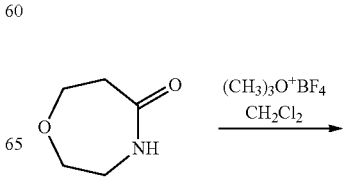

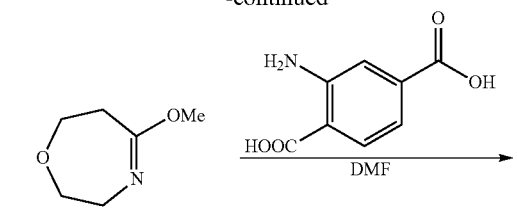

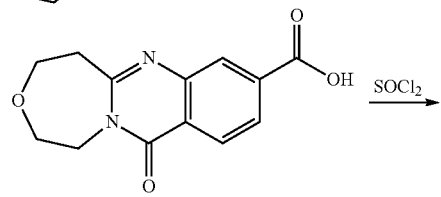

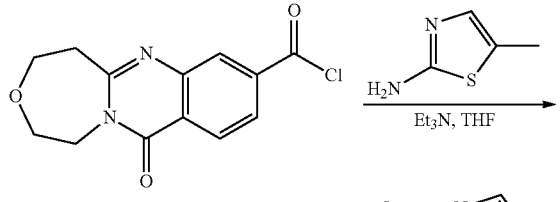

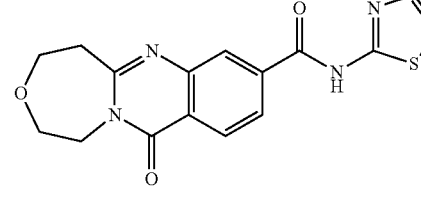

Example 23.2a. Synthesis of 5-methoxy-2,3,6,7-tetrahydro-1,4-oxazepine

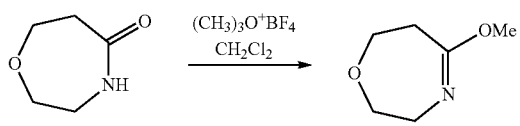 [SMILES: O=C1CCOCCN1 ; "(CH3)3O+BF4CH2Cl2" ; COC1=NCCOCC1]

A solution of 1,4-oxazepan-5-one (1 g, 8.7 mmol) and $(CH_3)_3O^+BF_4^-$ (1.9 g, 12.8 mmol) in DCM (30 mL) was stirred at room temperature for 20 h. The reaction mixture was then poured into water (60 mL) and extracted with DCM (2×50 mL). The combined organic layers were washed with brine, dried over anhydrous sodium sulfate. After filtration and concentration, the crude product was used for the next step without further purification.

Example 23.2b. Synthesis of (11-oxo-2,4,5,11-tetrahydro-1H-[1,4]oxazepino[5,4-b]quinazoline-8-carboxylic Acid

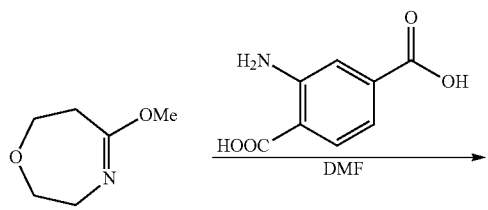

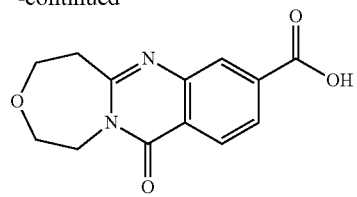

The title compound was prepared according to the experimental procedure as described in Example 23.1d.

Example 23.2c. Synthesis of N-(5-methylthiazol-2-yl)-11-oxo-2,4,5,11-tetrahyrdo-1H-[1,4]oxazepino[5,4-b]quinazoline-8-carboxamide

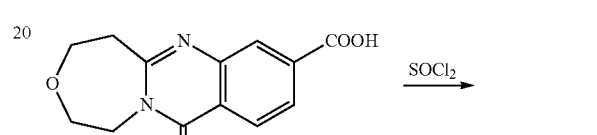

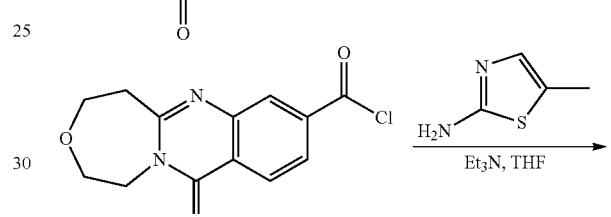

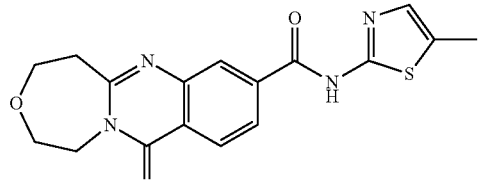

The title compound was prepared according to the experimental procedures as described in Example 22.1. MS (ESI): 357 (MH⁺); ¹H NMR (300 MHz, DMSO-d⁶+D₂O) δ 8.25-8.24 (d, J=1.4 Hz, 1H), 8.23-8.21 (d, J=8.3 Hz, 1H), 8.09-8.06 (dd, J=8.3, 1.7 Hz, 1H), 7.25-7.24 (d, J=1.32 Hz, 1H), 4.51-4.49 (m, 2H), 3.89-3.87 (t, J=4.8 Hz, 2H), 3.83-3.80 (t, J=4.5 Hz, 2H), 3.29-3.26 (t, J=4.8 Hz, 2H), 2.38-2.37 (d, J=1.20 Hz, 3H). mGluR5 PAM EC₅₀: ++.

Example 23.3. Synthesis of a Mixture of N-(4-fluorophenyl)-9-methyl-12-oxo-6,7,8,9,10,12-hexahydroazepino[2,1-b]quinazoline-3-carboxamide and N-(4-fluorophenyl)-7-methyl-12-oxo-6,7,8,9,10,12-hexahydroazepino[2,1-b]quinazoline-3-carboxamide

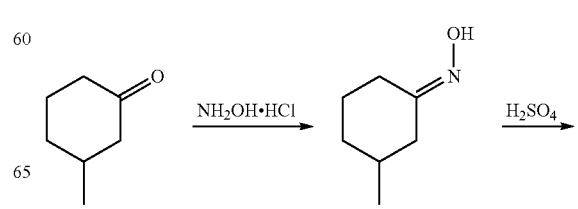

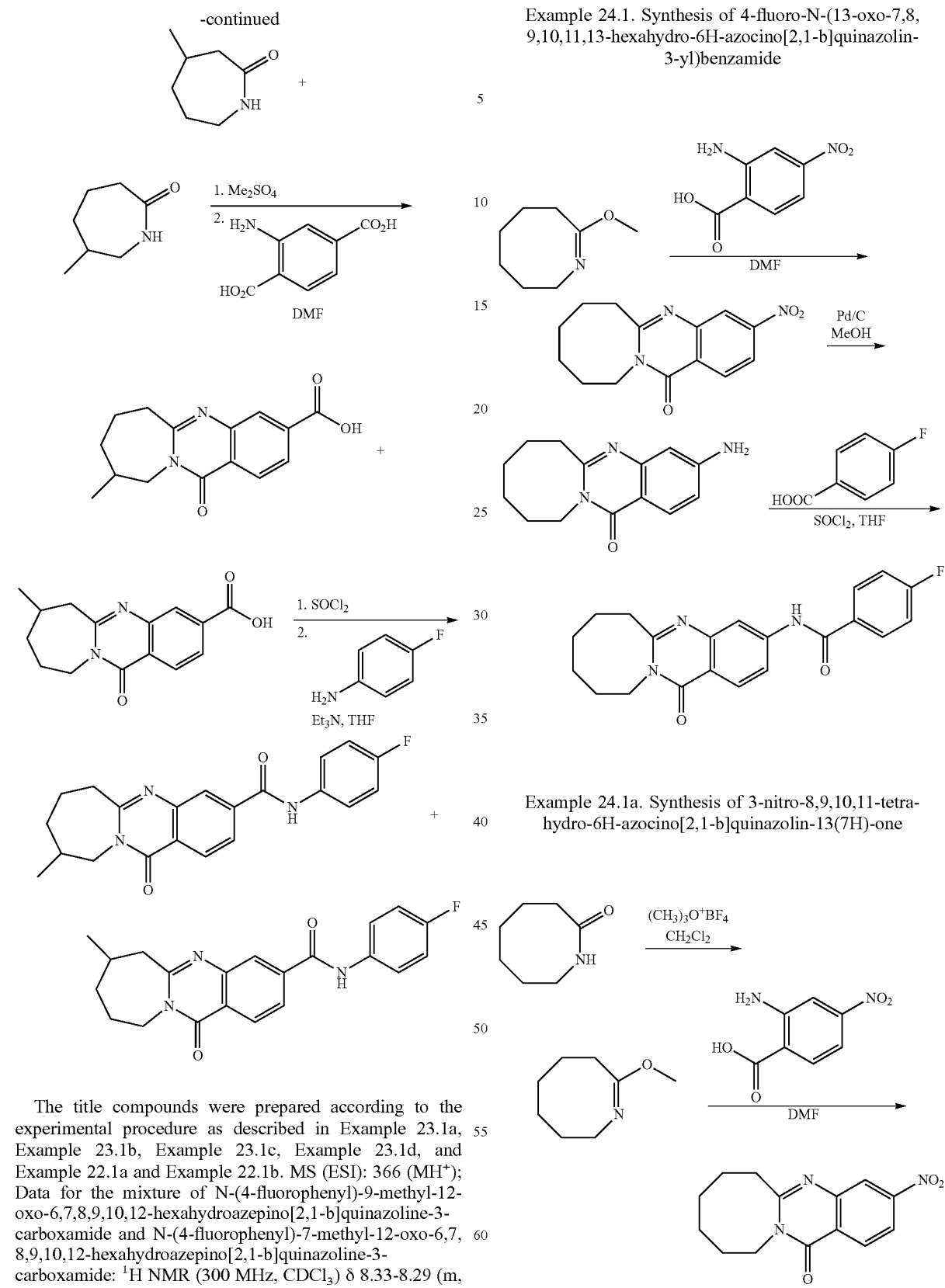

Example 24.1. Synthesis of 4-fluoro-N-(13-oxo-7,8,9,10,11,13-hexahydro-6H-azocino[2,1-b]quinazolin-3-yl)benzamide Example 24.1a. Synthesis of 3-nitro-8,9,10,11-tetrahydro-6H-azocino[2,1-b]quinazolin-13(7H)-one The title compounds were prepared according to the experimental procedure as described in Example 23.1a, Example 23.1b, Example 23.1c, Example 23.1d, and Example 22.1a and Example 22.1b. MS (ESI): 366 (MH+); Data for the mixture of N-(4-fluorophenyl)-9-methyl-12-oxo-6,7,8,9,10,12-hexahydroazepino[2,1-b]quinazoline-3-carboxamide and N-(4-fluorophenyl)-7-methyl-12-oxo-6,7,8,9,10,12-hexahydroazepino[2,1-b]quinazoline-3-carboxamide: $^1$H NMR (300 MHz, CDCl$_3$) δ 8.33-8.29 (m, 1H), 8.11 (s, 1H), 8.02-8.00 (m, 1H), 7.92-7.89 (m, 1H), 7.88-7.63 (m, 2H), 7.13-7.07 (m, 2H), 5.10-4.69 (m, 1H), 3.83-3.78 (m, 1H), 3.09-2.98 (m, 2H), 2.03-1.97 (m, 3H), 1.68-1.53 (m, 2H), 1.14-1.02 (m, 3H). mGluR5 PAM EC$_{50}$: +++. Fold shift at 10 μM: ++.

The title compound was prepared according to the experimental procedure as described in Example 23.2a and Example 23.2b. MS (ESI): 274 (MH+).

Example 24.1b. Synthesis of 13-oxo-7,8,9,10,11,13-hexahydro-6H-azocino[2,1-b]quinazoline-3-carboxamide

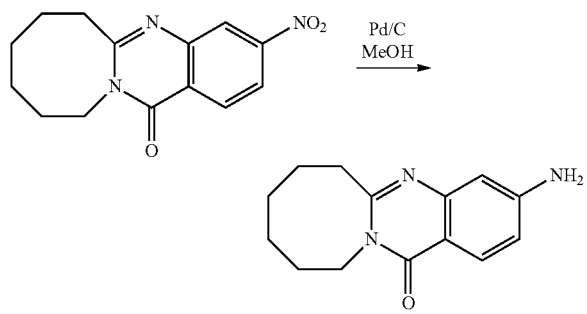

3-nitro-8,9,10,11-tetrahydro-6H-azocino[2,1-b]quinazolin-13(7H)-one (70 mg) was dissolved in MeOH (5 mL). To the solution was added a catalytic amount of Pd/C. The reaction mixture was vacuumed and then back filled with hydrogen gas three times. The solution was stirred under $H_2$ (1 atm) for 1 h. The reaction mixture was filtered and washed with methanol. The filtration was concentrated to give the desired product. MS (ESI): 244 (MH+).

Example 24.1c. Synthesis of 4-fluoro-N-(13-oxo-7,8,9,10,11,13-hexahydro-6H-azocino[2,1-b]quinazolin-3-yl)benzamide

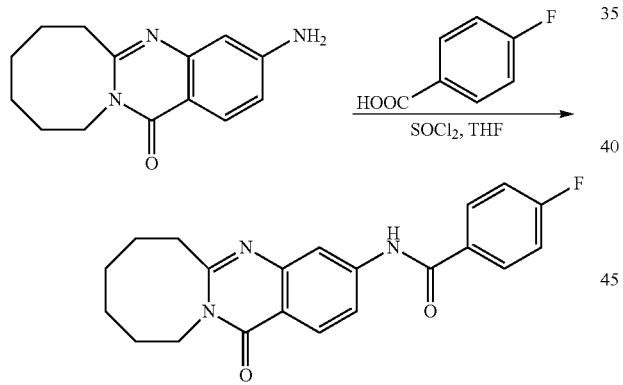

A solution of 4-fluorobenzoic acid (100 mg, 0.71 mmol) in $SOCl_2$ (2 mL) was stirred at reflux for 1 h. Excess $SOCl_2$ was removed and the residue was dissolved in THF (10 mL). The solution was added to a mixture of $Et_3N$ (1 mL) and 3-amino-8,9,10,11-tetrahydro-6H-azocino[2,1-b]quinazolin-13(7H)-one (22 mg, 0.09 mmol). After stirring for 1 h, the mixture was diluted with $H_2O$ (30 mL) and extracted with ethyl acetate (2×30 mL). The combined organic layers were washed with brine and dried over $Na_2SO_4$. After filtration and concentration, the crude product was purified by column chromatography to give the desired product (2 mg). MS (ESI): 366 (MH+); $^1H$ NMR (300 MHz, $CDCl_3$) δ 8.28 (d, J=8.70 Hz, 1H), 7.96-7.91 (m, 4H), 7.75-7.71 (dd, J=8.72 Hz, 2.12 Hz, 1H), 7.24-7.19 (t, J=8.60 Hz, 2H), 4.34 (broad, 2H), 3.06-3.02 (m, 2H), 1.99-1.87 (m, 4H), 1.68-1.66 (m, 2H), 1.47-1.46 (d, J=4.32 Hz, 2H). mGluR5 PAM $EC_{50}$: +.

Example 25.1. Synthesis of (E)-6-ethylidene-N-(5-methylthiazol-2-yl)-13-oxo-7,8,9,10,11,13-hexahydro-6H-azocino[2,1-b]quinazoline-3-carboxamide

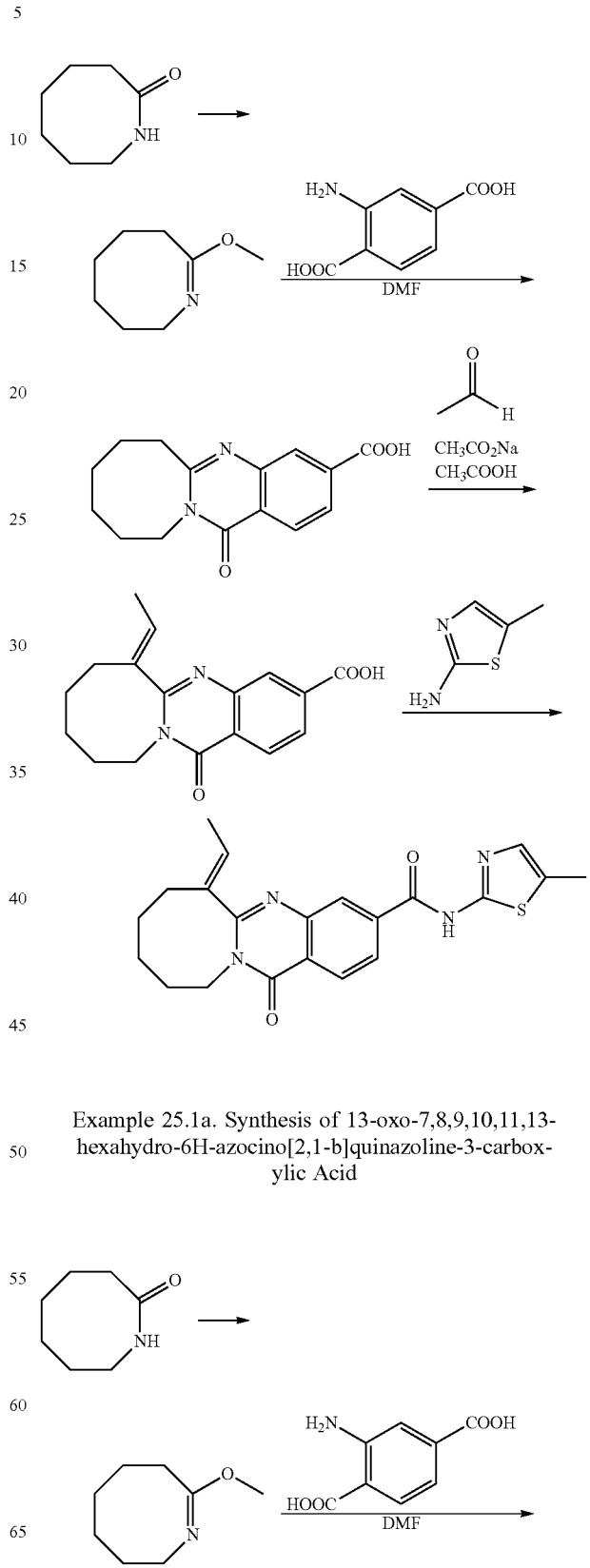

Example 25.1a. Synthesis of 13-oxo-7,8,9,10,11,13-hexahydro-6H-azocino[2,1-b]quinazoline-3-carboxylic Acid

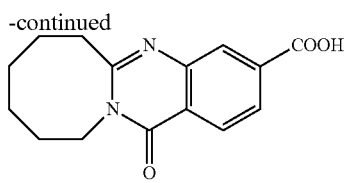

The title compound was synthesized from 2-aminoterephthalic acid according to the experimental procedure as described in Example 23.1c and Example 23.1d. MS (ESI): 273 (MH+).

Example 25.1b. Synthesis of (E)-6-ethylidene-13-oxo-7,8,9,10,11,13-hexahydro-6H-azocino[2,1-b]quinazoline-3-carboxylic Acid

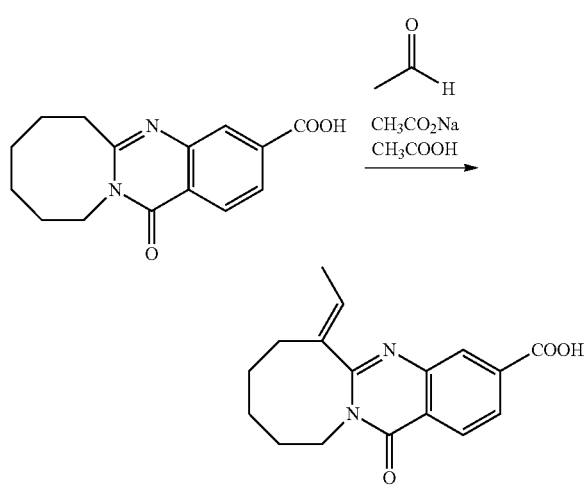

A solution of 13-oxo-7,8,9,10,11,13-hexahydro-6H-azocino[2,1-b]quinazoline-3-carboxylic acid (100 mg, 0.37 mmol), acetaldehyde (5 mL) and CH₃COONa (1 g) in acetic acid (10 mL) was stirred at 110° C. for 24 hours. After it was cooled to room temperature, the mixture was adjusted to pH around 8 with Na₂CO₃ and extracted with a mixture of dichloromethane/methanol (10/1) (3×30 mL). The combined organic layers were washed with brine and dried over Na₂SO₄. After filtration and concentration, the crude product obtained was used for the next step without further purification.

Example 25.1c. (E)-6-ethylidene-N-(5-methylthiazol-2-yl)-13-oxo-7,8,9,10,11,13-hexahydro-6H-azocino[2,1-b]quinazoline-3-carboxamide

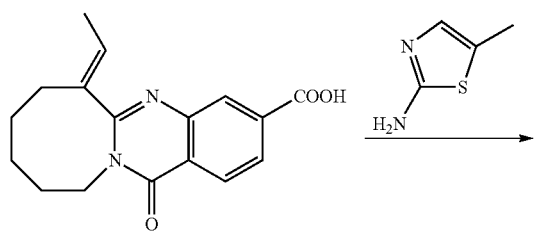

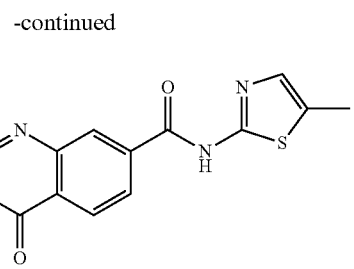

The title compound was prepared according to the experimental procedure as described in Example 22.1b. MS (ESI): 395 (MH+); ¹H NMR (300 MHz, CDCl₃) δ 8.44-8.41 (d, J=8.40 Hz, 1H), 8.30-8.27 (d, J=1.71 Hz, 1H), 8.03-7.99 (d, J=1.95 Hz, 1H), 6.95 (s, 1H), 5.82-5.80 (q, 1H), 4.33-4.30 (t, J=5.7 Hz, 2H), 2.62-2.60 (m, 2H), 2.40 (s, 3H), 1.90-1.87 (d, J=6.8 Hz, 4H), 1.71-1.61 (m, 3H), 1.56-1.53 (m, 2H). mGluR5 PAM EC₅₀: +++++.

Example 25.2. Synthesis of 6-methylene-N-(5-methylthiazol-2-yl)-13-oxo-7,8,9,10,11,13-hexahydro-6H-azocino[2,1-b]quinazoline-3-carboxamide

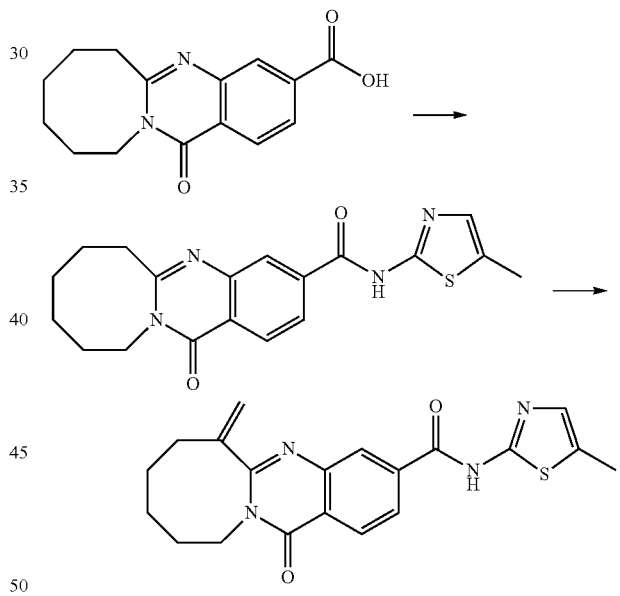

Example 25.2a. Synthesis of N-(5-methylthiazol-2-yl)-13-oxo-7,8,9,10,11,13-hexahydro-6H-azocino[2,1-b]quinazoline-3-carboxamide

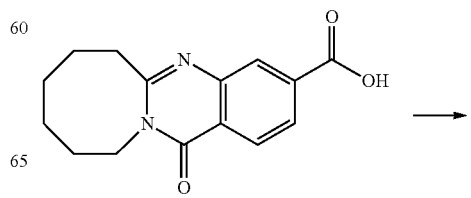

-continued

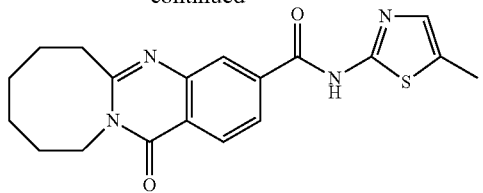

The title compound was prepared according to the experimental procedure as described in Example 22.1a and Example 22.1b. MS (ESI): 369 (MH$^+$).

Example 25.2b. Synthesis of 6-methylene-N-(5-methylthiazol-2-yl)-13-oxo-7,8,9,10,11,13-hexahydro-6H-azocino[2,1-b]quinazoline-3-carboxamide

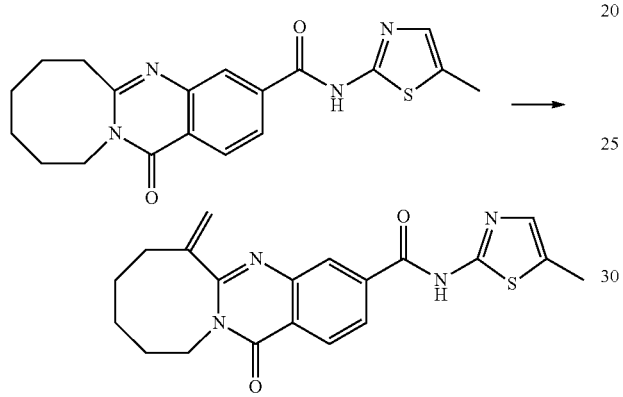

Paraformaldehyde (10 mg), N-(5-methylthiazol-2-yl)-13-oxo-7,8,9,10,11,13-hexahydro-6H-azocino[2,1-b]quinazoline-3-carboxamide (60 mg, 0.16 mmol) and NaOAc (3 mg, 0.0365 mmol) in 5 mL HOAc was stirred at 120° C. overnight in a sealed tube. The completion was monitored by TLC and LC-MS. The sealed tube was then placed in water until cool. The suspension was diluted with water (30 mL) and adjusted pH to 8, then extracted with ethyl acetate (3×50 mL). The organic phase was concentrated to give crude product and 20 mg of the desired product was obtained by column chromatography. MS (ESI): 381 (MH$^+$); $^1$H NMR (300 MHz, CDCl$_3$) δ 8.45-8.42 (d, J=8.22 Hz, 1H), 8.27 (s, 1H), 8.04-8.00 (dd, J=8.39, 1.61 Hz, 1H), 7.28 (s, 2H), 5.52 (s, 1H), 5.30 (s, 1H), 4.39-4.33 (m, 2H). 2.72-2.59 (m, 2H), 2.42 (s, 3H), 1.96-1.88 (m, 2H), 1.72-1.68 (m, 2H), 1.56-1.51 (m, 2H).

Example 25.3. Synthesis of 6-methyl-N-(5-methylthiazol-2-yl)-13-oxo-7,8,9,10,11,13-hexahydro-6H-azocino[2,1-b]quinazoline-3-carboxamide

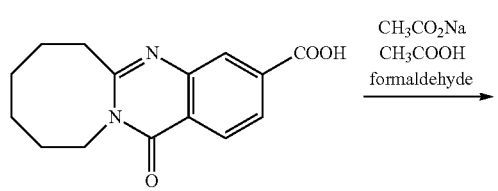

-continued

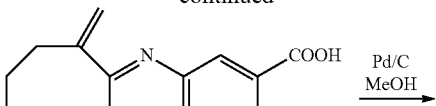

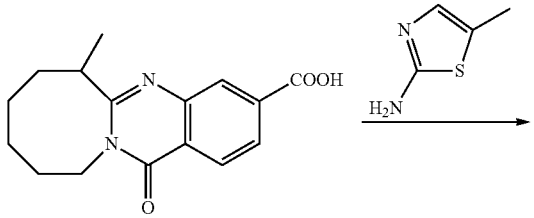

Example 25.3a. Synthesis of 6-methylene-13-oxo-7,8,9,10,11,13-hexahydro-6H-azocino[2,1-b]quinazoline-3-carboxylic Acid

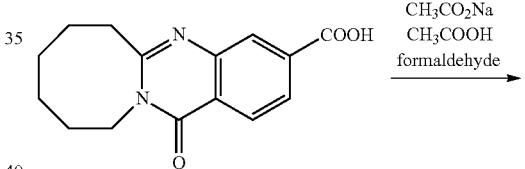

The title compound was prepared according to the experimental procedure as described in Example 25.1b. MS (ESI): 285 (MH$^+$).

Example 25.3b. Synthesis of 6-methyl-13-oxo-7,8,9,10,11,13-hexahydro-6H-azocino[2,1-b]quinazoline-3-carboxylic Acid

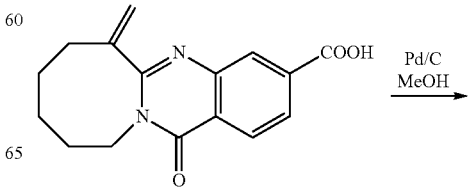

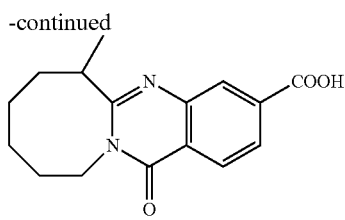

6-methylene-13-oxo-7,8,9,10,11,13-hexahydro-6H-azocino[2,1-b]quinazoline-3-carboxylic acid (50 mg) was dissolved in MeOH (5 mL). To the mixture was added a catalytic amount of Pd/C. The reaction mixture was vacuumed and then back filled with hydrogen gas three times. After completion, the reaction was filtered and washed with methanol. The filtrate was concentrated to give the desired product. MS (ESI): 287 (MH$^+$).

Example 25.3c. Synthesis of 6-methyl-N-(5-methyl-thiazol-2-yl)-13-oxo-7,8,9,10,11,13-hexahydro-6H-azocino[2,1-b]quinazoline-3-carboxamide

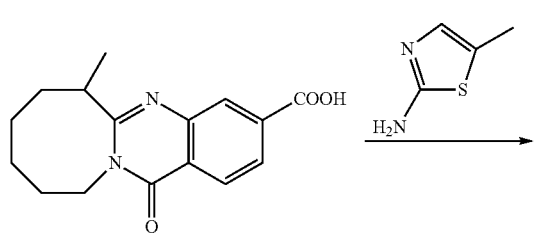

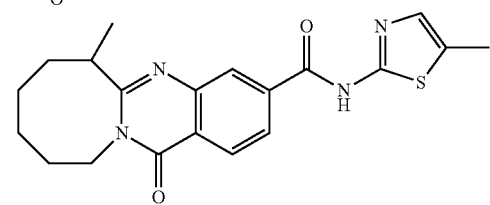

The title compound was prepared according to the experimental procedure as described in Example 22.1. MS (ESI): 383 (MH$^+$); $^1$H NMR (300 MHz, CDCl$_3$) δ 8.41-8.38 (d, J=8.37 Hz, 1H), 8.26-8.25 (d, J=1.47 Hz, 1H), 8.02-7.98 (dd, J=8.30, 1.68 Hz, 1H), 6.91 (s, 1H), 5.00-4.91 (dt, J=14.1, 3.6 Hz, 1H), 3.98-3.85 (m, 1H), 3.46-3.29 (m, 1H), 2.38 (s, 3H), 1.99-1.86 (m, 3H), 1.71-1.61 (m, 5H), 1.49-1.47 (d, J=6.36 Hz, 3H), 1.30-1.40 (m, 1H). mGluR5 PAM EC$_{50}$: ++++.

Example 25.4. Synthesis of 6-ethyl-N-(5-methylthiazol-2-yl)-13-oxo-7,8,9,10,11,13-hexahydro-6H-azocino[2,1-b]quinazoline-3-carboxamide

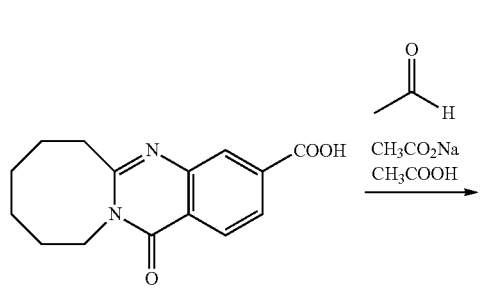

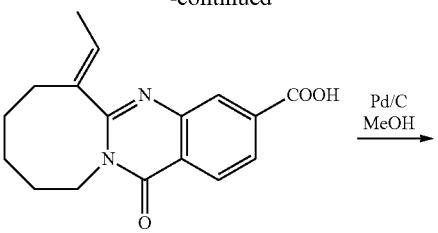

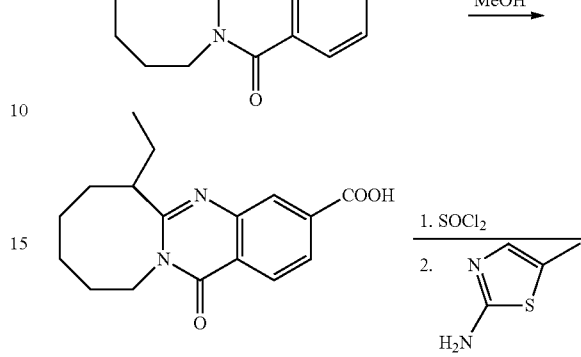

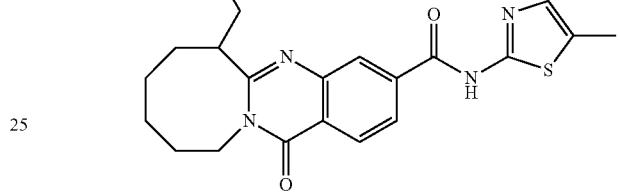

The title compound was prepared according to the experimental procedure as described in Example 25.1b, Example 25.3b, and Example 22.1a and Example 22.1b. MS (ESI): 397 (MH$^+$).

Example 26.1. Synthesis of N-(4-fluorophenyl)-7,8,9,10,11,13-hexahydro-6H-azocino[2,1-b]quinazoline-3-carboxamide

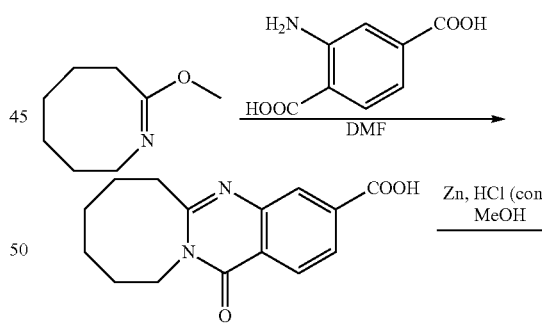

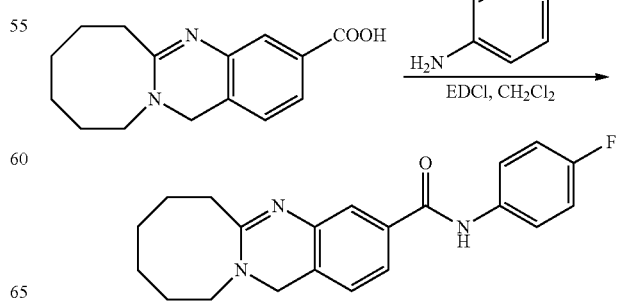

Example 26.1a. Synthesis of 13-oxo-7,8,9,10,11,13-hexahydro-6H-azocino[2,1-b]quinazoline-3-carboxylic Acid

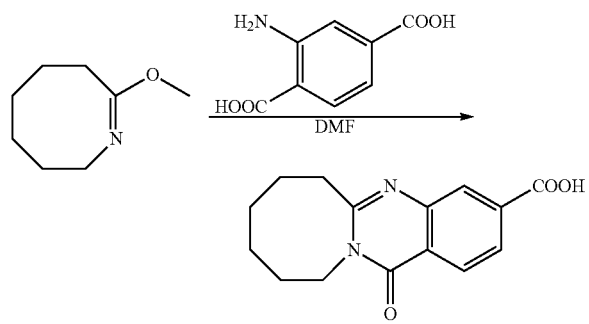

The title compound was prepared according to the experimental procedure as described for Example 23.1d. MS (ESI): 273 (MH$^+$).

Example 26.1b. Synthesis of 7,8,9,10,11,13-hexahydro-6H-azocino[2,1-b]quinazoline-3-carboxylic Acid

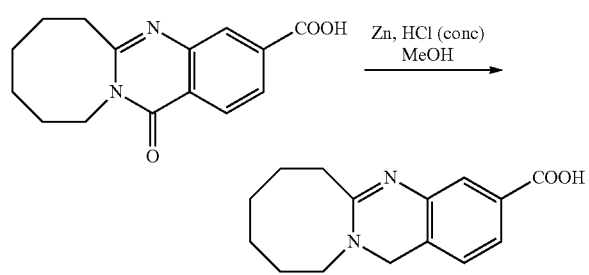

The title compound was prepared according to the experimental procedure as described for Example 19.1a. MS (ESI): 259 (MH+).

Example 26.1c. Synthesis of N-(4-fluorophenyl)-7,8,9,10,11,13-hexahydro-6H-azocino[2,1-b]quinazoline-3-carboxamide

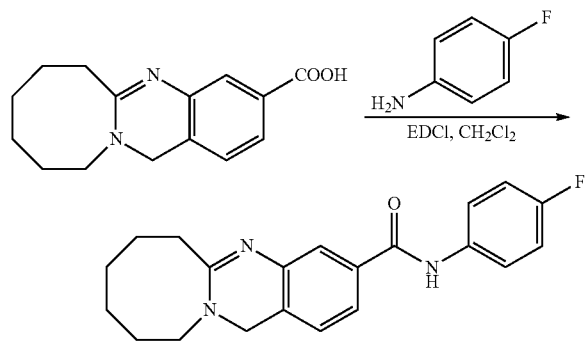

The title compound was prepared according to the experimental procedure as described for Example 28.1c. MS (ESI): 352 (MH$^+$); $^1$H NMR (300 MHz, CDCl$_3$) δ 7.94 (broad, 1H), 7.63-7.58 (m, 3H), 7.43-7.42 (d, J=1.8 Hz, 1H), 7.09-7.03 (m, 3H), 4.61 (s, 2H), 3.52-3.48 (t, J=5.7 Hz, 2H), 2.61-2.57 (t, J=6.0 Hz, 2H), 1.91-1.87 (m, 2H), 1.76-1.55 (m, 4H). mGluR5 PAM EC$_{50}$: +.

Example 27.1. Synthesis of 3-(3-(4-fluorophenyl)-1,2,4-oxadiazol-5-yl)-8,9,10,11-tetrahydro-6H-azocino[2,1-b]quinazolin-13(7H)-one

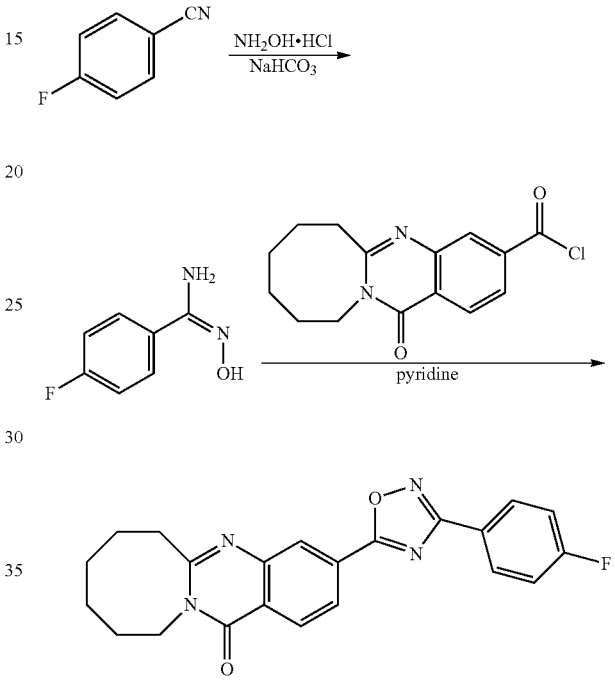

Example 27.1a. Synthesis of (E)-4-fluoro-N'-hydroxybenzimidamide

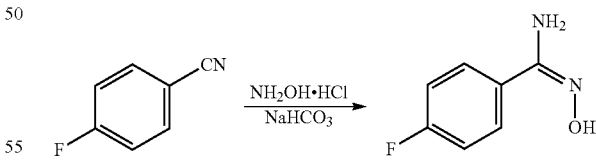

To a solution of 4-fluorobenzonitrile (1.21 g, 10 mmol) and NH$_2$OH.HCl (0.83 g, 12 mmol) in H$_2$O (5 mL) was added NaHCO$_3$ in portions. The reaction mixture was stirred at room temperature overnight. The mixture was then diluted with H$_2$O (50 mL) and extracted with ethyl acetate (2×50 mL). The combined organic layers were washed with brine and dried over Na$_2$SO$_4$. After filtration, the filtrate was concentrated under reduced pressure to give the desired product (1.2 g). MS (ESI): 155 (MH$^+$).

Example 27.1b. Synthesis of 3-(3-(4-fluorophenyl)-1,2,4-oxadiazol-5-yl)-8,9,10,11-tetrahydro-6H-azocino[2,1-b]quinazolin-13(7H)-one

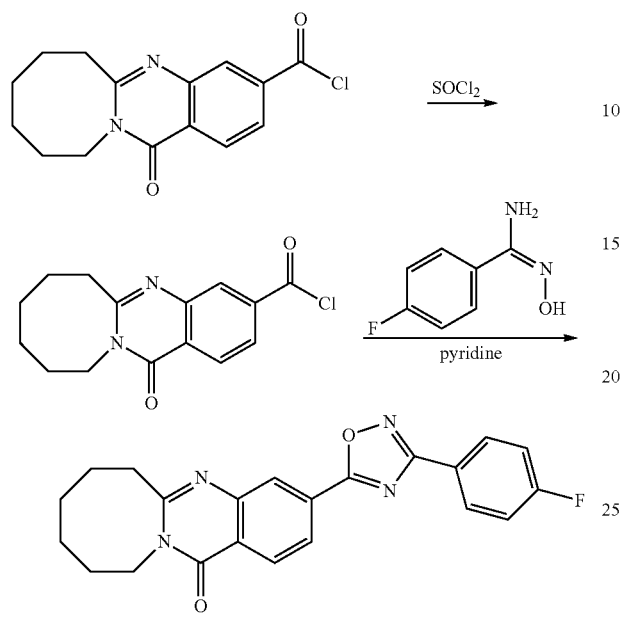

A solution of 13-oxo-7,8,9,10,11,13-hexahydro-6H-azocino[2,1-b]quinazoline-3-carboxylic acid (75 mg, 0.28 mmol) in SOCl₂ (3 mL) was stirred at reflux for 0.5 h. The excess SOCl₂ was removed and the residue was diluted with toluene (5 mL). The toluene solution was added dropwise to a solution of (E)-4-fluoro-N-hydroxybenzimidamide (51 mg, 0.33 mmol) in pyridine (2 mL). After stirring at room temperature for 0.5 h, the mixture was heated and kept at 60° C. overnight. The reaction mixture was concentrated and then diluted with water (25 mL). The aqueous mixture was extracted with ethyl acetate (2×25 mL). The combined organic layers were washed with brine and dried over Na₂SO₄. After concentration, the crude product was purified by column chromatography to give the desired product (13 mg). MS (ESI): 391 (MH⁺); ¹H NMR (300 MHz, CDCl₃) δ 8.52 (s, 1H), 8.45-8.42 (d, J=7.68 Hz, 1H), 8.25-8.18 (m, 3H), 7.23-7.20 (t, J=7.8 Hz, 2H), 4.38 (broad, 2H), 3.11-3.09 (m, 2H), 2.03 (broad, 2H), 1.94 (broad, 2H), 1.64 (broad, 2H), 1.48 (broad, 2H).

Example 27.2. Synthesis of 3-(5-(4-fluorophenyl)-1,3,4-oxadiazol-2-yl)-8,9,10,11-tetrahydro-6H-azocino[2,1-b]quinazolin-13(7H)-one

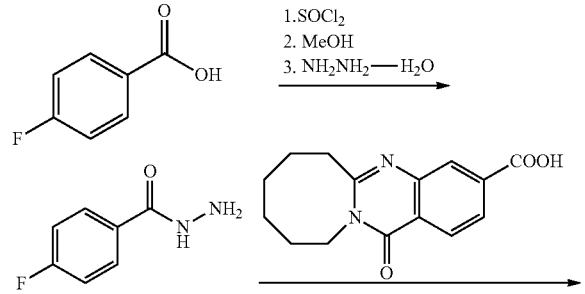

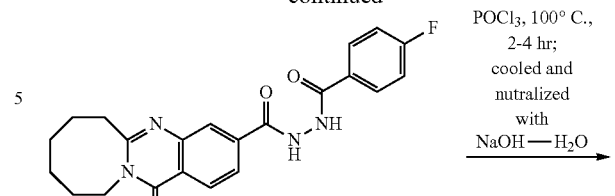

Example 27.2a. Synthesis of 4-fluorobenzohydrazide

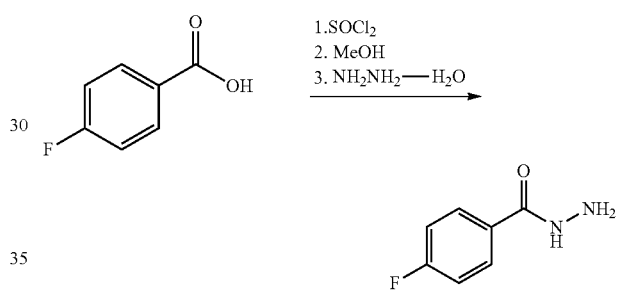

A solution of 4-fluorobenzoic acid (2.8 g, 0.02 mol) in SOCl₂ (6 mL) was stirred at reflux for 3 h. The reaction mixture was concentrated, then dissolved in MeOH and heated at reflux for 1 h. Hydrazine (20 mL) was added to the mixture and heated at reflux overnight. After it was cooled to room temperature, the reaction mixture was filtered to give the desired product as a white solid (3 g).

Example 27.2b. Synthesis of 3-(5-(4-fluorophenyl)-1,3,4-oxadiazol-2-yl)-8,9,10,11-tetrahydro-6H-azocino[2,1-b]quinazolin-13(7H)-one

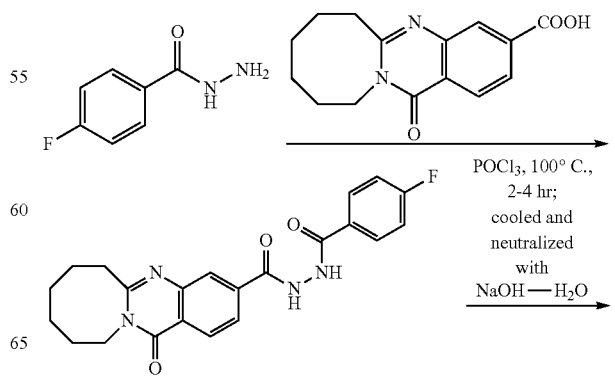

-continued

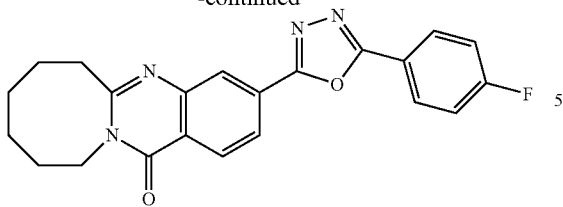

A solution of 13-oxo-7,8,9,10,11,13-hexahydro-6H-azocino[2,1-b]quinazoline-3-carboxylic acid (80 mg, 0.28 mmol) in SOCl$_2$ (3 mL) was stirred at reflux for 0.5 h. The reaction mixture was concentrated and diluted with toluene (5 mL). 4-fluorobenzohydrazide (54.4 mg, 0.35 mmol) was added to the solution and heated to 60° C. After stirring for 1.5 h, the toluene was evaporated. Phosphoryl trichloride (3 mL) was added to the residue and heated at 80° C. for 1.5 h. Excess phosphoryl trichloride was removed under reduced pressure and diluted with water (25 mL). The mixture was adjusted to pH around 7 with aqueous Na$_2$CO$_3$ solution. The aqueous mixture was extracted with ethyl acetate (3×20 mL), dried over Na$_2$SO$_4$. After filtration, the filtrate was concentrated and purified by column chromatography to give the desired product (7 mg). MS (ESI): 391 (MH$^+$); $^1$H NMR (300 MHz, CDCl$_3$) δ 8.43-8.39 (m, 2H), 8.23-8.16 (m, 3H), 7.29 (s, 1H), 7.24 (s, 1H), 4.38 (s, 2H), 3.11-3.07 (t, J=6.1 Hz, 2H), 2.05-1.93 (m, 4H), 1.65 (m, 2H), 1.49 (broad, 2H).

Example 27.3. Synthesis of 3-(4-phenyl-1H-imidazol-1-yl)-7,8,9,10-tetrahydrocyclohepta[d]pyrido[1,2-a]pyrimidin-11(6H)-one

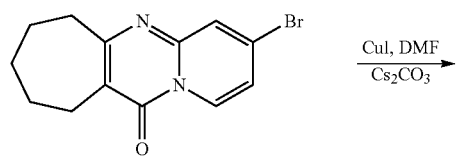

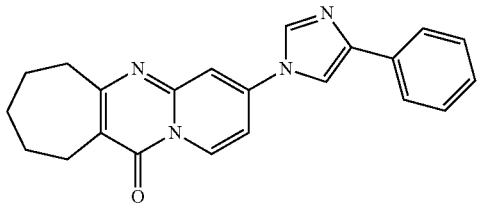

A solution of 3-bromo-7,8,9,10-tetrahydrocyclohepta[d]pyrido[1,2-a]pyrimidin-11(6H)-one (50 mg, 0.17 mmol), 4-phenyl-1H-imidazole (37.4 mg, 0.26 mmol), CuI (8 mg, 0.04 mmol) and Cs$_2$CO$_3$ in DMF was stirred at 80° C. under nitrogen. The completion of the reaction was monitored by TLC. After the suspension was diluted with water (30 mL) and extracted with ethyl acetate (3×50 mL), the combined organic phases were concentrated to crude product and 23 mg desired product was obtained by column chromatography purification. MS (ESI): 357 (MH$^+$); MS (ESI): 357 (MH$^+$); $^1$H NMR (300 MHz, CDCl$_3$) δ 9.15-9.13 (d, J=7.83 Hz, 1H), 8.16 (s, 1H), 7.87-7.85 (d, J=7.38 Hz, 2H), 7.72 (s, 1H), 7.57-7.56 (d, J=2.19 Hz, 1H), 7.48-7.44 (t, J=7.35 Hz, 2H), 7.38-7.35 (d, J=7.08 Hz, 1H), 7.26 (m, 1H), 3.00-2.97 (m, 4H), 1.93-1.91 (m, 2H), 1.79-1.77 (m, 2H), 1.71-1.69 (m, 2H).

Example 28.1. Synthesis of N-(5-methylthiazol-2-yl)-12-oxo-7,8,9,10,11,12-hexahydro-6H-cycloocta[d]pyrido[1,2-a]pyrimidine-3-carboxamide

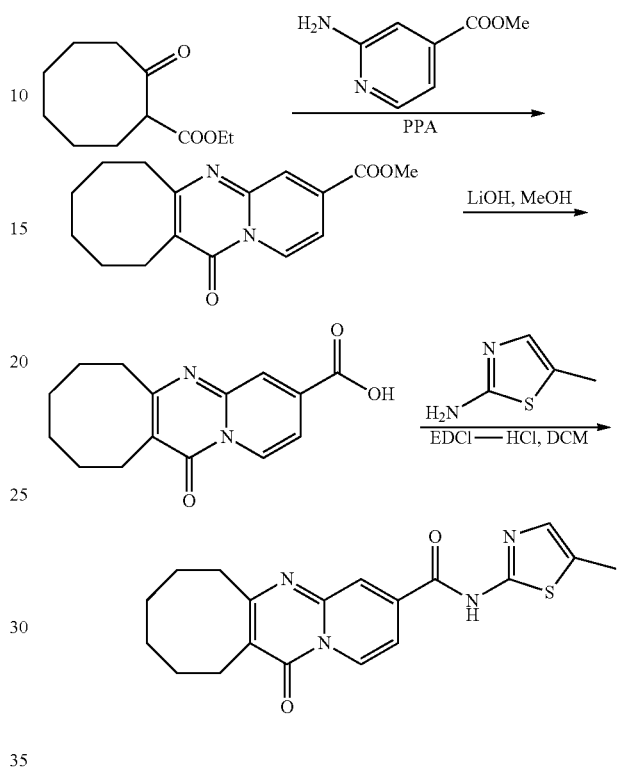

Example 28.1a. Synthesis of methyl-12-oxo-7,8,9,10,11,12-hexahydro-6H-cycloocta[d]pyrido[1,2-a]pyrimidine-3-carboxylate

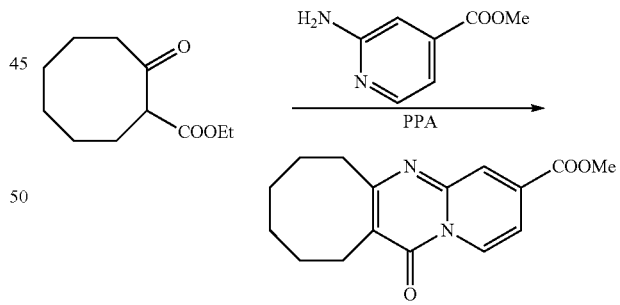

A solution of ethyl 2-oxocyclooctanecarboxylate (1 g, 5.05 mmol) and methyl 2-aminoisonicotinate (0.768 g, 5.05 mmol) in PPA (2.5 mL) and 1,2-dichloroethane (5 mL) was stirred at 85° C. for 18 hours. The reaction mixture was then cooled to ambient temperature. A chilled saturated sodium carbonate solution was added to adjust pH to 8. The resulting mixture was extracted with ethyl acetate (4×100 mL). The combined organic layers were washed with brine and dried over anhydrous sodium sulfate. After filtration and concentration, the crude product was purified by silica gel chromatography purification to afford 157 mg of desired product.

Example 28.1b. Synthesis of 12-oxo-7,8,9,10,11,12-hexahydro-6H-cycloocta[d]pyrido[1,2-a]pyrimidine-3-carboxylic Acid

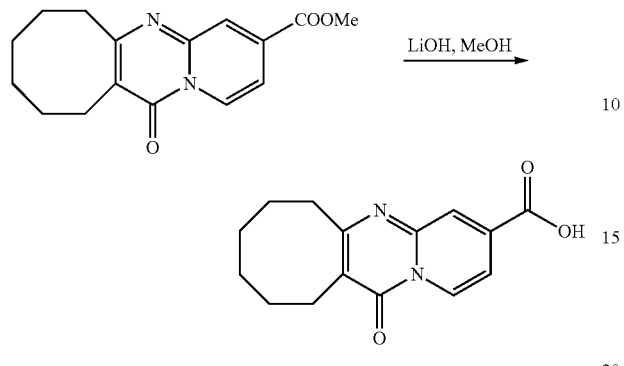

A solution of methyl 12-oxo-7,8,9,10,11,12-hexahydro-6H-cycloocta[d]pyrido[1,2-a]-pyrimidine-3-carboxylate (80 mg, 0.28 mmol) and LiOH·H$_2$O in MeOH (5 mL) was stirred at room temperature for 0.5 h. The reaction mixture was adjusted to pH around 6 with 1 N HCl and extracted with ethyl acetate (2×25 mL). The combined ethyl acetate layers were washed with brine and dried over anhydrous sodium sulfate. After filtration and concentration, the crude product was used for the next step without further purification.

Example 28.1c. Synthesis of N-(5-methylthiazol-2-yl)-12-oxo-7,8,9,10,11,12-hexahydro-6H-cycloocta[d]pyrido[1,2-a]pyrimidine-3-carboxamide

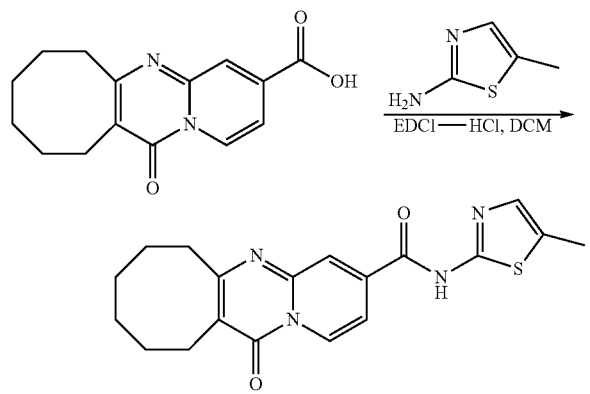

To a solution of the acid prepared from Example 28.1b and EDCl-HCl (80.2 mg, 0.42 mmol) in DCM (10 mL) was added 5-methylthiazol-2-amine (25.5 mg, 0.22 mmol). The mixture was stirred at room temperature for 10 min and then poured into 2 N HCl. The mixture was extracted with DCM (30 mL) and the organic layer was washed with aqueous NaHCO$_3$, brine, dried over anhydrous sodium sulfate. After filtration and concentration, the crude product was purified by preparative HPLC to afford 5.5 mg of desired product. MS (ESI): 369 (MH$^+$); $^1$H NMR (300 MHz, CDCl$_3$) δ 9.09-9.06 (d, J=7.38 Hz, 1H), 8.22 (s, 1H), 7.60-7.58 (J=6.57 Hz, 1H), 7.06 (t, J=5.4 Hz, 1H), 3.01-2.93 (m, 4H), 2.44 (s, 3H), 1.92-1.80 (m, 4H), 1.49 (broad, 4H). mGluR5 PAM EC$_{50}$: +++++. Fold shift at 10 μM: +.

Example 28.2. Synthesis of N-(4-fluorophenyl)-12-oxo-7,8,9,10,11,12-hexahydro-6H-cycloocta[d]pyrido[1,2-a]pyrimidine-3-carboxamide

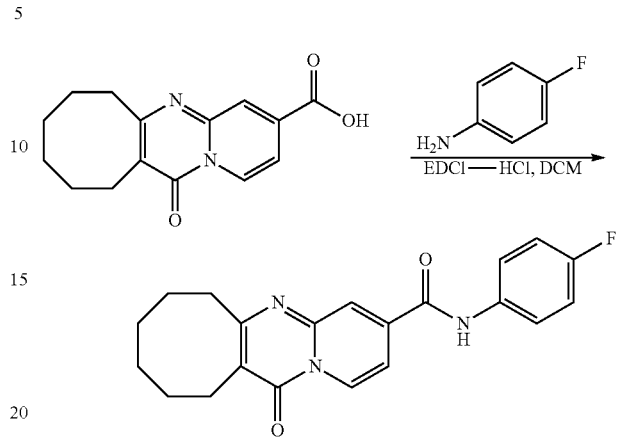

The title compound was prepared according to the experimental procedure as described in Example 28.1c. MS (ESI): 366 (MH$^+$); $^1$H NMR (300 MHz, CDCl$_3$) δ 9.08-9.05 (d, J=7.47 Hz, 1H), 7.96-7.88 (m, 2H), 7.65-7.58 (m, 2H), 7.52-7.48 (dd, J=7.38, 2.01 Hz, 1H), 7.16-7.10 (t, J=8.4 Hz, 2H), 3.00-2.87 (m, 4H), 1.96-1.75 (m, 4H), 1.49-1.45 (m, 4H). mGluR5 PAM EC$_{50}$: +.

Example 28.3. Synthesis of N-(5-methylthiazol-2-yl)-11-oxo-6,7,8,9,10,11-hexahydrocyclohepta[d]pyrido[1,2-a]pyrimidine-3-carboxamide

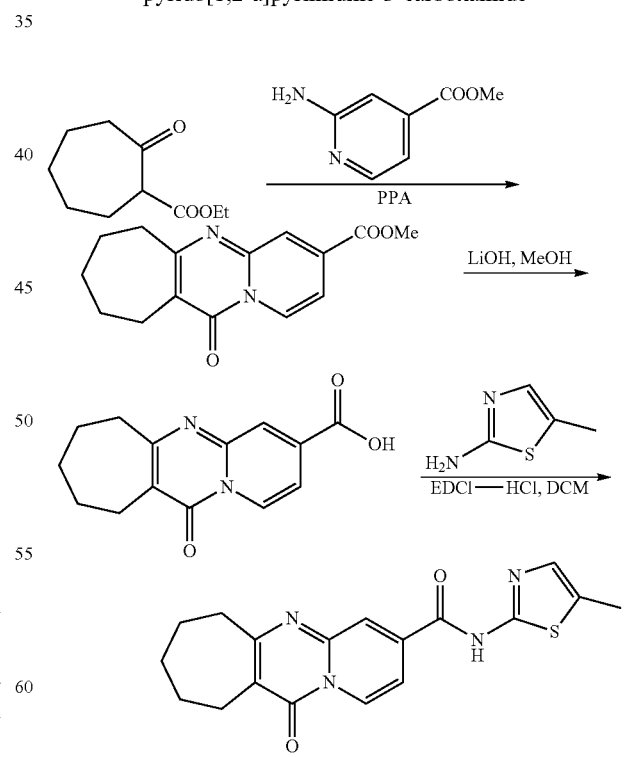

The title compound was prepared according to the experimental procedures as described in Example 28.1. MS (ESI): 355 (MH$^+$). mGluR5 PAM EC$_{50}$: +++.

Example 28.4. Synthesis of N-(3-methylisoxazol-5-yl)-11-oxo-6,7,8,9,10,11-hexahydrocyclohepta[d]pyrido[1,2-a]pyrimidine-3-carboxamide

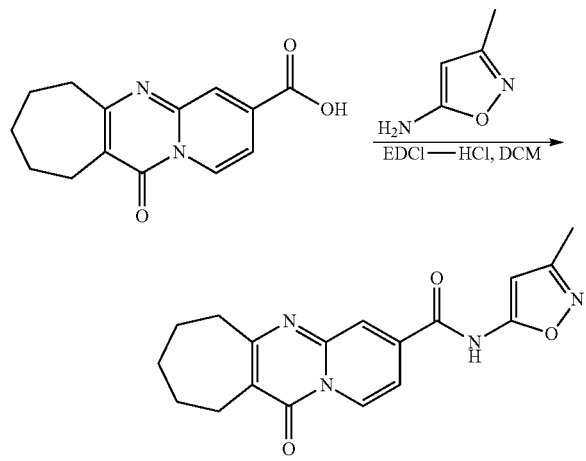

The title compound was prepared according to the experimental procedure as described in Example 28.1c. MS (ESI): 339 (MH+).

Example 28.5. Synthesis of N-(3-methylisoxazol-5-yl)-11-oxo-2,3,4,11-tetrahydro-1H-pyrido[2,1-b]quinazoline-7-carboxamide

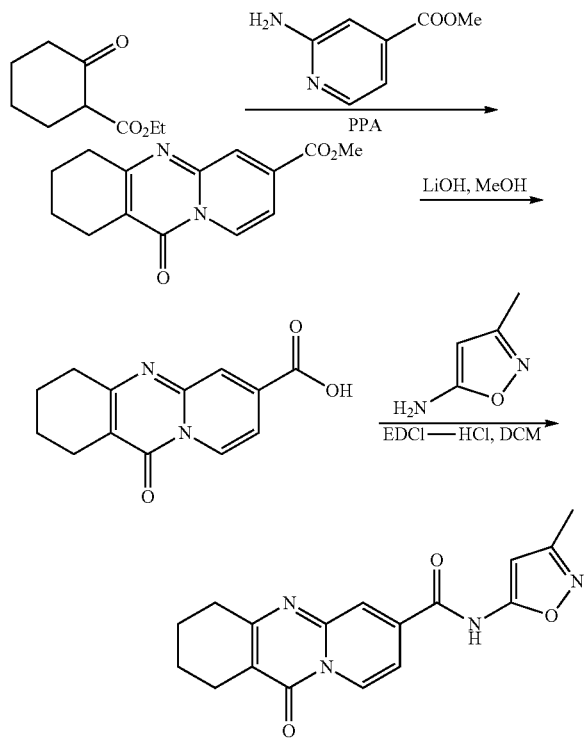

The title compound was prepared according to the experimental procedures as described in Example 28.1. MS (ESI): 325 (MH+).

Example 29. In Vitro Cell-Based Assay for Modulation of the Activation of mGluR5 by Glutamate The DNA sequences encoding the structural regions for rat mGluR5 [Abe T, Sugihara H, Nawa H, Shigemoto R, Mizuno N, Nakanishi S (1992) "Molecular characterization of a novel metabotropic glutamate receptor mGluR5 coupled to inositol phosphate/$Ca^{2+}$ signal transduction" *Journal of Biological Chemistry* vol. 267, no. 19, pp. 13361-8] and human mGluR5 [Daggett L P, Sacaan A I, Akong M, Rao S P, Hess S D, Liaw C, Urrutia A, Jachec C, Ellis S B, Dreessen J, Knöpfel T, Landwehrmeyer G B, Testa C M, Young A B, Varney M, Johnson E C, Veliçelebi (1995) "Molecular and functional characterization of recombinant human metabotropic glutamate receptor subtype 5" *Neuropharmacology* vol. 34, no. 8, pp. 871-886] were prepared synthetically and confirmed by DNA sequencing using standard methods at Genscript Inc., and inserted using standard molecular biology methods into the vector pcDNAzeo3.1 (purchased from Invitrogen Corporation). A HEK293 cell line that had previously been created which stably expresses the rat glial glutamate transporter GLAST (EAAT1) [Schlag B D, Vondrasek J R, Munir M, Kalandadze A, Zelenaia O A, Rothstein J D, Robinson M B (1998) "Regulation of the glial Na+-dependent glutamate transporters by cyclic AMP analogs and neurons" *Molecular Pharmacology* vol. 53, no. 3, pp. 355-369] was obtained from Dr. Michael Robinson of the Children's Hospital of Philadelphia under a Material Transfer Agreement. The pcDNAzeo3.1 vector DNA, carrying either rat mGluR5 or human mGluR5, was used to transfect a sample of the HEK293/GLAST cells, and single clones that express mGluR5 were isolated from the transfected cells using zeocin selection. Expression of mGluR5 was assessed by measurement of the transient fluorescence signal elicited from HEK293/GLAST/mGluR5 cells by glutamate following the loading of the cells with a calcium-sensitive dye using a FLIPR Tetra (Fluorometric Imaging Plate Reader) (Molecular Devices, Sunnyvale, Calif.) [O'Brien J A, Lemaire W, Chen T B, Chang R S, Jacobson M A, Ha S N, Lindsley C W, Schaffhauser H J, Sur C, Pettibone D J, Conn P J, Williams D L Jr. (2003) "A family of highly selective allosteric modulators of the metabotropic glutamate receptor subtype 5" *Molecular Pharmacology* vol. 64, no. 3, pp. 731-740; Assay Guidance Manual Version 5.0, 2008, Eli Lilly and Company and NIH Chemical Genomics Center; available online HEK293/GLAST/mGluR5 cells were grown in Dulbecco's Modified Eagle Medium (DMEM) supplemented with 10% dialyzed fetal bovine serum, 20 millimolar (mM) N-2-hydroxyethylpiperazine-N'-2-ethanesulfonic acid (HEPES), penicillin, streptomycin, 1% GlutaMax™ (Invitrogen) and 50 µg/ml zeocin. Cells were grown in the media to 70-80% confluency at 37° C. under 5% $CO_2$, 95% humidity in poly-D-lysine coated coated flasks. Cells for assays were plated into 96-well sterile standard microtiter plates (pre-coated with poly-D-lysine) at a density of 50,000 cells per well in 0.2 milliliters of media. Plated cells were allowed to settle and adhere for 30 minutes at ambient conditions, and then were incubated overnight at 37° C. under 5% $CO_2$, 95% humidity. Several such 96-well plates were typically prepared. On the day of the assays, the components of the FLIPR calcium 4 assay kit (Molecular Devices) were dissolved according to the instructions of the dye kit's manufacturer in assay buffer (Hank's balanced salt solution (HBSS) (Gibco) supplemented with 20 mM HEPES). After removal of the growth media from the first plate, cells were loaded with calcium dye by addition of calcium dye solution (50 microliters per well) and incubation at 25° C. for 45 to 60 minutes. The first plate was placed into the FLIPR Tetra, and a dilution series of glutamate solutions in assay buffer were added to wells on the plate, followed by acquisition of fluorescence data for several minutes. The fluorescence data (maximal signal as a 4-parameter sigmoidal function of log [glutamate]) were processed by non-linear regression methods using the software package GraphPad Prism 5.01 (GraphPad Software Inc.), to yield a glutamate concentration-response curve (CRC). These results allow the calculation of the $EC_{20}$, $EC_{50}$, and $EC_{80}$ values for glutamate for each day. These values were, respectively, the concentrations of glutamate that elicit 20%, 50%, and 80% of the maximal FLIPR signal (observed at saturating [glutamate]). The method for measuring the concentration response of a potentiator, or positive allosteric modulator (PAM), is described here as an example. For that purpose, subsequent assays were typically performed using assay buffer containing a glutamate concentration equal to that day's $EC_{20}$. The assays of test compounds to measure activity as positive modulators were typically done as follows: (1) test compound was added, (2) fluorescence signals were measured for 180 seconds, (3) glutamate at its $EC_{20}$ was added, and (4) fluorescence signals were measured for 120 seconds. For measurement of the $EC_{50}$ value of test compound as a positive modulator of mGluR5, the test compound was typically added in a volume of 50 microliters as a dilution (in assay buffer) of a stock solution of test compound in dimethylsulfoxide (DMSO), such that the final concentration of DMSO was 0.3% (previously demonstrated to be well tolerated by HEK293/GLAST/mGluR5 for the few minutes required for the assay). Addition to certain wells of the same buffer containing 0.3% DMSO, but without any test compound, provided a negative control. Addition to certain wells of a saturating concentration of glutamate (typically a final concentration of 15 micromolar) provided a positive control. The maximal fluorescence signals from the second time interval, from wells containing varying concentration of test compound, were analyzed to provide a CRC for that compound, and yielding a PAM $EC_{50}$ value and maximal stimulation value (normalized to that observed for saturating glutamate) for each test compound. The concentration response curve of a reference compound provided a quality control measurement on each plate.

Example 30. Measurement of Glutamate $EC_{50}$ Shift in the Presence of Test Compounds Shifts in the $EC_{50}$ for glutamate caused by the presence of 10 micromolar concentrations of test compounds (fold shift values) were measured in the following manner. Preparation of cell plates, incubation with dye prior to the assay and the FLIPR protocol were as described above. After incubation with the dye, the assay plates were transferred to the FLIPR. For each compound tested, sample was added to provide 10 micromolar final concentration, and after 180 sec, glutamate was added at varying concentrations. The FLIPR signal was monitored for another 120 sec. Three compounds were tested per plate, in duplicate rows, with the top 2 rows containing only 0.3% DMSO in buffer, which was the control without any test compound. The maximum FLIPR signal after addition of glutamate was plotted as a function of glutamate concentration, and the $EC_{50}$ values for glutamate were obtained as described above. The ratio of glutamate $EC_{50}$ for the control condition (in absence of test compound) to the $EC_{50}$ in the presence of 10 micromolar test compound was reported as "glutamate $EC_{50}$ fold-shift." Results from assays with cells expressing the recombinant human mGluR5 and with cells expressing the recombinant rat mGluR5 were similar but not identical; the values for mGluR5 PAM $EC_{50}$ and fold-shift provided herein were derived solely from assays performed with cells expressing the recombinant human mGluR5.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein by reference in their entireties. Citation or identification of any reference in this application is not an admission that such reference is available as prior art to this application. The full scope of the disclosure is understood with reference to the appended claims.

The invention claimed is:
1. A compound of formula I:

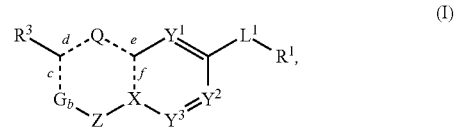

wherein:
  $R^1$ is cycloalkyl, heterocycloalkyl, aryl or heteroaryl, each of which is optionally substituted;
  $R^2$ and $R^3$, together with the atoms to which they are attached, form an optionally substituted hexahydroazepine ring;
  G is $NR^2$;
  Q is N;
  X is C;
  Z is C=O;
  b, c and e are single bonds; and d and f are double bonds;
  $Y^1$, $Y^2$ and $Y^3$ are each independently CH, C-halogen or C-lower alkyl; and
  $L^1$ is —C≡C—, —HC=CH—, or -(lower alkyl)C=C(lower alkyl)-;
  or a pharmaceutically acceptable salt thereof.
2. The compound of claim 1, or a pharmaceutically acceptable salt thereof, wherein $L^1$ is —C≡C— or —HC=CH—.
3. The compound of claim 1, or a pharmaceutically acceptable salt thereof, wherein $R^1$ is optionally substituted aryl.
4. The compound of claim 3, or a pharmaceutically acceptable salt thereof, wherein $R^1$ is selected from

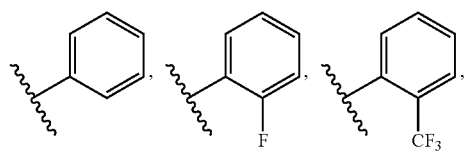

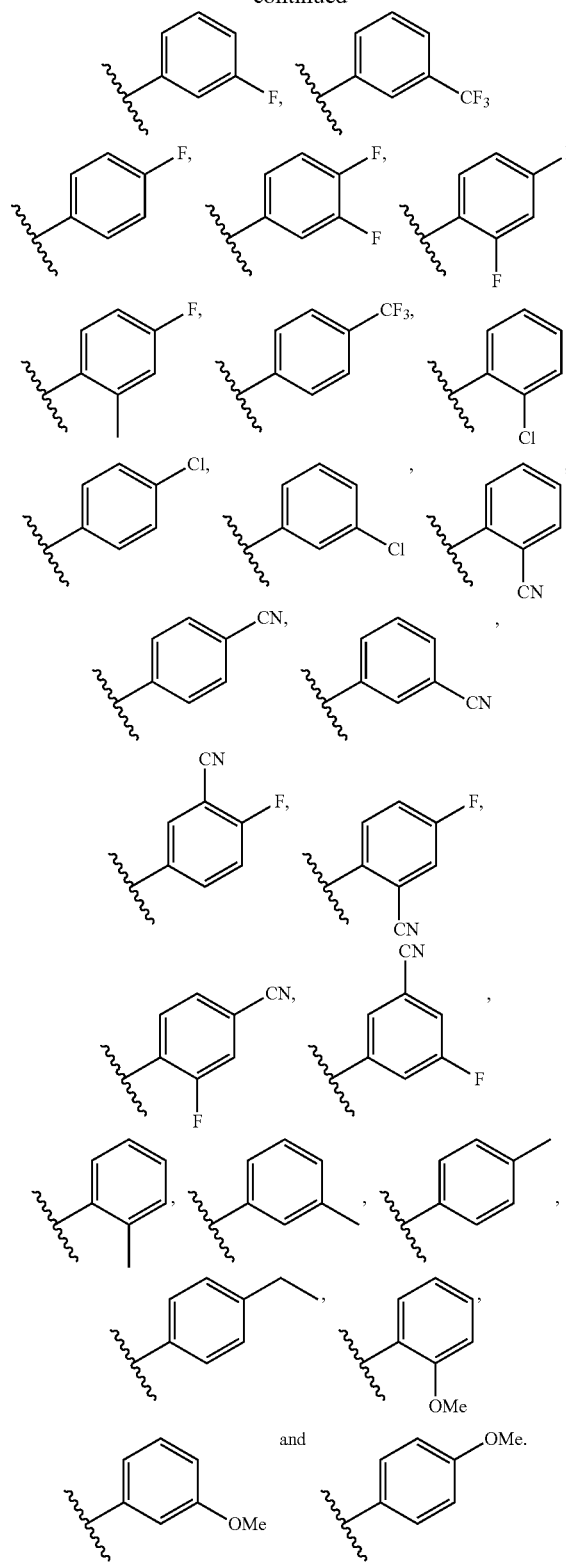
5. The compound of claim 1, or a pharmaceutically acceptable salt thereof, wherein $R^1$ is optionally substituted heteroaryl.
6. The compound of claim 5, or a pharmaceutically acceptable salt thereof, wherein $R^1$ is selected from 519
-continued
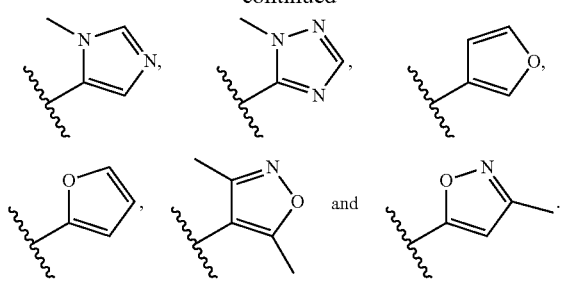
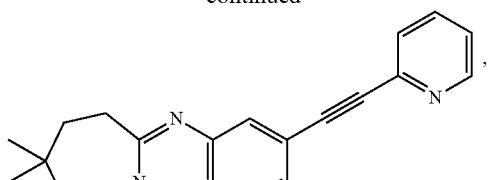
7. The compound of claim 1, or a pharmaceutically acceptable salt thereof, wherein R¹ is optionally substituted cycloalkyl.
8. The compound of claim 7, or a pharmaceutically acceptable salt thereof, wherein R¹ is selected from
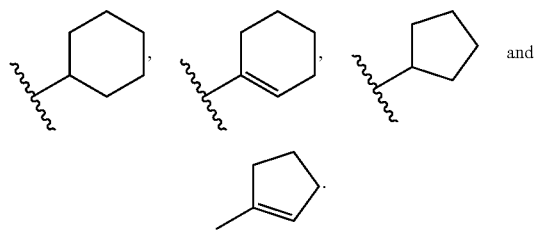
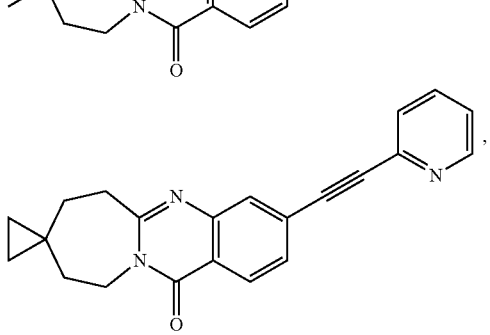
9. A compound, or a pharmaceutically acceptable salt thereof, wherein the compound is selected from:
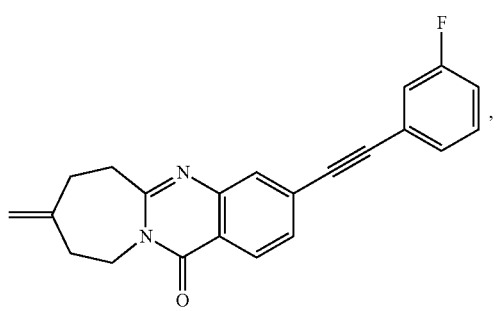
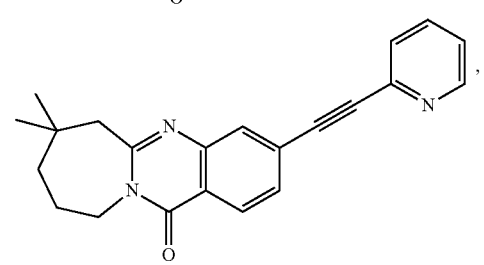
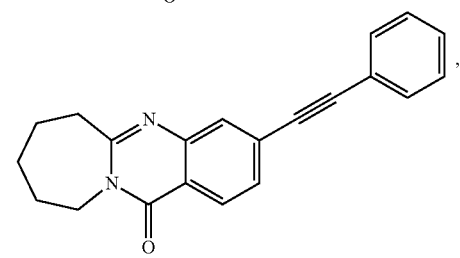
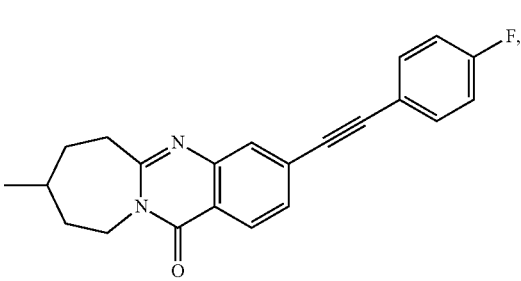
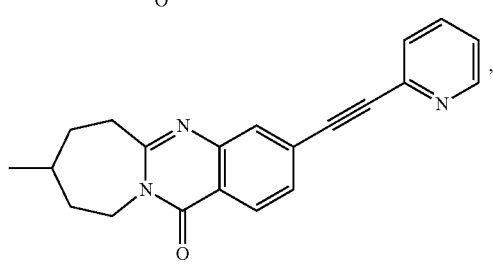
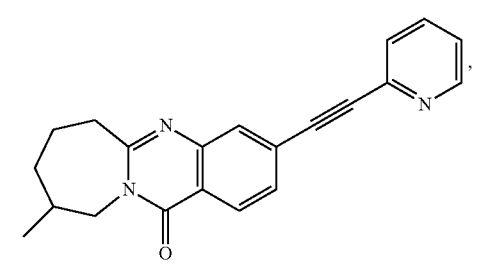
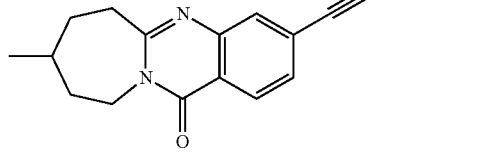
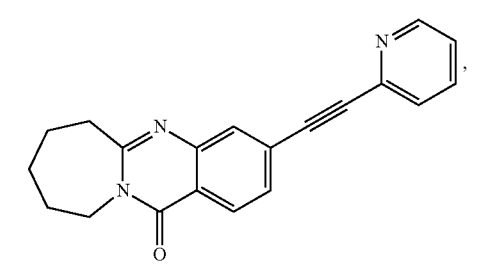
520
-continued 521
-continued
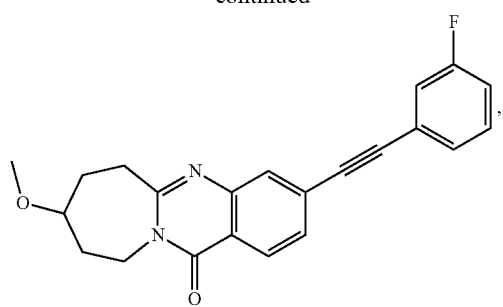
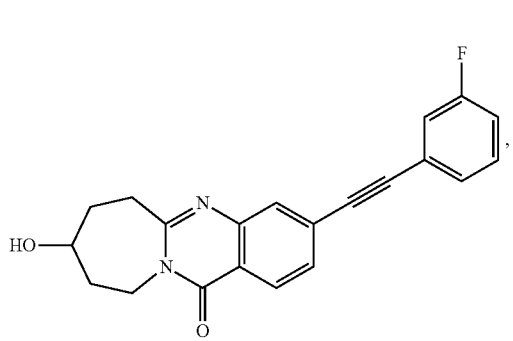
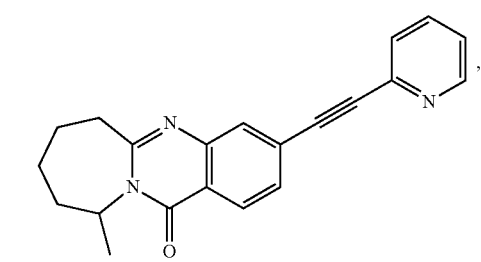
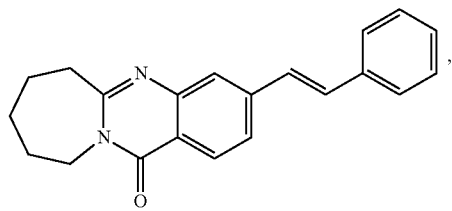
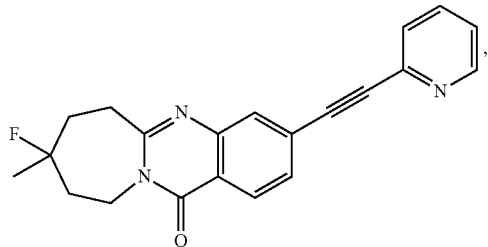
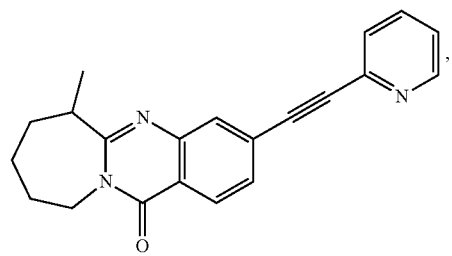
522
-continued
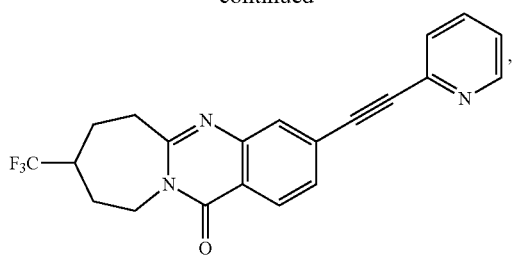
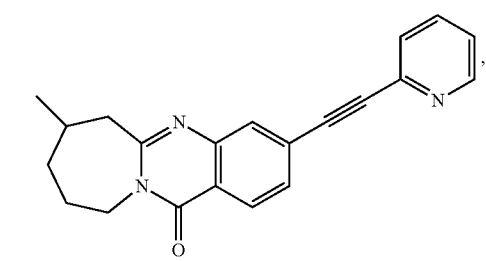
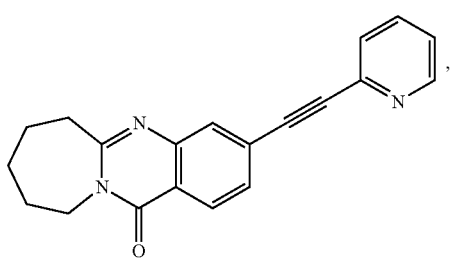
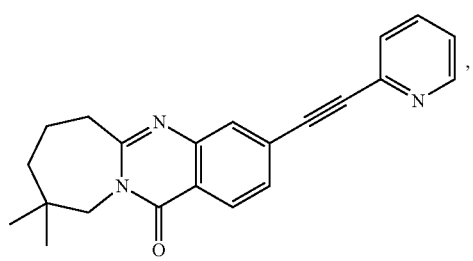
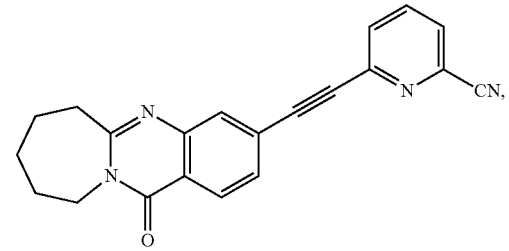
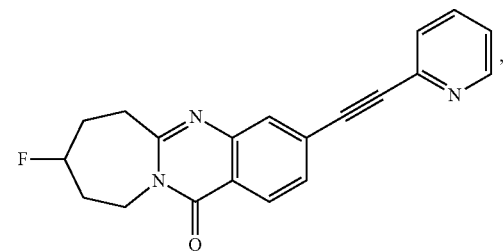

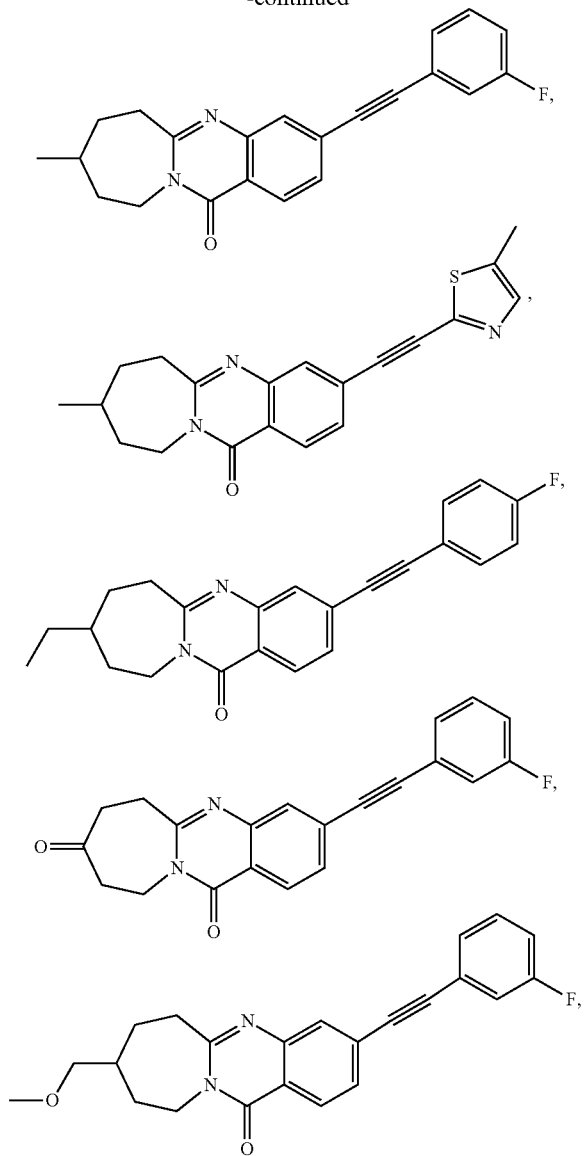
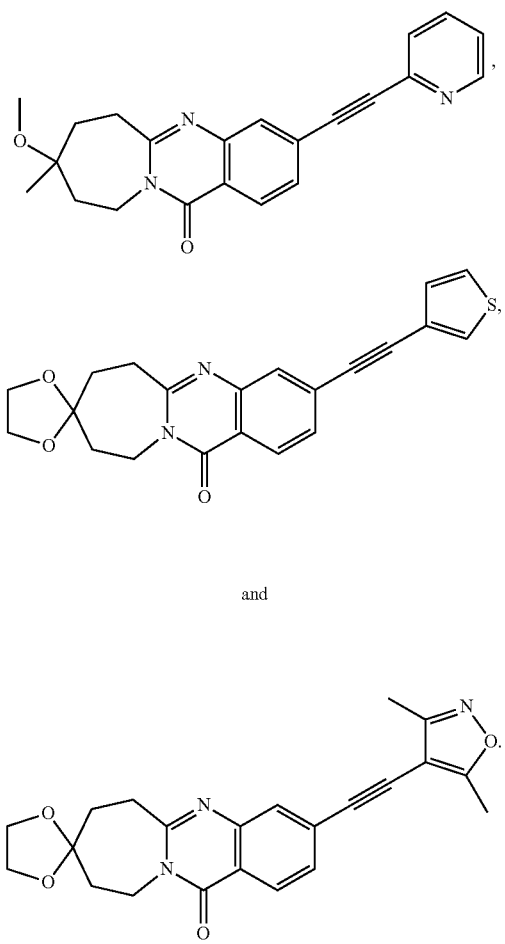
and
10. A pharmaceutical composition comprising a compound of claim 1, or a pharmaceutically acceptable salt thereof, and a pharmaceutically acceptable carrier.
11. The compound of claim 1, or a pharmaceutically acceptable salt thereof, wherein $Y^1$, $Y^2$ and $Y^3$ are each CH.
* * * * *